US007666898B2

(12) United States Patent
Chang et al.

(10) Patent No.: US 7,666,898 B2
(45) Date of Patent: Feb. 23, 2010

(54) MULTIVALENT INDOLE COMPOUNDS AND USE THEREOF AS PHOSPHOLIPASE-A2 INHIBITORS

(75) Inventors: Han-Ting Chang, Livermore, CA (US); Dominique Charmot, Campbell, CA (US); Tomasz Glinka, Cupertino, CA (US); Michael James Cope, Berkeley, CA (US); Elizabeth Goka, San Jose, CA (US); Jun Shao, Fremont, CA (US); Damien Cartigny, Cachen (FR); Shiah-yun Chen, Mountain View, CA (US); Jerry M. Buysse, Los Altos, CA (US)

(73) Assignee: Ilypsa, Inc., Thousand Oaks, CA (US)

( * ) Notice: Subject to any disclaimer, the term of this patent is extended or adjusted under 35 U.S.C. 154(b) by 81 days.

(21) Appl. No.: 11/593,177

(22) Filed: Nov. 3, 2006

(65) Prior Publication Data

US 2007/0135385 A1    Jun. 14, 2007

Related U.S. Application Data

(60) Provisional application No. 60/733,954, filed on Nov. 3, 2005.

(51) Int. Cl.
*A61K 31/404* (2006.01)
*C07D 209/04* (2006.01)
(52) U.S. Cl. ..................... 514/414; 548/455
(58) Field of Classification Search ........... 548/455
See application file for complete search history.

(56) References Cited

U.S. PATENT DOCUMENTS

| | | | |
|---|---|---|---|
| 5,504,073 A | 4/1996 | Homan | |
| 5,654,326 A | 8/1997 | Bach et al. | |
| 6,325,991 B1 | 12/2001 | Draheim | |
| 6,407,102 B1 | 6/2002 | Mahoobi et al. | |
| 6,451,839 B1 | 9/2002 | Bach et al. | |
| 6,608,099 B1 | 8/2003 | Mihelich et al. | |
| 6,630,496 B1 | 10/2003 | Seehra et al. | |
| 6,706,752 B1 | 3/2004 | Lin et al. | |
| 6,730,694 B1 | 5/2004 | Beight et al. | |
| 6,831,095 B1 | 12/2004 | Harper | |
| 2003/0087944 A1 | 5/2003 | Macias et al. | |
| 2004/0077704 A1 | 4/2004 | Beight | |

FOREIGN PATENT DOCUMENTS

| | | | |
|---|---|---|---|
| EP | 0315349 A1 | 10/1989 | |
| EP | 0620214 B1 | 10/1994 | |
| EP | 0620215 B1 | 10/1994 | |
| EP | 0675110 A1 | 10/1995 | |
| EP | 0675110 B1 | 10/1995 | |
| WO | WO 98 08818 A1 | 3/1998 | |
| WO | WO 99 43672 A1 | 9/1999 | |
| WO | WO0007590 A1 | 2/2000 | |
| WO | WO 0007591 B1 | 2/2000 | |
| WO | WO 0037358 B1 | 6/2000 | |
| WO | WO 0105761 B1 | 3/2001 | |
| WO | WO 0121587 B1 | 3/2001 | |
| WO | WO 01 51003 A3 | 7/2001 | |
| WO | WO 02074342 B1 | 9/2002 | |
| WO | WO 03 048122 A2 | 6/2003 | |
| WO | 2005/107766 B2 | 11/2005 | |

OTHER PUBLICATIONS

S. Hagishita et al; "Potent Inhibitors of Secretory Phospholipase A2. Synthesis and Inhibitory Activities of Indolizine and Indene Derivatives." Journal of Medicinal Chemistry; vol. 30, 1996, pp. 3636-3658, XP002395282.

D. ST. C. Black et al.; "Calix[3]indoles, New Macrocyclic Tris (indolylmethylene) Compounds with 2, 7-Linkages." Journal of the Chemical Society, Chemical Communications, vol. 1993, 1003, pp. 819-822, XP002265922.

J. Bloxham et al.; "Synthesis and Solid State Structures of N,N'-Linked Carbazoles and Indoles" Tetrahedron, vol. 58, 2002, pp. 3709-3720.

Robert D. Dillard et al; Indole Inhibitors of Human Nonpancreatic Secretory Phospholipase A-2. 2. Indole-3-acetamides with additional Functionality; Journal of Medicinal Chemistry; vol. 30, No. 26, 1996, pp. 5137-5158; XP002424901.

Susan E. Draheim et al; Indole Inhibitors oh Human Nonpancreatic secretory phospholipase A-2. 3. Indole-3-glyoxamides; Journal of Medicinal Chemistry; vol. 30, No. 26; 1996; pp. 5159-5175; XP002424902.

Scott J. Sawyer et al; Carbocyclic(g)indole Inhibitors of Human Nonpancreatic s-PLA2; Journal of Medicinal Chemistry; vol. 48, No. 3; Feb. 10, 2005; pp. 893-896; XP002424903.

Stokes, et al., Hypercholesterolemia Promotes Inflammation and Microvascular Dysfunction; Role of Nitric Oxide and Superoxide, vol. 33, Issue 8,Oct. 15, 2002, pp. 1026-1036.

Goyal & Shah, Novel Anti-Obesity Drugs in Type II Diabetes, Indian Journal of Pharmacology 2002; 34:372-373.

Richmond, et al., Compensatory Phospholipid Digestion is Required for Cholesterol Absorption in Pancreatic Phospholipase A2-Deficient Mice, Gastroenterology 2001:120:1193-1202.

Yedgar, et al., Control of Inflammatory Processes by Cell-Impermeable Inhibitors of Phospholipase A2, AAS 46, Novel Molecular Approaches to Anti-Inflammatory Theory, 1995 Birkhauser Verlag Basel, pp. 77-84.

Juhl, et al., Secretory Phospholipase A2 is Released From Pancreatic Beta-Cells and Stimulates Insulin Secretion Via Inhibition of ATP-Dependent K+ Channels, Biomedical and Biophysical Research Communications 310 (2003) 274-279.

Tanaka, et al., Enhancement of Insulin Release Due to Inhibition of Phospholipase A2 Activity, Horm. Metabol. Res. 15 (1983) 255-256.

Office Action mailed Dec. 16, 2008 for U.S. Appl. No. 11/593,176.

Response to Office Action Filed Mar. 16, 2009 for U.S. Appl. No. 11/593,176.

*Primary Examiner*—Rebecca L Anderson
*Assistant Examiner*—Shawquia Young
(74) *Attorney, Agent, or Firm*—McAndrews, Held & Malloy, Ltd.

(57) ABSTRACT

Indole and indole-related compounds, compositions and methods are disclosed. The compounds of the invention are useful as phospholipase inhibitors. The compounds and compositions of the invention are useful for treatment of phospholipase-related conditions, such as insulin-related, weight-related and/or cholesterol-related conditions in an animal subject.

15 Claims, 38 Drawing Sheets

POLAR INTERACTION WITH Ca

HYDROPHOBIC

SCHEME 1: CONTINUOUS FLUORIMETRIC ASSAY

PPyrPG: 1-HEXADECANOYL-2-(1-PYRENEDECANOYL)-SN-GLYCERO-3-PHOSPHOGLYCEROL
PyrPG 1-HEXADECANOYL-SN-GLYCERO-3-PHOSPHOGLYCEROL
PDA: 1-PYRENEDECANOIC ACID

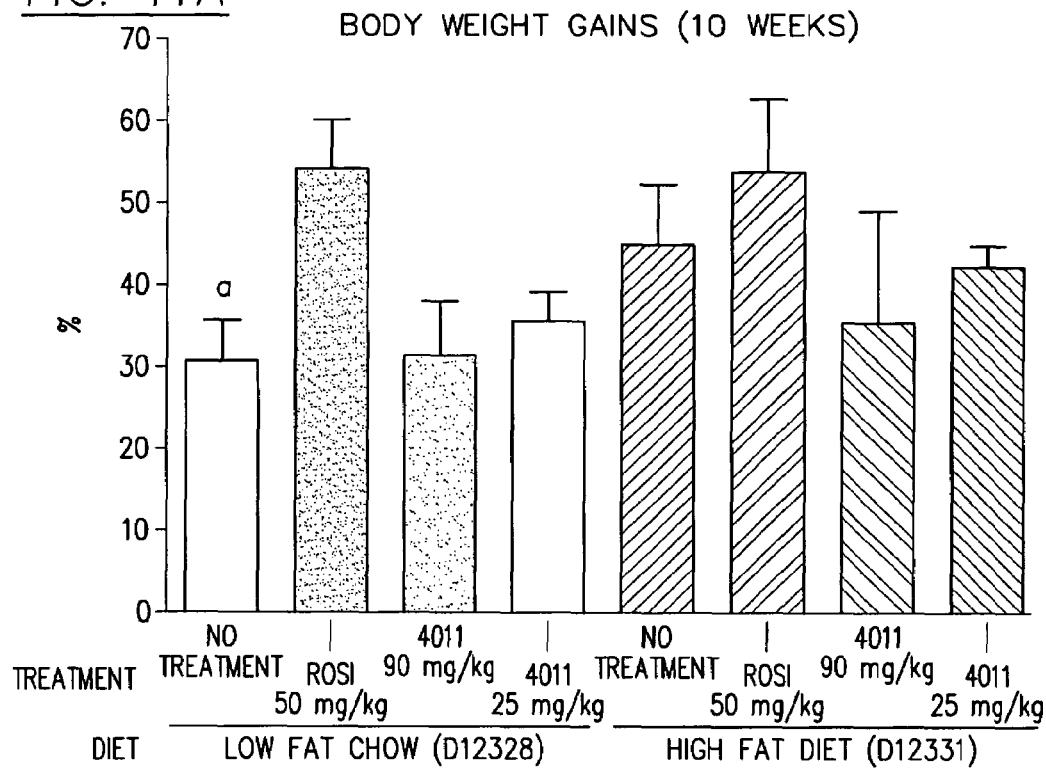
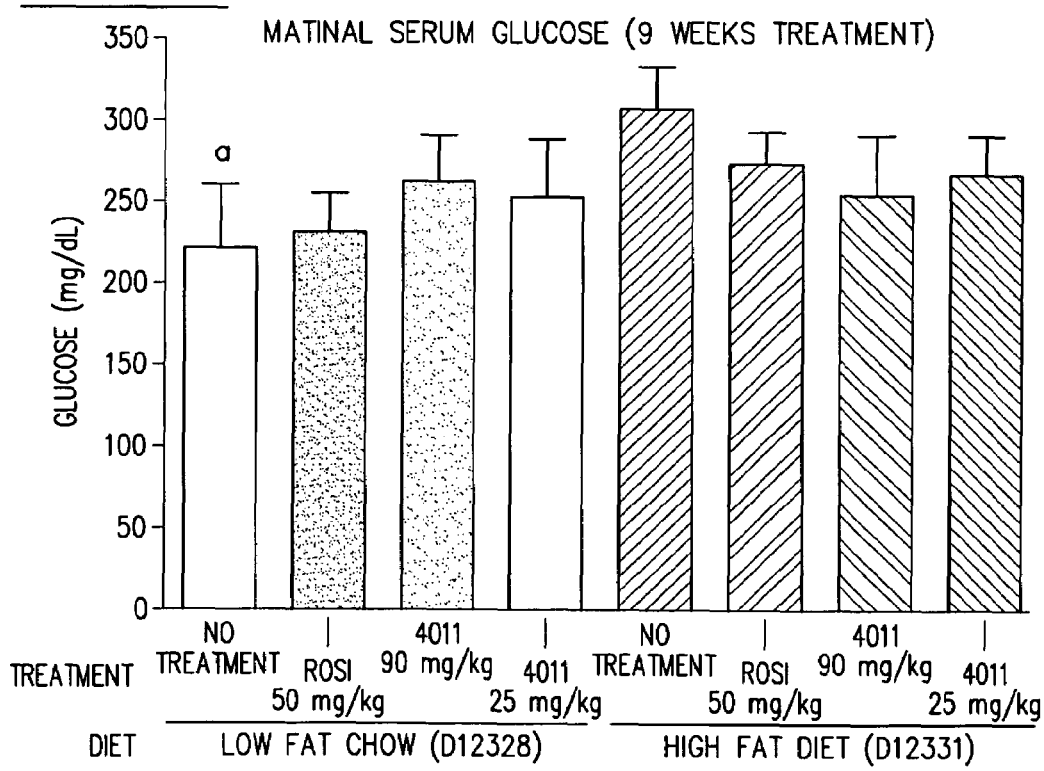

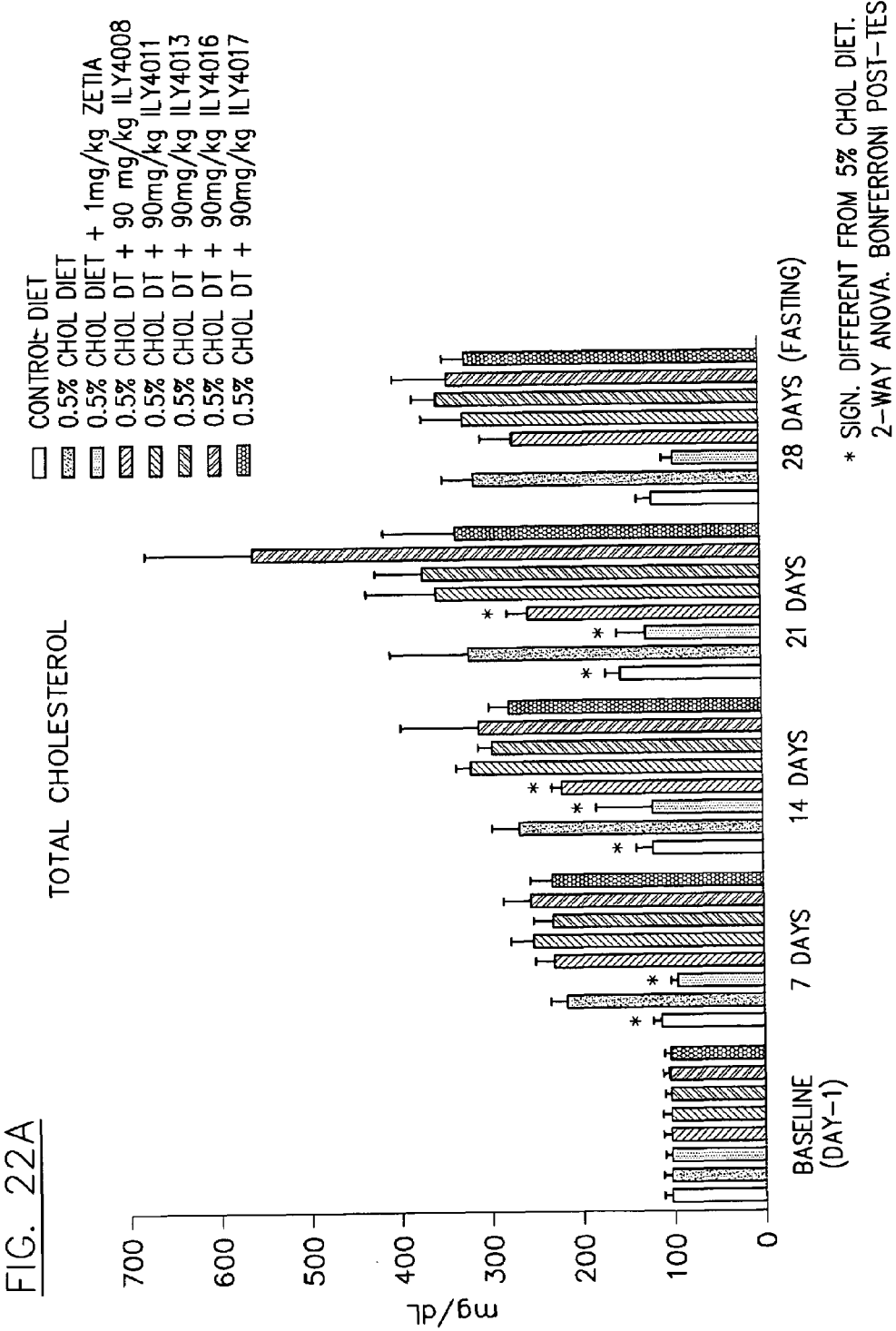

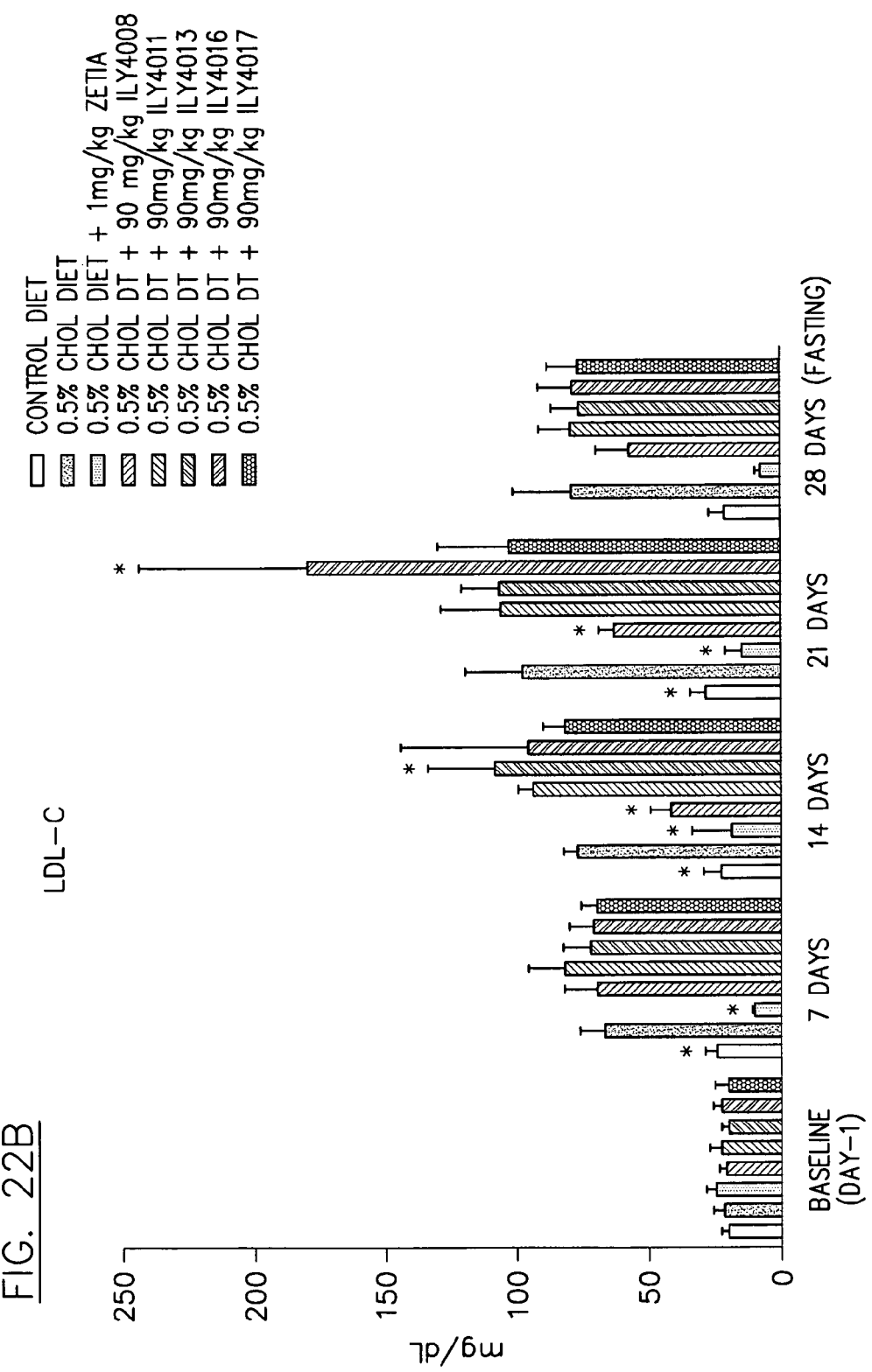

MULTIVALENT INDOLE COMPOUNDS AND USE THEREOF AS PHOSPHOLIPASE-A2 INHIBITORS

RELATED APPLICATION

This application is related to co-owned, co-pending U.S. patent application Ser. No. 10/838,879 entitled "Phospholipase Inhibitors Localized in the Gastrointestinal Lumen" filed May 3, 2004 by Hui et al. This application is also related to co-owned, co-pending PCT Patent Application No. US 2005/015418 entitled "Phospholipase Inhibitors Localized in the Gastrointestinal Lumen" filed May 3, 2005 by Ilypsa, Inc., as well as to co-owned, co-pending PCT Application No. US 2005/015416 entitled "Treatment of Diet-Related Conditions Using Phospholipase-A2 Inhibitors Comprising Indoles and Related Compounds" filed May 3, 2005 by Ilypsa, Inc. This application claims benefit of a provisional application of the same title, 60/733,954, filed Nov. 3, 2005. Each of such applications are incorporated herein by reference for all purposes.

BACKGROUND OF THE INVENTION

Phospholipases are a group of enzymes that play important roles in a number of biochemical processes, including regulation of membrane fluidity and stability, digestion and metabolism of phospholipids, and production of intracellular messengers involved in inflammatory pathways, hemodynamic regulation and other cellular processes. Phospholipases are themselves regulated by a number of mechanisms, including selective phosphorylation, pH, and intracellular calcium levels. Phospholipase activities can be modulated to regulate their related biochemical processes, and a number of phospholipase inhibitors have been developed.

A large number of phospholipase-A2 (PLA2 or $PLA_2$) inhibitors are known in the art. $PLA_2$ inhibiting moieties include, for example, small molecule inhibitors as well as phospholipid analog and transition state analog compounds. Many such small-molecule inhibitors were developed, for example, for indications related to inflammatory states. A non-exhaustive, exemplification of known phospholipase-A2 inhibitors include the following classes: Alkynoylbenzoic, -Thiophenecarboxylic, -Furancarboxylic, and -Pyridinecarboxylic acids (e.g. see U.S. Pat. No. 5,086,067); Amide carboxylate derivatives (e.g. see WO9108737); Aminoacid esters and amide derivatives (e.g. see WO2002008189); Aminotetrazoles (e.g. see U.S. Pat. No. 5,968,963); Aryoxyacle thiazoles (e.g. see WO00034254); Azetidinones (e.g. see WO9702242); Benzenesulfonic acid derivatives (e.g. see U.S. Pat. No. 5,470,882); Benzoic acid derivatives (e.g. see JP08325154); Benzothiaphenes (e.g. see WO02000641); Benzyl alcohols (e.g. see U.S. Pat. No. 5,124,334); Benzyl phenyl pyrimidines (e.g. see WO00027824); Benzylamines (e.g. see U.S. Pat. No. 5,039,706); Cinammic acid compounds (e.g. see JP07252187); Cinnamic acid derivatives (e.g. see U.S. Pat. No. 5,578,639); Cycloheptaindoles (e.g. see WO03016277); Ethaneamine-benzenes; Imidazolidinones, Thiazoldinones and Pyrrolidinones (e.g. see WO03031414); Indole glyoxamides (e.g. see U.S. Pat. No. 5,654,326); Indole glyoxamides (e.g. see WO9956752); Indoles (e.g. see U.S. Pat. No. 6,630,496 and WO9943672; Indoly (e.g. see WO003048122); Indoly containing sulfonamides; N-cyl-N-cinnamoylethylenediamine derivatives (e.g. see WO9603371); Naphyl acateamides (e.g. see EP77927); N-substituted glycines (e.g. see U.S. Pat. No. 5,298,652); Phosopholipid analogs (e.g. see U.S. Pat. No. 5,144,045 and U.S. Pat. No. 6,495,596); Piperazines (e.g. see WO03048139); Pyridones and Pyrimidones (e.g. see WO03086400); 6-carbamoylpicolinic acid derivatives (e.g. see JP07224038); Steroids and their cyclic hydrocarbon analogs with amino-containing sidechains (e.g. see WO8702367); Trifluorobutanones (e.g. see U.S. Pat. No. 6,350,892 and US2002068722); Abietic derivatives (e.g. see U.S. Pat. No. 4,948,813); Benzyl phosphinate esters (e.g. see U.S. Pat. No. 5,504,073).

Pancreatic phospholipase A2 IB (PLA2 IB) is thought to play a role in phospholipid digestion and processing. For example, PLA2 IB is an enzyme having activity for catabolizing phosphatidylcholine (PC) to form lysophosphatidylcholine (LPC) and free fatty acid (FFA) as reaction products. It has been reported that biliary phospholipids retard cholesterol uptake in the intestinal mucosa and that lypolysis of PC is a prerequisite for cholesterol absorption. (Rampone, A. J. and L. W. Long (1977). "The effect of phosphatidylcholine and lysophosphatidylcholine on the absorption and mucosal metabolism of oleic acid and cholesterol in vitro." *Biochim Biophys Acta* 486(3): 500-10. Rampone, A. J. and C. M. Machida (1981). "Mode of action of lecithin in suppressing cholesterol absorption." *J Lipid Res* 22(5): 744-52.) Further indication that phosphatidylcholine retards cholesterol absorption has been obtained in feeding studies in rats and man. For example, it has been reported that PLA2 IB catablolizing of PC within mixed micelles that carry cholesterol, bile acids, and triglycerides is an initial step for uptake of cholesterol into enterocytes. Mackay, K., J. R. Starr, et al. (1997). "Phosphatidylcholine Hydrolysis Is Required for Pancreatic Cholesterol Esterase- and Phospholipase A2-facilitated Cholesterol Uptake into Intestinal Caco-2 Cells." *Journal of Biological Chemistry* 272(20): 13380-13389. It has been reported as well that PLA2 IB activity is required for full activation of pancreatic lipase/colipase-mediated triacyl glycerol hydrolysis within phospholipid-containing vesicles, another preliminary step in the absorption of triglycerides from the GI tract. (Young, S. C. and D. Y. Hui (1999). "Pancreatic lipase/colipase-mediated triacylglycerol hydrolysis is required for cholesterol transport from lipid emulsions to intestinal cells." *Biochem J* 339 (Pt 3): 615-20). PLA2 IB inhibitors were shown to reduce cholesterol absorption in lymph fistula experiments in rats. (Homan, R. and B. R. Krause (1997). "Established and emerging strategies for inhibition of cholesterol absorption." *Current Pharmaceutical Design* 3(1): 29-44).

More recently, a study involving mice genetically engineered to be PLA2 deficient (PLA2 (−/−) mice, also referred to herein as PLA2 knock-out mice), in which the PLA2 (−/−) mice were fed with a normal chow, indicated that the cholesterol absorption efficiency and the plasma lipid level were similar to the wild-type mice PLA2 (+/+). (Richmond, B. L., A. C. Boileau, et al. (2001). "Compensatory phospholipid digestion is required for cholesterol absorption in pancreatic phospholipase A(2)-deficient mice." *Gastroenterology* 120 (5): 1193-202). The same study also showed that in the PLA2 (−/−) group, intestinal PC was fully hydrolyzed even in the absence of pancreatic PLA2 activity. This study supports the observation that one or more other enzymes with phospholipase activity compensates for PLA2 activity in catalyzing phospholipids and facilitating cholesterol absorption. From this observation, one can further deduce that previously reported PLA2 inhibitors used to blunt cholesterol absorption (See, e.g., WO 96/01253 of Homan et al.) are probably non-selective (non-specific) to PLA2; that is, these inhibitors are apparently also interfering with phospholipases other than PLA2 (e.g., phospholipase B) to prevent such other enzymes for compensating for the lack of PLA2 activity. Accordingly, one can conclude that PLA2 inhibition, while necessary for reducing cholesterol absorption, is not itself sufficient to reduce cholesterol absorption in mice fed with a normal chow diet.

Further studies using PLA2 knockout mice reported a beneficial impact on diet-induced obesity and obesity-related insulin resistance in mice on a high-fat and high-cholesterol diet. (Huggins, Boileau et al. 2002). Significantly, and consistent with the earlier work of (Richmond, Boileau et al. 2001), no difference in weight gain was observed between the wild-type and PLA2 (−/−) mice maintained on a normal chow diet. However, compared to wild-type PLA2 (+/+) mice, the PLA2 (−/−) mice on high-fat/high-cholesterol diet were reported to have: reduced body weight gain over a sixteen week period, with the observed weight difference being due to increased adiposity in the wild-type mice; substantially lower fasting plasma leptin concentrations; improved glucose tolerance; and improved protection against high-fat-diet induced insulin resistance. However, it was reported that no significant differences were observed between the wild-type PLA2 (+/+) mice and the PLA2 (−/−) mice on high-fat/high-cholesterol diet with respect to plasma concentrations of free-fatty acids, cholesterol and triglycerides. Although there was evidence of increased lipid content in the stools of the PLA2 (−/−) mice, the effect did not produce overt steatorrhea, suggesting only a slight reduction in fat absorption.

Diabetes affects 18.2 million people in the Unites States, representing over 6% of the population. Diabetes is characterized by the inability to produce or properly use insulin. Diabetes type 2 (also called non-insulin-dependent diabetes or NIDDM) accounts for 80-90% of the diagnosed cases of diabetes and is caused by insulin resistance. Insulin resistance in diabetes type 2 prevents maintenance of blood glucose within desirable ranges, despite normal to elevated plasma levels of insulin.

Obesity is a major contributor to diabetes type 2, as well as other illnesses including coronary heart disease, osteoarthritis, respiratory problems, and certain cancers. Despite attempts to control weight gain, obesity remains a serious health concern in the United States and other industrialized countries. Indeed, over 60% of adults in the United States are considered overweight, with about 22% of these being classified as obese.

Diet also contributes to elevated plasma levels of cholesterol, including non-HDL cholesterol, as well as other lipid-related disorders. Such lipid-related disorders, generally referred to as dislipidemia, include hypercholesterolemia and hypertriglyceridemia among other indications. Non-HDL cholesterol is firmly associated with atherogenesis and its sequalea including cardiovascular diseases such as arteriosclerosis, coronary artery disease myocardial infarction, ischemic stroke, and other forms of heart disease. These together rank as the most prevalent type of illness in industrialized countries. Indeed, an estimated 12 million people in the United States suffer with coronary artery disease and about 36 million require treatment for elevated cholesterol levels.

In patients with hypercholesteremia, lowering of LDL cholesterol is among the primary targets of therapy. Hydroxymethylglutaryl-coenzym A (HMG-CoA) reductase inhibitors ("statins") are reported to be used to reduce serum LDL cholesterol levels. However, severe and sometimes fatal adverse events, including liver failure and rhabdomyolysis (muscle condition) have been reported in connection with such use of statins. More recently, ezitimibe was introduced as a cholesterol absorption inhibitor, for use alone or in combination with statins. In patients with hypertriglyceridemia, fibrates (e.g. gemfibrozil) are used to lower high serum triglyceride concentrations. However, some patients report gastrointestinal side effects when using these drugs, and when gemfibrozil is used in combination with a statin, some patients develop significant myositis. Renal and/or liver failure or dysfunction are relative contraindications to gemfibrozil use as about 60-90% of the drug is reportedly cleared by the kidney, with the balance cleared by the liver. Notably, hypertriglyceridemia can be associatively linked with hypercholesterolemia; it has been reported that patients with triglyceride levels between 400 and 1000 mg/dl can have unwanted increases in LDL cholesterol by 10-30%. In patients with high triglycerides and low HDL cholesterol, nicotinic acid is used to increase serum HDL cholesterol and lower serum triglycerides. The main side effect is flushing of the skin in some patients. See generally, for example, Knopp, R H: Drug treatment of lipid disorders, New England Journal of Medicine 341:7 (1999) 498; Pasternak, R C et al: ACC/AHA/NHLBI Clinical Advisory on the use and safety of statins, Circulation 106 (2002) 1024; Grundy, S M et al: Implications of recent clinical trials for the National Cholesterol Education Program Adult Treatment Panel III Guidelines, Circulation 110 (2004) 227.

With the high prevalence of diabetes, obesity, and cholesterol-related conditions (including lipid disorders, generally), there remains a need for improved approaches to treat one or more of these conditions, including reducing unwanted side effects. Although a substantial number of studies have been directed to evaluating various phospholipase inhibitors for inflammatory-related indications, a relatively small effort has been directed to evaluating phospholipase-A2 inhibitors for efficacy in treating obesity, diabetes and cholesterol-related conditions. Notably, in this regard, particular pharmaceutical compounds effective as phospholipase-A2 inhibitors have not heretofore been identified that have a phenotypic effect approaching and/or comparable to the demonstrated beneficial effect of genetically deficient PLA2 (−/−) animals.

SUMMARY OF THE INVENTION

The present invention provides compositions of matter, methods, medicaments, foodstuffs and kits. The compositions can be phospholipase inhibitors, and can have a beneficial impact for treatment of phospholipase-related conditions, such as insulin-related conditions (e.g., diabetes), weight-related conditions (e.g., obesity) and/or cholesterol-related conditions.

One first aspect of the present invention relates to compositions of matter comprising a substituted organic compound or a salt thereof. Generally, in embodiments of this aspect of the invention, the substituted inorganic compound (or including a moiety thereof) comprises a multivalent indole or indole-related compound—having two or more indole or indole-related moieties linked with each other, preferably covalent linked with each other, for example through one or more linking moieties, optionally also through one or more multifunctional bridge moieties. Generally, the substituted organic compound can be a multivalent phospholipase inhibitor—having two or more phospholipase inhibiting moieties linked with each other, preferably covalent linked with each other, for example through one or more linking moieties, optionally also through one or more multifunctional bridge moieties.

The multivalent indole or indole-related compound can generally comprise two or more indole or indole-related moieties, each having a fused five-member ring and six-member ring, represented for example by the following formula (A)

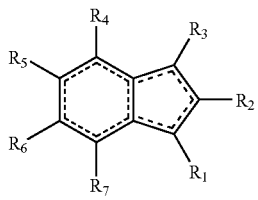

Preferably, the fused five-member and six-member ring can be an indole or an indole-related compound, for example as represented in formulas (I) and (II)

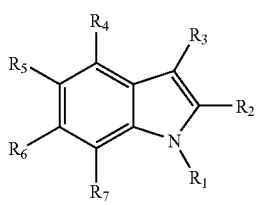

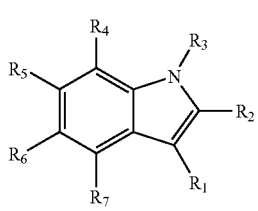

The fused five-member ring and six-member ring of formulas (A), (I) or (II) can in each case, independently considered, comprise one or more heteroatoms (e.g., nitrogen, oxygen, sulfur) substituted within the ring structure of the five-member ring, or within the ring structure of the six-member ring, or within the ring structure of each of the five-member ring and the six-member ring. In some embodiments, two or more heteroatoms are substituted within the fused multi-ring structure, for example, with one or two heteroatoms within the five-member ring or with one or two heteroatoms within the six-member ring. In any of the embodiments of the first aspect of the invention, nitrogen heteroatoms within the 5-member ring or within the six-member ring can optionally comprise a further substituent (e.g, hydrogen, alkyl, alkoxy, etc.), as a corresponding quaternized ammonium ion. For example, the N heteroatom can be substituted with the moiety selected from (i) oxygen, (ii) alkyl, and (iii) alkyl substituted with one or more substituents selected from carboxyl, sulfonic, phosphonic, hydroxyl and amine. In general, the particular substituent groups $R_1$ through $R_7$ of the fused mulit-ring structure are not narrowly critical. In some embodiments, the $R_1$ through $R_7$ substituents can each be independently selected from the group consisting of hydrogen, halide, oxygen, sulfur, phosphorus, hydroxyl, amine, thiol, alkyl, substituted alkyl, alkenyl, substituted alkenyl, alkynyl, substituted alkynyl, ether, carbonyl, acidic, carboxyl, ester, amide, carbocyclic, heterocyclic, acylamino, oximyl, hydrazyl and moieties comprising combinations thereof. In some preferred embodiments, each of the $R_1$ through $R_7$ substituents can be effective, collectively with the fused multi-ring structure, for imparting phospholipase-A2 inhibiting functionality to the multivalent compound (or moiety derived from such compound).

In a first general embodiment of the invention, for example, the multivalent indole or indole-related compounds of this first aspect of the invention can be represented by the formula D-I

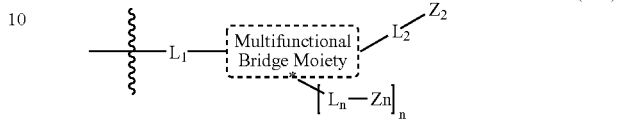

where L is generally a linking moiety, Z is generally an indole or indole-related moiety, each Z having a fused five-member ring and six-member ring (e.g., as described above and in further detail hereinafter), and n is zero or a non-zero integer. Z can generally be a phospholipase inhibiting moiety. The multifunctional bridge moiety can be a moiety having two or more, and preferably at least (n+2), reactive sites to which the two or more indole or indole-related moieties (e.g., phospholipase inhibiting moieties) are bonded, preferably covalently bonded. The multifunctional bridge moiety can preferably be a polymer moiety, or an oligomer moiety, or a non-repeating moiety, in each case having two or more, and preferably at least (n+2), reactive sites.

In preferred embodiments within the first general embodiment of the first aspect of the invention, the multifunctional bridge moiety can be a non-repeating moiety (considered as a whole). For example, the multifunctional bridge moiety can be a moiety selected from alkyl, phenyl, aryl, alkenyl, alkynyl, heterocyclic, amine, ether, sulfide, disulfide, hydrazine, and any of the foregoing substituted with oxygen, sulfur, sulfonyl, phosphonyl, hydroxyl, alkoxyl, amine, thiol, ether, carbonyl, carboxyl, ester, amide, alkyl, alkenyl, alkynyl, aryl, heterocyclic, and moieties comprising combinations thereof (in each permutation). A non-repeating moiety can include repeating units (e.g., methylene) within portions or segments thereof (e.g., within an alkyl segment), without having discrete repeat units that constitute the moiety as a whole (e.g., in the sense of a polymer or oligomer).

In other preferred embodiments within the first general embodiment of the first aspect of the invention, the multifunctional bridge moiety can be a polymer moiety or an oligomer moiety. The polymer or oligomer can in each case, independently considered, comprise repeat units consisting of a repeat moiety selected from alkyl (e.g., —CH$_2$—), substituted alkyl (e.g., —CHR—), alkenyl, substituted alkenyl, alkynyl, substituted alkynyl, phenyl, aryl, heterocyclic, amine, ether, sulfide, disulfide, hydrazine, and any of the foregoing substituted with oxygen, sulfur, sulfonyl, phosphonyl, hydroxyl, alkoxyl, amine, thiol, ether, carbonyl, carboxyl, ester, amide, alkyl, alkenyl, alkynyl, aryl, heterocyclic, as well as moieties comprising combinations thereof. Further and preferred polymer and oligomer moieties are described hereinafter.

In preferred embodiments within the first general embodiment of the first aspect of the invention, the integer n most preferably ranges from 0 to 10, such that the number of indole or indole-related moieties (e.g. phospholipase inhibitor moieties) ranges from 2 to 12; or alternatively, the integer n can range from 1 to 10, such that the number of indole or indole-related moieties (e.g. phospholipase inhibitor moieties) ranges from 3 to 12. In embodiments with n ranging from 0 to 10 or from 1 to 10, the multifunctional bridge moiety may be preferred to be an oligomer moiety or a non-repeating moiety. In alternative embodiments within the first general embodiment, n can generally range from 0 to about 500, or from 1 to about 500, preferably from 0 to about 400, or from 1 to about 400, preferably from 0 to about 300, or from 1 to about 300, preferably from 0 to about 200, or from 1 to about 200, preferably from 0 to about 100, or from 1 to about 100. In some such embodiments: n can range from 0 to about 50, or from 1 to about 50; or n can range from 0 to about 20, or from 1 to about 20. In some particular embodiments, the number of indole or indole-related moieties (e.g. phospholipase inhibitor moieties) can be lower, ranging for example: from 2 to about 10 (with the integer n correspondingly ranging from 0 to about 8); or from 3 to about 10 (correspondingly with n ranging from 1 to about 8). In some other embodiments, the number of indole or indole-related moieties (e.g. phospholipase inhibitor moieties) can range from 2 to about 6 (correspondingly with n ranging from 0 to about 4), or from 3 to about 6 (correspondingly with n ranging from 1 to about 4). In certain embodiments, the number of indole or indole-related moieties (e.g. phospholipase inhibitor moieties) can range from 2 to 4 (correspondingly with n ranging from 0 to 2), or from 3 to 4 (correspondingly with n ranging from 1 to 2).

In preferred embodiments within the first general embodiment of the first aspect of the invention, the total atomic distance between the multi-ring structures Z (e.g., including the multifunctional bridge moiety considered together with any linking moieties, L) can be a length of at least twenty atoms in the shortest chain through which at least two of the two or more multi-ring structures, Z, are joined.

In a second general embodiment within the first aspect of the invention, the substituted organic compound can comprise two or more independently selected multi-ring structures, $Z_1$, $Z_2$, joined by a linking moiety, L, as represented by the formula (D-I-A)

$$Z_1\text{-}L\text{-}Z_2 \quad\quad\quad\quad (D\text{-}I\text{-}A),$$

with each of the two or more multi-ring structures being covalently bonded to the linking moiety. The multi-ring structures, Z can each be indole or indole-related compounds (e.g., the multivalent phospholipase inhibitor) as described herein above, and as further detailed hereinafter.

In preferred embodiments within the second general embodiment of the first aspect of the invention, the linking moiety, L, can be a linking moiety having a total linker length of at least twenty atoms in the shortest chain through which at least two of the two or more multi-ring structures, $Z_1$, $Z_2$, are joined.

In preferred embodiments within the second general embodiment of the first aspect of the invention, the linking moiety, L, can be a linking moiety represented by the formula (D-II)

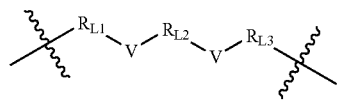

(D-II)

with $R_{L1}$, $R_{L2}$ and $R_{L3}$ each being a moiety independently selected from the group consisting of alkyl, substituted alkyl, alkenyl, substituted alkenyl, alkynyl, carbocyclic, heterocyclic, poly(ethylene oxyl), and polyester. In some embodiments, each $R_{L1}$, $R_{L2}$ and $R_{L3}$ can be an independently selected non-repeating moiety (e.g., a moiety other than an oligomer or polymer) and can be an independently selected from the group consisting of alkyl, substituted alkyl, alkenyl, substituted alkenyl, alkynyl, carbocyclic, heterocyclic. In these embodiments, V can be a multifunctional bridging moiety as generally and specifically described herein. V can be a moiety independently selected from the group consisting of N, O, S, disulfide, carbonyl, ester, amide, urethane, urea, hydrazine, alkene, and alkyne.

In preferred embodiments within the second general embodiment of the first aspect of the invention, the linking moiety, L, can be a linking moiety represented by the formula (D-II)

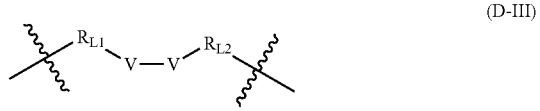

(D-III)

with $R_{L1}$ and $R_{L2}$ each being a moiety independently selected from the group consisting of alkyl, substituted alkyl, alkenyl, substituted alkenyl, alkynyl, carbocyclic, heterocyclic, poly(ethylene oxyl), and polyester. In some embodiments, each $R_{L1}$ and $R_{L2}$ can be an independently selected non-repeating moiety (e.g., a moiety other than an oligomer or polymer) and can be an independently selected from the group consisting of alkyl, substituted alkyl, alkenyl, substituted alkenyl, alkynyl, carbocyclic, heterocyclic. In these embodiments, V can be a multifunctional bridging moiety as generally and specifically described herein. V can be a moiety independently selected from the group consisting of N, O, S, disulfide, carbonyl, ester, amide, urethane, urea, hydrazine, alkene, and alkyne.

In preferred embodiments within the second general embodiment of the first aspect of the invention, the linking moiety, L, can be a linking moiety represented by the formula (D-IV)

(D-IV)

with $R_{L1}$ and $R_{L2}$ each being a moiety independently selected from the group consisting of alkyl, substituted alkyl, alkenyl, substituted alkenyl, alkynyl, carbocyclic, heterocyclic, poly(ethylene oxyl), and polyester. In some embodiments, each $R_{L1}$ and $R_{L2}$ can be an independently selected non-repeating moiety (e.g., a moiety other than an oligomer or polymer) and can be an independently selected from the group consisting of alkyl, substituted alkyl, alkenyl, substituted alkenyl, alkynyl, carbocyclic, heterocyclic. In these embodiments, V can be a multifunctional bridging moiety as generally and specifically described herein. V can be a moiety independently selected from the group consisting of N, O, S, disulfide, carbonyl, ester, amide, urethane, urea, hydrazine, alkene, and alkyne.

In a third general embodiment within the first aspect of the invention, the substituted organic compound can comprise three or more independently selected multi-ring structures, $Z_1$, $Z_2$, $Z_3$ joined by a linking moiety, L, where L can be a linking moiety represented by the formula (D-V)

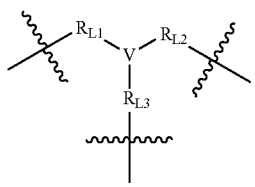

(D-V)

where the multi-ring structures $Z_1$, $Z_2$, $Z_3$ can be covalently bonded to the linking moiety. The multi-ring structures, $Z_1$, $Z_2$, $Z_3$ can each be indole or indole-related compounds (e.g., the multivalent phospholipase inhibitor) as described herein above, and as further detailed hereinafter. $R_{L1}$, $R_{L2}$ and $R_{L3}$ can each be a moiety independently selected from the group consisting of alkyl, substituted alkyl, alkenyl, substituted alkenyl, alkynyl, carbocyclic, heterocyclic, poly(ethylene oxyl), and polyester. In some embodiments, each $R_{L1}$, $R_{L2}$ and $R_{L3}$ can be an independently selected non-repeating moiety (e.g., a moiety other than an oligomer or polymer) and can be an independently selected from the group consisting of alkyl, substituted alkyl, alkenyl, substituted alkenyl, alkynyl, carbocyclic, heterocyclic. In these embodiments, V can be a multifunctional bridging moiety as generally and specifically described herein. V can be a moiety independently selected from the group consisting of N, O, S, disulfide, carbonyl, ester, amide, urethane, urea, hydrazine, alkene, and alkyne.

In preferred embodiments within the third general embodiment of the first aspect of the invention, the total atomic distance between the multi-ring structures $Z_1$, $Z_2$, $Z_3$ can be a length of at least twenty atoms in the shortest chain through which at least two of the two or more multi-ring structures, $Z_1$, $Z_2$, $Z_3$, are joined.

In preferred embodiments of the first aspect of the invention (applicable for each of the first through third general embodiments), $R_3$ of the multi-ring structure can be a moiety represented by formula (C3-I or C3-II)

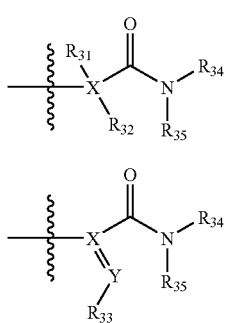

with, independently and as applicable: X being selected from the group consisting of O, C and N; $R_{31}$ being optional, and if present being selected from the group consisting of hydrogen, halide, hydroxyl and cyano; $R_{32}$ being optional, and if present being selected from the group consisting of hydrogen, halide, hydroxyl, and cyano; Y being selected from the group consisting of O, S, and N; $R_{33}$ being optional, and if present being selected from the group consisting of hydrogen, hydroxyl, $C_1$-$C_6$ alkyl, substituted $C_1$-$C_6$ alkyl, $C_1$-$C_6$ alkoxyl and substituted $C_1$-$C_6$ alkoxyl; and $R_{34}$ and $R_{35}$ each being independently selected from the group consisting of hydrogen, hydroxyl, alkoxyl, alkyl, substituted alkyl, amine, and alkylsulfonyl.

In a preferred embodiment of this first aspect of the invention (applicable for each of the first through third general embodiments), $R_4$ of the multi-ring structure can be a moiety selected from

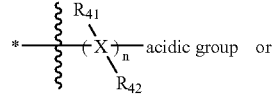

(C4-Acidic)

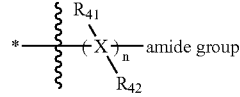

(C4-Amide)

with as applicable and independently selected for each formula: n being an integer ranging from 1 to 5; and for each n: X being independently selected from the group consisting of C, O, S, and N; and $R_{41}$ and $R_{42}$ each being optional, but if present being independently selected from the group consisting of hydrogen, halide, alkyl, substituted alkyl, phenyl, aryl, amine, alkoxyl, alkylsulfonyl, alkylphosphonyl, alkylcarbonyl, carboxyl, phosphonic, sulfonic, carboxamide, and cyano.

In a preferred embodiment of this first aspect of the invention (applicable for each of the first through third general embodiments), $R_2$ and $R_5$ of the multi-ring structure can each be independently selected from the group consisting of hydrogen, halide, hydroxyl, $C_1$-$C_3$ alkyl, substituted $C_1$-$C_3$ alkyl, and cyano.

In a preferred embodiment of this first aspect of the invention (applicable for each of the first through third general embodiments), $R_1$, $R_6$ and $R_7$ of the multi-ring structure can each be independently selected from the group consisting of hydrogen, halide, hydroxyl, amine, carboxyl, phosphonic, sulfonic, alkyl, substituted alkyl, alkoxyl, substituted alkoxyl, alkyl carbonyl, substituted alkyl carbonyl, carbocyclic, heterocyclic, and moieties comprising combinations thereof.

Each of these embodiments can be used in various and specific combination, and in each permutation, with each other aspects and embodiments described above or below herein.

In another, second aspect, the invention relates to methods of treating one or more conditions, comprising administering an effective amount of a pharmaceutical composition to a subject in need thereof, the pharmaceutical composition being an indole or indole-related compound or moiety as described in connection with the first aspect of the invention. In preferred embodiments, the indole or indole related compound or moiety can be a phospholipase-$A_2$ inhibitor. The compound or moiety (or pharmaceutically acceptable salt thereof) can be administered in an amount effective for treating diet-related conditions, including for example conditions selected from the group consisting of a weight-related condition, an insulin-related condition, a cholesterol-related condition and combinations thereof (preferably, including for example conditions selected from obesity, diabetes mellitus (e.g., diabetes type 2), insulin resistance, glucose intolerance, hypercholesterolemia, hypertriglyceridemia, and combinations thereof).

Another third aspect of the invention is directed to methods for modulating the metabolism of fat, glucose or cholesterol (or combinations thereof) in a subject. This method comprises, in one approach, administering an effective amount of an indole or indole-related compound or moiety as described in connection with the first aspect of the invention (or as a pharmaceutically-acceptable salt thereof).

In a fourth aspect, in one approach, the invention relates to methods comprising use of a substituted organic compound that is an indole or indole-related compound or moiety as described in connection with the first aspect of the invention (or as a pharmaceutically-acceptable salt thereof) for manufacture of a medicament for use as a pharmaceutical for treating a condition of a subject selected from a weight-related condition, an insulin-related condition, a cholesterol-related condition and combinations thereof (preferably, including for example conditions selected from obesity, diabetes mellitus, insulin resistance, glucose intolerance, hypercholesterolemia, hypertriglyceridemia and combinations thereof).

In a fifth aspect, in one approach, the invention relates to a food product composition comprising an edible foodstuff and a substituted organic compound being an indole or indole-related compound or moiety as described in connection with the first aspect of the invention. In some embodiments, the foodstuff can comprise (or can consist essentially of) a vitamin supplement and the indole or indole-related compound or moiety.

Generally, in embodiments of the invention, including for example for embodiments relating to each of the aforementioned first through fifth aspects of the invention, the an indole or indole-related compound or moiety as described in connection with the first aspect of the invention can be a phospholipase-A2 inhibitor, and additional or alternatively, can have lumen-localization functionality. For example, the phospholipase-A2 inhibitor can have chemical and physical properties that impart lumen-localization functionality to the inhibitor. Preferably in such embodiments, the inhibitors of these embodiments can have chemical and/or physical properties such that at least about 80% of the phospholipase inhibitor remains in the gastrointestinal lumen, and preferably at least about 90% of the phospholipase inhibitor remains in the gastrointestinal lumen (in each case, following administration of the inhibitor to the subject). Such chemical and/or physical properties can be realized, for example, by an inhibitor comprising at least one moiety selected from an oligomer moiety, a polymer moiety, a hydrophobic moiety, a hydrophilic moiety, a charged moiety and combinations thereof. These embodiments can be used in various and specific combination, and in each permutation, with other aspects and embodiments described above or below herein.

Generally, in embodiments of the invention, including for example for embodiments relating to each of the aforementioned first through fifth aspects of the invention, a phospholipase-A2 inhibitor can comprise or consist essentially of the substituted organic compound (i.e., the indole or indole-related compound or moiety) described in connection with the first aspect of the invention. In some embodiments, the phospholipase inhibitor can be a multivalent phospholipase inhibitor comprising the substituted organic compound or a moiety of the substituted organic compound, with the moiety being linked (e.g., covalently linked, directly or indirectly using a linking moiety) to multifunctional bridge moiety such as an oligomer moiety, a polymer moiety or a non-repeating moiety. The multivalent phospholipase inhibitor is preferably a non-absorbed or non-absorbable moiety. Each of these embodiments can be used in various and specific combination, and in each permutation, with other aspects and embodiments described above or below herein.

Generally, in embodiments of the invention, including for example for embodiments relating to each of the aforementioned first through fifth aspects of the invention, the phospholipase-$A_2$ inhibitor does not induce substantial steatorrhea following administration or ingestion thereof. These embodiments can be used in various and specific combination, and in each permutation, with other aspects and embodiments described above or below herein.

Although various features are described above to provide a summary of various aspects of the invention, it is contemplated that many of the details thereof as described below can be used with each of the various aspects of the invention, without limitation. Other features, objects and advantages of the present invention will be in part apparent to those skilled in art and in part pointed out hereinafter. All references cited in the instant specification are incorporated by reference for all purposes. Moreover, as the patent and non-patent literature relating to the subject matter disclosed and/or claimed herein is substantial, many relevant references are available to a skilled artisan that will provide further instruction with respect to such subject matter.

BRIEF DESCRIPTION OF THE DRAWINGS

FIGS. 11A, 11B, 11C and 11D are graphs depicting results for Test Article ILY4011 (ILY-V-30) in a C57BL/6J mouse model of obesity.

FIGS. 22A and 22B are graphs depicting results for Test Article ILY4016 (ILY-IV-40), Test Article ILY4008 (ILY-V-26), Test Article ILY4013 (ILY-V-32), Test Article ILY4011 (ILY-V-30), and Test Article ILY4017 (ILY-V-37) in a hamster diet-induced dyslipidemia model.

DETAILED DESCRIPTION OF THE INVENTION

Figure 1:
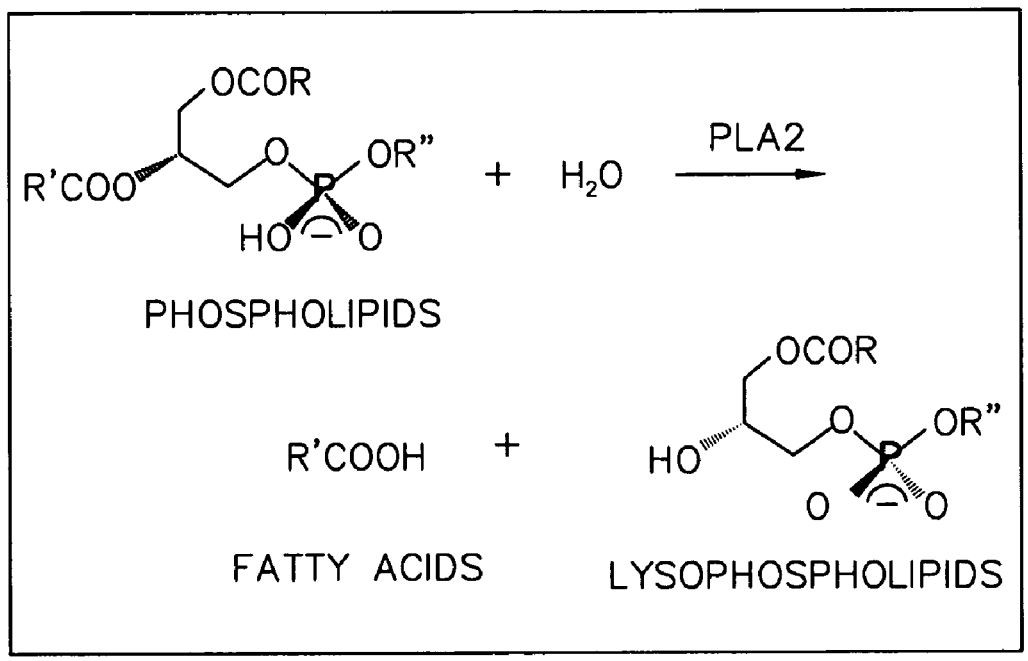
FIG. 1 is a schematic representation of a chemical reaction in which phospholipase-A2 enzyme (PLA2) catalyzes hydrolysis of phospholipids to corresponding lysophospholipids.

The present invention provides compositions of matter, including certain multivalent indole and indole-related compounds and salts thereof, multivalent phospholipase inhibitors, compositions (including pharmaceutical formulations, medicaments and foodstuffs) comprising such compositions of matter or such compounds or salts or such phospholipase inhibitors, methods for making such formulations, medicaments and foodstuffs, and methods for use thereof as pharmaceuticals for treatments of various conditions. The phospholipase inhibitors of the present invention can find use in treating a number of phospholipase-related conditions, including insulin-related conditions (e.g., diabetes), weight-related conditions (e.g., obesity), cholesterol-related disorders and any combination thereof, as described in detail below.

Overview

Advantageously, the inventors have identified particular indole and indole-related compounds having substantial promise as phospholipase inhibitors. In particular, compounds of the present invention can be (in one embodiment) multivalent phospholipase inhibitors. Multivalent phospholipase inhibitors can be advantageous with respect to lumen-localization, because they are generally physically of larger dimension and generally have a larger molecular weight than monovalent (e.g., small molecule) phospholipase inhibitors. Interestingly and unexpectedly, and without being bound by theory or to performance criteria not specifically recited in the claims, the activity (e.g., IC50) of multivalent phospholipase inhibitors can be comparable to or can exceed, on a per weight basis, the activity of monovalent (e.g., small molecule) phospholipase inhibitors. This is particularly surprising in view of the accepted wisdom within the art of phospholipase inhibitors, in which it is generally recognized to be little physical space for altering the dimensions of an inhibitor, since the inhibitor is thought to be active in a position situated between the enzyme and the bilipidic bilayer.

Hence, the invention comprises in one aspect, a multivalent indole or indole-related compound having multiple (two or more) multi-ring moieties comprising fused five-member ring and six-member ring structure. The invention comprises, in another aspect, a method of treating a condition by administering an effective amount of such multivalent compounds (e.g., as an enzymatic inhibitor such as a phospholipase inhibitor such as a phospholipase-$A_2$ IB inhibitor to a subject in need thereof). The invention also contemplates, in another aspect, a method for modulating the metabolism of fat, glucose or cholesterol in a subject by administering an effective amount of such compound to the subject. The invention includes as well, in a further aspect, methods of using such compound (e.g., having phospholipase-$A_2$ IB inhibitor activity) for manufacture of a medicament, where the medicament is indicated for use as a pharmaceutical for treating a condition of a subject (e.g., a weight-related condition, an insulin-related condition, a cholesterol-related condition and combinations thereof). The invention can include, moreover in another aspect, a food product composition comprising an edible foodstuff and a phospholipase-$A_2$ IB inhibitor, preferably where the phospholipase-$A_2$ IB inhibitor comprises the multivalent indole or indole-related compound.

Compounds

The composition of matter can comprise a substituted organic compound or a salt thereof (or a moiety derived from such a substituted organic compound). Generally, the substituted inorganic compound (or including a moiety thereof) comprises a multivalent indole or indole-related compound—having two or more indole or indole-related moieties linked with each other, preferably covalent linked with each other, for example through one or more linking moieties, optionally also through one or more multifunctional bridge moieties. Generally, the substituted organic compound can be a multivalent phospholipase inhibitor—having two or more phospholipase inhibiting moieties linked with each other, preferably covalent linked with each other, for example through one or more linking moieties, optionally also through one or more multifunctional bridge moieties.

The multivalent indole or indole-related compound can generally comprise two or more indole or indole-related moieties, each having a fused five-member ring and six-member ring, represented for example by the following formula (A)

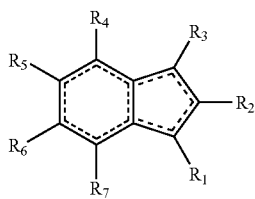

(A)

Preferably, the fused five-member and six-member ring can be an indole or an indole-related compound, for example as represented in formulas (I) and (II)

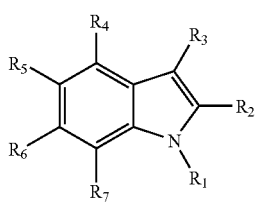

(I)

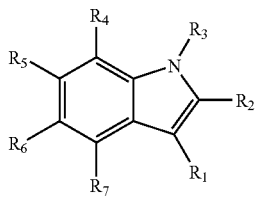

(II)

The fused five-member ring and six-member ring of formulas (A), (I) or (II) can in each case, independently considered, comprise one or more heteroatoms (e.g., nitrogen, oxygen, sulfur) substituted within the ring structure of the five-member ring, or within the ring structure of the six-member ring, or within the ring structure of each of the five-member ring and the six-member ring. In some embodiments, two or more heteroatoms are substituted within the fused multi-ring structure, for example, with one or two heteroatoms within the five-member ring or with one or two heteroatoms within the six-member ring.

In some embodiments of the first aspect of the invention, the fused five-member ring and six-member ring of formula (A) comprises two or more heteroatoms (e.g., nitrogen, oxygen, sulfur), preferably with at least one heteroatom being substituted within the ring structure of the five-member ring, and at least one heteroatom being substituted within the ring structure of the six-member ring. In some embodiments, two or more heteroatoms are substituted within the ring structure of the five-member ring.

In some embodiments, two or more heteroatoms are substituted within the ring structure of the six-member ring. Hence, for example, in some preferred embodiments of the first aspect of the invention, the compound can comprise a multi-ring structure represented by a formula selected from

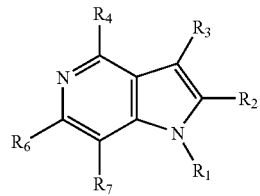

AI-5

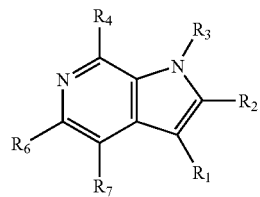

AII-5

AI-6

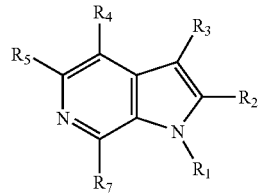

AII-6

AI-7

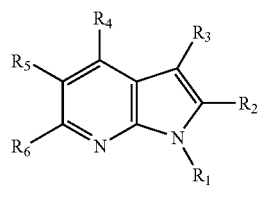

AII-7

AI-56

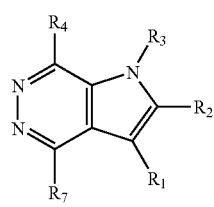

AII-56

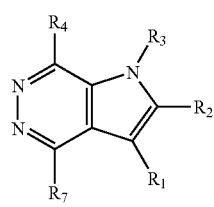

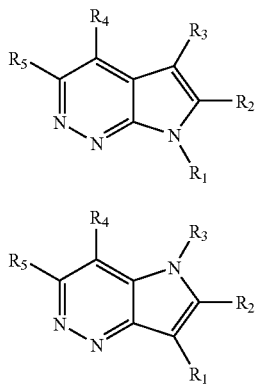

AI-67

AII-67

In any of the first embodiments of the first aspect of the invention, and particularly, in any of the preferred first through fifth general embodiments thereof, the nitrogen heteroatoms within the 5-member ring or within the six-member ring can optionally comprise a further substituent (e.g, hydrogen, alkyl, alkoxy, etc.), as a corresponding quaternized ammonium ion. For example, the N heteroatom can be substituted with the moiety selected from (i) oxygen, (ii) alkyl, and (iii) alkyl substituted with one or more substituents selected from carboxyl, sulfonic, phosphonic, hydroxyl and amine.

In a preferred embodiment of this first aspect of the invention (as applicable for each of the general embodiments), each of the $R_4$, $R_3$, $R_2$, $R_5$, $R_1$, $R_6$ and $R_7$ substituent groups can be effective, collectively with each other and with the multi-ring structure, for imparting phospholipase-A2 inhibiting functionality to the compound (or moiety).

In another preferred embodiment of this first aspect of the invention (as applicable for each of the first through fifth general embodiments), $R_1$ through $R_7$ can each be independently selected from the group consisting of hydrogen, halide, oxygen, sulfur, phosphorus, hydroxyl, amine, thiol, alkyl, substituted alkyl, alkenyl, substituted alkenyl, alkynyl, substituted alkynyl, ether, carbonyl, acidic, carboxyl, ester, amide, carbocyclic, heterocyclic, acylamino, oximyl, hydrazyl and moieties comprising combinations thereof. Specific preferred substituents for each of $R_1$ through $R_7$ are described hereinafter.

In a first general embodiment of the invention, for example, the multivalent indole or indole-related compounds of this first aspect of the invention can be represented by the formula D-I

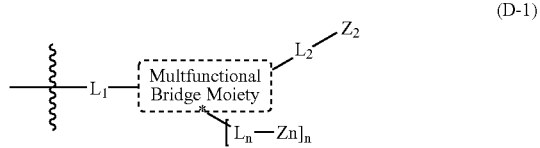

(D-1)

where L is generally a linking moiety, Z is generally an indole or indole-related moiety, each Z having a fused five-member ring and six-member ring (e.g., as described above and in further detail hereinafter), and n is zero or a non-zero integer. Z can generally be a phospholipase inhibiting moiety. The multifunctional bridge moiety can be a moiety having two or more, and preferably at least (n+2), reactive sites to which the two or more indole or indole-related moieties (e.g., phospholipase inhibiting moieties) are bonded, preferably covalently bonded. The multifunctional bridge moiety can preferably be a polymer moiety, or an oligomer moiety, or a non-repeating moiety, in each case having two or more, and preferably at least (n+2), reactive sites.

In preferred embodiments within the first general embodiment of the first aspect of the invention, the integer n most preferably ranges from 0 to 10, such that the number of indole or indole-related moieties (e.g. phospholipase inhibitor moieties) ranges from 2 to 12; or alternatively, the integer n can range from 1 to 10, such that the number of indole or indole-related moieties (e.g. phospholipase inhibitor moieties) ranges from 3 to 12. In embodiments with n ranging from 0 to 10 or from 1 to 10, the multifunctional bridge moiety may be preferred to be an oligomer moiety or a non-repeating moiety. In alternative embodiments within the first general embodiment, n can generally range from 0 to about 500, or from 1 to about 500, preferably from 0 to about 400, or from 1 to about 400, preferably from 0 to about 300, or from 1 to about 300, preferably from 0 to about 200, or from 1 to about 200, preferably from 0 to about 100, or from 1 to about 100. In some such embodiments: n can range from 0 to about 50, or from 1 to about 50; or n can range from 0 to about 20, or from 1 to about 20. In some particular embodiments, the number of indole or indole-related moieties (e.g. phospholipase inhibitor moieties) can be lower, ranging for example: from 2 to about 10 (with the integer n correspondingly ranging from 0 to about 8); or from 3 to about 10 (correspondingly with n ranging from 1 to about 8). In some other embodiments, the number of indole or indole-related moieties (e.g. phospholipase inhibitor moieties) can range from 2 to about 6 (correspondingly with n ranging from 0 to about 4), or from 3 to about 6 (correspondingly with n ranging from 1 to about 4). In certain embodiments, the number of indole or indole-related moieties (e.g. phospholipase inhibitor moieties) can range from 2 to 4 (correspondingly with n ranging from 0 to 2), or from 3 to 4 (correspondingly with n ranging from 1 to 2).

In a second general embodiment within the first aspect of the invention, the substituted organic compound can comprise two or more independently selected multi-ring structures, $Z_1$, $Z_2$, joined by a linking moiety, L, as represented by the formula (D-I-A)

$$Z_1\text{-L-}Z_2 \quad\quad\quad (\text{D-I-A}),$$

with each of the two or more multi-ring structures being covalently bonded to the linking moiety. The multi-ring structures, Z can each be indole or indole-related compounds (e.g., the multivalent phospholipase inhibitor) as described herein above, and as further detailed hereinafter.

In preferred embodiments within the second general embodiment of the first aspect of the invention, the linking moiety, L, can be a linking moiety represented by the formula selected from (D-II), (D-III) and (D-IV)

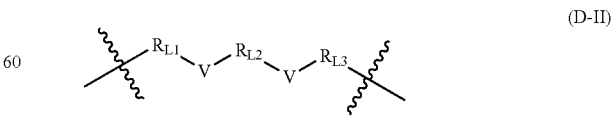

(D-II)

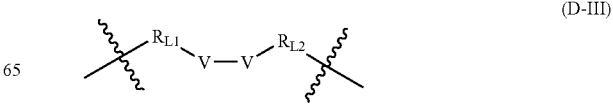

(D-III)

-continued (D-IV)

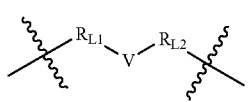

with in each case indpendently, and as applicable, $R_{L1}$, $R_{L2}$ and $R_{L3}$ can each be a moiety independently selected from the group consisting of alkyl, substituted alkyl, alkenyl, substituted alkenyl, alkynyl, carbocyclic, heterocyclic, poly(ethylene oxyl), and polyester. In some embodiments, each $R_{L1}$, $R_{L2}$ and $R_{L3}$ can be an independently selected non-repeating moiety (e.g., a moiety other than an oligomer or polymer) and can be an independently selected from the group consisting of alkyl, substituted alkyl, alkenyl, substituted alkenyl, alkynyl, carbocyclic, heterocyclic. In these embodiments, V can be a multifunctional bridging moiety as generally and specifically described herein. V can be a moiety independently selected from the group consisting of N, O, S, disulfide, carbonyl, ester, amide, urethane, urea, hydrazine, alkene, and alkyne.

For example, in some preferred embodiments, the linking moiety, L, can be a linking moiety represented by the formula selected from (D-II-A), (D-III-A) and (D-IV-A)

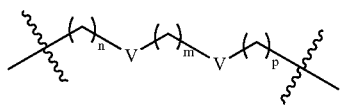
(D-II-A)

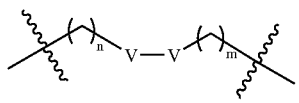
(D-III-A)

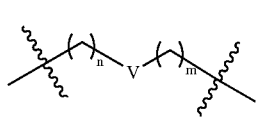
(D-IV-A)

with in each case indpendently, and as applicable, n, m and p are each independently selected non-zero integers. The integers n, m and p can each be independently selected as ranging from 1 to 50, preferably from 1 to 30, preferably from 1 to 20, or from 1 to 12, or from 1 to 8, or from 1 to 4. Preferably, the sum of n, m and p (as applicable in each case) is at least about 12, preferably at least about 16, more preferably at least about 20 and in some embodiments, at least about 24 or at least about 30. In each of the embodiments, the alkyl moieties (e.g., —(—C—)—) as shown can be substituted or unsubstitued alkyl moieties. In these embodiments, V can be a multifunctional bridging moiety as generally and specifically described herein. V can be a moiety independently selected from the group consisting of N, O, S, disulfide, carbonyl, ester, amide, urethane, urea, hydrazine, alkene, and alkyne.

In another (third) general embodiment, the substituted organic compound can comprise three or more independently selected multi-ring structures, $Z_1$, $Z_2$, $Z_3$, ... $Z_n$ each joined by a linking moiety, L. In one embodiment, for example, the multivalent compound of the invention can be a trimer comprising three or more independently selected multi-ring structures, $Z_1$, $Z_2$, $Z_3$, each bonded to a linking moiety, L, the where L can be a linking moiety represented by the formula (D-V)

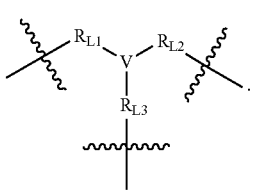
(D-V)

Here, the multi-ring structures $Z_1$, $Z_2$, $Z_3$ can be covalently bonded to the linking moiety. The multi-ring structures, $Z_1$, $Z_2$, $Z_3$ can each be indole or indole-related compounds (e.g., the multivalent phospholipase inhibitor) as described herein above, and as further detailed hereinafter. $R_{L1}$, $R_{L2}$ and $R_{L3}$ can each be a moiety independently selected from the group consisting of alkyl, substituted alkyl, alkenyl, substituted alkenyl, alkynyl, carbocyclic, heterocyclic, poly(ethylene oxyl), and polyester. In some embodiments, each $R_{L1}$, $R_{L2}$ and $R_{L3}$ can be an independently selected non-repeating moiety (e.g., a moiety other than an oligomer or polymer) and can be an independently selected from the group consisting of alkyl, substituted alkyl, alkenyl, substituted alkenyl, alkynyl, carbocyclic, heterocyclic. In these embodiments, V can be a multifunctional bridging moiety as generally and specifically described herein. V can be a moiety independently selected from the group consisting of N, O, S, disulfide, carbonyl, ester, amide, urethane, urea, hydrazine, alkene, and alkyne.

For example, in some preferred embodiments, the linking moiety, L, can be a linking moiety represented by the formula selected from (D-V-A)

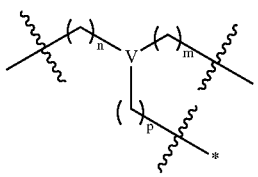
(D-V-A)

with n, m and p being independently selected non-zero integers. The integers n, m and p can each be independently selected as ranging from 1 to 50, preferably from 1 to 30, preferably from 1 to 20, or from 1 to 12, or from 1 to 8, or from 1 to 4. Preferably, the sum of any two of integers n, m and p (e.g., (n+m) or (n+p) or (m+p)) is at least about 12, preferably at least about 16, more preferably at least about 20 and in some embodiments, at least about 24 or at least about 30. In each of the embodiments, the alkyl moieties (e.g., —(—C—)—) as shown can be substituted or unsubstitued alkyl moieties. In these embodiments, V can be a multifunctional bridging moiety as generally and specifically described herein. V can be a moiety independently selected from the group consisting of N, O, S, disulfide, carbonyl, ester, amide, urethane, urea, hydrazine, alkene, and alkyne.

In general (for all embodiments), the total atomic distance between the multi-ring structures Z (e.g., including the multifunctional bridge moiety and/or any linking moieties, L) can be a length of at least twenty atoms in the shortest chain through which at least two of the two or more multi-ring structures, Z, are joined, and in some embodiments in each case, through which each of the two or more multi-ring structures, Z, are joined. Atomic distances for (e.g., carbocyclic or heterocylclic) ring structures is considered to be based on the nearest approximate number of C—C bond lengths in a straight line path across the (e.g., carbocyclic or heterocyclic) ring structures. In some embodiments, the total atomic distance between the multi-ring structures Z (e.g., including the multifunctional bridge moiety and/or any linking moieties, L) can be a length ranging from about 20 to about 500 atoms, preferably from about 20 to about 400 atoms, or from about 20 to about 300 atoms, or from about 20 to about 200 atoms, or from about 20 to about 100 atoms, or from about 20 to about 50 atoms, or from about 20 to about 40 atoms, or from about 20 to about 30 atoms, in each case, in the shortest chain through which at least two of the two or more multi-ring structures, Z, are joined, and in some embodiments in each case, through which each of the two or more multi-ring structures, Z, are joined.

The two or more moieties, $Z_1, Z_2 \ldots Z_n$, can be bonded, preferably covalently bonded, to the multifunctional bridge moiety through the corresponding linking moieties, $L_1$, $L_2 \ldots L_n$, respectively. Particularly preferred bonding sites for linking moieties, and generalized approaches are discussed hereinafter.

The multifunctional bridge moiety can be polymer moiety or a oligomer moiety or a non-repeating moiety.

In general, in one approach, the multifunctional bridge moiety can be a non-repeating moiety (considered as a whole). For example, the multifunctional bridge moiety can be a moiety selected from alkyl, phenyl, aryl, alkenyl, alkynyl, heterocyclic, amine, ether, sulfide, disulfide, hydrazine, and any of the foregoing substituted with oxygen, sulfur, sulfonyl, phosphonyl, hydroxyl, alkoxyl, amine, thiol, ether, carbonyl, carboxyl, ester, amide, alkyl, alkenyl, alkynyl, aryl, heterocyclic, and moieties comprising combinations thereof (in each permutation). A non-repeating moiety can include repeating units (e.g., methylene) within portions or segments thereof (e.g., within an alkyl segment), without having discrete repeat units that constitute the moiety as a whole (e.g., in the sense of a polymer or oligomer).

Examples of preferred multifunctional bridge moieties include, for example, sulfide moieties, disulfide moieties, amine moieties, aryl moieties, alkoxyl moieties, etc. Particularly preferred multifunctional bridge unit can be represented by a formula selected from

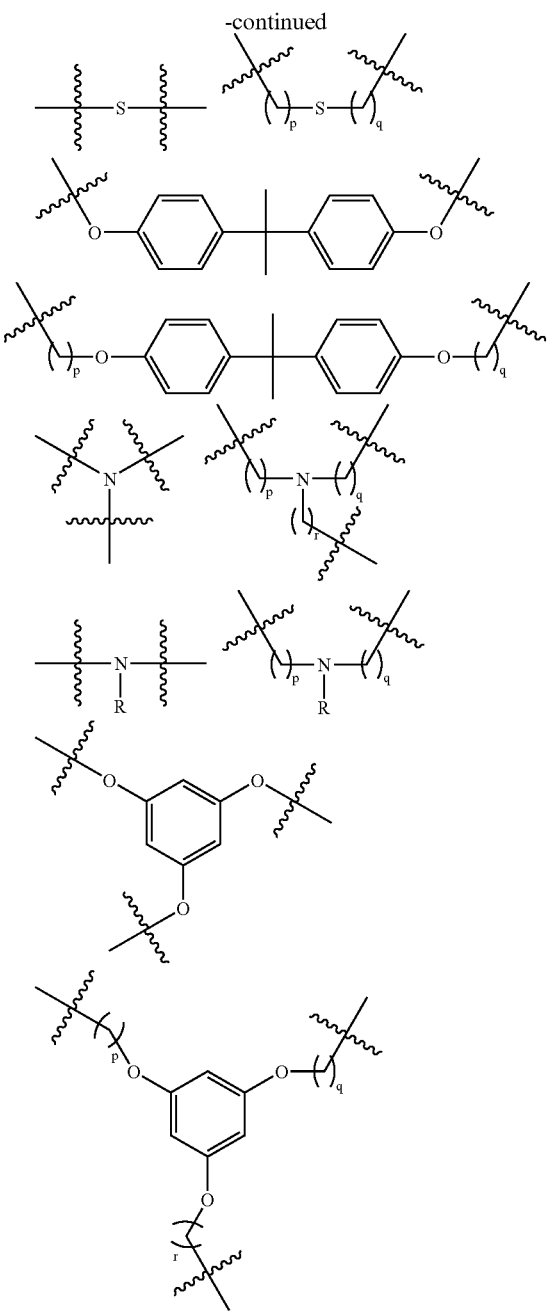

with each p, q and r each being an independently selected integer ranging from 0 to about 48, preferably from 0 to about 36, or from 0 to about 24, or from 0 to about 16. In some embodiments, each p, q and r can be an independently selected integer ranging from 0 to 12. R can be a substituent moiety. The substituent moiety can generally be selected from halide, hydroxyl, amine, thiol, ether, carbonyl, carboxyl, ester, amide, carbocyclic, heterocyclic, and moieties comprising combinations thereof.

In general, in another approach, the multifunctional bridge moiety can be a polymer moiety or an oligomer moiety. The polymer or oligomer can in each case, independently considered, comprise repeat units consisting of a repeat moiety selected from alkyl (e.g., —$CH_2$—), substituted alkyl (e.g., —CHR—), alkenyl, substituted alkenyl, alkynyl, substituted alkynyl, phenyl, aryl, heterocyclic, amine, ether, sulfide, disulfide, hydrazine, and any of the foregoing substituted with oxygen, sulfur, sulfonyl, phosphonyl, hydroxyl, alkoxyl, amine, thiol, ether, carbonyl, carboxyl, ester, amide, alkyl, alkenyl, alkynyl, aryl, heterocyclic, as well as moieties comprising combinations thereof.

Preferred polymers for polymer moieties useful in constructing multivalent indole or indole related compounds, preferably such as phospholipase inhibitors and especially preferably such as non-absorbed inhibitors can be prepared by any suitable technique, such a by free radical polymerization, condensation, addition polymerization, ring-opening polymerization, and/or can be derived from naturally occurring polymers, such as saccharide polymers. Further, in some embodiments, any of these polymer moieties may be functionalized.

Examples of polysaccharides useful in the present invention include materials from vegetal or animal origin, including cellulose materials, hemicellulose, alkyl cellulose, hydroxyalkyl cellulose, carboxymethylcellulose, sulfoethylcellulose, starch, xylan, amylopectine, chondroitin, hyarulonate, heparin, guar, xanthan, mannan, galactomannan, chitin, and/or chitosan. As noted above, more preferred are polymer moieties that do not degrade or that do not degrade significantly or essentially do not degrade under the physiological conditions of the GI tract, such as carboxymethylcellulose, chitosan, and sulfoethylcellulose.

When free radical polymerization is used, the polymer moiety can be prepared from various classes of monomers including, for example, acrylic, methacrylic, styrenic, vinylique dienic, whose typical examples are given thereafter: styrene, substituted styrene, alkyl acrylate, substituted alkyl acrylate, alkyl methacrylate, substituted alkyl methacrylate, acrylonitrile, methacrylonitrile, acrylamide, methacrylamide, N-alkylacrylamide, N-alkylmethacrylamide, N,N-dialkylacrylamide, N,N-dialkylmethacrylamide, isoprene, butadiene, ethylene, vinyl acetate, and combinations thereof. Functionalized versions of these monomers may also be used and any of these monomers may be used with other monomers as comonomers. For example, specific monomers or comonomers that may be used in this invention include methyl methacrylate, ethyl methacrylate, propyl methacrylate (all isomers), butyl methacrylate (all isomers), 2-ethylhexyl methacrylate, isobornyl methacrylate, methacrylic acid, benzyl methacrylate, phenyl methacrylate, methacrylonitrile, a-methylstyrene, methyl acrylate, ethyl acrylate, propyl acrylate (all isomers), butyl acrylate (all isomers), 2-ethylhexyl acrylate, isobornyl acrylate, acrylic acid, benzyl acrylate, phenyl acrylate, acrylonitrile, styrene, glycidyl methacrylate, 2-hydroxyethyl methacrylate, hydroxypropyl methacrylate (all isomers), hydroxybutyl methacrylate (all isomers), N,N-dimethylaminoethyl methacrylate, N,N-diethylaminoethyl methacrylate, triethyleneglycol methacrylate, itaconic anhydride, itaconic acid, glycidyl acrylate, 2-hydroxyethyl acrylate, hydroxypropyl acrylate (all isomers), hydroxybutyl acrylate (all isomers), N,N-dimethylaminoethyl acrylate, N,N-diethylaminoethyl acrylate, triethyleneglycol acrylate, methacrylamide, N-methylacrylamide, N,N-dimethylacrylamide, N-tert-butylmethacrylamide, N-n-butylmethacrylamide, N-methylolmethacrylamide, N-ethylolmethacrylamide, N-tert-butylacrylamide, N-n-butylacrylamide, N-methylolacrylamide, N-ethylolacrylamide, 4-acryloylmorpholine, vinyl benzoic acid (all isomers), diethylaminostyrene (all isomers), a-methylvinyl benzoic acid (all isomers), diethylamino α-methylstyrene (all isomers), p-vinylbenzene sulfonic acid, p-vinylbenzene sulfonic sodium salt, alkoxy and alkyl silane functional monomers, maleic anhydride, N-phenylmaleimide, N-butylmaleimide, butadiene, isoprene, chloroprene, ethylene, vinyl acetate, vinylformamide, allylamine, vinylpyridines (all isomers), fluorinated acrylate, methacrylates, and combinations thereof. Main chain heteroatom polymer moieties can also be used, including polyethyleneimine and polyethers such as polyethylene oxide and polypropylene oxide, as well as copolymers thereof.

The linking moiety L, in each of the described embodiments (including embodiments in which a phospholipase inhibiting moiety is linked to a multifunctional bridge such as a polymer moiety, an oligomer moiety, or a non-repeating moiety) can be a chemical linker, such as a bond or a other moiety, for example, comprising about 1 to about 10 atoms that can be hydrophilic and/or hydrophobic. In some embodiments, the linker can be longer, including for example where the linking moiety is also the bridge moiety, comprising for example from 1 to about 100 atoms that can be hydrophilic and/or hydrophobic. In some embodiments, the linker moiety can range from 10 to 300 atoms, or from 10 to 200 atoms or from 10 to 100 atoms, in each case along a shortest path between inhibiting moieties. In some embodiments the linking moiety length is at least 20 atoms along such a shortest path, preferably from about 20 to about 300 atoms, from 20 to about 200 atoms, from 20 to about 100 or from 20 to about 50 atoms, or from 20 to about 30 atoms along such a shortest path. The linking moiety links, couples, or otherwise attaches the phospholipase inhibiting moiety Z to another inhibiting moiety Z, or to a non-repeating bridge moiety, or to an oligomer moiety, or to a polymer moiety (for example to a backbone of the polymer moiety). In one embodiment, the linking moiety can be a polymer moiety grafted onto a polymer backbone, for example, using living free radical polymerization approaches known in the art.

The two or more moieties, $Z_1, Z_2 \ldots Z_n$, can be bonded, preferably covalently bonded, to the multifunctional bridge moiety through the corresponding linking moieties, $L_1$, $L_2 \ldots L_n$, respectively, through any reactive site. Preferably, the linking site does not affect the overall activity of the indole or indole-related compound or moieties, Z. Specifically, for phospholipase inhibitors of the invention, the site of attachment of an indole or indole related compound or moiety (e.g., an indole or indole-related phospholipase inhibiting compound or moiety) to a linking moiety or to a multifunctional bridge, e.g., a non-repeating moiety, a polymer moiety, or an oligomer moiety) can be selected so as to essentially not materially and adversely interfere with the inhibitory action of the phospholipase inhibiting moiety, e.g., its ability to blunt or reduce the catalytic activity of $PLA_2$. For instance preferred sites for covalently bonding an indole or indole-related compound or moiety (e.g., a phospholipase inhibiting moiety) can include a substituent groups of the multi-ring structure, preferably at $R_5$, $R_6$, $R_7$ and/or $R_1$. An example of such coupling sites is indicated with arrows below:

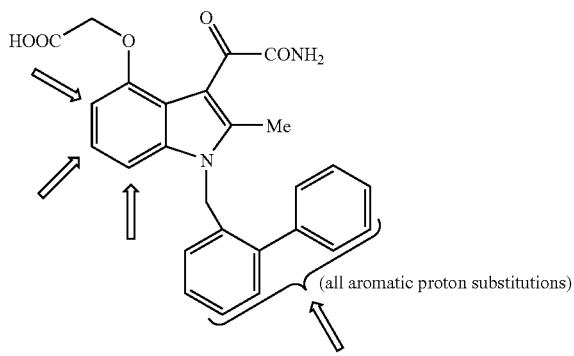

(all aromatic proton substitutions)

Those of skill in the art will recognize other suitable coupling sites and schema for indole or indole related moieties, such as novel or art-known phospholipase inhibiting moieties. For example, suitable points of coupling can be identified by available structural information. A co-crystal structure of a phospholipase inhibiting moiety bound to a phospholipase allows one to select one or more sites where attachment of a linking moiety would not preclude the interaction between the phospholipase inhibiting moiety and its target. Further, evaluation of binding of a phospholipase inhibitor to a phospholipase by nuclear magnetic resonance permits identification of sites non-essential for such binding interaction. Additionally, one of skill in the art can use available structure-activity relationship (SAR) for phospholipase inhibitors that suggest positions where structural variations are allowed. A library of candidate phospholipase inhibitors can be designed to feature different points of attachment of the phospholipase inhibiting moiety, e.g., chosen based on information described above as well as randomly, so as to present the phospholipase inhibiting moiety in multiple distinct orientations. Candidates can be evaluated for phospholipase inhibiting activity, as discussed in more detail below, to obtain phospholipase inhibitors with suitable coupling sites of the phospholipase inhibiting moiety to the polymer moiety or other non-absorbed moiety.

As a non-limiting example, one scheme for coupling an indole or indole related compound to a linking moiety or to a multifunctional bridge moiety can include alkylation of indole N1 position as shown in the following scheme:

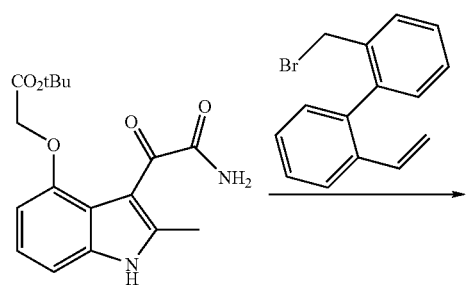

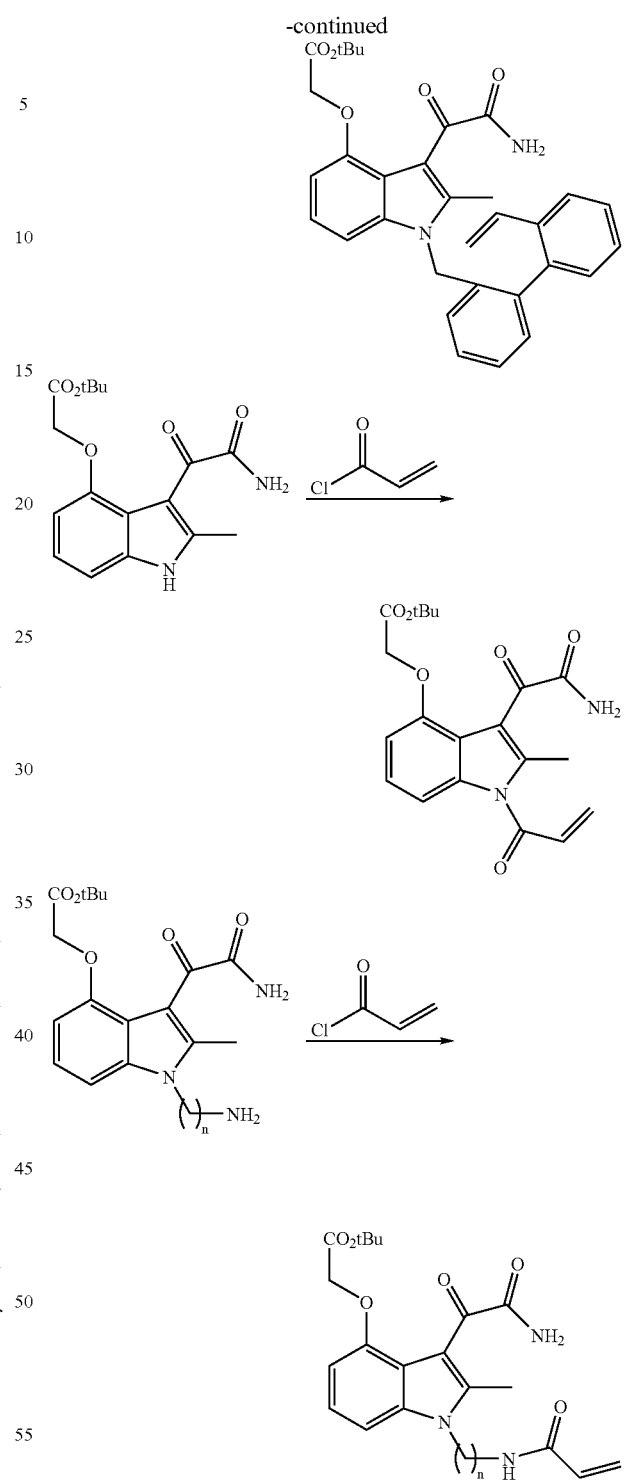

In another non-limiting example illustrating another scheme, a relatively short chain dimer can be achieved by the route outlined below. Generally, commercial available alkyl dibromide is used as the linker with bromide or thiol end functional group. Then two inhibitor can be jointed by a amine, sulfide, or a disulfide bond. Other jointing functional group also can be applied after derivatization of bromide linker.

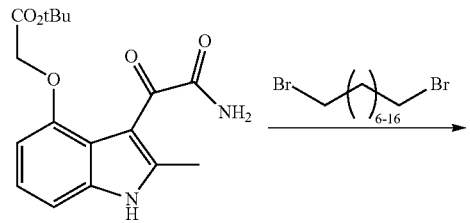
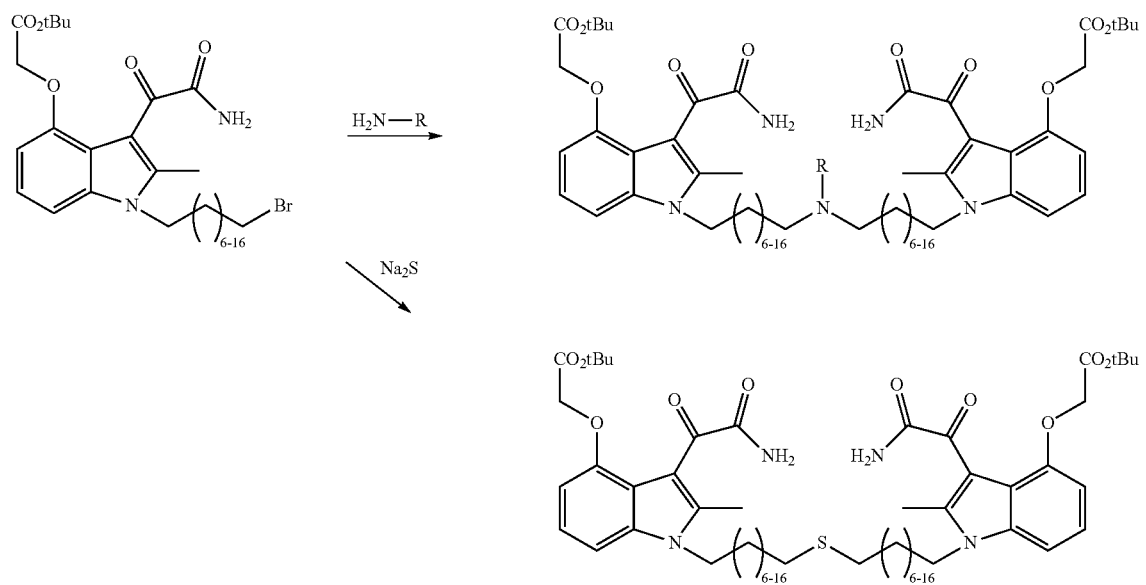
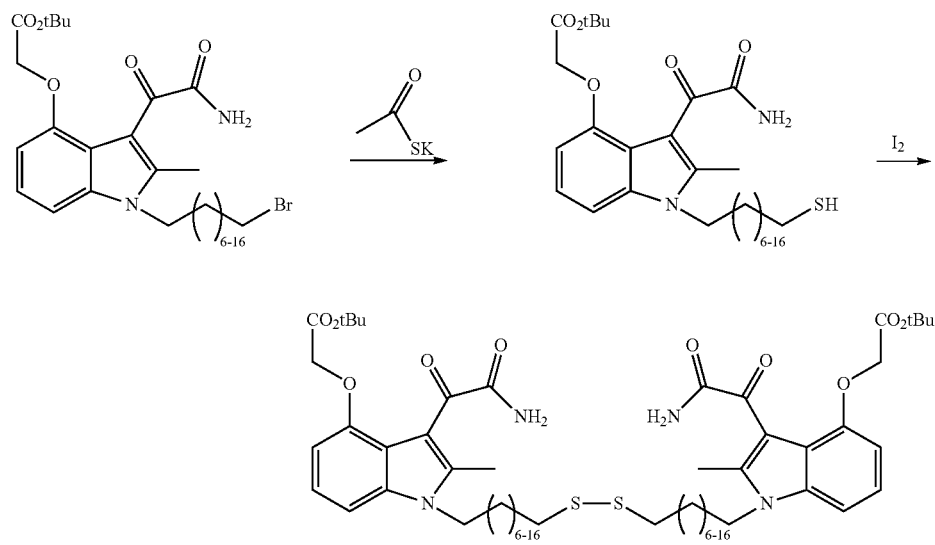

Further details for various schema are provided in the examples, which should be considered as non-limiting in this regard.

The multi-ring moiety of the multivalent compound can be more specifically described as follows. Such preferred embodiments are particularly suited for multivalent phospholipase inhibitor compounds of the invention.

In especially preferred embodiments, $R_3$ is a moiety represented by formula (C3-I or C3-II)

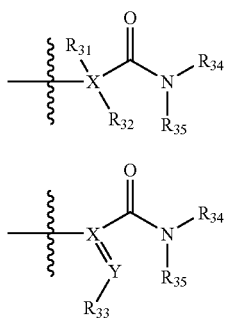

(C3-I)

(C3-II)

with: X being selected from the group consisting of O, C and N; $R_{31}$ being optional, and if present being selected from the group consisting of hydrogen, halide, hydroxyl and cyano; $R_{32}$ being optional, and if present being selected from the group consisting of hydrogen, halide, hydroxyl, and cyano; Y being selected from the group consisting of O, S, and N; $R_{33}$ being optional, and if present being selected from the group consisting of hydrogen, hydroxyl, $C_1$-$C_6$ alkyl, substituted $C_1$-$C_6$ alkyl, $C_1$-$C_6$ alkoxyl and substituted $C_1$-$C_6$ alkoxyl; and $R_{34}$ and $R_{35}$ each being independently selected from the group consisting of hydrogen, hydroxyl, alkoxyl, alkyl, substituted alkyl, amine, and alkylsulfonyl.

In some preferred embodiments, $R_3$ can preferably be a moiety represented by formula (C3-I-A or C3-II-A)

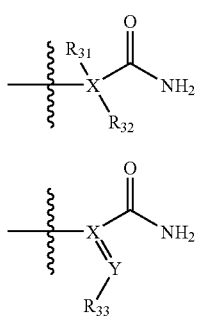

(C3-I-A)

(C3-II-A)

with: X being selected from the group consisting of O, C and N; $R_{31}$ being optional, and if present being selected from the group consisting of hydrogen, halide, hydroxyl and cyano; $R_{32}$ being optional, and if present being selected from the group consisting of hydrogen, halide, hydroxyl, and cyano; Y being selected from the group consisting of O, S, and N; $R_{33}$ being optional, and if present being selected from the group consisting of hydrogen, hydroxyl, $C_1$-$C_6$ alkyl, substituted $C_1$-$C_6$ alkyl, $C_1$-$C_6$ alkoxyl and substituted $C_1$-$C_6$ alkoxy.

$R_3$ can most preferably be a moiety represented by a formula selected from the group consisting of

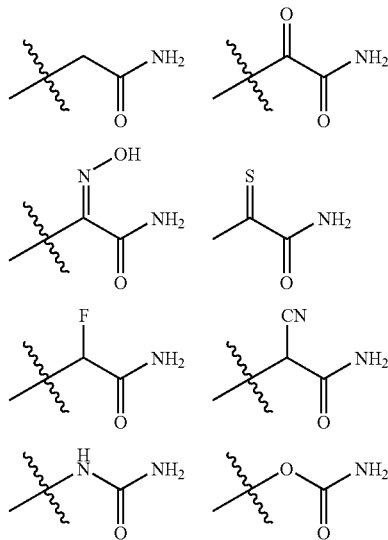

In especially preferred embodiments (including in embodiments with especially preferred $R_3$ as described in the immediately preceding paragraphs), $R_4$ can be a moiety selected from

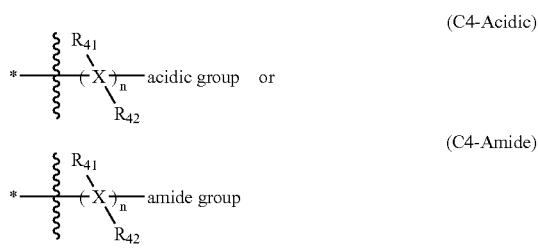

(C4-Acidic)

(C4-Amide)

with as applicable and independently selected for each formula: n being an integer ranging from 1 to 5; and for each n: X being independently selected from the group consisting of C, O, S, and N; and $R_{41}$ and $R_{42}$ each being optional, but if present being independently selected from the group consisting of hydrogen, halide, alkyl, substituted alkyl, phenyl, aryl, amine, alkoxyl, alkylsulfonyl, alkylphosphonyl, alkylcarbonyl, carboxyl, phosphonic, sulfonic, carboxamide, and cyano.

In particular, $R_4$ can be an acidic substituent, and can preferably be a moiety represented by formula selected from (C4-I-A), (C4-I-B) and (C4-I-C)

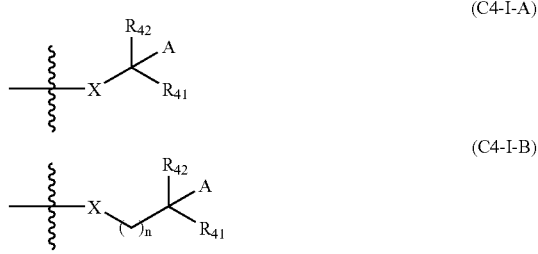

(C4-I-A)

(C4-I-B)

-continued

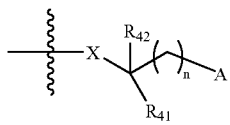
(C4-I-C)

in each case, independently selected for each of C4-I-A, C4-I-B and C4-I-C above with: n being an integer ranging from 0 to 5, and preferably ranging from 0 to 3; X being selected from the group consisting of O, C and N; A being an acidic group; $R_{41}$ being selected from the group consisting of hydrogen, halide, hydroxyl and cyano; and $R_{42}$ being selected from the group consisting of (i) $C_1$-$C_8$ alkyl, (ii) $C_1$-$C_8$ alkyl substituted with one or more substituents selected from halide, hydroxyl and amine, (iii) hydrogen, (iv) halide, and (v) carboxyl. Preferably, $R_{42}$ can be selected from the group consisting of (i) $C_2$-$C_6$ alkyl, (ii) $C_2$-$C_6$ alkyl substituted with one or more substituents selected from halide, hydroxyl and amine, (iii) halide, and (iv) carboxyl. Preferred $R_{42}$ can be selected from hydrogen, $C_1$-$C_6$ alkyl, and substituted $C_1$-$C_6$ alkyl. Preferred $R_{42}$ can be a moiety selected from $C_2$-$C_4$ alkyl and substituted $C_2$-$C_4$ alkyl. $R_{42}$ can be a moiety selected from $C_2$-$C_4$ alkyl and $C_2$-$C_4$ alkyl substituted with one or more substituents selected from halide, hydroxyl and amine. Especially preferred $R_{42}$ can be hydrogen, methyl, ethyl, propyl, isopropyl, isobutyl and tertbutyl. Particularly preferred $R_{42}$ can be ethyl, propyl, isopropyl, isobutyl and tertbutyl.

Especially preferred $R_4$ can be a moiety represented by formula selected from the group consisting of

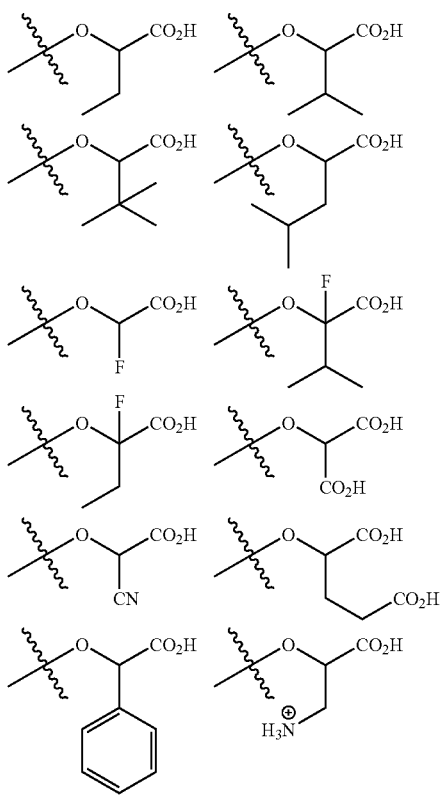

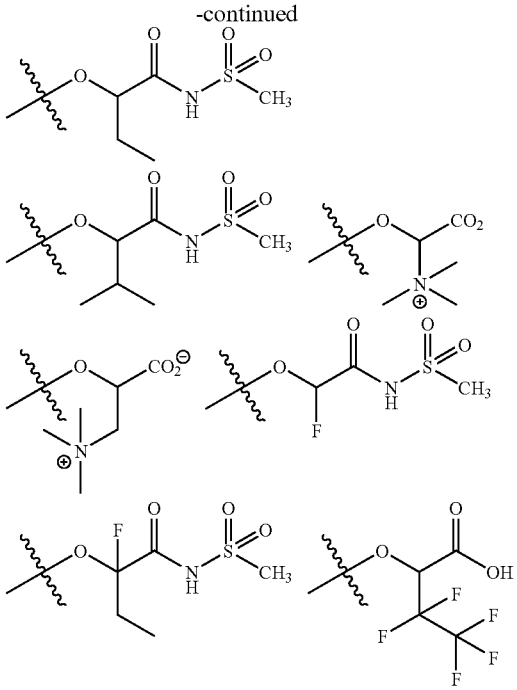

$R_4$ can in especially preferred embodiments, additionally or alternatively, be an amide substituent, and can be a moiety represented by formula selected from (C4-II-A), (C4-II-B), (C4-II-C) and (C4-II-D)

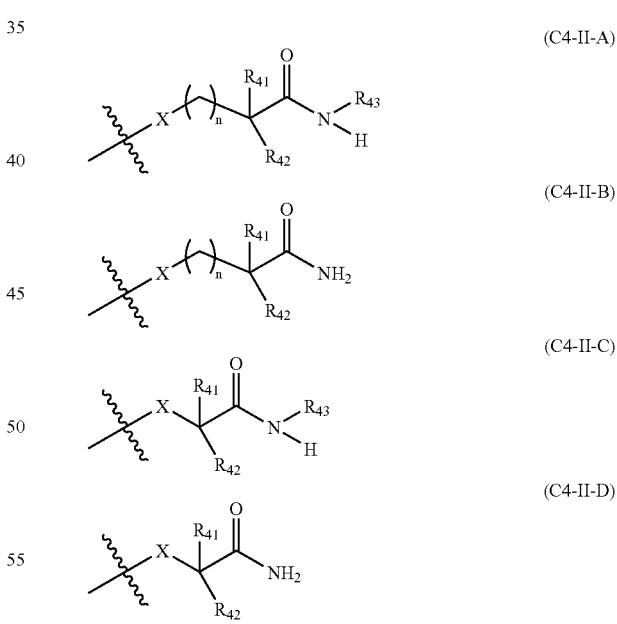

with as applicable and independently selected for each formula: n being an integer ranging from 0 to 5, preferably 0 to 3; X being selected from the group consisting of O, C, S and N; $R_{41}$ being selected from the group consisting of hydrogen, halide, hydroxyl, alkoxyl, alkyl, substituted alkyl, carboxyl, carboxamide, alkylcarbonyl, amine, alkylphosphonyl, alkylsulfonyl, sulfonic, phosphonic, and cyano; $R_{42}$ being selected from the group consisting of, halide, hydroxyl, alkoxyl, alkyl, substituted alkyl, carboxyl, carboxamide, alkylcarbonyl, amine, alkylphosphonyl, alkylsulfonyl, sulfonic, phosphonic, and cyano, and $R_{43}$ being selected from the group consisting of hydrogen, phenyl, aryl, $C_1$-$C_6$ alkyl, and $C_1$-$C_6$ alkyl substituted with a moiety selected from the group consisting of hydrogen, halide, hydroxyl, amine, sulfonic, phosphonic, and cyano.

In another especially preferred embodiment $R_4$, additionally or alternatively, be an amide substituent moiety represented by formula (C4-III-A), (C4-III-B), (C4-III-F) or (C4-III-G)

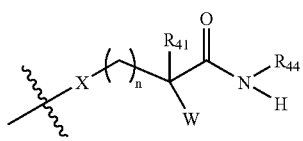
(C4-III-A)

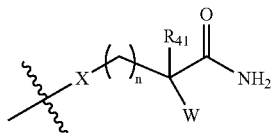
(C4-III-B)

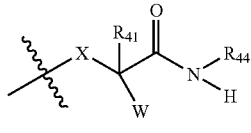
(C4-III-F)

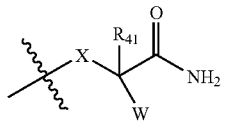
(C4-III-G)

with independently selected for each formula, as applicable: n being an integer ranging from 0 to 5, preferably 0 to 3; X being independently selected from the group consisting of O, C, S and N; W being an electron withdrawing group; $R_{41}$ being selected from the group consisting of hydrogen, halide, hydroxyl, alkoxyl, alkyl, substituted alkyl, carboxyl, carboxamide, alkylcarbonyl, amine, alkylphosphonyl, alkylsulfonyl, sulfonic, phosphonic, and cyano; and (for formulas C4-III-A and C4-III-F) $R_{44}$ being selected from the group consisting of hydrogen, phenyl, aryl, hydroxyl, alkoxyl, alkylsulfonyl, alkylphosphonyl, amine, $C_1$-$C_6$ alkyl, and $C_1$-$C_6$ alkyl substituted with a moiety selected from the group consisting of hydrogen, halide, hydroxyl, amine, carboxyl, sulfonic, phosphonic, and cyano.

In some embodiments, $R_4$ can be a moiety represented by formula (C4-III-C) or (C4-III-H)

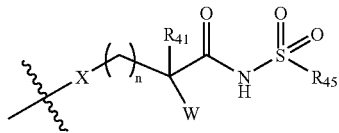
(C4-III-C)

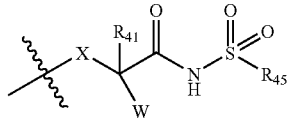
(C4-III-H)

with as applicable, and independently selected for each formula: n being an integer ranging from 0 to 5, preferably 0 to 3; X being independently selected from the group consisting of O, C, S and N; W being an electron withdrawing group; $R_{41}$ being selected from the group consisting of hydrogen, halide, hydroxyl, alkoxyl, alkyl, substituted alkyl, carboxyl, carboxamide, alkylcarbonyl, amine, alkylphosphonyl, alkylsulfonyl, sulfonic, phosphonic, and cyano; and $R_{45}$ being selected from the group consisting of hydrogen, phenyl, aryl, hydroxyl, alkoxyl, alkylsulfonyl, alkylphosphonyl, amine, $C_1$-$C_6$ alkyl, and $C_1$-$C_6$ alkyl substituted with a moiety selected from the group consisting of hydrogen, halide, hydroxyl, amine, carboxyl, sulfonic, phosphonic, and cyano.

In some embodiments, $R_4$ can be a moiety represented by formula (C4-III-D) or (C4-III-J)

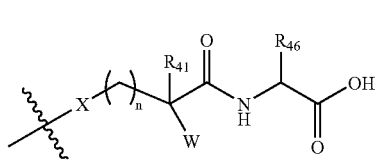
(C4-III-D)

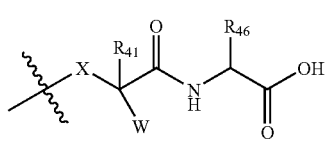
(C4-III-J)

with as applicable, and independently selected for each formula: n being an integer ranging from 0 to 5, preferably 0 to 3; X being independently selected from the group consisting of O, C, S and N; W being an electron withdrawing group; $R_{41}$ being selected from the group consisting of hydrogen, halide, hydroxyl, alkoxyl, alkyl, substituted alkyl, carboxyl, carboxamide, alkylcarbonyl, amine, alkylphosphonyl, alkylsulfonyl, sulfonic, phosphonic, and cyano; and $R_{46}$ being selected from the group consisting of hydrogen, phenyl, aryl, alkylsulfonyl, alkylphosphonyl, $C_1$-$C_6$ alkyl, and $C_1$-$C_6$ alkyl substituted with a moiety selected from the group consisting of hydrogen, halide, hydroxyl, amine, carboxyl, sulfonic, phosphonic, and cyano.

In some embodiments, $R_4$ can be a moiety represented by formula (C4-III-E) or (C4-III-K)

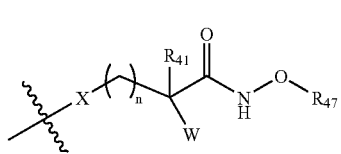
(C4-III-E)

-continued (C4-III-K)

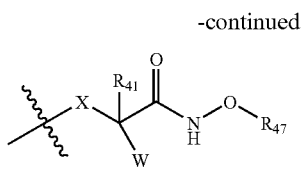

with as applicable, and independently for each formula: n being an integer ranging from 0 to 5, preferably 0 to 3; X being independently selected from the group consisting of O, C, S and N; W being an electron withdrawing group; $R_{41}$ being selected from the group consisting of hydrogen, halide, hydroxyl, alkoxyl, alkyl, substituted alkyl, carboxyl, carboxamide, alkylcarbonyl, amine, alkylphosphonyl, alkylsulfonyl, sulfonic, phosphonic, and cyano; and $R_{47}$ being selected from the group consisting of hydrogen, phenyl, aryl, $C_1$-$C_6$ alkyl, and $C_1$-$C_6$ alkyl substituted with a moiety selected from the group consisting of hydrogen, halide, hydroxyl, amine, carboxyl, sulfonic, phosphonic, and cyano.

In any of the aforementioned embodiments of formulas C4-III-A, -B, -C, -D, -E, -F, -G, -H, -J, -K, as applicable and in each case independently: $R_{41}$ is preferably selected from the group consisting of hydrogen, halide, haloalkyl, carboxyl, carboxamide, alkylcarbonyl, amine, alkyl alkylphosphonyl, alkylsulfonyl, sulfonic, phosphonic, and cyano; $R_{42}$ is preferably selected from the group consisting of halide, haloalkyl, carboxyl, carboxamide, alkylcarbonyl, amine, alkyl alkylphosphonyl, alkylsulfonyl, sulfonic, phosphonic, and cyano; $R_{43}$ is preferably selected from the group consisting of hydrogen, $C_1$-$C_6$ alkyl, and $C_1$-$C_6$ alkyl substituted with a moiety selected from the group consisting of hydrogen, hydroxyl, amine, sulfonic, and phosphonic; W is preferably selected from the group consisting of halide, hydroxyl, alkoxyl, haloalkyl, carboxyl, carboxamide, alkylcarbonyl, amine, alkylphosphonyl, alkylsulfonyl, sulfonic, phosphonic, and cyano; $R_{44}$ is preferably selected from the group consisting of hydrogen, hydroxyl, alkoxyl, alkylsulfonyl, $C_1$-$C_6$ alkyl, and $C_1$-$C_6$ alkyl substituted with a moiety selected from the group consisting of hydrogen, amine, carboxyl, sulfonic, and phosphonic; $R_{45}$ is preferably selected from the group consisting of $C_1$-$C_6$ alkyl substituted with a moiety selected from the group consisting of hydrogen, halide, hydroxyl, amine, carboxyl, sulfonic, phosphonic, and cyano; $R_{45}$ can be more preferably selected from the group consisting of $C_1$-$C_3$ alkyl substituted with a moiety selected from the group consisting of hydrogen, halide, hydroxyl, amine, carboxyl, sulfonic, phosphonic, and cyano; $R_{46}$ is preferably selected from the group consisting of $C_1$-$C_6$ alkyl substituted with a moiety selected from the group consisting of hydrogen, halide, hydroxyl, amine, carboxyl, sulfonic, phosphonic, and cyano. $R_{46}$ can be more preferably selected from the group consisting of $C_1$-$C_3$ alkyl substituted with a moiety selected from the group consisting of hydrogen, halide, hydroxyl, amine, carboxyl, sulfonic, phosphonic, and cyano; $R_{47}$ is preferably selected from the group consisting of $C_1$-$C_6$ alkyl substituted with a moiety selected from the group consisting of hydrogen, halide, hydroxyl, amine, carboxyl, sulfonic, phosphonic, and cyano; $R_{47}$ can be more preferably selected from the group consisting of $C_1$-$C_3$ alkyl substituted with a moiety selected from the group consisting of hydrogen, halide, hydroxyl, amine, carboxyl, sulfonic, phosphonic, and cyano.

In some embodiments, $R_4$ can be a moiety represented by a formula selected from the group consisting of

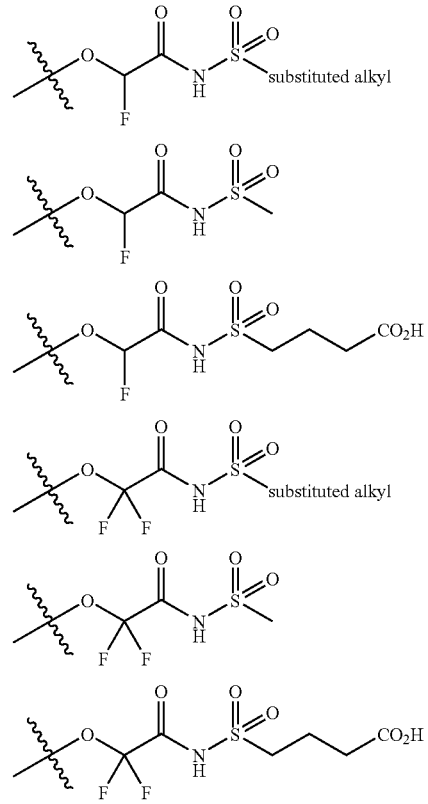

with: substituted alkyl being a $C_1$-$C_6$ alkyl substituted with a moiety selected from the group consisting of hydrogen, halide, hydroxyl, amine, carboxyl, sulfonic, phosphonic, and cyano.

In some embodiments, $R_4$ can be a moiety represented by a formula selected from the group consisting of

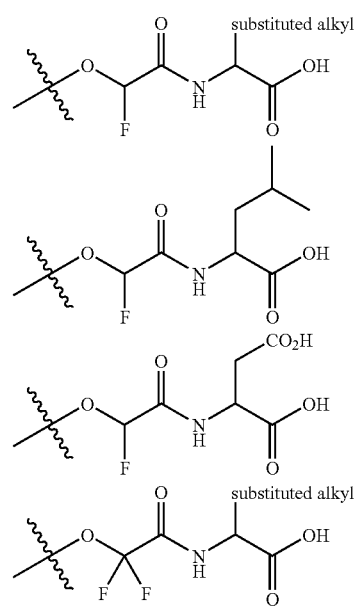

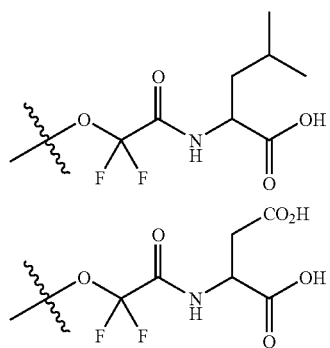

with: substituted alkyl being a $C_1$-$C_6$ alkyl substituted with a moiety selected from the group consisting of hydrogen, halide, hydroxyl, amine, carboxyl, sulfonic, phosphonic, and cyano.

In some embodiments, $R_4$ is a moiety represented by a formula selected from the group consisting of

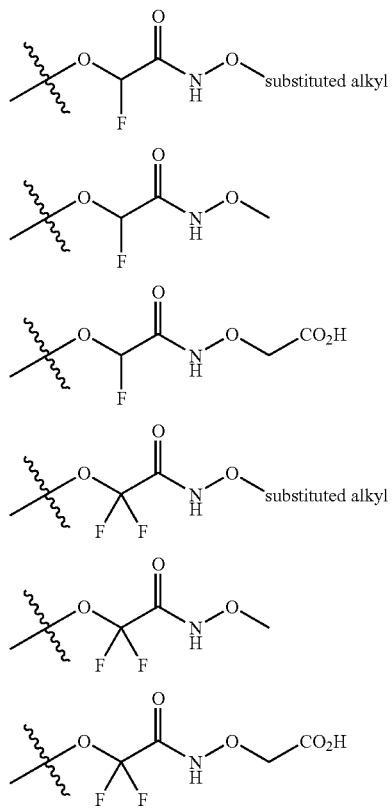

with: substituted alkyl being a $C_1$-$C_6$ alkyl substituted with a moiety selected from the group consisting of hydrogen, halide, hydroxyl, amine, carboxyl, sulfonic, phosphonic, and cyano.

In especially preferred embodiments, $R_4$ can be a moiety represented by a formula selected from the group consisting of

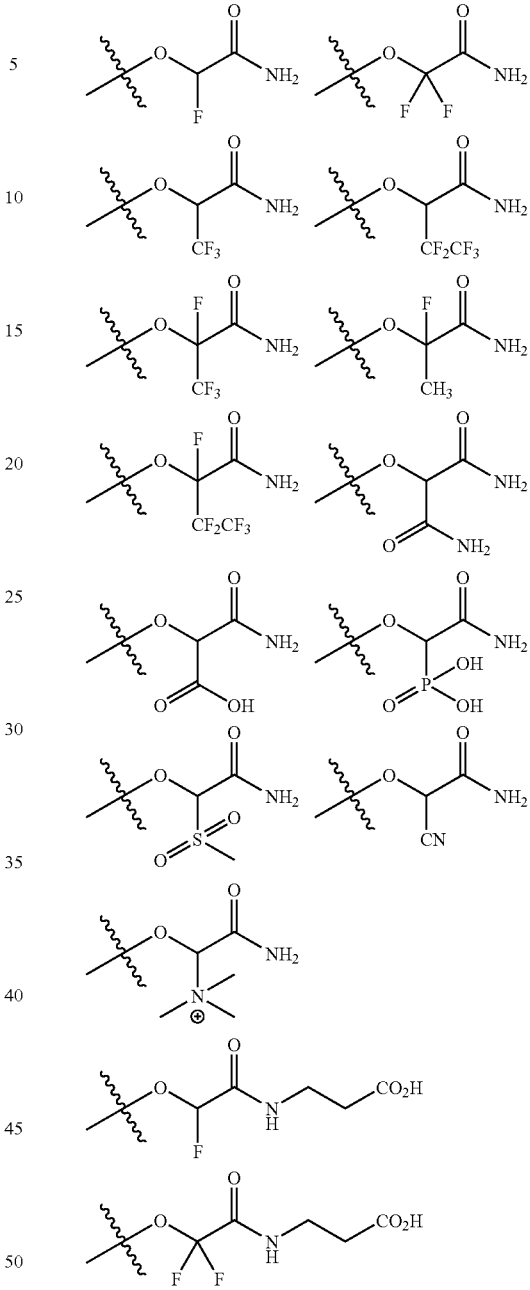

In a preferred embodiment of this first aspect of the invention, each of the other $R_2$, $R_5$, $R_1$, $R_6$ and $R_7$ substituent groups can be effective, collectively with each other and with $R_3$ and $R_4$ and with the multi-heterosubstituted multi-ring indole-based structure, for imparting phospholipase-A2 inhibiting functionality to the compound (or moiety).

In a preferred embodiment of this first aspect of the invention, $R_2$ and $R_5$ can each be independently selected from the group consisting of hydrogen, halide, hydroxyl, $C_1$-$C_3$ alkyl, substituted $C_1$-$C_3$ alkyl, and cyano.

$R_2$ can preferably be selected from the group consisting of hydrogen, halide, and $C_1$-$C_3$ alkyl. $R_2$ can be a moiety represented by a formula selected from the group consisting of

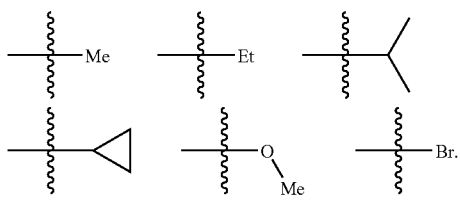

$R_5$ can preferably be selected from the group consisting of hydrogen, halide, hydroxyl, $C_1$-$C_3$ alkyl and cyano. $R_5$ can more preferably be selected from the group consisting of hydrogen, chloride, fluoride, hydroxyl, methyl and cyano.

In a preferred embodiment of this first aspect of the invention, $R_1$, $R_6$ and $R_7$ can each be independently selected from the group consisting of hydrogen, halide, hydroxyl, amine, carboxyl, phosphonic, sulfonic, alkyl, substituted alkyl, alkoxyl, substituted alkoxyl, alkyl carbonyl, substituted alkyl carbonyl, carbocyclic, heterocyclic, and moieties comprising combinations thereof.

For substitutents $R_1$ and $R_7$, preferable substituent groups can be non-polar, and additionally or alternatively can comprise functional group substituents effective for linking to a linking moiety and/or to a multifunctional bridge moiety (e.g., for preparing multivalent phospholipase inhibitors). For example, such substituents can be selected from halide, thiol, ether, carbocyclic, heterocyclic and moieties comprising combinations thereof.

$R_1$ can preferably be selected from the group consisting of $C_4$-$C_{36}$ alkyl, substituted $C_4$-$C_{36}$ alkyl, carbocyclic, heterocyclic, alkyl carbonyl, substituted alkyl carbonyl, and moieties comprising combinations thereof. $R_1$ can be selected from the group consisting of $C_4$-$C_{36}$ alkyl, substituted $C_4$-$C_{36}$ alkyl, carbocyclic, and moieties comprising combinations thereof.

$R_1$ can be a moiety represented by a formula selected from the group consisting of

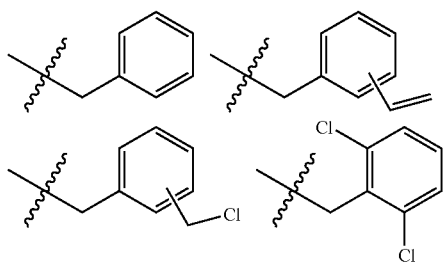

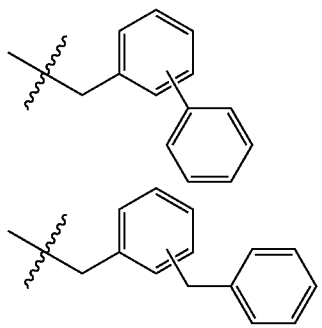

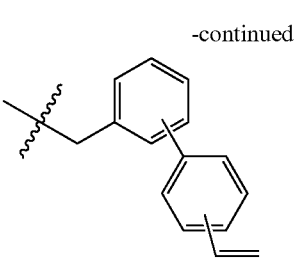

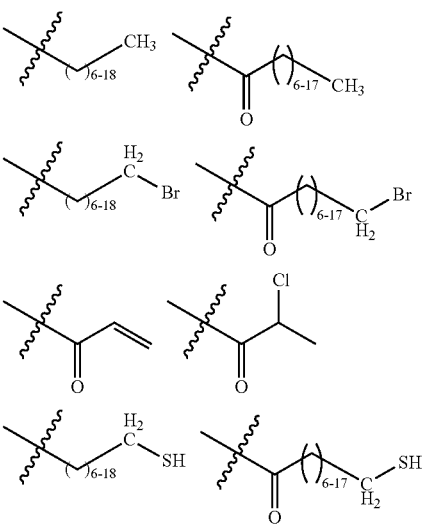

$R_1$ can be a moiety comprising a multifunctional bridge moiety or linked to a multifunctional bridge moiety.

$R_6$ can be selected from the group consisting of hydrogen, halide, amine, $C_1$-$C_3$ alkyl, substituted $C_1$-$C_3$ alkyl, acidic group, and moieties comprising combinations thereof. $R_6$ can be a moiety represented by a formula selected from the group consisting of

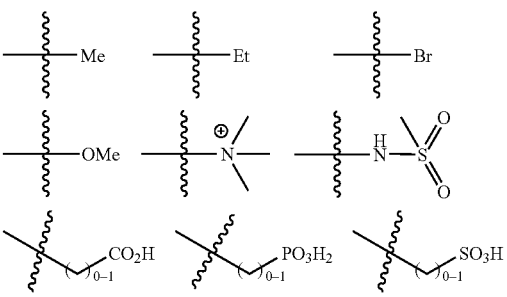

$R_6$ can be a moiety comprising a multifunctional bridge moiety.

$R_7$ can be selected from the group consisting of $C_4$-$C_{36}$ alkyl, substituted $C_4$-$C_{36}$ alkyl, carbocyclic, heterocyclic, alkyl carbonyl, substituted alkyl carbonyl, and moieties comprising combinations thereof. $R_7$ can be selected from the group consisting of $C_4$-$C_{36}$ alkyl, substituted $C_4$-$C_{36}$ alkyl, carbocyclic, and moieties comprising combinations thereof. $R_7$ can be a carbocyclic moiety.

$R_7$ can be a moiety represented by a formula selected from the group consisting of

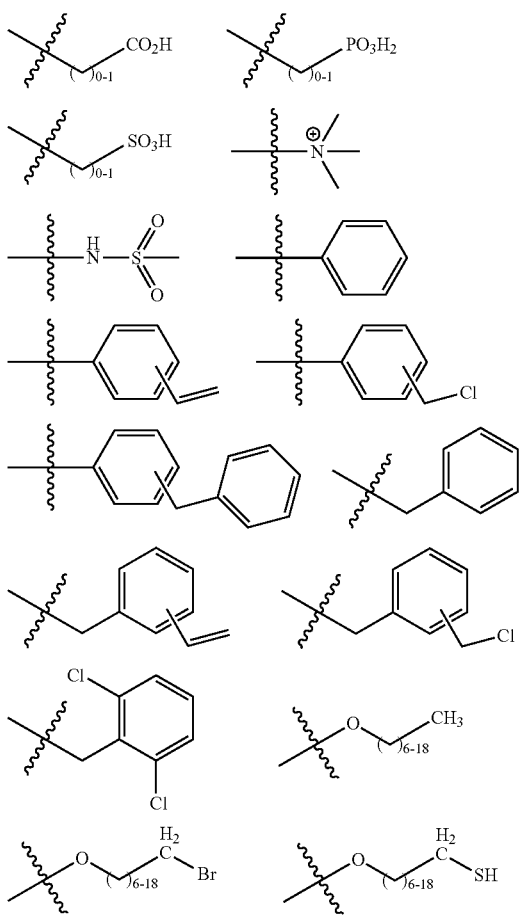

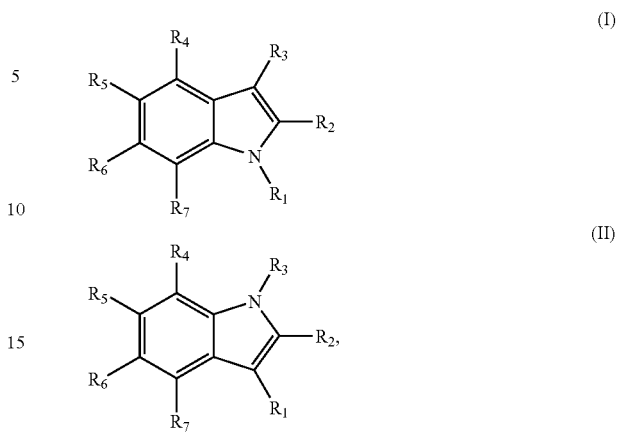

$R_7$ can be a moiety comprising a multifunctional bridge moiety.

As a non-limiting example, each of $R_1$, $R_6$ and $R_7$ can, independently, comprise a multifunctional bridge moiety, thereby forming a cross-linked network of multivalent indole or indole-related compounds. For example, each of $R_1$, $R_6$ and $R_7$ can, independently, comprise a multifunctional bridge moiety such as a moiety represented by a formula (D-I)

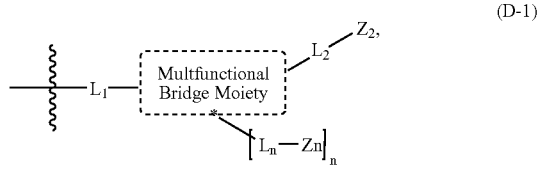

with: n being an integer ranging from 0 to 10, preferably 1 to 10; each of $L_1$, $L_2$ and $L_n$ being independently selected linking moieties; each of $Z_2$ and $Z_n$ being multi-ring structures covalently bonded to the multifunctional bridge moiety through corresponding linking moieties, each of the multi-ring structures including a fused five-membered ring and six-membered ring represented by formulas (I) or (II)

with the multi-ring structures independently optionally having one or more additional heteroatoms substituted within the ring structure of the five-member ring, within the ring structure of the six-member ring, or within the ring structure of each of the five-member and six-member rings, the one or more heteroatoms being selected from the group consisting of N, O, S and combinations thereof, and with $R_1$ through $R_7$ of the multi-ring structure each being independently selected from the group consisting of hydrogen, halide, oxygen, sulfur, phosphorus, hydroxyl, amine, thiol, alkyl, substituted alkyl, alkenyl, substituted alkenyl, alkynyl, substituted alkynyl, ether, carbonyl, acidic group, carboxyl, ester, amide, carbocyclic, heterocyclic, acylamino, oximyl, hydrazyl and moieties comprising combinations thereof, the multifunctional bridge moiety having at least (n+2) reactive sites to which the corresponding linking groups of the multi-ring structures are bonded, the multifunctional bridge moiety being selected from the group consisting of alkyl, phenyl, aryl, alkenyl, alkynyl, heterocyclic, amine, ether, sulfide, disulfide, hydrazine, and any of the foregoing substituted with oxygen, sulfur, sulfonyl, phosphonyl, hydroxyl, alkoxyl, amine, thiol, ether, carbonyl, carboxyl, ester, amide, alkyl, alkenyl, alkynyl, aryl, heterocyclic, and moieties comprising combinations thereof. Generally, in such multivalent embodiments, n can be an integer ranging from 0 to 10, or from 1 to 10 in preferred embodiments, such that the number of independently selected phospholipase inhibiting moieties can range from 2 to 12, or from 3 to 12. In alternative embodiments, n can generally range from 0 to about 500, or from 1 to about 500, preferably from 0 to about 100, or from 1 to about 100, and more preferably from 0 to about 50, or from 1 to about 50, and even more preferably from 0 to about 20, or from 1 to about 20. In some embodiments, the number of phospholipase inhibiting moieties can be lower, ranging for example from 2 to about 10 (correspondingly with n ranging from 0 to about 8), or from 3 to about 10 (correspondingly with n ranging from 1 to about 8). In some other embodiments, the number of phospholipase inhibiting moieties can range from 2 to about 6 (correspondingly with n ranging from 0 to about 4), or from 3 to about 6 (correspondingly with n ranging from 1 to about 4). In certain embodiments, the number of phospholipase inhibiting moieties can range from 2 to 4 (correspondingly with n ranging from 0 to 2), or from 3 to 4 (correspondingly with n ranging from 1 to 2).

Generally, in connection with the substituent groups described herein, a substituted moiety (e.g., substituted alkyl) means a moiety (e.g., alkyl) substituted with one or more substituents selected from halide, hydroxyl, amine, thiol, ether, carbonyl, carboxyl, ester, amide, carbocyclic, heterocyclic, and moieties comprising combinations thereof. Preferably, a substituted moiety can be a moiety substituted with one or more substituents selected from halide, hydroxyl, amine, thiol, ether, carbonyl, carbocyclic, heterocyclic, and moieties comprising combinations thereof. In some cases, a substituted moiety can be a moiety substituted with one or more substituents selected from halide, hydroxyl, amine, thiol, ether, carbonyl, and moieties comprising combinations thereof.

Generally, substituent groups can themselves be substituted. For example, unless specified otherwise, the recital of certain substituent moieties (e.g., "amine") is intended to refer to both unsubstituted moieties and where chemically reasonable also to substituted moieties (e.g., unsubstituted amine moieties and substituted amine moieties). Hence, as a non-limiting set of examples: reference to carbocyclic moieties can mean substituted or unsubstituted carbocycylic moieties; reference to heterocyclic moieties can mean substituted or Unsubstituted heterocyclic moieties; reference to amine moieties can mean substituted or unsubstituted amine moieties (e.g., primary, secondary, tertiary, quaternary ammonium ion); reference to alkoxyl moieties can mean substituted or unsubstituted alkoxyl moieties; reference to alkylcarbonyl moieties can mean substituted or unsubstituted alkylcarbonyl moieties; reference to alkylphosphonyl moieties can mean substituted or unsubstituted alkylphosphonyl moieties; reference to alkylsulphonyl moieties can mean substituted or unsubstituted alkylsulphonyl moieties; reference to carboxamide moieties can mean substituted or unsubstituted carboxamide moieties; etc.

Also, as used generally herein, including as used in connection with $R_1$ through $R_7$ in the indole or indole-related compounds shown above:

an amine group can include primary, secondary and tertiary amines;

a halide group can include fluoro, chloro, bromo, or iodo;

a carbonyl group can be a carbonyl moiety having a further substitution (defined below) as represented by the formula

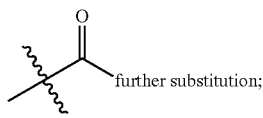

an acidic group can be an organic group as a proton donor and capable of hydrogen bonding, non-limiting examples of which include carboxylic acid, sulfate, sulfonate, phosphonates, substituted phosphonates, phosphates, substituted phosphates, 5-tetrazolyl,

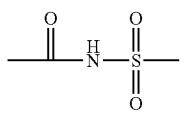 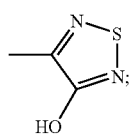

an alkyl group by itself or as part of another substituent can be a substituted or unsubstituted straight or branched chain hydrocarbon such as methyl, ethyl, n-propyl, isopropyl, n-butyl, tertiary butyl, sec-butyl, n-pentyl, n-hexyl, decyl, dodecyl, or octadecyl;

an alkenyl group by itself or in combination with other group can be a substituted or unsubstituted straight chain or branched hydrocarbon containing unsaturated bonds such as vinyl, propenyl, crotonyl, isopentenyl, and various butenyl isomers;

a carbocyclic group can be a substituted or unsubstituted, saturated or unsaturated, 5- to 14-membered organic nucleus whose ring forming atoms are solely carbon atoms, including cycloalkyl, cycloalkenyl, phenyl, spiro[5.5]undecanyl, naphthyl, norbornanyl, bicycloheptadienyl, tolulyl, xylenyl, indenyl, stilbenyl, terphenylyl, diphenylethylenyl, phenyl-cyclohexenyl, acenaphthylenyl, and anthracenyl, biphenyl, and bibenzylyl;

a heterocyclic group can be monocyclic or polycyclic, saturated or unsaturated, substituted or unsubstituted heterocyclic nuclei having 5 to 14 ring atoms and containing from 1 to 3 hetero atoms selected from the group consisting of nitrogen, oxygen or sulfur, including pyrrolyl, pyrrolodinyl, piperidinyl, furanyl, thiophenyl, pyrazolyl, imidazolyl, phenylimidazolyl, triazolyl, isoxazolyl, oxazolyl, thiazolyl, thiadiazolyl, indolyl, carbazolyl, norharmanyl, azaindolyl, benzofuranyl, dibenzofuranyl, dibenzothiophenyl, indazolyl, imidazo pyridinyl, benzotriazolyl, anthranilyl, 1,2-benzisoxazolyl, benzoxazolyl, benzothiazolyl, purinyl, pyridinyl, dipyridylyl, phenylpyridinyl, benzylpyridinyl, pyrimidinyl, phenylpyrimidinyl, pyrazinyl, 1,3,5-triazinyl, quinolinyl, phthalazinyl, quinazolinyl, morpholino, thiomorpholino, homopiperazinyl, tetrahydrofuranyl, tetrahydropyranyl, oxacanyl, 1,3-dioxolanyl, 1,3-dioxanyl, 1,4-dioxanyl, tetrahydrothiopheneyl, pentamethylenesulfadyl, 1,3-dithianyl, 1,4-dithianyl, 1,4-thioxanyl, azetidinyl, hexamethyleneiminium, heptamethyleneiminium, piperazinyl and quinoxalinyl;

an acylamino group can be an acylamino moiety having two further substitutions (defined below) as represented by the formula:

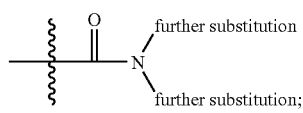

an oximyl group can be an oximyl moiety having two further substitutions (defined below) as represented by the formula:

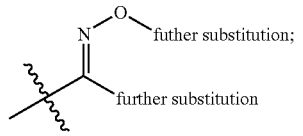

a hydrazyl group can be a hydrazyl moiety having three further substitutions (defined below) as represented by the formula:

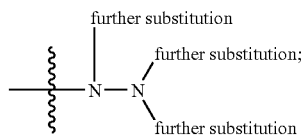

a substituted substitution group combines one or more of the listed substituent groups, preferably through moieties that include for example an -oxygene-alkyl-acidic moiety such as

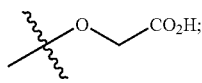

a -carbonyl-acyl amino-hydrogen moiety such as

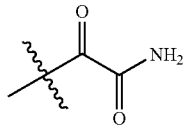

an -alkyl-carbocyclic-alkenyl moiety such as

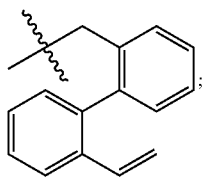

a -carbonyl-alkyl-thiol moiety such as

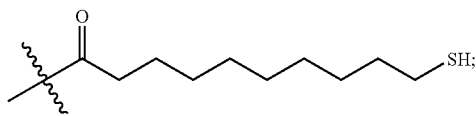

an -amine-carbonyl-amine moiety such as

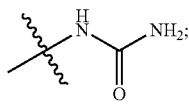

an alkylcarbonyl group can mean a moiety such as —C(=O)R; and a further substitution group can mean a group selected from hydrogen, oxygen, sulfur, phosphorus, amine, halide, hydroxyl (—OH), thiol (—SH), carbonyl, acidic group, alkyl, alkenyl, carbocyclic, heterocyclic, acylamino, oximyl, hydrazyl, substituted substitution group, and combinations thereof.

Each of these embodiments can be used in various and specific combination, and in each permutation, with each other aspects and embodiments described above or below herein.

The particular multiple indole and indole related moieties used in connection with the multivalent indole and indole related compounds can be the same or different on any given compound, and can be indole or indole related moieties known in the art. For example, many indole-based moieties are known in the art as having phospholipase inhibiting activity. Novel indole or indole related moieties can also be employed in connection with the present invention.

For example, particularly preferred indole or indole related moieties that can be employed as a Z moiety in connection with the present invention can be selected based on the guidance provided above.

Especially preferred moieties having phospholipase inhibiting activity can be selected, for example, from moieties having C-4 acidic groups, such as

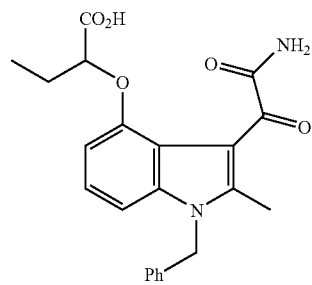
(4-20)

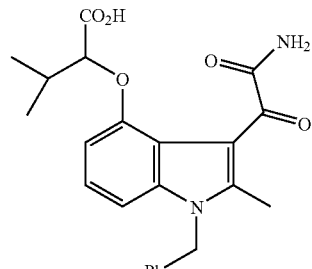
(4-22)

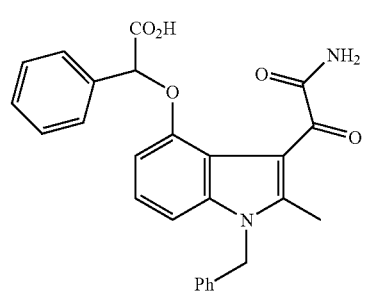
(4-32)

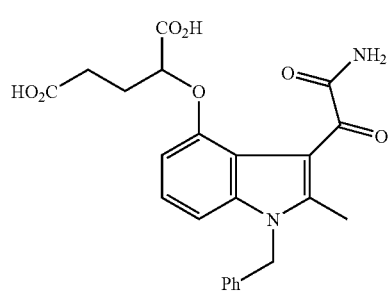
(4-33)

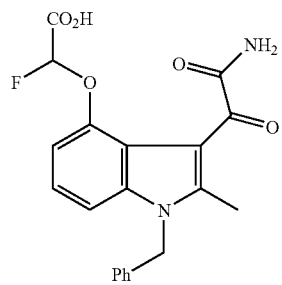
(4-24)

-continued
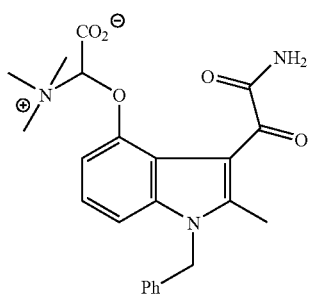 (4-48)
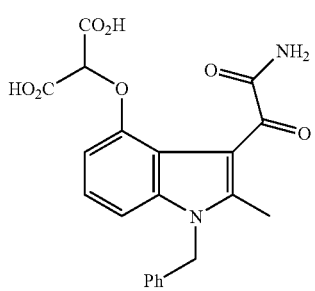 (4-8)
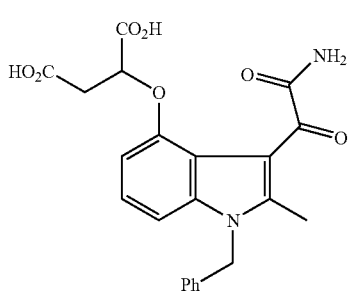 (4-1)
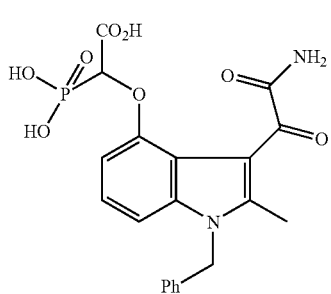 (4-19)
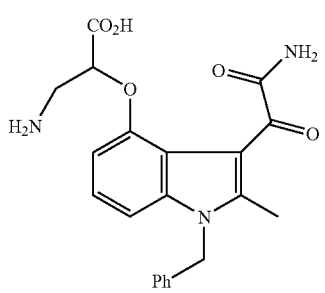 (4-44)
-continued
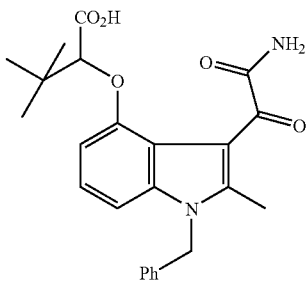 (4-46)
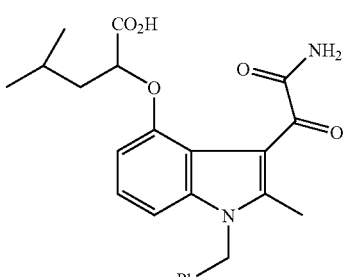 (4-47)
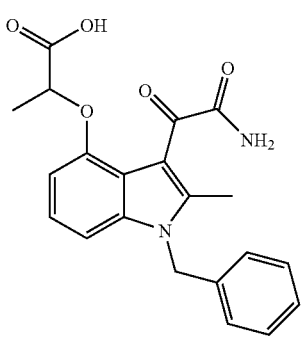 (5-19)
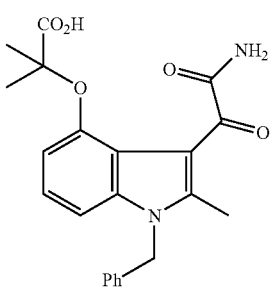 (4-23)
Especially preferred moieties having phospholipase inhibiting activity can also be selected, for example, from moieties having C-4 amide groups, such as
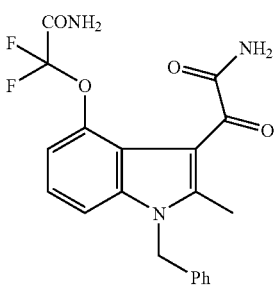 (4-41)

-continued
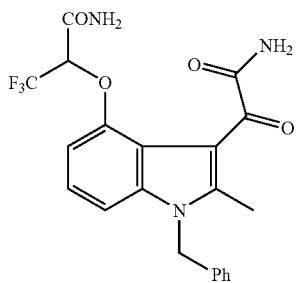 (4-42)
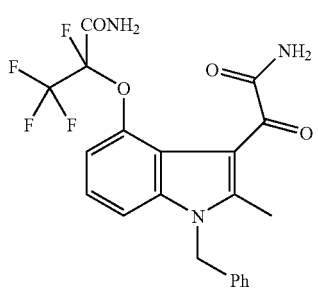 (4-43)
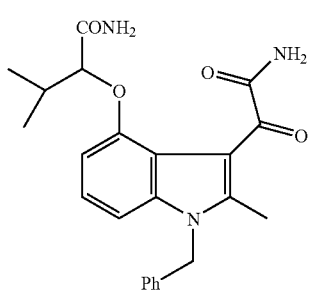 (4-45)
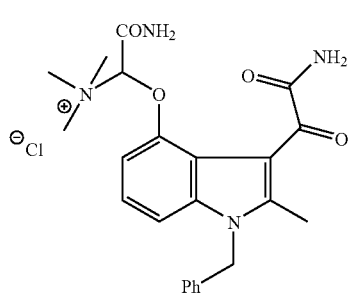 (4-49)
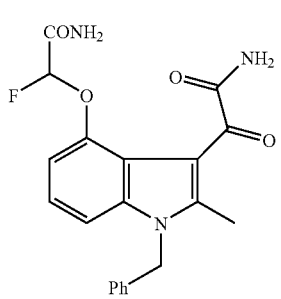 (4-28)
-continued
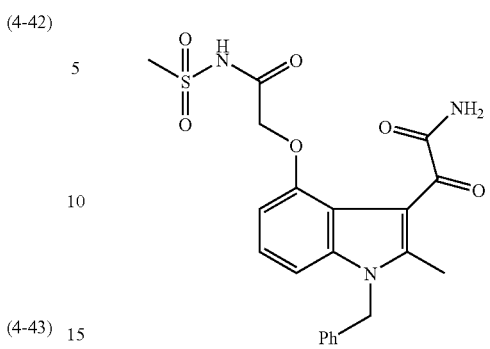 (4-21)
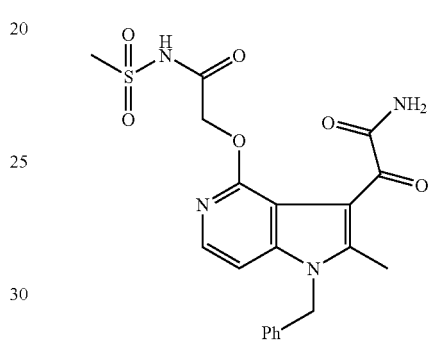 (2-7)
Especially preferred moieties having phospholipase inhibiting activity can also be selected, for example, from moieties having azaindole and azaindole related multi-ring structures, such as
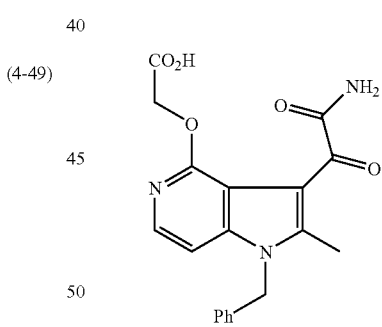 (2-1)
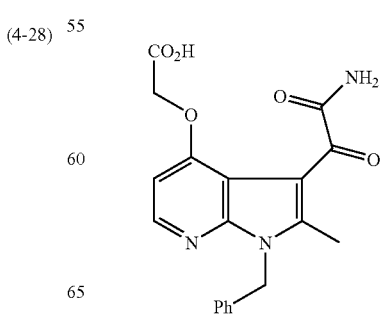 (7-1)

-continued
(2-7)
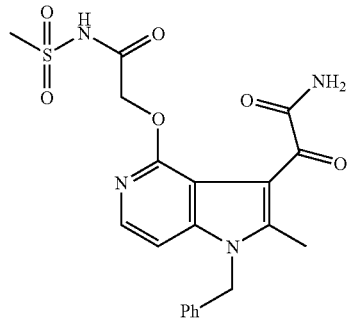
(2-4)
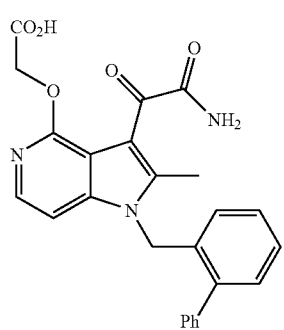
(2-8)
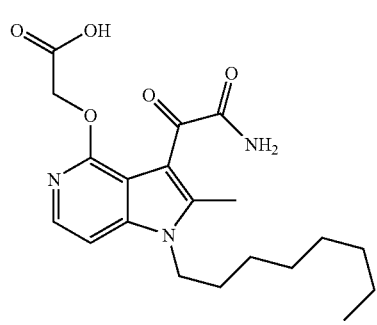
(2-11)
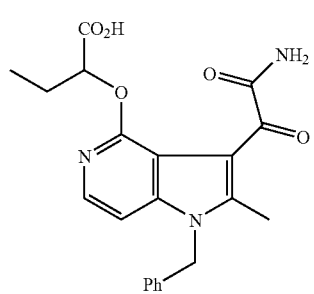
(2-9)
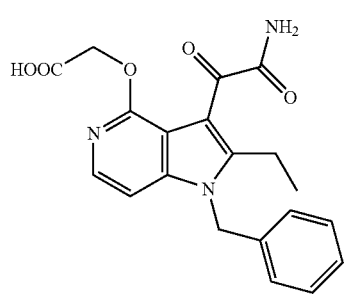
-continued
(2-10)
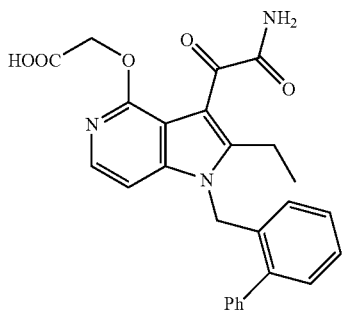
(2-12)
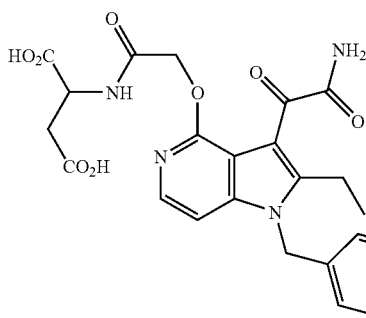
(2-13)
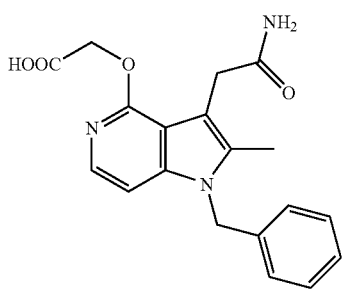
(2-14)
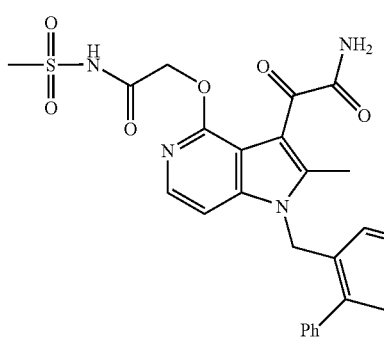
Other moieties having phospholipase inhibiting activity can also be selected, for example, including moieties such as

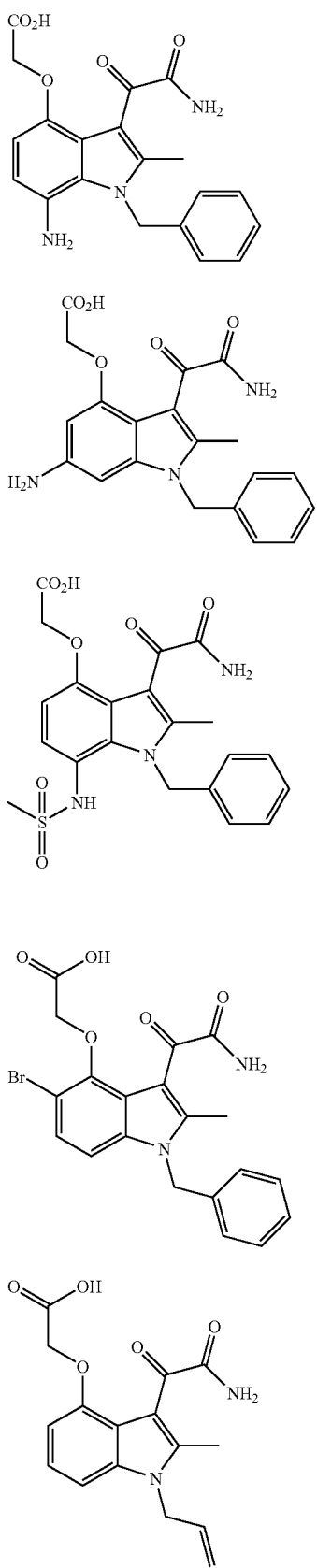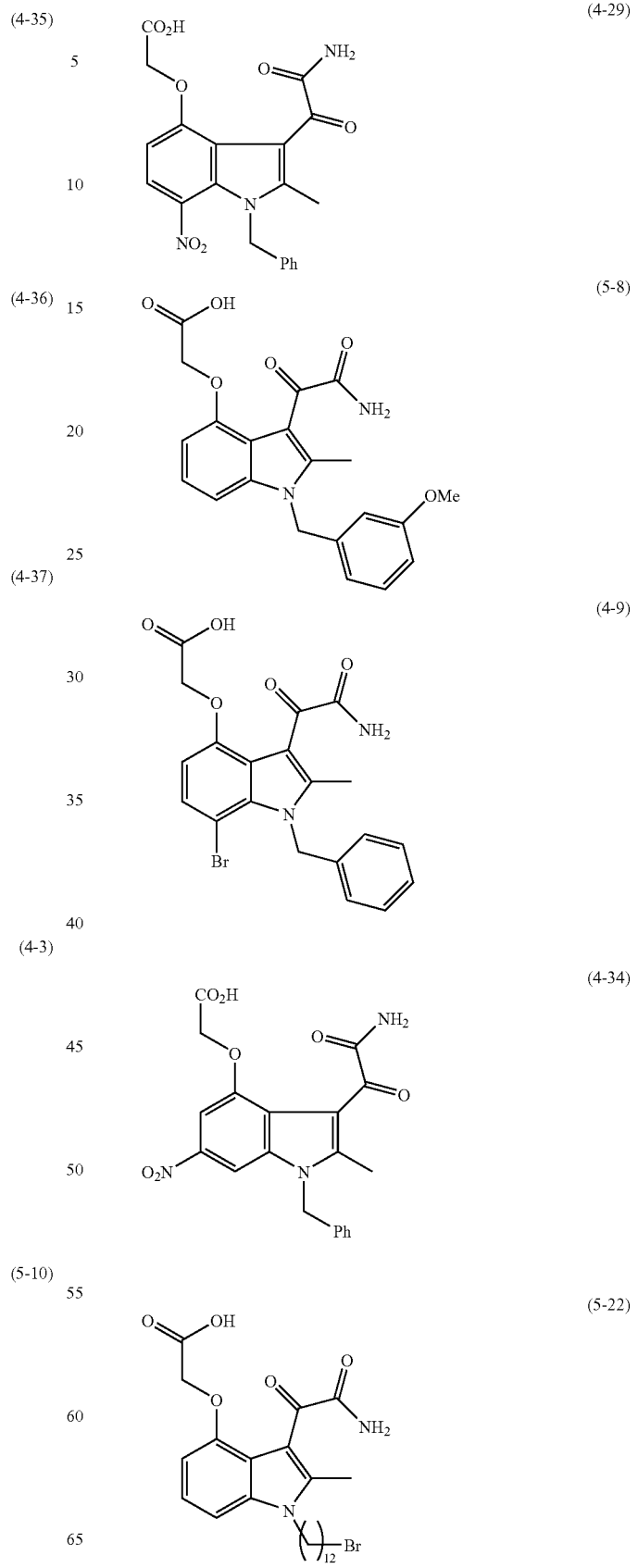

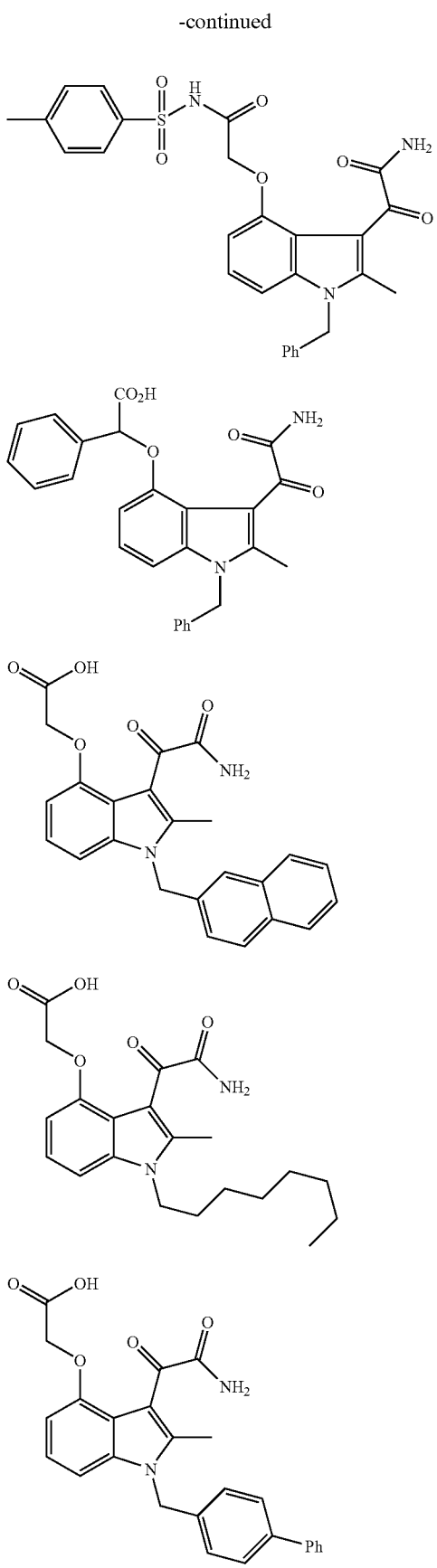

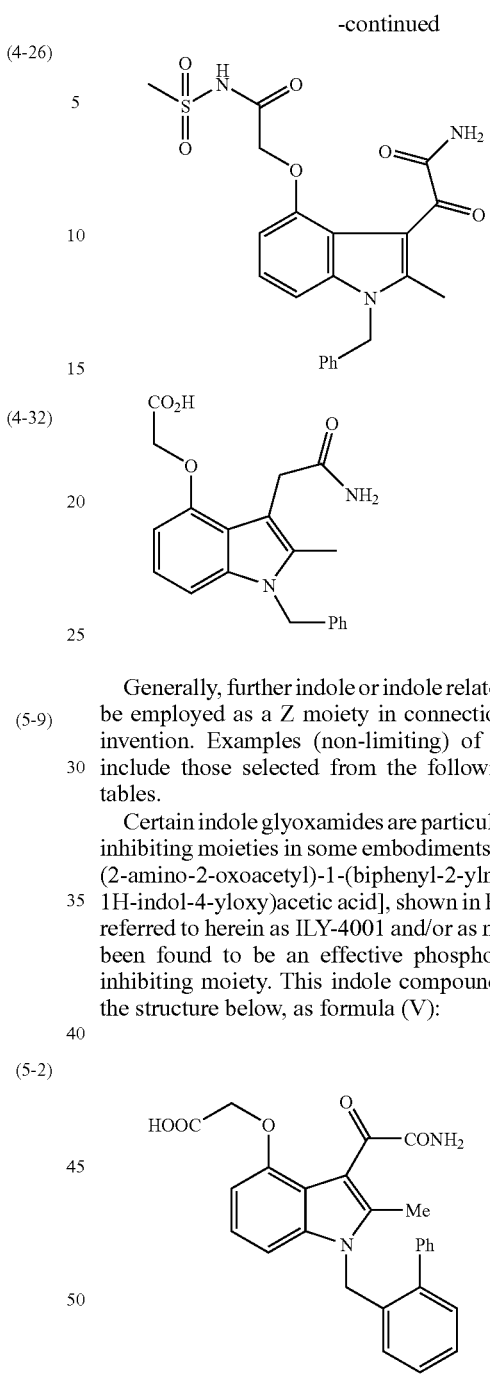

Generally, further indole or indole related moieties can also be employed as a Z moiety in connection with the present invention. Examples (non-limiting) of such moieties can include those selected from the following discussion and tables.

Certain indole glyoxamides are particularly useful as PLA$_2$ inhibiting moieties in some embodiments. Specifically [2-(3-(2-amino-2-oxoacetyl)-1-(biphenyl-2-ylmethyl)-2-methyl-1H-indol-4-yloxy)acetic acid], shown in FIG. 2, alternatively referred to herein as ILY-4001 and/or as methyl indoxam has been found to be an effective phospholipase inhibitor or inhibiting moiety. This indole compound is represented by the structure below, as formula (V):

This compound has been shown, based on in-vitro assays, to have phospholipase activity for a number of PLA2 classes, and is a strong inhibitor of mouse and human PLA21B enzymes in vitro (Singer, Ghomashchi et al. 2002; Smart, Pan et al. 2004). This indole compound was synthesized (See, Example 4) and as noted above, was evaluated in-vivo for phospholipase-A2 inhibition in a mice model. (See, Example 5, including Examples 5A through 5C). This indole compound was characterized with respect to inhibition activity, absorption and bioavailability. (See, Example 6, including Examples 6A through 6C).

Other indole compounds are also included within the scope of this invention. Many indoles have been described in the literature, for example, in connection with reported structure-activity-relationship studies (Schevitz, Bach et al. 1995; Dillard, Bach et al. 1996; Dillard, Bach et al. 1996; Draheim, Bach et al. 1996; Mihelich and Schevitz 1999). Table 1 lists various indole compounds, together with reported activity data against different phospholipase enzymes, including: human non-pancreatic PLA2 (hnp PLA2), human pancreatic secreted PLA2 (hps PLA2), and porcine pancreatic secreted PLA2 (pps PLA2).

TABLE 1

Indole Compounds

| Structure | IC$_{50}$ (μM) hnp PLA$_2$ | IC$_{50}$ (μM) hps PLA$_2$ | IC$_{50}$ (μM) pps PLA$_2$ |
|---|---|---|---|
| 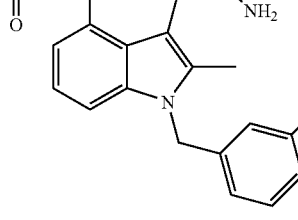 | 0.052 ± 0.012 | 1.2 | 0.02 |
| 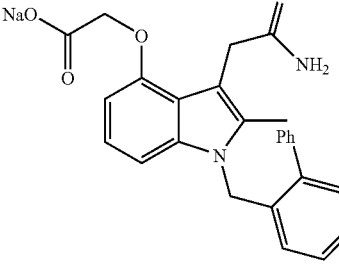 | 0.010 ± 0.001 | 4.09 | 0.014 |
| 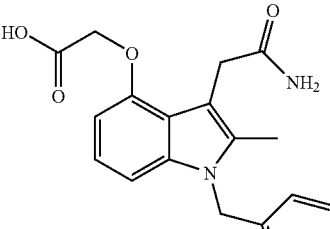 | 0.052 ± 0.010 | 1.4 | 0.15 |
| 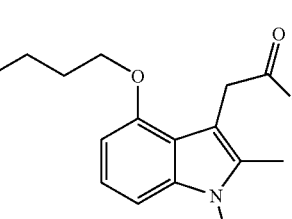 | 0.399 ± 0.045 | 3.66 | 0.61 |

TABLE 1-continued

Indole Compounds

| Structure | IC$_{50}$ (µM) hnp PLA$_2$ | IC$_{50}$ (µM) hps PLA$_2$ | IC$_{50}$ (µM) pps PLA$_2$ |
|---|---|---|---|
| (structure) | 0.152 ± 0.033 | 69 | 25 |
| (structure) | 0.147 ± 0.009 | 22.5 | 7.5 |
| (structure) | 0.024 ± 0.001 | 1.8 | 0.13 |
| (structure) | 0.189 ± 0.006 | 94 | 13.5 |

TABLE 1-continued

| Indole Compounds | | | |
|---|---|---|---|
| Structure | IC$_{50}$ (μM) hnp PLA$_2$ | IC$_{50}$ (μM) hps PLA$_2$ | IC$_{50}$ (μM) pps PLA$_2$ |
| [structure: 5-(3-carboxypropoxy)-2-bromo-1-benzyl-indole-3-acetamide] | 0.073 ± 0.016 | 15.9 | 2.86 |
| [structure: 4-(phosphonomethoxy)-2-methyl-1-benzyl-indole-3-acetamide] | 1.29 ± 0.16 | 73.5 | 5.55 |
| [structure: 5-(3-phosphonopropoxy)-2-methyl-1-benzyl-indole-3-acetamide] | 0.057 ± 0.004 | 67 | 27 |
| [structure: 5-(3-phosphonopropoxy)-2-ethyl-1-benzyl-indole-3-acetamide] | 0.023 ± 0.005 | 91.1 | 35.5 |

TABLE 1-continued

Indole Compounds

| Structure | IC$_{50}$ (µM) hnp PLA$_2$ | IC$_{50}$ (µM) hps PLA$_2$ | IC$_{50}$ (µM) pps PLA$_2$ |
|---|---|---|---|
| (5-(3-phosphonopropoxy)-2-bromo-1-benzyl-indol-3-yl acetamide) | 0.033 ± 0.004 | 6.2 | 2.2 |
| (5-(3-phosphonopropoxy)-2-ethyl-1-(3-chlorobenzyl)-indol-3-yl acetamide) | 0.016 ± 0.010 | 46.2 | |
| (5-(3-phosphonopropoxy)-2-methyl-1-(2-phenylbenzyl)-indol-3-yl acetamide) | 0.022 ± 0.006 | 39 | 7.6 |
| (5-(3-sulfopropoxy)-2-ethyl-1-benzyl-indol-3-yl acetamide) | 0.050 ± 0.015 | 135 | 5.8 |

TABLE 1-continued

Indole Compounds

| Structure | IC$_{50}$ (μM) hnp PLA$_2$ | IC$_{50}$ (μM) hps PLA$_2$ | IC$_{50}$ (μM) pps PLA$_2$ |
|---|---|---|---|
| 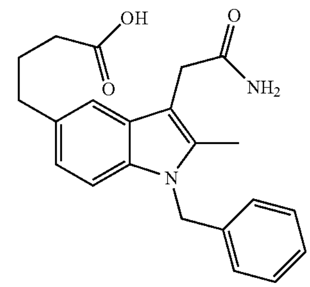 | 0.155 ± 0.029 | 94 | |
| 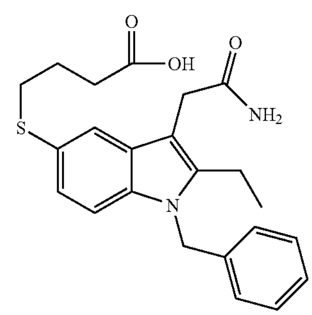 | 0.023 ± 0.005 | 16 | |
| 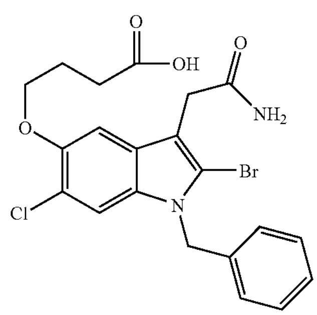 | 0.020 ± 0.003 | 3.2 | 1.3 |
| 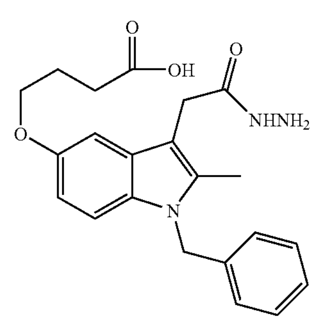 | 1.020 ± 0.150 | no activity | no activity |

TABLE 1-continued
Indole Compounds
| Structure | IC$_{50}$ (μM) hnp PLA$_2$ | IC$_{50}$ (μM) hps PLA$_2$ | IC$_{50}$ (μM) pps PLA$_2$ |
|---|---|---|---|
| 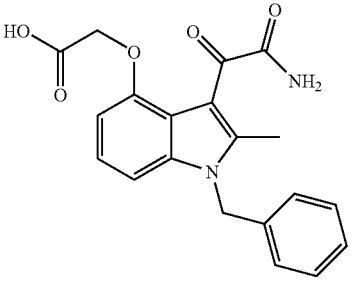 | 0.011 ± 0.004 | 0.761 | 0.015 |
| 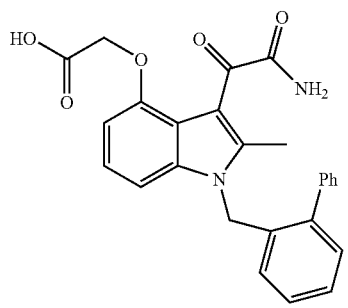 | 0.006 ± 0.001 | 0.364 | 0.097 |
| 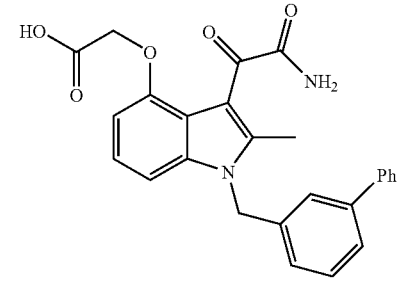 | 0.009 ± 0.001 | 0.57 | 0.007 |
| 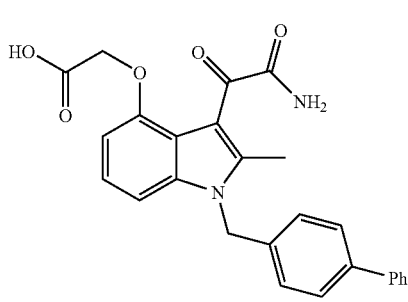 | 0.043 ± 0.003 | 1.09 | |
| 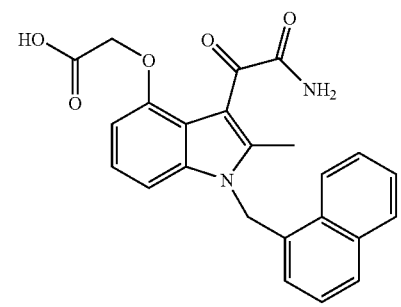 | 0.009 ± 0.004 | 1.2 | |

TABLE 1-continued

Indole Compounds

| Structure | IC$_{50}$ (μM) hnp PLA$_2$ | IC$_{50}$ (μM) hps PLA$_2$ | IC$_{50}$ (μM) pps PLA$_2$ |
|---|---|---|---|
| 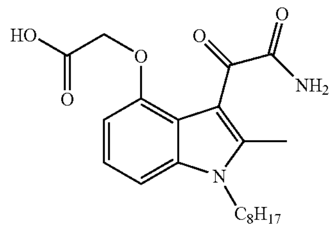 | 0.008 ± 0.003 | 0.78 | |
| 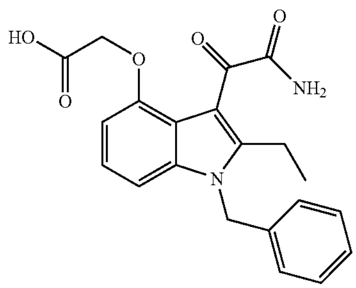 | 0.009 ± 0.001 | 0.228 | 0.048 |
| 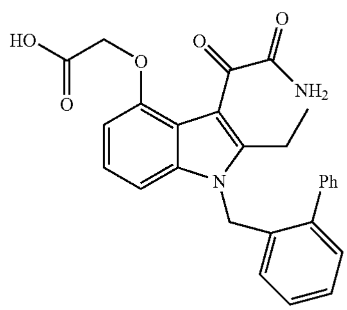 | 0.004 ± 0.001 | 0.062 | |
| 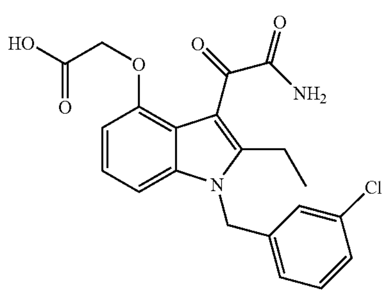 | 0.007 ± 0.002 | 0.39 | 0.003 |
| 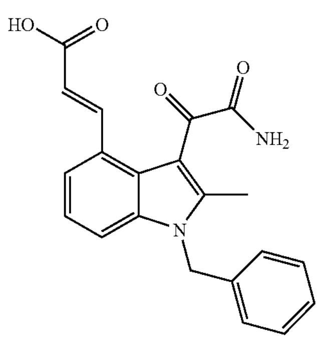 | 46 | >100 | |

TABLE 1-continued

Indole Compounds

| Structure | IC$_{50}$ (μM) hnp PLA$_2$ | IC$_{50}$ (μM) hps PLA$_2$ | IC$_{50}$ (μM) pps PLA$_2$ |
| --- | --- | --- | --- |
| (structure: 4-(2-carboxyethyl)-1-benzyl-2-methyl-3-(oxamoyl)indole) | 0.145 ± 0.006 | >100 | |
| (structure: 5-methoxy-1-benzyl-2-methylindole-3-acetic acid) | 13.6 ± 4.2 | | |
| (structure: 5-methoxy-1-benzyl-2-methylindole-3-acetamide) | 0.84 ± 0.17 | | |
| (structure: 5-methoxy-2-methylindole-3-acetamide) | | | |
| (structure: 5-(3-carboxypropoxy)-1-benzyl-2,7-dimethylindole-3-acetamide) | 0.075 ± 0.013 | | |

Other indole compounds can be employed within the scope of this invention. Table 2 lists some of such other indole compounds.

TABLE 2

Indole Compounds

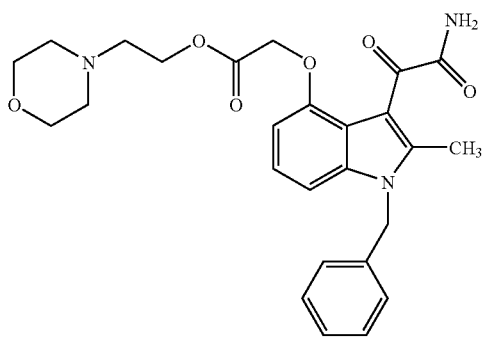

Indole glyoxamides

TABLE 2-continued

Indole Compounds

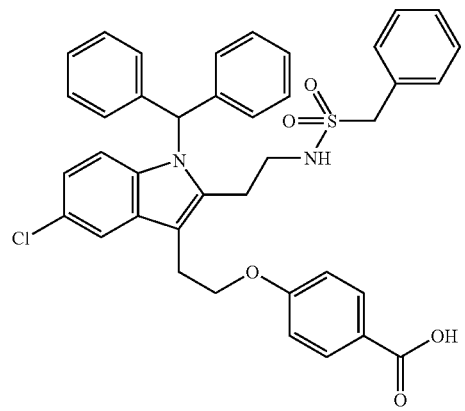

Indoly containing sulfonamides

Other compounds having fused five-membered rings and six-membered rings with at least one heteroatom (referred to herein generally as indole-related compounds) can also be used in connection with the present invention. Table 3 lists some of such other indole-related compounds, and as relevant, patent references.

TABLE 3

| Indole-Related Compounds | | |
|---|---|---|
| Scaffolds | Structures | Patent # |
| Indole acetamide/ glyoxamides | 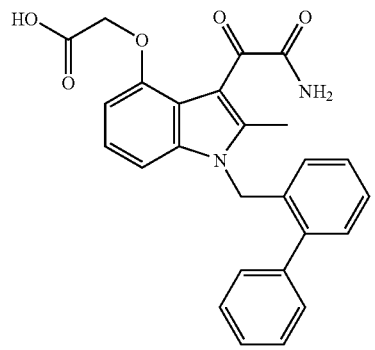<br>Methyl Indoxam | WO9921559 |
| Indole glyoxamides | 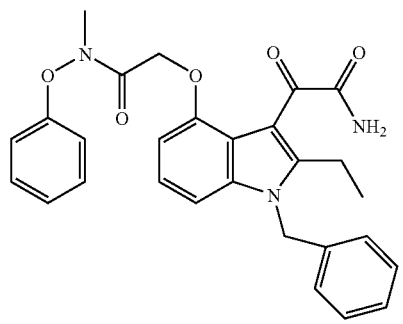 | WO0121587 |

TABLE 3-continued
Indole-Related Compounds
| Scaffolds | Structures | Patent # |
|---|---|---|
| Benzothiophene | 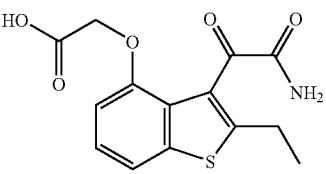 | |
| Indolizine | 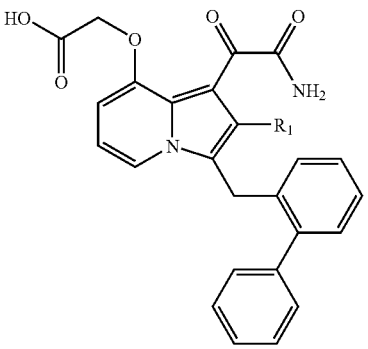 Methyl Indoxam | US 6645976 |
| Indene | 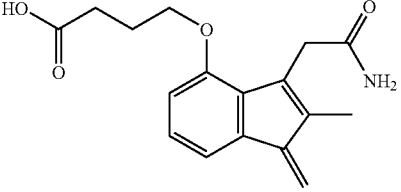 | US 6214876 |
| Substituted Tricyclic | 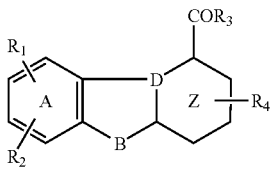<br>A: phenyl or pyridyl<br>B and D are independently N or C<br>Z is Cyclohexenyl, phenyl, pyridyl, etc, . . . | WO9818464 |
| Bicyclic Pyrrole-Pyrimidine | 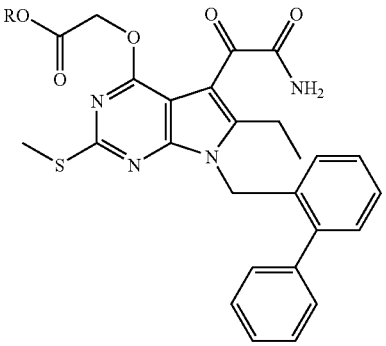 | |

TABLE 3-continued
Indole-Related Compounds
| Scaffolds | Structures | Patent # |
|---|---|---|
| Carbazole | 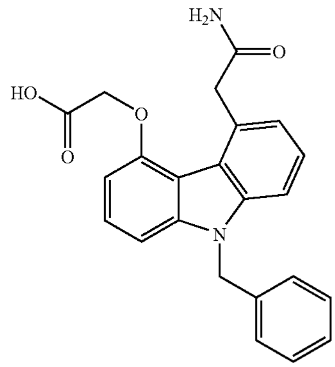 | WO03014082 |
| Cyclopenta-Indole | 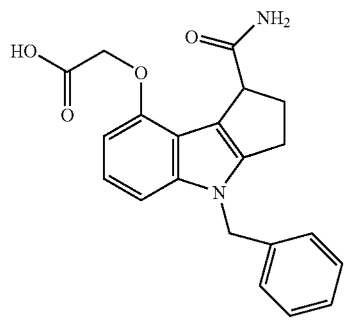 | |
| Cyclohepta-Indole | 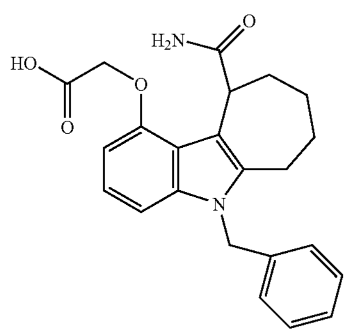 | WO03016277 |
Particularly preferred multivalent indole and indole related compounds of the invention can include, for example, compounds selected from
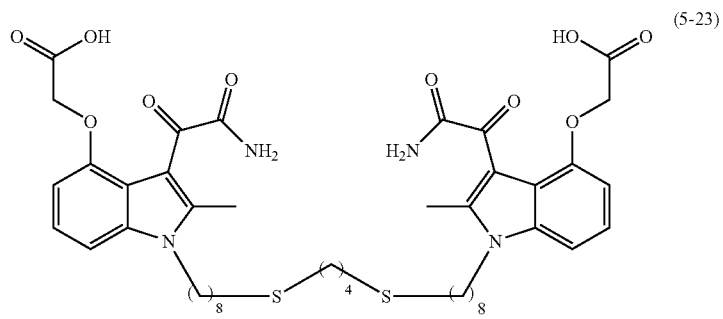
(5-23)

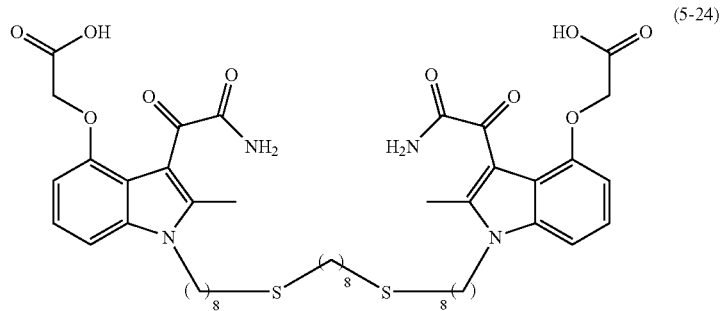
(5-24)
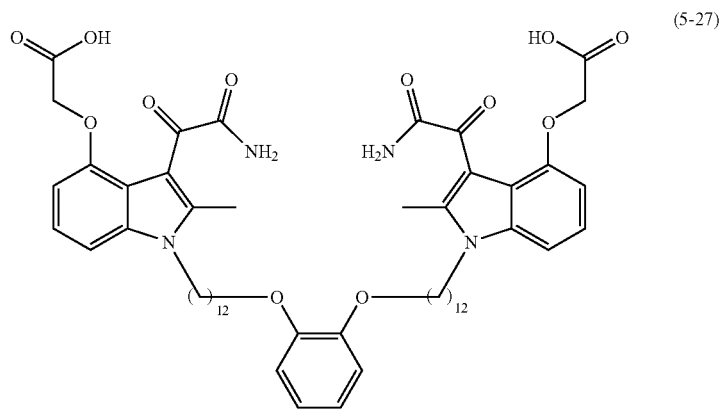
(5-27)
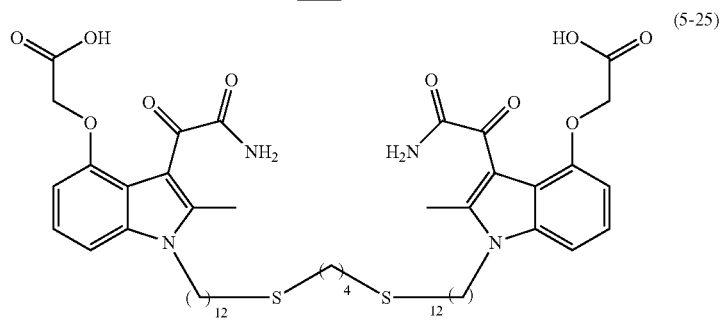
(5-25)
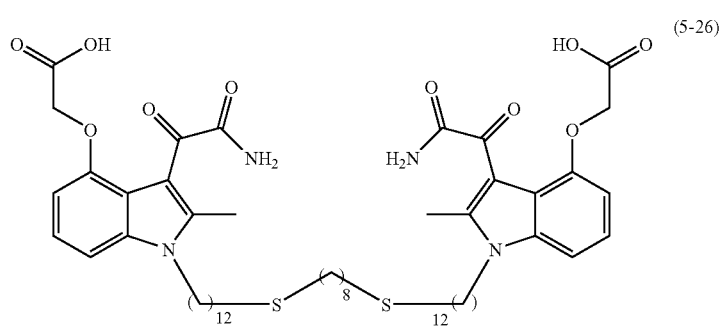
(5-26)
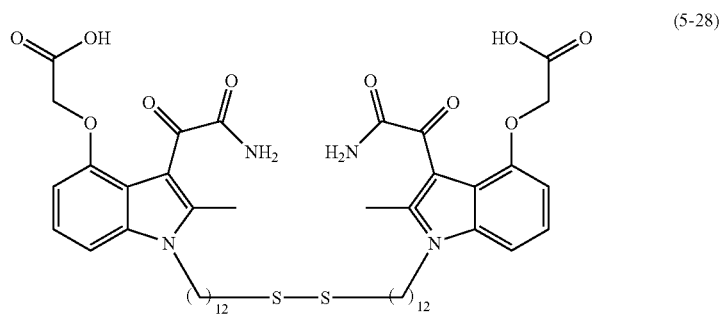
(5-28)

-continued
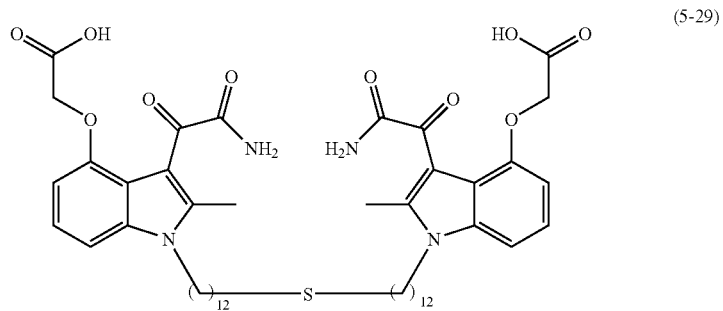
(5-29)
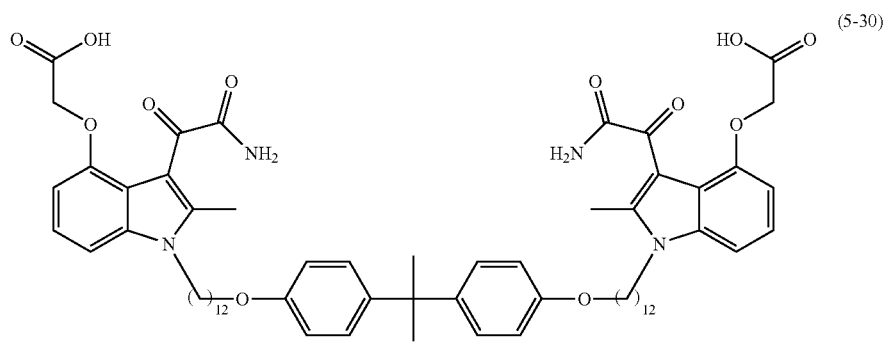
(5-30)
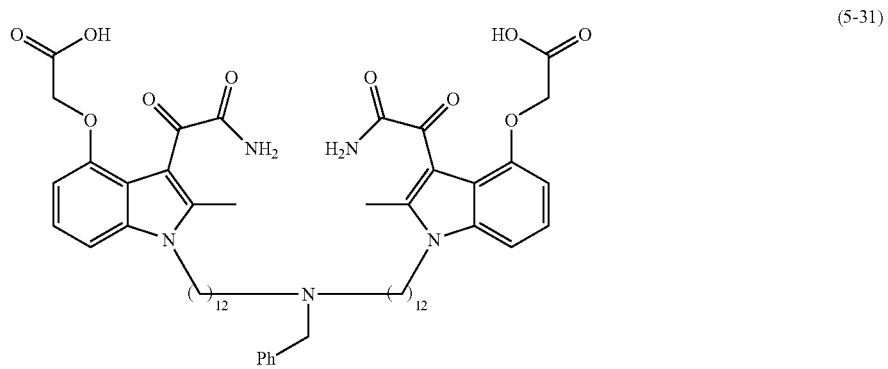
(5-31)
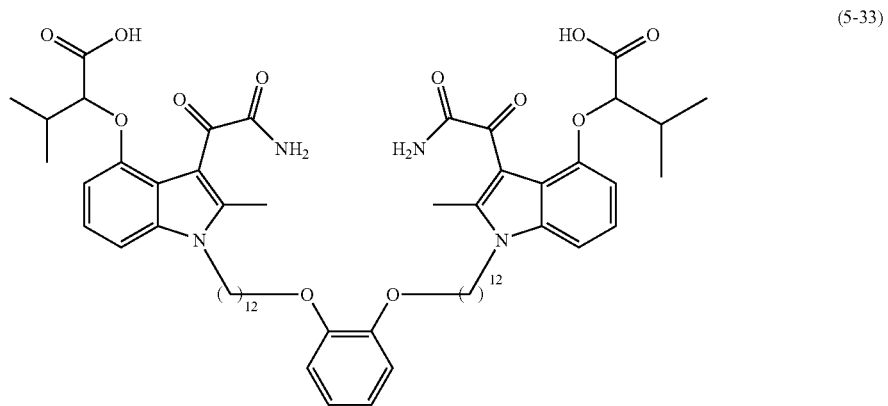
(5-33)

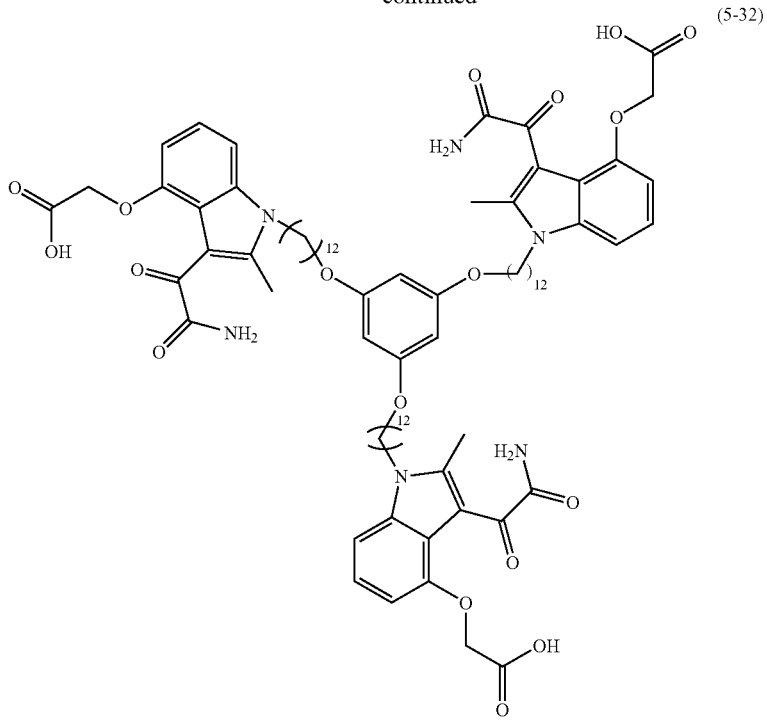

(5-32)

Figure 6A:
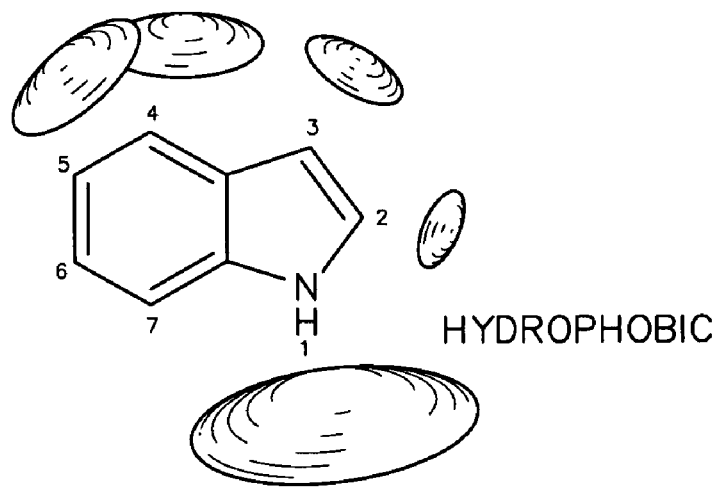
FIGS. 6A through 6D are schematic representations including chemical formulas illustrating indole compounds (FIG. 6A, FIG. 6C and FIG. 6D) and indole-related compounds (FIG. 6B).
Figure 6B:
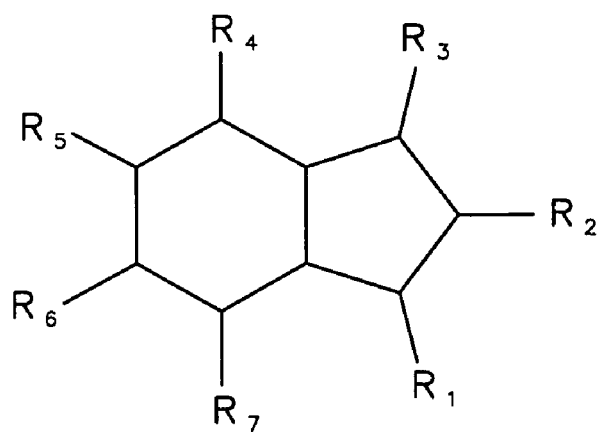
Figure 6C:
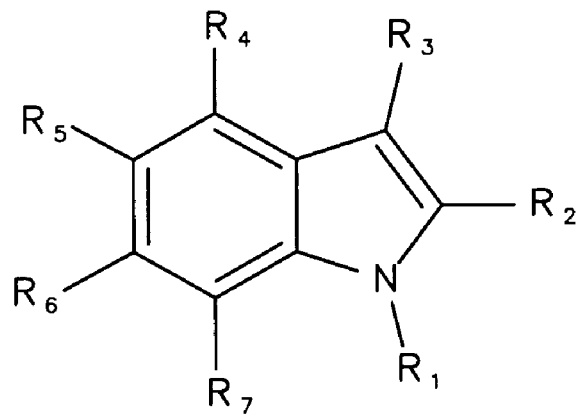
Figure 6D:
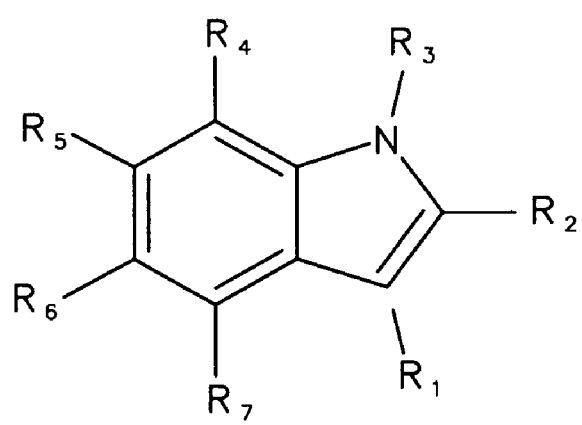

With reference to FIGS. 6C and 6D, indole-compounds of the invention can generally include "inverse indole compounds" that are mirror-image analogues of the core structure of the corresponding indole based on a reference axis taken orthogonal to and bisecting the fused bond between the five-membered and six-membered ring core, but that maintain the defined substituent groups at the same position. (See FIG. 6C compared to FIG. 6D). Indole compounds and indole-related compounds of the invention can also include "reciprocal indole compounds" and "reciprocal indole-related compounds" that are mirror-image analogues of the core structure of the corresponding indole based on a reference axis taken along the axis of the fused bond between the five-membered and six-membered ring core, but which maintain at least each of the —$R_3$ and —$R_4$ positions and each of the —$R_1$ and —$R_7$ at the same position, and that maintain —$R_2$ and at least one of —$R_5$ and —$R_6$ at the same position.

The salts of all of the above-described indole-related compounds and above-described indole compounds are an additional aspect of the invention. In those instances where the compounds of the invention possess acidic or basic functional groups various salts may be formed which are more water soluble and physiologically suitable than the parent compound.

Representative pharmaceutically acceptable salts, include but are not limited to, the alkali and alkaline earth salts such as lithium, sodium, potassium, calcium, magnesium, aluminum and the like. Salts are conveniently prepared from the free acid by treating the acid in solution with a base or by exposing the acid to an ion exchange resin. Included within the definition of pharmaceutically acceptable salts are the relatively non-toxic, inorganic and organic base addition salts of compounds of the present invention, for example, ammonium, quaternary ammonium, and amine cations, derived from nitrogenous bases of sufficient basicity to form salts with the compounds of this invention (see, for example, S. M. Berge, et al.,"Pharmaceutical Salts,"J. Phar. Sci., 66: 1-19 (1977)). Moreover, the basic group(s) of the compound of the invention may be reacted with suitable organic or inorganic acids to form salts such as acetate, benzenesulfonate, benzoate, bicarbonate, bisulfate, bitartrate, borate, bromide, camsylate, carbonate, chloride, clavulanate, citrate, chloride, edetate, edisylate, estolate, esylate, fluoride, fumarate, gluceptate, gluconate, glutamate, glycolylarsanilate, hexylresorcinate, bromide, chloride, hydroxynaphthoate, iodide, isothionate, lactate, lactobionate, laurate, malate, malseate, mandelate, mesylate, methylbromide, methylnitrate, methylsulfate, mucate, napsylate, nitrate, oleate, oxalate, palmitate, pantothenate, phosphate, polygalacturonate, salicylate, stearate, subacetate, succinate, tannate, tartrate, tosylate, trifluoroacetate, trifluoromethane sulfonate, and valerate.

Those of skill in the art will recognize that the compounds described herein may exhibit the phenomena of tautomerism, conformational isomerism, geometric isomerism and/or optical isomerism. It should be understood that the invention encompasses any tautomeric, conformational isomeric, optical isomeric and/or geometric isomeric forms of the compounds having one or more of the utilities described herein, as well as mixtures of these various different forms. Prodrugs and active metabolites of the compounds described herein are also within the scope of the present invention.

Phospholipase Inhibitors

The indole and indole-related compounds of the invention (or moieties derived therefrom) are useful as phospholipase inhibitors (or inhibiting moiety), and in particular as phospholipase-A2 inhibitor (or inhibiting moiety).

The indole and indole-related compounds of the invention (or moieties derived therefrom) can be effectively used in treating conditions such as weight-related conditions, insulin-related conditions, and cholesterol-related conditions, including in particular conditions such as obesity, diabetes mellitus, insulin resistance, glucose intolerance, hypercholesterolemia and hypertriglyceridemia.

As described below, the compounds of the invention can be used as a lumen-localized phospholipase-A2 inhibitor and/or as a lumen-localized pharmaceutical composition.

Certain indole glyoxamides are known in the art to be useful as $PLA_2$ inhibiting moieties; such known compounds can be used as control moieties in experiments evaluating compounds for phospholipase-A2 inhibiting activity. As shown in the various examples, the indole and indole-related compounds of the invention are active for phospholipase inhibition, and in preferred embodiments compare favorably to such a known indole compound. Specifically for example, [2-(3-(2-amino-2-oxoacetyl)-1-(biphenyl-2-ylmethyl)-2-methyl-1H-indol-4-yloxy)acetic acid], shown in FIG. 2, alternatively referred to herein as ILY-4001 and/or as methyl indoxam has been previously found to be an effective phospholipase inhibitor or inhibiting moiety. This indole compound is represented by the structure below, as formula (V):

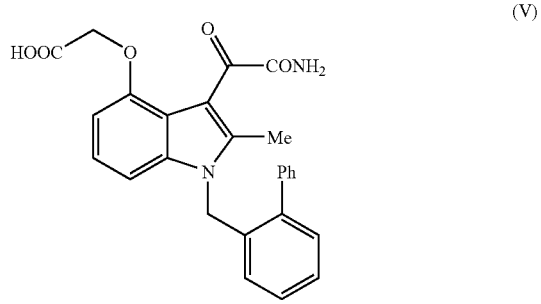

(V)

This compound has been shown, based on in-vitro assays, to have phospholipase activity for a number of PLA2 classes, and is a strong inhibitor of mouse and human PLA2IB enzymes in vitro (Singer, Ghomashchi et al. 2002; Smart, Pan et al. 2004). In previous work, this indole compound was synthesized (See, Example 4) and was evaluated in-vivo for phospholipase-A2 inhibition in a mice model. (See, Example 5, including Examples 5A through 5C, demonstrating effectiveness as a phospholipase-2A IB inhibitor, with phenotypic effects approaching and/or comparable to the effect of genetically deficient PLA2 (−/−) "knockout" mice). This indole compound was also characterized with respect to inhibition activity, absorption and bioavailability. (See, Example 6, including Examples 6A through 6C).

Generally, in embodiments included within the various aspects of the invention, phospholipase inhibitors of the present invention can modulate or inhibit (e.g., blunt or reduce) the catalytic activity of phospholipases, preferably phospholipases secreted or contained in the gastrointestinal tract, including the gastric compartment, and more particularly the duodenum and/or the small intestine. For example, such enzymes preferably include, but are not limited to, secreted Group IB phospholipase $A_2$ ($PLA_2$-IB), also referred to as pancreatic phospholipase $A_2$ (p-$PLA_2$) and herein referred to as "$PLA_2$ IB" or "phospholipase-$A_2$ IB. Such enzymes can also include other phospholipase A2's secreted, such as Group IIA phospholipase $A_2$ ($PLA_2$ IIA). In some embodiments, particularly in connection with preferred indole compounds of the invention and preferred indole-related compounds of the invention, other phospholipases can also be considered within the scope of invention, including for example: phospholipase A1 ($PLA_1$); phospholipase B (PLB); phospholipase C (PLC); and phospholipase D (PLD). The inhibitors of the invention preferably inhibit the activity at least the phospholipase-$A_2$ IB enzyme.

In some embodiments, the inhibitors of the present invention are specific, or substantially specific for inhibiting phospholipase activity, such as phospholipase $A_2$ activity (including for example phospholipase-$A_2$ IB). For example, in some preferred embodiments inhibitors of the present invention do not inhibit or do not significantly inhibit or essentially do not inhibit lipases, such as pancreatic triglyceride lipase (PTL) and carboxyl ester lipase (CEL). In some preferred embodiments, inhibitors of the present invention inhibit $PLA_2$, and preferably phospholipase-$A_2$ IB, but in each case do not inhibit or do not significantly inhibit or essentially do not inhibit any other phospholipases; in some preferred embodiments, inhibitors of the present invention inhibit $PLA_2$, and preferably phospholipase-$A_2$ IB, but in each case do not inhibit or do not significantly inhibit or essentially do not inhibit $PLA_1$; in some preferred embodiments, inhibitors of the present invention inhibit $PLA_2$, and preferably phospholipase-$A_2$ IB, but do not inhibit or do not significantly inhibit or essentially do not inhibit PLB. In some embodiments, the phospholipase inhibitor does not act on the gastrointestinal mucosa, for example, it does not inhibit or does not significantly inhibit or essentially does not inhibit membrane-bound phospholipases.

The different activities of $PLA_2$, $PLA_1$, and PLB are generally well-characterized and understood in the art. $PLA_2$ hydrolyzes phospholipids at the sn-2 position liberating 1-acyl lysophospholipids and fatty acids; $PLA_1$ acts on phospholipids at the sn-1 position to release 2-acyl lysophospholipids and fatty acids; and phospholipase B cleaves phospholipids at both sn-1 and sn-2 positions to form a glycerol and two fatty acids. See, e.g., Devlin, Editor, Textbook of Biochemistry with Clinical Correlations, $5^{th}$ ed. Pp 1104-1110 (2002).

Phospholipids substrates acted upon by gastrointestinal $PLA_1$, $PLA_2$ (including phospholipase-$A_2$ IB) and PLB are mostly of the phosphatidylcholine and phosphatidylethanolamine types, and can be of dietary or biliary origin, or may be derived from being sloughed off of cell membranes. For example, in the case of phosphatidylcholine digestion, $PLA_1$ acts at the sn-1 position to produce 2-acyl lysophosphatidylcholine and free fatty acid; $PLA_2$ acts at the sn-2 position to produce 1-acyl lysophosphatidylcholine and free fatty acid; while PLB acts at both positions to produce glycerol 3-phosphorylcholine and two free fatty acids (Devlin, 2002).

Pancreatic $PLA_2$ (and phospholipase-$A_2$ IB) is secreted by acinar cells of the exocrine pancreas for release in the duodenum via pancreatic juice. $PLA_2$ (and phospholipase-$A_2$ IB) is secreted as a proenzyme, carrying a polypeptide chain that is subsequently cleaved by proteases to activate the enzyme's catalytic site. Documented structure-activity-relationships (SAR) for $PLA_2$ isozymes illustrate a number of common features (see for instance, Gelb M., *Chemical Reviews*, 2001, 101:2613-2653; Homan, R., *Advances in Pharmacology*, 1995, 12:31-66; and Jain, M. K., *Intestinal Lipid Metabolism*, Biology, pathology, and interfacial enzymology of pancreatic phospholipase $A_2$, 2001, 81-104, each incorporated herein by reference).

The inhibitors of the present invention can take advantage of certain of these common features to inhibit phospholipase activity and especially $PLA_2$ activity. Common features of $PLA_2$ enzymes include sizes of about 13 to about 15 kDa; stability to heat; and 6 to 8 disulfides bridges. Common features of $PLA_2$ enzymes also include conserved active site architecture and calcium-dependent activities, as well as a catalytic mechanism involving concerted binding of His and Asp residues to water molecules and a calcium cation, in a His-calcium-Asp triad. A phospholipid substrate can access the catalytic site by its polar head group through a slot enveloped by hydrophobic and cationic residues (including lysine and arginine residues) described in more detail below. Within the catalytic site, the multi-coordinated calcium ion activates the acyl carbonyl group of the sn-2 position of the phospholipid substrate to bring about hydrolysis (Devlin, 2002). In some preferred embodiments, inhibitors of the present invention inhibit this catalytic activity of $PLA_2$ by interacting with its catalytic site.

PLA2 enzymes are active for catabolizing phospholipids substrates primarily at the lipid-water interface of lipid aggregates found in the gastrointestinal lumen, including, for example, fat globules, emulsion droplets, vesicles, mixed micelles, and/or disks, any one of which may contain triglycerides, fatty acids, bile acids, phospholipids, phosphatidylcholine, lysophospholipids, lysophosphatidylcholine, cholesterol, cholesterol esters, other amphiphiles and/or other diet metabolites. Such enzymes can be considered to act while "docked" to a lipid-water interface. In such lipid aggregates, the phospholipid substrates are typically arranged in a mono layer or in a bilayer, together with one or more other components listed above, which form part of the outer surface of the aggregate. The surface of a phospholipase bearing the catalytic site contacts this interface facilitating access to phospholipid substrates. This surface of the phospholipase is known as the i-face, i.e., the interfacial recognition face of the enzyme. The structural features of the i-face of $PLA_2$ have been well documented. See, e.g., Jain, M. K, et al, *Methods in Enzymology*, vol. 239, 1995, 568-614, incorporated herein by reference. The inhibitors of the present invention can take advantage of these structural features to inhibit $PLA_2$ activity. For instance, it is known that the aperture of the slot forming the catalytic site is normal to the i-face plane. The aperture is surrounded by a first crown of hydrophobic residues (mainly leucine and isoleucine residues), which itself is contained in a ring of cationic residues (including lysine and arginine residues).

As noted, $PLA_2$ enzymes share a conserved active site architecture and a catalytic mechanism involving concerted binding of His and Asp residues to water molecules and a calcium cation. Without being bound by theory, a phospholipid substrate can access the catalytic site of such enzymes with its polar head group directed through a slot enveloped by hydrophobic and cationic residues. Within the catalytic site, the multi-coordinated calcium ion activates the acyl carbonyl group of the sn-2 position of the phospholipid substrate to bring about hydrolysis.

In view of the substantial structure-activity-relationship studies for phospholipase-A2 enzymes, considered together with the significant experimental data demonstrated in the various examples, a skilled person can appreciate the observed inhibitive effect of the compounds of the invention.

Similarly, the skilled person can appreciate with reference to FIGS. 6C and 6D, that the above-described inverse indole compounds that are mirror-image analogues of the core structure of the corresponding indole of interest, and the above-described reciprocal indole compounds and reciprocal indole-related compounds that are alternative mirror-image analogues of the core structure of the corresponding indole or related compound can be similarly configured with polar substituents and hydrophobic substituents to provide alternative indole structures and alternative indole-related structures within the scope of the invention.

Moreover, a person skilled in the art can evaluate particular inhibitors within the scope of this invention using known assaying and evaluation approaches. For example, the extent of inhibition of the inhibitors of the invention can be evaluated using in-vitro assays and/or in-vivo studies as shown in the various examples. Binding of a phospholipase inhibitor to a phospholipase enzyme can be evaluated by nuclear magnetic resonance, for example to provide identification of sites essential or non-essential for such binding interaction. Additionally, one of skill in the art can use available structure-activity relationship (SAR) for phospholipase inhibitors that suggest positions where structural variations are allowed. A library of candidate phospholipase inhibitors can be designed to feature different points of attachment of the phospholipase inhibiting moiety, e.g., chosen based on information described above as well as randomly, so as to present the phospholipase inhibiting moiety in multiple distinct orientations. Candidates can be evaluated for phospholipase inhibiting activity to obtain phospholipase inhibitors with suitable attachment points of the phospholipase inhibiting moiety to the polymer moiety or other non-absorbed moiety.

Generally, the extent of inhibition is not narrowly critical to the invention, but can be of significance in particular embodiments. Hence, the term "inhibits" and its grammatical variations are not intended to require a complete inhibition of enzymatic activity. For example, it can refer to a reduction in enzymatic activity by at least about 30%, preferably at least about 50%, at least about 75%, preferably by at least about 90%, more preferably at least about 98%, and even more preferably at least about 99% of the activity of the enzyme in the absence of the inhibitor. Most preferably, it refers to a reduction in enzyme activity by an effective amount that is by an amount sufficient to produce a therapeutic and/or a prophylactic benefit in at least one condition being treated in a subject receiving phospholipase inhibiting treatment, e.g., as disclosed herein. Conversely, the phrase "does not inhibit" or "essentially does not inhibit" and its grammatical variations does not require a complete lack of effect on the enzymatic activity. For example, it refers to situations where there is less than about 10%, less than about 5%, preferably less than about 2%, and more preferably less than about 1% of reduction in enzyme activity in the presence of the inhibitor. Most preferably, it refers to a minimal reduction in enzyme activity such that a noticeable effect is not observed.

The inhibitors can modulate phospholipase activity by reversible and/or irreversible inhibition. Reversible inhibition by a phospholipase inhibitor of the present invention may be competitive (e.g. where the inhibitor binds to the catalytic site of a phospholipase), noncompetitive (e.g., where the inhibitor binds to an allosteric site of a phospholipase to effect an allosteric change), and/or uncompetitive (where the inhibitor binds to a complex between a phospholipase and its substrate). Inhibition may also be irreversible, where the phospholipase inhibitor remains bound, or significantly remains bound, or essentially remains bound to a site on a phospholipase without dissociating, without significantly dissociating, or essentially without dissociating from the enzyme.

Methods of Treating Phospholipase-Related Conditions

The present invention provides methods of treating phospholipase-related conditions. In preferred embodiments, the inhibitor can be localized in a gastrointestinal lumen. The term "phospholipase-related condition" as used herein refers to a condition in which modulating the activity and/or re-absorption of a phospholipase, and/or modulating the production and/or effects of one or more products of the phospholipase, is desirable. In preferred embodiments, an inhibitor of the present invention reduces the activity and/or re-absorption of a phospholipase, and/or reduces the production and/or effects of one or more products of the phospholipase. The term "phospholipase A2-related condition" as used herein refers to a condition in which modulating the activity and/or re-absorption of phospholipase A2 is desirable and/or modulating the production and/or effects of one or more products of phospholipase A2 activity is desirable. In preferred embodiments, an inhibitor of the present invention reduces the activity and/or re-absorption of phospholipase A2, and/or reduces the production and/or effects of one or more products of the phospholipase A2. Examples of phospholipase A2-related conditions include, but are not limited to, insulin-related conditions (e.g., diabetes), weight-related conditions (e.g., obesity) and/or cholesterol-related conditions, and any combination thereof.

The present invention provides methods, pharmaceutical compositions, and kits for the treatment of animal subjects. The term "animal subject" as used herein includes humans as well as other mammals. For example, the mammals can be selected from mice, rats, rabbits, guinea pigs, hamsters, cats, dogs, porcine, poultry, bovine and horses, as well as combinations thereof.

The term "treating" as used herein includes achieving a therapeutic benefit and/or a prophylactic benefit. By therapeutic benefit is meant eradication or amelioration of the underlying disorder being treated. For example, in a diabetic patient, therapeutic benefit includes eradication or amelioration of the underlying diabetes. Also, a therapeutic benefit is achieved with the eradication or amelioration of one or more of the physiological symptoms associated with the underlying disorder such that an improvement is observed in the patient, notwithstanding the fact that the patient may still be afflicted with the underlying disorder. For example, with respect to diabetes reducing $PLA_2$ activity can provide therapeutic benefit not only when insulin resistance is corrected, but also when an improvement is observed in the patient with respect to other disorders that accompany diabetes like fatigue, blurred vision, or tingling sensations in the hands or feet. For prophylactic benefit, a phospholipase inhibitor of the present invention may be administered to a patient at risk of developing a phospholipase-related condition, e.g., diabetes, obesity, or hypercholesterolemia, or to a patient reporting one or more of the physiological symptoms of such conditions, even though a diagnosis may not have been made.

The present invention provides compositions comprising a phospholipase inhibitor. In some embodiments, the inhibitor is not absorbed through a gastrointestinal mucosa and/or that is localized in a gastrointestinal lumen as a result of efflux from a gastrointestinal mucosal cell.

In preferred embodiments, the phospholipase inhibitors of the present invention produce a benefit, including either a prophylactic benefit, a therapeutic benefit, or both, in treating one or more conditions by inhibiting phospholipase activity.

The methods for effectively inhibiting phospholipase described herein can apply to any phospholipase-related condition, that is, to any condition in which modulating the activity and/or re-absorption of a phospholipase, and/or modulating the production and/or effects of one or more products of the phospholipase, is desirable. Preferably, such conditions include phospholipase-$A_2$-related conditions and/or phospholipase A2-related conditions induced by diet, that is, conditions which are brought on, accelerated, exacerbated, or otherwise influenced by diet. Phospholipase-$A_2$-related conditions include, but are not limited to, diabetes, weight gain, and cholesterol-related conditions, as well as hyperlipidemia, hypercholesterolemia, cardiovascular disease (such as heart disease and stroke), hypertension, cancer, sleep apnea, osteoarthritis, gallbladder disease, fatty liver disease, diabetes type 2 and other insulin-related conditions. In some embodiments, one or more of these conditions may be produced as a result of consumption of a high fat or Western diet; in some embodiments, one or more of these conditions may be produced as a result of genetic causes, metabolic disorders, environmental factors, behavioral factors, or any combination of these.

Western Diets and Western-Related Diets

Generally, some embodiments of the invention relate to one or more of a high-carbohydrate diet, a high-saccharide diet, a high-fat diet and/or a high-cholesterol diet, in various combinations. Such diets are generally referred to herein as a "high-risk diets" (and can include, for example, Western diets). Such diets can heighten the risk profile of a subject patient for one or more conditions, including an obesity-related condition, an insulin-related condition and/or a cholesterol-related condition. In particular, such high-risk diets can, in some embodiments, include at least a high-carbohydrate diet together with one or more of a high-saccharide diet, a high-fat diet and/or a high-cholesterol diet. A high-risk diet can also include a high-saccharide diet in combination with one or both of a high-fat diet and/or a high-cholesterol diet. A high-risk diet can also comprise a high-fat diet in combination with a high-cholesterol diet. In some embodiments, a high-risk diet can include the combination of a high-carbohydrate diet, a high-saccharide diet and a high-fat diet. In other embodiments, a high-risk diet can include a high-carbohydrate diet, a high-saccharide diet, and a high-cholesterol diet. In other embodiments, a high-risk diet can include a high-carbohydrate diet, a high-fat diet and a high-cholesterol diet. In yet further embodiments, a high-risk diet can include a high-saccharide diet, a high-fat diet and a high-cholesterol diet. In some embodiments, a high-risk diet can include a high-carbohydrate diet, a high-saccharide diet, a high-fat diet and a high-cholesterol diet.

Generally, the diet of a subject can comprise a total caloric content, for example, a total daily caloric content. In some embodiments, the subject diet can be a high-fat diet. In such embodiments, at least about 50% of the total caloric content can come from fat. In other such embodiments, at least about 40%, or at least about 30% or at least about 25%, or at least about 20% of the total caloric content can come from fat. In some embodiments, in which a high-fat diet is combined with one or more of a high-carbohydrate diet, a high-saccharide diet or a high-cholesterol diet, at least about 15% or at least about 10% of the total caloric content can come from fat.

Similarly, in some embodiments, the diet can be a high-carbohydrate diet. In such embodiments, at least about 50% of the total caloric content can come from carbohydrates. In other such embodiments, at least about 40%, or at least about 30% or at least about 25%, or at least about 20% of the total caloric content can come from carbohydrates. In some embodiments, in which a high-carbohydrate diet is combined with one or more of a high-fat diet, a high-saccharide diet or a high-cholesterol diet, at least about 15% or at least about 10% of the total caloric content can come from carbohydrate.

Further, in some embodiments, the diet can be a high-saccharide diet. In embodiments, at least about 50% of the total caloric content can come from saccharides. In other such embodiments, at least about 40%, or at least about 30% or at least about 25%, or at least about 20% of the total caloric content can come from saccharides. In some embodiments, in which a high-saccharide diet is combined with one or more of a high-fat diet, a high-carbohydrate diet or a high-cholesterol diet, at least about 15% or at least about 10% of the total caloric content can come from saccharides.

Similarly, in some embodiments, the diet can be a high-cholesterol diet. In such embodiments, the diet can comprise at least about 1% cholesterol (wt/wt, relative to fat). In other such embodiments, the diet can comprise at least about 0.5% or at least about 0.3% or at least about 0.1%, or at least about 0.07% cholesterol (wt/wt relative to fat). In some embodiments, in which a high-cholesterol diet is combined with one or more of a high-fat diet, a high-carbohydrate diet or a high-saccharide diet, the diet can comprise at least about 0.05% or at least about 0.03% cholesterol (wt/wt, relative to fat).

As an example, a high fat diet can include, for example, diets high in meat, dairy products, and alcohol, as well as possibly including processed food stuffs, red meats, soda, sweets, refined grains, deserts, and high-fat dairy products, for example, where at least about 25% of calories come from fat and at least about 8% come from saturated fat; or at least about 30% of calories come from fat and at least about 10% come from saturated fat; or where at least about 34% of calories came from fat and at least about 12% come from saturated fat; or where at least about 42% of calories come from fat and at least about 15% come from saturated fat; or where at least about 50% of calories come from fat and at least about 20% come from saturated fat. One such high fat diet is a "Western diet" which refers to the diet of industrialized countries, including, for example, a typical American diet, Western European diet, Australian diet, and/or Japanese diet. One particular example of a Western diet comprises at least about 17% fat and at least about 0.1% cholesterol (wt/wt); at least about 21% fat and at least about 0.15% cholesterol (wt/wt); or at least about 25% and at least about 0.2% cholesterol (wt/wt).

Such high-risk diets may include one or more high-risk foodstuffs.

Considered in the context of a foodstuff, generally, some embodiments of the invention relate to one or more of a high-carbohydrate foodstuff, a high-saccharide foodstuff, a high-fat foodstuff and/or a high-cholesterol foodstuff, in various combinations. Such foodstuffs are generally referred to herein as a "high-risk foodstuffs" (including for example Western foodstuffs). Such foodstuffs can heighten the risk profile of a subject patient for one or more conditions, including an obesity-related condition, an insulin-related condition and/or a cholesterol-related condition. In particular, such high-risk foodstuffs can, in some embodiments, include at least a high-carbohydrate foodstuff together with one or more of a high-saccharide foodstuff, a high-fat foodstuff and/or a high-cholesterol foodstuff. A high-risk foodstuff can also include a high-saccharide foodstuff in combination with one or both of a high-fat foodstuff and/or a high-cholesterol foodstuff. A high-risk foodstuff can also comprise a high-fat foodstuff in combination with a high-cholesterol foodstuff. In some embodiments, a high-risk foodstuff can include the combination of a high-carbohydrate foodstuff, a high-saccharide foodstuff and a high-fat foodstuff. In other embodiments, a high-risk foodstuff can include a high-carbohydrate foodstuff, a high-saccharide foodstuff, and a high-cholesterol foodstuff. In other embodiments, a high-risk foodstuff can include a high-carbohydrate foodstuff, a high-fat foodstuff and a high-cholesterol foodstuff. In yet further embodiments, a high-risk foodstuff can include a high-saccharide foodstuff, a high-fat foodstuff and a high-cholesterol foodstuff. In some embodiments, a high-risk foodstuff can include a high-carbohydrate foodstuff, a high-saccharide foodstuff, a high-fat foodstuff and a high-cholesterol foodstuff.

Hence, the food product composition can comprise a foodstuff having a total caloric content. In some embodiments, the food-stuff can be a high-fat foodstuff. In such embodiments, at least about 50% of the total caloric content can come from fat. In other such embodiments, at least about 40%, or at least about 30% or at least about 25%, or at least about 20% of the total caloric content can come from fat. In some embodiments, in which a high-fat foodstuff is combined with one or more of a high-carbohydrate foodstuff, a high-saccharide foodstuff or a high-cholesterol foodstuff, at least about 15% or at least about 10% of the total caloric content can come from fat.

Similarly, in some embodiments, the food-stuff can be a high-carbohydrate foodstuff. In such embodiments, at least about 50% of the total caloric content can come from carbohydrates. In other such embodiments, at least about 40%, or at least about 30% or at least about 25%, or at least about 20% of the total caloric content can come from carbohydrates. In some embodiments, in which a high-carbohydrate foodstuff is combined with one or more of a high-fat foodstuff, a high-saccharide foodstuff or a high-cholesterol foodstuff, at least about 15% or at least about 10% of the total caloric content can come from carbohydrate.

Further, in some embodiments, the food-stuff can be a high-saccharide foodstuff. In such embodiments, at least about 50% of the total caloric content can come from saccharides. In other such embodiments, at least about 40%, or at least about 30% or at least about 25%, or at least about 20% of the total caloric content can come from saccharides. In some embodiments, in which a high-saccharide foodstuff is combined with one or more of a high-fat foodstuff, a high-carbohydrate foodstuff or a high-cholesterol foodstuff, at least about 15% or at least about 10% of the total caloric content can come from saccharides.

Similarly, in some embodiments, the food-stuff can be a high-cholesterol foodstuff. In such embodiments, the food-stuff can comprise at least about 1% cholesterol (wt/wt, relative to fat). In other such embodiments, the foodstuff can comprise at least about 0.5%, or at least about 0.3% or at least about 0.1%, or at least about 0.07% cholesterol (wt/wt relative to fat). In some embodiments, in which a high-cholesterol foodstuff is combined with one or more of a high-fat foodstuff, a high-carbohydrate foodstuff or a high-saccharide foodstuff, the foodstuff can comprise at least about 0.05% or at least about 0.03% cholesterol (wt/wt, relative to fat).

As noted above, the methods of the invention can be used advantageously together with other methods, including for example methods broadly directed to treating insulin-related conditions, weight-related conditions and/or cholesterol-related conditions (including dislipidemia generally) and any combination thereof. Aspects of such conditions are described below.

Treatment of Insulin-Related Conditions

The term "insulin-related disorders" as used herein refers to a condition such as diabetes where the body does not produce and/or does not properly use insulin. Typically, a patient is diagnosed with pre-diabetes or diabetes by using a Fasting Plasma Glucose Test (FPG) and/or an Oral Glucose Tolerance Test (OGTT). In the case of the FPG test, a fasting blood glucose level between about 100 and about 125 mg/dl can indicate pre-diabetes; while a person with a fasting blood glucose level of about 126 mg/dl or higher can indicate diabetes. In the case of the OGTT test, a patient's blood glucose level can be measured after a fast and two hours after drinking a glucose-rich beverage. A two-hour blood glucose level between about 140 and about 199 mg/dl can indicate pre-diabetes; while a two-hour blood glucose level at about 200 mg/dl or higher can indicate diabetes.

In certain embodiments, a lumen localized phospholipase inhibitor of the present invention produces a benefit in treating an insulin-related condition, for example, diabetes, preferably diabetes type 2. For example, such benefits may include, but are not limited to, increasing insulin sensitivity and improving glucose tolerance. Other benefits may include decreasing fasting blood insulin levels, increasing tissue glucose levels and/or increasing insulin-stimulated glucose metabolism.

Without being limited to any particular hypothesis, these benefits may result from a number of effects brought about by reduced $PLA_2$ activity, including, for example, reduced membrane transport of phospholipids across the gastrointestinal mucosa and/or reduced production of 1-acyl lysophospholipids, such as 1-acyl lysophosphatydylcholine and/or reduced transport of lysophospholipids, 1-acyl lysophosphatydylcholine, that may act as a signaling molecule in subsequent pathways involved in diabetes or other insulin-related conditions.

In some embodiments, a lumen-localized phospholipase inhibitor is used that inhibits phospholipase A2 but does not inhibit or does not significantly inhibit or essentially does not inhibit phospholipase B. In some embodiments, the phospholipase inhibitor inhibits phospholipase A2 but no other gastrointestinal phospholipase, including not inhibiting or not significantly inhibiting or essentially not inhibiting phospholipase A1, and not inhibiting or not significantly inhibiting or essentially not inhibiting phospholipase.

Treatment of Weight-Related Conditions

The term "weight-related conditions" as used herein refers to unwanted weight gain, including overweight, obese and/or hyperlipidemic conditions, and in particular weight gain caused by a high fat or Western diet. Typically, body mass index (BMI) is used as the criteria in determining whether an individual is overweight and/or obese. An adult is considered overweight if, for example, he or she has a body mass index of at least about 25, and is considered obese with a BMI of at least about 30. For children, charts of Body-Mass-Index for Age are used, where a BMI greater than about the 85th percentile is considered "at risk of overweight" and a BMI greater than about the 95th percentile is considered "obese."

In certain embodiments, a lumen localized phospholipase A2 inhibitor of the present invention can be used to treat weight-related conditions, including unwanted weight gain and/or obesity. In certain embodiments, a lumen localized phospholipase A2 inhibitor decreases fat absorption after a meal typical of a Western diet. In certain embodiments, a lumen localized phospholipase A2 inhibitor increases lipid excretion from a subject on a Western diet. In certain preferred embodiments, the phospholipase inhibitor reduces weight gain in a subject on a (typical) Western diet. In certain embodiments, practice of the present invention can preferentially reduce weight gain in certain tissues and organs, e.g., in some embodiments, a phospholipase A2 inhibitor can decrease weight gain in white fat of a subject on a Western diet.

Without being limited to any particular hypothesis, these benefits may result from a number of effects brought about by reduced $PLA_2$ activity. For example, inhibition of $PLA_2$ activity may reduce transport of phospholipids through the gastrointestinal lumen, for example, through the small intestine apical membrane, causing a depletion of the pool of phospholipids (e.g. phosphatidylcholine) in enterocytes, particularly in mammals fed with a high fat diet. In such cases, the de novo synthesis of phospholipids may not be sufficient to sustain the high turnover of phospholipids, e.g. phosphatidylcholine, needed to carry triglycerides, for example by transport in chylomicrons (See Tso, in Fat Absorption, 1986, chapt. 6 177-195, Kuksis A., Ed.), incorporated herein by reference.

$PLA_2$ inhibition can also reduce production of 1-acyl lysophospholipids, such as 1-acyl lysophosphatydylcholine, that may act as a signaling molecule in subsequent up-regulation pathways of fat absorption, including, for example the release of additional digestive enzymes or hormones, e.g., secretin. See, Huggins, Protection against diet-induced obesity and obesity-related insulin resistance in Group 1B-$PLA_2$-deficient mice, Am. J. Physiol. Endocrinol. Metab. 283:E994-E1001 (2002), incorporated herein by reference.

Another aspect of the present invention provides composition, kits and methods for reducing or delaying the onset of diet-induced diabetes through weight gain. An unchecked high fat diet can produce not only weight gain, but also can contribute to diabetic insulin resistance. This resistance may be recognized by decreased insulin and leptin levels in a subject. The phospholipase inhibitors, compositions, kits and methods disclosed herein can be used in the prophylactic treatment of diet-induced diabetes, or other insulin-related conditions, e.g. in decreasing insulin and/or leptin levels in a subject on a Western diet.

In some embodiments, a lumen-localized phospholipase inhibitor is used that inhibits phospholipase A2 but does not inhibitor or does not significantly inhibit or essentially does not inhibit phospholipase B. In some embodiments, the phospholipase inhibitor inhibits phospholipase A2 but no other gastrointestinal phospholipase, including not inhibiting or not significantly inhibiting or essentially not inhibiting phospholipase A1, and not inhibiting or not significantly inhibiting or essentially not inhibiting phospholipase B.

Treatment of Cholesterol-Related Conditions

The term "cholesterol-related conditions" as used herein refers generally to a condition in which modulating the activity of HMG-CoA reductase is desirable and/or modulating the production and/or effects of one or more products of HMG-COA reductase is desirable, and can in any case, include dislipidemia generally. In preferred embodiments, a phospholipase inhibitor of the present invention reduces the activity of HMG-CoA reductase and/or reduces the production and/or effects of one or more products of HMG-CoA reductase. For example, a cholesterol-related condition may involve elevated levels of cholesterol, in particular, non-HDL cholesterol in plasma (e.g., elevated levels of LDL cholesterol and/or VLD/LDL levels). Typically, a patient is considered to have high or elevated cholesterol levels based on a number of criteria, for example, see Pearlman B L, The New Cholesterol Guidelines, Postgrad Med, 2002; 112(2):13-26, incorporated herein by reference. Guidelines include serum lipid profiles, such as LDL compared with HDL levels.

Examples of cholesterol-related conditions include hypercholesterolemia, lipid disorders such as hyperlipidemia, and atherogenesis and its sequelae of cardiovascular diseases, including atherosclerosis, other vascular inflammatory conditions, myocardial infarction, ischemic stroke, occlusive stroke, and peripheral vascular diseases, as well as other conditions in which decreasing cholesterol can produce a benefit.

Other cholesterol-related conditions of particular interest include dislipidemia conditions, such as hypertriglyceridemia. Hepatic triglyceride synthesis is regulated by available fatty acids, glycogen stores, and the insulin versus glucagon ratio. Patients with a high glucose diet (including, for example, patients on a high-carbohydrate or a high-saccharide diet, and/or patients in a population known to typically consume such diets) are likely to have a balance of hormones that maintains an excess of insulin and also build up glycogen stores, both of which enhance hepatic triglyceride synthesis. In addition, diabetic patients are particularly susceptible, since they are often overweight and are in a state of caloric excess. Hence, the present invention is particularly of interest, in each embodiment herein described, with respect to treatments directed to hypertriglyceridemia.

Without being bound by theory not specifically recited in the claims, the phospholipase A2 inhibitors of the present invention can modulate tryglycerides and cholesterol through more than one mechanistic path. For example, the phospholipase A2 inhibitors of the invention can modulate cholesterol absorption and triglyceride absorption from the gastrointestinal tract, and can also modulate the metabolism of fat and glucose, for example, via signaling molecules such as lysophosphatidylcholine (the reaction product of PLA2 catalyzed hydrolysis of phosphatidylcholine), operating directly and/or in conjunction with other hormones such as insulin. Such metabolic modulation can directly impact serum cholesterol and triglyceride levels in patients on a high fat/high disaccharide diet or on a high fat/high carbohydrate diet. VLDL is a lipoprotein packaged by the liver for endogenous circulation from the liver to the peripheral tissues. VLDL contains triglycerides, cholesterol, and phospholipase at its core along with apolipoproteins B100, C1, CII, CIII, and E at its perimeter. Triglycerides make up more than half of VLDL by weight and the size of VLDL is determined by the amount of triglyceride. Very large VLDL is secreted by the liver in states of caloric excess, in diabetes mellitus, and after alcohol consumption, because excess triglycerides are present. As such, inhibition of phospholipase A2 activity can impact metabolism, including for example hepatic triglyceride synthesis. Modulated (e.g., reduced or at least relatively reduced increase) in triglyceride synthesis can provide a basis for modulating serum triglyceride levels and/or serum cholesterol levels, and further can provide a basis for treating hypertriglyceridemia and/or hypercholesterolemia. Such treatments would be beneficial to both diabetic patients (who typically replace their carbohydrate restrictions with higher fat meals), and to hypertriglyceridemic patients (who typically substitute fat with high carbohydrate meals). In this regard, increased protein meals alone are usually not sustainable in the long term for most diabetic and/or hypertriglyceridemic patients.

Moreover, the modulation of serum triglyceride levels can have a beneficial effect on cardiovascular diseases such as atherosclerosis. Triglycerides included in VLDL packaged and released from the liver into circulation are in turn, hydrolyzed by lipoprotein lipase, such that VLDL are converted to VLDL remnants (=IDL). VLDL remnants can either enter the liver (the large ones preferentially do this) or can give rise to LDL. Hence, elevated VLDL in the circulation lowers HDL, which is responsible for reverse cholesterol transport. Since hypertriglyceridemia contributes to elevated LDL levels and also contributes to lowered HDL levels, hypertriglyceridemia is a risk factor for cardiovascular diseases such as atherosclerosis and coronary artery disease (among others, as noted above). Accordingly, modulating hypertriglyceridemia using the phospholipase-A2 inhibitors of the present invention also provide a basis for treating such cardiovascular diseases.

Other cholesterol-related conditions treatable with compositions, kits, and methods of the present invention include those currently treated with statins, as well as other conditions in which decreasing cholesterol absorption can produce a benefit.

In certain embodiments, a lumen-localized phospholipase inhibitor of the present invention can be used to reduce cholesterol levels, in particular non-HDL plasma cholesterol levels, as well as to treat hypertriglyceridemia.

In some preferred embodiments, the composition can inhibit phospholipase A2 and at least one other gastrointestinal phospholipase in addition to phospholipase A2, such as preferably phospholipase B, and also such as phospholipase A1, phospholipase C, and/or phospholipase D.

In other embodiments of the invention, the differential activities of phospholipases can be used to treat certain phospholipase-related conditions without undesired side effects resulting from inhibiting other phospholipases. For example, in certain embodiments, a phospholipase inhibitor that inhibits $PLA_2$, but not inhibiting or not significantly inhibiting or essentially not inhibiting, for example, PLA1, PLB, PLC, or PLD can be used to treat an insulin-related condition (e.g. diabetes) and/or a weight-related condition (e.g. obesity) without affecting, or without significantly affecting, or without essentially effecting, cholesterol absorption of a subject receiving phospholipase inhibiting treatment, e.g., when the subject is on a high fat diet.

The phospholipase inhibitors, methods, and kits disclosed herein can be used in the treatment of phospholipase-related conditions. In some preferred embodiments, these effects can be realized without a change in diet and/or activity on the part of the subject. For example, the activity of $PLA_2$ in the gastrointestinal lumen may be inhibited to result in a decrease in fat absorption and/or a reduction in weight gain in a subject on a Western diet compared to if the subject was not receiving $PLA_2$ inhibiting treatment. More preferably, this decrease and/or reduction occurs without a change, without a significant change, or essentially without a change, in energy expenditure and/or food intake on the part of the subject, and without a change, or without a significant change, or essentially without a change in the body temperature of the subject. Further, in preferred embodiments, a phospholipase inhibitor of the present invention can be used to offset certain negative consequences of high fat diets without affecting normal aspects of metabolism on non-high fat diets.

The present invention also includes kits that can be used to treat phospholipase-related conditions, preferably phospholipase A2-related conditions or phospholipase-related conditions induced by diet, including, but not limited to, insulin-related conditions (e.g., diabetes, particularly diabetes type 2), weight-related conditions (e.g., obesity) and/or cholesterol-related conditions. These kits comprise at least one composition of the present invention and instructions teaching the use of the kit according to the various methods described herein.

Inhibitor Formulations, Routes of Administration, and Effective Doses

The phospholipase inhibitors useful in the present invention, or pharmaceutically acceptable salts thereof, can be delivered to a patient using a number of routes or modes of administration. The term "pharmaceutically acceptable salt" means those salts which retain the biological effectiveness and properties of the compounds used in the present invention, and which are not biologically or otherwise undesirable. Such salts include salts with inorganic or organic acids, such as hydrochloric acid, hydrobromic acid, phosphoric acid, nitric acid, sulfuric acid, methanesulfonic acid, p-toluenesulfonic acid, acetic acid, fumaric acid, succinic acid, lactic acid, mandelic acid, malic acid, citric acid, tartaric acid or maleic acid. In addition, if the compounds used in the present invention contain a carboxyl group or other acidic group, it may be converted into a pharmaceutically acceptable addition salt with inorganic or organic bases. Examples of suitable bases include sodium hydroxide, potassium hydroxide, ammonia, cyclohexylamine, dicyclohexyl-amine, ethanolamine, diethanolamine and triethanolamine.

If necessary or desirable, the phospholipase inhibitor may be administered in combination with one or more other therapeutic agents. The choice of therapeutic agent that can be co-administered with a composition of the invention will depend, in part, on the condition being treated. For example, for treating obesity, or other weight-related conditions, a phospholipase inhibitor of some embodiments of the present invention can be used in combination with a statin, a fibrate, a bile acid binder, an ezitimibe (e.g., Zetia, etc), a saponin, a lipase inhibitor (e.g. Orlistat, etc), and/or an appetite suppressant, and the like. With respect to treating insulin-related conditions, e.g., diabetes, a phospholipase inhibitor of some embodiments the present invention can be used in combination with a biguanide (e.g., Metformin), thiazolidinedione, and/or α-glucosidase inhibitor, and the like.

The phospholipase inhibitors (or pharmaceutically acceptable salts thereof) may be administered per se or in the form of a pharmaceutical composition wherein the active compound(s) is in admixture or mixture with one or more pharmaceutically acceptable carriers, excipients or diluents. Pharmaceutical compositions for use in accordance with the present invention may be formulated in conventional manner using one or more physiologically acceptable carriers compromising excipients and auxiliaries which facilitate processing of the active compounds into preparations which can be used pharmaceutically. Proper formulation is dependent upon the route of administration chosen.

The phospholipase inhibitors can be administered by direct placement, orally, and/or rectally. Preferably, the phospholipase inhibitor or the pharmaceutical composition comprising the phospholipase inhibitor is administered orally. The oral form in which the phospholipase inhibitor is administered can include a powder, tablet, capsule, solution, or emulsion. The effective amount can be administered in a single dose or in a series of doses separated by appropriate time intervals, such as hours.

For oral administration, the compounds can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions, wafers, and the like, for oral ingestion by a patient to be treated. In some embodiments, the inhibitor may be formulated as a sustained release preparation. Pharmaceutical preparations for oral use can be obtained as a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinyl pyrrolidone (PVP). If desired, disintegrating agents may be added, such as the cross-linked polyvinyl pyrrolidone, agar, or alginic acid or a salt thereof such as sodium alginate.

Dragee cores can be provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. In some embodiments, the oral formulation does not have an enteric coating.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for administration.

Suitable carriers used in formulating liquid dosage forms for oral as well as parenteral administration include non-aqueous, pharmaceutically-acceptable polar solvents such as hydrocarbons, alcohols, amides, oils, esters, ethers, ketones, and/or mixtures thereof, as well as water, saline solutions, electrolyte solutions, dextrose solutions (e.g., DW5), and/or any other aqueous, pharmaceutically acceptable liquid.

Suitable nonaqueous, pharmaceutically-acceptable polar solvents include, but are not limited to, alcohols (e.g., aliphatic or aromatic alcohols having 2-30 carbon atoms such as methanol, ethanol, propanol, isopropanol, butanol, t-butanol, hexanol, octanol, benzyl alcohol, amylene hydrate, glycerin (glycerol), glycol, hexylene glycol, lauryl alcohol, cetyl alcohol, stearyl alcohol, tetrahydrofurfuryl alcohol, fatty acid esters of fatty alcohols such as polyalkylene glycols (e.g., polyethylene glycol and/or polypropylene glycol), sorbitan, cholesterol, sucrose and the like); amides (e.g., dimethylacetamide (DMA), benzyl benzoate DMA, N,N-dimethylacetamide amides, 2-pyrrolidinone, polyvinylpyrrolidone, 1-methyl-2-pyrrolidinone, and the like); esters (e.g., 2-pyrrolidinone, 1-methyl-2-pyrrolidinone, acetate esters (such as monoacetin, diacetin, and triacetin and the like), and the like, aliphatic or aromatic esters (such as dimethylsulfoxide (DMSO), alkyl oleate, ethyl caprylate, ethyl benzoate, ethyl acetate, octanoate, benzyl benzoate, benzyl acetate, esters of glycerin such as mono, di, or tri-glyceryl citrates or tartrates, ethyl carbonate, ethyl oleate, ethyl lactate, N-methyl pyrrolidinone, fatty acid esters such as isopropyl myristrate, fatty acid esters of sorbitan, glyceryl monostearate, glyceride esters such as mono, di, or tri-glycerides, fatty acid derived PEG esters such as PEG-hydroxystearate, PEG-hydroxyoleate, and the like, pluronic 60, polyoxyethylene sorbitol oleic polyesters, polyoxyethylene sorbitan esters such as polyoxyethylene-sorbitan monooleate, polyoxyethylene-sorbitan monostearate, polyoxyethylene-sorbitan monolaurate, polyoxyethylene-sorbitan monopalmitate, alkyleneoxy modified fatty acid esters such as polyoxyl 40 hydrogenated castor oil and polyoxyethylated castor oils, saccharide fatty acid esters (i.e., the condensation product of a monosaccharide, disaccharide, or oligosaccharide or mixture thereof with a fatty acid(s) (e.g., saturated fatty acids such as caprylic acid, myristic acid, palmitic acid, capric acid, lauric acid, and stearic acid, and unsaturated fatty acids such as palmitoleic acid, oleic acid, elaidic acid, erucic acid and linoleic acid)), or steroidal esters and the like); alkyl, aryl, or cyclic ethers (e.g., diethyl ether, tetrahydrofuran, diethylene glycol monoethyl ether, dimethyl isosorbide and the like); glycofurol (tetrahydrofurfuryl alcohol polyethylene glycol ether); ketones (e.g., acetone, methyl isobutyl ketone, methyl ethyl ketone and the like); aliphatic, cycloaliphatic or aromatic hydrocarbons (e.g., benzene, cyclohexane, dichloromethane, dioxolanes, hexane, n-hexane, n-decane, n-dodecane, sulfolane, tetramethylenesulfoxide, tetramethylenesulfon, toluene, tetramethylenesulfoxide dimethylsulfoxide (DMSO) and the like); oils of mineral, animal, vegetable, essential or synthetic origin (e.g., mineral oils such as refined paraffin oil, aliphatic or wax-based hydrocarbons, aromatic hydrocarbons, mixed aliphatic and aromatic based hydrocarbons, and the like, vegetable oils such as linseed, soybean, castor, rapeseed, coconut, tung, safflower, cottonseed, groundnut, palm, olive, corn, corn germ, sesame, persic, peanut oil, and the like, as well as glycerides such as mono-, di- or triglycerides, animal oils such as cod-liver, haliver, fish, marine, sperm, squalene, squalane, polyoxyethylated castor oil, shark liver oil, oleic oils, and the like); alkyl or aryl halides e.g., methylene chloride; monoethanolamine; trolamine; petroleum benzin; omega-3 polyunsaturated fatty acids (e.g., α-linolenic acid, docosapentaenoic acid, docosahexaenoic acid, eicosapentaenoic acid, and the like); polyglycol ester of 12-hydroxystearic acid; polyethylene glycol; polyoxyethylene glycerol, and the like.

Other pharmaceutically acceptable solvents that can be used in formulating pharmaceutical compositions of a phospholipase inhibitor of the present invention including, for example, for direct placement, are well known to those of ordinary skill in the art, e.g. see Modern Pharmaceutics, (G. Banker et al., eds., 3d ed.) (Marcel Dekker, Inc., New York, N.Y., 1995), The Handbook of Pharmaceutical Excipients, (American Pharmaceutical Association, Washington, D.C.; The Pharmacological Basis of Therapeutics, (Goodman & Gilman, McGraw Hill Publishing), Remington's Pharmaceutical Sciences (A. Gennaro, ed., 19th ed.) (Mack Publishing, Easton, Pa., 1995), Pharmaceutical Dosage Forms, (H. Lieberman et al., eds.,) (Marcel Dekker, Inc., New York, N.Y., 1980); and The United States Pharmacopeia 24, The National Formulary 19, (National Publishing, Philadelphia, Pa., 2000).

Formulations for rectal administration may be prepared in the form of a suppository, an ointment, an enema, a tablet, or a cream for release of the phospholipase inhibitor in the gastrointestinal tract, e.g., the small intestine. Rectal suppositories can be made by mixing one or more phospholipase inhibitors of the present invention, or pharmaceutically acceptable salts thereof, with acceptable vehicles, for example, cocoa butter, with or without the addition of waxes to alter melting point. Acceptable vehicles can also include glycerin, salicylate and/or polyethylene glycol, which is solid at normal storage temperature, and a liquid at those temperatures suitable to release the phospholipase inhibitor inside the body, such as in the rectum. Oils may also be used in rectal formulations of the soft gelatin type and in suppositories. Water soluble suppository bases, such as polyethylene glycols of various molecular weights, may also be used. Suspension formulations may be prepared that use water, saline, aqueous dextrose and related sugar solutions, and glycerols, as well as suspending agents such as pectins, carbomers, methyl cellulose, hydroxypropyl cellulose or carboxymethyl cellulose, as well as buffers and preservatives.

Pharmaceutical compositions suitable for use in the present invention include compositions wherein the active ingredients are present in an effective amount, i.e., in an amount sufficient to produce a therapeutic and/or a prophylactic benefit in at least one condition being treated. The actual amount effective for a particular application will depend on the condition being treated and the route of administration. Determination of an effective amount is well within the capabilities of those skilled in the art, especially in light of the disclosure herein. For example, the IC50 values and ranges provided in Table 1 above provide guidance to enable one of ordinary skill in the art to select effective dosages of the corresponding phospholipase inhibiting moieties.

The effective amount when referring to a phospholipase inhibitor will generally mean the dose ranges, modes of administration, formulations, etc., that have been recommended or approved by any of the various regulatory or advisory organizations in the medical or pharmaceutical arts (eg, FDA, AMA) or by the manufacturer or supplier. Effective amounts of phospholipase inhibitors can be found, for example, in the Physicians Desk Reference. The effective amount when referring to producing a benefit in treating a phospholipase-related condition, such as insulin-related conditions (e.g., diabetes), weight-related conditions (e.g., obesity), and/or cholesterol related-conditions will generally mean the levels that achieve clinical results recommended or approved by any of the various regulatory or advisory organizations in the medical or pharmaceutical arts (eg, FDA, AMA) or by the manufacturer or supplier.

A person of ordinary skill using techniques known in the art can determine the effective amount of the phospholipase inhibitor. In the present invention, the effective amount of a phospholipase inhibitor localized in the gastrointestinal lumen can be less than the amount administered in the absence of such localization. Even a small decrease in the amount of phospholipase inhibitor administered is considered useful for the present invention. A significant decrease or a statistically significant decrease in the effective amount of the phospholipase inhibitor is particularly preferred. In some embodiments of the invention, the phospholipase inhibitor reduces activity of phospholipase to a greater extent compared to non-lumen localized inhibitors. Lumen-localization of the phospholipase inhibitor can decrease the effective amount necessary for the treatment of phospholipase-related conditions, such as insulin-related conditions (e.g., diabetes), weight-related conditions (e.g., obesity) and/or cholesterol-related conditions by about 5% to about 95%. The amount of phospholipase inhibitor used could be the same as the recommended dosage or higher than this dose or lower than the recommended dose.

In some embodiments, the recommended dosage of a phospholipase inhibitor is between about 0.1 mg/kg/day and about 1,000 mg/kg/day. The effective amount for use in humans can be determined from animal models. For example, a dose for humans can be formulated to achieve circulating and/or gastrointestinal concentrations that have been found to be effective in animals, e.g. a mouse model as the ones described in the samples below.

A person of ordinary skill in the art can determine phospholipase inhibition by measuring the amount of a product of a phospholipase, e.g., lysophosphatidylcholine (LPC), a product of $PLA_2$. The amount of LPC can be determined, for example, by measuring small intestine, lymphatic, and/or serum levels post-prandially. Another technique for determining amount of phospholipase inhibition involves taking direct fluid samples from the gastrointestinal tract. A person of ordinary skill in the art would also be able to monitor in a patient the effect of a phospholipase inhibitor of the present invention, e.g., by monitoring cholesterol and/or triglyceride serum levels. Other techniques would be apparent to one of ordinary skill in the art. Other approaches for measuring phospholipase inhibition and/or for demonstrating the effects of phospholipase inhibitors of some embodiments are further illustrated in the examples below.

Lumen-Localized PLA2-Inhibitors

As noted above, in some embodiments, the PLA2 inhibitors of the invention are preferably lumen-localized PLA2 inhibitors. Such phospholipase inhibitors can be adapted for having both lumen-localization functionality as well as enzyme-inhibition functionalization. In some schema, certain aspects of such dual functionality can be achieved synergistically (e.g., by using the same structural features and/or charge features); in other schema, the lumen-localization functionality can be achieved independently (e.g., using different structural and/or charge features) from the enzyme-inhibition functionality.

Figure 2:
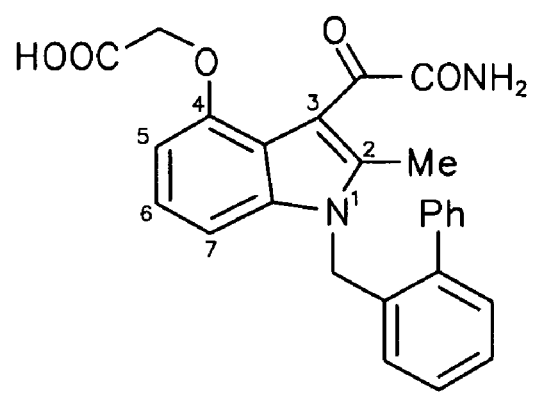
FIG. 2 is a chemical formula for [2-(3-(2-amino-2-oxoacetyl)-1-(biphenyl-2-ylmethyl)-2-methyl-1H-indol-4-yloxy)acetic acid], also referred to herein as ILY-4001 and as methyl indoxam.

The compound 2-(3-(2-amino-2-oxoacetyl)-1-(biphenyl-2-ylmethyl)-2-methyl-1H-indol-4-yloxy)acetic acid, shown in FIG. 2, and referred to herein as ILY-4001 (or methyl indoxam) was evaluated to consider its absorption using in-vitro Caco-2 cell assays (See Example 6B) and using bioavailability in in-vivo studies (See, for example, Example 6C). Bioavailability of this compound can be reduced, and reciprocally, lumen-localization can be improved, according to this preferred embodiment of the invention, for example, by charge modification and/or by covalently linking this indole moiety to a polymer. (See, for example, co-owned PCT Application No. US/2005/015418 entitled "Phospholipase Inhibitors Localized in the Gastrointestinal Lumen" filed on May 3, 2005 by Charmot et al.), incorporated herein by reference.

The phospholipase inhibitors of the invention are preferably localized in the gastrointestinal lumen, such that upon administration to a subject, the phospholipase inhibitors remain substantially in the gastrointestinal lumen. Following administration, the localized phospholipase inhibitors can remain in and pass naturally through the gastrointestinal tract, including the stomach, the duodenum, the small intestine and the large intestine (until passed out of the body via the gastrointestinal tract). The phospholipase inhibitors are preferably substantially stable (e.g., with respect to composition and/or with respect to functionality for inhibiting phospholipase) while passing through at least the stomach and the duodenum, and more preferably, are substantially stable while passing through the stomach, the duodenum and the small intestine of the gastrointestinal tract, and most preferably, are substantially stable while passing through the entire gastrointestinal tract. The phospholipase inhibitors can act in the gastrointestinal lumen, for example to catabolize phospholipase substrates or to modulate the absorption and/or downstream activities of products of phospholipase digestion.

Phospholipase inhibitors are localized within the gastrointestinal lumen, in one approach, by being not absorbed through a gastrointestinal mucosa. As another approach, the phospholipase inhibitors can be localized in the gastrointestinal lumen by being absorbed into a mucosal cell and then effluxed back into a gastrointestinal lumen.

Generally, without being constrained by categorization into one or more of the aforementioned general approaches by which the phospholipase inhibitor can be lumen-localized, preferred phospholipase inhibitors of the invention (as contemplated in the various aspects of the invention) can be realized by several general lumen-localization embodiments. In one general lumen-localization embodiment, for example, the phospholipase inhibitor can comprise a multifunctional bridge moiety (such as an oligomer moiety or polymer moiety or a non-repeating moiety) covalently linked, directly or indirectly through a linking moiety, to a phospholipase inhibiting moiety of the invention—including the afore-described indole-related compounds and indole-compounds described herein. In a further general embodiment, the lumen-localized phospholipase inhibitor can be a substituted small organic molecule itself—including the indole-related compounds and indole-compounds described above.

In general for each various aspects and embodiments included within the various aspects of the invention, the inhibitor can be localized, upon administration to a subject, in the gastrointestinal lumen of the subject, such as an animal, and preferably a mammal, including for example a human as well as other mammals (e.g., mice, rats, rabbits, guinea pigs, hamsters, cats, dogs, porcine, poultry, bovine and horses). The term "gastrointestinal lumen" is used interchangeably herein with the term "lumen," to refer to the space or cavity within a gastrointestinal tract, which can also be referred to as the gut of the animal. In some embodiments, the phospholipase inhibitor is not absorbed through a gastrointestinal mucosa. "Gastrointestinal mucosa" refers to the layer(s) of cells separating the gastrointestinal lumen from the rest of the body and includes gastric and intestinal mucosa, such as the mucosa of the small intestine. In some embodiments, lumen localization is achieved by efflux into the gastrointestinal lumen upon uptake of the inhibitor by a gastrointestinal mucosal cell. A "gastrointestinal mucosal cell" as used herein refers to any cell of the gastrointestinal mucosa, including, for example, an epithelial cell of the gut, such as an intestinal enterocyte, a colonic enterocyte, an apical enterocyte, and the like. Such efflux achieves a net effect of non-absorbedness, as the terms, related terms and grammatical variations, are used herein.

In preferred approaches, the phosphate inhibitor can be an inhibitor that is substantially not absorbed from the gastrointestinal lumen into gastrointestinal mucosal cells. As such, "not absorbed" as used herein can refer to inhibitors adapted such that a significant amount, preferably a statistically significant amount, more preferably essentially all of the phospholipase inhibitor, remains in the gastrointestinal lumen. For example, at least about 80% of phospholipase inhibitor remains in the gastrointestinal lumen, at least about 85% of phospholipase inhibitor remains in the gastrointestinal lumen, at least about 90% of phospholipase inhibitor remains in the gastrointestinal lumen, at least about 95%, at least about 98%, preferably at least about 99%, and more preferably at least about 99.5% remains in the gastrointestinal lumen. Reciprocally, stated in terms of serum bioavailability, a physiologically insignificant amount of the phospholipase inhibitor is absorbed into the blood serum of the subject following administration to a subject. For example, upon administration of the phospholipase inhibitor to a subject, not more than about 20% of the administered amount of phospholipase inhibitor is in the serum of the subject (e.g., based on detectable serum bioavailability following administration), preferably not more than about 15% of phospholipase inhibitor, and most preferably not more than about 10% of phospholipase inhibitor is in the serum of the subject. In some embodiments, not more than about 5%, not more than about 2%, preferably not more than about 1%, and more preferably not more than about 0.5% is in the serum of the subject. In some cases, localization to the gastrointestinal lumen can refer to reducing net movement across a gastrointestinal mucosa, for example, by way of both transcellular and paracellular transport, as well as by active and/or passive transport. The phospholipase inhibitor in such embodiments is hindered from net permeation of a gastrointestinal mucosal cell in transcellular transport, for example, through an apical cell of the small intestine; the phospholipase inhibitor in these embodiments is also hindered from net permeation through the "tight junctions" in paracellular transport between gastrointestinal mucosal cells lining the lumen. The term "not absorbed" is used interchangeably herein with the terms "non-absorbed," "non-absorbedness," "non-absorption" and its other grammatical variations.

In some embodiments, an inhibitor or inhibiting moiety can be adapted to be non-absorbed by modifying the charge and/or size, particularly, as well as additionally other physical or chemical parameters of the phospholipase inhibitor. For example, in some embodiments, the phospholipase inhibitor is constructed to have a molecular structure that minimizes or nullifies absorption through a gastrointestinal mucosa. The absorption character of a drug can be selected by applying principles of pharmacodynamics, for example, by applying Lipinsky's rule, also known as "the rule of five." As a set of guidelines, Lipinsky shows that small molecule drugs with (i) molecular weight, (ii) number of hydrogen bond donors, (iii) number of hydrogen bond acceptors, and (iv) water/octanol partition coefficient (Moriguchi logP) each greater than a certain threshold value generally do not show significant systemic concentration. See Lipinsky et al, Advanced Drug Delivery Reviews, 46, 2001 3-26, incorporated herein by reference. Accordingly, non-absorbed phospholipase inhibitors can be constructed to have molecule structures exceeding one or more of Lipinsky's threshold values, and preferably two or more, or three or more, or four or more or each of Lipinsky's threshold values. See also Lipinski et al., Experimental and computational approaches to estimate solubility and permeability in drug discovery and development settings, Adv. Drug Delivery Reviews, 46:3-26 (2001); and Lipinski, Drug-like properties and the causes o poor solubility and poor permeability, J. Pharm. & Toxicol. Methods, 44:235-249 (2000), incorporated herein by reference. In some preferred embodiments, for example, a phospholipase inhibitor of the present invention can be constructed to feature one or more of the following characteristics: (i) having a MW greater than about 500 Da; (ii) having a total number of NH and/or OH and/or other potential hydrogen bond donors greater than about 5; (iii) having a total number of O atoms and/or N atoms and/or other potential hydrogen bond acceptors greater than about 10; and/or (iv) having a Moriguchi partition coefficient greater than about $10^5$, i.e., logP greater than about 5. Any art known phospholipase inhibitors and/or any phospholipase inhibiting moieties described below can be used in constructing a non-absorbed molecular structure.

Preferably, the permeability properties of the compounds are screened experimentally: permeability coefficient can be determined by methods known to those of skill in the art, including for example by Caco-2 cell permeability assay. The human colon adenocarcinoma cell line, Caco-2, can be used to model intestinal drug absorption and to rank compounds based on their permeability. It has been shown, for example, that the apparent permeability values measured in Caco-2 monolayers in the range of $1 \times 10^{-7}$ cm/sec or less typically correlate with poor human absorption (Artursson P, K. J. (1991). Permeability can also be determined using an artificial membrane as a model of a gastrointestinal mucosa. For example, a synthetic membrane can be impregnated with e.g. lecithin and/or dodecane to mimic the net permeability characteristics of a gastrointestinal mucosa. The membrane can be used to separate a compartment containing the phospholipase inhibitor from a compartment where the rate of permeation will be monitored. "Correlation between oral drug absorption in humans and apparent drug." *Biochemical and Biophysical Research Communications* 175(3): 880-885.) Also, parallel artificial membrane permeability assays (PAMPA) can be performed. Such in vitro measurements can reasonably indicate actual permeability in vivo. See, for example, Wohnsland et al. J. Med. Chem., 2001, 44:923-930; Schmidt et al., Millipore corp. Application note, 2002, n° AN1725EN00, and n° AN1728EN00, incorporated herein by reference. The permeability coefficient is reported as its decimal logarithm, Log Pe.

In some embodiments, the phospholipase inhibitor permeability coefficient Log Pe is preferably lower than about −4, or lower than about −4.5, or lower than about −5, more preferably lower than about −5.5, and even more preferably lower than about −6 when measured in the permeability experiment described in Wohnsland et al. J. Med. Chem. 2001, 44. 923-930.

As noted, in one general lumen-localization embodiment, a phospholipase inhibitor can comprise a phospholipase inhibiting moiety such as the indole-related compounds and indole compounds described above, that are linked, coupled or otherwise attached to a larger moiety, such as a multifunctional bridge moiety (e.g., an oligomer moiety or polymer moiety or non-repeating moiety), where such oligomer moiety or polymer moiety or non-repeating moiety can be a hydrophobic moiety, hydrophilic moiety, and/or charged moiety. Generally, multivalent inhibitor moieties or monovalent inhibitor moieties of the invention can be sized to be non-absorbed, and can be adapted to be enzyme-inhibiting, for example based on one or more or a combination of features, such as charge characteristics, relative balance and/or distribution of hydrophilic/hydrophobic character, and molecular structure. The oligomer or polymer or non-repeating unit in this general embodiment is preferably soluble, and can preferably be a copolymer (including polymers having two monomer-repeat-units, terpolymers and higher-order polymers), including for example random copolymer or block copolymer. The oligomer or polymer can generally include one or more ionic monomer moieties such as one or more anionic monomer moieties. The oligomer or polymer can generally include one or more hydrophobic monomer moieties.

In one more specific approach within this general embodiment, the polymer moiety may be of relatively high molecular weight, for example ranging from about 1000 Da to about 500,000 Da, preferably in the range of about 5000 to about 200,000 Da, and more preferably sufficiently high to hinder or preclude (net) absorption through a gastrointestinal mucosa. Large polymer moieties may be advantageous, for example, in scavenging approaches involving relatively large, soluble or insoluble (e.g., cross-linked) polymers having multiple inhibiting moieties (e.g., as discussed below in connection with FIG. 2).

In an alternative more specific approach within this general embodiment, the oligomer or polymer moiety may be of low molecular weight, for example not more than about 5000 Da, and preferably not more than about 3000 Da and in some cases not more than about 1000 Da. Preferably within this approach, the oligomer or polymer moiety can consist essentially of or can comprise a block of hydrophobic polymer, allowing the inhibitor to associate with a water-lipid interface.

BIBLIOGRAPHY

The following references describe knowledge known in the art that relates to the present invention, for example, as indicated above. In some cases, these references are cited above in the description of the invention by reference to the first two authors and the year. These references are incorporated by reference herein.

Baker, R. R. and H. Chang (2000). "A metabolic path for the degradation of lysophosphatidic acid, an inhibitor of lysophosphatidylcholine lysophospholipase, in neuronal nuclei of cerebral cortex." *Biochim Biophys Acta* 1483(1): 58-68.

Baker, R. R. and H. Y. Chang (1999). "Evidence for two distinct lysophospholipase activities that degrade lysophosphatidylcholine and lysophosphatidic acid in neuronal nuclei of cerebral cortex." *Biochim Biophys Acta* 1438(2): 253-63.

Carriere (1993). "Secretion and contribution to Lipolysis of Gastic and Pancreatic Lipases During a Test Meal in Humans." *Gastroenterology*: 876-888.

Carriere, F., C. Renou, et al. (2000). "The specific activities of human digestive lipases measured from the in vivo and in vitro lipolysis of test meals." *Gastroenterology* 119(4): 949-60.

Duan, R. D. and B. Borgstrom (1993). "Is there a specific lysophospholipase in human pancreatic juice?" *Biochim Biophys Acta* 1167(3): 326-30.

Dunlop, M. E., E. Muggli, et al. (1997). "Differential disposition of lysophosphatidylcholine in diabetes compared with raised glucose: implications for prostaglandin production in the diabetic kidney glomerulus in vivo." *Biochim Biophys Acta* 1345(3): 306-16.

el Soda, M., L. Pannell, et al. (1989). "Microencapsulated enzyme systems for the acceleration of cheese ripening." *J Microencapsul* 6(3): 319-26.

Flieger, A., S. Gong, et al. (2001). "Novel lysophospholipase A secreted by *Legionella pneumophila*." *J Bacteriol* 183 (6): 2121-4.

Flieger, A., B. Neumeister, et al. (2002). "Characterization of the gene encoding the major secreted lysophospholipase A of *Legionella pneumophila* and its role in detoxification of lysophosphatidylcholine." *Infect Immun* 70(11): 6094-106.

Gesta, S., M. F. Simon, et al. (2002). "Secretion of a lysophospholipase D activity by adipocytes: involvement in lysophosphatidic acid synthesis." *J Lipid Res* 43(6): 904-10.

McMorn, P. and G. J. Hutchings (2004). "Heterogeneous enantioselective catalysts: strategies for the immobilisation of homogeneous catalysts." *Chem Soc Rev* 33(2): 108-22.

Millan, C. G., M. L. Marinero, et al. (2004). "Drug, enzyme and peptide delivery using erythrocytes as carriers." *J Control Release* 95(1): 27-49.

Muzykantov, V. R. (2001). "Delivery of antioxidant enzyme proteins to the lung." *Antioxid Redox Signal* 3(1): 39-62.

Ross, B. M. and S. J. Kish (1994). "Characterization of lysophospholipid metabolizing enzymes in human brain." *J Neurochem* 63(5): 1839-48.

Sakagami, H., J. Aoki, et al. (2005). "Biochemical and molecular characterization of a novel choline-specific glycerophosphodiester phosphodiesterase belonging to the nucleotide pyrophosphatase/phosphodiesterase (NPP) family." *J Biol Chem*.

Shah, N. P. (2000). "Probiotic bacteria: selective enumeration and survival in dairy foods." *J Dairy Sci* 83(4): 894-907.

Shanado, Y., M. Kometani, et al. (2004). "Lysophospholipase I identified as a ghrelin deacylation enzyme in rat stomach." *Biochem Biophys Res Commun* 325(4): 1487-94.

Sunaga, H., H. Sugimoto, et al. (1995). "Purification and properties of lysophospholipase isoenzymes from pig gastric mucosa." *Biochem J* 308 (Pt 2): 551-7.

Taniyama, Y., S. Shibata, et al. (1999). "Cloning and expression of a novel lysophospholipase which structurally resembles lecithin cholesterol acyltransferase." *Biochem Biophys Res Commun* 257(1): 50-6.

Tokumura, A., Y. Kanaya, et al. (2002). "Increased formation of lysophosphatidic acids by lysophospholipase D in serum of hypercholesterolemic rabbits." *J Lipid Res* 43(2): 307-15.

Tokumura, A., E. Majima, et al. (2002). "Identification of human plasma lysophospholipase D, a lysophosphatidic acid-producing enzyme, as autotaxin, a multifunctional phosphodiesterase." *J Biol Chem* 277(42): 39436-42.

Tosti, E., L. Dahl, et al. (1999). "Endothelial degradation of extracellular lysophosphatidylcholine." *Scand J Clin Lab Invest* 59(4): 249-57.

Toyoda, T., H. Sugimoto, et al. (1999). "Sequence, expression in *Escherichia coli*, and characterization of lysophospholipase II." *Biochim Biophys Acta* 1437(2): 182-93.

Walde, P. and S. Ichikawa (2001). "Enzymes inside lipid vesicles: preparation, reactivity and applications." *Biomol Eng* 18(4): 143-77.

Wang, A. and E. A. Dennis (1999). "Mammalian lysophospholipases." *Biochim Biophys Acta* 1439(1): 1-16.

Wang, A., H. C. Yang, et al. (1999). "A specific human lysophospholipase: cDNA cloning, tissue distribution and kinetic characterization." *Biochim Biophys Acta* 1437(2): 157-69.

Witt, W., A. Mertsching, et al. (1984). "Secretion of phospholipase B from *Saccharomyces cerevisiae*." *Biochim Biophys Acta* 795(1): 117-24.

Witt, W., M. E. Schweingruber, et al. (1984). "Phospholipase B from the plasma membrane of *Saccharomyces cerevisiae*. Separation of two forms with different carbohydrate content." *Biochim Biophys Acta* 795(1): 108-16.

Wright, L. C., J. Payne, et al. (2004). "Cryptococcal phospholipases: a novel lysophospholipase discovered in the pathogenic fungus *Cryptococcus gattii*." *Biochem J* 384(Pt 2): 377-84.

EXAMPLES

Example 1

Reduction in Insulin Resistance in a Mouse Model

A phospholipase inhibitor, for example a composition comprising a phospholipase inhibiting moiety disclosed herein, can be used in a mouse model to demonstrate, for example, suppression of diet-induced insulin resistance, relating to, for example, diet-induced onset of diabetes. The phospholipase inhibitor can be administered to subject animals either as a chow supplement and/or by oral gavage BID in a certain dosage (e.g., less than about 1 ml/kg body weight, or about 25 to about 50 µl/dose). A typical vehicle for inhibitor suspension comprises about 0.9% carboxymethylcellulose, about 9% PEG-400, and about 0.05% Tween 80, with an inhibitor concentration of about 5 to about 13 mg/ml. This suspension can be added as a supplement to daily chow, e.g., less than about 0.015% of the diet by weight, and/or administered by oral gavage BID, e.g., with a daily dose of about 10 mg/kg to about 90 mg/kg body weight.

The mouse chow used may have a composition representative of a Western (high fat and/or high cholesterol) diet. For example, the chow may contain about 21% milk fat and about 0.15% cholesterol by weight in a diet where 42% of total calories are derived from fat. See, e.g., Harlan Teklad, diet TD88137. When the inhibitor is mixed with the chow, the vehicle, either with or without the inhibitor, can be mixed with the chow and fed to the mice every day for the duration of the study.

The duration of the study is typically about 6 to about 8 weeks, with the subject animals being dosed every day during this period. Typical dosing groups, containing about 6 to about 8 animals per group, can be composed of an untreated control group, a vehicle control group, and dose-treated groups ranging from about 10 mg/kg body weight to about 90 mg/kg body weight.

At the end of the about 6 to about 8 week study period, an oral glucose tolerance test and/or an insulin sensitivity test can be conducted as follows:

Oral glucose tolerance test—after an overnight fast, mice from each dosing group can be fed a glucose bolus (e.g., by stomach gavage using about 2 g/kg body weight) in about 50 µl of saline. Blood samples can be obtained from the tail vein before, and about 15, about 30, about 60, and about 120 minutes after glucose administration; blood glucose levels at the various time points can then be determined.

Insulin sensitivity test—after about a 6 hour morning fast, mice in each of the dosing groups can be administered bovine insulin (e.g., about 1 U/kg body weight, using, e.g., intraperitoneal administration. Blood samples can be obtained from the tail vein before, and about 15, about 30, about 60, and about 120 minutes after insulin administration; plasma insulin levels at the various time points can then be determined, e.g., by radioimmunoassay.

The effect of the non-absorbed phospholipase inhibitor, e.g., a phospholipase A2 inhibitor, is a decrease in insulin resistance, i.e., better tolerance to glucose challenge by, for example, increasing the efficiency of glucose metabolism in cells, and in the animals of the dose-treated groups fed a Western (high fat/high cholesterol) diet relative to the animals of the control groups. Effective dosages can also be determined.

Example 2

Reduction in Fat Absorption in a Mouse Model

A phospholipase inhibitor, for example a composition comprising a phospholipase inhibiting moiety disclosed herein, can be used in a mouse model to demonstrate, for example, reduced lipid absorption in subjects on a Western diet. The phospholipase inhibitor can be administered to subject animals either as a chow supplement and/or by oral gavage BID in a certain dosage (e.g., less than about 1 ml/kg body weight, or about 25 to about 50 µl/dose). A typical vehicle for inhibitor suspension comprises about 0.9% carboxymethylcellulose, about 9% PEG-400, and about 0.05% Tween 80, with an inhibitor concentration of about 5 to about 13 mg/ml. This suspension can be added as a supplement to daily chow, e.g., less than about 0.015% of the diet by weight, and/or administered by oral gavage BID, e.g., with a daily dose of about 10 mg/kg to 90 mg/kg body weight.

The mouse chow used may have a composition representative of a Western-type (high fat and/or high cholesterol) diet. For example, the chow may contain about 21% milk fat and about 0.15% cholesterol by weight in a diet where 42% of total calories are derived from fat. See, e.g., Harlan Teklad, diet TD88137. When the inhibitor is mixed with the chow, the vehicle, either with or without the inhibitor, can be mixed with the chow and fed to the mice every day for the duration of the study.

Triglyceride measurements can be taken for a duration of about 6 to about 8 weeks, with the subject animals being dosed every day during this period. Typical dosing groups, containing about 6 to about 8 animals per group, can be composed of an untreated control group, a vehicle control group, and dose-treated groups ranging from about 10 mg/kg body weight to about 90 mg/kg body weight. On a weekly basis, plasma samples can be obtained from the subject animals and analyzed for total triglycerides, for example, to determine the amount of lipids absorbed into the blood circulation.

The effect of the non-absorbed phospholipase inhibitor, e.g., a phospholipase A2 inhibitor, is a net decrease in lipid plasma levels, which indicates reduced fat absorption, in the animals of the dose-treated groups fed a Western (high fat/high cholesterol) diet relative to the animals of the control groups. Effective dosages can also be determined.

Example 3

Reduction in Diet-Induced Hypercholesterolemia in a Mouse Model

A phospholipase inhibitor, for example a composition comprising a phospholipase inhibiting moiety disclosed herein, can be used in a mouse model to demonstrate, for example, suppression of diet-induced hypercholesterolemia. The phospholipase inhibitor can be administered to subject animals either as a chow supplement and/or by oral gavage BID (e.g., less than about 1 ml/kg body weight, or about 25 to about 50 µl/dose). A typical vehicle for inhibitor suspension comprises about 0.9% carboxymethylcellulose, about 9% PEG-400, and about 0.05% Tween 80, with an inhibitor concentration of about 5 to about 13 mg/ml. This suspension can be added as a supplement to daily chow, e.g., less than about 0.015% of the diet by weight, and/or administered by oral gavage BID, e.g., with a daily dose of about 10 mg/kg to about 90 mg/kg body weight.

The mouse chow used may have a composition representative of a Western-type (high fat and/or high cholesterol) diet. For example, the chow may contain about 21% milk fat and about 0.15% cholesterol by weight in a diet where 42% of total calories are derived from fat. See, e.g., Harlan Teklad, diet TD88137. When the inhibitor is mixed with the chow, the vehicle, either with or without the inhibitor, can be mixed with the chow and fed to the mice every day for the duration of the study.

Cholesterol and/or triglyceride measurements can be taken for a duration of about 6 to about 8 weeks, with the subject animals being dosed every day during this period. Typical dosing groups, containing about 6 to about 8 animals per group, can be composed of a untreated control group, a vehicle control group, and dose-treated groups ranging from about 10 mg/kg body weight to about 90 mg/kg body weight. On a weekly basis, plasma samples can be obtained from the subject animals and analyzed for total cholesterol and/or triglycerides, for example, to determine the amount of cholesterol and/or lipids absorbed into the blood circulation. Since most plasma cholesterol in a mouse is associated with HDL (in contrast to the LDL association of most cholesterol in humans), HDL and non-HDL fractions can be separated to aid determination of the effectiveness of the non-absorbed phospholipase inhibitor in lowering plasma non-HDL levels, for example VLDL/LDL.

The effect of the non-absorbed phospholipase inhibitor, e.g., a phospholipase A2 inhibitor, is a net decrease in hypercholesterolemia in the animals of the dose-treated groups fed a Western (high fat/high cholesterol) diet relative to the animals of the control groups. Effective dosages can also be determined.

Example 4

Synthesis of ILY-4001 [2-(3-(2-AMINO-2-OXOACETYL)-1-(BIPHENYL-2-YLMETHYL)-2-METHYL-1H-INDOL-4-YLOXY)ACETIC ACID] (ME INDOXAM)

This example synthesized a compound for use as a phospholipase inhibitor or inhibiting moiety. Specifically, the compound 2-(3-(2-amino-2-oxoacetyl)-1-(biphenyl-2-ylmethyl)-2-methyl-1H-indol-4-yloxy)acetic acid, shown in FIG. 2 was synthesized. This compound is designated in these examples as ILY-4001, and is alternatively referred to herein as methyl indoxam.

Figure 9:
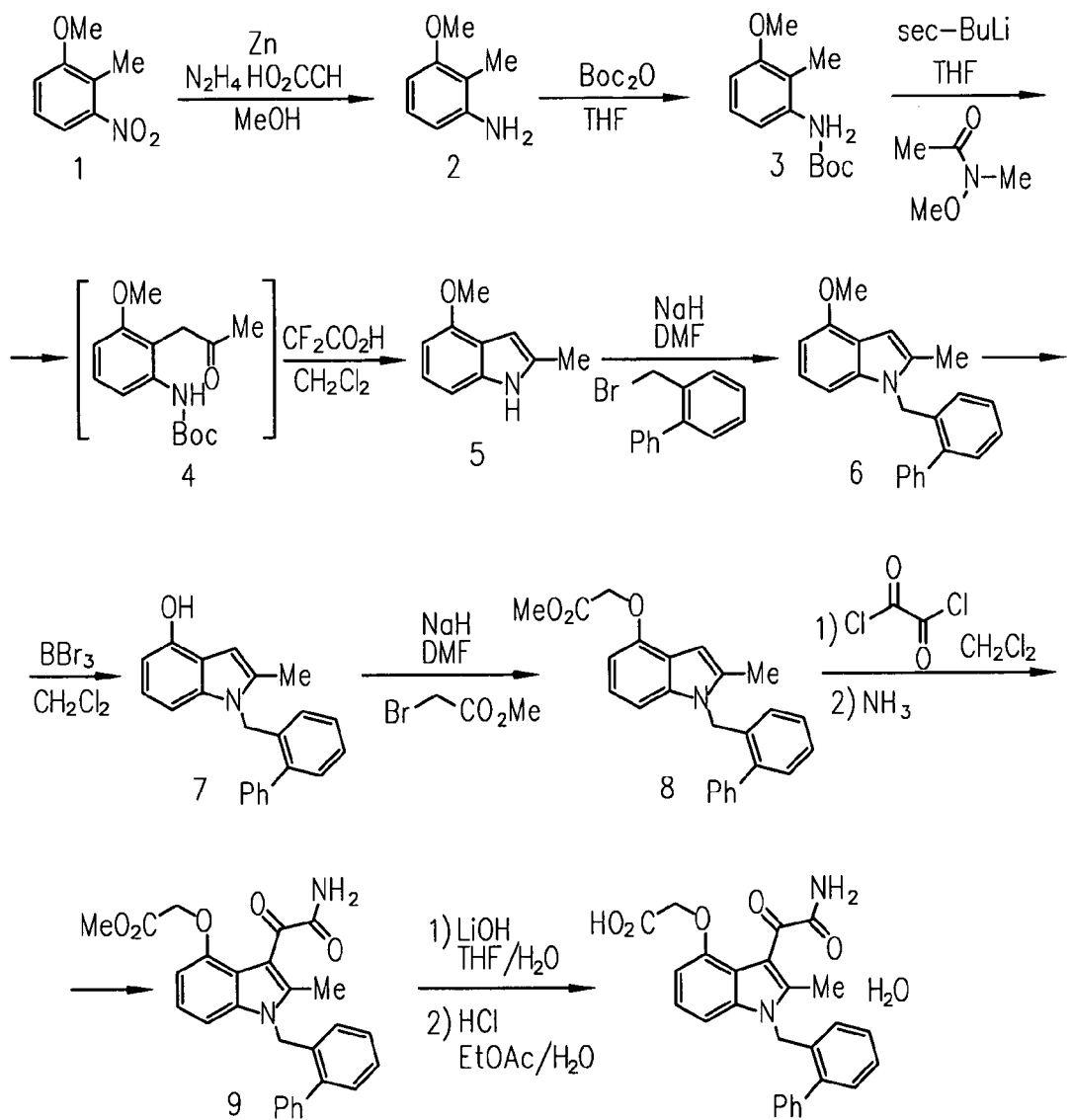
FIG. 9 is a schematic illustration, including chemical formulas, which outlines the overall synthesis scheme for ILY-4001 [2-(3-(2-amino-2-oxoacetyl)-1-(biphenyl-2-ylmethyl)-2-methyl-1H-indol-4-yloxy)acetic acid] as described in Example 4.
Figure 10A:
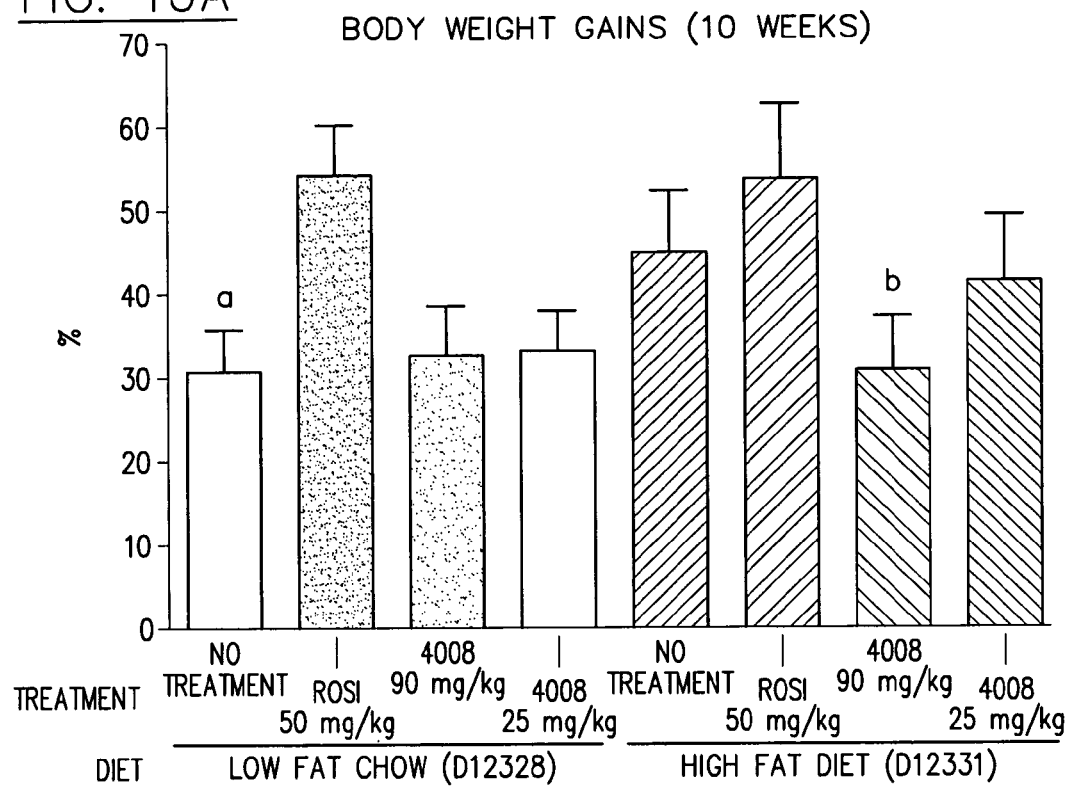
FIGS. 10A, 10B, 10C and 10D are graphs depicting results for Test Article ILY4008 (ILY-V-26) in a C57BL/6J mouse model of obesity.
Figure 10B:
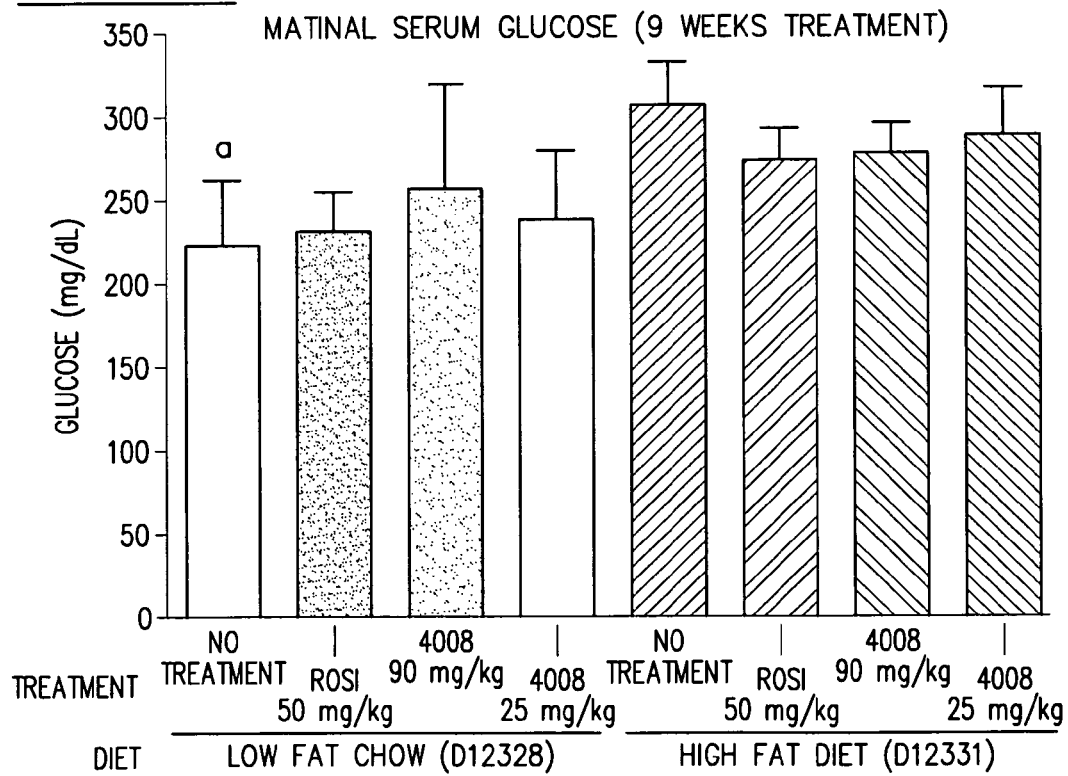
Figure 10C:
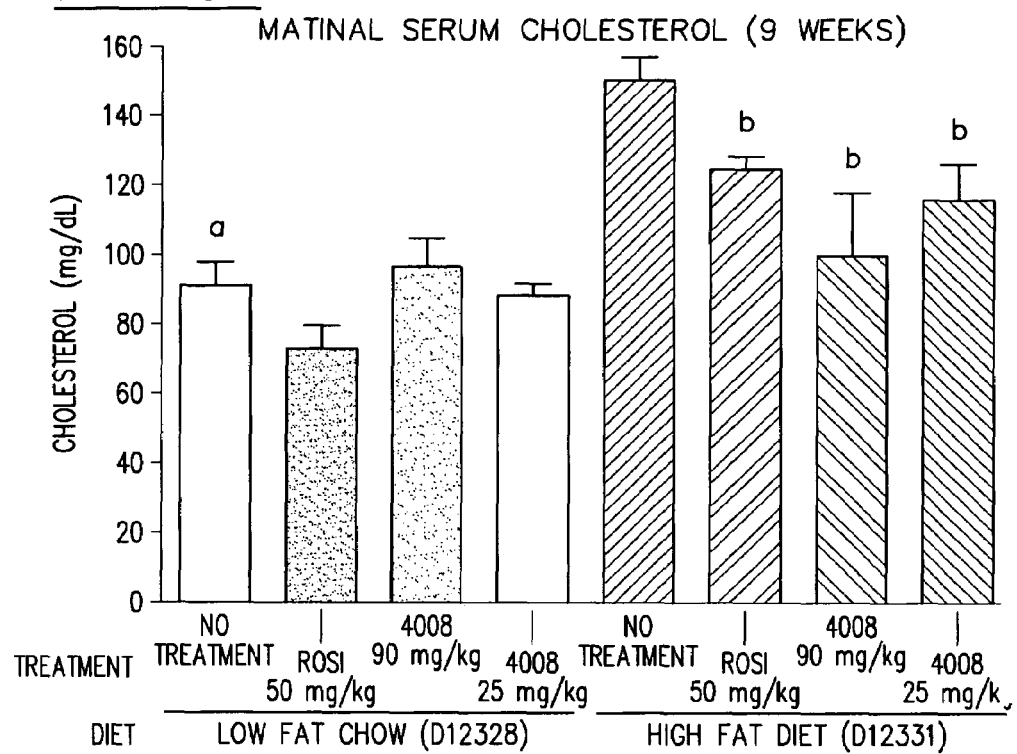
Figure 10D:
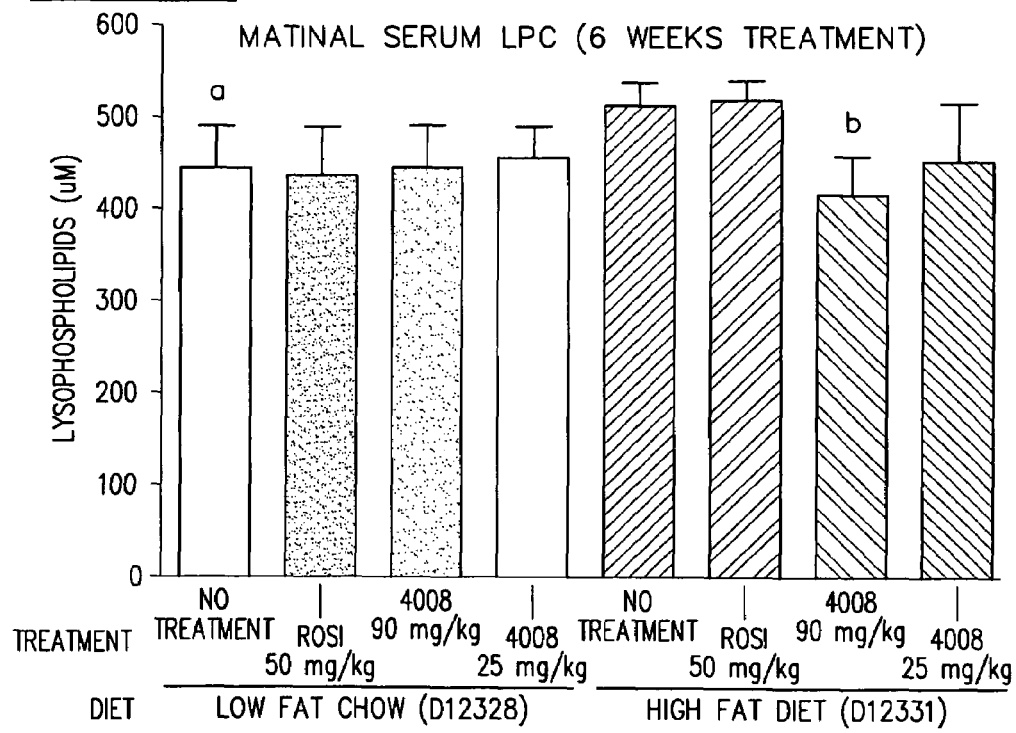
Figure 11C:
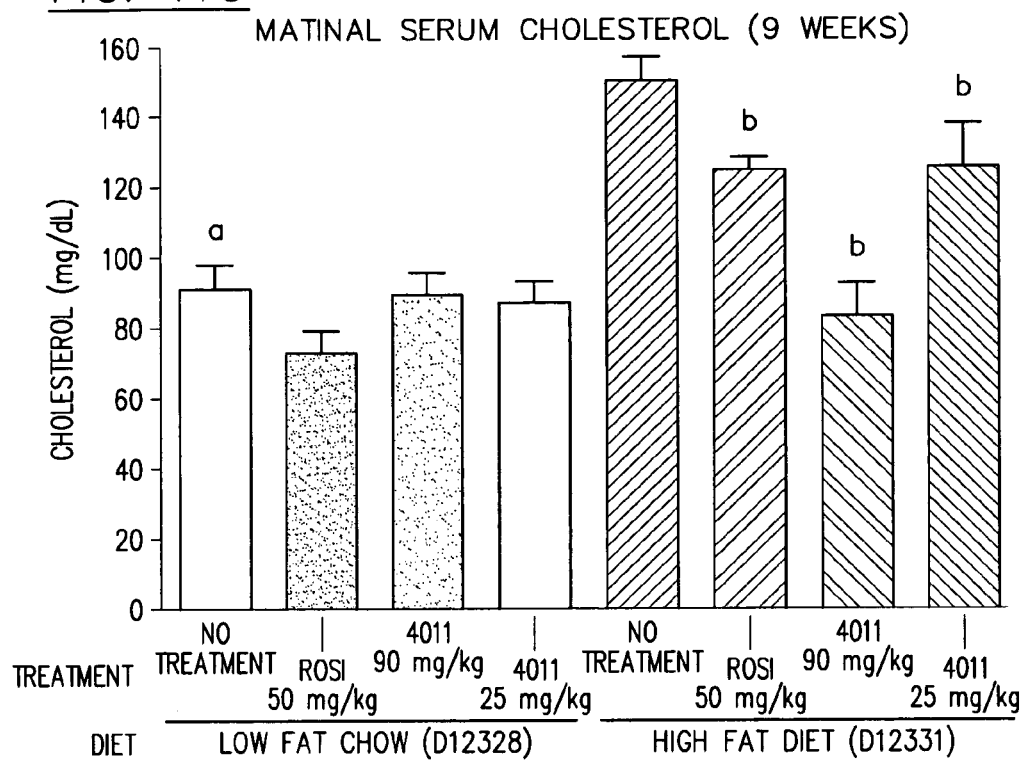
Figure 11D:
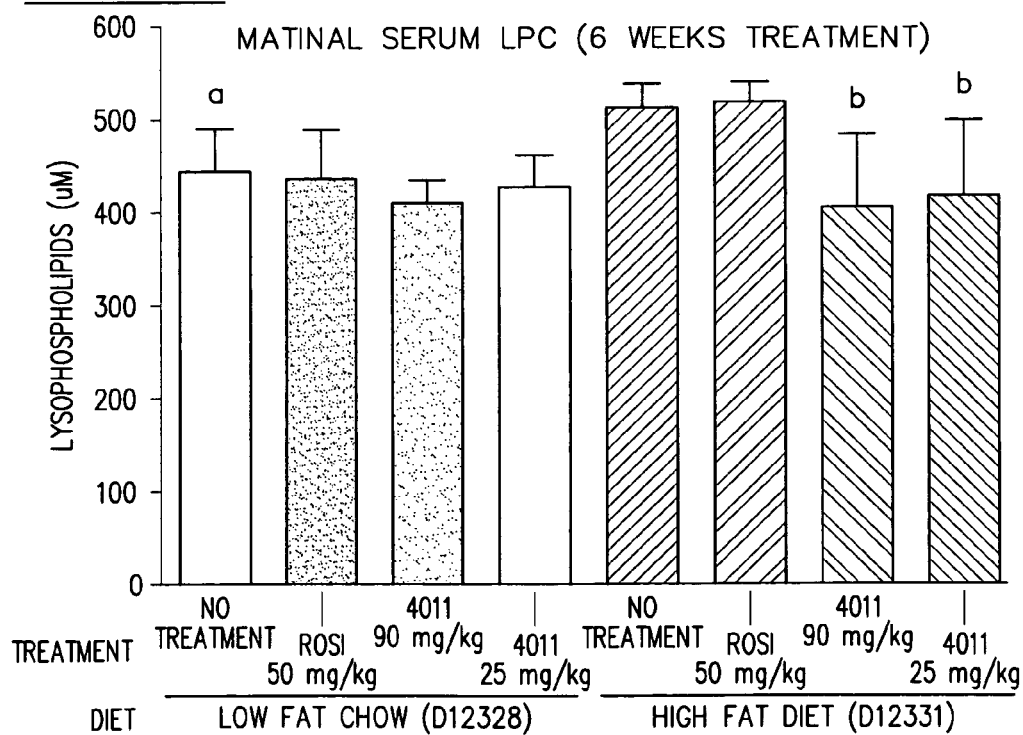

Reference is made to FIG. 9, which outlines the overall synthesis scheme for ILY-4001. The numbers under each compound shown in FIG. 9 correspond to the numbers in parenthesis associated with the chemical name for each compound in the following experimental description.

2-Methyl-3-methoxyaniline (2) [04-035-11]. To a stirred cooled (ca. 5° C.) hydrazine hydrate (159.7 g, 3.19 mol), 85% formic acid (172.8 g, 3.19 mol) was added drop wise at 10-20° C. The resultant mixture was added drop wise to a stirred suspension of zinc dust (104.3 g, 1.595 mol) in a solution of 2-methyl-3-nitroanisole (1) (53.34 g, 0.319 mol) in methanol (1000 mL). An exothermic reaction occurred. After the addition was complete, the reaction mixture was stirred for additional 2 h (until temperature dropped from 61° C. to RT) and the precipitate was filtered off and washed with methanol (3×150 mL). The filtrate was concentrated under reduced pressure to a volume of ca. 250 mL. The residue was treated with EtOAc (500 ml) and saturated aqueous NaHCO$_3$ (500 mL). The aqueous phase was separated off and discarded. The organic phase was washed with water (300 mL) and extracted with 1N HCl (800 mL). The acidic extract was washed with EtOAc (300 mL) and was basisified with K$_2$CO$_3$ (90 g). The free base 2 was extracted with EtOAc (3×200 mL) and the combined extracts were dried over MgSO$_4$. After filtration and removal of the solvent from the filtrate, product 2 was obtained as a red oil, which was used in the next step without further purification. Yield: 42.0 g (96%).

N-tert-Butyloxycarbonyl-2-methyl-3-methoxyaniline (3) [04-035-12]. A stirred solution of amine 2 (42.58 g, 0.31 mol) and di-tert-butyl dicarbonate (65.48 g, 0.30 mol) in THF (300 mL) was heated to maintain reflux for 4 h. After cooling to RT, the reaction mixture was concentrated under reduced pressure and the residue was dissolved in EtOAc (500 mL). The resultant solution was washed with 0.5 M citric acid (2×100 mL), water (100 mL), saturated aqueous NaHCO$_3$ (200 mL), brine (200 mL) and dried over MgSO$_4$. After filtration and removal of the solvent from the filtrate, the residue (red oil, 73.6 g) was dissolved in hexanes (500 mL) and filtered through a pad of Silica Gel (for TLC). The filtrate was evaporated under reduced pressure to provide N-Boc aniline 3 as a yellow solid. Yield: 68.1 g (96%).

4-Methoxy-2-methyl-1H-indole (5) [04-035-13]. To a stirred cooled (−50° C.) solution of N-Boc aniline 3 (58.14 g, 0.245 mol) in anhydrous THF (400 mL), a 1.4 M solution of sec-BuLi in cyclohexane (0.491 mol, 350.7 mL) was added drop wise at −48-−50° C. and the reaction mixture was allowed to warm up to −20° C. After cooling to −60° C., a solution of N-methoxy-N-methylacetamide (25.30 g, 0.245 mol) in THF (25 mL) was added drop wise at −57-−60° C. The reaction mixture was stirred for 1 h at −60° C. and was allowed to warm up to 15° C. during 1 h. After cooling to −15° C., the reaction was quenched with 2N HCl (245 mL) and the resultant mixture was adjusted to pH of ca. 7 with 2N HCl. The organic phase was separated off and saved. The aqueous phase was extracted with EtOAc (3×100 mL). The organic solution was concentrated under reduced pressure and the residual pale oil was dissolved in EtOAc (300 mL) and combined with the EtOAc extracts. The resultant solution was washed with water (2×200 mL), 0.5 M citric acid, (100 mL), saturated aqueous NaHCO$_3$ (100 mL), brine (200 mL) and dried over MgSO$_4$. After filtration and removal of the solvent from the filtrate, a mixture of starting N-Boc aniline 3 and intermediate ketone 4 (ca. 1:1 mol/mol) was obtained as a pale oil (67.05 g).

The obtained oil was dissolved in anhydrous CH$_2$Cl$_2$ (150 mL) and the solution was cooled to 0-−5° C. Trifluoroacetic acid (65 mL) was added drop wise and the reaction mixture was allowed to warm up to RT. After 16 h of stirring, an additional portion of trifluoroacetic acid (35 mL) was added and stirring was continued for 16 h. The reaction mixture was concentrated under reduced pressure and the red oily residue was dissolved in CH$_2$Cl$_2$ (500 mL). The resultant solution was washed with water (3×200 mL) and dried over MgSO$_4$. Filtration through a pad of Silica Gel 60 and evaporation of the filtrate under reduced pressure provided crude product 5 as a yellow solid (27.2 g). Purification by dry chromatography (Silica Gel for TLC, 20% EtOAc in hexanes) afforded indole 5 as a white solid. Yield: 21.1 g (53%)

1-[(1,1'-Biphenyl)-2-ylmethyl]-4-methoxy-2-methyl-1H-indole (6) [04-035-14]. A solution of indole 5 (16.12 g, 0.10 mol) in anhydrous DMF (100 mL) was added drop wise to a stirred cooled (ca. 15° C.) suspension of sodium hydride (0.15 mol, 6.0 g, 60% in mineral oil, washed with 100 mL of hexanes before the reaction) in DMF (50 mL) and the reaction mixture was stirred for 0.5 h at RT. After cooling the reaction mixture to ca. 5° C., 2-phenylbenzyl bromide (25.0 g, 0.101 mol) was added drop wise and the reaction mixture was stirred for 18 h at RT. The reaction was quenched with water (10 mL) and EtOAc (500 mL) was added. The resultant mixture was washed with water (2×200 mL+3×100 mL), brine (200 mL) and dried over MgSO$_4$. After filtration and removal of the solvent from the filtrate under reduced pressure, the residue (35.5 g, thick red oil) was purified by dry chromatography (Silica Gel for TLC, 5%→25% CH$_2$Cl$_2$ in hexanes) to afford product 6 as a pale oil. Yield: 23.71 g (72%).

1-[(1,1'-Biphenyl)-2-ylmethyl]-4-hydroxy-2-methyl-1H-indole (7) [04-035-15]. To a stirred cooled (ca. 10° C.) solution of the methoxy derivative 6 (23.61 g, 72.1 mmol) in anhydrous CH$_2$Cl$_2$ (250 mL), a 1M solution of BBr$_3$ in CH$_2$Cl$_2$ (300 mmol, 300 mL) was added drop wise at 15-20° C. and the dark reaction mixture was stirred for 5 h at RT. After concentrating of the reaction mixture under reduced pressure, the dark oily residue was cooled to ca. 5° C. and was dissolved in precooled (15° C.) EtOAc (450 mL). The resultant cool solution was washed with water (3×200 mL), brine (200 mL) and dried over MgSO$_4$. After filtration and removal of the solvent from the filtrate under reduced pressure, the residue (26.1 g, dark semi-solid) was purified by dry chromatography (Silica Gel for TLC, 5%→25% EtOAc in hexanes) to afford product 7 as a brown solid. Yield: 4.30 g (19%)

2-{1-[(1,1'-Biphenyl)-2-ylmethyl]-2-methyl-1H-indol-4-yl]oxy}-acetic acid methyl ester (8) [04-035-16]. To a stirred suspension of sodium hydride (0.549 g, 13.7 mmol, 60% in mineral oil) in anhydrous DMF (15 mL), a solution of compound 7 (4.30 g, 13.7 mmol) in DMF (30 mL) was added drop wise and the resultant mixture was stirred for 40 min at RT. Methyl bromoacetate (2.10 g, 13.7 mmol) was added drop wise and stirring was continued for 21 h at RT. The reaction mixture was diluted with EtOAc (200 mL) and washed with water (4×200 mL), brine (200 mL) and dried over $MgSO_4$. After filtration and removal of the solvent from the filtrate under reduced pressure, the residue (5.37 g, dark semi-solid) was purified by dry chromatography (Silica Gel for TLC, 5%→30% EtOAc in hexanes) to afford product 8 as a yellow solid. Yield: 4.71 g (89%).

2-{[3-(2-Amino-1,2-dioxoethyl)-1-[(1,1'-biphenyl)-2-yl-methyl)-2-methyl-1H-indol-4-yl]oxy}-acetic acid methyl ester (9) [04-035-17]. To a stirred solution of oxalyl chloride (1.55 g, 12.2 mmol) in anhydrous $CH_2Cl_2$ (20 mL), a solution of compound 8 in $CH_2Cl_2$ (40 mL) was added drop wise and the reaction mixture was stirred for 80 min at RT. After cooling the reaction mixture to −10° C., a saturated solution of $NH_3$ in $CH_2Cl_2$ (10 mL) was added drop wise and then the reaction mixture was saturated with $NH_3$ (gas) at ca. 0° C. Formation of a precipitate was observed. The reaction mixture was allowed to warm up to RT and was concentrated under reduced pressure to dryness. The dark solid residue (6.50 g) was subjected to dry chromatography (Silica Gel for TLC, 30% EtOAc in hexanes→100% EtOAc) to afford product 9 as a yellow solid. Yield: 4.64 g (83%).

2-{[3-(2-Amino-1,2-dioxoethyl)-1-[(1,1'-biphenyl)-2-yl-methyl)-2-methyl-1H-indol-4-yl]oxy}-acetic acid (ILY-4001) [04-035-18]. To a stirred solution of compound 9 (4.61 g, 10.1 mmol) in a mixture of THF (50 mL) and water (10 mL), a solution of lithium hydroxide monohydrate (0.848 g, 20.2 mmol) in water (20 mL) was added portion wise and the reaction mixture was stirred for 2 h at RT. After addition of water (70 mL), the reaction mixture was concentrated under reduced pressure to a volume of ca. 100 mL. Formation of a yellow precipitate was observed. To the residual yellow slurry, 2N HCl (20 mL) and EtOAc (200 mL) were added and the resultant mixture was stirred for 16 h at RT. The yellow-ish-greenish precipitate was filtered off and washed with EtOAc (3×20 mL), $Et_2O$ (20 mL) and hexanes (20 mL). After drying in vacuum, the product (2.75 g) was obtained as a pale solid. MS: 443.27 ($M^+$+1). Elemental Analysis: Calcd for $C_{26}H_{22}N_2O_5$+$H_2O$: C, 67.82; H, 5.25; N, 6.08. Found: C, 68.50; H, 4.96; N, 6.01. HPLC: 96.5% purity. $^1$H NMR (DMSO-$d_6$) 7.80 (br s, 1H), 7.72-7.25 (m, 9H), 7.07 (t, 1H), 6.93 (d, 1H), 6.57 (d, 1H), 6.43 (d, 1H), 5.39 (s, 2H), 4.68 (s, 2H), 2.38 (s, 3H).

The aqueous phase of the filtrate was separated off and the organic one was washed with brine (100 mL) and dried over $MgSO_4$. After filtration and removal of the solvent from the filtrate under reduced pressure, the greenish solid residue was washed with EtOAc (3×10 mL), $Et_2O$ (10 mL) and hexanes (10 mL). After drying in vacuum, an additional portion (1.13 g) of product was obtained as a greenish solid.

Total yield: 2.75 g+1.13 g=3.88 g (87%).

Example 5

In-vivo Evaluation of ILY-4001 [2-(3-(2-amino-2-OXOACETYL)-1-(BIPHENYL-2-YLMETHYL)-2-METHYL-1H-INDOL-4-YLOXY)ACETIC ACID] as PLA2-IB Inhibitor and for Treatment of Diet-Related Conditions This example demonstrated that the compound 2-(3-(2-amino-2-oxoacetyl)-1-(biphenyl-2-ylmethyl)-2-methyl-1H-indol-4-yloxy)acetic acid, shown in FIG. 2, was an effective phospholipase-2A IB inhibitor, with phenotypic effects approaching and/or comparable to the effect of genetically deficient PLA2 (−/−) mice. This example also demonstrated that this compound is effective in treating conditions such as weight-related conditions, insulin-related conditions, and cholesterol-related conditions, including in particular conditions such as obesity, diabetes mellitus, insulin resistance, glucose intolerance, hypercholesterolemia and hypertriglyc-eridemia. In this example, the compound 2-(3-(2-amino-2-oxoacetyl)-1-(biphenyl-2-ylmethyl)-2-methyl-1H-indol-4-yloxy)acetic acid is designated as ILY-4001 (and is alternatively referred to herein as methyl indoxam).

ILY-4001 (FIG. 2) was evaluated as a PLA2 IB inhibitor in a set of experiments using wild-type mice and genetically deficient PLA2 (−/−) mice (also referred to herein as PLA2 knock-out (KO) mice). In these experiments, wild-type and PLA2 (−/−) mice were maintained on a high fat/high sucrose diet, details of which are described below.

ILY-4001 has a measured IC50 value of around 0.2 uM versus the human PLA2 IB enzyme and 0.15 uM versus the mouse PLA2 IB enzyme, in the context of the 1-palmitoyl-2-(10-pyrenedecanoyl)-sn-glycero-3-phosphoglycerol assay, which measures pyrene substrate release from vesicles treated with PLA2 IB enzyme (Singer, Ghomashchi et al. 2002). An IC-50 value of around 0.062 was determined in experimental studies. (See Example 6A). In addition to its activity against mouse and human pancreatic PLA2, methyl indoxam is stable at low pH, and as such, would be predicted to survive passage through the stomach. ILY-4001 has relatively low absorption from the GI lumen, based on Caco-2 assays (See Example 6B), and based on pharmokinetic studies (See Example 6C).

In the study of this Example 5, twenty-four mice were studied using treatment groups as shown in Table 4, below. Briefly, four groups were set up, each having six mice. Three of the groups included six wild-type PLA2 (+/+) mice in each group (eighteen mice total), and one of the groups included six genetically deficient PLA2 (−/−) mice. One of the wild-type groups was used as a wild-type control group, and was not treated with ILY-4001. The other two wild-type groups were treated with ILY-4001—one group at a lower dose (indicated as "L" in Table 1) of 25 mg/kg/day, and the other at a higher dose (indicated as "H" in Table 1) of 90 mg/kg/day. The group comprising the PLA2 (−/−) mice was used as a positive control group.

TABLE 4

Treatment Groups for ILY-4001 Study

| Group Number | Treatment Groups | Number of Animals | ILY-4001 Dose Levels (mg/kg/day) | Duration (weeks) |
|---|---|---|---|---|
| 1 | C57BL/6(wt) | 6 | 0 | 10 |
| 2 | C57BL/6(wt) | 6 | 25 (L) | 10 |
| 3 | C57BL/6(wt) | 6 | 90 (H) | 10 |
| 4 | C57BL/6($PLA_2$-KO) | 6 | 0 | 10 |

The experimental protocol used in this study was as follows. The four groups of mice, including wild type and isogenic PLA2 (−/−) C57BL/J mice were acclimated for three days on a low fat/low carbohydrate diet. After the three day acclimation phase, the animals were fasted overnight and serum samples taken to establish baseline plasma cholesterol, triglyceride, and glucose levels, along with baseline body weight. The mice in each of the treatment groups were then fed a high fat/high sucrose diabetogenic diet (Research Diets D12331). 1000 g of the high fat/high sucrose D12331 diet was composed of casein (228 g), DL-methionine (2 g), maltodextrin 10 (170 g), sucrose (175 g), soybean oil (25 g), hydrogenated coconut oil (333.5 g), mineral mix S10001 (40 g), sodium bicarbonate (10.5 g), potassium citrate (4 g), vitamin mix V10001 (10 g), and choline bitartrate (2 g). This diet was supplemented with ILY-4001 treatments such that the average daily dose of the compound ingested by a 25 g mouse was: 0 mg/kg/day (wild-type control group and PLA2 (−/−) control group); 25 mg/kg/day (low-dose wild-type treatment group), or 90 mg/kg/day (high-dose wild-type treatment group). The animals were maintained on the high fat/high sucrose diet, with the designated ILY-4001 supplementation, for a period of ten weeks.

Body weight measurements were taken for all animals in all treatment and control groups at the beginning of the treatment period and at 4 weeks and 10 weeks after initiation of the study. (See Example 5A). Blood draws were also taken at the beginning of the treatment period (baseline) and at 4 weeks and 10 weeks after initiation of the study, in order to determine fasting glucose (See Example 5B). Cholesterol and triglyceride levels were determined from blood draws taken at the beginning of the treatment (baseline) and at ten weeks. (See Example 5C).

Example 5A

Body-weight Gain in In-vivo Evaluation of ILY-4001 [2-(3-(2-AMINO-2-OXOACETYL)-1-(BIPHENYL-2-YLMETHYL)-2-METHYL-1H-INDOL-4-YLOXY)ACETIC ACID] as PLA2-IB Inhibitor In the study generally described above in Example 5, body weight measurements were taken for all animals in all treatment and control groups at the beginning of the treatment period and at 4 weeks and 10 weeks after initiation of the study. Using the treatment protocol described above with ILY-4001 supplemented into a high fat/high sucrose diabetogenic diet, notable decreases were seen in body weight gain.

Figure 3:
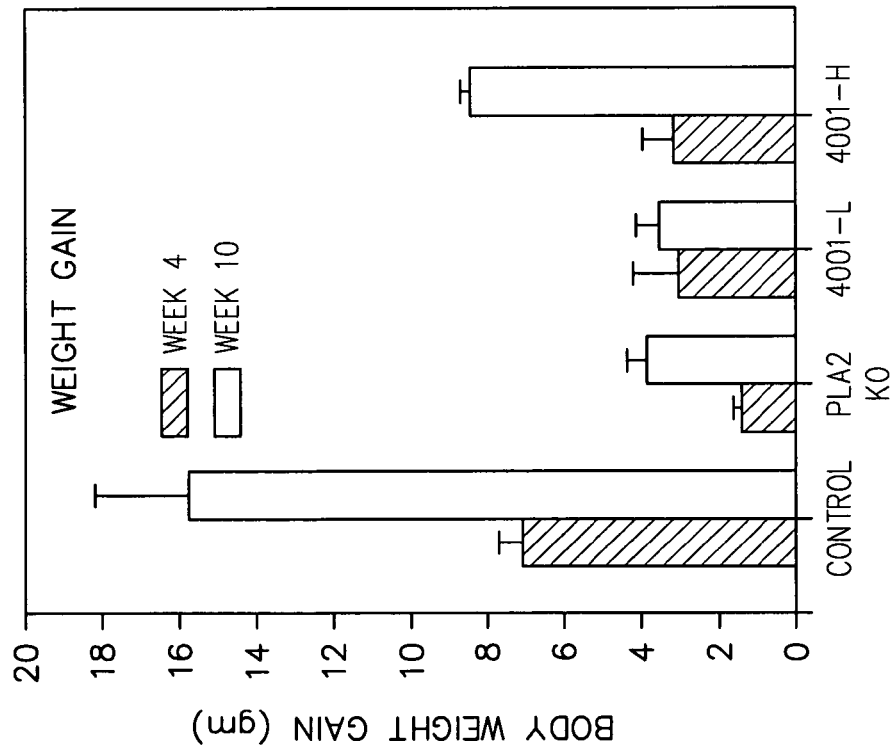
FIG. 3 is a graph illustrating the results of Example 5A, showing body weight gain in groups of mice receiving ILY-4001 at low dose (4001-L) and high dose (4001-H) as compared to wild-type control group (Control) and as compared to genetically deficient PLA2 (−/−) knock-out mice (PLA2 KO).

With reference to FIG. 3, body weight gain in the wild-type mice receiving no ILY-4001 (group 1, wild-type control) followed the anticipated pattern of a substantial weight gain from the beginning of the study to week 4, and a further doubling of weight gain by week 10. In contrast, body weight gain for the PLA2 (−/−) mice (PLA2 KO mice) also receiving no ILY-4001 and placed on the same diet (group 4, PLA2 (−/−) control) did not show statistically significant changes from week 4 to week 10, and only a marginal increase in body weight over the extent of the study (<5 g). The two treatment groups (25 mg/kg/d and 90 mg/kg/d) showed significantly reduced body weight gains at week 4 and week 10 of the study compared to the wild-type control group. Both treatment groups showed body weight gain at four weeks modulated to an extent approaching that achieved in the PLA2 (−/−) mice. The low-dose treatment group showed body weight gain at ten weeks modulated to an extent comparable to that achieved in the PLA2 (−/−) mice.

Example 5B

Fasting Serum Glucose in In-vivo Evaluation of ILY-4001 [2-(3-(2-AMINO-2-OXOACETYL)-1-(BIPHENYL-2-YLMETHYL)-2-METHYL-1H-INDOL-4-YLOXY)ACETIC ACID] as PLA2-IB Inhibitor In the study generally described above in Example 5, blood draws were taken at the beginning of the treatment period (baseline) and at 4 weeks and 10 weeks after initiation of the study, in order to determine fasting glucose. Using the treatment protocol described above with ILY-4001 supplemented into a high fat/high sucrose diabetogenic diet, notable decreases were seen in fasting serum glucose levels.

Figure 4:
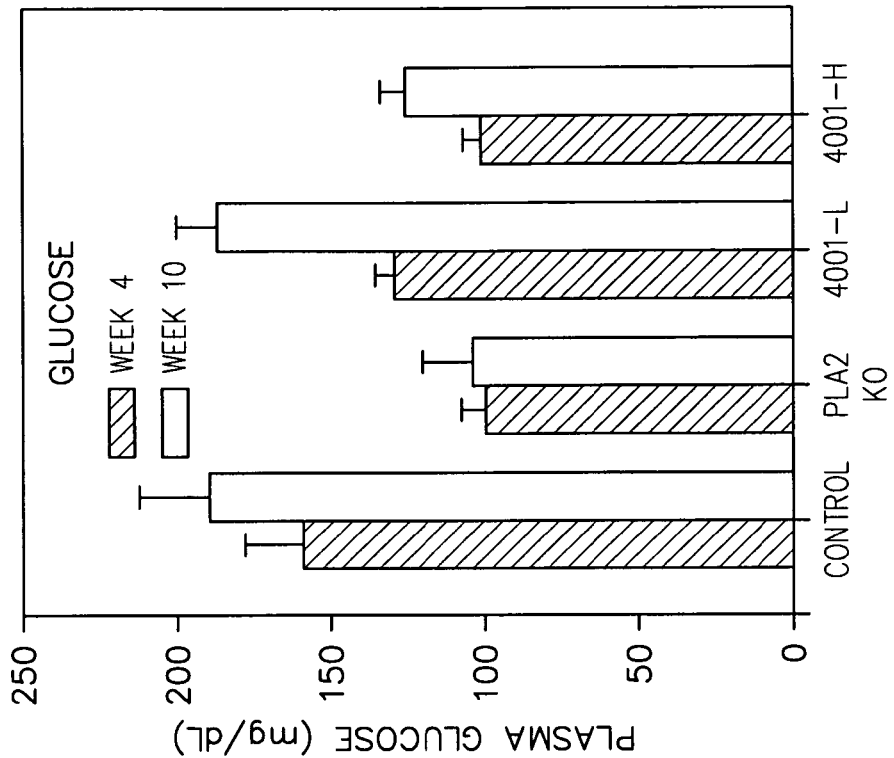
FIG. 4 is a graph illustrating the results of Example 5B, showing fasting serum glucose levels in groups of mice receiving ILY-4001 at low dose (4001-L) and high dose (4001-H) as compared to wild-type control group (Control) and as compared to genetically deficient PLA2 (−/−) knock-out mice (PLA2 KO).

Referring to FIG. 4, the wild-type control mice (group 1) showed a sustained elevated plasma glucose level, consistent with and indicative of the high fat/high sucrose diabetogenic diet at both four weeks and ten weeks. In contrast, the PLA2 (−/−) KO mice (group 4) showed a statistically significant decrease in fasting glucose levels at both week 4 and week 10, reflecting an increased sensitivity to insulin not normally seen in mice placed on this diabetogenic diet. The high dose ILY-4001 treatment group (group 3) showed a similar reduction in fasting glucose levels at both four weeks and ten weeks, indicating an improvement in insulin sensitivity for this group as compared to wild-type mice on the high fat/high sucrose diet, and approaching the phenotype seen in the PLA2 (−/−) KO mice. In the low dose ILY-4001 treatment group (group 2), a moderately beneficial effect was seen at week four; however, a beneficial effect was not observed at week ten.

Example 5C

Serum Cholesterol and Triglycerides in In-vivo Evaluation of ILY-4001 [2-(3-(2-AMINO-2-OXOACETYL)-1-(BIPHENYL-2-YLMETHYL)-2-METHYL-1H-INDOL-4-YLOXY)ACETIC ACID] as PLA2-IB Inhibitor In the study generally described above in Example 5, blood draws were taken at the beginning of the treatment period (baseline) and at 10 weeks after initiation of the study, in order to determine cholesterol and triglyceride levels. Using the treatment protocol described above with ILY-4001 supplemented into a high fat/high sucrose diabetogenic diet, notable decreases were seen in both serum cholesterol levels and serum triglyceride levels.

Figure 5A:
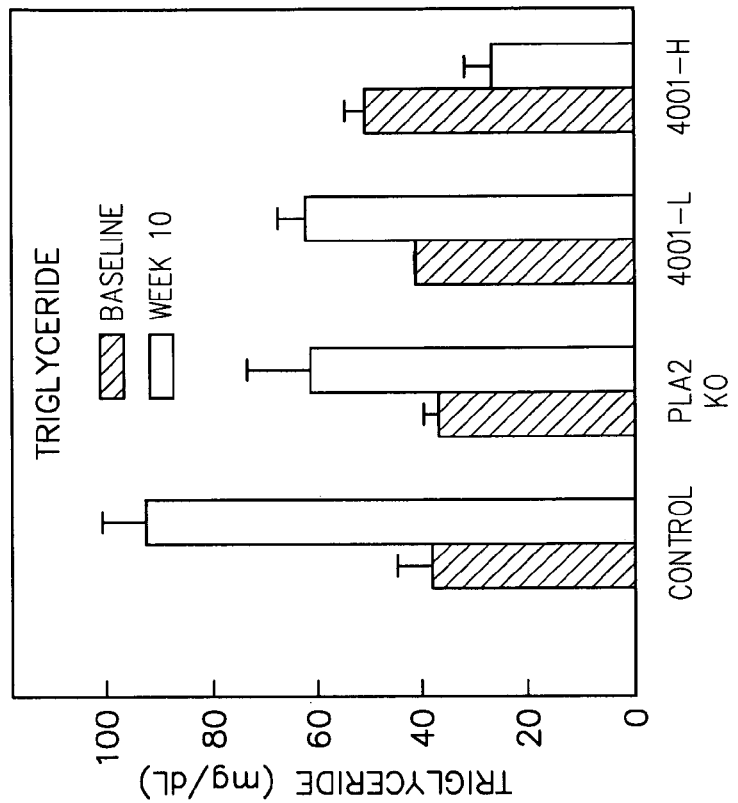
FIGS. 5A and 5B are graphs illustrating the results of Example 5C, showing serum cholesterol levels (FIG. 5A) and serum triglyceride levels (FIG. 5B) in groups of mice receiving ILY-4001 at low dose (4001-L) and high dose (4001-H) as compared to wild-type control group (Control) and as compared to genetically deficient PLA2 (−/−) knock-out mice (PLA2 KO).
Figure 5B:
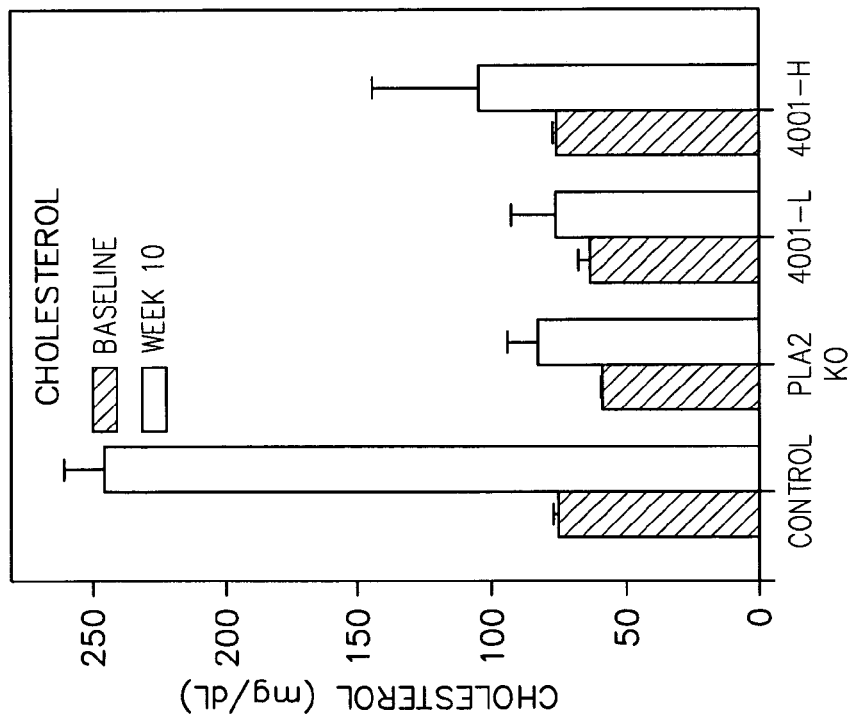

With reference to FIGS. 5A and 5B, after 10 weeks on the high fat/high sucrose diet, the wild-type control animals (group 1) had notable and substantial increases in both circulating cholesterol levels (FIG. 5A) and triglyceride levels (FIG. 5B), relative to the baseline measure taken at the beginning of the study. The PLA2 (−/−) KO animals (group 4), in contrast, did not show the same increase in these lipids, with cholesterol and triglyceride values each 2 to 3 times lower than those found in the wild-type control group. Significantly, treatment with ILY-4001 at both the low and high doses (groups 2 and 3, respectively) substantially reduced the plasma levels of cholesterol and triglycerides, mimicking the beneficial effects at levels comparable to the PLA2 (−/−) KO mice.

Example 6

Characterization Studies—ILY-4001 [2-(3-(2-AMINO-2-OXOACETYL)-1-(BIPHENYL-2-YLMETHYL)-2-METHYL-1H-INDOL-4-YLOXY)ACETIC ACID]

This example characterized ILY-4001 [2-(3-(2-amino-2-oxoacetyl)-1-(biphenyl-2-ylmethyl)-2-methyl-1H-indol-4-yloxy)acetic acid], alternatively referred to herein as methyl indoxam, with respect to activity, as determined by IC50 assay (Example 6A), with respect to cell absorption, as determined by in-vitro Caco-2 assay (Example 6B) and with respect to bioavailability, as determined using in-vivo mice studies (Example 6C).

Example 6A

IC-50 Study—ILY-4001 [2-(3-(2-AMINO-2-OXOACETYL)-1-(BIPHENYL-2-YLMETHYL)-2-METHYL-1H-INDOL-4-YLOXY)ACETIC ACID]

This example evaluated the IC50 activity value of ILY-4001 [2-(3-(2-amino-2-oxoacetyl)-1-(biphenyl-2-ylmethyl)-2-methyl-1H-indol-4-yloxy)acetic acid], alternatively referred to herein as methyl indoxam.

A continuous fluorimetric assay for PLA2 activity described in the literature was used to determine IC (Leslie, C C and Gelb, M H (2004) Methods in Molecular Biology "Assaying phospholipase A2 activity", 284: 229-242, Singer, A G, et al. (2002) Journal of Biological Chemistry "Interfacial kinetic and binding properties of the complete set of human and mouse groups I, II, V, X, and XII secreted phospholipases A2", 277: 48535-48549, Bezzine, S, et al. (2000) Journal of Biological Chemistry "Exogenously added human group X secreted phospholipase A(2) but not the group IB, IIA, and V enzymes efficiently release arachidonic acid from adherent mammalian cells", 275: 3179-3191) and references therein.

Figure 7A:
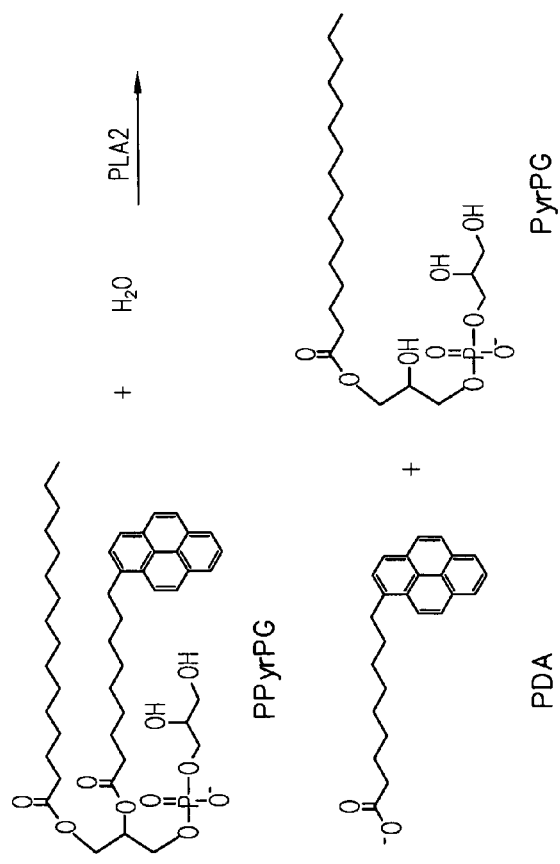
FIGS. 7A and 7B are a schematic representation (FIG. 7A) of an in-vitro fluorometric assay for evaluating PLA2 IB enzyme inhibition, and a graph (FIG. 7B) showing the results of Example 6A in which the assay was used to evaluate ILY-4001 [2-(3-(2-amino-2-oxoacetyl)-1-(biphenyl-2-ylmethyl)-2-methyl-1H-indol-4-yloxy)acetic acid].

Generally, this assay used a phosphatidylglycerol (or phosphatidylmethanol) substrate with a pyrene fluorophore on the terminal end of the sn-2 fatty acyl chain. Without being bound by theory, close proximity of the pyrenes from neighboring phospholipids in a phospholipid vesicle caused the spectral properties to change relative to that of monomeric pyrene. Bovine serum albumin was present in the aqueous phase and captured the pyrene fatty acid when it is liberated from the glycerol backbone owing to the PLA2-catalyzed reaction. In this assay, however, a potent inhibitor can inhibit the liberation of pyrene fatty acid from the glycerol backbone. Hence, such features allow for a sensitive PLA2 inhibition assay by monitoring the fluorescence of albumin-bound pyrene fatty acid, as represented in Scheme 1 shown in FIG. 7A. The effect of a given inhibitor and inhibitor concentration on any given phospholipase can be determined.

In this example, the following reagents and equipment were obtained from commercial vendors:
1. Porcine PLA2 IB
2. 1-hexadecanoyl-2-(1-pyrenedecanoyl)-sn-glycero-3-phosphoglycerol (PPyrPG)
3. 1-hexadecanoyl-2-(1-pyrenedecanoyl)-sn-glycero-3-phosphomethanol (PPyrPM)
4. Bovine serum albumin (BSA, fatty acid free)
5. 2-Amino-2-(hydroxymethyl)-1,3-propanediol, hydrochloride (Tris-HCl)
6. Calcium chloride
7. Potassium chloride
8. Solvents: DMSO, toluene, isopropanol, ethanol
9. Molecular Devices SPECTRAmax microplate spectrofluorometer
10. Costar 96 well black wall/clear bottom plate In this example, the following reagents were prepared:
1. PPyrPG (or PPyrPM) stock solution (1 mg/ml) in toluene:isopropanol (1:1)
2. Inhibitor stock solution (10 mM) in DMSO
3. 3% (w/v) bovine serum albumin (BSA)
4. Stock buffer: 50 mM Tris-HCl, pH 8.0, 50 mM KCl and 1 mM $CaCl_2$ In this example, the procedure was performed as follows:
1. An assay buffer was prepared by adding 3 ml 3% BSA to 47 ml stock buffer.
2. Solution A was prepared by adding serially diluted inhibitors to the assay buffer. Inhibitor were three-fold diluted in a series of 8 from 15 uM.
3. Solution B was prepared by adding PLA2 to the assay buffer. This solution was prepared immediately before use to minimize enzyme activity loss.
4. Solution C was prepared by adding 30 ul PPyrPG stock solution to 90 ul ethanol, and then all 120 ul of PPyrPG solution was transferred drop-wise over approximately 1 min to the continuously stirring 8.82 ml assay buffer to form a final concentration of 4.2 uM PPyrPG vesicle solution.
5. The SPECTRAmax microplate spectrofluorometer was set at 37° C.
6. 100 ul of solution A was added to each inhibition assay well of a costar 96 well black wall/clear bottom plate.
7. 100 ul of solution B was added to each inhibition assay well of a costar 96 well black wall/clear bottom plate.
8. 100 ul of solution C was added to each inhibition assay well of a costar 96 well black wall/clear bottom plate.
9. The plate was incubated inside the spectrofluorometer chamber for 3 min.
10. The fluorescence was read using an excitation of 342 nm and an emission of 395 nm.

In this example, the IC50 was calculated using the BioDataFit 1.02 (Four Parameter Model) software package. The equation used to generate the curve fit is:

$$y_j = \beta + \frac{\alpha - \beta}{1 + \exp(-\kappa(\log(x_j) - \gamma))}$$

wherein: $\alpha$ is the value of the upper asymptote; $\beta$ is the value of the lower asymptote; $\kappa$ is a scaling factor; $\gamma$ is a factor that locates the x-ordinate of the point of inflection at $$\exp\left[\frac{\kappa\gamma - \log\left(\frac{1+\kappa}{\kappa-1}\right)}{\kappa}\right]$$

with constraints $\alpha$, $\beta$, $\kappa$, $\gamma > 0$, $\beta < \alpha$, and $\beta < \gamma < \alpha$.

Figure 7B:
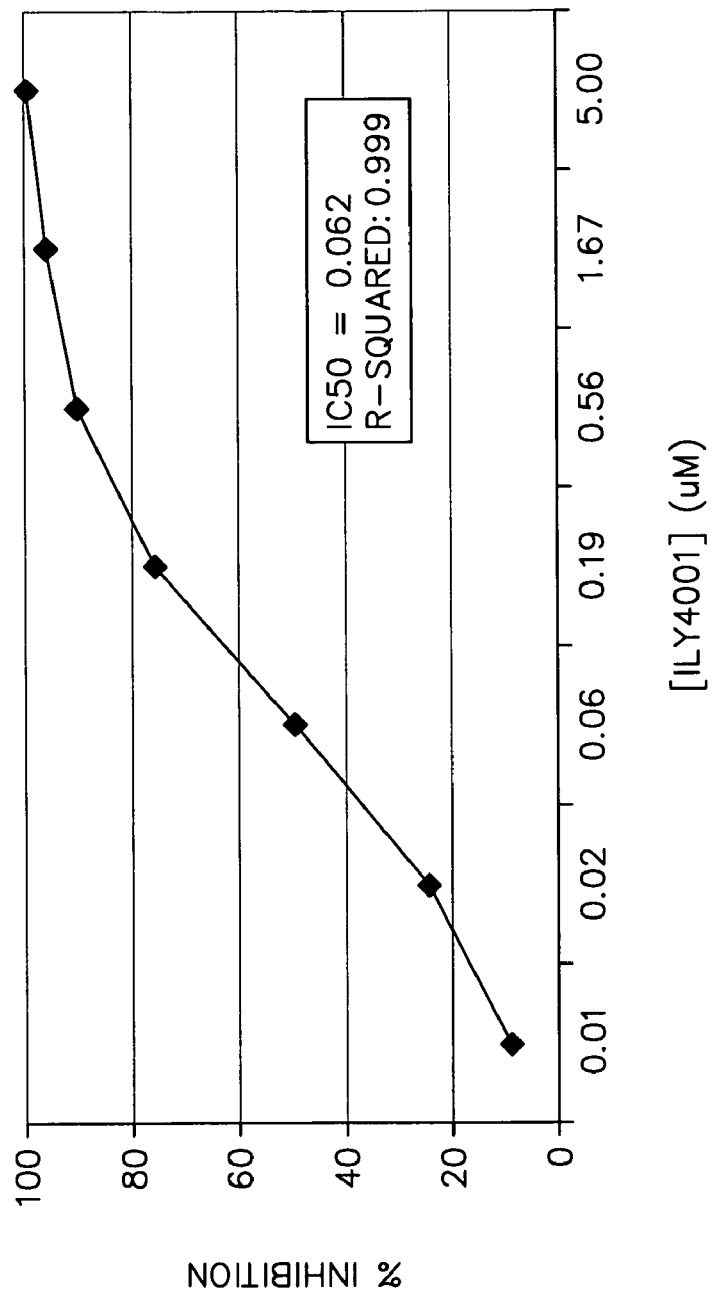

The results, shown in FIG. 7B, indicate that the concentration of ILY4001 resulting in 50% maximal PLA2 activity was calculated to be 0.062 uM.

Example 6B

Caco-2 Absorption Study—ILY-4001 [2-(3-(2-AMINO-2-OXOACETYL)-1-(BIPHENYL-2-YLMETHYL)-2-METHYL-1H-INDOL-4-YLOXY)ACETIC ACID]

This example evaluated the intestinal absorption of ILY-4001 [2-(3-(2-amino-2-oxoacetyl)-1-(biphenyl-2-ylmethyl)-2-methyl-1H-indol-4-yloxy)acetic acid], alternatively referred to herein as methyl indoxam using in-vitro assays with Caco-2 cells.

Briefly, the human colon adenocarcinoma cell line, Caco-2, was used to model intestinal drug absorption. It has been shown that the apparent permeability values measured in Caco-2 monolayers in the range of $1 \times 10^{-7}$ cm/sec or less typically correlate with relatively poor human absorption. (Artursson, P., K. Palm, et al. (2001). "Caco-2 monolayers in experimental and theoretical predictions of drug transport." *Adv Drug Deliv Rev* 46(1-3): 27-43.).

In order to determine the compound permeability, Caco-2 cells (ATCC) were seeded into 24-well transwells (Costar) at a density of $6\times10^4$ cells/cm$^2$. Monolayers were grown and differentiated in MEM (Mediatech) supplemented with 20% FBS, 100 U/ml penicillin, and 100 ug/ml streptomycin at 37° C., 95% humidity, 95% air, and 5% $CO_2$. The culture medium was refreshed every 48 hours. After 21 days, the cells were washed in transport buffer made up of HBSS with HEPES and the monolayer integrity was evaluated by measuring the trans-epithelial electrical resistance (TEER) of each well. Wells with TEER values of 350 ohm-cm$^2$ or better were assayed.

ILY-4001 and Propranolol (a transcellular transport control) were diluted to 50 ug/ml in transport buffer and added to the apical wells separately. 150 ul samples were collected for LC/MS analysis from the basolateral well at 15 min, 30 min, 45 min, 1 hr, 3 hr, and 6 hr time points; replacing the volume with pre-warmed transport buffer after each sampling. The apparent permeabilities in cm/s were calculated based on the equation:

$$P_{app}=(dQ/dt)\times(1/C_0)\times(1/A)$$

where dQ/dt is the permeability rate corrected for the sampling volumes over time, $C_0$ is the initial concentration, and A is the surface area of the monolayer (0.32 cm$^2$). At the end of the experiment, TEER measurements were retaken and wells with readings below 350 ohm-cm$^2$ indicated diminished monolayer integrity such that the data from these wells were not valid for analysis. Finally, wells were washed with transport buffer and 100 uM of Lucifer Yellow was added to the apical wells. 15 min, 30 min, and 45 min time points were sampled and analyzed by LC/MS to determine paracellular transport.

Figure 8A:
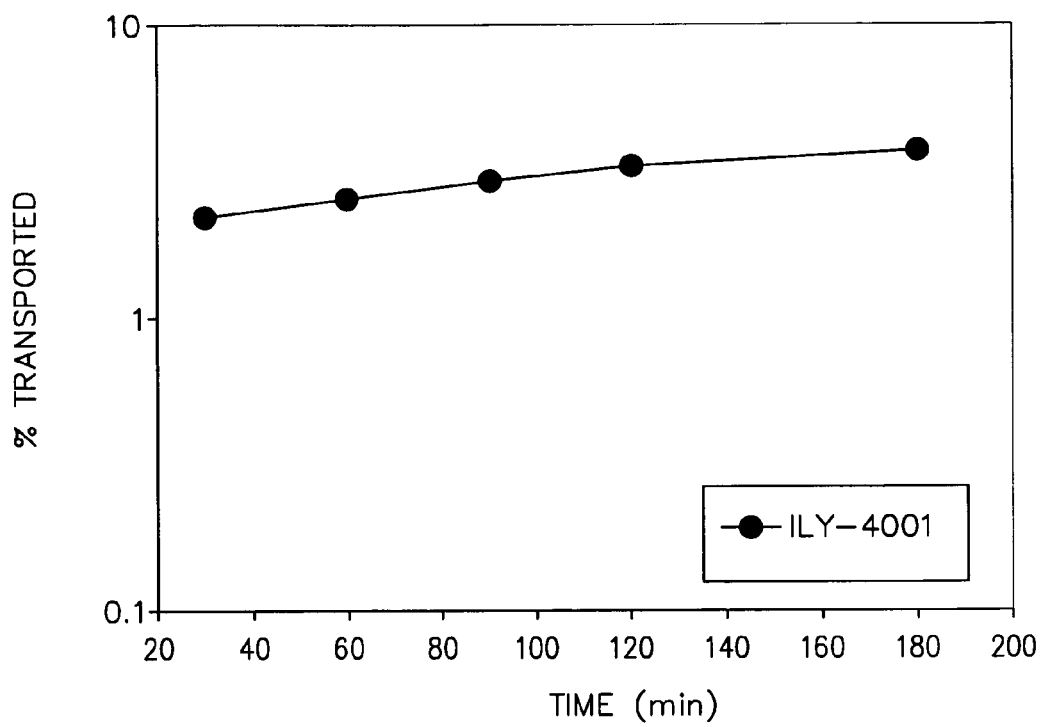
FIGS. 8A and 8B are graphs showing the results from the in-vitro Caco-2 permeability study of Example 6B for ILY-4001 [2-(3-(2-amino-2-oxoacetyl)-1-(biphenyl-2-ylmethyl)-2-methyl-1H-indol-4-yloxy)acetic acid] (FIG. 8A) and for Lucifer Yellow and Propranolol as paracellular and transcellular transport controls (FIG. 8B).
Figure 8B:
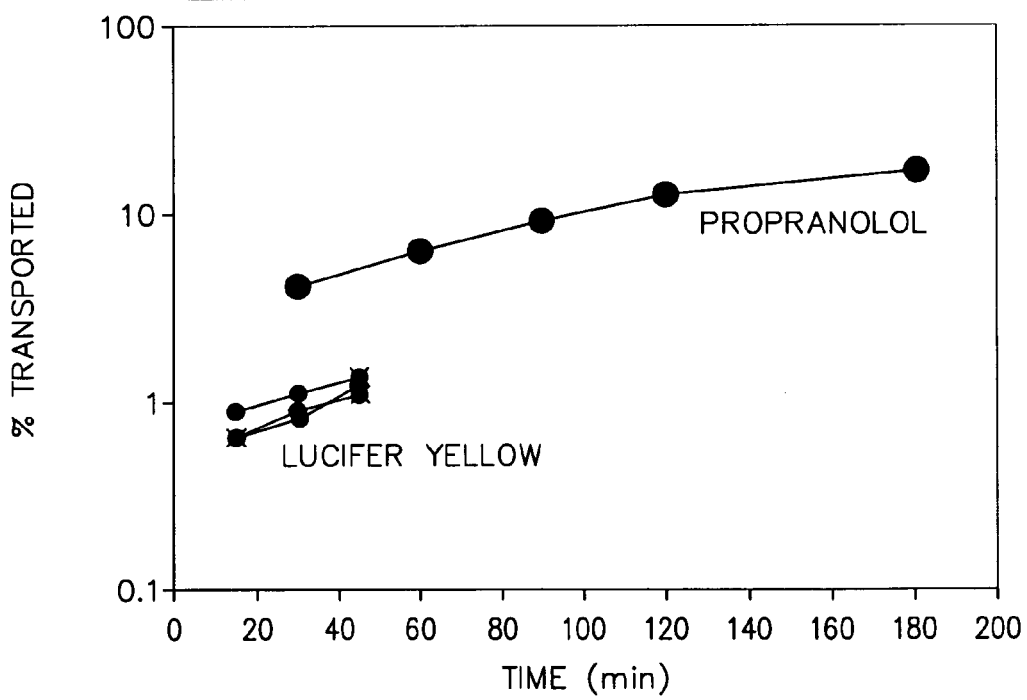

Results from the Caco-2 permeability study for ILY-4001 are shown in FIG. 8A, in which the apparent permeability (cm/s) for ILY-4001 was determined to be around $1.66\times10^{-7}$. The results for Lucifer Yellow and Propranolol permeability as paracellular and transcellular transport controls were also determined, and are shown in FIG. 8B, with determined apparent permeability (cm/s) of around $1.32\times10^{-5}$ for Propranolol and around $2.82\times10^{-7}$ +/− $0.37\times10^{-7}$ for Lucifer Yellow.

Example 6C

Pharmokinetic Study—ILY-4001 [2-(3-(2-AMINO-2-OXOACETYL)-1-(BIPHENYL-2-YLMETHYL)-2-METHYL-1H-INDOL-4-YLOXY)ACETIC ACID] (METHYL INDOXAM)

This example evaluated the bioavailability of ILY-4001 [2-(3-(2-amino-2-oxoacetyl)-1-(biphenyl-2-ylmethyl)-2-methyl-1H-indol-4-yloxy)acetic acid], alternatively referred to herein as methyl indoxam. Specifically, a pharmokinetic study was conducted to determine the fraction of unchanged ILY-4001 in systemic circulation following administration.

Bioavailability was calculated as a ratio of AUC-oral/AUC-intravenous (IV). To determine this ratio, a first set of subject animals were given a measured intravenous (IV) dose of ILY-4001, followed by a determination of ILY-4001 levels in the blood at various time points after administration (e.g., 5 minutes through 24 hours). Another second set of animals was similarly dosed using oral administration, with blood levels of ILY-4001 determined at various time points after administration (e.g., 30 minutes through 24 hours). The level of ILY-4001 in systemic circulation were determined by generally accepted methods (for example as described in Evans, G., A Handbook of Bioanalysis and Drug Metabolism. Boca Raton, CRC Press (2004)). Specifically, liquid scintillation/mass spectrometry/mass spectrometry (LC/MS/MS) analytical methods were used to quantitate plasma concentrations of ILY-4001 after oral and intravenous administration. Pharmacokinetic parameters that were measured include $C_{max}$, AUC, $t_{max}$, $t_{1/2}$, and F (bioavailability).

In this procedure, ILY-4001 was dosed at 3 mg/kg IV and 30 mg/kg oral. The results of this study, summarized in Table 5, showed a measured bioavailability of 28% of the original oral dose. This indicated about a 72% level of non-absorption of ILY-4001 from the GI tract into systemic circulation.

TABLE 5

Results of Pharmokinetic Study for ILY-4001

| | IV | ORAL |
| --- | --- | --- |
| t½ (h) | 1.03 | 1.25 |
| Cmax (ng/mL) | 3168 | 2287 |
| Tmax (h) | 0.083 | 1 |
| AUC 0-24) (h * ng/mL) | 2793 | 5947 |
| AUC(0-inf) (h * ng/mL) | 2757 | 5726 |
| % F | | 28.0 |

Example 7

Synthesis of Multivalent Indole and Indole Related Compounds

This example shows the preparation of multivalent indole or indole-related compounds comprising two or more indole or indole-related moieties (e.g., phospholipase inhibiting moieties) each covalently linked to a multifunctional bridge moiety.

Example 7.1

(Intermediate) TERT-BUTYL 2-(3-(2-AMINO-2-OXOACETYL)-1-(8-BROMOOCTYL)-2-METHYL-1H-INDOL-4-YLOXY)ACETATE

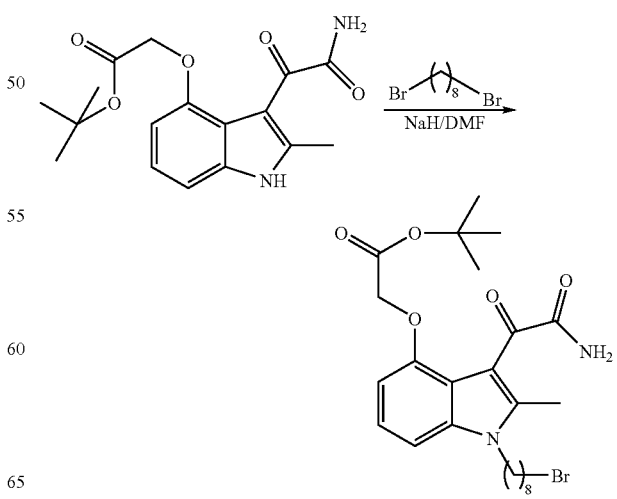

tert-Butyl 2-(3-(2-amino-2-oxoacetyl)-1-(8-bromooctyl)-2-methyl-1H-indol-4-yloxy)acetate was prepared as follows, as a starting material for later examples:

A solution of the starting indole (3.3 g, 10 mmol) in 10 mL of anhydrous DMF was cooled in an ice bath and dry sodium hydride (290 mg, 12 mmol, 1.2 equiv) was added. After stirring under nitrogen for 30 min at 0° C., the mixture was transferred dropwise into a solution of 1,8-dibromooctane (2.2 mL, 3.3 g, 12 mmol, 1.2 equiv) in 5 mL of anhydrous DMF also cooled in an ice bath. The resulting orange mixture was stirred under nitrogen for 4 h at 0° C., and it was then allowed to warm to RT. After an overnight stirring at RT, the reaction mixture was quenched with 15 mL of NH$_4$Cl and concentrated under reduced pressure. It was then diluted with 100 mL of DCM, washed with NH$_4$Cl (40 mL) and twice with brine (2×40 mL), dried over MgSO$_4$ and concentrated in vacuo to afford the crude product as an orange oil. Purification by flash-chromatography (H/EA: 3/2, 1/1 then 2/3) yielded pure bromoalkyl (2.6 g, 50%) as a yellow solid.

$^1$H NMR (CD$_3$OD, 300 MHz): δ 7.10 (dd, 1H, J=9.0, 8.1 Hz, H-6), 7.08 (dd, 1H, J=8.1, 1.5 Hz, H-5), 6.44 (dd, 1H, J=9.0, 1.5 Hz, H-7), 4.63 (s, 2H, H-10), 4.17 (t, 2H, J=7.5 Hz, H-14), 3.41 (t, 2H, J=6.9 Hz, H-15), 2.60 (s, 3H, H-9), 1.80-1.75 (m, 4H, H-16+H-17), 1.44 (s, 9H, C(CH$_3$)$_3$), 1.41-1.33 (m, 8H, CH$_2$). $^{13}$C NMR (CD$_3$OD, 75.5 MHz): δ 188.8 (12), 170.2 (11), 169.2 (13), 152.0 (4), 145.2 (1), 138.0 (8), 123.1 (3), 116.7 (6), 110.1 (5), 104.1 (7+2), 82.1 (C(CH$_3$)$_3$), 65.6 (10), 43.3 (14), 33.2 (15), 32.7 (17), 29.4 (16), 29.0 (CH$_2$), 28.5 (CH$_2$), 27.8 (CH$_2$), 27.1 (C(CH$_3$)$_3$), 26.6 (CH$_2$), 10.7 (9). MS (ESI, MeOH): m/z 545.2 [M+Na]$^+$ (100%, $^{79}$Br isotope), 547.2 [M+Na]$^+$ (97%, $^{81}$Br isotope).

Example 7.2

(Intermediate) Synthesis of TERT-BUTYL 2-(3-(2-AMINO-2-OXOACETYL)-1-(12-BROMODODE-CYL)-2-METHYL-1H-INDOL-4-YLOXY)AC-ETATE

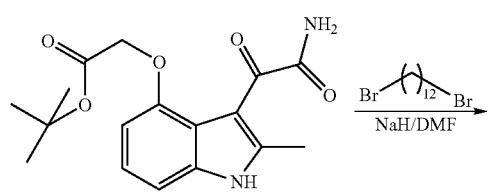

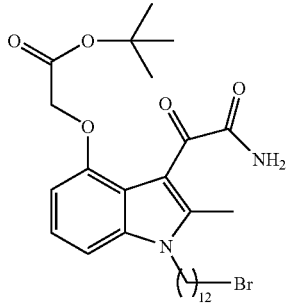

tert-Butyl 2-(3-(2-amino-2-oxoacetyl)-1-(12-bromododecyl)-2-methyl-1H-indol-4-yloxy)acetate was prepared as follows as a starting material for use in other examples.

The starting indole intermediate (2.54 g, 7.65 mmole) in dry DMF (10 mL), at 0° C. under nitrogen, had 95% sodium hydride (0.233 g., 9.22 mmole) added. The dark mixture was stirred at 0° C. for 0.5 h and then added dropwise over 10 minutes to a solution of 1,12-dibromododecane (4.5 g, 13.71 mmole) in dry DMF (20 mL) at 0° C. The mixture was stirred at 0° C. for 5 h and at room temperature for 19 h. The reaction was cooled to 0° C., quenched with ammonium chloride solution (10 mL), and diluted with dichloromethane (100 mL). The mixture was washed with ammonium chloride solution (50 mL) and the aqueous phase extracted with dichloromethane (4×25 mL). The combined organic phase was washed with brine (100 mL), dried (Na$_2$SO$_4$), filtered and evaporated to a red/brown liquid which was further evaporated under high vacuum. The residue was a thick red/brown semi-solid, which was purified by chromatography over silica gel, using chloroform/hexanes (8:1) as the eluant, gave the product as an orange/brown semi-solid (2.00 g, 45%).

Example 7.3

Compound (5-27)

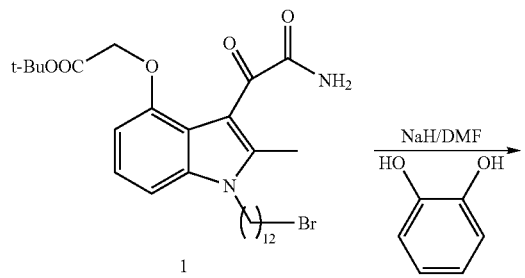

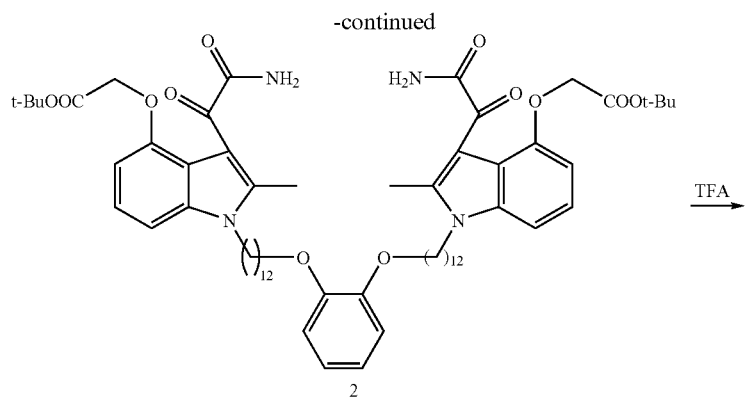

First, the t-Bu protected compound, [3-Aminooxalyl-1-(12-{2-[12-(3-aminooxalyl-4-tert-butoxycarbonylmethoxy-2-methyl-indol-1-yl)-dodecyloxy]-phenoxy}-dodecyl)-2-methyl-1H-indol-4-yloxy]-acetic acid tert-butyl ester, 2 was prepared as follows.

Catechol (0.054 g, 0.49 mmole) in dry DMF (6 mL), at 0° C. under nitrogen, had 95% sodium hydride (0.027 g, 1.08 mmole) added. The mixture was stirred at 0° C. for 0.5 h and then the bromide 1 (0.600 g, 1.03 mmole) (prepared as in Example 11B) in dry DMF (7 mL) was added over 3 minutes. The mixture was stirred at 0° C. for 8 h and slowly warmed to room temperature overnight. The mixture was cooled to 0° C., quenched with ammonium chloride solution (5 mL), diluted with dichloromethane (100 mL) and ammonium chloride (45 mL). The organic phase was separated and the aqueous phase extracted with dichloromethane (6×50 mL). The combined organic phase was evaporated to near dryness, dissolved in dichloromethane (100 mL) and washed with water (50 mL). The aqueous phase was extracted with dichloromethane (2×50 mL). The combined organic phase was dried (Na$_2$SO$_4$), filtered and evaporated to a red/brown semi-solid. Purification by chromatography over silica gel, using chloroform/hexanes (7:1 to 4:1) as the eluant, gave the product as an orange/brown semi-solid (0.029 g, 5%).

The diester 2 in above scheme was deprotected to form [3-Aminooxalyl-1-(12-{2-[12-(3-aminooxalyl-4-carboxymethoxy-2-methyl-indol-1-yl)-dodecyloxy]-phenoxy}-dodecyl)-2-methyl-1H-indol-4-yloxy]-acetic acid, 3 (Compound 5-27) as follows.

The diester 2 (0.029 g, 0.026 mmole) and 1,3-dimethoxybenzene (0.02 ml, 0.152 mmole) in dry dichloromethane (3 mL), at room temperature under nitrogen, had trifluoroacetic acid (3 mL, 38.9 mmole) added. The solution was stirred for 1 h and the solvents evaporated below 25° C. The residue was triturated with ether (10 mL) and the solid removed by filtration. The solid was washed with ether (20 mL) and dried in vacuo to give the desired compound as a beige solid (0.012 g, 46%).

$^1$H nmr (400 MHz, DMSO-d$_6$) δ 7.71 (brs, 2H), 7.38 (brs, 2H), 7.11 (dd, 2H), 7.06 (dd, 2H), 6.91 (m, 2H), 6.83 (m, 2H), 6.51 (d, 2H), 4.62 (s, 4H), 4.14 (m, 4H), 3.90 (m, 4H), 2.54 (s, 6H), 1.66 (m, 8H), 1.40 (m, 4H), 1.28, 1.23 (2m, 28H). MS (ES+) 1017.58 (M+Na), 996.51 (M+1), 995.54 (M).

Example 7.4

Compound (5-25)

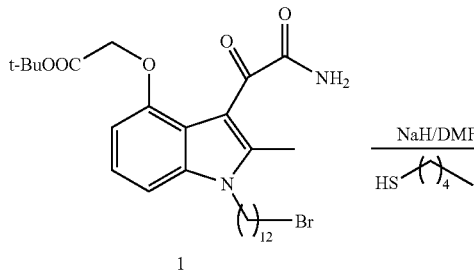

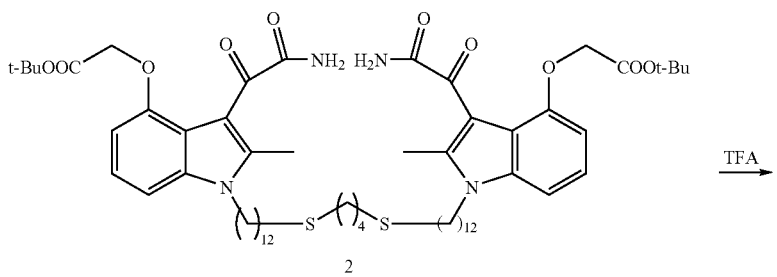

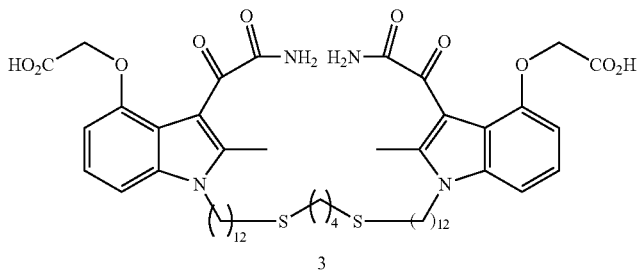

The t-Bu protected compound, tert-Butyl 2,2'-(1,1'-(12,12'-(butane-1,4-diylbis(sulfanediyl))bis(dodecane-12,1-diyl))bis(3-(2-amino-2-oxoacetyl)-2-methyl-1H-indole-4,1-diyl))bis(oxy)diacetate, 2 was first prepared as follows.

1,4-Butanedithiol (0.06 mL, 0.51 mmole) was added to 95% sodium hydride (0.028 g, 1.10 mmole) in dry DMF (4 mL), at 0° C. under nitrogen. After 0.5 h this mixture was added to the bromide 1 (0.602 g, 1.03 mmole) (prepared as in Example 11B) in dry DMF (6 mL), at 0° C. under nitrogen. The reaction was maintained at 0° C. for 9 h and slowly warmed to room temperature overnight. The mixture was cooled to 0° C., quenched with ammonium chloride solution (5 mL), diluted with dichloromethane (50 mL) and ammonium chloride solution (40 mL). The organic phase was separated and the aqueous phase extracted with dichloromethane (5×40 mL). The combined organic phase was washed with brine (50 mL), dried ($Na_2SO_4$), filtered and evaporated to a red/brown syrup. Purification by chromatography over silica gel, using chloroform/ethyl acetate (2:1 to 1:1) as the eluant, gave the product as an orange/brown semi-solid (0.224 g, 39%).

The resulting diester 2 in above scheme was then deprotected to form 2,2'-(1,1'-(12,12'-(Butane-1,4-diylbis(sulfanediyl))bis(dodecane-12,1-diyl))bis(3-(2-amino-2-oxoacetyl)-2-methyl-1H-indole-4,1-diyl))bis(oxy)diacetic acid, 3 (Compound 5-25)

The diester 2 (0.051 g, 0.045 mmole) and 1,3-dimethoxybenzene (0.02 ml, 0.152 mmole) in dry dichloromethane (2 mL), at room temperature under nitrogen, had trifluoroacetic acid (2 mL, 25.9 mmole) added. The solution was stirred for 1 h and the solvents evaporated below 25° C. The residue was triturated with ether (20 mL) and the solid removed by filtration. The solid was washed with ether (20 mL) and stirred with ether (7 mL) for 1 h. The product was removed by filtration and dried in vacuo to give the desired compound as a beige solid (0.029 g, 64%).

[1]H nmr (400 MHz, DMSO-$d_6$) δ 7.71 (brs, 2H), 7.38 (brs, 2H), 7.12 (dd, 2H), 7.07 (dd, 2H), 6.52 (d, 2H), 4.62 (s, 4H), 4.15 (m, 4H), 2.54 (s, 6H), 2.45 (m, 8H), 1.66 (m, 4H), 1.57 (m, 4H), 1.48 (m, 4H), 1.29, 1.23 (2m, 32H). MS (ES+) 1030.35 (M+Na), 1008.35 (M+1), 1007.39 (M).

Example 7.5

Compound (5-26)

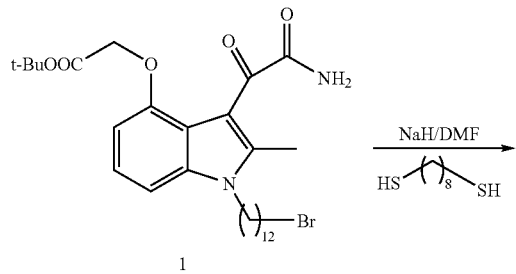

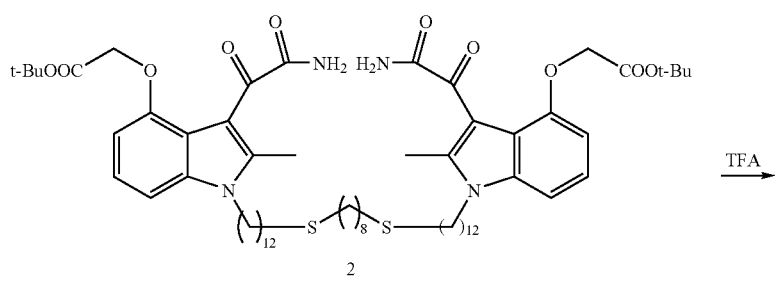

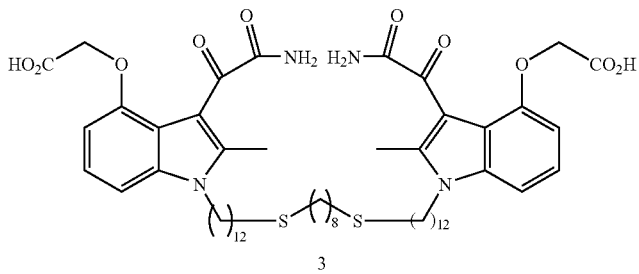

The t-Bu protected compound tert-Butyl 2,2'-(1,1'-(12,12'-(octane-1,8-diylbis(sulfanediyl))bis(dodecane-12,1-diyl)) bis(3-(2-amino-2-oxoacetyl)-2-methyl-1H-indole-4,1-diyl)) bis(oxy)diacetate, 2 was prepared as follows.

1,8-Octanedithiol (0.115 mL, 0.62 mmole) was added to 95% sodium hydride (0.035 g, 1.38 mmole) in dry DMF (3 mL), at 0° C. under nitrogen. After 0.5 h this mixture was added to the bromide 1 (0.760 g, 1.31 mmole) (prepared as in Example 11B) in dry DMF (9 mL), at 0° C. under nitrogen. The reaction was maintained at 0° C. for 9 h and slowly warmed to room temperature overnight. The mixture was cooled to 0° C., quenched with ammonium chloride solution (10 mL), diluted with dichloromethane (100 mL) and washed with ammonium chloride solution (2×50 mL). The organic phase was separated and the aqueous phase extracted with dichloromethane (3×30 mL). The combined organic phase was dried ($Na_2SO_4$), filtered and evaporated to a brown syrup. Purification by chromatography over silica gel, using chloroform/ethyl acetate (2:1 to 1:1) as the eluant, gave the product as yellow solid (0.422 g, 58%).

The resulting diester 2 in the above schema was deprotected to form 2,2'-(1,1'-(12,12'-(Octane-1,8-diylbis(sulfanediyl))bis(dodecane-12,1-diyl))bis(3-(2-amino-2-oxoacetyl)-2-methyl-1H-indole-4,1-diyl))bis(oxy)diacetic acid, 3 (Compound 5-26) as follows.

The diester 2 (0.092 g, 0.078 mmole) and 1,3-dimethoxybenzene (0.04 ml, 0.312 mmole) in dry dichloromethane (3 mL), at room temperature under nitrogen, had trifluoroacetic acid (3 mL, 38.9 mmole) added. The solution was stirred for 2 h and the solvents evaporated below 25° C. The residue was triturated with ether (30 mL) and the solid removed by filtration. The solid was washed with ether (20 mL) and stirred with ether (6 mL) for 1 h. The product was removed by filtration washed with ether (20 mL) and dried in vacuo to give the desired compound as a beige solid (0.060 g, 72%).

$^1$H nmr (400 MHz, DMSO-$d_6$) δ 7.71 (brs, 2H), 7.38 (brs, 2H), 7.12 (dd, 2H), 7.08 (dd, 2H), 6.52 (d, 2H), 4.63 (s, 4H), 4.16 (m, 4H), 2.55 (s, 6H), 2.45 (m, 8H), 1.66 (m, 4H), 1.49 (m, 8H), 130, 1.23 (2m, 40H). MS (ES+) 1064.42 (M+1), 1063.45 (M).

Example 7.6

Compound (5-24)

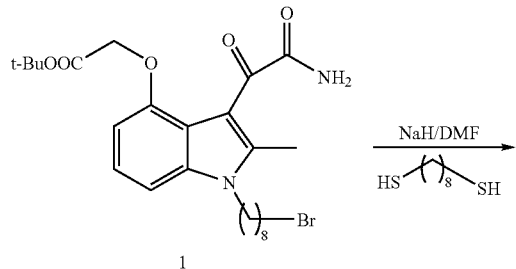

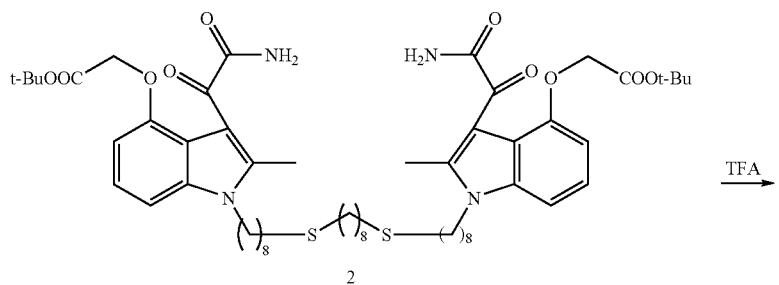

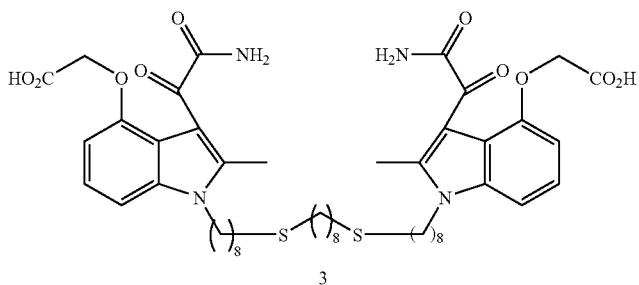

The t-Bu protected compound tert-Butyl 2,2'-(1,1'-(8,8'-(octane-1,8-diylbis(sulfanediyl))bis(octane-8,1-diyl))bis(3-(2-amino-2-oxoacetyl)-2-methyl-1H-indole-4,1-diyl))bis(oxy)diacetate, 2 was prepared as follows.

1,8-Octanedithiol (0.73 mL, 3.94 mmole) was added to sodium hydride (0.21 g, 8.75 mmole) in dry DMF (12 mL), at 0° C. under nitrogen. After 0.5 h this mixture was added to the bromide 1 (4.3 g, 8.21 mmole) (prepared as in Example 11A) in dry DMF (20 mL), at 0° C. under nitrogen. The reaction was maintained at 0° C. for 8 h and stored in the freezer overnight. The mixture was cooled to 0° C., quenched with ammonium chloride solution (15 mL), diluted with dichloromethane (100 mL) and washed with ammonium chloride solution (50 mL). The organic phase was separated and the aqueous phase extracted with dichloromethane (2×25 mL). The combined organic phase was washed with brine (75 mL) dried (Na$_2$SO$_4$), filtered and evaporated to a yellow/orange syrup. Purification by chromatography over silica gel, using chloroform/ethyl acetate (2:1 to 3:2) as the eluant, gave the product as yellow solid (2.79 g, 32%).

The resulting diester 2 in the above schema was deprotected to form 2,2'-(1,1'-(8,8'-(Octane-1,8-diylbis(sulfanediyl))bis(octane-8,1-diyl))bis(3-(2-amino-2-oxoacetyl)-2-methyl-1H-indole-4,1-diyl))bis(oxy)diacetic acid, 3 (Compound 5-24) as follows.

The diester 2 (1.97 g, 1.85 mmole) and 1,3-dimethoxybenzene (0.74 mL, 5.65 mmole) in dry dichloromethane (20 mL), at room temperature under nitrogen, had trifluoroacetic acid (20 mL, 38.9 mmole) added. The solution was stirred for 1 h and the solvents evaporated below 25° C. The residue was triturated with ether (50 mL) and the solid removed by filtration and washed with ether (100 mL). The solid was triturated with ether (50 mL), filtered and washed with ether (50 mL). The product was dried in vacuo to give the desired compound as a beige solid (1.57 g, 89%).

$^1$H nmr (400 MHz, DMSO-d$_6$) δ 7.70 (brs, 2H), 7.38 (brs, 2H), 7.13 (dd, 2H), 7.08 (dd, 2H), 6.52 (d, 2H), 4.63 (s, 4H), 4.15 (m, 4H), 2.54 (s, 6H), 2.44 (m, 8H), 1.66 (m, 4H), 1.48 (m, 8H), 1.29, 1.26 (2m, 24H). MS (ES+) 952.26 (M+1), 951.26 (M).

Example 7.7a

Compound (5-28)

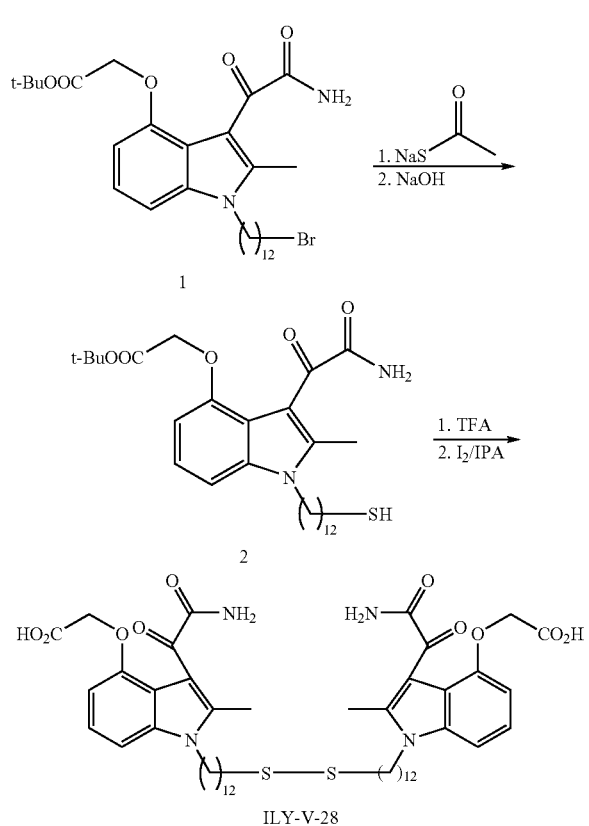

Example 7.7b

Compound (5-28)

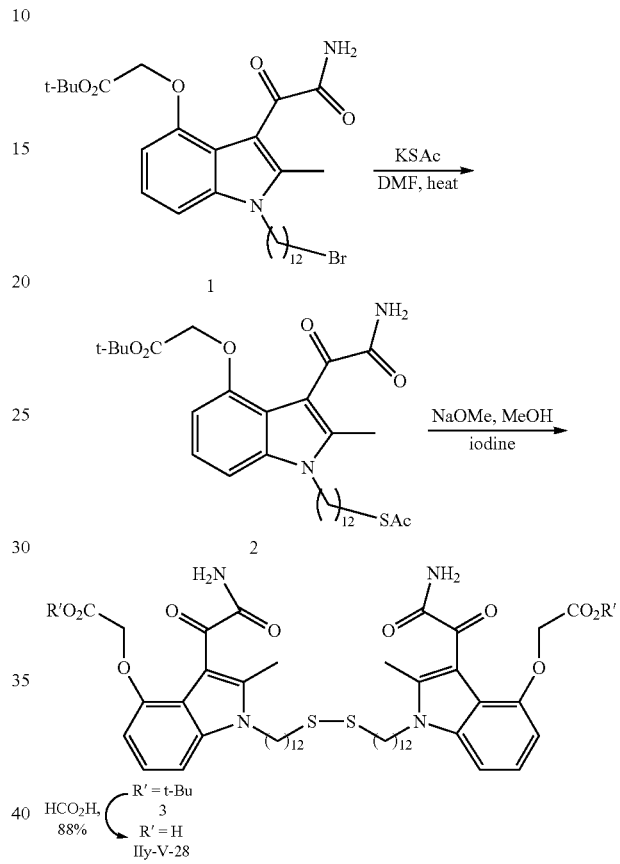

2,2'-(1,1'-(12,12'-disulfanediylbis(dodecane-12,1-diyl)) bis(3-(2-amino-2-oxoacetyl)-2-methyl-1H-indole-4,1-diyl)) bis(oxy)diacetic acid (ILY-V-28) To the solution of (1 mmol) of 1 in 30 mL of EtOH is added 1.1 mmol of thioacetate sodium salt. This mixture is stirred for 12 hour and then the reaction is heated to 45° C. To the resulted yellow solution 2 mL of 10% NaOH solution is added and stirred for an additional 8 hours. After the reaction is cooled to rt, solvent is removed and extracted with EtOAc. The resulted mixture is washed with water, brine, and dried over MgSO$_4$ to obtain a crude product. To the solution of (1 mmol) of the crude product in 15 mL of CH$_2$Cl$_2$ is added 2 mL of trifluoroacetic acid. This mixture is stirred for 1.5 hour, the solvent is evaporated at reduced pressure, and the residue is diluted with EtOAc and water. The organic phase is washed with brine, dried over MgSO$_4$, evaporated at reduced pressure, and purified by column chromatography to obtain the deprotected compound. To a solution of the deprotected compound (1 mmol) in isopropanol (10 mL) is added iodine (127 mg, 0.5 mmol). After 2 hours, the reaction mixture is concentrated and redissolved in EtOAc (25 mL). The solution is washed with Na$_2$S$_2$O$_4$ (2×10 mL) and brine (10 mL), is dried over sodium sulfate, filtered, and is concentrated in vacuo. The product is to be purified by column chromatography to provide disulfide ILY-V-28.

[3-Aminooxalyl-1-(12-methoxycarbonylsulfanyl-dodecyl)-2-methyl-1H-indol-4-yloxy]-acetic acid tert-butyl ester (2): A mixture of [3-aminooxalyl-1-(12-bromo-dodecyl)-2-methyl-1H-indol-4-yloxy]-acetic acid tert-butyl ester (1) (0.18 g, 0.32 mmol) and potassium acetate (0.036 g, 0.32 mmol) were heated in dry DMF (5 mL) at 70° C. for 5 h under N$_2$. The mixture was cooled and concentrated to dryness under high vacuum. The resulted syrup was suspended in saturated aqueous NH$_4$Cl solution and then extracted with EtOAc (10×3 mL). The combined organic layers were washed with water (10×2 mL) and dried (Na$_2$SO$_4$). The solvent was removed under reduced pressure, and the residue was chromatographed on a silica gel column eluting with 70% ethyl acetate in hexane to afford intermediate 2 as colorless syrup. Yield: 0.18 g, 98%.

(3-Aminooxalyl-1-{12-[11-(3-aminooxalyl-4-tert-butoxycarbonylmethoxy-2-methyl-indol-1-yl)-undecyldisulfanyl]-dodecyl}-2-methyl-1H-indol-4-yloxy)-acetic acid tert-butyl ester (3): A mixture of intermediate (2) (0.10 g, 0.17 mmol) in dry MeOH (5 mL) and a catalytic amount of iodine (0.001 g) was treated with 1N NaOMe methanol solution. The mixture was stirred at room temperature for 18 h. The solvent was removed and the residue was chromatographed on a silica gel column eluting with 70% ethyl acetate in hexane to afford intermediate 3 as an off-white solid. Yield: 0.07 g, 38%.

(3-Aminooxalyl-1-{12-[11-(3-aminooxalyl-4-carboxymethoxy-2-methyl-indol-1-yl)-undecyldisulfanyl]-dodecyl}-2-methyl-1H-indol-4-yloxy)-acetic acid (Ily-V-28): A mixture of intermediate (3) (0.06 g, 0.056 mmol) in aqueous HCO$_2$H (88%, 2 mL) was stirred at room temperature for 6 h. The mixture was concentrated to dryness under high vacuum and co-evaporated with water (2×2 mL). The flask containing the gummy material was then transferred to freeze dryer and was kept under high vacuum overnight to get the title compound Ily-V-28 as a pale green solid. Yield: 0.05 g, 92%. $^1$H NMR: (DMSO-d$_6$), δ, ppm: (5-37-159) δ 7.72 (bs, 1H), 7.41 (bs, 1H), 7.17 (t, 1H), 7.10 (t, 1H), 6.46 (d, 1H), 4.62 (s, 2H), 4.08 (t, 3H), 2.62 (t, 2H), 2.45 (s, 3H), 1.70-1.60 (m, 2H), 1.48-1.41 (m, 2H), 1.38-1.15 (m, 40H). ES-MS: m/z=951.3 (M+1)

Example 7.8a

Compound (5-29)

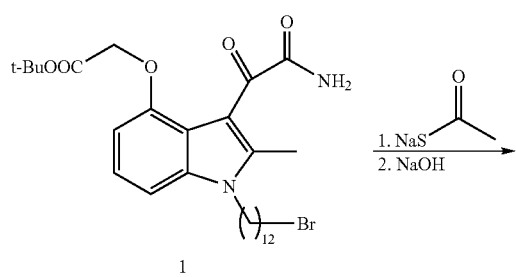

1

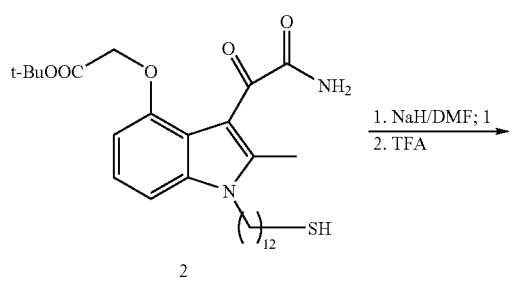

2

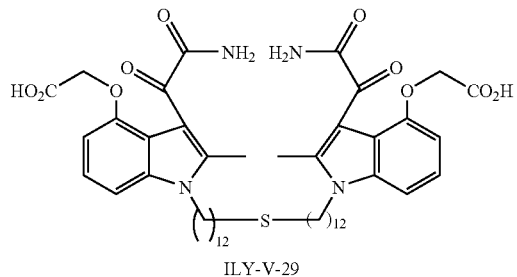

ILY-V-29

2,2'-(1,1'-(12,12'-thiobis(dodecane-12,1-diyl))bis(3-(2-amino-2-oxoacetyl)-2-methyl-1H-indole-4,1-diyl))bis(oxy)diacetic acid (ILY-V-29) To the solution of (1 mmol) of 1 in 30 mL of EtOH is added 1.1 mmol of thioacetate sodium salt. This mixture is stirred for 12 hour and then the reaction is heated to 45° C. To the resulted yellow solution 2 mL of 10% NaOH solution is added and stirred for an additional 8 hours. After the reaction is cooled to rt, solvent is removed and extracted with EtOAc. The resulting mixture is to be washed with water, brine, and dried over MgSO$_4$ to obtain a crude product of. The material then is purified by column chromatography to give 2.

Compound 2 (0.9 mmole) is added to sodium hydride (1.2 mmole) in dry DMF (12 mL), at 0° C. under nitrogen. After 0.5 h this mixture is added to the bromide 1 (0.95 mmole) in dry DMF (20 mL), at 0° C. under nitrogen. The reaction is maintained at 0° C. for 8 h and quenched with ammonium chloride solution (15 mL), diluted With dichloromethane (100 mL) and washed with ammonium chloride solution (50 mL). The organic phase is separated and the aqueous phase extracted with dichloromethane (2×25 mL). The combined organic phase is washed with brine (75 mL) dried (Na$_2$SO$_4$), filtered and evaporated to a yellow/orange syrup. Purification by chromatography over silica gel, using chloroform/ethyl acetate as the eluant, can give the protected dimer product.

The dimer product (0.9 mmole) and 1,3-dimethoxybenzene (3 mmole) in dry dichloromethane (20 mL), at room temperature under nitrogen, is added with trifluoroacetic acid (10 mL). The solution is stirred for 1 h and the solvents evaporated below 25° C. The residue is triturated with ether (50 mL) and the solid is removed by filtration and is washed with ether (100 mL). The solid is triturated with ether (50 mL), filtered and washed with ether (50 mL). The product is dried in vacuo to give ILY-V-29.

Example 7.8b

Compound (5-29)

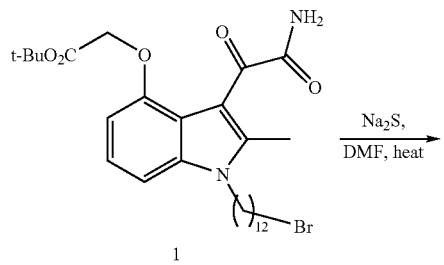

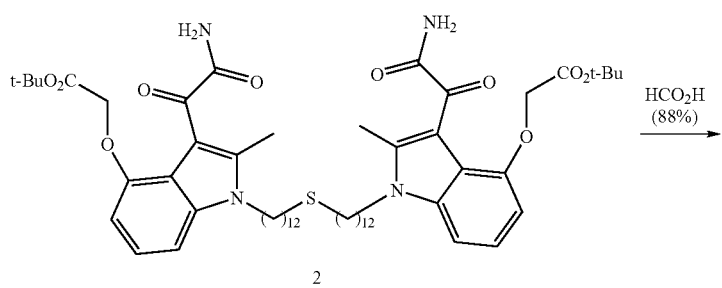

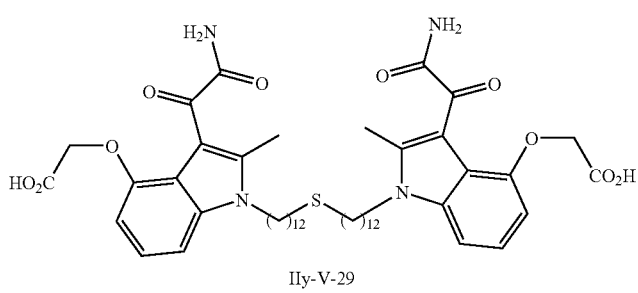

(3-Aminooxalyl-1-{12-[12-(3-aminooxalyl-4-tert-butoxycarbonylmethoxy-2-methyl-indoyl-1-yl)-dodecylsulfanyl]-dodecyl}-2-methyl-1H-4-yloxy-acetic acid tert-butyl ester (2): A mixture of [3-aminooxalyl-1-(12-bromo-dodecyl)-2-methyl-1H-indol-4-yloxy]-acetic acid tert-butyl ester (1) (0.285 g, 0.38 mmol) and sodium sulfide (0.01 g, 0.12 mmol) were heated in dry DMF (5 mL) at 70° C. for 5 h under $N_2$. The reaction mixture was cooled and concentrated. The resulted syrup was suspended in saturated aqueous $NH_4Cl$ solution, extracted with $CH_2Cl_2$ (10×3 mL) and the combined organic layers were washed with water (5×2 mL) and dried over $Na_2SO_4$. The solvent was removed under reduced pressure, and the residue was chromatographed on a silica gel column, eluting with 70% ethyl acetate in hexanes to afford intermediate 5 as an off-white solid. Yield: 0.13 g, 96%.

(3-Aminooxalyl-1-{12-[12-(3-aminooxalyl-4-carboxymethoxy-2-methyl-indol-1-yl)-dodecylsulfanyl]-dodecyl}-2-methyl-1H-indol-4-yloxy)-acetic acid (Ily-V-29): A solution of intermediate (2) (0.04 g, 0.038 mmol) in aqueous $HCO_2H$ (88%, 2 mL) was stirred at room temperature for 6 h. The mixture was concentrated to dryness under high vacuum and co-evaporated with water (2×2 mL). The flask containing the gummy material was then transferred to freeze dryer and was kept under high vacuum overnight to get the title compound Ily-V-29 as a pale yellow powder. Yield: 0.03 g, 90% $^1$H NMR: (DMSO-$d_6$), δ, ppm: (5-37-145) δ 7.70 (bs, 1H), 7.40 (bs, 1H), 7.15 (t, 1H), 7.10 (t, 1H), 6.46 (d, 1H), 4.62 (s, 2H), 4.18 (t, 3H), 2.45 (s, 3H), 2.20 (t, 2H), 1.70-1.60 (m, 2H), 1.48-1.41 (m, 2H), 1.39-1.15 (m, 40H). ES-MS: m/z=920.3 (M+1)

Example 7.9a

Compound (5-30)

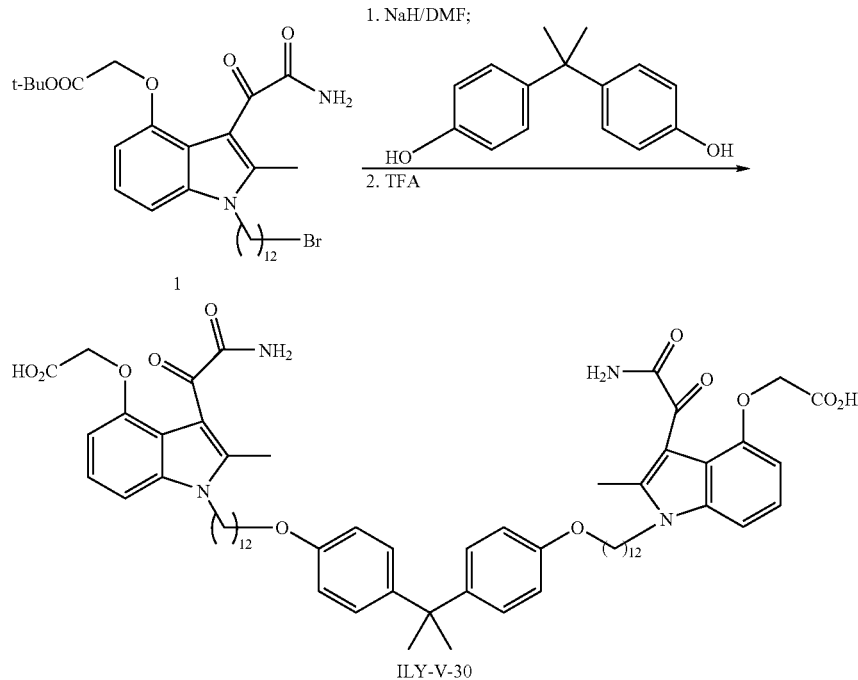

2,2'-(1,1'-(12,12'-(4,4'-(propane-2,2-diyl)bis(4,1-phenylene))bis(oxy)bis(dodecane-12,1-diyl))bis(3-(2-amino-2-oxoacetyl)-2-methyl-1H-indole-4,1-diyl))bis(oxy)diacetic acid (ILY-V-30) Bisphenol A (1 mmole) is added to sodium hydride (2.2 mmole) in dry DMF (12 mL), at 0° C. under nitrogen. After 0.5 h this mixture is added to the bromide 1 (2.05 mmole) in dry DMF (20 mL), at 0° C. under nitrogen. The reaction is maintained at 0° C. for 8 h and quenched with ammonium chloride solution (15 mL), diluted with dichloromethane (100 mL) and is washed with ammonium chloride solution (50 mL). The organic phase is separated and the aqueous phase extracted with dichloromethane (2×25 mL). The combined organic phase is washed with brine (75 mL) dried ($Na_2SO_4$), filtered and evaporated to a yellow/orange syrup. Purification by chromatography over silica gel, using chloroform/ethyl acetate as the eluant, give the protected dimer product.

The dimer product (0.9 mmole) and 1,3-dimethoxybenzene (3 mmole) in dry dichloromethane (20 mL), at room temperature under nitrogen, is added with trifluoroacetic acid (10 mL). The solution is stirred for 1 h and the solvents evaporated below 25° C. The residue is triturated with ether (50 mL) and the solid is removed by filtration and is washed with ether (100 mL). The solid is triturated with ether (50 mL), filtered and washed with ether (50 mL). The product is to be dried in vacuo to give ILY-V-30.

Example 7.9b

Compound (5-30)

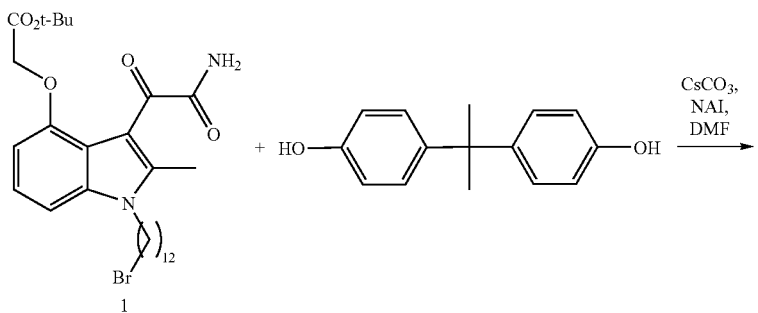

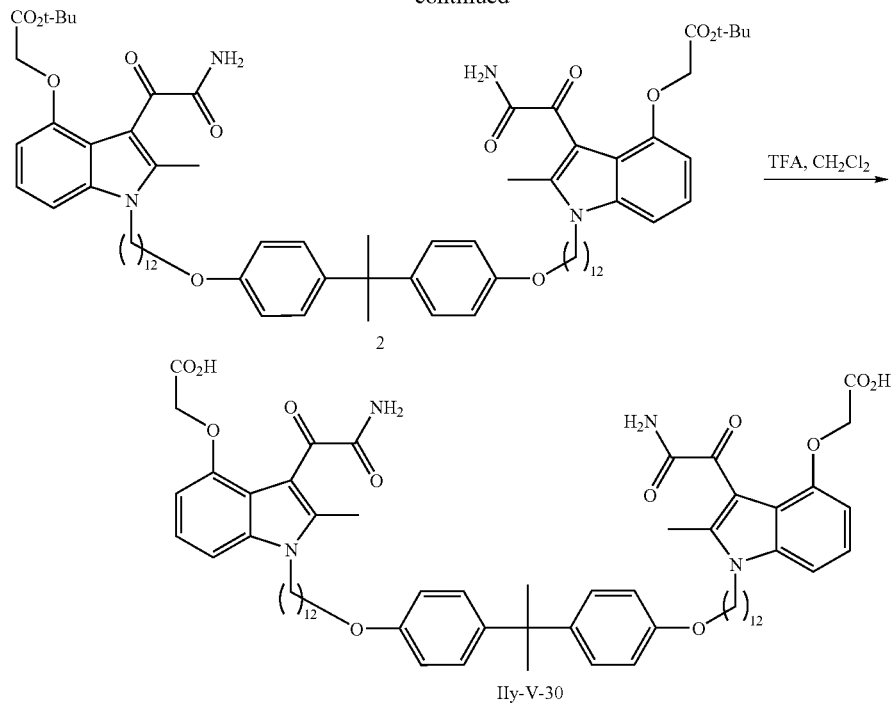

(3-Aminooxalyl-1-{12-[4-(1-{4-[12-(3-aminooxalyl-4-tert-butoxycarbonylmethoxy-2-methyl-indol-1-yl)-dodecyloxy]-phenyl}-1-methyl-ethyl)-phenoxy]-dodecyl}-2-methyl-1H-indol-4-yloxy)-acetic acid tert-butyl ester (2): To a solution of bisphenol (10.27 g, 0.045 mole) in anhydrous DMF (700 mL), cesium carbonate (147 g, 0.45 mole) was added. The mixture was stirred at room temperature for 30 minutes. To the mixture [3-aminooxalyl-1-(12-bromo-dodecyl)-2-methyl-1H-indol-4-yloxy]-acetic acid tert-butyl ester (1) (57.8 g, 0.10 mole) and sodium iodide (33.5 g, 0.225 mole) were added. The reaction mixture was stirred at room temperature for 18 h. The mixture was diluted with ethyl acetate (3.5 L) and washed with water (4×700 mL) and brine (1×700 mL). The organic layer was separated and dried with sodium sulphate, then concentrated. The residue was purified by column chromatography (2:1 EtOAc:CHCl$_3$) to afford intermediate (2) as a white solid. Yield: 48 g, 87%

(3-Aminooxalyl-1-{12-[4-(1-{4-[12-(3-aminooxalyl-4-carboxymethoxy-2-methyl-indol-1-yl)-dodecyloxy]-phenyl}-1-methyl-ethyl)-phenoxy]-dodecyl}-2-methyl-1H-indol-4-yloxy)-acetic acid (Ily-V-30): To a solution of intermediate (2) (23 g, 0.0187 mole) in dichloromethane (1 L), trifluoroacetic acid (230 mL, 1.131 mole) was added dropwise. The reaction mixture was stirred at room temperature for 3 h. The reaction solvent was evaporated and the brown sticky residue was stirred in diethyl ether (700 mL) for 2 h. The resulting solid was collected by filtration and dried under high vacuum for 18 h to afford Ily-V-30 as a pink solid. Yield: 22.1 g >100% (contains some inorganic salts). $^1$H NMR (400 MHz, DMSO-d$_6$) δ, ppm: 12.86 (brs, 2H), 7.72 (s, 2H), 7.40 (s, 2H), 7.18-7.04 (m, 8H), 6.78 (d, 4H), 6.50 (d, 2H), 4.42 (s, 4H), 4.17 (brt, 4H), 3.87 (t, 4H), 2.50 (s, 6 H), 1.78-1.20 (m, 22 H). ES-MS: m/z=1113.28 (M+1)

Example 7.10.1a

Compound (5-31)

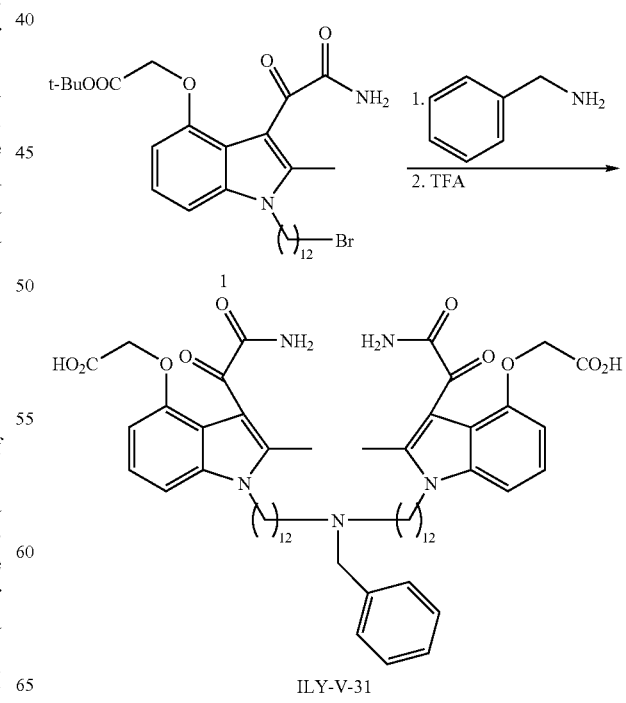

2,2'-(1,1'-(12,12'-(benzylazanediyl)bis(dodecane-12,1-diyl))bis(3-(2-amino-2-oxoacetyl)-2-methyl-1H-indole-4,1-diyl))bis(oxy)diacetic acid (ILY-V-31) Benzyl amine (1 mmole) is added to the bromide 1 (2.05 mmole) in dry DMF (12 mL) at rt under nitrogen. The reaction is maintained at 50° C. for 8 h and is quenched with ammonium chloride solution (15 mL), is diluted with dichloromethane (100 mL) and is washed with ammonium chloride solution (50 mL). The organic phase is separated and the aqueous phase is extracted with dichloromethane (2×25 mL). The combined organic phase is washed with brine (75 mL) dried ($Na_2SO_4$), is fil- The protected dimer product (0.9 mmole) and 1,3-dimethoxybenzene (3 mmole) in dry dichloromethane (20 mL), at room temperature under nitrogen, is added with trifluoroacetic acid (10 mL). The solution is stirred for 1 h and the solvents evaporated below 25° C. The residue is triturated with ether (50 mL) and the solid removed by filtration and washed with ether (100 mL). The solid is triturated with ether (50 mL), filtered and washed with ether (50 mL). The product is dried in vacuo to give ILY-V-31.

Example 7.10.1b and 7.10.2

Compound (5-31) and (5-45)

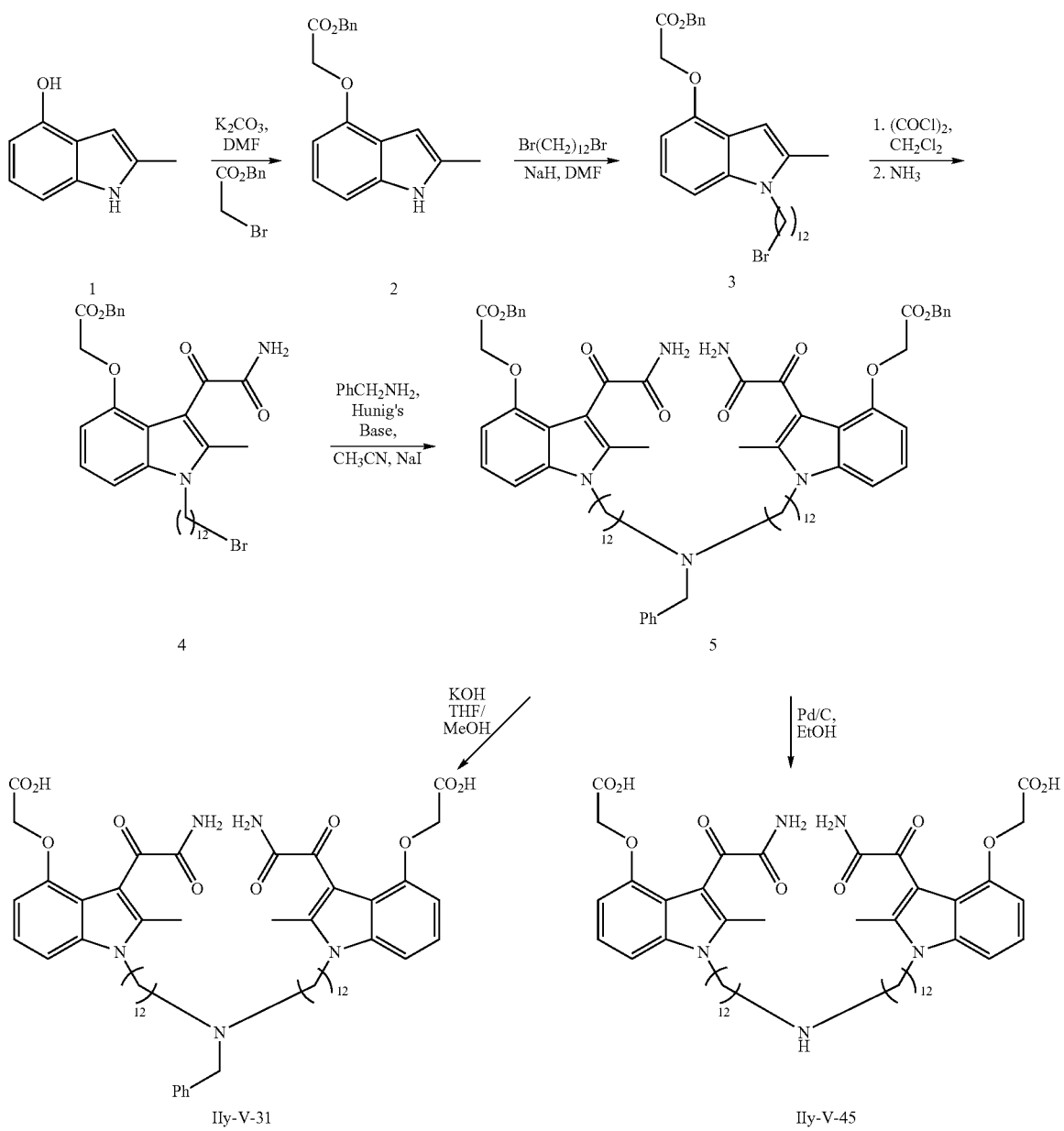

tered and is evaporated to a yellow/orange syrup. Purification by chromatography over silica gel, using chloroform/ethyl acetate as the eluant, can give the protected dimer product.

(2-Methyl-1H-indol-4-yloxy)-acetic acid benzyl ester (2): A mixture of 4-hydroxy-2-methylindole (3.0 g, 0.02 mole), bromo-acetic acid benzyl ester (4.6 g, 0.02 mole), potassium carbonate (2.8 g, 0.02 mole) in acetone was refluxed for 48 h. The reaction mixture was filtered and the filtrate was concentrated. The residue was purified by column chromatography (10:1 Hex:EtOAc) to afford intermediate (2). Yield: 3.5 g, 58%.

[1-(12-Bromododecyl)-2-methyl-1H-indol-4-yloxy]-acetic acid benzyl ester (3): To a suspension of sodium hydride (60% in mineral oil, 0.093 g, 6.45 mmole) in DMF (10 mL), (2-methyl-1H-indol-4-yloxy)-acetic acid benzyl ester (2) (0.845 g, 2.3 mmole) was added. The mixture was stirred at room temperature for 1 h. To the mixture, dibromododecane (0.765 g, 2.3 mmole) was added and the reaction mixture was stirred at room temperature for 18 h. The reaction was diluted with ethyl acetate and washed with water. The organic layer was separated, dried with sodium sulphate and concentrated. The residue was purified by column chromatography (10:1, hexane: EtOAc) to afford intermediate 3. Yield: 0.708 g, 45%.

[3-Aminooxalyl-1-(12-bromododecyl)-2-methyl-1H-indol-4-yloxy]-acetic acid benzyl ester (4): To a solution of intermediate 3 (0.708 g, 1.31 mmole) in anhydrous dichloromethane (20 mL), oxalyl chloride (0.166 g, 1.31 mmole) was added dropwise. The mixture was stirred for 2 h, and then ammonia was bubbled through the mixture for 15 min. The reaction mixture was evaporated to afford intermediate 4 (1.0 g) as a crude mixture which was used in the subsequent reaction without further purification.

[3-Aminooxalyl-1-(12-{[12-(3-aminooxalyl-4-benzyloxycarbonylmethoxy-2-methyl-indol-1-yl)-dodecyl]-benzylamino}-dodecyl)-2-methyl-1H-indol-4-yloxy]-acetic acid benzyl ester (5): A mixture of intermediate 4 (1.0 g, crude martial from the previous step), benzylamine (0.08 g, 0.74 mmole), sodium iodide (0.005 g) and Hunig's base (0.084 g, 0.65 mmole) in acetonitrile (10 mL) was refluxed for 12 h. The mixture was concentrated and the residue was purified by column chromatography (100% CH$_3$CN) to afford intermediate 5 as a solid. Yield 0.41 g, 26% for 2 steps.

(3-Aminooxalyl-1-{12-[12-(3-aminooxalyl-4-carboxymethoxy-2-methyl-indol-1-yl)-dodecylamino]-dodecyl}-2-methyl-1H-indol-4-yloxy)-acetic acid (Ily-V-45): To a solution of intermediate 5 (0.098 g, 0.084 mmole) in ethanol (10 mL), Pd/C (10%, 50 mg) was added. The mixture was stirred under hydrogen atmosphere using a balloon for 30 minutes. The mixture was filtered through Celite and the filtrate was evaporated. The resulting solid was washed with chloroform and hexane to afford Ily-V-45. Yield: 0.022 g, 27%. $^1$H NMR (400 MHz, DMSO-d$_6$) δ, ppm: 8.40 (brs, 1H), 7.78 (brs, 2H), 7.41 (brs, 2H), 7.01-7.12 (m, 4H), 6.45 (d, 2H), 4.61 (s, 4H), 4.18 (t, 4H), 2.80 (t, 4H), 2.54(s, 6H), 1.62(m, 4H), 1.45(m, 4H), 1.11-1.18(m, 32H) ppm. ES-MS: m/z=902.15 (M+1).

[3-Aminooxalyl-1-(12-{[12-(3-aminooxalyl-4-carboxymethoxy-2-methyl-indol-1-yl)-dodecyl]-benzylamino}-dodecyl)-2-methyl-1H-indol-4-yloxy]-acetic acid (Ily-V-31): To a solution of intermediate 5 (0.204 g, 0.204 mmole) in THF/MeOH (5 mL/5 mL), a solution of potassium hydroxide (0.20 g, 3.57 mmole) in water (1 mL) was added. The reaction mixture was stirred at room temperature for 18 h. The reaction was acidified to pH 5 with 2 M HCl. The solvent was evaporated and the residue was washed with diethyl ether (2×10 mL). The solid was collected by filtration and dried to afford Ily-V-31 as a yellow solid. Yield: 0.190 g, 93%. $^1$H NMR (400 MHz, DMSO-d$_6$) δ, ppm: 7.78 (brs, 2H), 7.40-7.00 (m, 11H), 6.50 (d, 2H), 4.60 (s, 4H), 4.18 (brs, 4H), 3.63 (brs, 2H), 3.42-3.20 (m, 4H), 2.55 (s, 6H), 1.65 (brs, 4H), 1.42 (brs, 4H), 1.38-1.08 (m, 14H). ES-MS: m/z=993.38 (M+1).

Example 7.11a

Compound (5-32)

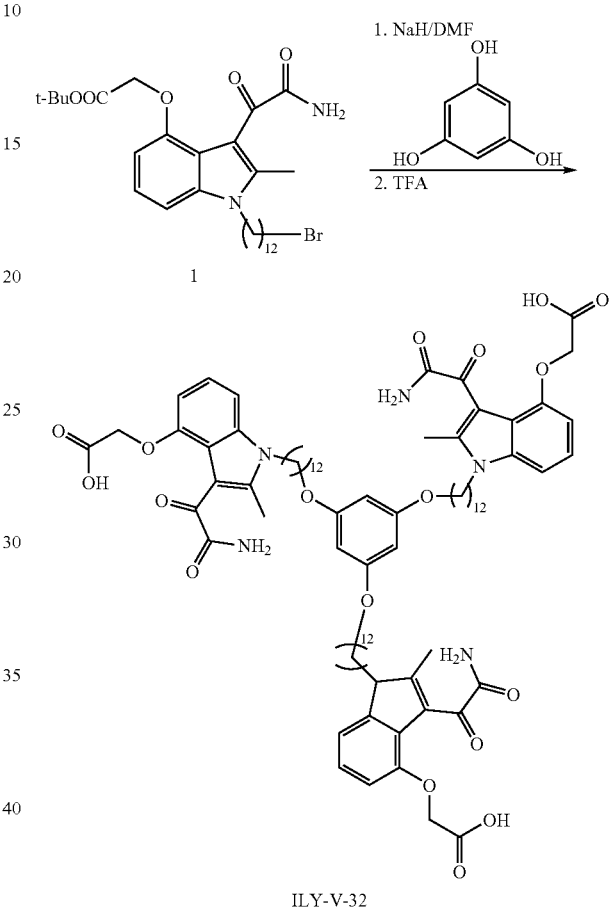

ILY-V-32

2,2',2''-(1,1',1''-(12,12',12''-(benzene-1,3,5-triyltris(oxy))tris(dodecane-12,1-diyl))tris(3-(2-amino-2-oxoacetyl)-2-methyl-1H-indole-4,1-diyl))tris(oxy)triacetic acid (ILY-V-32) Dehydrated phloroglucinol (1 mmole) is added to sodium hydride (3.3 mmole) in dry DMF (12 mL), at 0° C. under nitrogen. After 0.5 h this mixture is added to the bromide 1 (3.1 mmole) in dry DMF (20 mL), at 0° C. under nitrogen. The reaction is maintained at 0° C. for 8 h and is quenched with ammonium chloride solution (15 mL), is diluted with dichloromethane (100 mL) and is washed with ammonium chloride solution (50 mL). The organic phase is separated and the aqueous phase extracted with dichloromethane (2×25 mL). The combined organic phase is washed with brine (75 mL) dried (Na$_2$SO$_4$), filtered and evaporated to a yellow/orange syrup. Purification by chromatography over silica gel, using chloroform/ethyl acetate as the eluant, can give the protected dimer product.

The protected dimer product (0.9 mmole) and 1,3-dimethoxybenzene (3 mmole) in dry dichloromethane (20 mL), at room temperature under nitrogen, is added with trifluoroacetic acid (10 mL). The solution is stirred for 1 h and the solvents evaporated below 25° C. The residue is triturated with ether (50 mL) and the solid removed by filtration and washed with ether (100 mL). The solid is triturated with ether (50 mL), is filtered and is washed with ether (50 mL). The product is dried in vacuo to give ILY-V-32.

Example 7.11b

Compound (5-32)

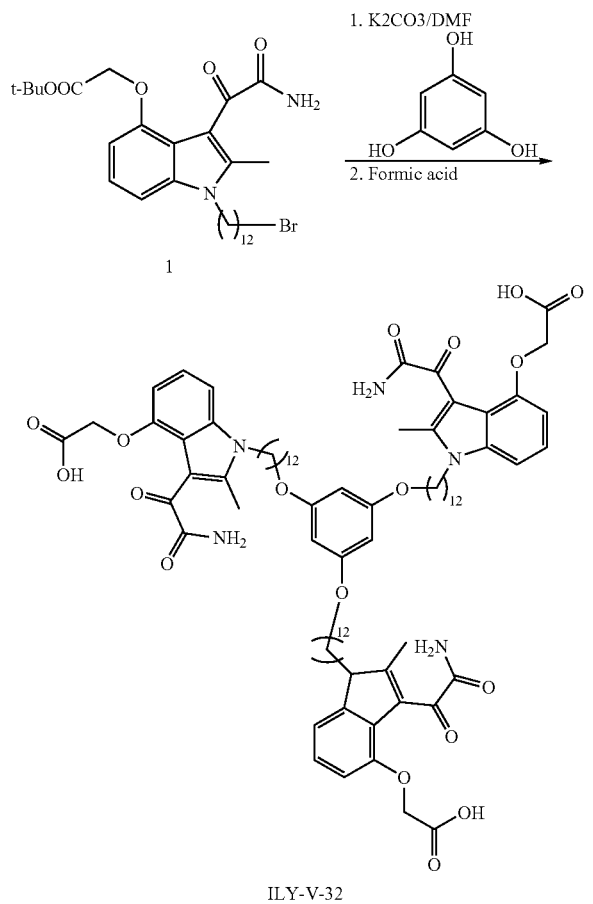

ILY-V-32

[3-Aminooxalyl-1-(12-{3,5-bis-[12-(3-aminooxalyl-4-tert-butoxycarbonylmethoxy-2-methyl-indol-1-yl)-dodecyloxy]-phenoxy}-dodecyl)-2-methyl-1H-indol-4-yloxy]-acetic acid tert-butyl ester: A mixture of [3-aminooxalyl-1-(12-bromododecyl)-2-methyl-1H-indol-4-yloxy]-acetic acid tert-butyl ester (1) (0.70 g, 1.11 mmol), $K_2CO_3$ (1.0 g, excess) and phloroglucinol (0.03 g, 0.18 mmol) were heated in dry DMF (8 mL) at 55° C. for 12 h under $N_2$. The mixture was cooled and concentrated to dryness. The syrup was suspended in $CH_2Cl_2$ (50 mL) and filtered through Celite. The filtrate was washed with water (10×2 mL) and dried ($Na_2SO_4$). The solvent was removed under reduced pressure, and the residue was chromatographed on a silica gel column eluting with 70% ethyl acetate in hexane to afford the intermediate as an off-white solid. Yield: 0.09 g, 30%.

[3-Aminooxalyl-1-(12-{3,5-bis-[12-(3-aminooxalyl-4-carboxymethoxy-2-methyl-indol-1-yl)-dodecyloxy]-phenoxy}-dodecyl)-2-methyl-1H-indol-4-yloxy]-acetic acid (Ily-V-32): The intermediate (0.08 g, 0.049 mmol) was dissolved in aqueous $HCO_2H$ (88%, 2 mL) and the mixture was stirred at room temperature for 6 h. The mixture was concentrated to dryness under high vacuum and co-evaporated with water (2×2 mL). The flask containing the gummy material was then transferred to freeze dryer and was under high vacuum overnight to get the title compound Ily-V-32 as a pale green gum. Yield: 0.03 g, 40%. $^1$H NMR: (DMSO-$d_6$), δ, ppm: (5-37-147) δ 7.71 (bs, 3H), 7.40 (bs, 3H), 7.20-7.05 (m, 6H), 6.48 (d, 3H), 6.01 (s, 3H), 4.62 (s, 6H), 4.18 (t, 6H), 3.83 (t, 6H), 2.47 (s, 9H), 1.70-1.60 (m, 6H), 1.38-1.05 (m, 60H). ES-MS: m/z=1452.8 (M+1).

Example 7.12a

Compound (5-33)

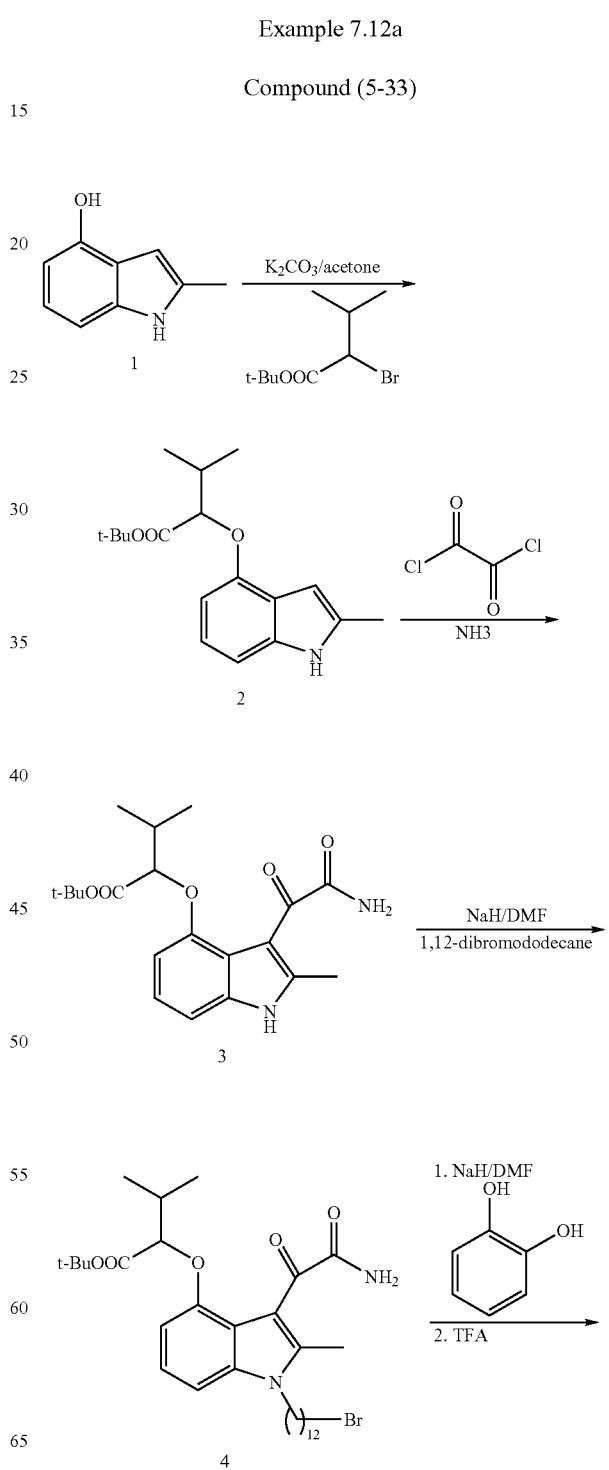

-continued

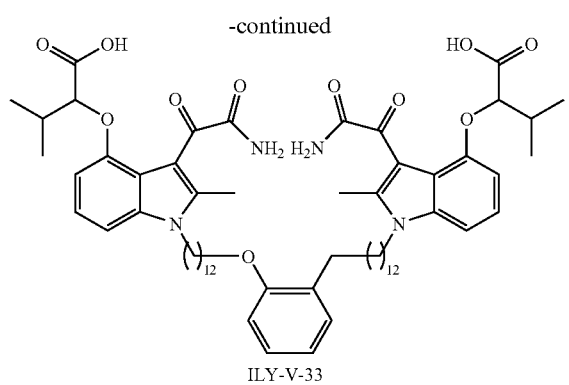

ILY-V-33

2,2'-(1,1'-(12,12'-(1,2-phenylenebis(oxy))bis(dodecane-12,1-diyl))bis(3-(2-amino-2-oxoacetyl)-2-methyl-1H-indole-4,1-diyl))bis(oxy)bis(3-methylbutanoic acid) (ILY-V-33) Hydroxy indole 1 (1 mmol) and tert-butyl 2-bromo-3-methylbutanoate (1 mmol) is dissolved in 10 mL acetone. To this solution at room temperature is added anhydrous potassium carbonate (2 mmol) and the stirred mixture is refluxed for 12 hours. The solid is removed by filtration and followed by column chromatography to give 2.

Compound 2 (1 mmole) is dissolved in anhydrous dichloromethane (50 mL). To the solution oxalyl chloride (1.1 mmole) is added. The mixture is left to stir at room temperature for 2 h. $NH_3$ gas is then bubbled through the solution for 30 minutes. The mixture is left to stir at room temperature for 1 h. The dichloromethane is evaporated and the residue is dissolved in ethyl acetate (200 mL) and washed with $H_2O$ (3×200 mL) and brine (1×300 mL). The organic layer is separated, dried with magnesium sulfate and concentrated to afford 3.

The indole intermediate 3 (1 mmole) in dry DMF (10 mL), at 0° C. under nitrogen, is added with 95% sodium hydride (1.2 mmole). The mixture is stirred at 0° C. for 0.5 h and then added dropwise over 10 minutes to a solution of 1,12-dibromododecane (1.5 mmole) in dry DMF (20 mL) at 0° C. The mixture is stirred at 0° C. for 5 h and at room temperature for 19 h. The reaction is cooled to 0° C., quenched with ammonium chloride solution (10 mL), and diluted with dichloromethane (100 mL). The mixture is washed with ammonium chloride solution (50 mL) and the aqueous phase extracted with dichloromethane (4×25 mL). The combined organic phase is washed with brine (100 mL), dried ($Na_2SO_4$), filtered and evaporated to a red/brown liquid which is further evaporated under high vacuum. The residue is purified by chromatography over silica gel to give 4.

Catechol (1 mmole) is added to sodium hydride (2.2 mmole) in dry DMF (12 mL), at 0° C. under nitrogen. After 0.5 h this mixture is added to the bromide 4 (2.05 mmole) in dry DMF (20 mL), at 0° C. under nitrogen. The reaction is maintained at 0° C. for 8 h and quenched with ammonium chloride solution (15 mL), diluted with dichloromethane (100 mL) and washed with ammonium chloride solution (50 mL). The organic phase is separated and the aqueous phase extracted with dichloromethane (2×25 mL). The combined organic phase is washed with brine (75 mL) dried ($Na_2SO_4$), filtered and evaporated to a yellow/orange syrup. Purification by chromatography over silica gel, using chloroform/ethyl acetate as the eluant, give the protected dimer product.

The protected dimer product (0.9 mmole) and 1,3-dimethoxybenzene (3 mmole) in dry dichloromethane (20 mL), at room temperature under nitrogen, is added with trifluoroacetic acid (10 mL). The solution is stirred for 1 h and the solvents evaporated below 25° C. The residue is triturated with ether (50 mL) and the solid removed by filtration and washed with ether (100 mL). The solid is triturated with ether (50 mL), filtered and washed with ether (50 mL). The product is dried in vacuo to give ILY-V-33.

Example 7.12b

Compound (5-33)

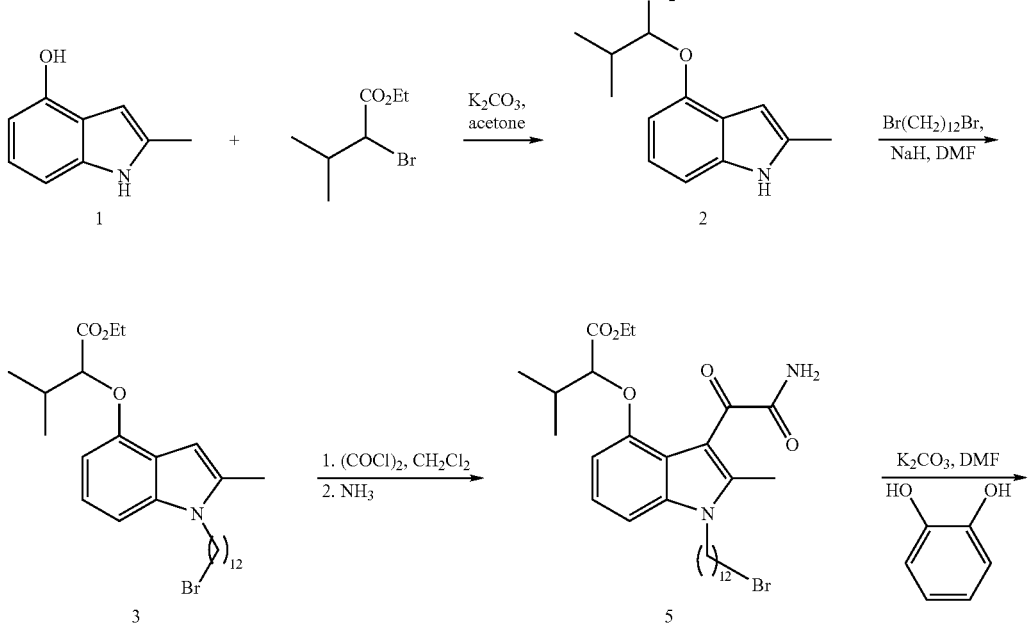

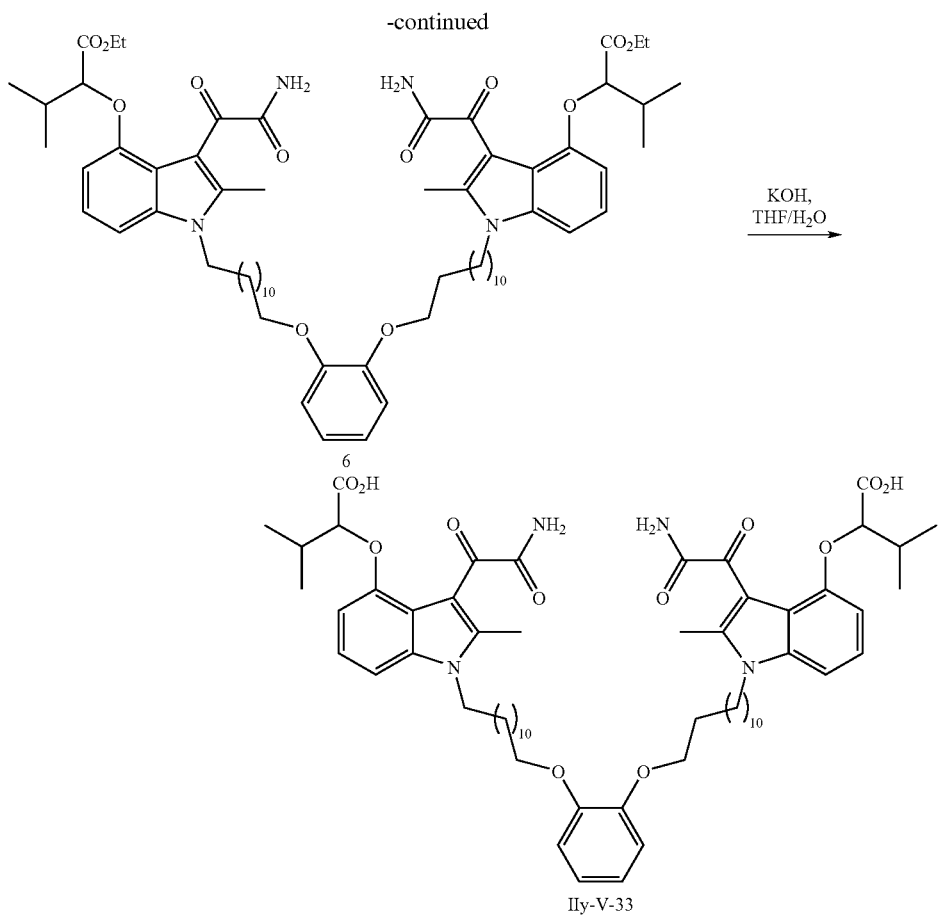

3-Methyl-2-(2-methyl-1H-indol-4-yloxy)-butyric acid ethyl ester (2): A mixture of 4-hydroxy-2-methylindole (1) (1.5 g, 0.010 mole), 2-bromo-3-methyl-butyric acid ethyl ester (2.2 g, 0.010 mole) and potassium carbonate (excess) in acetone (50 mL) was refluxed for 3 days. The reaction mixture was filtered, and the filtrate was concentrated. The residue was purified by column chromatography (20:1 Hex: EtOAc) to afford intermediate 2. Yield: 1.88 g, 71%

2-[1-(12-Bromo-dodecyl)-2-methyl-1H-indol-4-yloxy]-3-methylbutyric acid ethyl ester (3): To a mixture of NaH (60% in mineral oil, 0.42 g, 10 mmole) in anhydrous DMF (20 mL), 3-methyl-2-(2-methyl-1H-indol-4-yloxy)-butyric acid ethyl ester (2) (1.88 g, 7.0 mmole) and dibromododecane (2.30 g, 7.0 mmole) were added. The mixture was stirred at room temperature for 18 h. The reaction was diluted with ethyl acetate (50 mL) and washed with water (3×30 mL). The organic layer was separated, dried over sodium sulphate and concentrated. The residue was purified by column chromatography (10:1 Hex:EtOAc) to afford intermediate (3) Yield: intermediate (3) 1.32 g, 35%, by-product (4) 1.56 g, 31%.

2-[3-Aminooxalyl-1-(12-bromo-dodecyl)-2-methyl-1H-indol-4-yloxy]-3-methyl-butyric acid ethyl ester (5): To a solution of intermediate 3 (0.50 g, 0.959 mmole) in anhydrous dichloromethane (200 mL), oxalyl chloride (0.12 g, 0.95 mmole) was added at 0° C. The mixture was stirred for 1 h. Ammonia gas was bubbled through the reaction mixture for 20 minutes. The mixture was stirred for an addition hour and then concentrated. The residue was diluted with ethyl acetate (30 mL) and washed with water (3×30 mL). The organic layer was separated, dried over sodium sulphate and concentrated to afford intermediate (5) as a yellow solid. Yield: 0.44 g, 77%

2-{3-Aminooxalyl-1-[12-(2-{12-[3-aminooxalyl-4-(1-ethoxycarbonyl-2-methyl-propoxy)-2-methyl-indol-1-yl]-dodecyloxy}-phenoxy)-dodecyl]-2-methyl-1H-indol-4-yloxy}-3-methyl-butyric acid ethyl ester (6): A mixture of intermediate 5 (474 mg, 0.8 mmol), catechol (40 mg, 0.36 mmol) and potassium carbonate (excess) in DMF (5 mL) was stirred at room temperature for 72 h. The reaction was filtered and the filtrate was poured onto crushed ice (20 mL). The mixture was extracted with dichloromethane (3×30 mL). The organic layer was separated, dried over sodium sulphate and concentrated. The residue was purified by column chromatography (1% MeOH in CHCl$_3$) to afford intermediate (6) and recovered intermediate (5) (205 mg). Yield: 0.060 g, 7%.

2-{3-Aminooxalyl-1-[12-(2-{12-[3-aminooxalyl-4-(1-carboxy-2-methyl-propoxy)-2-methyl-indol-1-yl]-dodecyloxy}-phenoxy)-dodecyl]-2-methyl-1H-indol-4-yloxy}-3-methyl-butyric acid (Ily-V-33): To a solution of intermediate 6 (55 mg, 0.05 mmol) in THF/CH$_3$OH/H$_2$O (1:1:1, 2 mL:2 mL:2 mL), potassium hydroxide (0.06 g, 0.11 mmole) was added. The mixture was stirred at room temperature for 4 h. The solution was evaporated and the residue was neutralized with 1M HCl at 0° C. The solid was collected by filtration and washed with water and then hexane to afford Ily-V-33 as a yellow solid. Yield: 0.035 g, 67%. $^1$H NMR (400 MHz, DMSO-d$_6$), δ, ppm: δ 12.51 (brs, 2H),8.10(brs, 2H),7.62 (brs, 2H), 7.11-7.14(m, 4H),7.92-7.96 (m, 2H), 7.81-7.84 (m, 2H), 6.42(d, 2H), 4.68(d, 2H),4.15 (t, 4H), 3.92 (t, 4H), 2.44 (s, 6H), 2.23(m, 2H), 1.62(m, 4H), 1.20-1.43(m, 36H), 1.08(d, 6H), 0.98(d, 6H) ppm. ES-MS: m/z=1079.44(M+1).

Example 7.13

Compound (5-23)

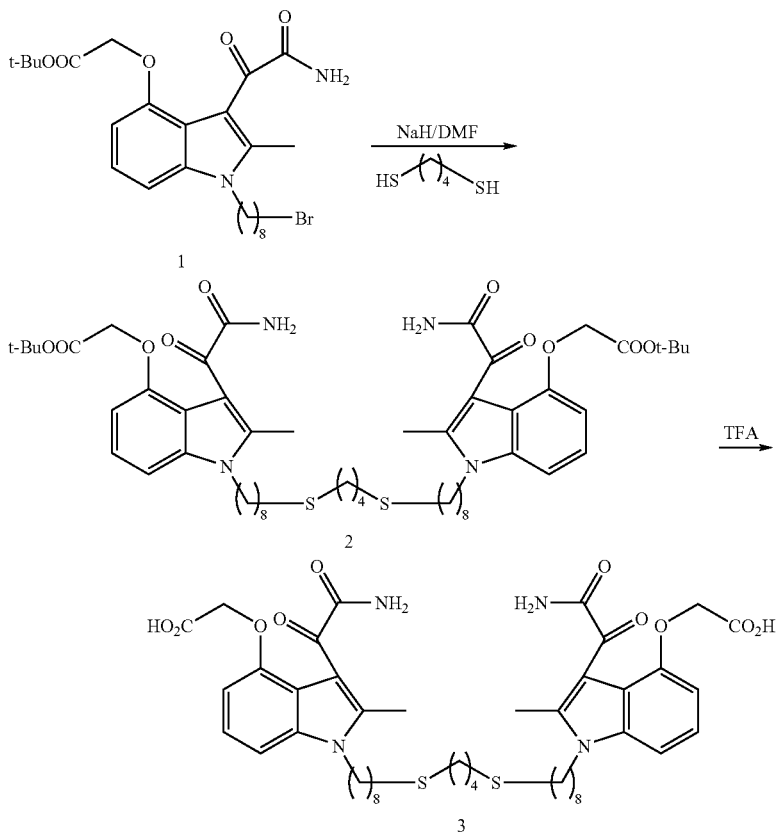

2,2'-(1,1'-(8,8'-(butane-1,4-diylbis(sulfanediyl))bis(octane-8,1-diyl))bis(3-(2-amino-2-oxoacetyl)-2-methyl-1H-indole-4,1-diyl))bis(oxy)diacetic acid (ILY-V-23) A solution of 1,4-butanedithiol (280 µL, 2.4 mmol, 290 mg) in 5 mL of anhydrous DMF was cooled in an ice bath and dry sodium hydride (125 mg, 5.23 mmol, 2.2 equiv) was added. After stirring under nitrogen for 15 min at 0° C., the mixture was transferred drop wise into a solution of N1-bromoalkyl indole 1 (2.6 g, 5.0 mmol, 2.1 equiv) in 10 mL of anhydrous DMF also cooled in an ice bath. The resulting orange mixture was stirred under nitrogen for 8 h at 0° C. After an overnight refrigerating at −20° C., the reaction mixture was quenched with 10 mL of NH$_4$Cl, and it was then allowed to warm to RT. It was diluted with 50 mL of DCM, washed with NH$_4$Cl (25 mL) and twice with brine (2×30 mL), dried over MgSO$_4$ and concentrated in vacuo to afford the crude product as an orange oil. Purification by flash-chromatography (H/EA: 2/3, 3/7 and 1/4) yielded the pure dimer (1.2 g, 51%) as a yellow solid.

$^1$H NMR (CD$_2$Cl$_2$, 300 MHz): δ 7.14 (dd, 2H, J=8.1, 8.1 Hz, H-6), 7.08 (d, 2H, J=8.1, H-5), 6.6 (br s, 2H, NH$_2$), 6.51 (d, 2H, J=8.1 Hz, H-7), 6.0 (br s, 2H, NH$_2$), 4.59 (s, 4H, H-10), 4.09 (t, 4H, J=7.8 Hz, H-14), 2.59 (s, 6H, H-9), 2.50 (m, 8H, S—CH$_2$), 1.78 (m, 4H, CH$_2$), 1.66 (m, 4H, CH$_2$), 1.57 (m, 4H, CH$_2$), 1.47 (s, 18H, C(CH$_3$)$_3$), 1.36 (m, 16H, CH$_2$). $^{13}$C NMR (CD$_2$Cl$_2$, 75.5 MHz): δ 188.5 (12), 168.3 (11), 167.5 (13), 152.0 (4), 144.2 (1), 137.8 (8), 123.2 (3), 117.0 (6), 110.3 (5), 104.1 (7+2), 82.1 (C(CH$_3$)$_3$), 66.3 (10), 44.0 (14), 36.4 (CH$_2$), 32.1 (CH$_2$), 31.7 (CH$_2$), 31.2 (CH$_2$), 29.8 (CH$_2$), 29.4 (CH$_2$), 29.3 (CH$_2$), 29.0 (CH$_2$), 28.0 (C(CH$_3$)$_3$), 27.1 (CH$_2$), 11.6 (9). MS (ESI, MeOH): m/z 1029.5 [M+Na]$^+$.

The protected dimer 2 (1.0 g, 1 mmol) was stirred under nitrogen with TFA (7.5 mL, 11 g, 100 mmol, 100 equiv) for 45 mn at RT. TFA in excess was then evaporated under reduced pressure to afford the crude product as a brown-yellow oil. Purification by reversed-phase chromatography (Water/Acetonitrile: continuous gradient from 75/25 to 55/45 over the course of 120 mn; product was eluted at 65/35) yielded pure 2,2'-(1,1'-(8,8'-(butane-1,4-diylbis(sulfanediyl))bis(octane-8,1-diyl))bis(3-(2-amino-2-oxoacetyl)-2-methyl-1H-indole-4,1-diyl))bis(oxy)diacetic acid (ILY-V-23), (70 mg, 8%).

$^1$H NMR ((CD$_3$)$_2$CS, 300 MHz): δ 7.70 (br s, 2H, NH$_2$), 7.35 (br s, 2H, NH$_2$), 7.08 (m, 4H, H-6+H-5), 6.49 (d, 2H, J=7.51 Hz, H-7), 4.57 (s, 4H, H-10), 4.12 (t, 4H, J=7.2 Hz, H-14), 2.51 (s, 6H, H-9), 2.44 (m, 8H, S—CH$_2$), 1.65 (m, 4H, CH$_2$), 1.54 (m, 4H, CH$_2$), 1.46 (m, 4H, CH$_2$), 1.26 (m, 16H, CH$_2$). $^{13}$C NMR ((CD$_3$)$_2$CS, 75.5 MHz): δ 189.9 (12), 171.4 (11), 169.2 (13), 152.5 (4), 144.2 (1), 137.8 (8), 123.4 (3), 116.7 (6), 110.7 (5), 104.5 (7+2), 67.8 (10), 43.6 (14), 31.7 (CH$_2$), 31.3 (CH$_2$), 29.9 (CH$_2$), 29.7 (CH$_2$), 29.3 (CH$_2$), 29.2

(CH$_2$), 28.8 (CH$_2$), 26.9 (CH$_2$), 25.8 (CH$_2$), 11.9 (9). MS (ESI, MeOH): m/z 917.4 [M+Na]$^+$.
Example 7.14
Compound (5-44)
2-(3-Aminooxalyl-1-{12-[3-aminooxalyl-4-(1-ethoxy-carbonyl-2-methyl-propoxy)-2-methyl-indol-1-yl]-dodecyl}-2-methyl-1H-indol-4-yloxy)-3-methyl-butyric acid ethyl ester (4): To a solution of intermediate 3 (0.20 g, 0.278 mmole) in anhydrous dichloromethane (20 mL) oxalyl chloride (0.035 g, 0.278 mmole) in anhydrous dichloromethane
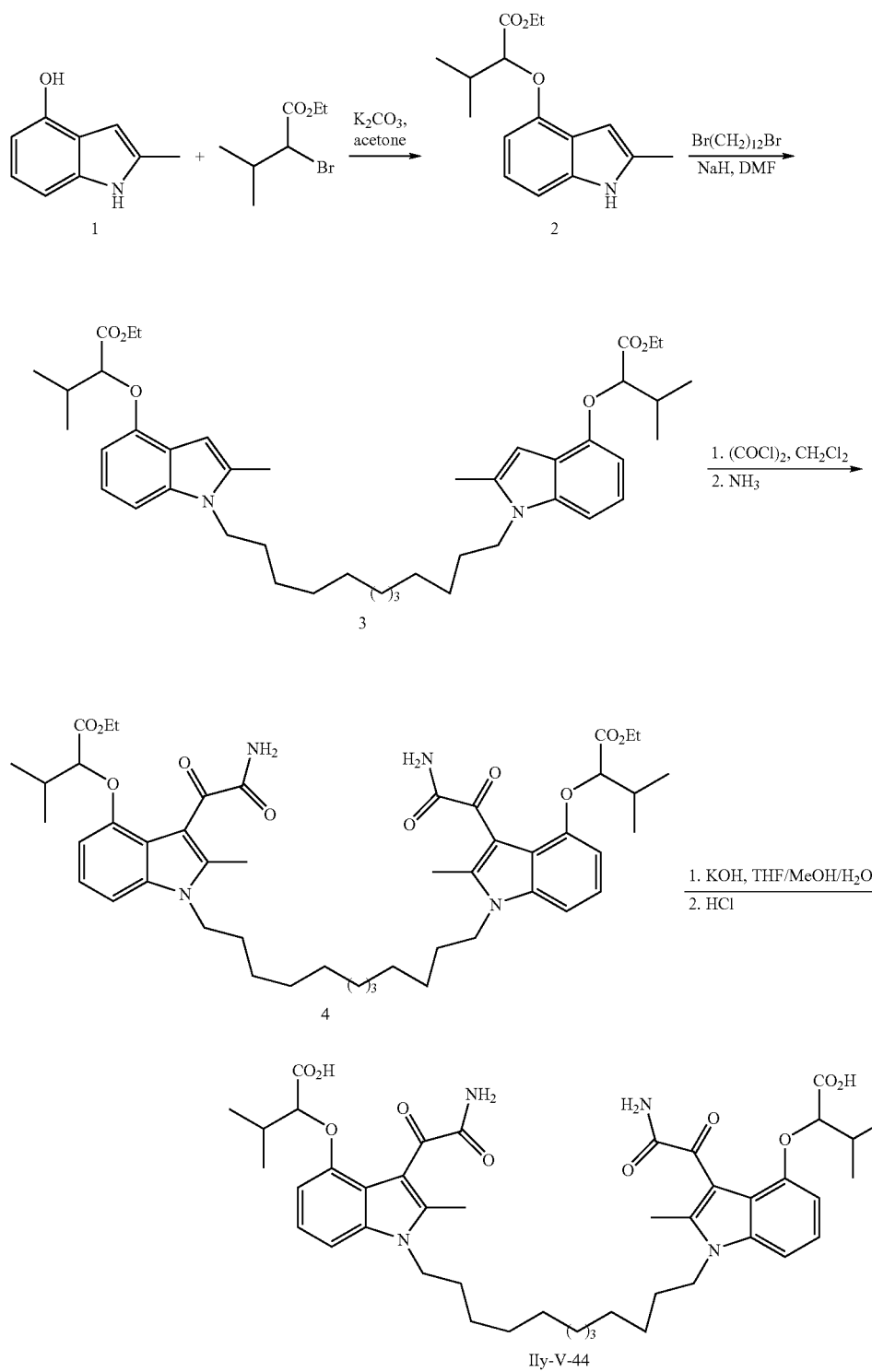

(20 mL) was added dropwise at 0° C. The mixture was stirred for 1 h. Ammonia was bubbled through the mixture for 20 minutes and stirred for 1 h. The reaction mixture was evaporated. The residue was purified by column chromatography (10:1 CHCl$_3$:MeOH) to afford intermediate (4) as a yellow solid. Yield: 0.212 g, 91%

2-(3-Aminooxalyl-1-{12-[3-aminooxalyl-4-(1-carboxy-2-methyl-propoxy)-2-methyl-indol-1-yl]-dodecyl}-2-methyl-1H-indol-4-yloxy)-3-methyl-butyric acid (Ily-V-44): A solution of intermediate 4 (100 mg, 0.12 mmol) in THF/CH$_3$OH/H$_2$O (1:1:1, 3 mL:3 mL:3 mL) was stirred with 2.2 equivalent of KOH for 4 hr at room temperature. The solution was evaporated and resulting residue was neutralized with 5% HCl at 0° C. The resulting solid was collected by filtration and washed with water and then hexane to afford Ily-V44 as a yellow solid. Yield: 0.067 g, 72%. $^1$H NMR (400 MHz, DMSO-d$_6$) δ, ppm: 12.51(brs, 2H), 8.02 (brs, 2H),7.61 (brs, 2H), 7.11-7.14(m, 4H), 6.42(d, 2H), 4.42 (d, 2H), 4.16(t, 4H), 2.41 (s,6H), 2.23(m, 2H), 1.62(m, 4H), 1.20-1.32 (m, 16H), 1.07(d, 6H), 0.96(d, 6H) ppm. ES-MS: m/z=803.12(M+1).

Example 7.15

Compound (5-41)

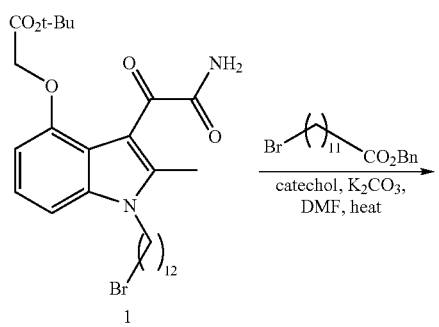

1

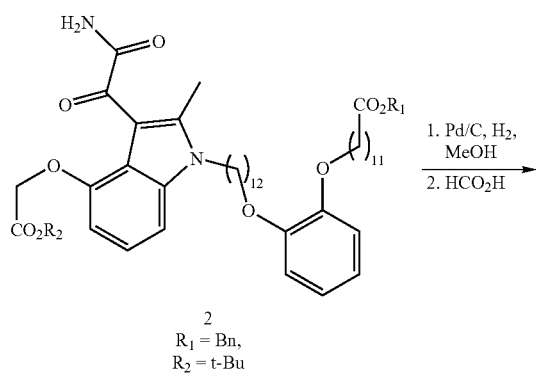

2
R$_1$ = Bn,
R$_2$ = t-Bu

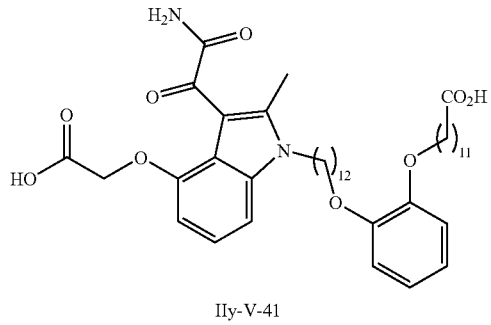

Ily-V-41

12-{2-[12-(3-Aminooxalyl-4-tert-butoxycarbonyl-methoxy-2-methyl-indol-1-yl)-dodecyloxy]-phenoxy}-dodecanoic acid benzyl ester (2): A mixture of [3-aminooxalyl-1-(12-bromo-dodecyl)-2-methyl-1H-indol-4-yloxy]-acetic acid tert-butyl ester (1) (0.654 g, 1.12 mmol), 12-bromobenzyldodecetate (0.416 g, 1.12 mmol), catechol (0.098 g, 0.89 mmol) and K$_2$CO$_3$ (2.0 g, excess) were heated in dry DMF (10 mL) at 55° C. for 12 h under N$_2$. The mixture was cooled and concentrated to dryness. The syrup was suspended in CH$_2$Cl$_2$ (15 mL) and filtered through celite. The filtrate was washed with water (10×2 mL) and dried (Na$_2$SO$_4$). The solvent was removed under reduced pressure, and the residue was chromatographed on a silica gel column eluting with 80% ethyl acetate in hexane to afford intermediate 2 as an off-white solid. Yield: 0.18 g, 18%.

12-{2-[12-(3-Aminooxalyl-4-carboxymethoxy-2-methyl-indol-1-yl)-dodecyloxy]-phenoxy}-dodecanoic acid (Ily-V-41): Compound 2 (0.12 g, 0.133 mmol) was hydrogenated in presence of Pd—C (10%, 0.01 g) in MeOH (10 mL) for 1 h, then filtered through celite. The filtrate was concentrated to provide colorless syrup. It was then dissolved in aqueous HCO$_2$H (88%, 2 mL) and the mixture was stirred at room temperature for 6 h. The mixture was concentrated to dryness under high vacuum and co-evaporated with water (2×2 mL). The flask containing the gummy material was then transferred to freeze dryer and was under high vacuum overnight to afford the title compound Ily-V-41 as a white powder. Yield: 0.8 g, 79%. $^1$H NMR: (DMSO-d$_6$), δ, ppm: (5-37-191) δ 7.70 (bs, 3H), 7.40 (bs, 3H), 7.20-7.05 (m, 2H), 6.95-6.80 (m, 4H), 4.62 (s, 2H), 4.18 (t, 2H), 3.83 (t, 4H), 2.47 (s, 3H), 2.09 (t, 2H), 1.70-1.05 (m, 54H). ES-MS: m/z=751.2 (M+1)

Example 7.16

Compound (5-36)

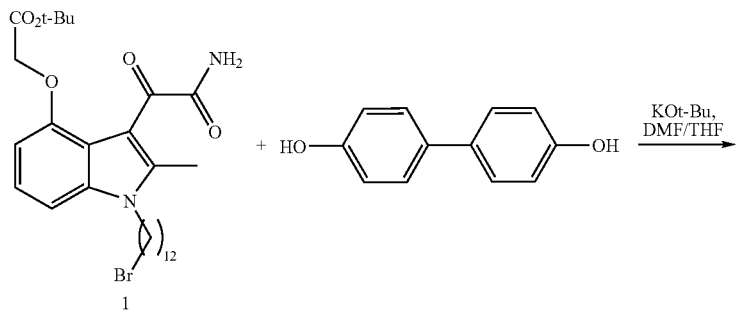

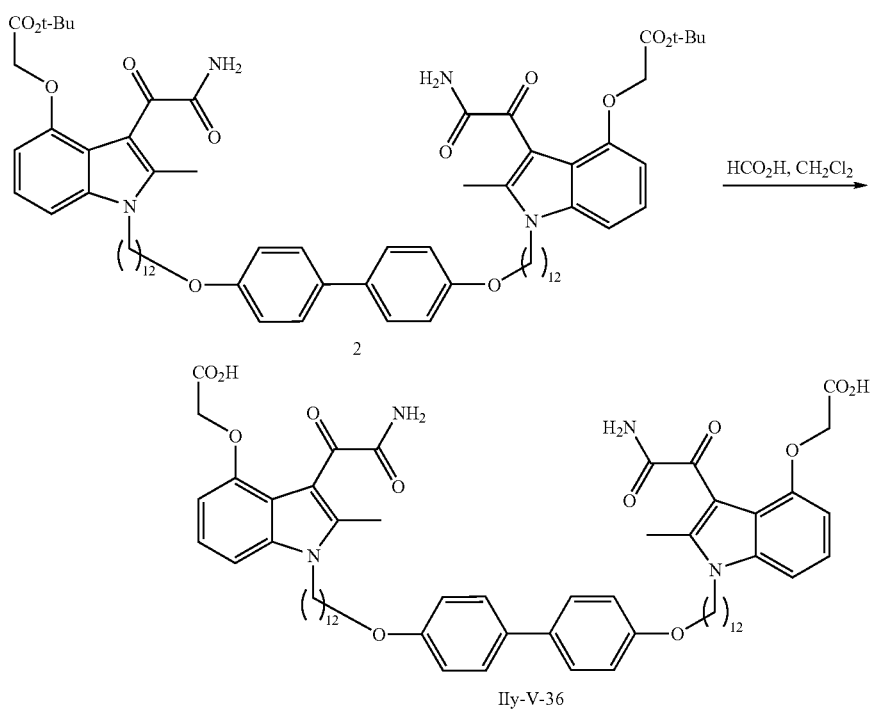

[3-Aminooxalyl-1-(12-{4'-[12-(3-aminooxalyl-4-tert-butoxycarbonylmethoxy-2-methyl-indol-1-yl)-dodecyloxy]-biphenyl-4-yloxy}-dodecyl)-2-methyl-1H-indol-4-yloxy]-acetic acid tert-butyl ester (2): To a solution of 4,4'-dihydroxybiphenyl (0.18 g, 0.966 mmole) in DMF (4 mL) potassium tert-butoxide (1M in THF, 2.12 mL, 2.12 mmole) was added dropwise. The mixture was stirred at 0° C. for 20 minutes. A solution of [3-aminooxalyl-1-(12-bromo-dodecyl)-2-methyl-1H-indol-4-yloxy]-acetic acid tert-butyl ester (1) (1.1 g, 1.89 mmole) in DMF/THF (10 mL/5 mL) was added rapidly to the mixture. The mixture was stirred at 0° C. for 10 h. The reaction was quenched at 0° C. with ammonium chloride solution (20 mL), diluted with water (10 mL) and extracted with ethyl acetate (3×20 mL). The organic layer was separated, washed with brine, dried over sodium sulphate and concentrated. The residue was purified by column chromatography (2:1 CHCl$_3$:EtOAc) to afford intermediate (2) as a golden brown semi solid. Yield: 0.157 g, 14%.

[3-Aminooxalyl-1-(12-{4'-[12-(3-aminooxalyl-4-carboxymethoxy-2-methyl-indol-1-yl)-dodecyloxy]-biphenyl-4-yloxy}-dodecyl)-2-methyl-1H-indol-4-yloxy]-acetic acid (IIy-V-36): To a solution of intermediate (2) (0.125 g, 0.105 mmole) in dichloromethane, 90% formic acid (35 mL) was added. The reaction mixture was stirred at room temperature for 8 h. The reaction mixture was evaporated and the residue was stirred in diethyl ether (30 mL). The formed solid was collected by filtration and dried under high vacuum to afford IIy-V-36 as a solid. Yield: 0.076 g, 68%. $^1$H NMR (400 MHz, DMSO-d$_6$) δ, ppm: 7.72 (s, 2H), 7.50 (s, 4H), 7.40 (s, 2H), 7.15-7.05 (m, 4H), 6.95 (d, 4H), 6.50 (d, 2H), 4.62 (s, 4H), 4.17 (m, 4H), 3.97 (m, 4H), 2.55 (s, 6H), 1.75-1.60 (m, 8H), 1.45-1.20 (m, 32H). ES-MS: m/z=1070.33 (M−1).

Example 7.17

Compound (5-37)

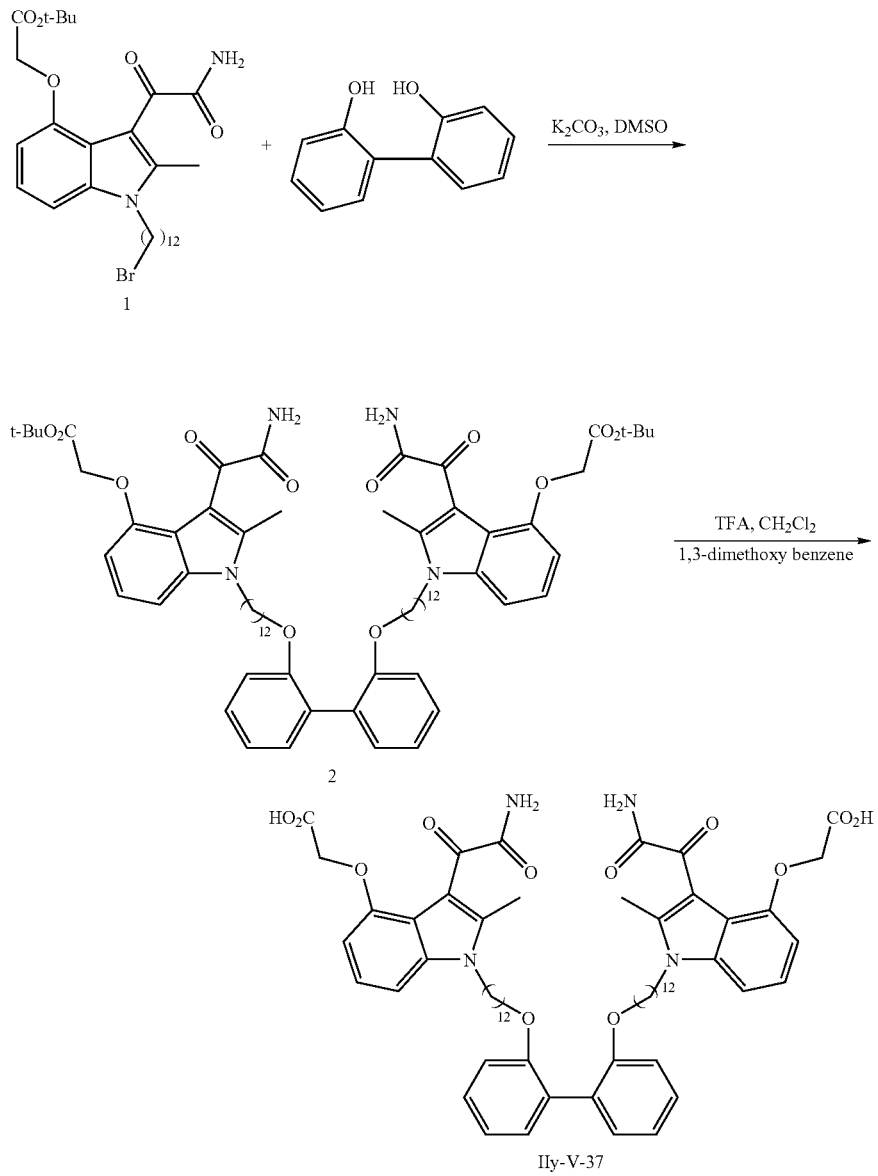

[3-Aminooxalyl-1-(12-{2'-[12-(3-aminooxalyl-4-tert-butoxycarbonylmethoxy-2-methyl-indol-1-yl)-dodecyloxy]-biphenyl-2-yloxy}-dodecyl)-2-methyl-1H-indol-4-yloxy]-acetic acid tert-butyl ester (2): A solution of intermediate 1 (32.62 g, 56.28 mmol) in dimethyl sulfoxide (300 mL) was prepared. To the mixture 2,2'-hydroxybiphenyl (3.52 g, 18.76 mmol) and potassium carbonate (26.45 g, 0.187 mole) was added. The mixture was stirred at 55° C. for 18 h. The reaction mixture was diluted with ethyl acetate (1 L) and washed with ammonium chloride solution (3×1 L). The organic layer was separated, dried with magnesium sulphate and concentrated. The residue was purified by column chromatography (1:1 CHCl$_3$:EtOAc) affording intermediate 2 as a yellow solid. Yield: 17.63 g, 80%.

[3-Aminooxalyl-1-(12-{2'-[12-(3-aminooxalyl-4-carboxymethoxy-2-methyl-indol-1-yl)-dodecyloxy]-biphenyl-2-yloxy}-dodecyl)-2-methyl-1H-indol-4-yloxy]-acetic acid (Ily-V-37): A solution of intermediate 2 (1.0 g, 0.846 mmol) in anhydrous dichloromethane (40 mL) was prepared. To the mixture, 1,3-dimethoxybenzene (0.25 mL, 1.71 mmol) and trifluoroacetic acid (3 mL) were added. The mixture was stirred at room temperature for 3 h. The solvent was evaporated and the residue was stirred in diethyl ether (50 mL) for 30 minutes. The solid was collected by filtration, washed with diethyl ether and dried to afford Ily-V-37 as a green solid. Yield: 0.8 g, 88%. $^1$H NMR (400 MHz, DMSO-d$_6$) δ, ppm:

12.85 (br, 2H), 7.70 (s, 2H), 7.50 (d, 4H), 7.38 (s, 2H), 7.18-7.05 (m, 4H), 6.95 (d, 4H), 6.55 (d, 2H), 4.62 (s, 4H), 4.20-4.05 (m, 4H), 4.00-3.90 (m, 4H), 2.55 (s, 6H), 1.78-1.60 (m, 8 H), 1.40-1.15 (m, 32H). ES-MS: m/z=1071.26 (M+1).

Example 8

In-vitro Assay for the Inhibition of Human, Mouse and Porcine Phospholipase $A_2$ In this example, a fluorimetric assay procedure was used to evaluate the indole and indole-related compounds of the invention as inhibitors of group 1B phospholipase $A_2$ ($PLA_2$) from human, mouse and porcine. A description of this assay is found in articles: Leslie, C C and Gelb, M H (2004) Methods in Molecular Biology "Assaying phospholipase A2 activity", 284:229-242; Singer, A G, et al. (2002) Journal of Biological Chemistry "Interfacial kinetic and binding properties of the complete set of human and mouse groups I, II, V, X, and XII secreted phospholipases A2", 277:48535-48549, which are incorporated herein as references.

In general, this assay used a phosphatidylmethanol substrate with a pyrene fluorophore on the terminal end of the sn-2 fatty acyl chain. Without being bound by theory, close proximity of the pyrenes from neighboring phospholipids in a phospholipid vesicle caused the spectral properties to change relative to that of monomeric pyrene. Bovine serum albumin was present in the aqueous phase and captured the pyrene fatty acid when it is liberated from the glycerol backbone owing to the PLA2-catalyzed reaction. However, a potent inhibitor can inhibit the liberation of pyrene fatty acid from the glycerol backbone. Hence, such features allow for a sensitive PLA2 inhibition assay by monitoring the fluorescence of albumin-bound pyrene fatty acid. The effect of a given inhibitor and inhibitor concentration on human, mouse and porcine phospholipase was determined.

Recombinant human and mouse group 1B $PLA_2$ were cloned and expressed in E. coli as insoluble inclusion bodies. The inclusion bodies were isolated and purified by sonicating cell pellet in lysis buffer (50 mM Tris-HCl pH 7.0, 250 mM NaCl, 0.5% Triton 100), centrifugation at 12,000×g, and washing three times in washing buffer (20 mM Tris-HCl pH 7.0, 250 mM NaCl, 0.5% Triton 100). Then the inclusion bodies were dissolved in dissolving buffer (50 mM Tris-HCl pH 7.0, 250 mM NaCl, 6 M Guanidine-HCl, 1 mM DTT) and dialyzed four times against 10 volumes of refolding buffer (20 mM Tris-HCl pH 7.0, 250 mM NaCl, 0.5M Guanidine-HCl, 5% (w/w) Glycerol, 2 mM reduced glutathione and 0.4 mM oxidized glutathione) at 4° C. The correctly refolded proteins were concentrated using Amicon Stirred cell under nitrogen pressure (<70 psi) and dialyzed against 10 volumes of 50 mM Tris-HCl pH 7.0, 250 mM NaCl and 5% (w/w) glycerol. Human and mouse group 1B PLA2 were further purified by High S ion exchange and gel filtration columns.

The following reagents and equipments were obtained from commercial vendors:
1. Porcine group 1 B phospholipase $A_2$
2. 1-hexadecanoyl-2-(1-pyrenedecanoyl)-sn-glycero-3-phosphomethanol (PPyrPM)
3. Bovine serum albumin (BSA, fatty acid free)
4. 2-Amino-2-(hydroxymethyl)-1,3-propanediol, hydrochloride (Tris-HCl)
5. Calcium chloride
6. Potassium chloride
7. Solvents: DMSO, toluene, isopropanol, ethanol
8. Molecular Devices SPECTRAmax microplate spectrofluorometer
9. Costar 96 well black wall/clear bottom plate The following reagents were prepared:
1. PPyrPM stock solution (1 mg/ml) in toluene:isopropanol (1:1)
2. ILY104 inhibitor stock solution (10 mM) in DMSO
3. 3% (w/v) bovine serum albumin (BSA)
4. Stock buffer: 50 mM Tris-HCl, pH 8.0, 50 mM KCl and 1 mM $CaCl_2$ The following procedure was performed to evaluate the inhibitory potency of the evaluated compounds.
1. An assay buffer was prepared by adding 3 ml 3% BSA to 47 ml stock buffer.
2. Solution A was prepared by adding serially diluted inhibitors to the assay buffer. Inhibitors were three-fold diluted in stock buffer in a series of 8 from 15 uM.
3. Solution B was prepared by adding human, mouse or porcine PLA2 to the assay buffer. This solution was prepared immediately before use to minimize enzyme activity loss.
4. Solution C was prepared by adding 30 ul PPyrPM stock solution to 90 ul ethanol, and then all 120 ul of PPyrPM solution was transferred drop-wise over approximately 1 min to the continuously stirring 8.82 ml assay buffer to form a final concentration of 4.2 uM PPyrPM vesicle solution.
5. The SPECTRAmax microplate spectrofluorometer was set at 37° C.
6. 100 ul of solution A was added to each inhibition assay well of a costar 96 well black wall/clear bottom plate
7. 100 ul of solution B was added to each inhibition assay well of a costar 96 well black wall/clear bottom plate.
8. 100 ul of solution C was added to each inhibition assay well of a costar 96 well black wall/clear bottom plate.
9. The plate was incubated inside the spectrofluorometer chamber for 3 min.
10. The fluorescence was read using an excitation of 342 nm and an emission of 395 nm.

Evaluated compounds were tested in duplicate and their values were averaged to plot the inhibition curve and calculate the IC50. Compared to uninhibited controls, lower fluorescent signal at an emission of 395 nm in test reactions evidenced inhibition of $PLA_2$. Although the final concentration of compounds in reactions typically ranged from 15 uM to 0.007 uM, the more potent inhibitors were diluted to a much lower concentration. Compounds initially found to be active were repeated to confirm their inhibitory activity. The IC50 was calculated using the BioDataFit 1.02 (Four Parameter Model) software package. The equation used to generate the inhibition curve fit is:

$$y_j = \beta + \frac{\alpha - \beta}{1 + \exp(-\kappa(\log(x_j) - \gamma))}$$

wherein: $\alpha$ is the value of the upper asymptote; $\beta$ is the value of the lower asymptote; $\kappa$ is a scaling factor; $\gamma$ is a factor that locates the x-ordinate of the point of infection at $$\exp\left[\frac{\kappa\gamma - \log\left(\frac{1+\kappa}{\kappa-1}\right)}{\kappa}\right]$$

with constraints α, β, κ, γ>0, β<α, and β<y<α. In experiments in which the IC 50 value was not reached at concentrations of 15 uM of the compound under test, the % inhibition at 15 uM was reported.

The results of the inhibition assay for pancreas secreted human, mouse and porcine group 1B PLA$_2$ by the evaluated compounds are summarized in Table 6.

TABLE 6

Inhibition of pancreas secreted human, mouse and porcine PLA$_2$

| structure | Compound ID | MW | ILYPSA IC50 (µM) hps PLA$_2$ | pps PLA$_2$ | mps PLA$_2$ | ILYPSA % inhibition at 15 µM hps PLA$_2$ | pps PLA$_2$ | mps PLA$_2$ |
|---|---|---|---|---|---|---|---|---|
| [structure] | ILY-v-23 (5-23) | 894.39 | 2.16 | 1.12 | 0.55 | | | |
| [structure] | ILY-v-24 (5-24) | 951.24 | 0.54 | 0.8 | 1.05 | | | |
| [structure] | ILY-v-27 (5-27) | 995.21 | 0.15 | 0.15 | 0.2 | | | |
| [structure] | ILY-v-25 (5-25) | 1007.35 | 0.15 | 0.19 | 0.35 | | | |

TABLE 6-continued

Inhibition of pancreas secreted human, mouse and porcine PLA$_2$

| structure | Compound ID | MW | ILYPSA IC50 (μM) hps PLA$_2$ | pps PLA$_2$ | mps PLA$_2$ | ILYPSA % inhibition at 15 μM hps PLA$_2$ | pps PLA$_2$ | mps PLA$_2$ |
|---|---|---|---|---|---|---|---|---|
| 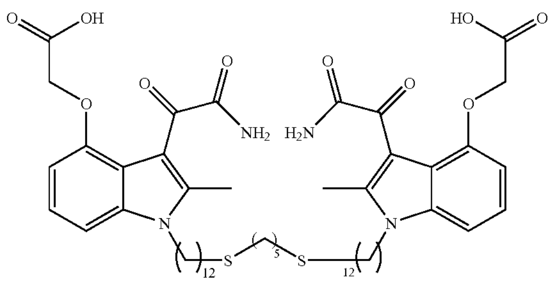 | ILY-v-26 (5-26) | 1063.45 | 0.24 | 0.26 | 0.34 | | | |
| 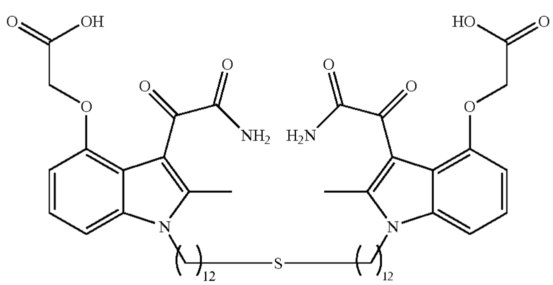 | ILY-v-29 (5-29) | 919.18 | 0.46 | 0.53 | 0.79 | | | |
| 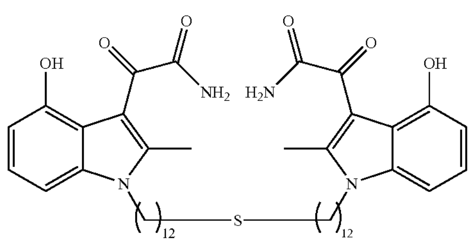 | ILY-v-35 (5-35) | 803.1 | 1.52 | 2.09 | 3.65 | | | |
| unreadable goes to query | ILY-v-32 (5-32) | 1453.75 | 0.06 | 0.09 | 0.13 | | | |
| 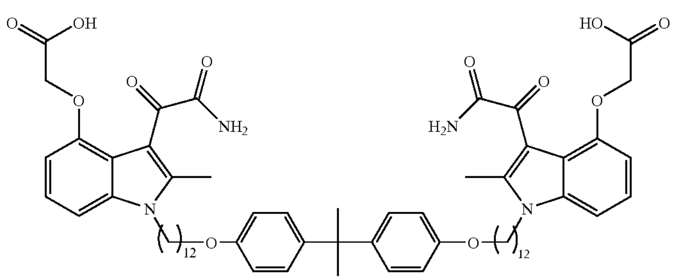 | ILY-v-30 (5-30) | 1113.41 | 0.43 | <0.02 | 0.19 | | | |

TABLE 6-continued
Inhibition of pancreas secreted human, mouse and porcine $PLA_2$
| structure | Compound ID | MW | ILYPSA IC50 (μM) hps $PLA_2$ | pps $PLA_2$ | mps $PLA_2$ | ILYPSA % inhibition at 15 μM hps $PLA_2$ | pps $PLA_2$ | mps $PLA_2$ |
|---|---|---|---|---|---|---|---|---|
| 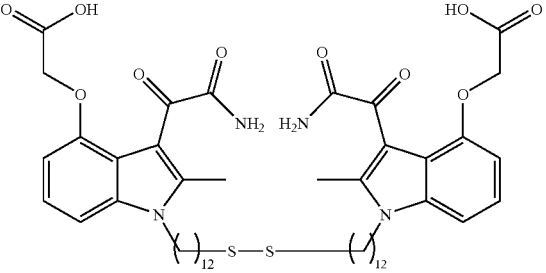 | ILY-v-28 (5-28) | 951.2 | 0.6 | 0.73 | 1 | | | |
| 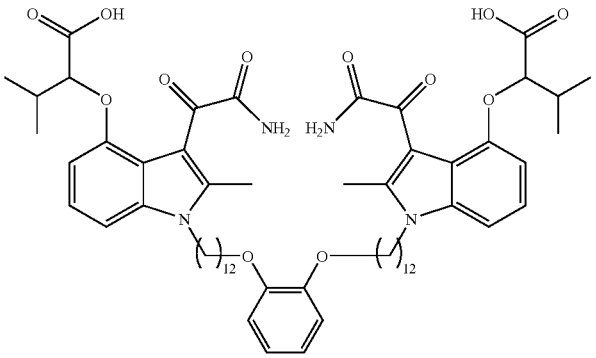 | ILY-v-33 (5-33) | 1079.37 | 0.22 | 0.24 | 0.3 | | | |
| 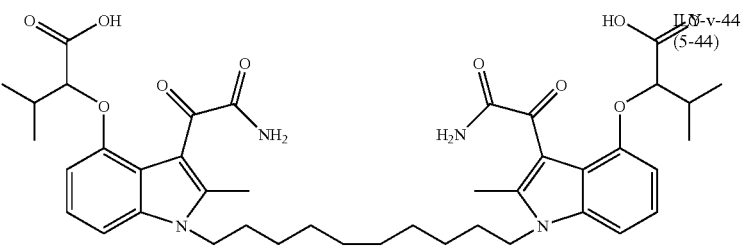 | ILY-v-44 (5-44) | 802 | 0.28 | 0.05 | 0.48 | | | |
| 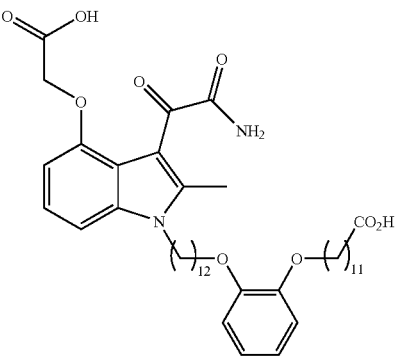 | ILY-v-41 (5-41) | 751 | 1.54 | 1.14 | 1.6 | | | |

TABLE 6-continued

Inhibition of pancreas secreted human, mouse and porcine PLA$_2$

| structure | Compound ID | MW | ILYPSA IC50 (μM) hps PLA$_2$ | ILYPSA IC50 (μM) pps PLA$_2$ | ILYPSA IC50 (μM) mps PLA$_2$ | ILYPSA % inhibition at 15 μM hps PLA$_2$ | ILYPSA % inhibition at 15 μM pps PLA$_2$ | ILYPSA % inhibition at 15 μM mps PLA$_2$ |
|---|---|---|---|---|---|---|---|---|
| (structure) | ILY-v-45 (5-45) | 902.15 | 0.12 | 0.04 | 0.07 | | | |
| (structure) | ILY-v-31 (5-31) | 992.25 | 0.1 | 0.02 | 0.03 | | | |
| (structure) | ILY-v-36 (5-36) | 1071.3 | 1.25 | 0.44 | 0.92 | | | |
| (structure) | ILY-v-37 (5-37) | 1071.3 | 0.27 | 0.2 | 0.23 | | | |

These data demonstrate that the multivalent indole and indole related compounds of the invention are active for inhibiting phospholipase A2.

Example 9

Bioavailability of Multivalent Indole or Indole Related Compounds

This example shows that the multivalent indole or indole related compounds of the invention that are phospholipase inhibitors (See Example 8) are not significantly absorbed (i.e., are substantially lumen-localized).

Bioavailability was determined for Compound 5-24 (ILY-V-24) as follows. Generally, the bioavailability was calculated by comparing a timecourse of the concentration of the test compound in the serum of mice after an intra-venous (IV) dosing, versus the timecourse of the concentration following an oral dosing of the test compound. The IV dose was ~3 mg/kg, the oral dose was ~30 mg/kg.

Materials. The following materials were used for preparing the oral and IV formulations:

| Material | Vendor | Cat or Lot# |
| --- | --- | --- |
| ILY-V-24 | Ilypsa | |
| CMC Medium Viscosity USP | Sigma-Aldrich | C9481 |
| Ethanol ESP/NF | Sigma-Aldrich | 493538 |
| PEG 300 - Ultra Grade | Sigma-Aldrich | 90878 |
| PEG 400 - Ultra Grade | Sigma-Aldrich | 91893 |
| Tween-80 Ultra. 100 ML | Sigma-Aldrich | P8074 |
| DMSO Hybri-MAX | Sigma-Aldrich | D2650 |

Oral Formulation. The oral formulation was prepared as follows. To sterile flask, 90 ml of sterile Milli-Q water was added. 9 ml of PEG-400 was added (final concentration of 9%). 50 ul of Tween-80 was added (final concentration of 0.05%). 0.9 g of CMC was weighed and added (final concentration of 0.9% w/v). A clean stir-bar was added and the CMC was dissolved effectively by stirring overnight at RT. ~30 mg of test compound was weighed into a 40 ml glass vial. ~10 ml of oral formulation was added (final test article concentration of 3 mg/ml). The vial was vortexed and then sonicated in a warming, sonicating bath for 30 minutes. At the end of this period, much of the test article was in suspension, but some particulates were observed in the bottom of the vial. This preparation was sonicated for a further hour, checked for precipitating particulates before dosing and was kept well mixed during dosing.

Intravenous (IV) Formulation. The intravenous formulation was prepared as follows. To sterile flask, 60 ml of sterile Milli-Q water was added. 30 ml of PEG-300 was added (final concentration of 30%). 5 ml of EtOH was added (final concentration of 5%). This resulted in the IV formulation, minus DMSO. The test compound was dissolved as follows. ~3 mg of test article was weighed into a 10 ml glass vial and ~500 ul of DMSO was added. ~9.5 ml of the above IV formulation (minus DMSO) was added to a 40 ml glass vial, for a final concentration of 3 mg test article in 10 ml IV formulation (containing 5% DMSO). The formulation was vortexed before dosing.

Study Design. The bioavailability study was designed as follows. Three groups (N=18, 24 or 3) of male CD-1 *Mus Musculus* mice were used for each study. On study day 0, all the animals were weighed, dosages were calculated and the animals were dosed by oral route (PO) or (IV) as outlined below in Table 7. PO formulation was sonicated in a warm sonication bath for an hour prior to dosing. IV formulation was vortexed for 5 mins immediately prior to dosing. Blood for plasma (0.5 mL/sample) was collected at specified time intervals and placed into labeled Eppendorf® tubes with Potassium-EDTA as an anti-coagulant, centrifuged and pipetted off into labeled Eppendorf® tubes (for at least 0.2 ml plasma) and frozen at −80° C.

TABLE 7

Bioavailability Study Details

| Compound | Dose | Group Number | Time Points (hr) | Mice Per time point |
| --- | --- | --- | --- | --- |
| Test Article | PO 30 mg/kg 10 ml/kg | 1 | 0.5, 1, 2, 4, 8, 24 | 3 |
| Test Article | IV 3 mg/kg 10 ml/kg | 2 | 5 min, 15 min, 0.5, 1, 2, 4, 8, 24 | 3 |
| None | None | 3 | N/A | 3 |

Calculations. Bioavailabilty was calculated as follows. Individual doses were calculated based on an average of body weights taken on the day of dosing. Serum concentrations of test compound, as well as the actual concentration of dosing solutions, were measured using 2-dimensional Mass Spectrophotometry after Liquid Chromatography (LC MS/MS). Methods were optimized for each test article and internal standards were used in all cases.

The maximum concentration ($C_{max}$) in plasma and the time to reach maximum concentration ($T_{max}$) were obtained by visual inspection of the raw data. Pharmacokinetic parameters were calculated using GraphPad Prism 4.0 software and included half-life ($t_{1/2}$) and area under the concentration-time curve from time 0 to the last time point ($AUC_{0-t}$). Visual inspection of the data shows in all cases that $AUC_{0-t}$ was very similar in the case of all test articles to the area under the concentration-time curve from 0 to infinity ($AUC_{0-\infty}$)

Bioavailability (% F) was calculated using the following relationship:

$$\% F = (AUC_{0-t,\ oral}/AUC_{0-t,\ iv}) \times (Dose_{iv}/Dose_{oral}) \times 100$$

where: % F is bioavailability; $AUC_{0-t}$ is area under the concentration-time curve at the last measurable time-point, and IV refers to intravenous.

Results. The bioavailability for Compound 5-24 (ILY-V-24) was determined to be about 4-8%.

Example 10

Synthesis of C4-Acidic Indole and Indole Related Compounds, and In-vitro Assay for Certain of Such Compounds for the Inhibition of Human, Mouse and Porcine Phospholipase $A_2$ In this example, various preferred indole and indole-related compounds having specific C4-acidic moieties are prepared.

Example 10.1

Compound (4-20)

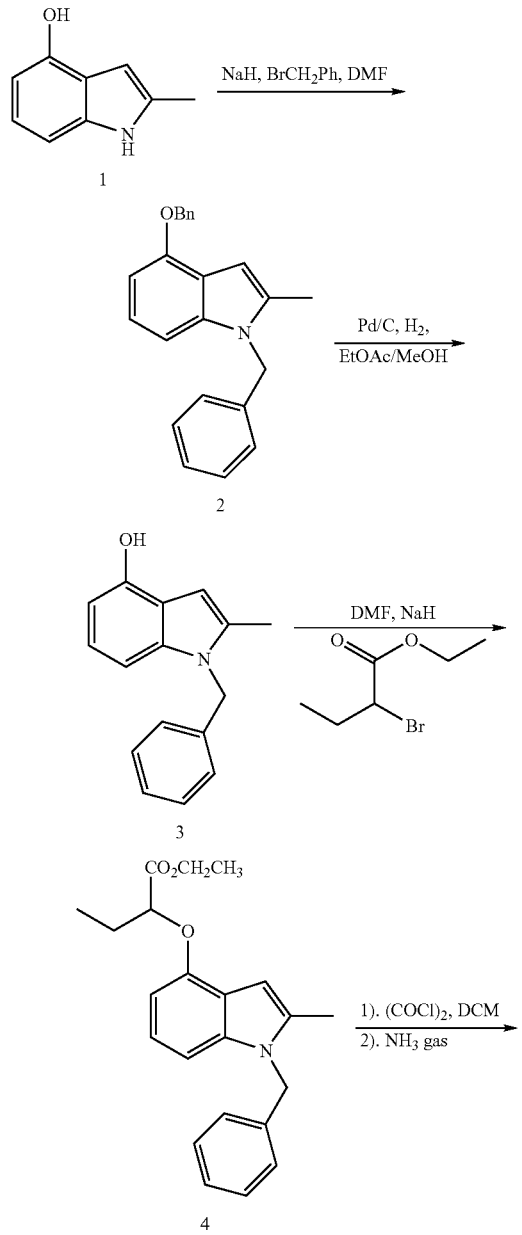

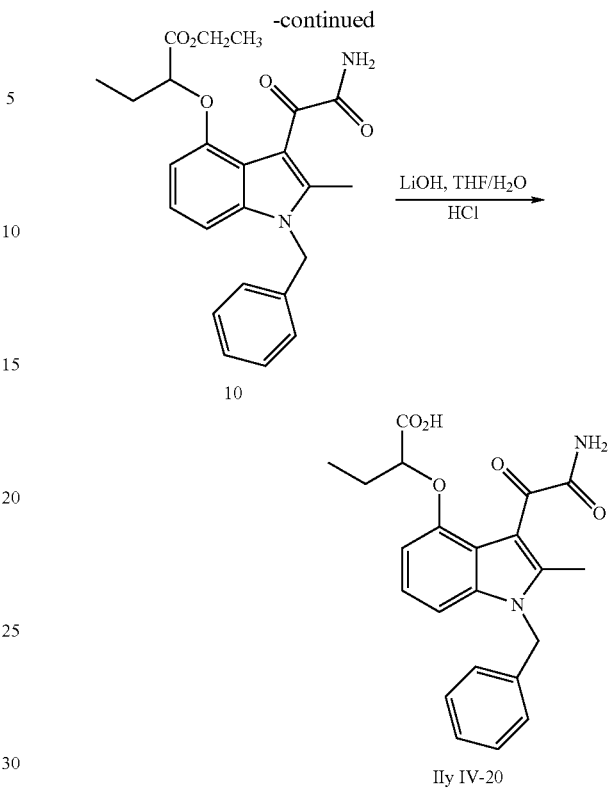

1-Benzyl-4-benzyloxy-2-methyl-1H-indole 2: 4-hydroxy-2-methyl indole 1 (50 g, 0.339 mole) was dissolved in anhydrous DMF (1 L). To the mixture sodium hydride 60% in mineral oil (27.9 g, 0.697 mole) was added. The mixture was left to stir at rt. for 1 h. To the mixture benzyl bromide (82.7 mL, 0.697 mole) was added drop-wise. The mixture was left to stir at room temperature for 18 h. The reaction was diluted with ethyl acetate (4 L) and washed with water (5×500 mL) then brine (1 L). The organic layer was separated and dried with magnesium sulphate and concentrated. The orange oily residue was purified by column chromatography (6:1 Hexane:EtOAc) to afford 86 g (72%) of 2 as an yellow oil.

1-Benzyl-2-methyl-1H-indol-4-ol 3: 1-Benzyl-4-benzyloxy-2-methyl-1H-indole 2 (86 g, 0.263 mole) was dissolved with ethyl acetate (1.5 L) and methanol (300 mL). To the mixture 10% Pd/C wet (18 g) was added to the solution. The reaction was then subjected to $H_2$ gas passed through a mercury bubbler at room temperature and 1 atm. The mixture was left to stir for 6 h. The reaction mixture was filtered through Celite and concentrated. The residue was purified by column chromatography (3:1 Hexane:EtOAc) to afford 3 (30 g, 49%) as a cream solid.

2-(1-Benzyl-2-methyl-1H-indol-4-yloxy)-butric acid ethyl ester 4: 1-Benzyl-2-methyl-1H-indol-4-ol 3 (0.5 g 2.1 mmole) was dissolved in anhydrous dimethylformamide (100 mL). To the solution sodium hydride 60% in mineral oil (0.11 g 2.73 mmole) was added. The mixture was stirred at room temperature for 1 h. To the mixture ethyl-2-bromobutyrate (0.4 mL, 2.73 mmole) was added. The mixture was stirred at room temperature for 72 h. The reaction was diluted with ethyl acetate (500 mL) and washed with $H_2O$ (5×100 mL) and brine (1×100 mL). The organic layer was separated, dried with magnesium sulfate and concentrated. The residue was purified by column chromatography (8:1 Hexane:EtOAc) to afford 4 (0.32 g, 43%) as an orange oil.

2-(3-Aminooxalyl-1-benzyl-2-methyl-1H-indol-4-yloxy)-butyric acid ethyl ester 10: To a solution of oxalyl chloride (0.1 mL, 1.09 mmole) in anhydrous dichloromethane (100 mL) a solution of 2-(1-Benzyl-2-methyl-1H-indol-4-yloxy)-butric acid ethyl ester 4 (0.32 g, 0.914 mmole) in anhydrous dichloromethane (100 mL) was added drop-wise. The mixture was left to stir at room temperature for 1 h. NH$_3$ gas was then bubbled through the solution for 30 minutes. The mixture was left to stir at room temperature for 18 h. The dichloromethane was evaporated and the residue was dissolved in ethyl acetate 300 mL) and washed with H$_2$O (2×300 mL) and brine (1×300 mL). The organic layer was separated, dried with magnesium sulfate and concentrated to afford 10 (0.35 g, 91%) as a green solid.

2-(3-Aminooxalyl-1-benzyl-2-methyl-1H-indol-4-yloxy)-butyric acid Ily-IV-20: 2-(3-Aminooxalyl-1-benzyl-2-methyl-1H-indol-4-yloxy)-butyric acid ethyl ester 10 (0.2 g, 0.477 mmole) was dissolved in THF:H$_2$O 4:1 (10 mL). To the mixture lithium hydroxide monohydrate (0.024 g, 0.573 mmole) was added. The mixture was left to stir at room temperature for 18 h. The mixture was acidified to pH 3 with 2M HCl. The resulting precipitate was collected by filtration and washed with water and dried to afford Ily-IV-20 (0.043 g, 23%) as a yellow solid.

Ref: 04-090-249.1: $^1$H NMR (DMSO) δ 12.63 (s, broad, 1H), 7.95 (s, 1H), 7.55 (s, broad, 1H), 7.35-7.00 (m, 7H), 6.47 (d, 1H), 5.50 (s, 2H), 3.4 (m, 1H), 2.50 (s, 3H), 1.95 (m, 2H), 1.00 (m, 3H). MS (ES+) 395.02

Example 10.2

Compound (4-24)

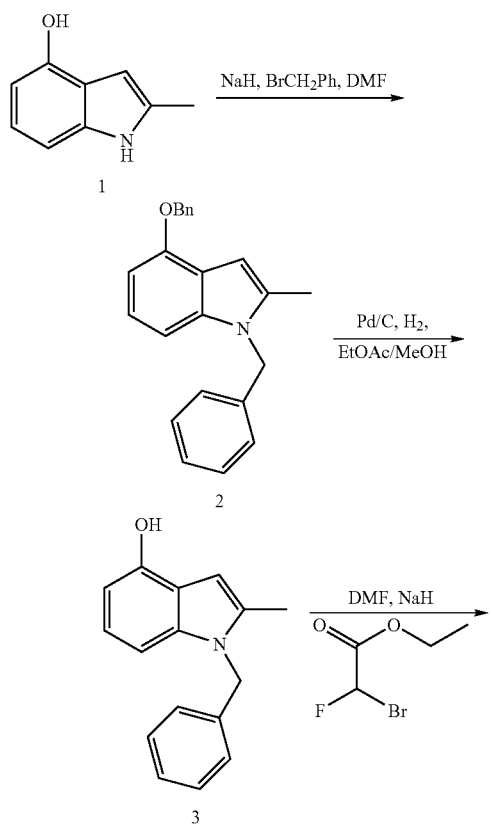

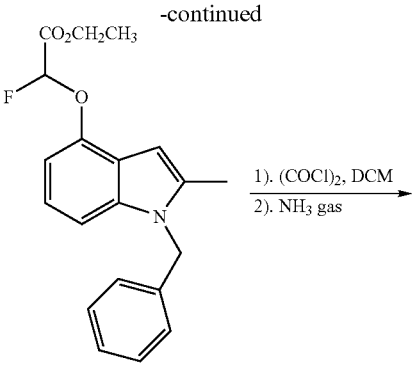

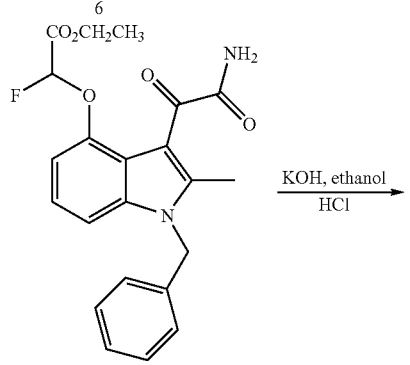

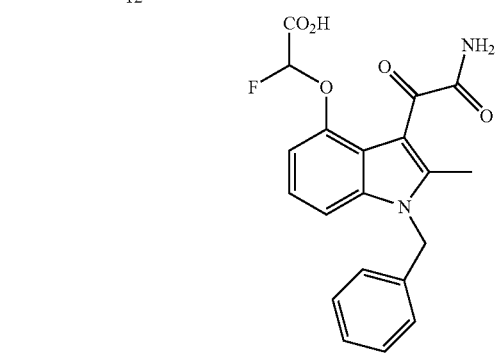

1-Benzyl-4-benzyloxy-2-methyl-1H-indole 2: 4-hydroxy-2-methyl indole 1 (50 g, 0.339 mole) was dissolved in anhydrous DMF (1 L). To the mixture sodium hydride 60% in mineral oil (27.9 g, 0.697 mole) was added. The mixture was left to stir at rt. for 1 h. To the mixture benzyl bromide (82.7 mL, 0.697 mole) was added drop-wise. The mixture was left to stir at room temperature for 18 h. The reaction was diluted with ethyl acetate (4 L) and washed with water (5×500 mL) then brine (1 L). The organic layer was separated and dried with magnesium sulphate and concentrated. The orange oily residue was purified by column chromatography (6:1 Hexane:EtOAc) to afford 86 g (72%) of 2 as an yellow oil.

1-Benzyl-2-methyl-1H-indol-4-ol 3: 1-Benzyl-4-benzyloxy-2-methyl-1H-indole 2 (86 g, 0.263 mole) was dissolved with ethyl acetate (1.5 L) and methanol (300 mL). To the mixture 10% Pd/C wet (18 g) was added to the solution. The reaction was then subjected to H$_2$ gas passed through a mercury bubbler at room temperature and 1 atm. The mixture was left to stir for 6 h. The reaction mixture was filtered through Celite and concentrated. The residue was purified by column chromatography (3:1 Hexane:EtOAc) to afford 3 (30 g, 49%) as a cream solid.

(1-Benzyl-2-methyl-1H-indol-4-yloxy)-fluoro-acetic acid ethyl ester 6: 1-Benzyl-2-methyl-1H-indol-4-ol 3 (0.3 g 1.26 mmole) was dissolved in anhydrous dimethylformamide (50 mL). To the solution sodium hydride 60% in mineral oil (66 mg 1.65 mmole) was added. The mixture was stirred at room temperature for 1 h. To the mixture ethyl-2-bromofluoroacetate (0.2 mL, 1.65 mmole) was added. The mixture was stirred at room temperature for 18 h. The reaction was diluted with ethyl acetate (500 mL) and washed with $H_2O$ (5×100 mL) and brine (1×100 mL). The organic layer was separated, dried with magnesium sulfate and concentrated. The residue was purified by column chromatography (6:1 Hexane: EtOAc) to afford 6 (0.14 g, 32%) as an yellow oil.

(3-Aminooxalyl-1-benzyl-2-methyl-1H-indol-4-yloxy)-fluoro-acetic acid ethyl ester 12: To a solution of oxalyl chloride (0.042 mL, 0.478 mmole) was diluted in anhydrous dichloromethane (25 mL). To the solution (1-Benzyl-2-methyl-1H-indol-4-yloxy)-fluoro-acetic acid ethyl ester 6 (0.14 g, 0.398 mmole) in anhydrous dichloromethane (25 mL) was added drop-wise. The mixture was left to stir at room temperature for 2 h. $NH_3$ gas was then bubbled through the solution for 30 minutes. The mixture was left to stir at room temperature for 1.5 h. The dichloromethane was evaporated and the residue was dissolved in ethyl acetate 300 mL) and washed with $H_2O$ (2×300 mL) and brine (1×300 mL). The organic layer was separated, dried with magnesium sulfate and concentrated. The residue was purified by preparative TLC (3:1 EtOAc:Hex) to afford 12 (0.02 g, 12%) as a yellow solid. Also isolated as a polar product (Rf ~0.2)

(3-Aminooxalyl-1-benzyl-2-methyl-1H-indol-4-yloxy)-fluoro-acetic acid Ily-IV-24: (3-Aminooxalyl-1-benzyl-2-methyl-1H-indol-4-yloxy)-fluoro-acetic acid ethyl ester 12 (0.06 g, 0.145 mmole) was dissolved in anhydrous ethanol (10 mL). To the mixture 0.5054 N potassium hydroxide solution was added (0.15 mL, 0.152 mmole). The mixture was left to stir at room temperature for 30 min. The ethanol was evaporated and $H_2O$ (5 mL) was added. The solution was acidified to pH 2 with 0.5 M HCl. The mixture was extracted with ethyl acetate (100 mL). The organic was washed with $H_2O$ (100 mL), separated, dried with magnesium sulfate and concentrated to afford Ily-IV-24 (5 mg, 9%) as a green solid. Ref: 04-090-287.1: $^1$H NMR (DMSO) δ 7.70 (s, 1H), 7.40-6.90 (m, 9H), 6.20 (d, 1H), 5.50 (s, 2H), 2.50 (s, 3H). MS (ES+) 384.94

Example 10.3

Compound (4-22)

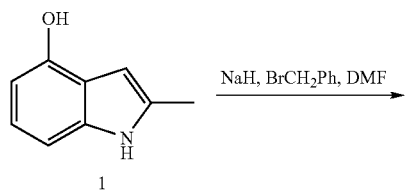

1

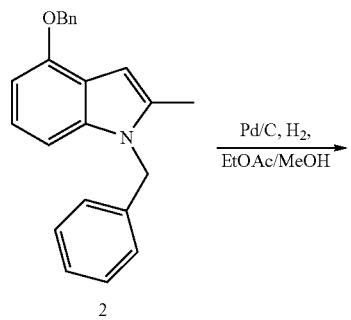

2

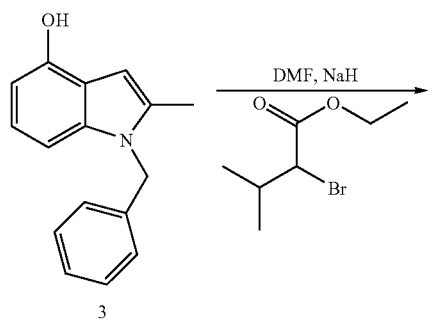

3

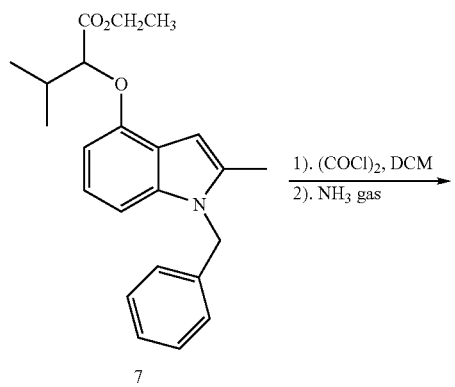

7

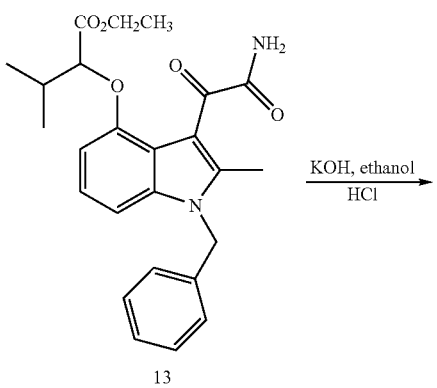

13

-continued

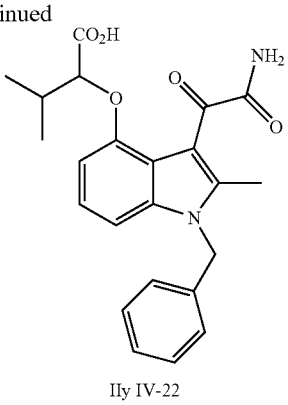

Ily IV-22

1-Benzyl-4-benzyloxy-2-methyl-1H-indole 2: 4-hydroxy-2-methyl indole 1 (50 g, 0.339 mole) was dissolved in anhydrous DMF (1 L). To the mixture sodium hydride 60% in mineral oil (27.9 g, 0.697 mole) was added. The mixture was left to stir at rt. for 1 h. To the mixture benzyl bromide (82.7 mL, 0.697 mole) was added drop-wise. The mixture was left to stir at room temperature for 18 h. The reaction was diluted with ethyl acetate (4 L) and washed with water (5×500 mL) then brine (1 L). The organic layer was separated and dried with magnesium sulphate and concentrated. The orange oily residue was purified by column chromatography (6:1 Hexane:EtOAc) to afford 86 g (72%) of 2 as an yellow oil.

1-Benzyl-2-methyl-1H-indol-4-ol 3: 1-Benzyl-4-benzyloxy-2-methyl-1H-indole 2 (86 g, 0.263 mole) was dissolved with ethyl acetate (1.5 L) and methanol (300 mL). To the mixture 10% Pd/C wet (18 g) was added to the solution. The reaction was then subjected to $H_2$ gas passed through a mercury bubbler at room temperature and 1 atm. The mixture was left to stir for 6 h. The reaction mixture was filtered through Celite and concentrated. The residue was purified by column chromatography (3:1 Hexane:EtOAc) to afford 3 (30 g, 49%) as a cream solid.

2-(1-Benzyl-2-methyl-1H-indol-4-yloxy)-3-methyl-butyric acid ethyl ester 7: 1-Benzyl-2-methyl-1H-indol-4-ol 3 (0.3 g 1.26 mmole) was dissolved in anhydrous dimethylformamide (20 mL). To the solution sodium hydride 60% in mineral oil (66 mg 1.65 mmole) was added. The mixture was stirred at room temperature for 1 h. To the mixture ethyl-2-bromoisovalerate (0.344 mL, 1.65 mmole) was added. The mixture was stirred at room temperature for 18 h. The reaction was diluted with ethyl acetate (300 mL) and washed with $H_2O$ (4×100 mL) and brine (1×100 mL). The organic layer was separated, dried with magnesium sulfate and concentrated. The residue was purified by column chromatography (10:1 Hexane:EtOAc) to afford a 1:1 mixture of 7: ethyl-2-bromoisovalerate. Further purification by column chromatography (10:1 Hexane:EtOAc) afforded 7 (0.09 g, 19%) as a yellow oil.

2-(3-Aminooxalyl-1-benzyl-2-methyl-1H-indol-yloxy)-3-methyl-butyric acid ethyl ester 13: 2-(1-Benzyl-2-methyl-1H-indol-4-yloxy)-3-methyl-butyric acid ethyl ester 7 (0.09 g, 0.247 mmole) was dissolved in anhydrous dichloromethane (50 mL). To the solution oxalyl chloride (0.026 mL, 0.296 mmole) was added. The mixture was left to stir at room temperature for 1 h. $NH_3$ gas was then bubbled through the solution for 30 minutes. The mixture was left to stir at room temperature for 1 h. The dichloromethane was evaporated and the residue was dissolved in ethyl acetate (200 mL) and washed with $H_2O$ (3×200 mL) and brine (1×300 mL). The organic layer was separated, dried with magnesium sulfate and concentrated to afford 13 (0.23 g, >100%) as a yellow solid (contained inorganic salt). The material was used in next step without further purification.

2-(3-Aminooxalyl-1-benzyl-2-methyl-1H-indol-4-yloxy)-3-methyl-butyric acid Ily-IV-22: 2-(3-Aminooxalyl-1-benzyl-2-methyl-1H-indol-yloxy)-3-methyl-butyric acid ethyl ester 13 (0.15 g, 0345 mmole) was dissolved in anhydrous ethanol (10 mL). To the mixture 0.5054 N potassium hydroxide solution (0.4 mL, 0.403 mmole) was added. The mixture was left to stir at room temperature for 72 h. The reaction mixture was evaporated under high vacuum. The residue was dissolved in $H_2O$ (5 mL) and acidified with 2M HCl. The mixture was left to stir for 30 min. The precipitate was collected by filtration washed and with $H_2O$ to afford Ily-IV-22 (0.03 g, 21%) as a yellow solid.

Ref: 04-090-270.1: $^1$H NMR (DMSO) δ 12.60 (s, broad, 1H), 8.00 (s, 1H), 7.60 (s, 1H), 7.40-7.00 (m, 7H), 6.50 (d, 1H), 5.50 (s, 2H), 4.47 (d, 1H), 2.42 (s, 3H), 2.30 (m, 1H), 1.10-0.90 (m, 6H). MS (ES+) 409.00

Example 10.4

Compound (4-33)

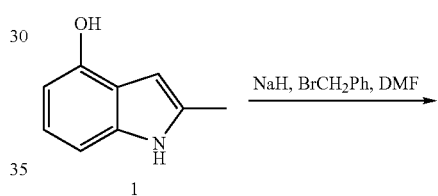

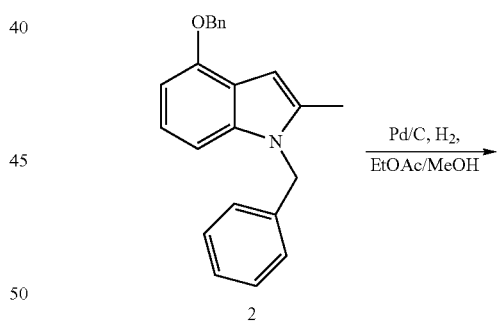

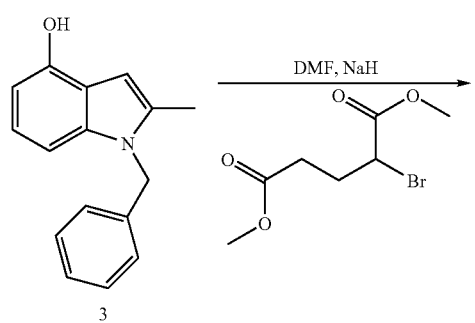

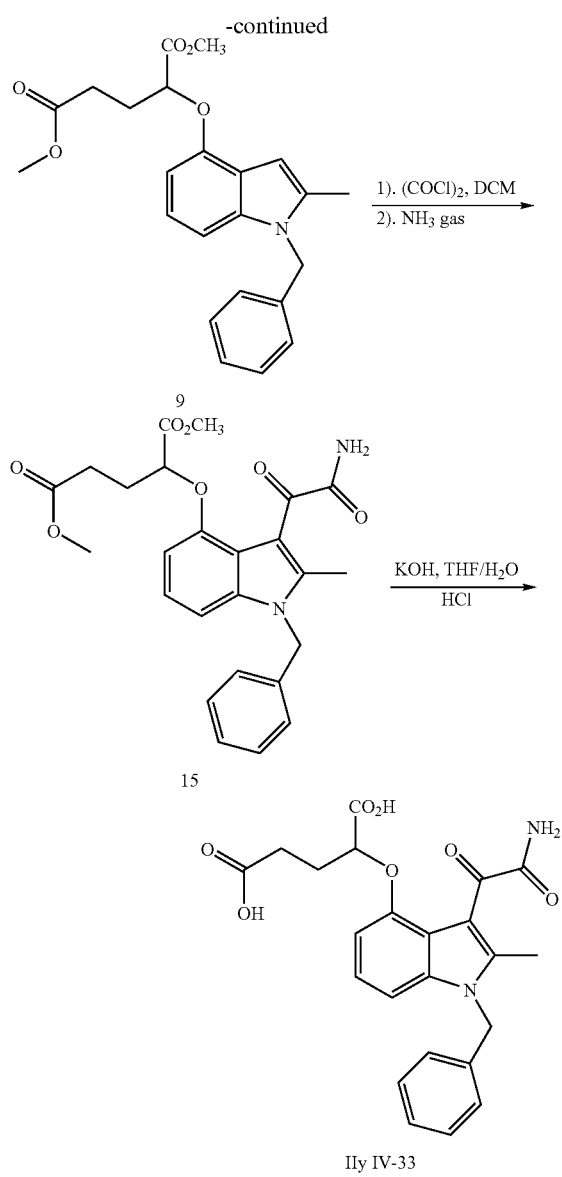

Celite and concentrated. The residue was purified by column chromatography (3:1 Hexane:EtOAc) to afford 3 (30 g, 49%) as a cream solid.

2-(1-Benzyl-2-methyl-1H-indol-4-yloxy)-pentanedioic acid 1-methyl ester 5-methyl ester 9: 1-Benzyl-2-methyl-1H-indol-4-ol 3 (0.3 g 1.26 mmole) was dissolved in anhydrous dimethylformamide (20 mL). To the solution sodium hydride 60% in mineral oil (66 mg 1.65 mmole) was added. The mixture was stirred at room temperature for 1 h. To the mixture dimethyl-2-bromoglutarate (0.3 mL, 1.25 mmole) was added. The mixture was stirred at room temperature for 18 h. The reaction was diluted with ethyl acetate (300 mL) and washed with $H_2O$ (4×100 mL) and brine (1×100 mL). The organic layer was separated, dried with magnesium sulfate and concentrated. The residue was purified by column chromatography (6:1 Hexane:EtOAc) to afford 9 (0.49 g, 97%) as a white solid.

2-(3-Aminooxalyl-1-benzyl-2-methyl-1H-indol-4-yloxy)-pentaedioic acid dimethyl ester 15: 2-(1-Benzyl-2-methyl-1H-indol-4-yloxy)-pentanedioic acid 1-methyl ester 5-methyl ester 9 (0.15 g, 0.38 mmole) was dissolved in anhydrous dichloromethane (50 mL). To the solution oxalyl chloride (0.037 mL, 0.396 mmole) was added. The mixture was left to stir at room temperature for 2 h. $NH_3$ gas was then bubbled through the solution for 30 minutes. The mixture was left to stir at room temperature for 1 h. The dichloromethane was evaporated and the residue was dissolved in ethyl acetate (200 mL) and washed with $H_2O$ (3×200 mL) and brine (1×300 mL). The organic layer was separated, dried with magnesium sulfate and concentrated to afford 15 (0.17 g, 96%) as a yellow solid.

2-(3-Aminooxalyl-1-benzyl-2-methyl-1H-indol-4-yloxy)-pentaedioic acid Ily-IV-33: 2-(3-Aminooxalyl-1-benzyl-2-methyl-1H-indol-4-yloxy)-pentaedioic acid dimethyl ester 15 (0.08 g, 0.172 mmole) was dissolved in THF: $H_2O$ 4:1 (10 mL). To the mixture 0.5054 N potassium hydroxide solution (0.48 mL, 0.495 mmole) was added. The mixture was left to stir at room temperature for 72 h. The reaction mixture was evaporated to dryness, then dissolved in $H_2O$ (5 mL) and acidified to pH 4 with 2M HCl. The resulting precipitate was collected by filtration and dried to afford Ily-IV-33 (0.03 g, 40%) as a yellow solid.

Ref: 04-090-288.2: $^1$H NMR (DMSO) δ 8.40 (s, broad, 1H), 7.92 (s, 1H), 7.40-7.20 (m, 3H), 7.10-6.90 (m, 4H), 6.40 (d, 1H), 5.45 (s, 2H), 4.20 (t, broad, 1H), 2.50 (s, 3H), 2.40-1.90 (m, 4H). MS (ES−) 436.98 (ES+) 460.91 (M+Na$^+$).

1-Benzyl-4-benzyloxy-2-methyl-1H-indole 2: 4-hydroxy-2-methyl indole 1 (50 g, 0.339 mole) was dissolved in anhydrous DMF (1 L). To the mixture sodium hydride 60% in mineral oil (27.9 g, 0.697 mole) was added. The mixture was left to stir at rt. for 1 h. To the mixture benzyl bromide (82.7 mL, 0.697 mole) was added drop-wise. The mixture was left to stir at room temperature for 18 h. The reaction was diluted with ethyl acetate (4 L) and washed with water (5×500 mL) then brine (1 L). The organic layer was separated and dried with magnesium sulphate and concentrated. The orange oily residue was purified by column chromatography (6:1 Hexane:EtOAc) to afford 86 g (72%) of 2 as an yellow oil.

1-Benzyl-2-methyl-1H-indol-4-ol 3: 1-Benzyl-4-benzyloxy-2-methyl-1H-indole 2 (86 g, 0.263 mole) was dissolved with ethyl acetate (1.5 L) and methanol (300 mL). To the mixture 10% Pd/C wet (18 g) was added to the solution. The reaction was then subjected to $H_2$ gas passed through a mercury bubbler at room temperature and 1 atm. The mixture was left to stir for 6 h. The reaction mixture was filtered through Example 10.5

Compound (4-32)

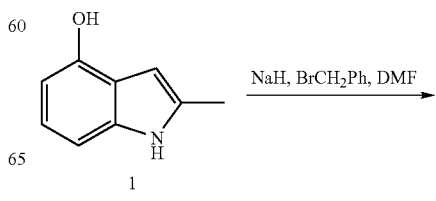

-continued

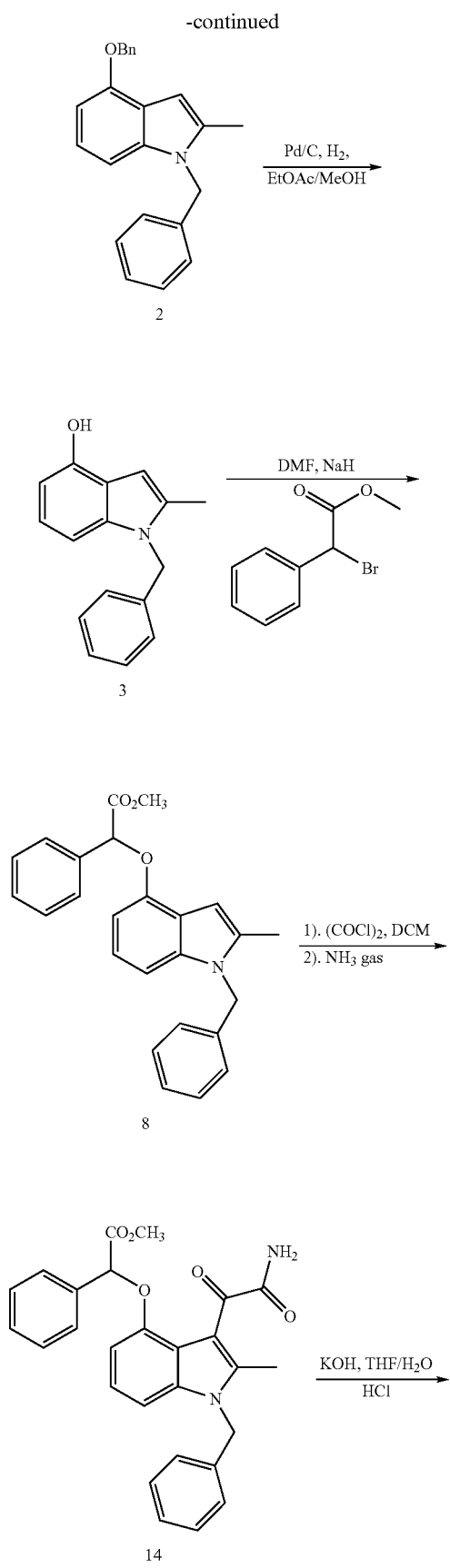

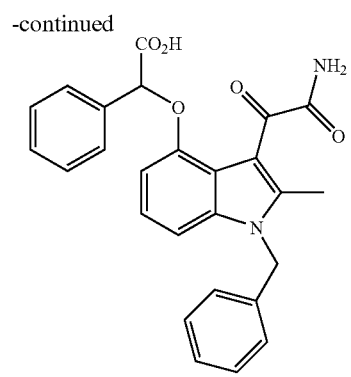

IIy IV-32

1-Benzyl-4-benzyloxy-2-methyl-1H-indole 2: 4-hydroxy-2-methyl indole 1 (50 g, 0.339 mole) was dissolved in anhydrous DMF (1 L). To the mixture sodium hydride 60% in mineral oil (27.9 g, 0.697 mole) was added. The mixture was left to stir at rt. for 1 h. To the mixture benzyl bromide (82.7 mL, 0.697 mole) was added drop-wise. The mixture was left to stir at room temperature for 18 h. The reaction was diluted with ethyl acetate (4 L) and washed with water (5×500 mL) then brine (1 L). The organic layer was separated and dried with magnesium sulphate and concentrated. The orange oily residue was purified by column chromatography (6:1 Hexane:EtOAc) to afford 86 g (72%) of 2 as an yellow oil.

1-Benzyl-2-methyl-1H-indol-4-ol 3: 1-Benzyl-4-benzyloxy-2-methyl-1H-indole 2 (86 g, 0.263 mole) was dissolved with ethyl acetate (1.5 L) and methanol (300 mL). To the mixture 10% Pd/C wet (18 g) was added to the solution. The reaction was then subjected to $H_2$ gas passed through a mercury bubbler at room temperature and 1 atm. The mixture was left to stir for 6 h. The reaction mixture was filtered through Celite and concentrated. The residue was purified by column chromatography (3:1 Hexane:EtOAc) to afford 3 (30 g, 49%) as a cream solid.

(1-Benzyl-2-methyl-1H-indol-4-yloxy)-phenyl-acetic acid methyl ester 8: 1-Benzyl-2-methyl-1H-indol-4-ol 3 (0.3 g 1.26 mmole) was dissolved in anhydrous dimethylformamide (20 mL). To the solution sodium hydride 60% in mineral oil (66 mg 1.65 mmole) was added. The mixture was stirred at room temperature for 1 h. To the mixture bromo-phenyl-acetic acid methyl ester (0.24 mL, 1.512 mmole) was added. The mixture was stirred at room temperature for 18 h. The reaction was diluted with ethyl acetate (300 mL) and washed with $H_2O$ (4×100 mL) and brine (1×100 mL). The organic layer was separated, dried with magnesium sulfate and concentrated. The residue was purified by column chromatography (10:1 Hexane:EtOAc) to afford 8 (0.3 g, 62%) as a white solid.

(3-Aminooxalyl-1-benzyl-2-methyl-1H-indol-4-yloxy)-2-phenyl-acetic acid methyl ester 14: (1-Benzyl-2-methyl-1H-indol-4-yloxy)-phenyl-acetic acid methyl ester 8 (0.15 g, 0.389 mmole) was dissolved in anhydrous dichloromethane (50 mL). To the solution oxalyl chloride (0.04 mL, 0.428 mmole) was added. The mixture was left to stir at room temperature for 2 h. $NH_3$ gas was then bubbled through the solution for 30 minutes. The mixture was left to stir at room temperature for 1 h. The dichloromethane was evaporated and the residue was dissolved in ethyl acetate (200 mL) and washed with $H_2O$ (3×200 mL) and brine (1×300 mL). The organic layer was separated, dried with magnesium sulfate and concentrated to afford 14 (0.15 g, 85%) as a yellow solid.

(3-Aminooxalyl-1-benzyl-2-methyl-1H-indol-4-yloxy)-phenyl-acetic acid Ily-IV-32: (3-Aminooxalyl-1-benzyl-2-methyl-1H-indol-4-yloxy)-2-phenyl-acetic acid methyl ester 14 (0.15 g, 0.33 mmole) was dissolved in THF:H$_2$O 4:1 (10 mL). To the mixture 0.5054 N potassium hydroxide solution (0.48 mL, 0.495 mmole) was added. The mixture was left to stir at room temperature for 18 h. The reaction mixture was evaporated to dryness. The residue was dissolved in H$_2$O (5 mL) and acidified to pH 4 with 2M HCl. The resulting precipitate was collected by filtration washed with H$_2$O and dried to afford Ily-IV-32 (0.08 g, 55%) as a yellow solid.

Ref: 04-090-281.1: $^1$H NMR (DMSO) δ 12.90 (s, broad, 1H), 7.90 (s, broad, 1H), 7.65 (d, 2H), 7.50-7.00 (m, 11H), 6.60 (d, 1H), 6.85 (s, 1H), 5.50 (s, 2H), 2.45 (s, 3H). MS (ES+) 443.02

Examples 10.6a, 10.7a, 10.8-10.10

Compounds (4-47, 4-46, 4-8, 4-1 and 4-19)

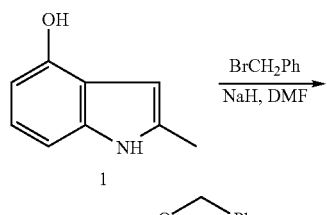

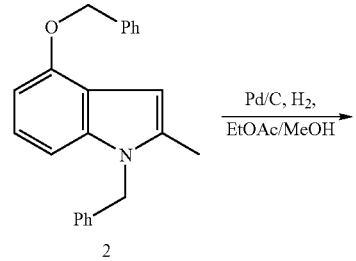

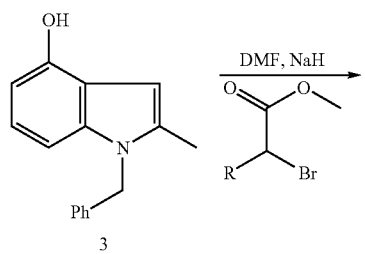

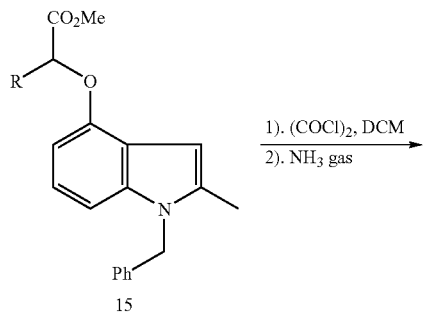

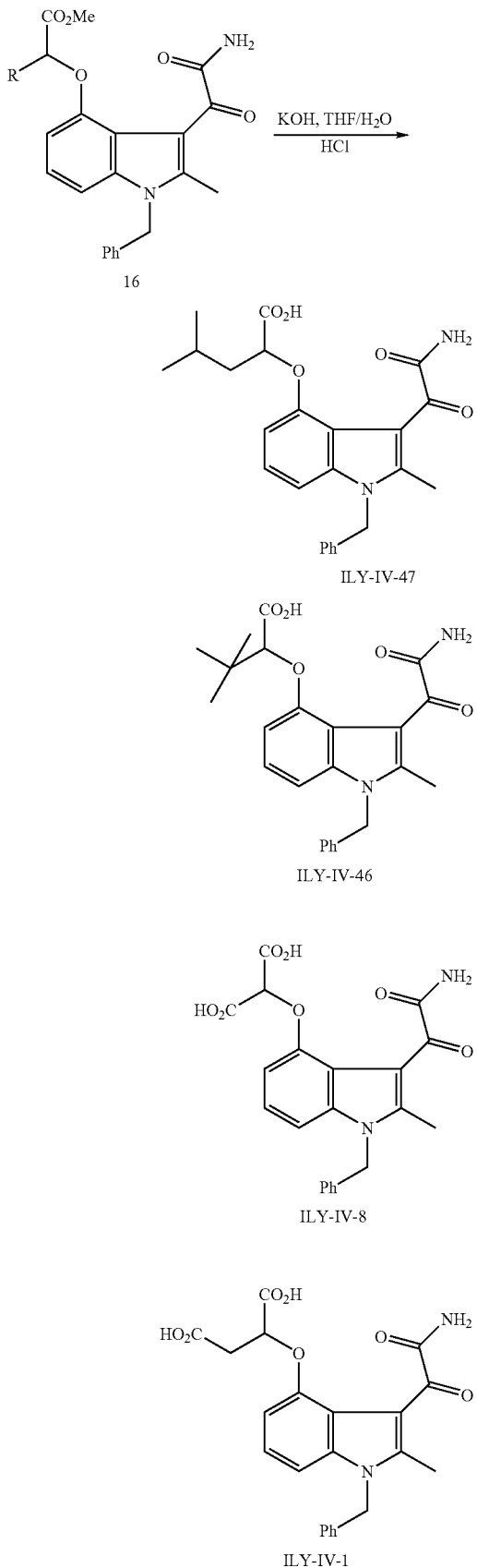

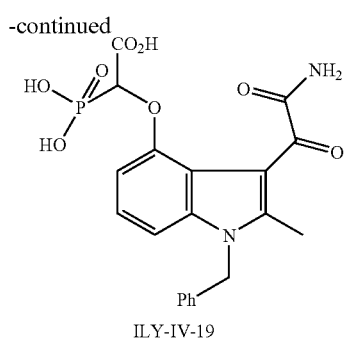

ILY-IV-19

2-(3-(2-amino-2-oxoacetyl)-1-benzyl-2-methyl-1H-indol-4-yloxy)-4-methylpentanoic acid (ILY-IV-47); 2-(3-(2-amino-2-oxoacetyl)-1-benzyl-2-methyl-1H-indol-4-yloxy)-3,3-dimethylbutanoic acid (ILY-IV-46); 2-(3-(2-amino-2-oxoacetyl)-1-benzyl-2-methyl-1H-indol-4-yloxy)malonic acid (ILY-IV-8); 2-(3-(2-amino-2-oxoacetyl)-1-benzyl-2-methyl-1H-indol-4-yloxy)-2-phosphonoacetic acid (ILY-IV-1); 2-(3-(2-amino-2-oxoacetyl)-1-benzyl-2-methyl-1H-indol-4-yloxy)succinic acid (ILY-IV-19) can be prepared according to the schema shown above and the following description.

Alkylation: 1-Benzyl-2-methyl-1H-indol-4-ol 3 (1 mmole) is dissolved in anhydrous dimethylformamide (20 mL). To the solution, sodium hydride 60% in mineral oil (1.2 mmole) is added. The mixture is stirred at room temperature for 1 h. To the mixture the corresponding bromo-acetic acid methyl ester (1.2 mmole) is added. The mixture is stirred at room temperature for 18 h. The reaction is diluted with ethyl acetate (300 mL) and washed with $H_2O$ (4×100 mL) and brine (1×100 mL). The organic layer is to be separated, dried with magnesium sulfate and concentrated. The residue is purified by column chromatography to afford 15.

Glyoxamidation: The corresponding acetic acid methyl ester 15 (1 mmole) is dissolved in anhydrous dichloromethane (50 mL). To the solution oxalyl chloride (1.1 mmole) is added. The mixture is left to stir at room temperature for 2 h. $NH_3$ gas is then bubbled through the solution for 30 minutes. The mixture is left to stir at room temperature for 1 h. The dichloromethane is evaporated and the residue is dissolved in ethyl acetate (200 mL) and washed with $H_2O$ (3×200 mL) and brine (1×300 mL). The organic layer is separated, dried with magnesium sulfate and concentrated to afford 16.

Deprotection: Compound 16 (1 mmole) is dissolved in $THF:H_2O$ 4:1 (10 mL). To the mixture 0.5054 N potassium hydroxide solution is added. The mixture is left to stir at room temperature for 18 h. The reaction mixture is evaporated to dryness. The residue is dissolved in $H_2O$ (5 mL) and is acidified to pH 4 with 2M HCl. The resulting precipitate is collected by filtration washed with $H_2O$ and dried to afford Ily-IV-47, Ily-IV-46, Ily-IV-8, Ily-IV-1, and Ily-IV-19.

Example 10.6b

Compound (4-47)

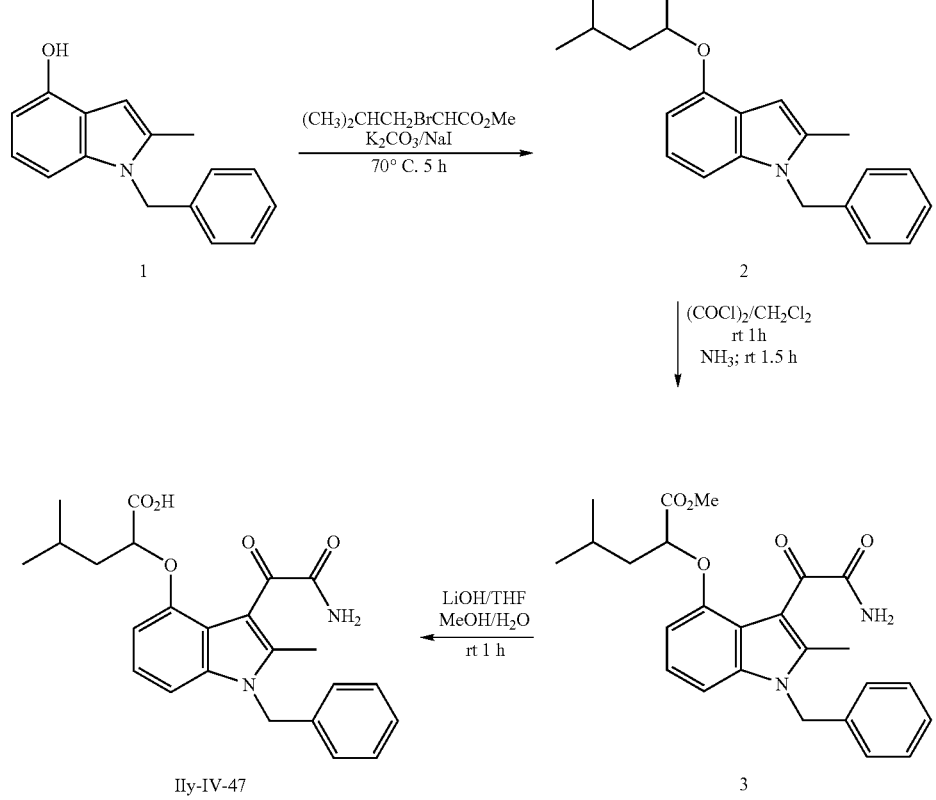

2-(1-Benzyl-2-methyl-1H-indol-4-yloxy)-4-methyl-pentanoic acid methyl ester (2): To a stirred suspension of K₂CO₃ (0.563 g, 4.22 mmol), NaI (0.031 g, 0.21 mmol) and 1-benzyl-2-methyl-1H-indol-4-ol (1) (0.500 g, 2.11 mmol) in dry DMF (15 mL), a solution of (CH₃)₂CHCH₂BrCHCO₂Me (0.66 g, 3.2 mmol) in DMF (5 mL) was added dropwise. The reaction mixture was heated at 70° C. for 7 h, cooled to room temperature and water (30 mL) was added. The mixture was extracted with EtOAc (3×50 mL). The combined organic extracts were washed with water (50 mL), brine (50 mL), dried over Na₂SO₄ and evaporated. Flash chromatography of the residue over silica gel, using 10% EtOAc in hexanes to 20% EtOAc in hexanes, gave product 2 as a pale yellow solid. Yield: 0.54 g (70%).

2-(3-Aminooxalyl-1-benzyl-2-methyl-1H-indol-4-yloxy)-4-methyl-pentanoic acid methyl ester (3): A solution of 2-(1-benzyl-2-methyl-1H-indol-4-yloxy)-4-methyl-pentanoic acid methyl ester (2) (243 mg, 0.671 mmol) in CH₂Cl₂ (10 mL) was prepared. To this mixture, oxalyl chloride (0.075 mL, 0.85 mmol) was added dropwise, and the mixture was stirred at room temperature for 1 h. Ammonia was bubbled through the mixture for 30 minutes and stirred for another 1 h. The reaction mixture was diluted with EtOAc (100 mL), washed with water (50 mL), brine (50 mL), dried over Na₂SO₄ and concentrated. The residue was purified by crystallization from CHCl₃/hexanes (1:1) to afford intermediate (3) as a yellow solid. Yield: 0.220 g (76%).

2-(3-Aminooxalyl-1-benzyl-2-methyl-1H-indol-4-yloxy)-4-methyl-pentanoic acid (Ily-IV-47): To a solution of 2-(3-aminooxalyl-1-benzyl-2-methyl-1H-indol-4-yloxy)-4-methyl-pentanoic acid methyl ester (3) (150 mg, 0.344 mmol) in THF/MeOH/H₂O (5 mL/5 mL/5 mL) lithium hydroxide monohydrate (0.041 g, 1.72 mmol) was added. The reaction mixture was stirred at room temperature for 1 h, evaporated and then acidified (pH=4) with 1 N HCl to form a white precipitate, which was filtered off, washed with water and dried in vacuum to afford product Ily-IV-47 as a yellow solid. Yield: 125 mg (86%). ¹H NMR: 05-056-069 (DMSO-d₆, 400 MHz) δ, ppm: 0.88 (d, 3 H), 0.95 (d, 3 H), 1.55-1.65 (m, 1 H), 1.76-2.04 (m, 2 H), 2.45 (s, 3 H), 4.70 (m, 1 H), 5.48 (s, 2 H), 6.54 (d, 1 H), 7.00-7.18 (m, 4 H), 7.20-7.38 (m, 3 H), 7.58 (s, 1 H), 8.02 (s, 1 H) (COOH not shown). ES-MS: m/z=422.99 (M+1).

Example 10.7b

Compound (4-8)

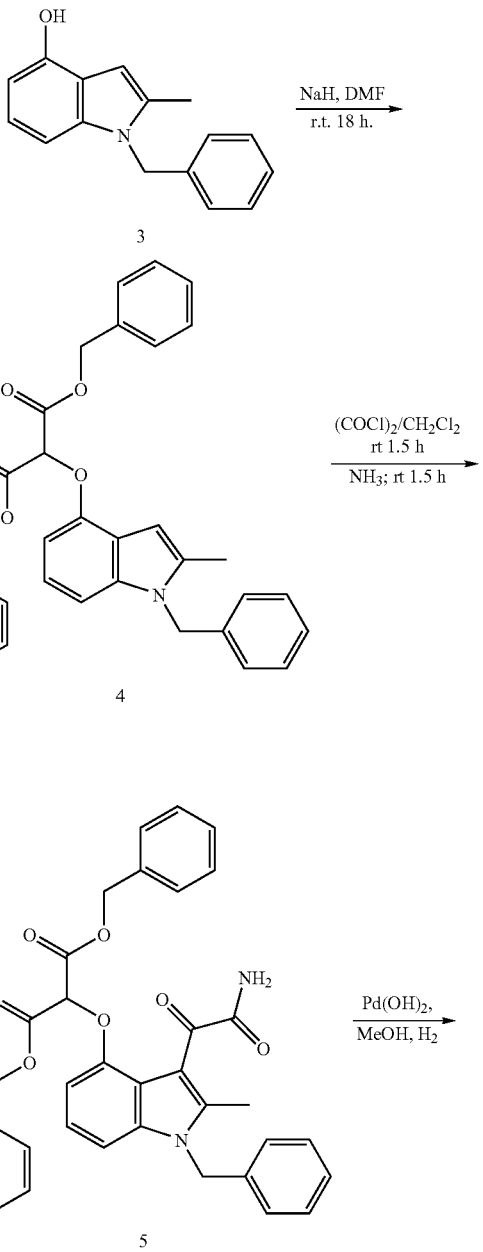

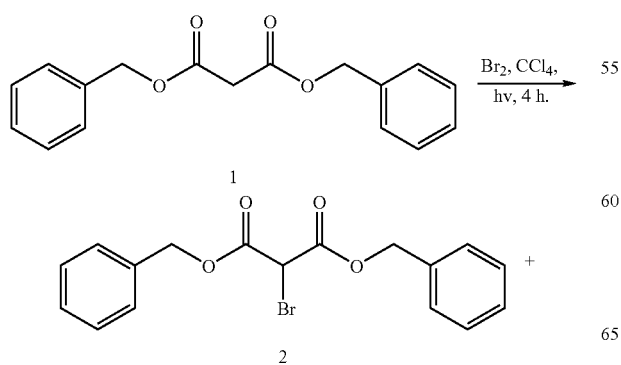

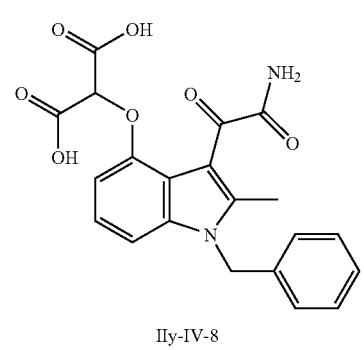

Ily-IV-8

2-Bromo-malonic acid dibenzyl ester (2): To a solution of dibenzyl malonate (9.8 g, 34.46 mmole) in carbon tetrachloride (25 mL), bromine (10.14 g, 63.4 mmole) was added dropwise at room temperature over 4 h. The reaction mixture was irradiated with a 150 W lamp during the addition. The reaction mixture was quenched with water. The organic layer was separated and the aqueous layer was further extracted with dichloromethane (3 ×30 mL). The organic extracts were combined, washed with sodium hydrogen carbonate solution (3×50 mL) and brine solution 3×50 mL). The organic layer was dried over magnesium sulphate and concentrated. The residue was purified by column chromatography (9:1 Hex: EtOAc) to afford intermediate 2 as an orange oil. Yield 3.8 g, 30%

2-(1-Benzyl-2-methyl-1H-indol-4-yloxy)-malonic acid dibenzyl ester (4): To a solution of 1-benzyl-2-methyl-1H-indol-4-ol (3) (1.0 g, 4.22 mmole) in DMF (30 mL), sodium hydride (0.285 g, 5.48 mmole, 60% in mineral oil) was added. The mixture was stirred at room temperature for 45 minutes. To the reaction mixture a solution of 2-bromo-malonic acid dibenzyl ester (2) (1.9 g, 5.48 mmole) in DMF (20 mL) was added dropwise. The mixture was stirred at room temperature for 18 h. The reaction mixture was diluted with ethyl acetate (50 mL) and washed with water (3×50 mL) and brine (3×50 mL). The organic layer was separated and dried over magnesium sulphate and concentrated. The residue was purified by column chromatography (3:1 Hex:EtOAc) to afford a mixture of starting material (2) and intermediate (4). The crude material was used in the following step without further purification.

2-(3-Aminooxalyl-1-benzyl-2-methyl-1H-indol-4-yloxy)-malonic acid dibenzyl ester (5): To a solution of 2-(1-benzyl-2-methyl-1H-indol-4-yloxy)-malonic acid dibenzyl ester (4) (0.2 g, crude material) in dichloromethane (50 mL), oxalyl chloride (0.1 mL, 1.06 mmole) was added. The mixture was stirred at room temperature for 1.5 h. Ammonia gas was bubbled through the solution for 30 min. Then the mixture was stirred for an additional 1 h. The solvent was evaporated. The residue was dissolved in ethyl acetate (50 mL) and washed with water (3×50 mL) and brine (3×50 mL). The organic layer was separated, dried over magnesium sulphate and concentrated. The residue was purified by preparative TLC (1:1 Hex:EtOAc) to afford intermediate (4) as a yellow solid. Yield: 0.12 g 2-(3-Aminoooxalyl-1-benzyl-2-methyl-1H-indol-4-yloxy)-malonic acid (Ily-IV-8): To a solution of 2-(3-aminooxalyl-1-benzyl-2-methyl-1H-indol-4-yloxy)-malonic acid dibenzyl ester (5) (0.07 g, 0.1206 mmole) in methanol (75 mL), palladium hydroxide (0.017 mg, 50% water wet) was added. Hydrogen was then bubbled through the mixture at 1 atm and room temperature for 30 minutes. The reaction mixture was filtered through Celite and the filtrate was concentrated to afford a yellow solid (0.030 mg). Analysis by $^1$H NMR indicated that approximately 30% mono decarboxlyation had occurred. $^1$H NMR (400 MHz, DMSO-$d_6$) δ, ppm: 7.47 (brs, 1H), 7.35-6.95 (m, 8H), 6.28 (d, 1H), 5.50 (s, 2H), 4.92 (s, 1H), 2.50 (s, 3H). ES-MS: m/z=410.94 (M+1).

Example 10.11

Compound (4-44)

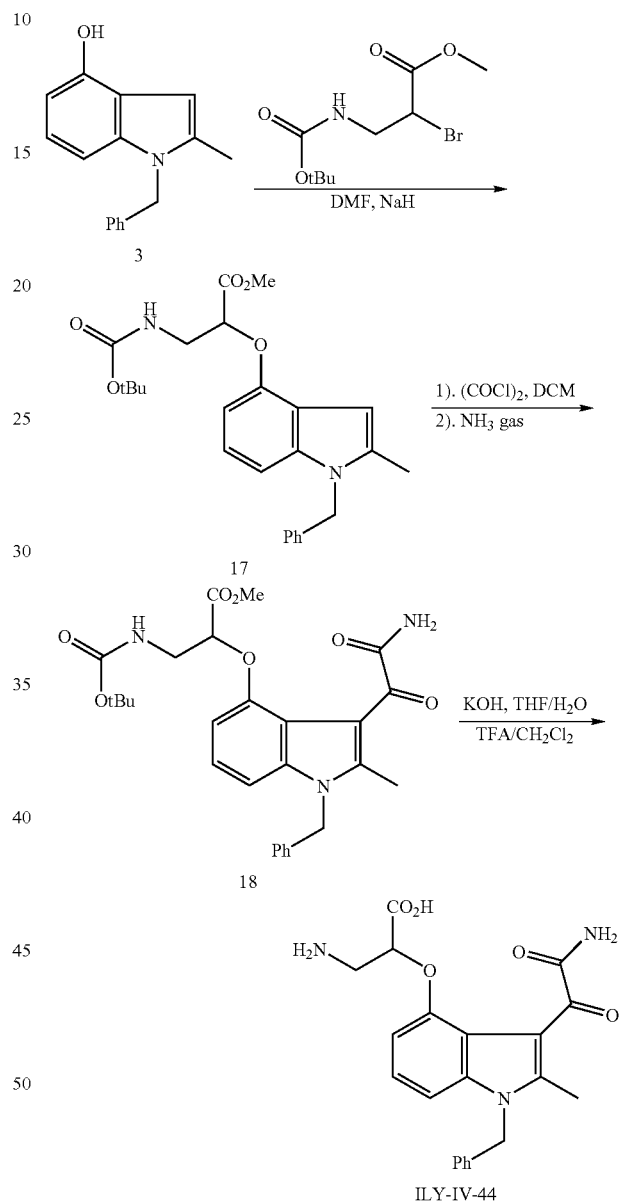

3-amino-2-(3-(2-amino-2-oxoacetyl)-1-benzyl-2-methyl-1H-indol-4-yloxy)propanoic acid (ILY-IV-44) 1-Benzyl-2-methyl-1H-indol-4-ol 3 (1 mmole) is dissolved in anhydrous dimethylformamide (20 mL). To the solution sodium hydride, 60% in mineral oil (1.2 mmole) is added. The mixture is stirred at room temperature for 1 h. To the mixture the corresponding bromo-acetic acid methyl ester (1.2 mmole) is added. The mixture is stirred at room temperature for 18 h. The reaction is diluted with ethyl acetate (300 mL) and is washed with H$_2$O (4×100 mL) and brine (1×100 mL). The organic layer is separated, dried with magnesium sulfate and concentrated. The residue is purified by column chromatography to afford 17.

The corresponding acetic acid methyl ester 17 (1 mmole) is dissolved in anhydrous dichloromethane (50 mL). To the solution oxalyl chloride (1.1 mmole) is added. The mixture was left to stir at room temperature for 2 h. $NH_3$ gas is then bubbled through the solution for 30 minutes. The mixture is left to stir at room temperature for 1 h. The dichloromethane is evaporated and the residue is dissolved in ethyl acetate (200 mL) and washed with $H_2O$ (3×200 mL) and brine (1×300 mL). The organic layer is to be separated, dried with magnesium sulfate and concentrated to afford 18.

Compound 18 (1 mmole) is dissolved in THF:$H_2O$ 4:1 (10 mL). To the mixture 0.5054 N potassium hydroxide solution is added. The mixture is left to stir at room temperature for 18 h. The reaction mixture is evaporated to dryness. The dried mixture and 1,3-dimethoxybenzene (7 mmole) in dry dichloromethane (30 mL), at room temperature under nitrogen, is added with trifluoroacetic acid (30 mL). The solution is stirred for 1 h and the solvents evaporated below 25° C. The residue is dissolved in $H_2O$ (5 mL) and acidified to pH 4 with 2M HCl. The resulting precipitate is collected by filtration washed with $H_2O$ and dried to afford Ily-IV-44.

Example 10.12

Compound (4-48)

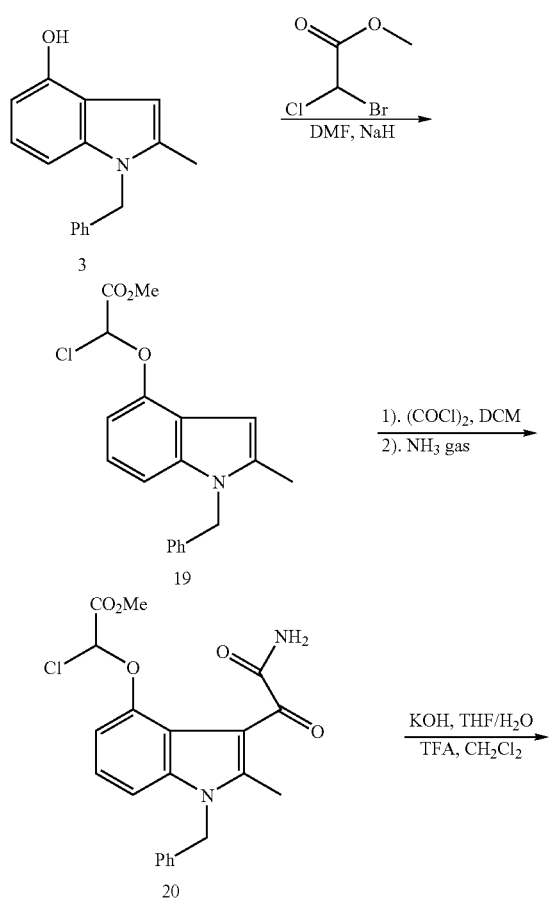

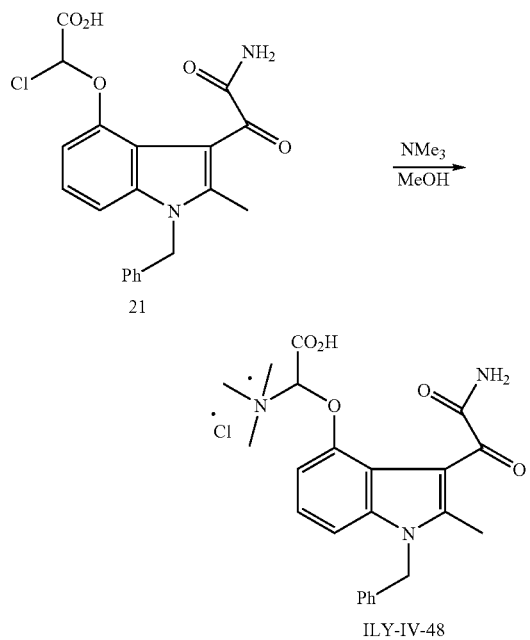

2-(3-(2-amino-2-oxoacetyl)-1-benzyl-2-methyl-1H-indol-4-yloxy)-2-(trimethylamino)acetic acid hydrochloride salt (ILY-IV-48) 1-Benzyl-2-methyl-1H-indol-4-ol 3 (1 mmole) is dissolved in anhydrous dimethylformamide (20 mL). To the solution sodium hydride 60% in mineral oil (1.2 mmole) is added. The mixture is stirred at room temperature for 1 h. To the mixture chloro-bromo-acetic acid methyl ester (1.2 mmole) is added. The mixture is stirred at room temperature for 18 h. The reaction is diluted with ethyl acetate (300 mL) and washed with $H_2O$ (4×100 mL) and brine (1×100 mL). The organic layer is separated, dried with magnesium sulfate and concentrated. The residue is purified by column chromatography to afford 19.

The corresponding acetic acid methyl ester 19 (1 mmole) is dissolved in anhydrous dichloromethane (50 mL). To the solution oxalyl chloride (1.1 mmole) is added. The mixture is left to stir at room temperature for 2 h. $NH_3$ gas is then bubbled through the solution for 30 minutes. The mixture is left to stir at room temperature for 1 h. The dichloromethane is evaporated and the residue is dissolved in ethyl acetate (200 mL) and washed with $H_2O$ (3×200 mL) and brine (1×300 mL). The organic layer is to be separated, dried with magnesium sulfate and concentrated to afford 20.

Compound 20 (1 mmole) is dissolved in THF:$H_2O$ 4:1 (10 mL). To the mixture 0.5054 N potassium hydroxide solution is added. The mixture is left to stir at room temperature for 18 h. The reaction mixture is evaporated to dryness. The residue is dissolved in $H_2O$ (5 mL) and acidified to pH 4 with 2M HCl. The resulting precipitate is collected by filtration washed with $H_2O$ and dried to afford 21.

Compound 21 (1 mmole) is dissolved in trimethylamine methanol solution (15 mL) in a pressure tube. The mixture is

Example 10.13

Compound (2-11)

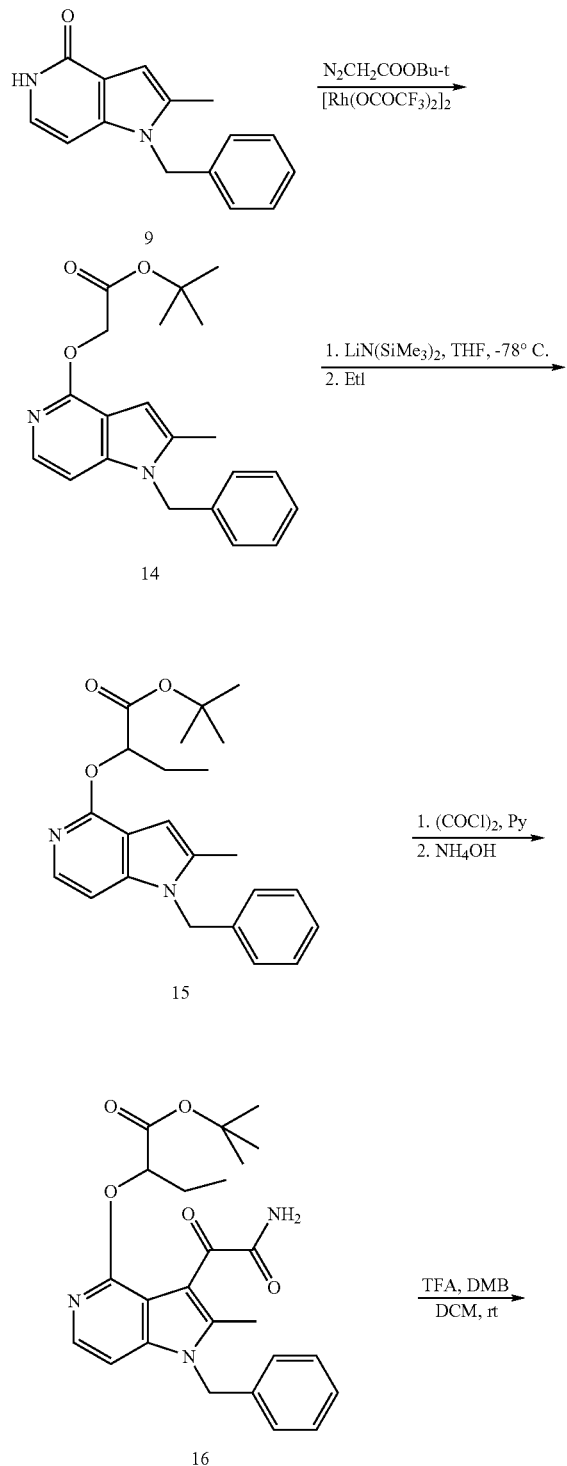

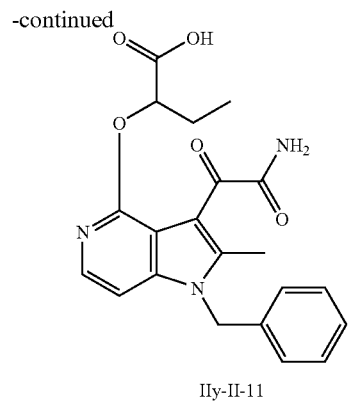

IIy-II-11 stirred 50° C. for 12 h. The reaction mixture is evaporated to dryness. The residue is triturated with ether and dried to afford ILY-IV-48.

(1-Benzyl-2-methyl-1H-pyrrolo[3,2-c]pyridin-4-yloxy)-acetic acid tert-butyl ester, 14: 1-Benzyl-2-methyl-1,5-dihydro-pyrrolo[3,2-c]pyridin-4-one, 9 (1.0 g, 4.20 mmol) was dissolved in a dry dichloroethane (500 mL). To the mixture $Rh_2(OCOCF_3)_4$ (132 mg, 0.202 mmol) was added. The reaction mixture was heated to reflux and then to the reaction mixture a solution of tert-butyl diazoacetate (0.65 mL, 4.20 mmol) in dry dichloroethane (50 mL) was added dropwise over 16 h under refluxing. After addition the reaction mixture was stirred for 1 h under refluxing. Then the reaction mixture was cooled to room temperature. The mixture was concentrated and the residue was purified by silica gel chromatography (hexane to hexane:ethyl acetate, 3:1) to afford (1-benzyl-2-methyl-1H-pyrrolo[3,2-c]pyridin-4-yloxy)-acetic acid tert-butyl ester, 14 Yield: 700 mg, (51%)

2-(1-Benzyl-2-methyl-1H-pyrrolo[3,2-c]pyridin-4-yloxy)-butyric acid tert-butyl ester, 15: (1-Benzyl-2-methyl-1H-pyrrolo[3,2-c]pyridin-4-yloxy)-acetic acid tert-butyl ester, 14 (200 mg, 0.568 mmol) was dissolved in a dry tetrahydrofuran (10 mL) and then cooled to −78° C. To the mixture the tetrahydrofuran solution (1.0 M) of $LiN(Si(CH_3)_3)_2$ (1.70 mL) was added dropwise at −78° C. The reaction mixture was stirred from −78° C. to −5° C. for 1 h and then the tetrahydrofuran solution (5 mL) of iodoethane (0.15 mL, 1.84 mmol) was added dropwise at −50° C. The mixture was stirred for 4 h from −50° C. to room temperature. The mixture was concentrated and the residue was purified by silica gel chromatography (hexane to hexane:ethyl acetate, 4:1) to afford 2-(1-benzyl-2-methyl-1H-pyrrolo[3,2-c]pyridin-4-yloxy)-butyric acid tert-butyl ester, 15 Yield: 50 mg, (23%)

2-(3-Aminooxalyl-1-benzyl-2-methyl-1H-pyrrolo[3,2-c]pyridin-4-yloxy)-butyric acid tert-butyl ester, 16: 2-(1-benzyl-2-methyl-1H-pyrrolo[3,2-c]pyridin-4-yloxy)-butyric acid tert-butyl ester, 15 (134 mg, 0.352 mmol) was dissolved in a dry chloroform (10 mL). To the mixture the solution of oxalyl chloride (0.10 mL, 1.13 mmol) in chloroform (5 mL) was added dropwise at room temperature. Then pyridine (0.05 mL) was added slowly to the mixture at room temperature. After addition the mixture was stirred at room temperature for 18 h. The mixture was poured into icy 20% $NH_4OH$ solution (100 mL) and stirred for 1 h. The mixture was diluted with dichloromethane (20 mL). The organic layer was separated and aqueous layer was extracted with dichloromethane (2×20 mL). The organic layers were combined and dried over anhydrous $MgSO_4$. The mixture was filtered. The filtrate was concentrated and the residue was purified by silica gel chromatography (hexan to hexane:ethyl acetate, gradient 1:1) to afford 2-(3-aminooxalyl-1-benzyl-2-methyl-1H-pyrrolo[3, 2-c]pyridin-4-yloxy)-butyric acid tert-butyl ester, 16 as a yellow solid. Yield: 62 mg, (39%)

2-(3-Aminooxalyl-1-benzyl-2-methyl-1H-pyrrolo[3,2-c]pyridin-4-yloxy)-butyric acid, Ily-II-11: 2-(3-aminooxalyl-1-benzyl-2-methyl-1H-pyrrolo[3,2-c]pyridin-4-yloxy)-butyric acid tert-butyl ester, 16 (26 mg, 0.0576 mmol) was dissolved in dichloromethane (2 mL). To the mixture 1,3-dimethoxybenzene (0.023 mL, 0.172 mmol) was added at room temperature. The mixture was cooled to 0° C. for 30 min. To the mixture trifluoroacetic acid (0.015 mL, 0.234 mmol) was added at 0° C. After addition the mixture was stirred at 0° C. for 1 h. Then mixture was warmed up to room temperature and stirred for 2 h at room temperature. Then more trifluoroacetic acid (0.1 mL) was added and the mixture was stirred at room temperature for 18 h. The mixture was concentrated and H-NMR indicated the reaction was not completed. The residue was redissolved in dichloromethane (5 mL) and then trifluoroacetic acid (0.5 mL) was added at room temperature. The mixture was stirred at room temperature for 6 h. The mixture was concentrated and the residue was purified by silica gel preparative thin layer chromatography (hexane:ethyl acetate, 1:1) to afford 2-(3-aminooxalyl-1-benzyl-2-methyl-1H-pyrrolo[3,2-c]pyridin-4-yloxy)-butyric acid, Ily-II-11 as a light yellow solid. Yield: 11 mg, (48%) $^1$H NMR: 05-43-128-2, (400 MHz, DMSO-d6) δ, 8.09 (br, s, 1H, NH), 7.72 (d, 1H), 7.54 (br, s, 1H, NH), 7.20-7.38 (m, 3H), 7.18 (d, 1H), 7.08 (d, 2H), 5.50 (br, s, 2H, PhCH$_2$N), 5.02 (t, 1H, CHOAr), 2.41 (br, s, 3H, Me), 1.92 (q, 2H, Et), 1.02 (t, 3 H, Et), ppm. MS (ES): 395.98 [M+1].

Example 10.14A

Compound (5-33)

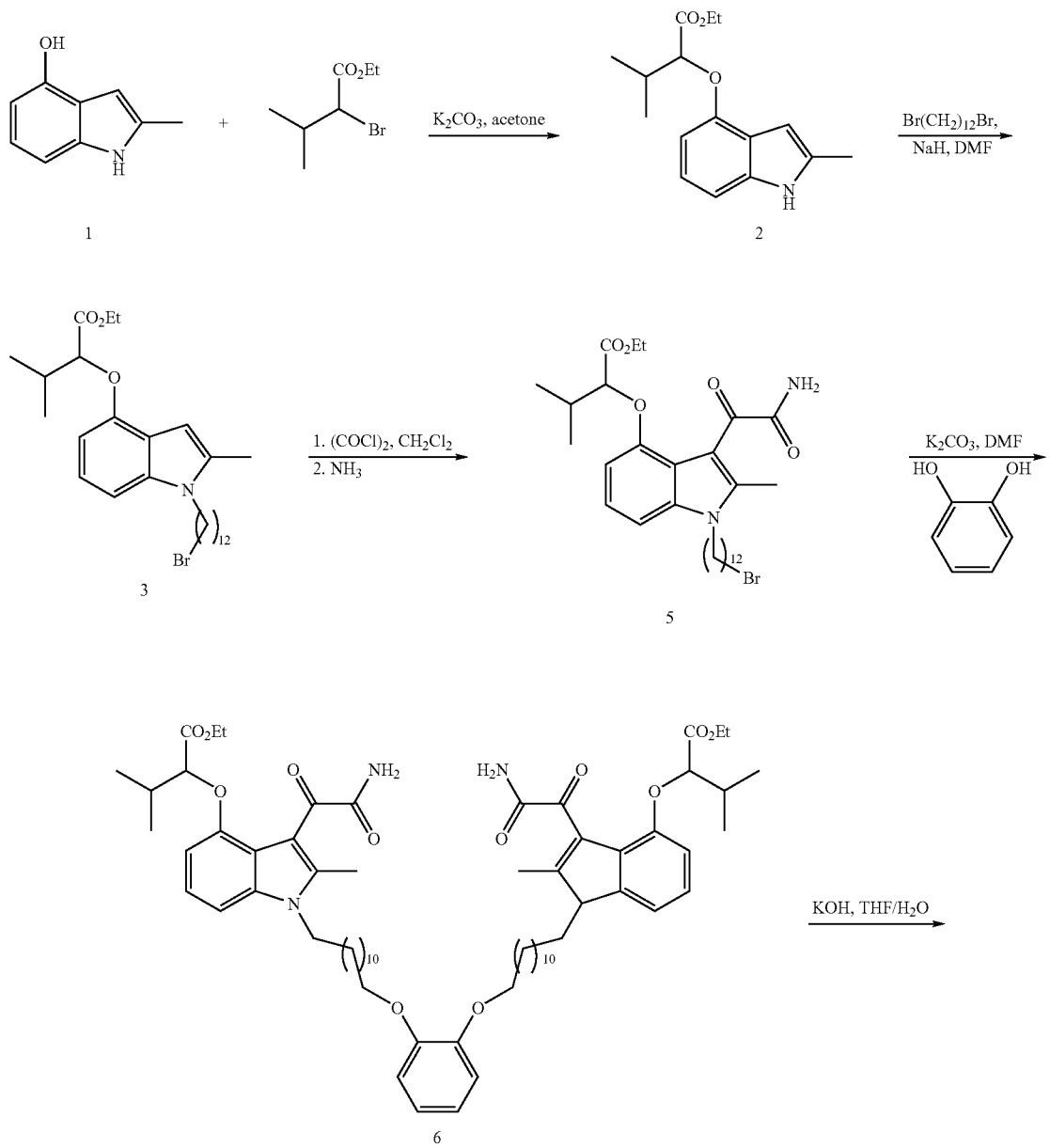

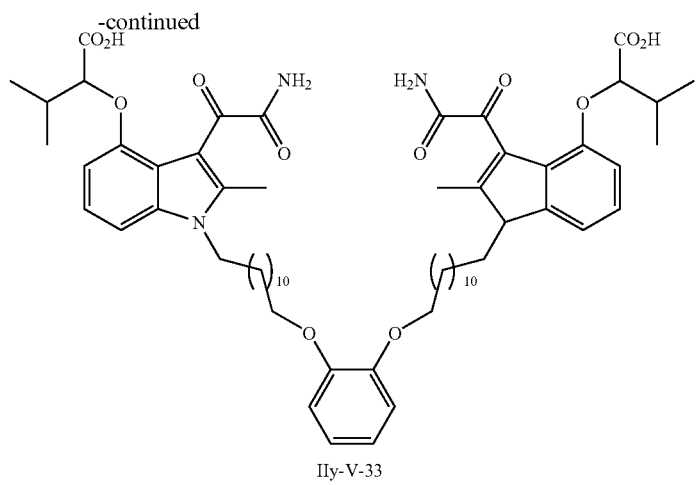

IIy-V-33

2,2'-(1,1'-(12,12'-(1,2-phenylenebis(oxy))bis(dodecane-12,1-diyl))bis(3-(2-amino-2-oxoacetyl)-2-methyl-1H-indole-4,1-diyl))bis(oxy)bis(3-methylbutanoic acid) (ILY-V-33) Hydroxy indole 1 (1 mmol) and tert-butyl 2-bromo-3-methylbutanoate (1 mmol) is dissolved in 10 mL acetone. To this solution at room temperature is added anhydrous potassium carbonate (2 mmol) and the stirred mixture is refluxed for 12 hours. The solid is removed by filtration and followed by column chromatography to give 2.

Compound 2 (1 mmole) is dissolved in anhydrous dichloromethane (50 mL). To the solution, oxalyl chloride (1.1 mmole) is added. The mixture is left to stir at room temperature for 2 h. $NH_3$ gas is then bubbled through the solution for 30 minutes. The mixture is left to stir at room temperature for 1 h. The dichloromethane is evaporated and the residue is dissolved in ethyl acetate (200 mL) and washed with $H_2O$ (3×200 mL) and brine (1×300 mL). The organic layer is separated, dried with magnesium sulfate and concentrated to afford 3.

The indole intermediate 3 (1 mmole) in dry DMF (10 mL), at 0° C. under nitrogen, is added with 95% sodium hydride (1.2 mmole). The mixture is stirred at 0° C. for 0.5 h and then added dropwise over 10 minutes to a solution of 1,12-dibromododecane (1.5 mmole) in dry DMF (20 mL) at 0° C. The mixture is stirred at 0° C. for 5 h and at room temperature for 19 h. The reaction is cooled to 0° C., quenched with ammonium chloride solution (10 mL), and diluted with dichloromethane (100 mL). The mixture is washed with ammonium chloride solution (50 mL) and the aqueous phase extracted with dichloromethane (4×25 mL). The combined organic phase is washed with brine (100 mL), dried ($Na_2SO_4$), filtered and evaporated to a red/brown liquid which is further evaporated under high vacuum. The residue is purified by chromatography over silica gel to give 4.

Catechol (1 mmole) is added to sodium hydride (2.2 mmole) in dry DMF (12 mL), at 0° C. under nitrogen. After 0.5 h this mixture is added to the bromide 4 (2.05 mmole) in dry DMF (20 mL), at 0° C. under nitrogen. The reaction is maintained at 0° C. for 8 h and quenched with ammonium chloride solution (15 mL), diluted with dichloromethane (100 mL) and washed with ammonium chloride solution (50 mL). The organic phase is separated and the aqueous phase extracted with dichloromethane (2×25 mL). The combined organic phase is washed with brine (75 mL) dried ($Na_2SO_4$), filtered and evaporated to a yellow/orange syrup. Purification can be effected by chromatography over silica gel, using chloroform/ethyl acetate as the eluant, give the protected dimer product.

The dimer product (0.9 mmole) and 1,3-dimethoxybenzene (3 mmole) in dry dichloromethane (20 mL), at room temperature under nitrogen, is added with trifluoroacetic acid (10 mL). The solution is stirred for 1 h and the solvents evaporated below 25° C. The residue is triturated with ether (50 mL) and the solid removed by filtration and washed with ether (100 mL). The solid is triturated with ether (50 mL), filtered and washed with ether (50 mL). The product is dried in vacuo to give ILY-V-33.

Example 10.14B

Compound (5-33)

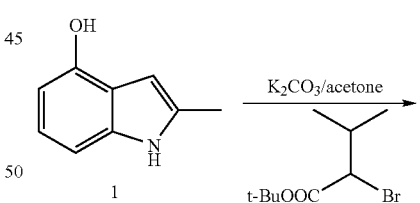

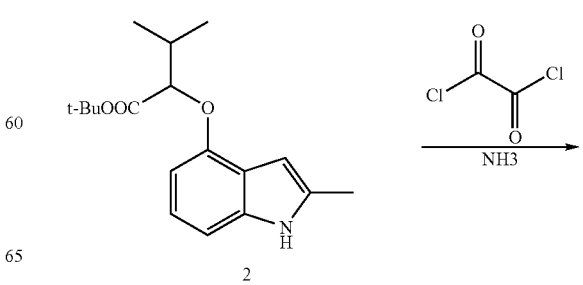

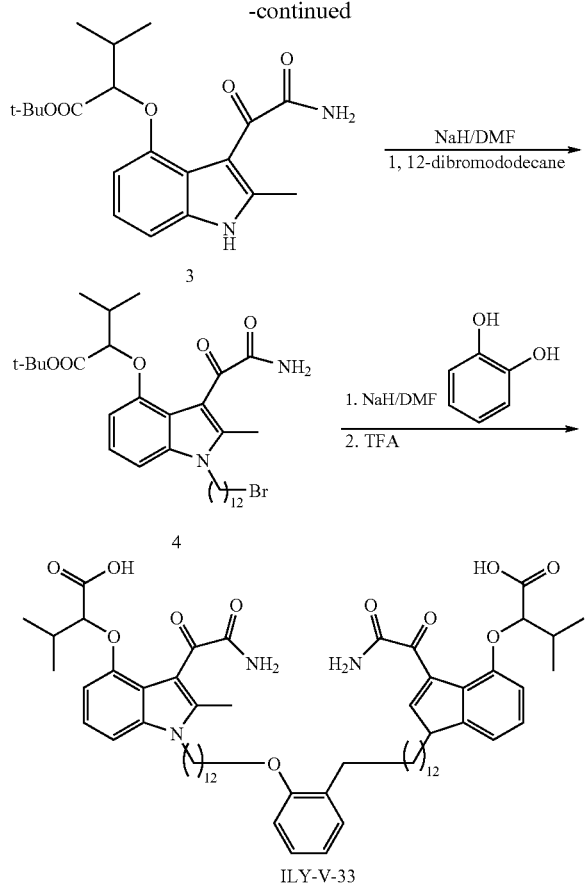

ILY-V-33

3-Methyl-2-(2-methyl-1H-indol-4-yloxy)-butyric acid ethyl ester (2): A mixture of 4-hydroxy-2-methylindole (1) (1.5 g, 0.010 mole), 2-bromo-3-methyl-butyric acid ethyl ester (2.2 g, 0.010 mole) and potassium carbonate (excess) in acetone (50 mL) was refluxed for 3 days. The reaction mixture was filtered, and the filtrate was concentrated. The residue was purified by column chromatography (20:1 Hex:EtOAc) to afford intermediate 2. Yield: 1.88 g, 71%

2-[1-(12-Bromo-dodecyl)-2-methyl-1H-indol-4-yloxy]-3-methylbutyric acid ethyl ester (3): To a mixture of NaH (60% in mineral oil, 0.42 g, 10 mmole) in anhydrous DMF (20 mL), 3-methyl-2-(2-methyl-1H-indol-4-yloxy)-butyric acid ethyl ester (2) (1.88 g, 7.0 mmole) and dibromododecane (2.30 g, 7.0 mmole) were added. The mixture was stirred at room temperature for 18 h. The reaction was diluted with ethyl acetate (50 mL) and washed with water (3×30 mL). The organic layer was separated, dried over sodium sulphate and concentrated. The residue was purified by column chromatography (10:1 Hex:EtOAc) to afford intermediate (3) Yield: intermediate (3) 1.32 g, 35%, by-product (4) 1.56 g, 31%.

2-[3-Aminooxalyl-1-(12-bromo-dodecyl)-2-methyl-1H-indol-4-yloxy]-3-methyl-butyric acid ethyl ester (5): To a solution of intermediate 3 (0.50 g, 0.959 mmole) in anhydrous dichloromethane (200 mL), oxalyl chloride (0.12 g, 0.95 mmole) was added at 0° C. The mixture was stirred for 1 h. Ammonia gas was bubbled through the reaction mixture for 20 minutes. The mixture was stirred for an addition hour and then concentrated. The residue was diluted with ethyl acetate (30 mL) and washed with water (3×30 mL). The organic layer was separated, dried over sodium sulphate and concentrated to afford intermediate (5) as a yellow solid. Yield: 0.44 g, 77%

2-{3-Aminooxalyl-1-[12-(2-{12-[3-aminooxalyl-4-(1-ethoxycarbonyl-2-methyl-propoxy)-2-methyl-indol-1-yl]-dodecyloxy}-phenoxy)-dodecyl]-2-methyl-1H-indol-4-yloxy}-3-methyl-butyric acid ethyl ester (6): A mixture of intermediate 5 (474 mg, 0.8 mmol), catechol (40 mg, 0.36 mmol) and potassium carbonate (excess) in DMF (5 mL) was stirred at room temperature for 72 h. The reaction was filtered and the filtrate was poured onto crushed ice (20 mL). The mixture was extracted with dichloromethane (3×30 mL). The organic layer was separated, dried over sodium sulphate and concentrated. The residue was purified by column chromatography (1% MeOH in CHCl$_3$) to afford intermediate (6) and recovered intermediate (5) (205 mg). Yield: 0.060 g, 7%.

2-{3-Aminooxalyl-1-[12-(2-{12-[3-aminooxalyl-4-(1-carboxy-2-methyl-propoxy)-2-methyl-indol-1-yl]-dodecyloxy}-phenoxy)-dodecyl]-2-methyl-1H-indol-4-yloxy}-3-methyl-butyric acid (Ily-V-33): To a solution of intermediate 6 (55 mg, 0.05 mmol) in THF/CH$_3$OH/H$_2$O (1:1:1, 2 mL:2 mL:2 mL), potassium hydroxide (0.06 g, 0.11 mmole) was added. The mixture was stirred at room temperature for 4 h. The solution was evaporated and the residue was neutralized with 1M HCl at 0° C. The solid was collected by filtration and washed with water and then hexane to afford Ily-V-33 as a yellow solid. Yield: 0.035 g, 67%. $^1$H NMR (400 MHz, DMSO-d$_6$), δ, ppm: δ 12.51(brs, 2H),8.10(brs, 2H),7.62 (brs, 2H), 7.11-7.14(m, 4H), 7.92-7.96 (m, 2H),7.81-7.84 (m, 2H), 6.42(d, 2H), 4.68(d, 2H), 4.15 (t, 4H),3.92 (t, 4H), 2.44 (s, 6H), 2.23(m, 2H), 1.62(m, 4H),1.20-1.43(m, 36H), 1.08(d, 6H), 0.98(d, 6H) ppm. ES-MS: m/z=1079.44 (M+1).

Example 10.15

Compound (4-55)

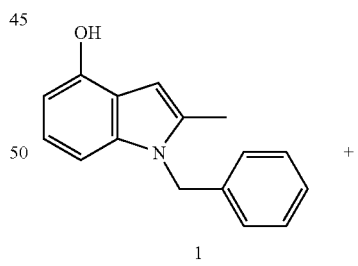

1

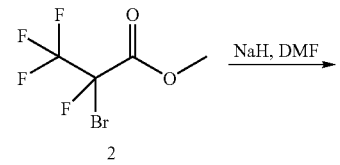

2

201

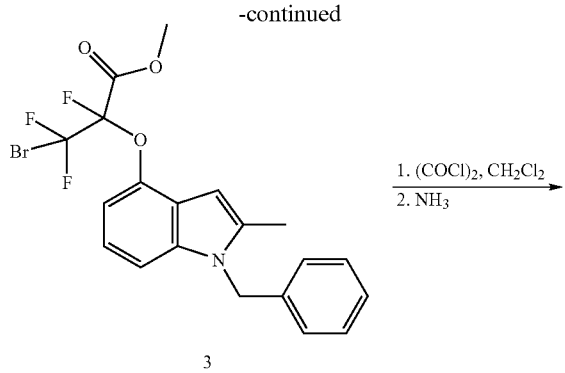

1. (COCl)₂, CH₂Cl₂
2. NH₃

3

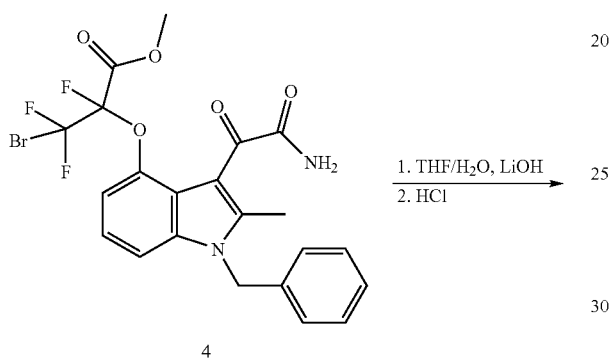

1. THF/H₂O, LiOH
2. HCl

4

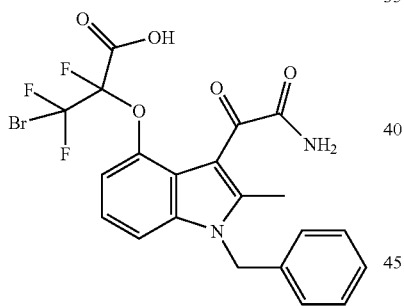

Ily-IV-55

202

Methyl 2-(1-benzyl-2-methyl-1H-indol-4-yloxy)-3-bromo-2,3,3-trifluoropropanoate (3): To a solution of 1-benzyl-2-methyl-1H-indol-4-ol (1) (0.5 g, 2.1 mmole) in DMF (25 mL), sodium hydride (60% in mineral oil, 0.11 g, 2.75 mmole) was added and the mixture was stirred for 30 minutes at room temperature. Methyl-2-bromo-2,3,3,3-tetrafluoropropionate (0.5 mL, 2.90 mmole) was added to the mixture and stirring was continued at room temperature for 18 h. The reaction was diluted with ethyl acetate (50 mL) and washed with water (3×50 mL) and brine (3×50 mL). The organic layer was separated, dried over magnesium sulphate and concentrated. The residue was purified by preparative TLC (4:1 Hex:EtOAc) to afford intermediate (3) Yield: 0.140 g (17%)

Methyl 2-(3-(2-amino-2-oxoacetyl)-1-benzyl-2-methyl-1H-indol-4-yloxy)-3-bromo-2,3,3-trifluoropropanoate (4): To a solution of the methyl ester (3) (0.14 g, 0.31 mmole) in dichloromethane (60 mL) oxalyl chloride (0.39 g, 0.31 mmole) in dichloromethane (5 mL) was added dropwise at 0° C. The mixture was stirred for 2 h. Ammonia gas was bubbled through the solution for 30 minutes, and then stirred for an additional 1 h. The reaction solvent was evaporated and the residue was purified by column chromatography intermediate (4) as a solid. 0.122 g, 75%.

2-(3-(2-amino-2-oxoacetyl)-1-benzyl-2-methyl-1H-indol-4-yloxy)-3-bromo-2,3,3-trifluoropropanoic acid (ILY-IV-55): To a solution of the methyl ester (4) (0.95 g, 0.18 mmole) in THF:H2O (4:1, 10 mL), lithium hydroxide mono hydrate (0.01 g, 0.24 mmole) was added. The mixture was stirred at room temperature for 30 minutes. THF was evaporated and the mixture was acidified with 2M HCl to pH 3. The aqueous layer was extracted with ethyl acetate (3×10 mL). The organic layer was separated, dried over magnesium sulphate and concentrated to afford intermediate (ILY-IV-55) as a solid. Yield: (0.09 g, 98%).

Example 10.16

Compound (5-44)

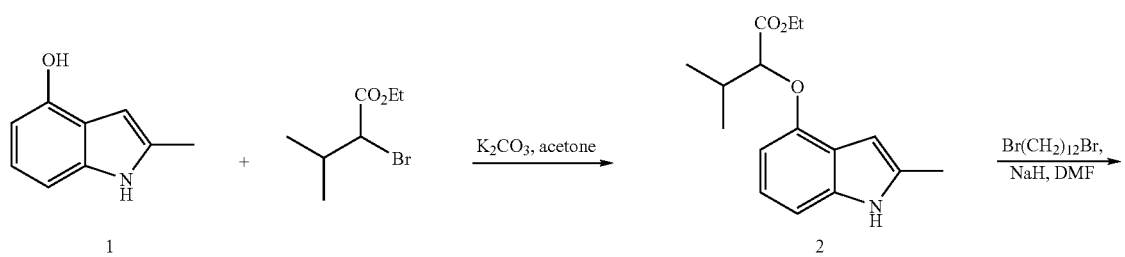

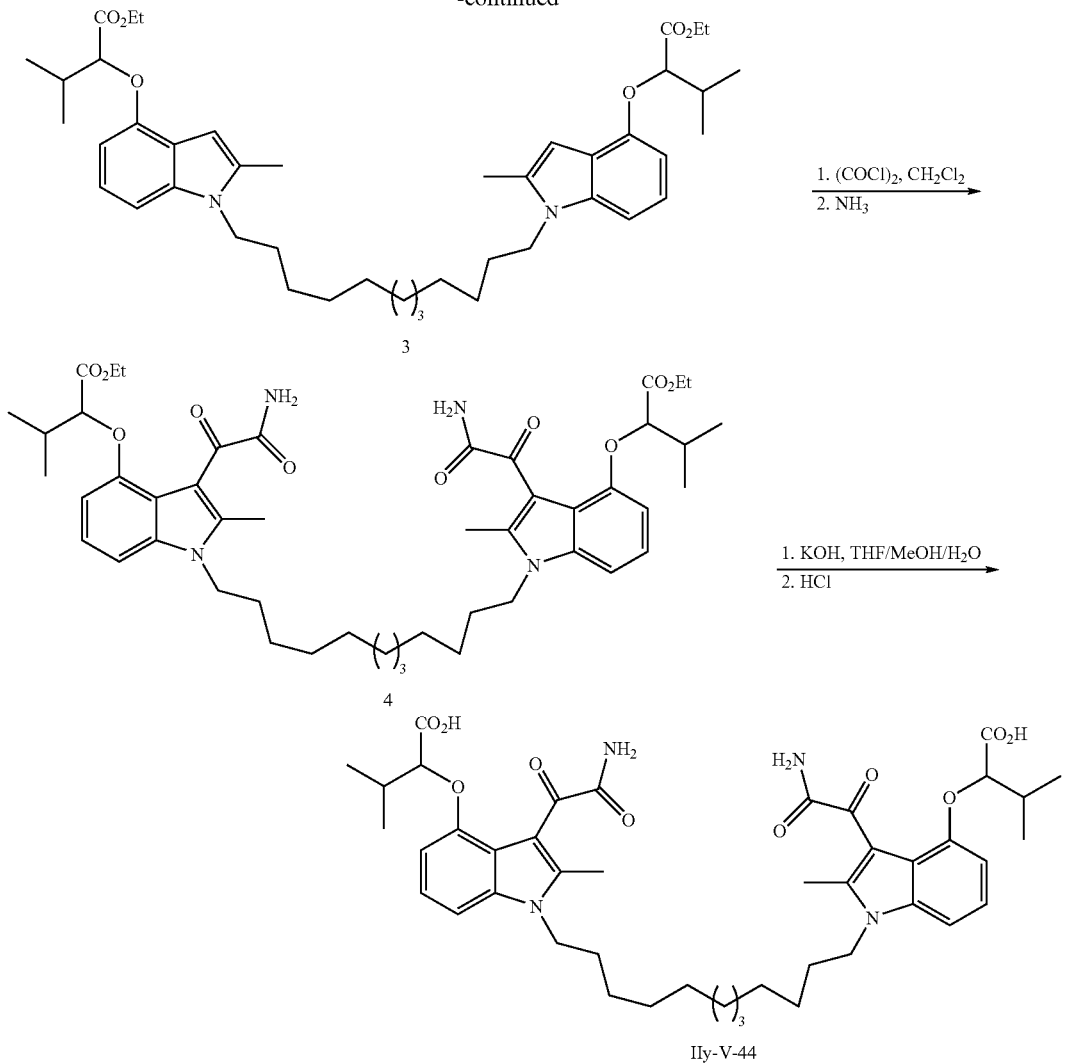

2-(3-Aminooxalyl-1-{12-[3-aminooxalyl-4-(1-ethoxycarbonyl-2-methyl-propoxy)-2-methyl-indol-1-yl]-dodecyl}-2-methyl-1H-indol-4-yloxy)-3-methyl-butyric acid ethyl ester (4): To a solution of intermediate 3 (0.20 g, 0.278 mmole) in anhydrous dichloromethane (20 mL) oxalyl chloride (0.035 g, 0.278 mmole) in anhydrous dichloromethane (20 mL) was added dropwise at 0° C. The mixture was stirred for 1 h. Ammonia was bubbled through the mixture for 20 minutes and stirred for 1 h. The reaction mixture was evaporated. The residue was purified by column chromatography (10:1 CHCl$_3$:MeOH) to afford intermediate (4) as a yellow solid. Yield: 0.212 g, 91%

2-(3-Aminooxalyl-1-{12-[3-aminooxalyl-4-(1-carboxy-2-methyl-propoxy)-2-methyl-indol-1-yl]-dodecyl}-2-methyl-1H-indol-4-yloxy)-3-methyl-butyric acid (Ily-V-44): A solution of intermediate 4 (100 mg, 0.12 mmol) in THF/CH$_3$OH/H$_2$O (1:1:1, 3 mL:3 mL:3 mL) was stirred with 2.2 equivalent of KOH for 4 hr at room temperature. The solution was evaporated and resulting residue was neutralized with 5% HCl at 0° C. The resulting solid was collected by filtration and washed with water and then hexane to afford Ily-V-44 as a yellow solid. Yield: 0.067 g, 72%. $^1$H NMR (400 MHz, DMSO-d$_6$) δ, ppm: 12.51(brs, 2H), 8.02 (brs, 2H), 7.61 (brs, 2H), 7.11-7.14(m, 4H), 6.42(d, 2H), 4.42 (d, 2H), 4.16(t, 4H), 2.41 (s,6H), 2.23(m, 2H), 1.62(m, 4H), 1.20-1.32 (m, 16H), 1.07(d, 6H), 0.96(d, 6H) ppm. ES-MS: m/z=803.12 (M+1).

Example 10.17

Compound (4-40)

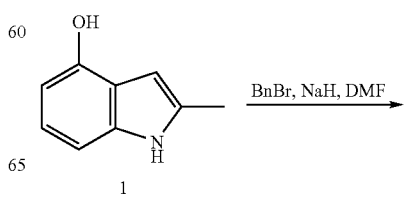

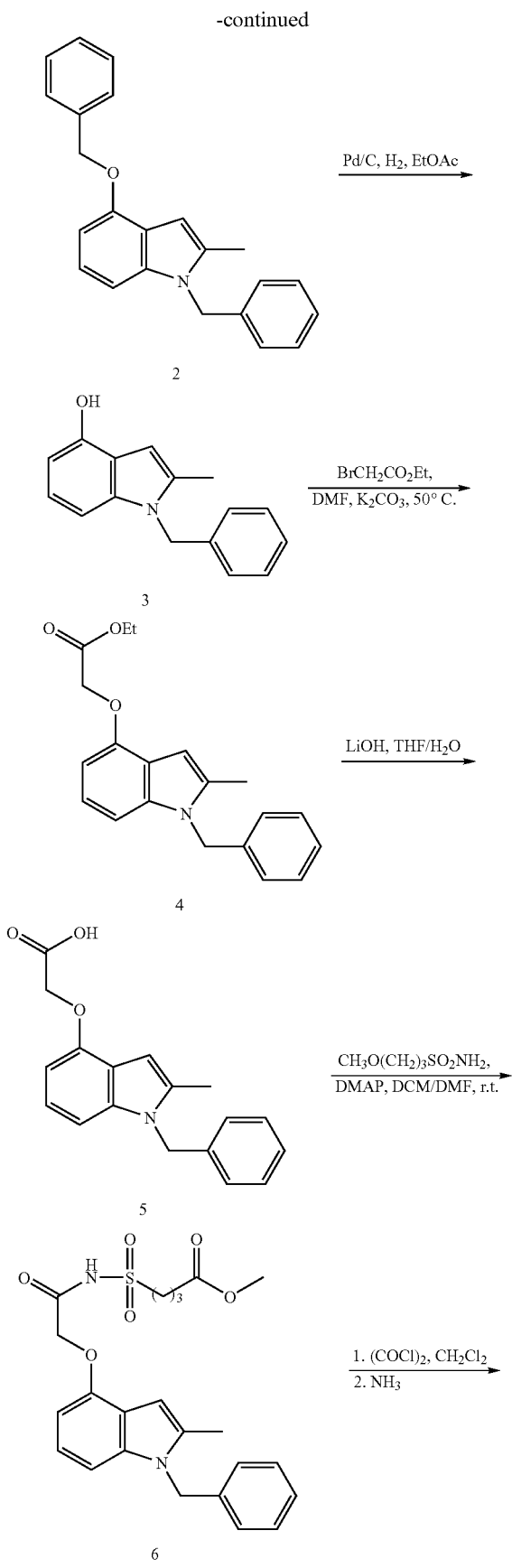

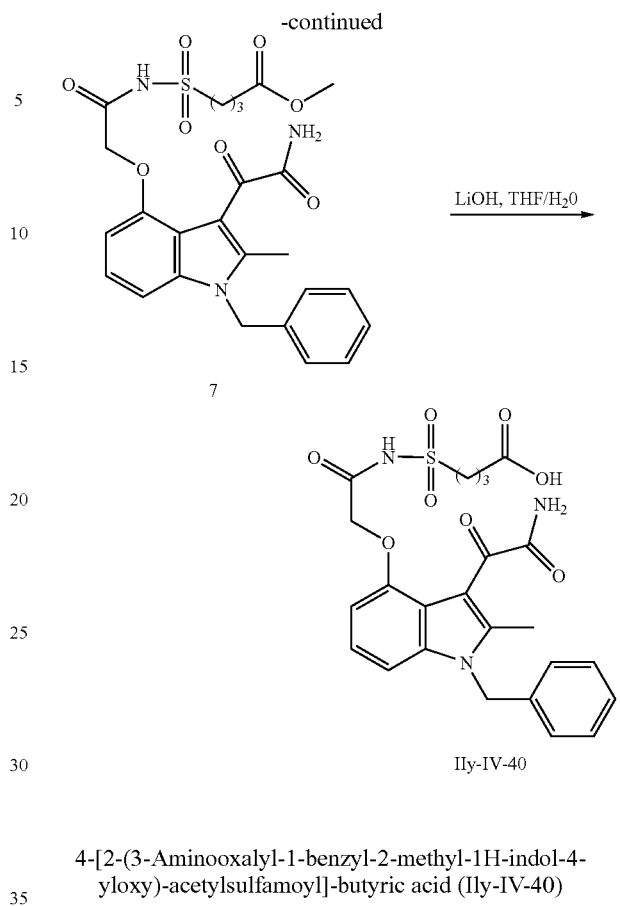

4-[2-(3-Aminooxalyl-1-benzyl-2-methyl-1H-indol-4-yloxy)-acetylsulfamoyl]-butyric acid (IIy-IV-40)

1-Benzyl-4-benzyloxy-2-methyl-1H-indole (2): To a suspension of sodium hydride (60% in mineral oil, 27.9 g, 0.69 mole) in anhydrous DMF (500 mL) 4-hydroxyl-2-methyl indole was added and stirred at room temperature for 1 h. A solution of benzyl bromide (82.7 mL, 0.69 mole) in DMF (500 mL) was added dropwise to the mixture. The reaction was stirred at room temperature for 18 h. The reaction mixture was diluted with ethyl acetate (4 L) and washed with water (7×500 mL) and brine (1×500 mL). The organic layer was separated and concentrated. The residue was purified by column chromatography (3:1 Hex:EtOAc) to afford intermediate (2) as an orange oil. Yield: 65 g (58%)

1-Benzyl-2-methyl-1H-indol-4-ol (3): To a solution of 1-Benzyl-4-benzyloxy-2-methyl-1H-indole (2) (35 g, 0.107 mole) in methanol (1 L) and ethyl acetate (500 mL), Pd/C (10%, 17 g) was added. Hydrogen was bubbled through the mixture at room pressure and temperature for 6 h. The reaction mixture was filtered through Celite. The filtrate was concentrated and the residue was purified by column chromatography (6:1 Hex:EtOAc) to afford intermediate (3) as an orange solid. Yield: 22 g (60%)

(1-Benzyl-2-methyl-1H-indol-4-yloxy)-acetic acid ethyl ester (4): To a stirred suspension of K2CO3 (11.7 g, 84.7 mmol), NaI (0.633 g, 4.22 mmol) and 1-benzyl-2-methyl-1H-indol-4-ol (3) (10.0 g, 42.2 mmol) in dry DMF (100 mL) ethyl bromoacetate (5.10 mL, 46.0 mmol) was added dropwise. The reaction mixture was stirred at room temperature for 20 h. The reaction was quenched with water (150 mL) and the mixture was extracted with EtOAc (3×150 mL). The combined organic extracts were washed with water (100 mL), brine (100 mL), dried over Na2SO4 and evaporated. The residue was purified by flash chromatography over silica gel, using 10% EtOAc in hexanes to 25% EtOAc in hexanes) to afford intermediate 4 as a pale yellow solid. Yield: 10.3 g (76%).

(1-Benzyl-2-methyl-1H-indol-4-yloxy)-acetic acid (5): To a solution of (1-benzyl-2-methyl-1H-indol-4-yloxy)-acetic acid ethyl ester (4) (0.80 g, 2.48 mmole) in THF:H2O (4:1, 10 mL), lithium hydroxide monohydrate was added (0.118 g, 4.96 mmole). The mixture was stirred at room temperature for 1 h. THF was evaporated and then crushed ice was added to the aqueous mixture; the resulting solid was collected by filtration to afford intermediate (5) as a solid. Yield: 0.67 g, 92% 1H NMR: 05-038-055

4-[2-(1-Benzyl-2-methyl-1H-indol-4-yloxy)-acetylsulfamoyl]-butyric acid methyl ester (6): To a solution of (1-benzyl-2-methyl-1H-indol-4-yloxy)-acetic acid (5) (0.189 g, 0.64 mmole) in dichloromethane (15 mL), 4-sulfamoyl-butyric acid methyl ester (0.232 g, 1.28 mmole), EDCI (0.122 g, 0.64 mmole) and DMAP (0.078 g, 0.64 mmole) were added. The mixture was stirred at room temperature for 18 h. The dichloromethane was evaporated to half of the original volume and the mixture was washed with water (2×10 mL). The organic layer was separated and evaporated. The residue was purified by column chromatography (10:1 CHCl$_3$:MeOH) to afford intermediate (6) as a solid. Yield: 0.15 g, 51%

4-[2-(3-Aminooxalyl-1-benzyl-2-methyl-1H-indol-4-yloxy)-acetylsulfamoyl]-butyric acid methyl ester (7): To a solution of 4-[2-(1-benzyl-2-methyl-1H-indol-4-yloxy)-acetylsulfamoyl]-butyric acid methyl ester (6) (0.15 g, 0.32 mmole) in dichloromethane (60 mL) oxalyl chloride (0.41 g, 0.32 mmole) in dichloromethane (5 mL) was added dropwise at 0° C. The mixture was stirred for 2 h. Ammonia gas was bubbled through the solution for 30 minutes, and then stirred for an additional 1 h. The reaction solvent was evaporated and the residue was purified by column chromatography (2% MeOH in CHCl$_3$) to afford intermediate (7) as a solid. Yield: 0.125 g, 72%.

4-[2-(3-Aminooxalyl-1-benzyl-2-methyl-1H-indol-4-yloxy)-acetylsulfamoyl]-butyric acid (Ily-IV-40): To a solution of intermediate (7) (125 mg, 0.24 mmol) in THF/H2O (4:1, 10 mL) lithium hydroxide monohydrate (0.012 g, 0.528 mmole) was added. The mixture was stirred at room temperature for 30 minutes. THF was evaporated and the resulting residue was neutralized with 5% HCl at 0° C. The green solid was collected by filtration and washed with water (2×20 mL) and hexane (2×20 mL). The colour impurity was removed by dissolving the residue in methanol and stirring with charcoal for 30 minutes. The mixture was filtered through Celite and the filtrate was concentrated to afford Ily-IV-40 as a light yellow solid. Yield: 0.065 g, 53% yield. 1H NMR (400 MHz, DMSO-d6) δ, ppm: 12.21(brs, 1H), 11.45(brs, 1H),7.98 (brs, 1H), 7.61 (brs, 1H), 7.23-7.35 (m, 4H), 7.03-7.18 (m, 3H), 6.46 (d, 1H), 5.45 (s, 2H), 4.62(s, 2H), 3.40(t, 2H), 2.54(s, 3H), 2.32(t, 2H), 1.68 (t, 2H). ES-MS: m/z=515.98 (M+1).

Certain such C4-acidic indole and indole related compounds were evaluated for phospholipase activity using the protocol of Example 8. The results are shown in Table 8.

TABLE 8

Inhibition of pancreas secreted human, mouse and porcine PLA2

| structure | Compound ID | MW | ILYPSA IC50 (µM) | | | ILYPSA % inhibition at 15 µM | | |
|---|---|---|---|---|---|---|---|---|
| | | | hps PLA$_2$ | pps PLA$_2$ | mps PLA$_2$ | hps PLA$_2$ | pps PLA$_2$ | mps PLA$_2$ |
| [structure] | ILY-IV-20 (4-20) | 394.42 | 0.18 | <0.02 | <0.02 | | | |
| [structure] | ILY-IV-22 (4-22) | 408.45 | 0.07 | <0.02 | <0.02 | | | |

TABLE 8-continued

Inhibition of pancreas secreted human, mouse and porcine PLA2

| structure | Compound ID | MW | ILYPSA IC50 (µM) | | | ILYPSA % inhibition at 15 µM | | |
|---|---|---|---|---|---|---|---|---|
| | | | hps PLA$_2$ | pps PLA$_2$ | mps PLA$_2$ | hps PLA$_2$ | pps PLA$_2$ | mps PLA$_2$ |
| [structure] | ILY-IV-32 (4-32) | 442.48 | | | | 41.73 | 38.5 | 47.49 |
| [structure] | ILY-IV-33 (4-33) | 438.43 | | 3.76 | | 35.91 | | 50.34 |
| [structure] | ILY-IV-24 (4-24) | 384.36 | | 1.42 | | 52.36 | | 63.66 |
| [structure] | ILY-IV-8 (4-8) | 410.38 | | 2.25 | | 41 | | 61.22 |
| [structure] | ILY-IV-47 (4-47) | 422.47 | 2.94 | 0.02 | 2.43 | | | |

TABLE 8-continued

Inhibition of pancreas secreted human, mouse and porcine PLA2

| structure | Compound ID | MW | ILYPSA IC50 (μM) ||| ILYPSA % inhibition at 15 μM |||
| | | | hps PLA$_2$ | pps PLA$_2$ | mps PLA$_2$ | hps PLA$_2$ | pps PLA$_2$ | mps PLA$_2$ |
|---|---|---|---|---|---|---|---|---|
| 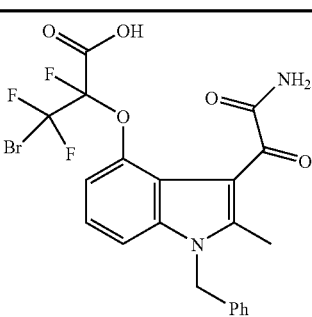 | ILY-IV-55 (4-55) | 513.27 | | | | 33.98 | 74.51 | 42.61 |
| 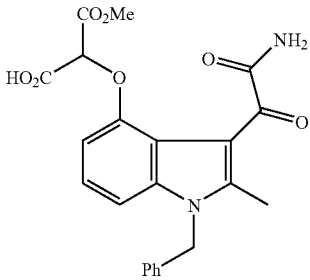 | ILY-IV-59 (4-59) | 424.41 | | | | 10.17 | 56.84 | 35.72 |

Example 11

Synthesis of C4-Amide Indole and Indole Related Compounds, and In-vitro Assay for Certain of Such Compounds for the Inhibition of Human, Mouse and Porcine Phospholipase A$_2$ In this example, various preferred indole and indole-related compounds having specific C4-amide moieties are prepared.

Example 11.1

Compound (4-28)

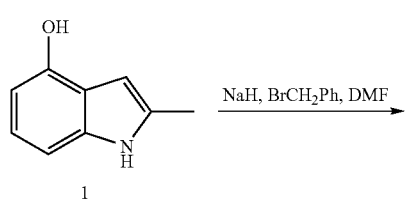

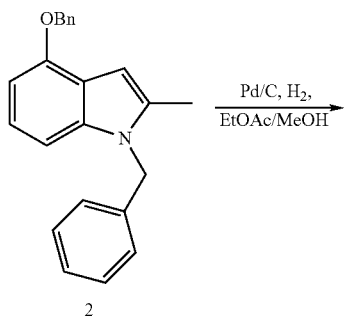

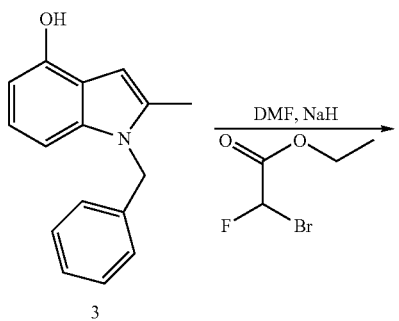

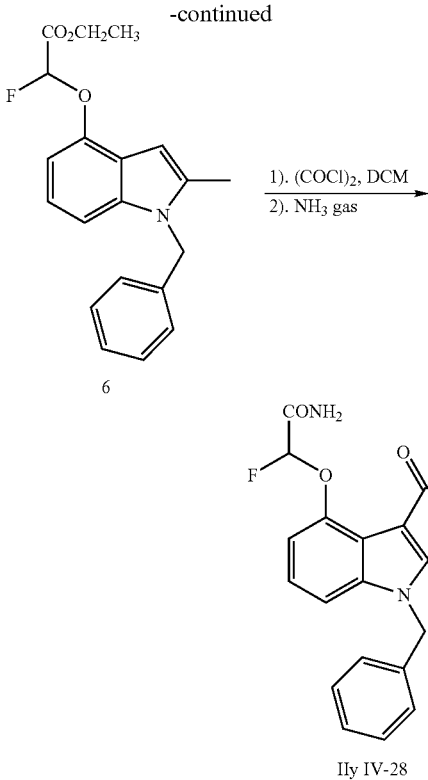

6

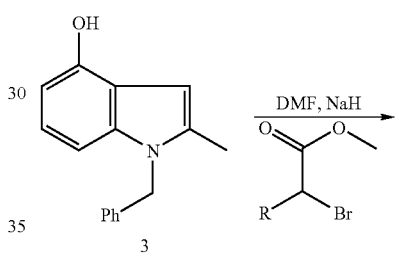

Ily IV-28

1-Benzyl-4-benzyloxy-2-methyl-1H-indole, 2: 4-hydroxy-2-methyl indole 1 (50 g, 0.339 mole) was dissolved in anhydrous DMF (1 L). To the mixture sodium hydride 60% in mineral oil (27.9 g, 0.697 mole) was added. The mixture was left to stir at rt. for 1 h. To the mixture benzyl bromide (82.7 mL, 0.697 mole) was added drop-wise. The mixture was left to stir at room temperature for 18 h. The reaction was diluted with ethyl acetate (4 L) and washed with water (5×500 mL) then brine (1 L). The organic layer was separated and dried with magnesium sulphate and concentrated. The orange oily residue was purified by column chromatography (6:1 Hexane:EtOAc) to afford 86 g (72%) of 2 as an yellow oil.

1-Benzyl-2-methyl-1H-indol-4-ol 3: 1-Benzyl-4-benzyloxy-1H-indole 2 (86 g, 0.263 mole) was dissolved with ethyl acetate (1.5 L) and methanol (300 mL). To the mixture 10% Pd/C wet (18 g) was added to the solution. The reaction was then subjected to $H_2$ gas passed through a mercury bubbler at room temperature and 1 atm. The mixture was left to stir for 6 h. The reaction mixture was filtered through Celite and concentrated. The residue was purified by column chromatography (3:1 Hexane:EtOAc) to afford 3 (30 g, 49%) as a cream solid.

(1-Benzyl-2-methyl-1H-indol-4-yloxy)-fluoro-acetic acid ethyl ester 6: 1-Benzyl-2-methyl-1H-indol-4-ol 3 (0.3 g 1.26 mmole) was dissolved in anhydrous dimethylformamide (50 mL). To the solution sodium hydride 60% in mineral oil (66 mg 1.65 mmole) was added. The mixture was stirred at room temperature for 1 h. To the mixture ethyl-2-bromofluoroacetate (0.2 mL, 1.65 mmole) was added. The mixture was stirred at room temperature for 18 h. The reaction was diluted with ethyl acetate (500 mL) and washed with $H_2O$ (5×100 mL) and brine (1×100 mL). The organic layer was separated, dried with magnesium sulfate and concentrated. The residue was purified by column chromatography (6:1 Hexane:EtOAc) to afford 6 (0.14 g, 32%) as an yellow oil.

2-(3-Aminooxalyl-1-benzyl-2-methyl-1H-indol-4-yloxy)-2-fluoro-acetamide Ily-IV-28: To a solution of oxalyl chloride (0.042 mL, 0.478 mmole) was diluted in anhydrous dichloromethane (25 mL). To the solution (1-Benzyl-2-methyl-1H-indol-4-yloxy)-fluoro-acetic acid ethyl ester 6 (0.14 g, 0.398 mmole) in anhydrous dichloromethane (25 mL) was added drop-wise. The mixture was left to stir at room temperature for 2 h. $NH_3$ gas was then bubbled through the solution for 30 minutes. The mixture was left to stir at room temperature for 1.5 h. The dichloromethane was evaporated and the residue was dissolved in ethyl acetate 300 mL) and washed with $H_2O$ (2×300 mL) and brine (1×300 mL). The organic layer was separated, dried with magnesium sulfate and concentrated. The residue was purified by preparative TLC (3:1 EtOAc:Hex) to afford Ily-IV-28 (0.050 g, 33%).

Examples 11.2-11.4 and 11.5a

Compounds (4-41, 4-42, 4-43 and 4-45)

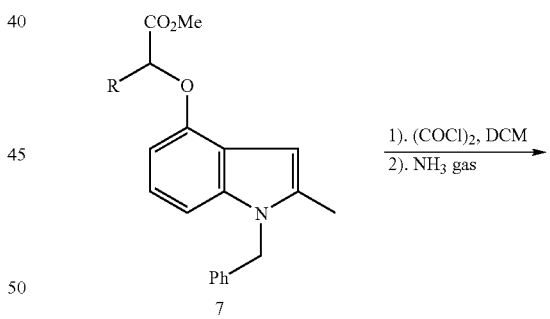

3

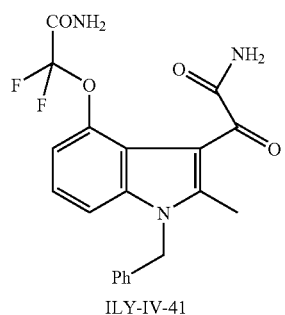

ILY-IV-41

215

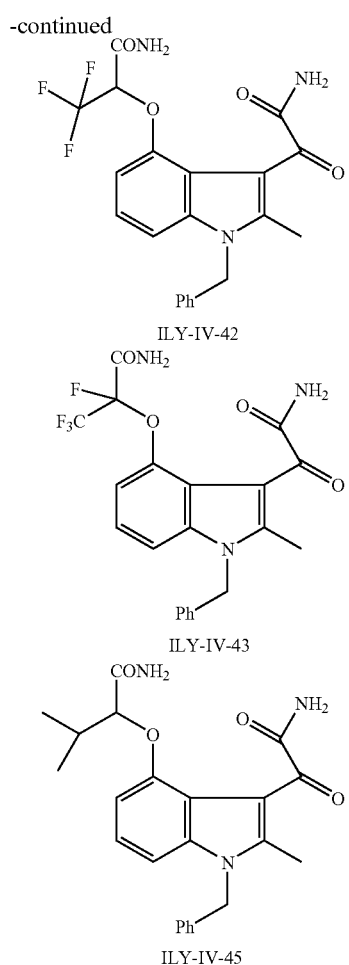

ILY-IV-42

ILY-IV-43

ILY-IV-45

2-(3-(2-amino-2-oxoacetyl)-1-benzyl-2-methyl-1H-indol-4-yloxy)-2,2-difluoroacetamide (ILY-IV-41); 2-(3-(2-amino-2-oxoacetyl)-1-benzyl-2-methyl-1H-indol-4-yloxy)-3,3,3-trifluoropropanamide (ILY-IV-42); 2-(3-(2-amino-2-oxoacetyl)-1-benzyl-2-methyl-1H-indol-4-yloxy)-2,3,3,3-tetrafluoropropanamide (ILY-IV-43); 2-(3-(2-amino-2-oxoacetyl)-1-benzyl-2-methyl-1H-indol-4-yloxy)-3-methylbutanamide (ILY-IV-45)

Alkylation: 1-Benzyl-2-methyl-1H-indol-4-ol 3 (1 mmole) is dissolved in anhydrous dimethylformamide (20 mL). To the solution sodium hydride 60% in mineral oil (1.2 mmole) is added. The mixture is stirred at room temperature for 1 h. To the mixture the corresponding bromo-acetic acid methyl ester (1.2 mmole) is added. The mixture is stirred at room temperature for 18 h. The reaction is diluted with ethyl acetate (300 mL) and washed with $H_2O$ (4×100 mL) and brine (1×100 mL). The organic layer is to be separated, dried with magnesium sulfate and concentrated. The residue is purified by column chromatography to afford 7.

Glyoxamidation and amidation: The corresponding acetic acid methyl ester 7 (1 mmole) is dissolved in anhydrous dichloromethane (50 mL). To the solution oxalyl chloride (1.1 mmole) is added. The mixture is left to stir at room temperature for 2 h. $NH_3$ gas is then bubbled through the solution for 30 minutes. The mixture is left to stir at room temperature for 5 h. The dichloromethane is evaporated and the residue is dissolved in ethyl acetate (200 mL) and washed with $H_2O$ (3×200 mL) and brine (1×300 mL). The organic layer is separated, dried with magnesium sulfate and concentrated to afford Ily-IV-41, Ily-IV-42, Ily-IV-43, and Ily-IV-45.

Examples 11.5b

Compound (4-45)

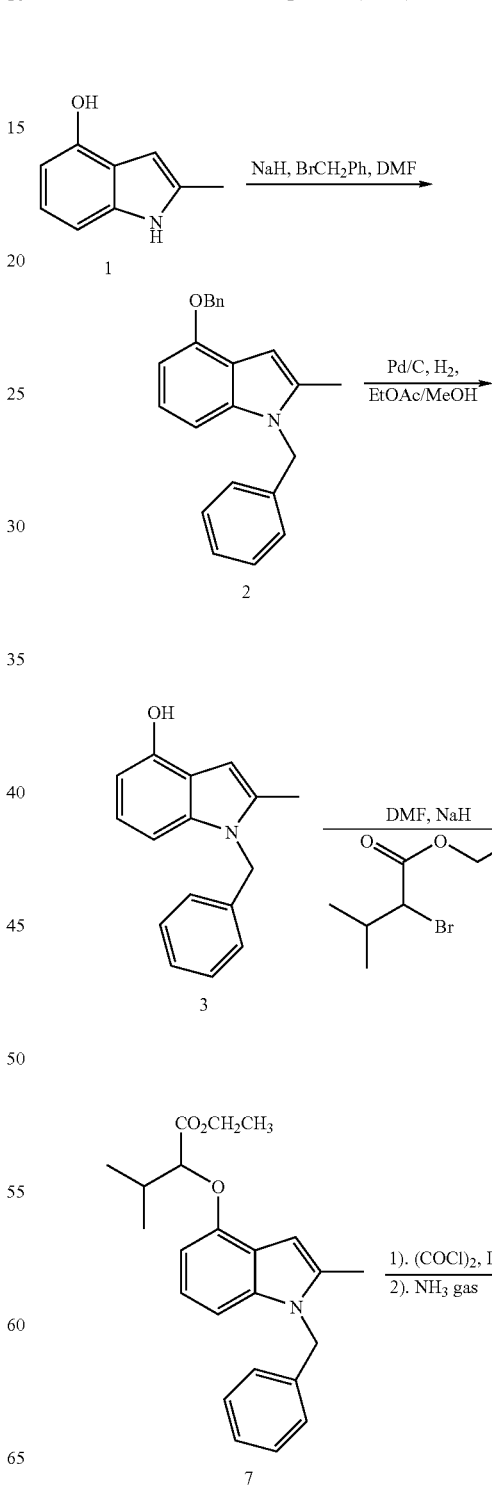

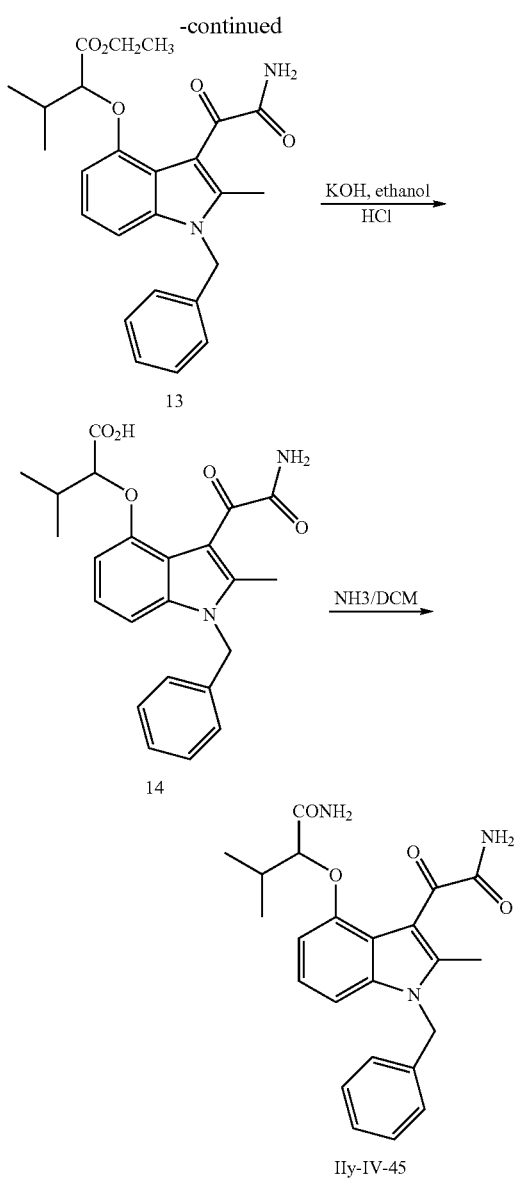

1-Benzyl-4-benzyloxy-2-methyl-1H-indole 2: 4-hydroxy-2-methyl indole 1 (50 g, 0.339 mole) was dissolved in anhydrous DMF (1 L). To the mixture sodium hydride 60% in mineral oil (27.9 g, 0.697 mole) was added. The mixture was left to stir at rt. for 1 h. To the mixture benzyl bromide (82.7 mL, 0.697 mole) was added drop-wise. The mixture was left to stir at room temperature for 18 h. The reaction was diluted with ethyl acetate (4 L) and washed with water (5×500 mL) then brine (1 L). The organic layer was separated and dried with magnesium sulphate and concentrated. The orange oily residue was purified by column chromatography (6:1 Hexane:EtOAc) to afford 86 g (72%) of 2 as an yellow oil.

1-Benzyl-2-methyl-1H-indol-4-ol 3: 1-Benzyl-4-benzyloxy-2-methyl-1H-indole 2 (86 g, 0.263 mole) was dissolved with ethyl acetate (1.5 L) and methanol (300 mL). To the mixture 10% Pd/C wet (18 g) was added to the solution. The reaction was then subjected to $H_2$ gas passed through a mercury bubbler at room temperature and 1 atm. The mixture was left to stir for 6 h. The reaction mixture was filtered through Celite and concentrated. The residue was purified by column chromatography (3:1 Hexane:EtOAc) to afford 3 (30 g, 49%) as a cream solid.

2-(1-Benzyl-2-methyl-1H-indol-4-yloxy)-3-methyl-butyric acid ethyl ester 7: 1-Benzyl-2-methyl-1H-indol-4-ol 3 (0.3 g 1.26 mmole) was dissolved in anhydrous dimethylformamide (20 mL). To the solution sodium hydride 60% in mineral oil (66 mg 1.65 mmole) was added. The mixture was stirred at room temperature for 1 h. To the mixture ethyl-2-bromoisovalerate (0.344 mL, 1.65 mmole) was added. The mixture was stirred at room temperature for 18 h. The reaction was diluted with ethyl acetate (300 mL) and washed with $H_2O$ (4×100 mL) and brine (1×100 mL). The organic layer was separated, dried with magnesium sulfate and concentrated. The residue was purified by column chromatography (10:1 Hexane:EtOAc) to afford a 1:1 mixture of 7: ethyl-2-bromoisovalerate. Further purification by column chromatography (10:1 Hexane:EtOAc) afforded 7 (0.09 g, 19%) as a yellow oil.

2-(3-Aminooxalyl-1-benzyl-2-methyl-1H-indol-yloxy)-3-methyl-butyric acid ethyl ester 13: 2-(1-Benzyl-2-methyl-1H-indol-4-yloxy)-3-methyl-butyric acid ethyl ester 7 (0.09 g, 0.247 mmole) was dissolved in anhydrous dichloromethane (50 mL). To the solution oxalyl chloride (0.026 mL, 0.296 mmole) was added. The mixture was left to stir at room temperature for 1 h. $NH_3$ gas was then bubbled through the solution for 30 minutes. The mixture was left to stir at room temperature for 1 h. The dichloromethane was evaporated and the residue was dissolved in ethyl acetate (200 mL) and washed with $H_2O$ (3×200 mL) and brine (1×300 mL). The organic layer was separated, dried with magnesium sulfate and concentrated to afford 13 (0.23 g, >100%) as a yellow solid (contained inorganic salt). The material was used in next step without further purification.

2-(3-Aminooxalyl-1-benzyl-2-methyl-1H-indol-4-yloxy)-3-methyl-butyric acid 14: 2-(3-Aminooxalyl-1-benzyl-2-methyl-1H-indol-yloxy)-3-methyl-butyric acid ethyl ester 13 (0.15 g, 0345 mmole) was dissolved in anhydrous ethanol (10 mL). To the mixture 0.5054 N potassium hydroxide solution (0.4 mL, 0.403 mmole) was added. The mixture was left to stir at room temperature for 72 h. The reaction mixture was evaporated under high vacuum. The residue was dissolved in $H_2O$ (5 mL) and acidified with 2M HCl. The mixture was left to stir for 30 min. The precipitate was collected by filtration washed and with $H_2O$ to afford 14 (0.03 g, 21%) as a yellow solid.

2-(3-(2-amino-2-oxoacetyl)-1-benzyl-2-methyl-1H-indol-4-yloxy)-3-methylbutanamide (ILY-IV-45) 2-(3-Aminooxalyl-1-benzyl-2-methyl-1H-indol-4-yloxy)-3-methyl-butyric acid 14 (0.03 g, 0.074 mmole) was dissolved in anhydrous dichloromethane (20 mL). To the solution $NH_3$ gas was bubbled through the solution for 30 minutes. The mixture was left to stir at room temperature for 2 h. The dichloromethane was evaporated and the residue was dissolved in ethyl acetate (50 mL) and washed with $H_2O$ (3×50 mL) and brine (1×30 mL). The organic layer was separated, dried with magnesium sulfate and concentrated to afford the crude ILY- IV-45. After flash column chromatography, the pure product was isolated in 0.029 g (99%) as a yellow solid.

Example 11.6

Compound (4-49)

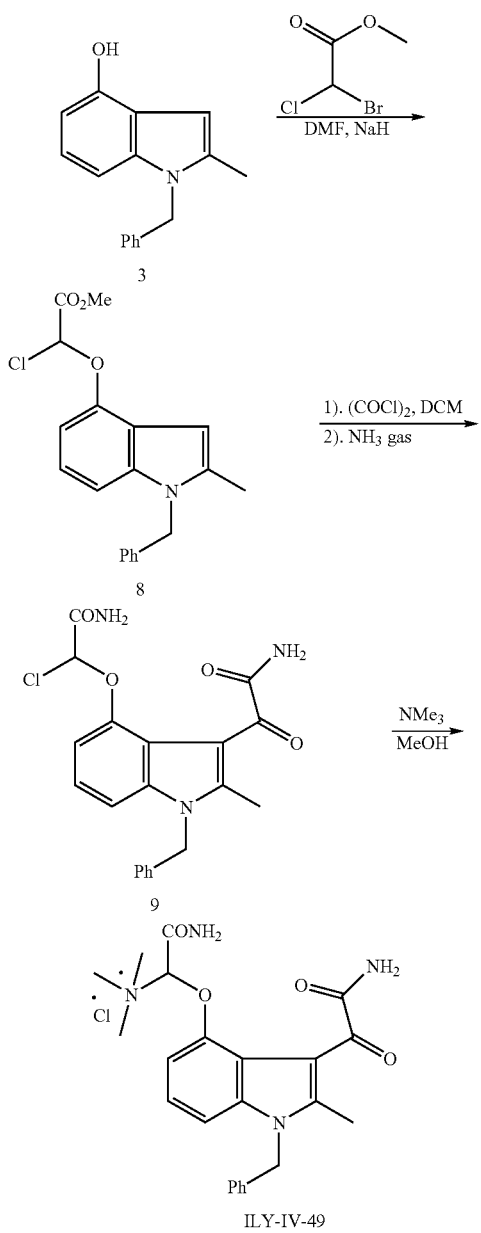

2-(4-(2-amino-1-(trimethylamino)-2-oxoethoxy)-1-benzyl-2-methyl-1H-indol-3-yl)-2-oxoacetamide hydrochloride salt (ILY-IV-49) 1-Benzyl-2-methyl-1H-indol-4-ol 3 (1 mmole) is dissolved in anhydrous dimethylformamide (20 mL). To the solution sodium hydride 60% in mineral oil (1.2 mmole) is added. The mixture is stirred at room temperature for 1 h. To the mixture chloro-bromo-acetic acid methyl ester (1.2 mmole) is added. The mixture is stirred at room temperature for 18 h. The reaction is diluted with ethyl acetate (300 mL) and washed with $H_2O$ (4×100 mL) and brine (1×100 mL). The organic layer is separated, dried with magnesium sulfate and concentrated. The residue is purified by column chromatography to afford 8.

The corresponding acetic acid methyl ester 8 (1 mmole) is dissolved in anhydrous dichloromethane (50 mL). To the solution oxalyl chloride (1.1 mmole) is added. The mixture is left to stir at room temperature for 2 h. $NH_3$ gas is then bubbled through the solution for 30 minutes. The mixture is left to stir at room temperature for 3 h. The dichloromethane is evaporated and the residue is dissolved in ethyl acetate (200 mL) and washed with $H_2O$ (3×200 mL) and brine (1×300 mL). The organic layer is separated, dried with magnesium sulfate and concentrated to afford 9.

Compound 9 (1 mmole) is dissolved in trimethylamine methanol solution (15 mL) in a pressure tube. The mixture is stirred 50° C. for 12 h. The reaction mixture is evaporated to dryness. The residue is triturated with ether and dried to afford ILY-IV-49.

Example 11.7

Compound (4-52)

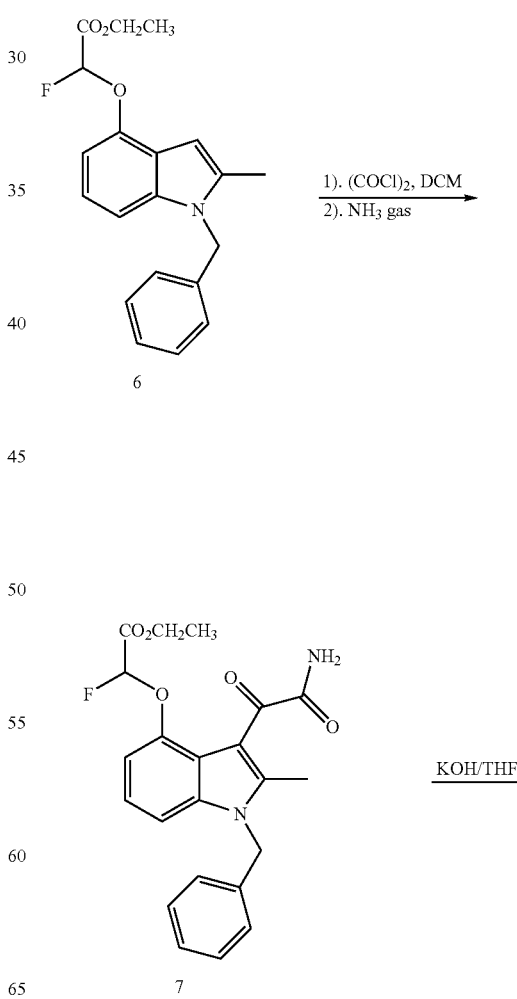

-continued

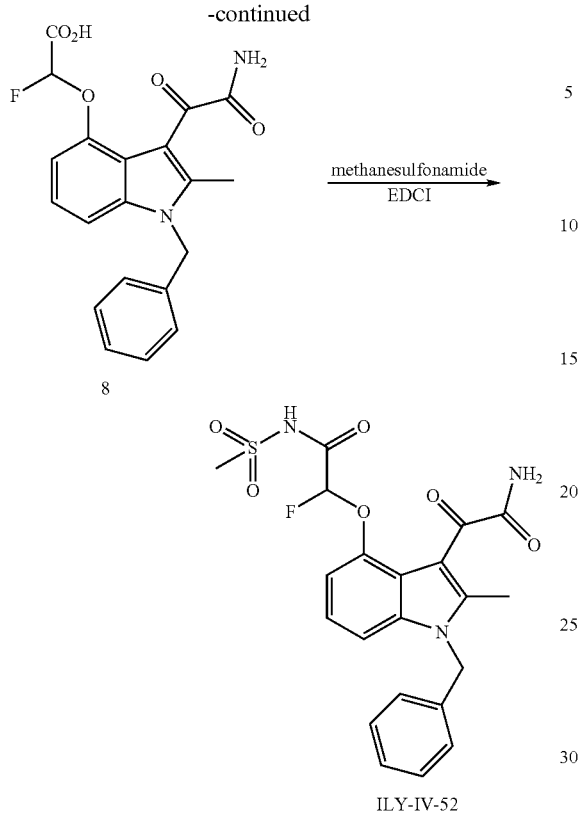

8

ILY-IV-52

2-(3-(2-amino-2-oxoacetyl)-1-benzyl-2-methyl-1H-indol-4-yloxy)-2-fluoro-N-(methylsulfonyl)acetamide (ILY-IV-52) To a solution of oxalyl chloride (0.478 mmole) is diluted in anhydrous dichloromethane (25 mL). To the solution (1-Benzyl-2-methyl-1H-indol-4-yloxy)-fluoro-acetic acid ethyl ester 6 (0.398 mmole) in anhydrous dichloromethane (25 mL) is added drop-wise. The mixture is left to stir at room temperature for 2 h, and then is cooled to 0° C. $NH_3$ gas is then bubbled through the solution for 30 minutes. The mixture is left to stir at 0° C. for 2 h. The dichloromethane is evaporated and the residue is dissolved in ethyl acetate 300 mL) and washed with $H_2O$ (2×300 mL) and brine (1×300 mL). The organic layer is to be separated, dried with magnesium sulfate and concentrated. The residue is purified by to afford 7.

Compound 7 (1 mmole) is dissolved in $THF:H_2O$ 4:1 (10 mL). To the mixture 0.5054 N potassium hydroxide solution is added. The mixture is left to stir at room temperature for 18 h. The reaction mixture is evaporated to dryness. The residue is dissolved in $H_2O$ (5 mL) and acidified to pH 4 with 2M HCl. The resulting precipitate is collected by filtration washed with $H_2O$ and dried to afford 8.

To a solution of 2-(3-(2-amino-2-oxoacetyl)-1-benzyl-2-methyl-1H-indol-4-yloxy)-2-fluoroacetic acid 8 (2.3 mmol) in dichloromethane/dimethylformamide mixture (4:1, 10 mL) is added 4-dimethylaminopyridine (3.4 mmol), methanesulfonamide (4.5 mmol) and 1-(3-dimethylaminopropyl)-3-ethylcarbodiimide hydrochloride (2.3 mmol) and the reaction mixture is stirred at room temperature. After 24 h the reaction mixture is diluted with dichloromethane and washed twice with 1N HCl and brine. The organic layer is dried with $Na_2SO_4$ and evaporated in vacuum. The residue is chromatographed on silica gel to give ILY-IV-52.

Examples 11.8

Compound (4-53)

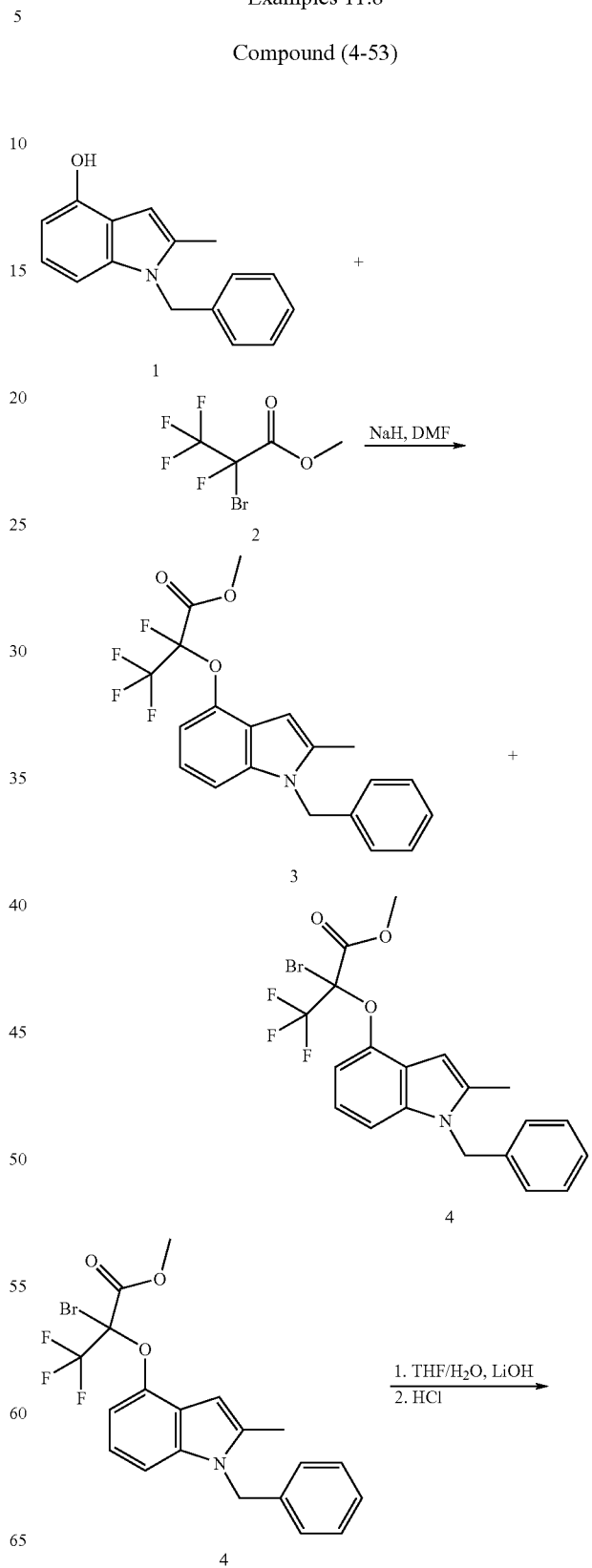

-continued

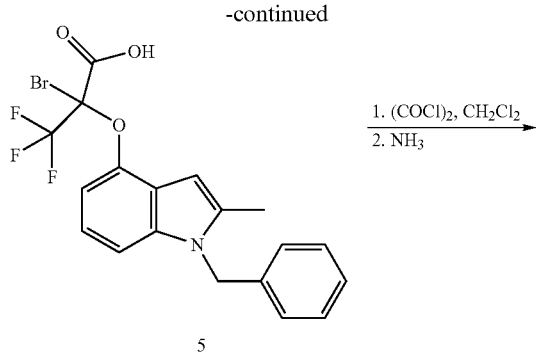

5

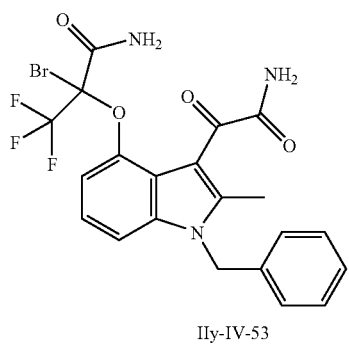

Ily-IV-53

2-(1-Benzyl-2-methyl-1H-indol-4-yloxy)-2-bromo-3,3,3-trifluoro-propionic acid methyl ester (4): To a solution of 1-benzyl-2-methyl-1H-indol-4-ol (1) (0.5 g, 2.1 mmole) in DMF (25 mL), sodium hydride (60% in mineral oil, 0.11 g, 2.75 mmole) was added and the mixture was stirred for 30 minutes at room temperature. Methyl-2-bromo-2,3,3,3-tetrafluoro propionate (0.5 mL, 2.90 mmole) was added to the mixture and stirring was continued at room temperature for 18 h. The reaction was diluted with ethyl acetate (50 mL) and washed with water (3×50 mL) and brine (3×50 mL). The organic layer was separated, dried over magnesium sulphate and concentrated. The residue was purified by preparative TLC (4:1 Hex:EtOAc) to afford intermediate (4) as an orange oil. Intermediate (3) was not the product as expected. Yield: 0.140 g (17%)

2-(1-Benzyl-2-methyl-1H-indol-4-yloxy)-2-bromo-3,3,3-trifluoro-propionic acid (5): To a solution of 2-(1-benzyl-2-methyl-1H-indol-4-yloxy)-2-bromo-3,3,3-trifluoro-propionic acid methyl ester (4) (0.07 g, 0.177 mmole) in THF:H$_2$O (4:1, 10 mL), lithium hydroxide mono hydrate (0.01 g, 0.238 mmole) was added. The mixture was stirred at room temperature for 30 minutes. THF was evaporated and the mixture was acidified with 2M HCl to pH 3. The aqueous layer was extracted with ethyl acetate (3×10 mL). The organic layer was separated, dried over magnesium sulphate and concentrated to afford intermediate (5) as a pink solid. Yield: (0.066 g, 97%).

2-(3-Aminooxalyl-1-benzyl-2-methyl-1H-indol-4-yloxy)-2-bromo-3,3,3-trifluoro-propionamide (Ily-IV-53): To a solution of 2-(1-benzyl-2-methyl-1H-indol-4-yloxy)-2-bromo-3,3,3-trifluoro-propionic acid (5) (0.066 g, 0.173 mmole) in dichloromethane (20 mL), oxalyl chloride (0.035 mL, 0.381 mmole) was added. The mixture was stirred at room temperature for 1 h. Ammonia was bubbled through the reaction mixture for 30 minutes and stirred for 1 h. at room temperature. The dichloromethane was evaporated. The residue was diluted in ethyl acetate (50 mL) and washed with water (3×50 mL) and brine (3×50 mL). The organic layer was separated, dried over magnesium sulphate and concentrated. The residue was purified by preparative TLC (3:1 EtOAc:Hex) to afford Ily-V-53 as a yellow solid. Yield: 0.02 g (22%), $^1$H NMR (400 MHz, DMSO-d$_6$) δ, ppm: 8.25 (brs, 1H), 8.15 (brs, 1H), 7.90 (brs, 1H), 7.62 (brs, 1H), 7.52 (d, 1H), 7.38-7.18 (m, 4H), 7.10-6.95 (m, 2H), 5.57 (s, 2H), 2.50 (s, 3H). ES-MS: m/z=513.84 (M+1).

Certain such C4-amide indole and indole related compounds were evaluated for phospholipase activity using the protocol of Example 8. The results are shown in Table 9.

TABLE 9

| | | | Inhibition of pancreas secreted human, mouse and porcine PLA$_2$ | | | | | |
| --- | --- | --- | --- | --- | --- | --- | --- | --- |
| | | | ILYPSA IC50 (μM) | | | ILYPSA % inhibition at 15 μM | | |
| structure | Compound ID | MW | hps PLA$_2$ | pps PLA$_2$ | mps PLA$_2$ | hps PLA$_2$ | pps PLA$_2$ | mps PLA$_2$ |
| [structure] | ILY-IV-28 (4-28) | 383.37 | 2.6 | 0.16 | 1.44 | | | |

TABLE 9-continued

| | | | Inhibition of pancreas secreted human, mouse and porcine PLA$_2$ | | | | | |
| | | | ILYPSA IC50 (μM) | | | ILYPSA % inhibition at 15 μM | | |
| structure | Compound ID | MW | hps PLA$_2$ | pps PLA$_2$ | mps PLA$_2$ | hps PLA$_2$ | pps PLA$_2$ | mps PLA$_2$ |
| --- | --- | --- | --- | --- | --- | --- | --- | --- |
| (structure) | ILY-IV-53 (4-53) | 512.28 | | 16.01 | | | 49 | 49.68 |
| (structure) | ILY-IV-45 (4-45) | 407.47 | | 1.03 | | | 73.95 | 65.52 |

Example 12

Synthesis of Azaindole and Azaindole Related Compounds, and In-vitro Assay for Certain of Such Compounds for the Inhibition of Human, Mouse and Porcine Phospholipase A$_2$ In this example, various preferred azaindole and azaindole-related compounds are prepared.

Example 12.1

Compound (7-1)

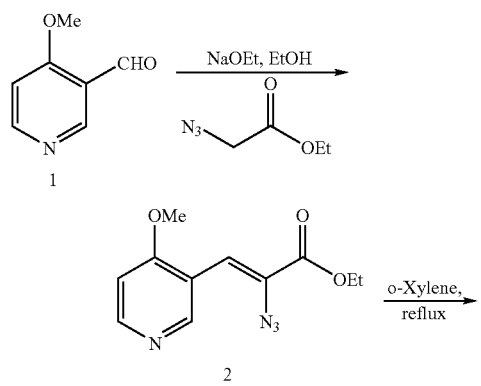

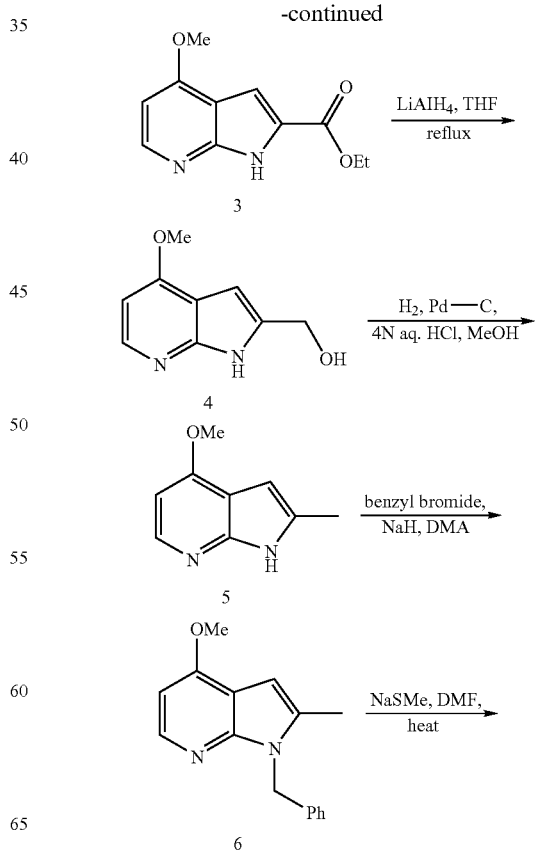

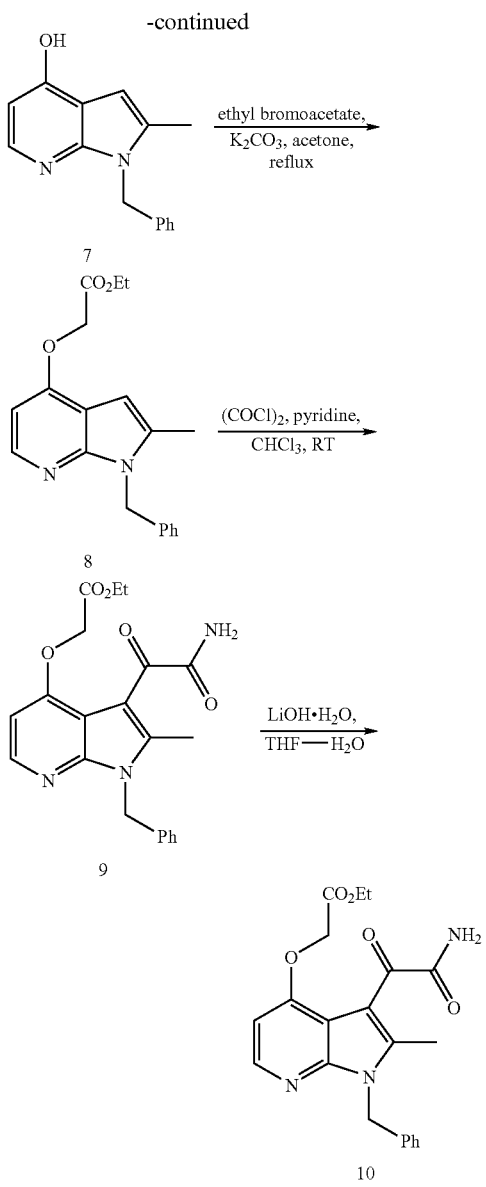

Ethyl α-Azido-β-(4-methoxypyrid-3-yl)-acrylate 2. A homogeneous mixture of 3-formyl-4-methoxypyridine 1 (7.0 g, 54.7 mmol) and ethyl azidoacetate (5.0 g, 36.4 mmol) in anhydrous EtOH (50 mL) was added through a dropping funnel to a well-stirred solution containing Na (0.1.24 g, 54.7 mmol) in anhydrous EtOH (30 mL) under $N_2$ at −15° C. The mixture was stirred at that temperature for 4 h. During this time the precipitated solid was filtered and washed with ice cooled ethanol (30 mL). The compound was dried under vacuum oven for 3 h to get pure title compound 2 as white crystalline solid. Mp 92-95° C.; Yield: 4.8 g, 53%; ESI MS: m/z 248.9 (M+1).

2-Ethoxycarbonyl-4-methoxypyrrolo-[2,3-b]pyridine 3. A stirred solution of ethyl-α-azido-β-(4-methoxypyrid-3-yl)-acrylate 2 (3.7 g, 14.9 mmol) in dry o-xylene (35 mL) was heated in an oil bath at 170° C. for 25 min. During this time the contents of the flask gained brick red color. After cooling, the mixture was concentrated under high vacuum. The resultant brown residue was purified on silica gel column using 5% methanol in $CH_2Cl_2$ to give 3 as brick red solid. Mp 195-197° C.; Yield: 3.3 g, 82%; ESI MS: m/z 220.9 (M+1).

(4-Methoxy-1H-pyrrolo[2,3-b]pyridin-2-yl)methanol 4. To a suspension of 2-ethoxycarbonyl-4-methoxypyrrolo-[2,3-b]pyridine 3 (1.90 g, 8.62 mmol) in anhydrous THF (25 mL) was added $LiAlH_4$ (0.218 g, 17.2 mmol) in small portions under $N_2$ atmosphere. The mixture was stirred at reflux temperature for 50 min. After cooling, it was poured into cool $H_2O$ (20 mL) and extracted with EtOAc (4×15 mL). The combined organic layers were washed with brine (20 mL) and dried ($Na_2SO_4$). After filtration, the filtrate was concentrated to dryness and the residue was chromatographed on a silica gel column using 5% methanol in $CH_2Cl_2$ to give 4 as white solid. Mp 210-212° C.; Yield: 1.10 g, 71%; ESI MS: m/z 178.9 (M+1).

4-Methoxy-2-methyl-1H-pyrrolo[2,3-b]pyridine 5. A suspension of (4-methoxy-1H-pyrrolo[2,3-b]pyridin-2-yl)methanol 4 (0.90 g, 5.05 mmol) and $Pd(OH)_2$ (100 mg) in methanol containing 4N aq. HCl solution (10 mL) was hydrogenated under hydrogen pressure (50 psi) for 36 h. The acidic mixture was quenched with 1N NaOH solution. Filtration through celite, concentration and purification on silica gel column using 5% methanol in $CH_2Cl_2$ to gave 5 as pale yellow syrup. Yield: 0.68 g, 83%; ESI MS: m/z 163.01 (M+1).

1-Benzyl-4-methoxy-2-methyl-1H-pyrrolo[2,3-b]pyridine 6. To a suspension of sodium hydride (0.292 g, 9.24 mmol) in dry N,N-dimethyl acetamide (10 mL) was added drop-wise under $N_2$, a solution of 4-methoxy-2-methyl-1H-pyrrolo[2,3-b]pyridine 5 (0.60 g, 3.70 mmol) in the same solvent (5 mL). The mixture was stirred at room temperature for 45 min. After this time, the solution was cooled in an ice bath, and benzyl bromide (1.25 g, 7.30 mmol) was slowly added. The solution was allowed to warm at room temperature and stirred for 12 h. Then, it was poured into ice water (30 mL) and stirred for 30 min, and the precipitated solid was extracted with ethylacetate (3×20 mL). The organic layer was washed with water and brine. Concentration and purification on silica gel column using 20% ethylacetate in hexanes gave pure title compound 6 as a white solid. Yield: 0.70 g, 68%; mp 129-131° C.; ESI MS: m/z 253.0 (M+1).

1-Benzyl-2-methyl-1H-pyrrolo[2,3-b]pyridin-4-ol 7. To a solution of compound 1-benzyl-4-methoxy-2-methyl-1H-pyrrolo[2,3-b]pyridine 6 (0.45 g, 1.78 mmol) in anhydrous DMF (10 mL) was added NaSMe (0.37 g, 5.35 mmol) under $N_2$. The reaction mixture was stirred at 80° C. for 45 min. After cooling, the mixture was poured into a saturated solution of $NH_4Cl$ (20 mL), and 1 N HCl (3-4 mL) was added until pH 4-5. The resultant mixture was extracted with EtOAc (5×30 mL), the combined organic extracts were washed with $H_2O$ (2×10 mL) and dried ($Na_2SO_4$). The solvent was removed under reduced pressure, and the residue was chromatographed on a silica gel column using 5% methanol in $CH_2Cl_2$ as eluent to give 7 as an amorphous white solid. Yield: 0.30 g, 70%; ESI MS: m/z 238.9 (M+1).

Ethyl 2-(1-benzyl-2-methyl-1H-pyrrolo[2,3-b]pyridin-4-yloxy)acetate 8. A mixture of 1-benzyl-2-methyl-1H-pyrrolo[2,3-b]pyridin-4-ol 7 (0.30 g, 1.26 mmol), 2-bromoethylacetate (1.05 g, 6.29 mmol) and $K_2CO_3$ (2.0 g) in anhydrous acetone (15 mL) were heated at reflux for 6 h under $N_2$. After cooling, the mixture was filtered through celite and the filtrate was concentrated to yield a syrup. It was then re-dissolved in ethyl acetate and washed with water (10×2 mL), brine and dried ($Na_2SO_4$). The solvent was removed under reduced pressure, and the residue was chromatographed on a silica gel column eluting with 40% ethylacetate in hexanes afforded the title compound 8 as an amorphous white solid. Yield: 0.25 g, 61%; ESI MS: m/z 325.0 (M+1).

2-(1-Benzyl-4-yloxyacetic acid ethyl ester-2-methyl-1H-pyrrolo[2,3-b]pyridin-3-yl)-2-oxoacetamide 9. To an ice-cooled solution of ethyl 2-(1-benzyl-2-methyl-1H-pyrrolo[2,3-b]pyridin-4-yloxy)acetate 8 (0.10 g, 0.31 mmol) in anhydrous CHCl₃ (5 mL), oxalyl chloride (0.05 mL, 0.61 mmol) followed by anhydrous pyridine (0.04 mL, 0.60 mmol) was added. The mixture was allowed to attain room temperature and further stirred for 5 h. The mixture was concentrated under vacuum to remove excess unreacted oxalyl chloride. The resultant syrup was and resuspended in CHCl₃ (20 mL) and ammonia gas was passed by cooling to 0° C. for 15 min. The organic layer was washed with water (10×2 mL), dried (Na₂SO₄). The solvent was removed under reduced pressure, and the residue was chromatographed on a silica gel column eluting with 2% ethanol in CH₂Cl₂ to get the title compound 9 as a white solid. Yield: 0.065 g, 53%; mp 139-141° C.; ESI MS: m/z 395.9 (M+1).

2-(1-Benzyl-4-yloxyacetic acid-2-methyl-1H-pyrrolo[2,3-b]pyridin-3-yl)-2-oxoacetamide 10 (Ily-VII-1). To a suspension of 2-(1-benzyl-4-yloxyacetic acid ethyl ester-2-methyl-1H-pyrrolo[2,3-b]pyridin-3-yl)-2-oxoacetamide 9 (0.035 g, 0.08 mmol) in THF-H₂O (1:1, 3 mL), a solution of LiOH.H₂O (0.005 g, 0.13 mmol) was added and the mixture was stirred for 6 h at room temperature. During this time the contents were homogeneous. The pH of the basic solution was set to 4-5 using 1N HCl solution (0.5 mL). The pale yellow solid separated was filtered and washed with H₂O (1 mL) and dried in vacuum oven at 50° C. overnight to get the title compound 10 as a pale yellow solid in high purity. Yield: 0.026 g, 79%; ESI MS: m/z 367.9 (M+1); HPLC: 91.7% purity; ¹H NMR (DMSO-d₆): (5-37-75) δ 8.20 (d, 1H), 7.92 (s, 1H), 7.43 (s, 1H), 7.32-7.22 (m, 3H), 7.18-7.10 (m, 2H), 6.70 (d, 1H), 5.58 (s, 2H), 4.76 (s, 2H), 2.45 (s, 3H) ppm.

Example 12.2

Compound (2-1)

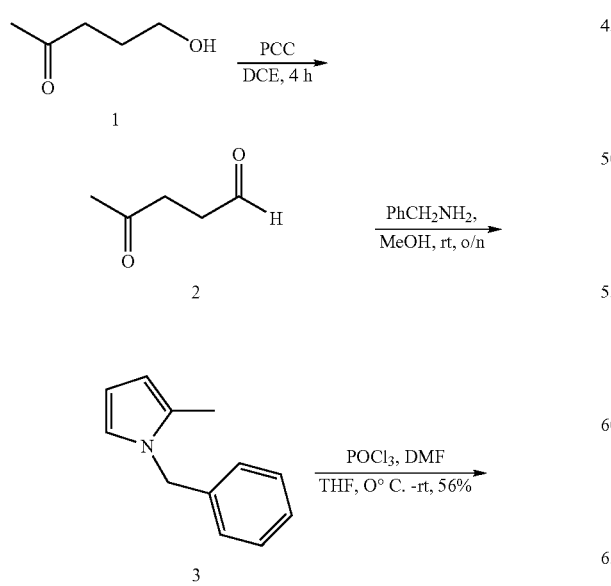

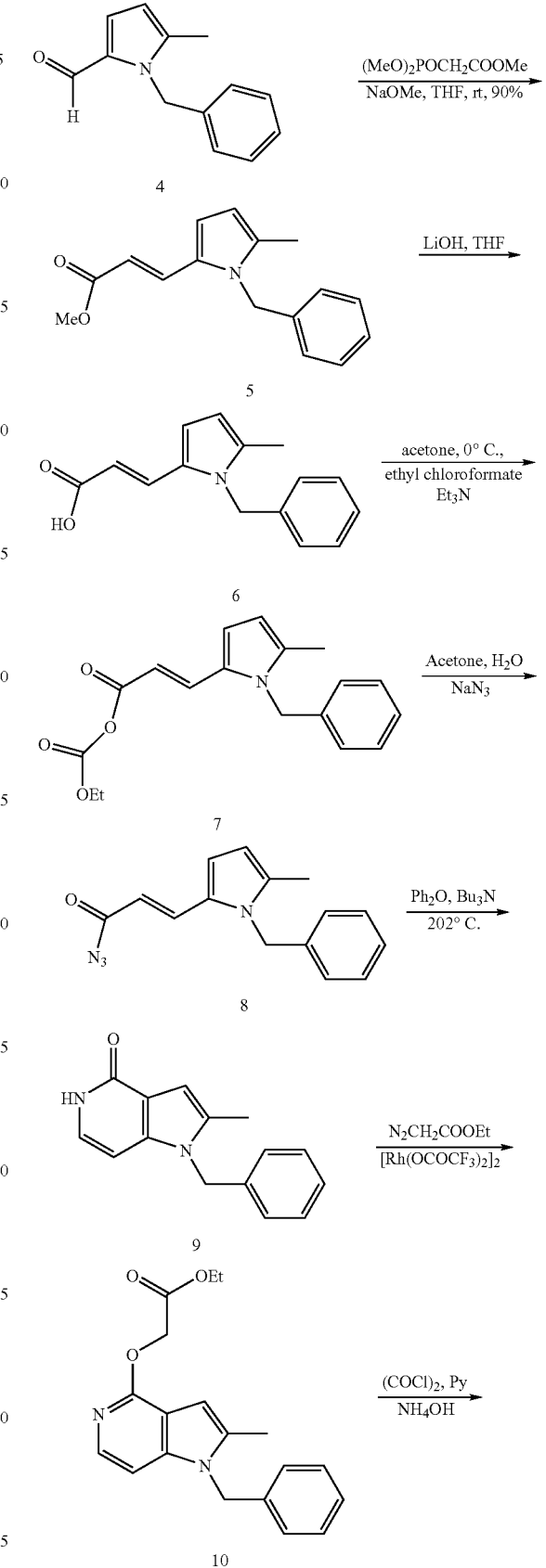

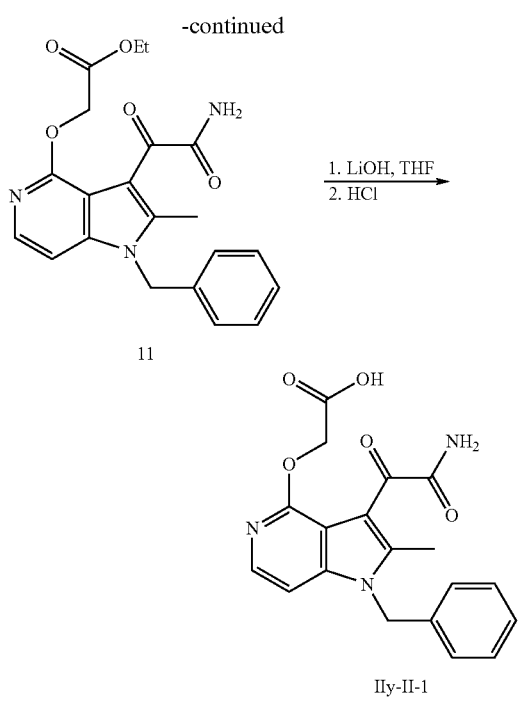

4-Oxo-pentanal, 2: To a stirred suspension of pyridinium chlorochromate (538 g, 2.49 mol) in dichloromethane (4000 mL) at room temperature was added dropwise 3-acetyl-1-propanol (200 g, 1.96 mol) over 5 h. The formed dark mixture was stirred for 1 h at room temperature and then filtered through a pad of silica gel. The silica gel pad was washed with dichloromethane till no product left. The dichloromethane solution was concentrated to afford the crude product as a green liquid. The crude product was purified by distillation under vacuum to afford 4-oxo-pentanal, 2 as clear colorless oil. Yield: 94.6 g (51%).

1-Benzyl-2-methyl-1H-pyrrole, 3: To a stirred mixture of 4-oxo-pentanal (94.6 g, 0.945 mol) in dry methanol (400 mL) and molecular sieve (4A, 100 g) at room temperature was added dropwise benzylamine solution (125 mL, 1.13 mol) in dry methanol (125 mL). The formed dark solution was stirred for 18 h at room temperature and then the reaction mixture was filtered and concentrated. The crude product was purified by silica gel chromatography (hexane to hexane:ethyl acetate, 3:1) to afford 1-benzyl-2-methyl-1H-pyrrole, 3 as a light yellow oil. Yield: 94 g (58%).

1-Benzyl-5-methyl-1H-pyrrole-2-carbaldehyde, 4: POCl$_3$ (23.46 mL, 246 mmol) was added dropwise to a stirred N,N-dimethyformamide (204 mL) at 0° C. After addition the mixture was stirred for additional 90 minutes. To the mixture was added dropwise the solution of 1-benzyl-2-methyl-1H-pyrrole, 3 (2.71 g, 45 mmol) in tetrahydrofuran (1150 mL). The reaction mixture was allowed to be stirred for 18 h from 0° C. to room temperature. The mixture was concentrated and redissolved in ethyl acetate (2 L). The mixture was washed with saturated Na$_2$CO$_3$ (2×500 mL). The Na$_2$CO$_3$ solution was extracted with ethyl acetate (7×1 L). The organic layers were combined and concentrated. The crude product was purified by silica gel chromatography (hexane to hexane: ethyl acetate, 7:1) to afford 1-benzyl-5-methyl-1H-pyrrole-2-carbaldehyde, 4 as a light yellow liquid. Yield: 30.8 g (81%).

3-(1-Benzyl-5-methyl-1H-pyrrol-2-yl)-acrylic acid methyl ester, 5: Sodium (14.45 g, 628 mmol) was added in portions to a dry methanol (420 mL). To the fresh formed sodium methoxide solution was added dropwise the solution of trimethyl phosphonoacetate (50 mL, 302 mmol) in tetrahydrofuran (105 mL) at room temperature. After addition the mixture was stirred for additional 60 min at room temperature. Then to the reaction mixture was added dropwise the solution of 1-benzyl-5-methyl-1H-pyrrole-2-carbaldehyde, 4 (30.8 g, 154 mmol) in tetrahydrofuran (630 mL) at room temperature. The reaction mixture was stirred for 2 h at room temperature. The mixture was concentrated and redissolved in ethyl acetate (1 L). The mixture was washed with 1 M HCl solution, then saturated NaHCO$_3$, H$_2$O. The organic solution were dried over MgSO$_4$ and then filtered, concentrated to afford the crude product, 3-(1-benzyl-5-methyl-1H-pyrrol-2-yl)-acrylic acid methyl ester, 5 as a light yellow solid. Yield: 40 g 1-Benzyl-2-methyl-1,5-dihydro-pyrrolo[3,2-c]pyridin-4-one, 6: 3-(1-Benzyl-5-methyl-1H-pyrrol-2-yl)-acrylic acid methyl ester, 5 (40 g) was dissolved in a mixture of tetrahydrofuran (400 mL) and methanol (400 mL). To the mixture a solution of lithium hydroxide monohydrate (20 g, 476 mmol) in H$_2$O (200 mL) was added. After addition the reaction mixture was stirred for 18 h at room temperature. The reaction mixture was acidified by 2M HCl to pH=4-5. The mixture was concentrated and redissolved in ethyl acetate (2 L). The mixture was washed with H$_2$O. The water layer was extracted with ethyl acetate (2×1 L). The organic was combined and concentrated to afford a yellow solid which was washed with dichloromethane to afford the product (22.66 g). The washing dichloromethane solution were concentrated and the residue was purified by silica gel chromatography (hexane to hexane:ethyl acetate, 1:3, followed by neat ethyl acetate) to afford 3-(1-Benzyl-5-methyl-1H-pyrrol-2-yl)-acrylic acid, 6 as a light yellow solid (5.9 g). Yield: 28.56 g, (77%, 2 steps)

1-Benzyl-2-methyl-1,5-dihydro-pyrrolo[3,2-c]pyridin-4-one, 9: 3-(1-Benzyl-5-methyl-1H-pyrrol-2-yl)-acrylic acid, 6 (26.72 g, 110.9 mmol) was dissolved in a dry acetone (1050 mL). To the suspension mixture triethylamine (35 mL) was added to form a clear solution. The reaction mixture was cooled to 0° C. and then to the cooled reaction mixture a solution of ethyl chlorofomate (30 mL, 304 mmol) in dry acetone (650 mL) was added dropwise over 1 hour. After addition the reaction mixture was stirred for 4 h at 0° C. Then to the reaction mixture was added dropwise the solution of sodium azide (14.52 g, 223 mmol) in H$_2$O (175 mL) over 30 minutes. The reaction mixture was stirred at 0° C. for 2 h. The reaction mixture was poured into ice-water (1 L). Then the mixture was extracted with dichloromethane (3×1 L). The organic layers were combined and dried over MgSO$_4$. The mixture was filtered and concentrated to afford a crude 8 as a yellow solid (32 g). To the mixture of diphenyl ether (175 mL) and tributylamine (31 mL) which was preheated to 205° C. was added dropwise the solution of crude 8 in diphenyl ether (250 mL) at 205° C. for 1 hour. After addition the mixture was stirred for another hour at 205° C. The mixture was cooled to room temperature and solid was formed. Diethyl ether (500 mL) was added into the reaction mixture to form more solid. The mixture was filtered and the solid was washed with diethyl ether to afford the product (8.81 g). The filtrate was concentrated and the residue was purified by silica gel chromatography (hexane to hexane:ethyl acetate, gradient 1:1 to 1:3; then methanol in dichloromethane, 1% to 5%) to afford 1-benzyl-2-methyl-1,5-dihydro-pyrrolo[3,2-c]pyridin-4-one, 9 as a yellow solid (4.7 g). Yield: 13.51 g, (51%)

(1-Benzyl-2-methyl-1H-pyrrolo[3,2-c]pyridin-4-yloxy)-acetic acid ethyl ester, 10: 1-Benzyl-2-methyl-1,5-dihydro-pyrrolo[3,2-c]pyridin-4-one, 9 (512 mg, 2.15 mmol) was dissolved in a dry dichloroethane (300 mL). To the mixture Rh$_2$(OCOCF$_3$)$_4$ (64 mg, 0.097 mmol) was added. The reaction mixture was heated to reflux and then to the reaction mixture a solution of ethyl diazoacetate (0.25 mL, 2.15 mmol) in dry dichloroethane (30 mL) was added dropwise over 6 h under refluxing. After addition the reaction mixture was stirred for 1.5 h under refluxing. Then the reaction mixture was cooled to room temperature. The mixture was concentrated and the residue was purified by silica gel chromatography (hexane to hexane:ethyl acetate, 5:1) to afford (1-benzyl-2-methyl-1H-pyrrolo[3,2-c]pyridin-4-yloxy)-acetic acid ethyl ester, 10. Yield: 345 mg, (49%)

(3-Aminooxalyl-1-benzyl-2-methyl-1H-pyrrolo[3,2-c]pyridin-4-yloxy)-acetic acid ethyl ester, 11: (1-Benzyl-2-methyl-1H-pyrrolo[3,2-c]pyridin-4-yloxy)-acetic acid ethyl ester, 10 (370 mg, 1.14 mmol) was dissolved in a dry chloroform (37 mL). To the mixture the solution of oxalyl chloride (0.30 mL, 3.43 mmol) in chloroform (10 mL) was added dropwise at room temperature. Then pyridine (0.133 mL) was added slowly to the mixture at room temperature. After addition the mixture was stirred at room temperature for 18 h. The mixture was concentrated and the residue was purified by silica gel chromatography (hexan to hexane:ethyl acetate, gradient 1:1 to 1:3) to afford (3-aminooxalyl-1-benzyl-2-methyl-1H-pyrrolo[3,2-c]pyridin-4-yloxy)-acetic acid ethyl ester, 11 as a yellow solid. Yield: 280 mg, (62%)

(3-Aminooxalyl-1-benzyl-2-methyl-1H-pyrrolo[3,2-c]pyridin-4-yloxy)-acetic acid, Ily-II-1: (3-Aminooxalyl-1-benzyl-2-methyl-1H-pyrrolo[3,2-c]pyridin-4-yloxy)-acetic acid ethyl ester, 11 (90 mg, 0.227 mmol) was dissolved in methanol (20 mL). To the mixture the solution of KOH (1M, 0.25 mL) was added at room temperature. After addition the mixture was stirred at room temperature for 18 h. Then solution of lithium hydroxide monohydrate (90 mg) in H$_2$O (5 mL) was added. After another hour stirring the mixture was concentrated and the residue was redissolved in methanol (10 mL) and ethanol (10 mL). The mixture was filtered and the filtrate was acidified by hydrogen chloride in ether (1.0 M) to pH=3-4. Solvent was evaporated and the residue was washed with a mixture of dichloromethane: ether (1:1), then water (5 mL) and ether to afford (3-aminooxalyl-1-benzyl-2-methyl-1H-pyrrolo[3,2-c]pyridin-4-yloxy)-acetic acid, Ily-II-1 as a light yellow solid. Yield: 29 mg, (35%)

$^1$H NMR: 05-43-67, (400 MHz, DMSO-d6) δ, 12.96 (br, s, 1H, COOH), 7.97 (br, s, 1H, NH), 7.79 (d, 1H), 7.56 (br, s, 1H, NH), 7.22-7.39 (m, 4H), 7.08-7.12 (m, 2H), 5.57 (br, s, 2H, PhCH$_2$N), 4.80 (br, s, 2H, CH$_2$OAr) ppm. MS (ES): 367.99 [M+1].

Example 12.3

Compound (2-7)

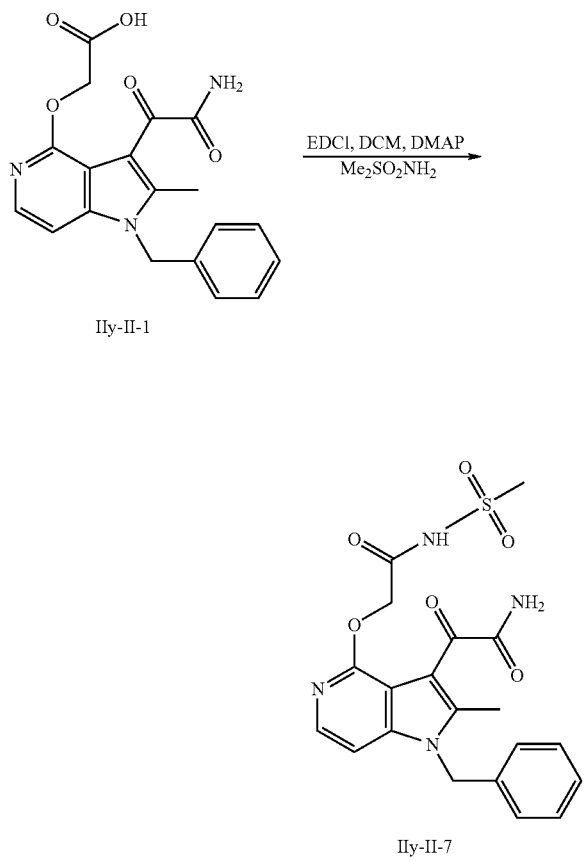

2-[1-Benzyl-4-(2-methanesulfonylamino-2-oxo-ethoxy)-2-methyl-1H-pyrrolo[3,2-c]pyridin-3-yl]-2-oxo-acetamide, Ily-II-7: (3-Aminooxalyl-1-benzyl-2-methyl-1H-pyrrolo[3,2-c]pyridin-4-yloxy)-acetic acid, Ily-II-1 (27 mg, 0.0736 mmol) was suspended in dichloromethane (2 mL). To the mixture 4-dimethylaminopyridine (35 mg, 0.286 mmol) was added at room temperature, followed by methanesulfonamide (30 mg, 0.296 mmol) and N-(3-dimethylaminopropyl)-N"-ethylcarbodiimide hydrochloride (45 mg, 0.234 mmol). After addition the mixture was stirred at room temperature for 24 h. Dichloromethane (20 mL) was added to dilute the reaction mixture. Then reaction mixture solution was washed with 1.0 M HCl, water and dried over MgSO$_4$. The mixture was filtered. The filtrate was concentrated and the residue was purified by silica gel chromatography (hexane to hexane: ethyl acetate, gradient 1:1 to 1:2; then methanol in dichloromethane, 5% to 15%) to afford 2-[1-benzyl-4-(2-methanesulfonylamino-2-oxo-ethoxy)-2-methyl-1H-pyrrolo[3,2-c]pyridin-3-yl]-2-oxo-acetamide, Ily-II-7 as an off-white solid. Yield: 9 mg, (28%)

$^1$H NMR: 05-43-101-2, (400 MHz, DMSO-d6) δ, 11.62 (br, s, 1H, NHSO$_2$), 8.16 (br, s, 1H, NH), 7.80 (d, 1H), 7.68 (br, s, 1H, NH), 7.26-7.40 (m, 4H), 7.06-7.12 (m, 2H), 5.58 (br, s, 2H, PhCH$_2$N), 4.85 (br, s, 2H, CH$_2$OAr), 3.20 (br, s, 3H, SO$_3$CH$_3$) ppm. MS (EI): 444.85 [M+1], 442.84 [M−1]

Example 12.4
Compound (2-4)
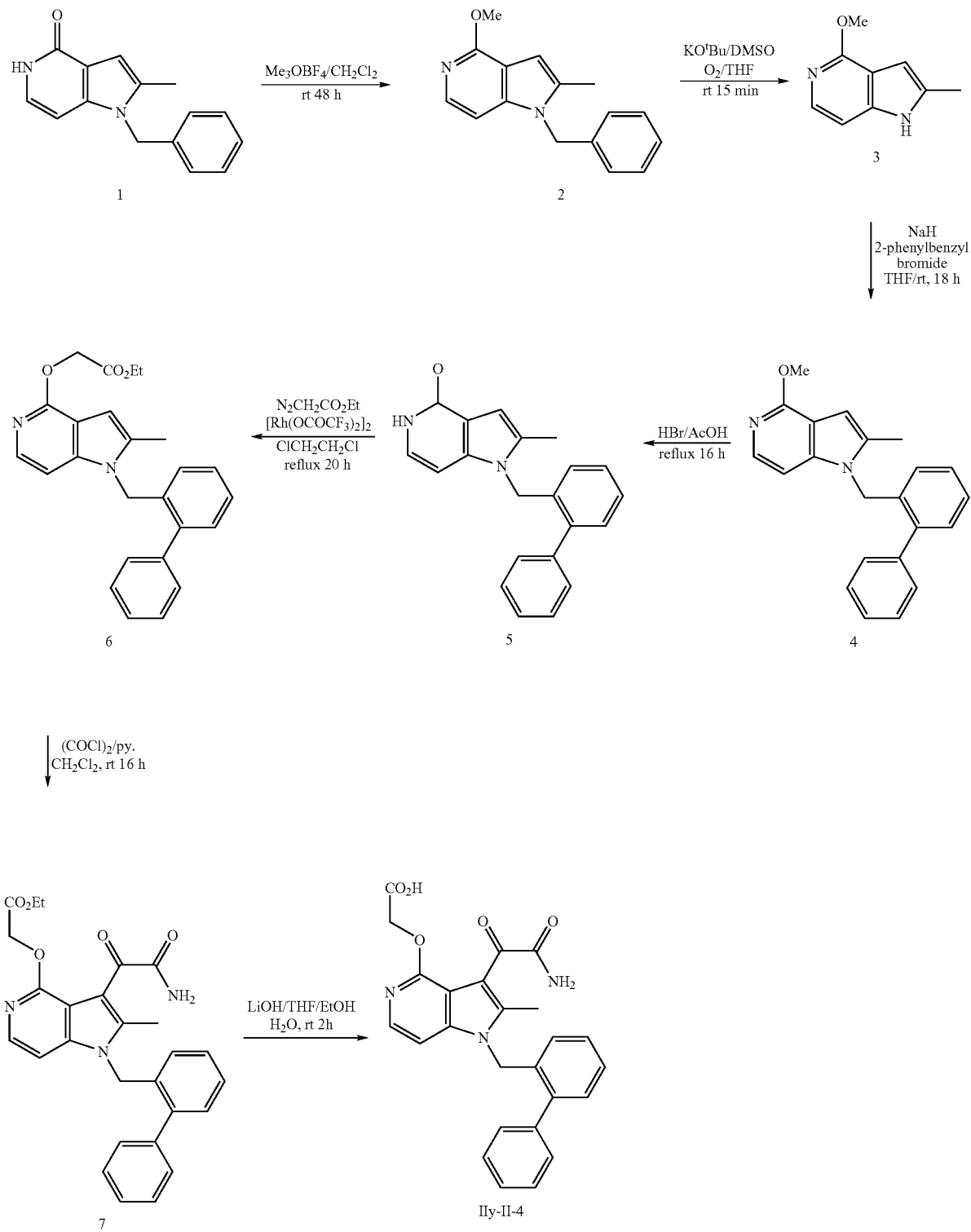

(1-Benzyl-4-methoxy-2-methyl-1H-pyrrolo[3,2-c]pyridine 2. To a stirred suspension of 1-benzyl-2-methyl-1,5-dihydro-pyrrolo[3,2-c]pyridin-4-one 1 (2.0 g, 8.4 mmol) in CH$_2$Cl$_2$ (70 mL), Me$_3$OBF$_4$ (3.8 g, 25.6 mmol) was added and the reaction mixture was stirred for 48 h, then diluted with CH$_2$Cl$_2$ (70 mL). The mixture was washed with water (100 mL), brine (100 mL), dried over Na$_2$SO$_4$ and evaporated. Flash chromatography of the residue over silica gel, using 10% EtOAc in hexanes to 25% EtOAc in hexanes) gave product 2 as a pale yellow solid. Yield: 1.6 g (75%).

4-Methoxy-2-methyl-1H-pyrrolo[3,2-c]pyridine 3. To a stirred solution of (1-benzyl-4-methoxy-2-methyl-1H-pyrrolo[3,2-c]pyridine 2 (0.887 mg, 3.52 mmol) in THF (10 mL), DMSO (2.5 mL), followed by KO$^t$Bu (25 mL, 1.0 M in THF) was added dropwise, and then the reaction mixture was treated with O$_2$ for 15 min at room temperature, quenched with saturated NH$_4$Cl (20 mL), extracted with EtOAc (3×60 mL). The combined organic extracts were washed with water (50 mL), brine (50 mL), dried over Na$_2$SO$_4$ and evaporated. Flash chromatography of the residue over silica gel, using 20% EtOAc in hexanes to 40% EtOAc in hexanes) gave product 3 as a yellow solid. Yield: 560 mg (98%).

1-Biphenyl-2-ylmethyl-4-methoxy-2-methyl-1H-pyrrolo[3,2-c]pyridine 4. To a stirred suspension of NaH (98 mg, 2.5 mmol, 60% in mineral oil) in THF (10 mL), 4-methoxy-2-methyl-1H-pyrrolo[3,2-c]pyridine 3 (280 mg, 1.72 mmol) in THF (3 mL) was added. The mixture was stirred at room temperature for 30 min, and then 2-phenylbenzyl bromide (0.40 mL, 2.2 mmol) was added, stirring was continued for 18 h. The reaction mixture was quenched with saturated NH$_4$Cl (20 mL), extracted with EtOAc (3×40 mL). The combined organic extracts were washed with water (40 mL), brine (40 mL), dried over Na$_2$SO$_4$ and evaporated. Flash chromatography of the residue over silica gel, using 10% EtOAc in hexanes to 25% EtOAc in hexanes) gave product 4 as a yellow foam. Yield: 375 mg (66%).

1-Biphenyl-2-ylmethyl-2-methyl-1,5-dihydro-pyrrolo[3,2-c]pyridin-4-one 5. To a stirred solution of 1-biphenyl-2-ylmethyl-4-methoxy-2-methyl-1H-pyrrolo[3,2-c]pyridine 4 (370 mg, 1.13 mmol) in AcOH (15 mL), 48% of HBr (5 mL) was added. The reaction mixture was heated to 105° C., and then stirred for 16 h, cooled to room temperature and evaporated. The obtained residue was dissolved in CH$_2$Cl$_2$ (100 mL), washed with saturated NaHCO$_3$ (30 mL), brine (30 mL), dried over Na$_2$SO$_4$ and evaporated to afford crude product 5, which was used without further purification for next step. Yield: 355 mg (100%).

(1-Biphenyl-2-ylmethyl-2-methyl-1H-pyrrolo[3,2-c]pyridin-4-yloxy)-acetic acid ethyl ester 6. To a stirred solution of 1-biphenyl-2-ylmethyl-2-methyl-1,5-dihydro-pyrrolo[3,2-c]pyridin-4-one 5 (0.355 g, 1.13 mmol) in ClCH$_2$CH$_2$Cl (40 mL), [Rh(OCOCF$_3$)$_2$]$_2$ (48 mg, 0.073 mmol) was added, and then a solution of N$_2$CH$_2$CO$_2$Et (0.13 mL. 1.3 mmol) in ClCH$_2$CH$_2$Cl (8 mL) was added over 16 h via a syringe pump. The reaction mixture was cooled to room temperature and evaporated. Flash chromatography of the residue over silica gel, using 10% EtOAc in hexanes to 25% EtOAc in hexanes) gave product 6 as a yellow solid. Yield: 105 mg (22%).

(3-Aminooxalyl-1-biphenyl-2-ylmethyl-2-methyl-1H-pyrrolo[3,2-c]pyridin-4-yloxy)-acetic acid ethyl ester 7. To a stirred solution of (1-biphenyl-2-ylmethyl-2-methyl-1H-pyrrolo[3,2-c]pyridin-4-yloxy)-acetic acid ethyl ester 6 (100 mg, 0.250 mmol) in CH$_2$Cl$_2$ (10 mL), (COCl)$_2$ (80 μL, 0.91 mmol), followed by pyridine (40 μL) was added dropwise, and then the reaction mixture was stirred at room temperature for 16 h, treated with NH$_3$ (g) for 30 min and stirred for another 1 h. The obtained mixture was diluted with EtOAc (40 mL), washed with water (20 mL), brine (20 mL), dried over Na$_2$SO$_4$ and evaporated. Flash chromatography of the residue over silica gel, using 50% hexanes in EtOAc to 25% hexanes in EtOAc) gave product 7 as a yellow solid. Yield: 30 mg (25%).

(3-Aminooxalyl-1-biphenyl-2-ylmethyl-2-methyl-1H-pyrrolo[3,2-c]pyridin-4-yloxy)-acetic acid Ily-II-4. To a stirred solution of (3-Aminooxalyl-1-biphenyl-2-ylmethyl-2-methyl-1H-pyrrolo[3,2-c]pyridin-4-yloxy)-acetic acid ethyl ester (7) (30 mg, 0.064 mmol) in THF/EtOH/H$_2$O (2 mL/2 mL/2 mL), LiOH (16 mg, 0.67 mmol) was added. The reaction mixture was stirred at room temperature for 2 h, evaporated and then acidified (pH=4) with 1 N HCl to form a precipitate, which was filtered off, washed with water and dried in vacuum to afford product Ily-II-4 as a yellow solid. Yield: 12 mg (43%). $^1$H NMR: 05-056-043 (DMSO-d$_6$, 400 MHz) δ 2.32 (s, 3 H), 4.78 (s, 2 H), 5.39 (s, 2 H), 6.42 (d, 1 H), 7.04 (d, 1 H), 7.20-7.60 (m, 9 H), 7.74 (d, 1 H), 7.88 (s, 1 H), 12.6 (s, 1 H). MS: 444.02 (M+H).

Example 12.5

Compound (2-8)

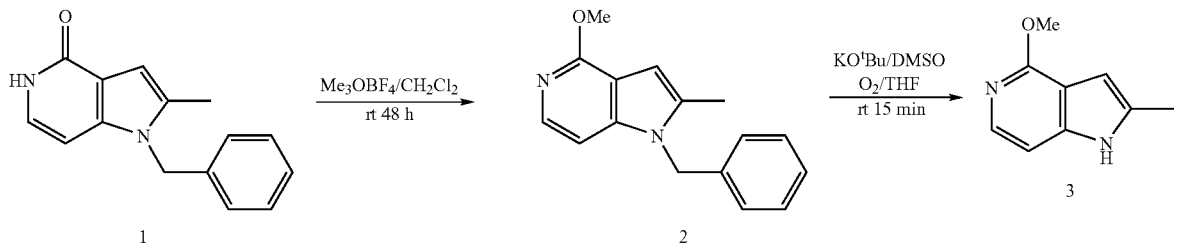

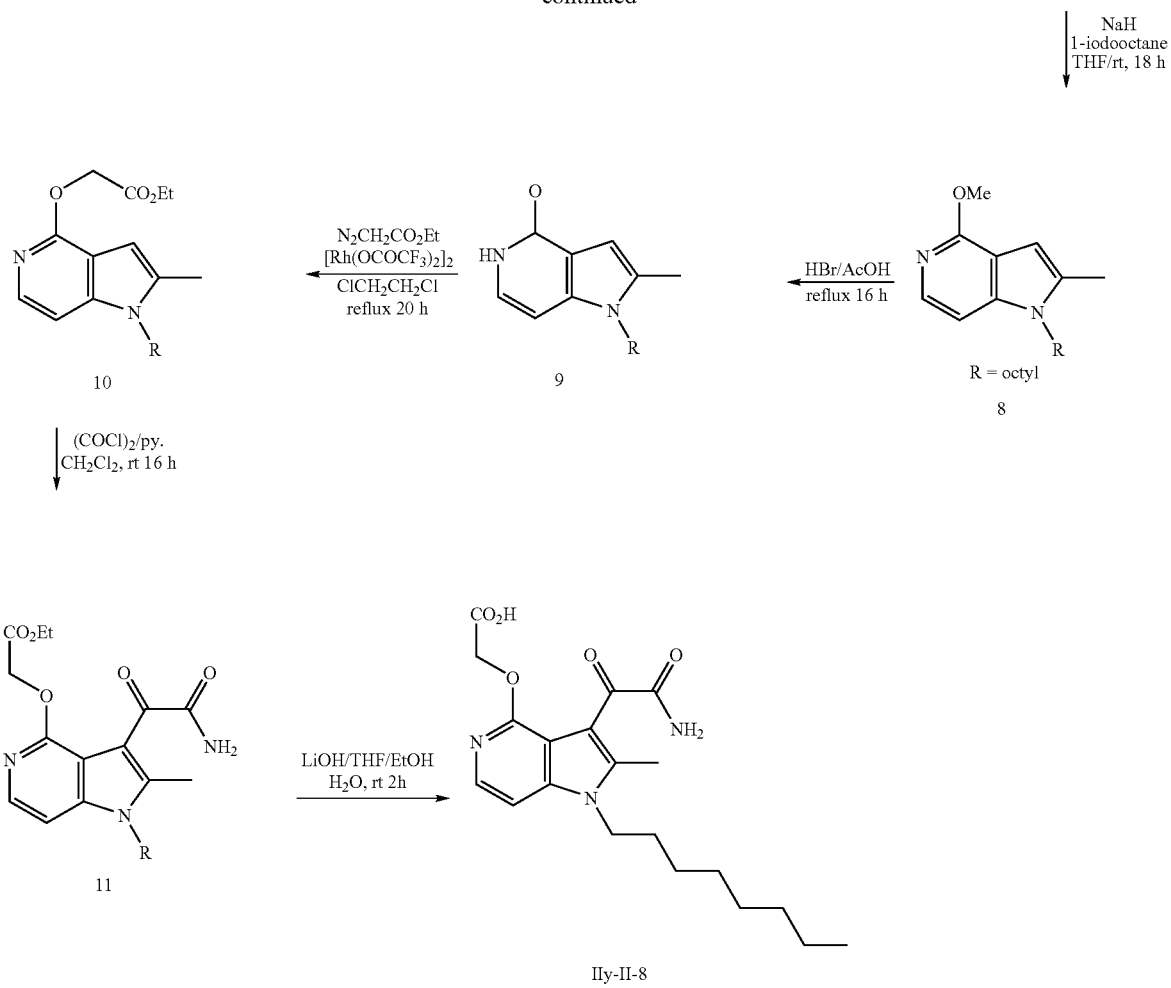

(1-Benzyl-4-methoxy-2-methyl-1H-pyrrolo[3,2-c]pyridine 2. To a stirred suspension of 1-benzyl-2-methyl-1,5-dihydro-pyrrolo[3,2-c]pyridin-4-one 1 (2.0 g, 8.4 mmol) in $CH_2Cl_2$ (70 mL), $Me_3OBF_4$ (3.80 g, 25.6 mmol) was added and the reaction mixture was stirred for 48 h, then diluted with $CH_2Cl_2$ (70 mL). The mixture was washed with water (100 mL), brine (100 mL), dried over $Na_2SO_4$ and evaporated. Flash chromatography of the residue over silica gel, using 10% EtOAc in hexanes to 25% EtOAc in hexanes) gave product 2 as a pale yellow solid. Yield: 1.6 g (75%).

4-Methoxy-2-methyl-1H-pyrrolo[3,2-c]pyridine 3. To a stirred solution of (1-benzyl-4-methoxy-2-methyl-1H-pyrrolo[3,2-c]pyridine 2 (0.887 mg, 3.52 mmol) in THF (10 mL), DMSO (2.5 mL), followed by KO$^t$Bu (25 mL, 1.0 M in THF) was added dropwise, and then the reaction mixture was treated with $O_2$ for 15 min at room temperature, quenched with saturated $NH_4Cl$ (20 mL), extracted with EtOAc (3×60 mL). The combined organic extracts were washed with water (50 mL), brine (50 mL), dried over $Na_2SO_4$ and evaporated. Flash chromatography of the residue over silica gel, using 20% EtOAc in hexanes to 40% EtOAc in hexanes) gave product 3 as a yellow solid. Yield: 560 mg (98%).

4-Methoxy-2-methyl-1-octyl-1H-pyrrolo[3,2-c]pyridine 8. To a stirred suspension of NaH (98 mg, 2.5 mmol, 60% in mineral oil) in THF (10 mL), 4-methoxy-2-methyl-1H-pyrrolo[3,2-c]pyridine 3 (280 mg, 1.72 mmol) in THF (3 mL) was added. The mixture was stirred at room temperature for 30 min, and then 1-iodooctane (0.41 mL, 2.2 mmol) was added, stirring was continued for 18 h. The reaction mixture was quenched with saturated $NH_4Cl$ (20 mL), extracted with EtOAc (3×40 mL). The combined organic extracts were washed with water (40 mL), brine (40 mL), dried over $Na_2SO_4$ and evaporated. Flash chromatography of the residue over silica gel, using 10% EtOAc in hexanes to 20% EtOAc in hexanes) gave product 8 as a yellow oil. Yield: 231 mg (49%).

2-Methyl-1-octyl-1,5-dihydro-pyrrolo[3,2-c]pyridin-4-one 9. To a stirred solution of 4-methoxy-2-methyl-1-octyl-1H-pyrrolo[3,2-c]pyridine 8 (0.22 g, 0.80 mmol) in AcOH (10 mL), 48% of HBr (5 mL) was added. The reaction mixture was heated to 105° C., and then stirred for 16 h, cooled to room temperature and evaporated. The obtained residue was dissolved in $CH_2Cl_2$ (80 mL), washed with saturated $NaHCO_3$ (30 mL), brine (30 mL), dried over $Na_2SO_4$ and evaporated to afford crude product 9, which was used without further purification for next step. Yield: 207 mg (100%).

(2-Methyl-1-octyl-1H-pyrrolo[3,2-c]pyridin-4-yloxy)-acetic acid ethyl ester 10. To a stirred solution of 2-methyl-1-octyl-1,5-dihydro-pyrrolo[3,2-c]pyridin-4-one 9 (0.207 g, 0.800 mmol) in $ClCH_2CH_2Cl$ (40 mL), [Rh(OCOCF$_3$)$_2$]$_2$ (30 mg, 0.046 mmol) was added, and then a solution of N₂CH₂CO₂Et (0.10 mL. 0.96 mmol) in ClCH₂CH₂Cl (8 mL) was added over 16 h via a syringe pump. The reaction mixture was cooled to room temperature and evaporated. Flash chromatography of the residue over silica gel, using 10% EtOAc in hexanes to 25% EtOAc in hexanes) gave product 10 as a yellow oil. Yield: 70 mg (25%).

(3-Aminooxalyl-2-methyl-1-octyl-1H-pyrrolo[3,2-c]pyridin-4-yloxy)-acetic acid ethyl ester 11. To a stirred solution of (2-methyl-1-octyl-1H-pyrrolo[3,2-c]pyridin-4-yloxy)-acetic acid ethyl ester 10 (68 mg, 0.20 mmol) in CH₂Cl₂ (10 mL), (COCl)₂ (60 μL, 0.68 mmol), followed by pyridine (30 μL) was added dropwise, and then the reaction mixture was stirred at room temperature for 16 h, treated with NH₃ (g) for 30 min and stirred for another 1 h. The precipitated mixture was diluted with EtOAc (40 mL), washed with water (20 mL), brine (20 mL), dried over Na₂SO₄ and evaporated. Flash chromatography of the residue over silica gel, using 50% hexanes in EtOAc to 25% hexanes in EtOAc) gave product 11 as a yellow solid. Yield: 45 mg (55%).

(3-Aminooxalyl-2-methyl-1-octyl-1H-pyrrolo[3,2-c]pyridin-4-yloxy)-acetic acid (Ily-II-8). To a stirred solution of (3-aminooxalyl-2-methyl-1-octyl-1H-pyrrolo[3,2-c]pyridin-4-yloxy)-acetic acid ethyl ester 11 (42 mg, 0.10 mmol) in THF/EtOH/H₂O (3 mL/3 mL/3 mL), LiOH (17 mg, 0.70 mmol) was added. The reaction mixture was stirred at room temperature for 2 h, evaporated and then acidified (pH=4) with 1 N HCl to form a precipitate, which was filtered off, washed with water and dried in vacuum to afford product Ily-II-8 as a yellow solid. Yield: 30 mg (77%).

¹H NMR: 05-056-041 (DMSO-d₆, 400 MHz) δ 0.85 (t, 3 H), 1.20-1.40 (m, 10 H), 1.55-1.75 (m, 2 H), 2.58 (s, 3 H), 4.20 (t, 2 H), 4.78 (s, 2 H), 7.24 (d, 1 H), 7.49 (s, 1 H), 7.78 (d, 1 H), 7.87 (s, 1 H), 12.7 (s, 1 H). MS: 390.04 (M+H).

Example 12.6

Compound (2-11)

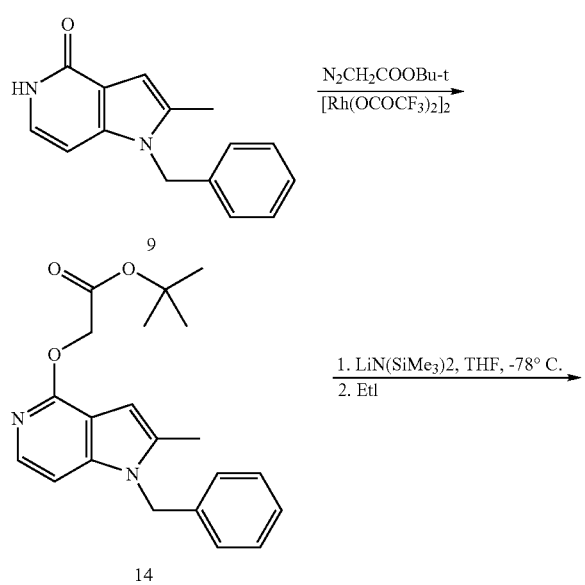

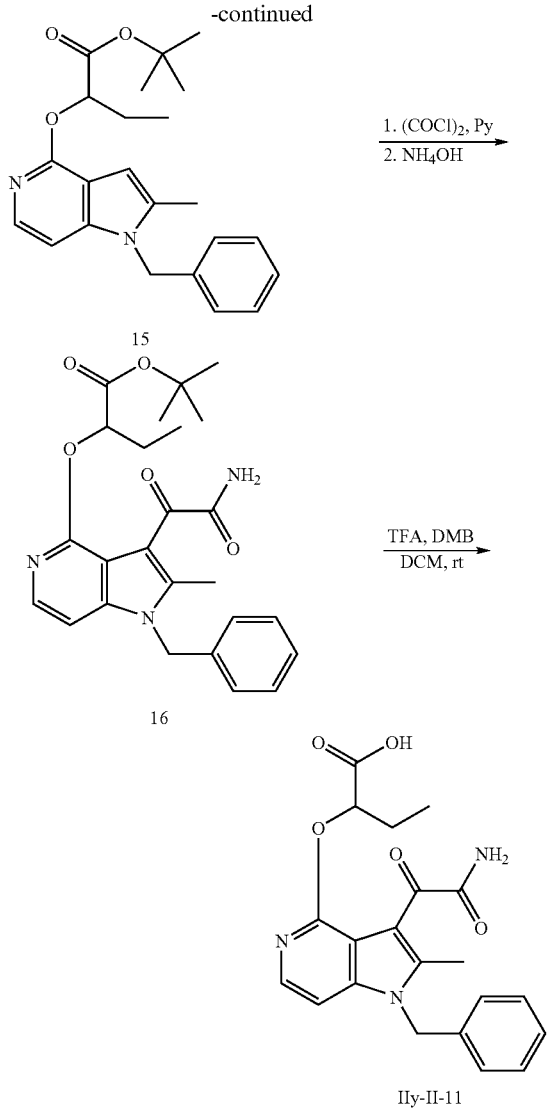

(1-Benzyl-2-methyl-1H-pyrrolo[3,2-c]pyridin-4-yloxy)-acetic acid tert-butyl ester, 14: 1-Benzyl-2-methyl-1,5-dihydro-pyrrolo[3,2-c]pyridin-4-one, 9 (1.0 g, 4.20 mmol) was dissolved in a dry dichloroethane (500 mL). To the mixture Rh₂(OCOCF₃)₄ (132 mg, 0.202 mmol) was added. The reaction mixture was heated to reflux and then to the reaction mixture a solution of tert-butyl diazoacetate (0.65 mL, 4.20 mmol) in dry dichloroethane (50 mL) was added dropwise over 16 h under refluxing. After addition the reaction mixture was stirred for 1 h under refluxing. Then the reaction mixture was cooled to room temperature. The mixture was concentrated and the residue was purified by silica gel chromatography (hexane to hexane:ethyl acetate, 3:1) to afford (1-benzyl-2-methyl-1H-pyrrolo[3,2-c]pyridin-4-yloxy)-acetic acid tert-butyl ester, 14 Yield: 700 mg, (51%)

2-(1-Benzyl-2-methyl-1H-pyrrolo[3,2-c]pyridin-4-yloxy)-butyric acid tert-butyl ester, 15: (1-Benzyl-2-methyl-1H-pyrrolo[3,2-c]pyridin-4-yloxy)-acetic acid tert-butyl ester, 14 (200 mg, 0.568 mmol) was dissolved in a dry tetrahydrofuran (10 mL) and then cooled to −78° C. To the mixture the tetrahydrofuran solution (1.0 M) of LiN(Si(CH₃)₃)₂ (1.70 mL) was added dropwise at −78° C. The reaction mixture was stirred from −78° C. to −5° C. for 1 h and then the tetrahydrofuran solution (5 mL) of iodoethane (0.15 mL, 1.84 mmol) was added dropwise at −50° C. The mixture was stirred for 4 h from −50° C. to room temperature. The mixture was concentrated and the residue was purified by silica gel chromatography (hexane to hexane:ethyl acetate, 4:1) to afford 2-(1-benzyl-2-methyl-1H-pyrrolo[3,2-c]pyridin-4-yloxy)-butyric acid tert-butyl ester, 15 Yield: 50 mg, (23%)

2-(3-Aminooxalyl-1-benzyl-2-methyl-1H-pyrrolo[3,2-c]pyridin-4-yloxy)-butyric acid tert-butyl ester, 16: 2-(1-benzyl-2-methyl-1H-pyrrolo[3,2-c]pyridin-4-yloxy)-butyric acid tert-butyl ester, 15 (134 mg, 0.352 mmol) was dissolved in a dry chloroform (10 mL). To the mixture the solution of oxalyl chloride (0.10 mL, 1.13 mmol) in chloroform (5 mL) was added dropwise at room temperature. Then pyridine (0.05 mL) was added slowly to the mixture at room temperature. After addition the mixture was stirred at room temperature for 18 h. The mixture was poured into icy 20% NH$_4$OH solution (100 mL) and stirred for 1 h. The mixture was diluted with dichloromethane (20 mL). The organic layer was separated and aqueous layer was extracted with dichloromethane (2×20 mL). The organic layers were combined and dried over anhydrous MgSO$_4$. The mixture was filtered. The filtrate was concentrated and the residue was purified by silica gel chromatography (hexan to hexane:ethyl acetate, gradient 1:1) to afford 2-(3-aminooxalyl-1-benzyl-2-methyl-1H-pyrrolo[3,2-c]pyridin-4-yloxy)-butyric acid tert-butyl ester, 16 as a yellow solid. Yield: 62 mg, (39%)

2-(3-Aminooxalyl-1-benzyl-2-methyl-1H-pyrrolo[3,2-c]pyridin-4-yloxy)-butyric acid, Ily-II-11: 2-(3-aminooxalyl-1-benzyl-2-methyl-1H-pyrrolo[3,2-c]pyridin-4-yloxy)-butyric acid tert-butyl ester, 16 (26 mg, 0.0576 mmol) was dissolved in dichloromethane (2 mL). To the mixture 1,3-dimethoxybenzene (0.023 mL, 0.172 mmol) was added at room temperature. The mixture was cooled to 0° C. for 30 min. To the mixture trifluoroacetic acid (0.015 mL, 0.234 mmol) was added at 0° C. After addition the mixture was stirred at 0° C. for 1 h. Then mixture was warmed up to room temperature and stirred for 2 h at room temperature. Then more trifluoroacetic acid (0.1 mL) was added and the mixture was stirred at room temperature for 18 h. The mixture was concentrated and H-NMR indicated the reaction was not completed. The residue was redissolved in dichloromethane (5 mL) and then trifluoroacetic acid (0.5 mL) was added at room temperature. The mixture was stirred at room temperature for 6 h. The mixture was concentrated and the residue was purified by silica gel preparative thin layer chromatography (hexane:ethyl acetate, 1:1) to afford 2-(3-aminooxalyl-1-benzyl-2-methyl-1H-pyrrolo[3,2-c]pyridin-4-yloxy)-butyric acid, Ily-II-11 as a light yellow solid. Yield: 11 mg, (48%)

$^1$H NMR: 05-43-128-2, (400 MHz, DMSO-d6) δ, 8.09 (br, s, 1H, NH), 7.72 (d, 1H), 7.54 (br, s, 1H, NH), 7.20-7.38 (m, 3H), 7.18 (d, 1H), 7.08 (d, 2H), 5.50 (br, s, 2H, PhCH$_2$N), 5.02 (t, 1H, CHOAr), 2.41 (br, s, 3H, Me), 1.92 (q, 2H, Et), 1.02 (t, 3 H, Et), ppm. MS (ES): 395.98 [M+1].

Example 12.7

Compound (2-9)

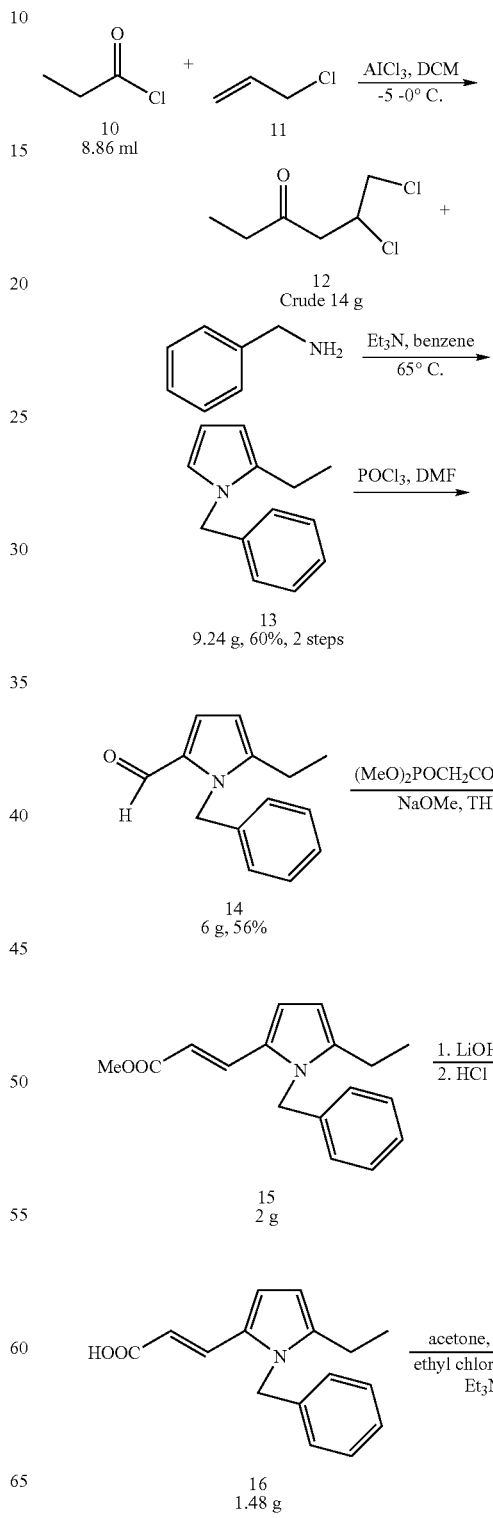

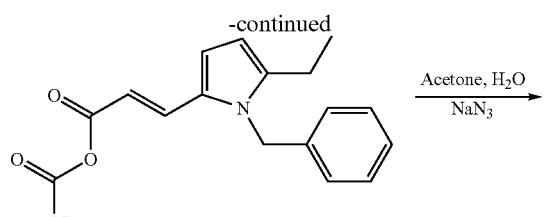

17

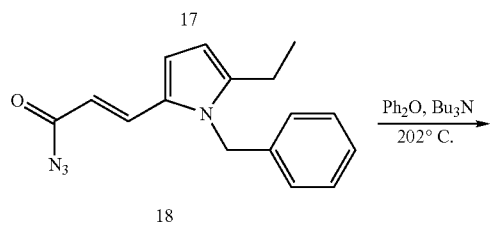

18

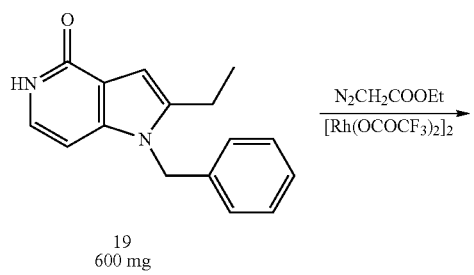

19
600 mg

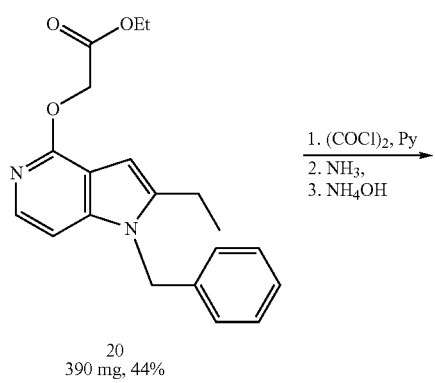

20
390 mg, 44%

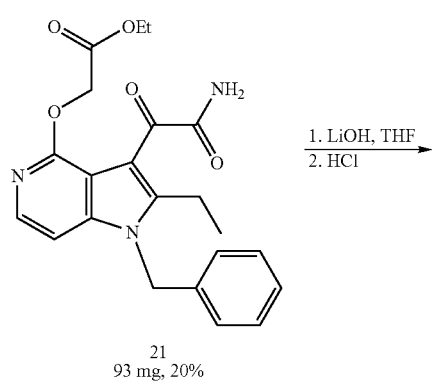

21
93 mg, 20%

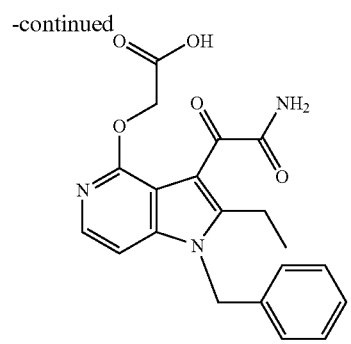

IIy-II-9

2-(3-(2-amino-2-oxoacetyl)-1-benzyl-2-ethyl-1H-pyrrolo[3,2-c]pyridin-4-yloxy)acetic acid (ILY-II-9)

5,6-dichlorohexan-3-one, 12 To a solution of propionyl chloride (8.86 mL, 102 mmol) and ally chloride (115 mmol) in dichloromethane (500 mL) at −5° C. aluminum chloride (115 mmol) was added. The resulted solution was stirred for 5 hr, then was allowed to warmed up to 0° C. After evaporating solvent the residue was extracted by ether (3×150 mL). The combined extracts was washed with water (2×200 mL), followed by removing solvent and drying to give 14 g of crude 12.

1-benzyl-2-ethyl-1H-pyrrole, 13: To the crude 12 (14 g, 83 mmol) in dry benzene (200 mL) at room temperature was added benzylamine solution (12.5 mL, 100 mmol) and triethylamine (11 g, 110 mmol). The solution was heated to reach 65° C. and stirred for 18 h. The resulted reaction mixture was filtered and concentrated. The crude product was purified by silica gel chromatography to afford 1-benzyl-2-ethyl-1H-pyrrole 13 (9.24 g (50 mmol), 60% for two step).

1-benzyl-5-ethyl-1H-pyrrole-2-carbaldehyde, 14: $POCl_3$ (23.46 mL, 246 mmol) was added dropwise to a stirred N,N-dimethyformamide (204 mL) at 0° C. After addition the mixture was stirred for additional 90 minutes. To the mixture was added dropwise the solution of 1-benzyl-2-ethyl-1H-pyrrole, 13 (8.33 g, 45 mmol) in tetrahydrofuran (1150 mL). The reaction mixture was allowed to be stirred for 18 h from 0° C. to room temperature. The mixture was concentrated and redissolved in ethyl acetate (2 L). The mixture was washed with saturated $Na_2CO_3$ (2×500 mL). The $Na_2CO_3$ solution was extracted with ethyl acetate (7×1 L). The organic layers were combined and concentrated. The crude product was purified by silica gel chromatography (hexane to hexane:ethyl acetate, 7:1) to afford 1-benzyl-5-ethyl-1H-pyrrole-2-carbaldehyde, 14 Yield: 6 g (56%).

(E)-methyl 3-(1-benzyl-5-ethyl-1H-pyrrol-2-yl)acrylate, 15: Sodium (0.75 g, 32 mmol) was added in portions to a dry methanol (30 mL). To the fresh formed sodium methoxide solution was added dropwise the solution of trimethyl phosphonoacetate (2.6 mL, 15.2 mmol) in tetrahydrofuran (7 mL) at room temperature. After addition the mixture was stirred for additional 60 min at room temperature. Then to the reaction mixture was added dropwise the solution of 1-benzyl-5-ethyl-1H-pyrrole-2-carbaldehyde, 14 (2 g) in tetrahydrofuran (50 mL) at room temperature. The reaction mixture was stirred for 2 h at room temperature. The mixture was concentrated and redissolved in ethyl acetate (200 L). The mixture was washed with 1 M HCl solution, then saturated $NaHCO_3$, $H_2O$. The organic solution were dried over $MgSO_4$ and then filtered, concentrated to afford the crude product, (E)-methyl 3-(1-benzyl-5-ethyl-1H-pyrrol-2-yl)acrylate, 15.Yield: 2 g (E)-3-(1-benzyl-5-ethyl-1H-pyrrol-2-yl)acrylic acid, 16: (E)-methyl 3-(1-benzyl-5-ethyl-1H-pyrrol-2-yl)acrylate, 15 (2 g) was dissolved in a mixture of tetrahydrofuran (40 mL) and methanol (40 mL). To the mixture a solution of lithium hydroxide monohydrate (1 g, 25 mmol) in H₂O (20 mL) was added. After addition the reaction mixture was stirred for 18 h at room temperature. The reaction mixture was acidified by 2M HCl to pH=4-5. The mixture was concentrated and redissolved in ethyl acetate. The mixture was washed with H₂O. The water layer was extracted with ethyl acetate (2×250 mL). The organic was combined and concentrated to afford a yellow solid which was washed with dichloromethane, followed by purification on silica gel chromatography (hexane to hexane:ethyl acetate, 1:3, followed by neat ethyl acetate) to afford (E)-3-(1-benzyl-5-ethyl-1H-pyrrol-2-yl)acrylic acid, 16 (1.48 g).

1-benzyl-2-ethyl-1H-pyrrolo[3,2-c]pyridin-4(5H)-one, 19: 3(E)-3-(1-benzyl-5-ethyl-1H-pyrrol-2-yl)acrylic acid, 16 (1.48 g, 5.8 mmol) was dissolved in a dry acetone (70 mL). To the suspension mixture triethylamine (1.9 mL) was added to form a clear solution. The reaction mixture was cooled to 0° C. and then to the cooled reaction mixture a solution of ethyl chlorofomate (16 mmol) in dry acetone (65 mL) was added dropwise over 1 hour. After addition the reaction mixture was stirred for 4 h at 0° C. Then to the reaction mixture was added dropwise the solution of sodium azide (770 mg, 11.7 mmol) in H₂O (17 mL) over 30 minutes. The reaction mixture was stirred at 0° C. for 2 h. The reaction mixture was poured into ice-water (500 mL). Then the mixture was extracted with dichloromethane (3×250 mL). The organic layers were combined and dried over MgSO₄. The mixture was filtered and concentrated to afford a crude 18. To the mixture of diphenyl ether (17 mL) and tributylamine (1.65 mL) which was preheated to 205° C. was added dropwise the solution of crude 18 in diphenyl ether (25 mL) at 205° C. for 1 hour. After addition the mixture was stirred for another hour at 205° C. The mixture was cooled to room temperature and solid was formed. Diethyl ether (50 mL) was added into the reaction mixture to form more solid. The mixture was filtered and the solid was washed with diethyl ether to afford the product. The filtrate was concentrated and the residue was purified by silica gel chromatography to afford 1-benzyl-2-ethyl-1H-pyrrolo[3,2-c]pyridin-4(5H)-one, 19 (600 mg).

ethyl 2-(1-benzyl-2-ethyl-1H-pyrrolo[3,2-c]pyridin-4-yloxy)acetate, 20: 1-benzyl-2-ethyl-1H-pyrrolo[3,2-c]pyridin-4(5H)-one, 19 (600 mg, 2.38 mmol) was dissolved in a dry dichloroethane (300 mL). To the mixture Rh₂(OCOCF₃)₄ (71 mg, 0.103 mmol) was added. The reaction mixture was heated to reflux and then to the reaction mixture a solution of ethyl diazoacetate (2.37 mmol) in dry dichloroethane (30 mL) was added dropwise over 6 h under refluxing. After addition the reaction mixture was stirred for 1.5 h under refluxing. Then the reaction mixture was cooled to room temperature. The mixture was concentrated and the residue was purified by silica gel chromatography to afford ethyl 2-(1-benzyl-2-ethyl-1H-pyrrolo[3,2-c]pyridin-4-yloxy)acetate, 20. Yield: 390 mg, (44%)

ethyl 2-(3-(2-amino-2-oxoacetyl)-1-benzyl-2-ethyl-1H-pyrrolo[3,2-c]pyridin-4-yloxy)acetate, 21: ethyl 2-(1-benzyl-2-ethyl-1H-pyrrolo[3,2-c]pyridin-4-yloxy)acetate, 20 (390 mg, 1.15 mmol) was dissolved in a dry chloroform (37 mL). To the mixture the solution of oxalyl chloride (0.30 mL, 3.45 mmol) in chloroform (10 mL) was added dropwise at room temperature. Then pyridine (0.140 mL) was added slowly to the mixture at room temperature. After addition the mixture was stirred at room temperature for 18 h. The mixture was concentrated and the residue was purified by silica gel chromatography to afford ethyl 2-(3-(2-amino-2-oxoacetyl)-1-benzyl-2-ethyl-1H-pyrrolo[3,2-c]pyridin-4-yloxy)acetate, 21 Yield: 93 mg, (20%)

2-(3-(2-amino-2-oxoacetyl)-1-benzyl-2-ethyl-1H-pyrrolo[3,2-c]pyridin-4-yloxy)acetic acid, Ily-II-9: ethyl 2-(3-(2-amino-2-oxoacetyl)-1-benzyl-2-ethyl-1H-pyrrolo[3,2-c]pyridin-4-yloxy)acetate, 21 (93 mg, 0.227 mmol) is dissolved in methanol (20 mL). To the mixture the solution of KOH (1M, 0.25 mL) is added at room temperature. After addition the mixture was stirred at room temperature for 18 h. Then solution of lithium hydroxide monohydrate (90 mg) in H₂O (5 mL) is added. After another hour stirring the mixture was concentrated and the residue is redissolved in methanol (10 mL) and ethanol (10 mL). The mixture is filtered and the filtrate was acidified by hydrogen chloride in ether (1.0 M) to pH=3-4. Solvent is evaporated and the residue is washed with a mixture of dichloromethane: ether (1:1), then water (5 mL) and ether to afford 2-(3-(2-amino-2-oxoacetyl)-1-benzyl-2-ethyl-1H-pyrrolo[3,2-c]pyridin-4-yloxy)acetic acid, Ily-II-9.

Example 12.8

Compound (2-10)

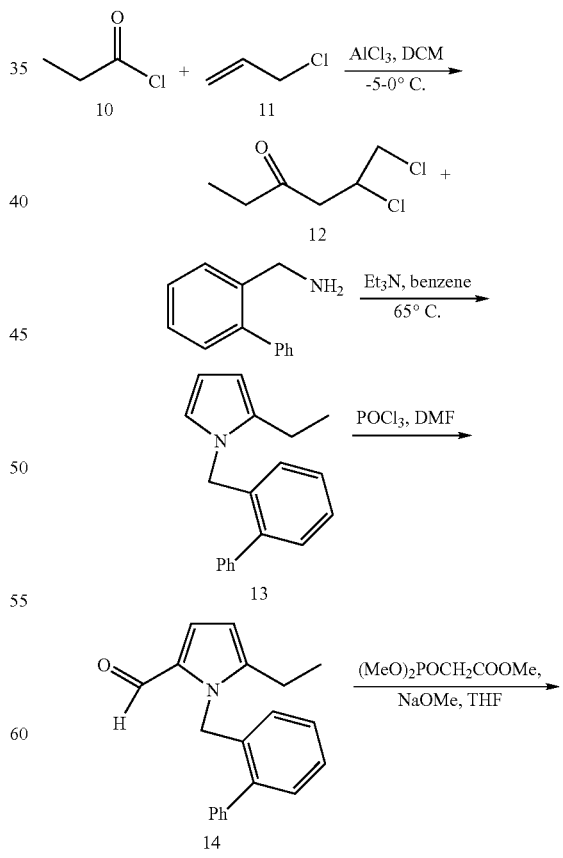

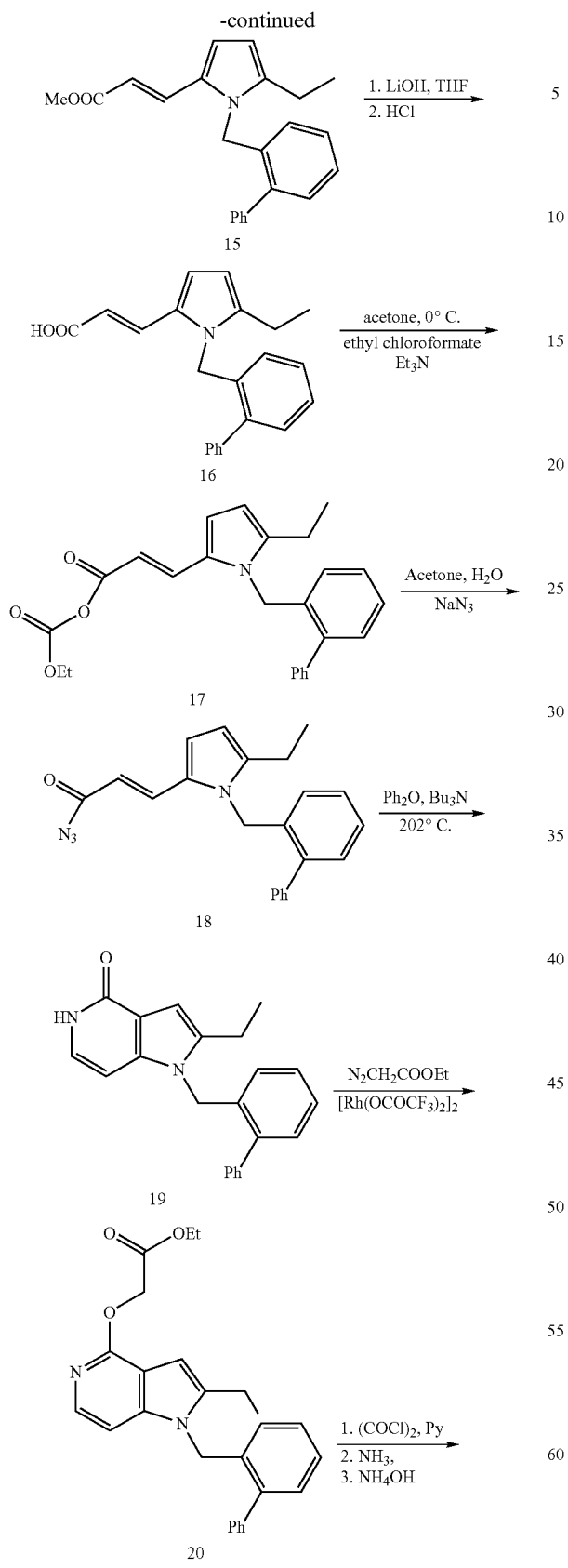
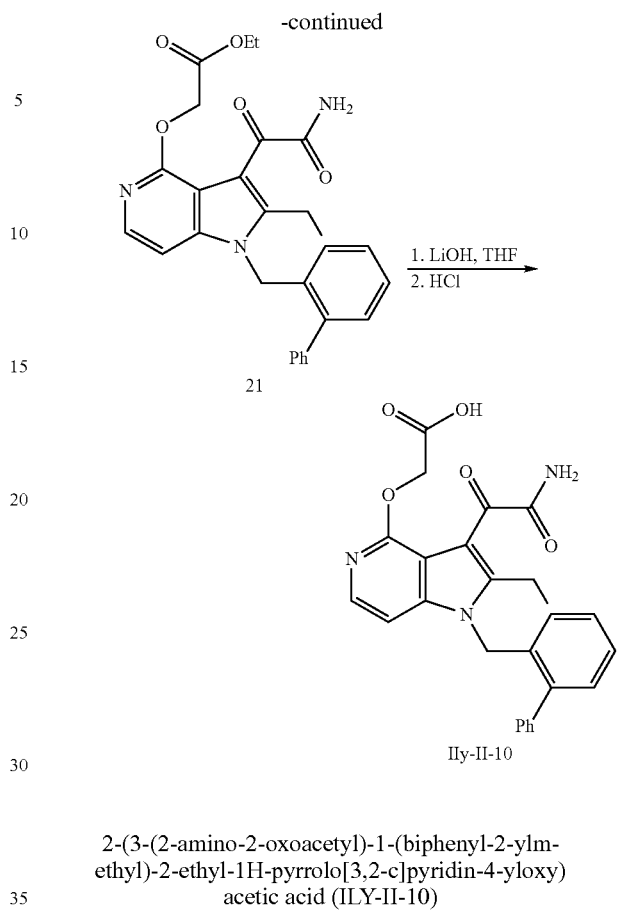

2-(3-(2-amino-2-oxoacetyl)-1-(biphenyl-2-ylmethyl)-2-ethyl-1H-pyrrolo[3,2-c]pyridin-4-yloxy) acetic acid (ILY-II-10)

5,6-dichlorohexan-3-one, 12 To a solution of propionyl chloride (8.86 mL, 102 mmol) and ally chloride (115 mmol) in dichloromethane (500 mL) at −5° C. aluminum chloride (115 mmol) was added. The resulted solution was stirred for 5 hr, then was allowed to warmed up to 0° C. After evaporating solvent the residue was extracted by ether (3×150 mL). The combined extracts was washed with water (2×200 mL), followed by removing solvent and drying to give 14 g of crude 12.

1-(biphenyl-2-ylmethyl)-2-ethyl-1H-pyrrole, 13: To the crude 12 (14 g, 83 mmol) in dry benzene (200 mL) at room temperature is added biphenyl-2-ylmethanamine solution (100 mmol) and triethylamine (110 mmol). The solution is heated to reach 65° C. and stirred for 18 h. The resulted reaction mixture is filtered and concentrated. The crude product was purified by silica gel chromatography to afford 13

1-(biphenyl-2-ylmethyl)-5-ethyl-1H-pyrrole-2-carbaldehyde, 14: POCl$_3$ (23.46 mL, 246 mmol) is added dropwise to a stirred N,N-dimethyformamide (204 mL) at 0° C. After addition the mixture is stirred for additional 90 minutes. To the mixture is added dropwise the solution of 13 (45 mmol) in tetrahydrofuran (1150 mL). The reaction mixture was allowed to be stirred for 18 h from 0° C. to room temperature. The mixture was concentrated and redissolved in ethyl acetate (2 L). The mixture was washed with saturated Na$_2$CO$_3$ (2×500 mL). The Na$_2$CO$_3$ solution was extracted with ethyl acetate (7×1 L). The organic layers were combined and concentrated. The crude product was purified by silica gel chromatography to afford 14.

(E)-methyl 3-(1-(biphenyl-2-ylmethyl)-5-ethyl-1H-pyrrol-2-yl)acrylate, 15: Sodium (0.75 g, 32 mmol) is added in portions to a dry methanol (30 mL). To the fresh formed sodium methoxide solution is added dropwise the solution of trimethyl phosphonoacetate (2.6 mL, 15.2 mmol) in tetrahydrofuran (7 mL) at room temperature. After addition the mixture is stirred for additional 60 min at room temperature. Then to the reaction mixture is added dropwise the solution of 14 (2 g) in tetrahydrofuran (50 mL) at room temperature. The reaction mixture is stirred for 2 h at room temperature. The mixture is concentrated and redissolved in ethyl acetate (200 mL). The mixture is washed with 1 M HCl solution, then saturated NaHCO$_3$, H$_2$O. The organic solution is dried over MgSO$_4$ and then filtered, concentrated to afford the crude product 15.

(E)-3-(1-(biphenyl-2-ylmethyl)-5-ethyl-1H-pyrrol-2-yl)acrylic acid, 16: Compound 15 (2 g) is dissolved in a mixture of tetrahydrofuran (40 mL) and methanol (40 mL). To the mixture a solution of lithium hydroxide monohydrate (1 g, 25 mmol) in H$_2$O (20 mL) is added. After addition the reaction mixture is stirred for 18 h at room temperature. The reaction mixture is acidified by 2M HCl to pH=4-5. The mixture is concentrated and redissolved in ethyl acetate. The mixture is washed with H$_2$O. The water layer is extracted with ethyl acetate (2×250 mL). The organic is combined and concentrated to afford a yellow solid which is washed with dichloromethane, followed by purification on silica gel chromatography to afford 16.

1-(biphenyl-2-ylmethyl)-2-ethyl-1H-pyrrolo[3,2-c]pyridin-4(5H)-one, 19: Compound 16 (5.8 mmol) is dissolved in a dry acetone (70 mL). To the suspension mixture triethylamine (1.9 mL) is added to form a clear solution. The reaction mixture is cooled to 0° C. and then to the cooled reaction mixture a solution of ethyl chlorofomate (16 mmol) in dry acetone (65 mL) is added dropwise over 1 hour. After addition the reaction mixture is stirred for 4 h at 0° C. Then to the reaction mixture is added dropwise the solution of sodium azide (770 mg, 11.7 mmol) in H$_2$O (17 mL) over 30 minutes. The reaction mixture is stirred at 0° C. for 2 h. The reaction mixture is poured into ice-water (500 mL). Then the mixture is extracted with dichloromethane (3×250 mL). The organic layers are combined and dried over MgSO$_4$. The mixture is filtered and concentrated to afford a crude 18. To the mixture of diphenyl ether (17 mL) and tributylamine (1.65 mL) which is preheated to 205° C. is added dropwise the solution of crude 18 in diphenyl ether (25 mL) at 205° C. for 1 hour. After addition the mixture is stirred for another hour at 205° C. The mixture is cooled to room temperature and solid is formed. Diethyl ether (50 mL) is added into the reaction mixture to form more solid. The mixture is filtered and the solid is washed with diethyl ether to afford the product. The filtrate is concentrated and the residue was purified by silica gel chromatography to afford 19.

ethyl 2-(1-(biphenyl-2-ylmethyl)-2-ethyl-1H-pyrrolo[3,2-c]pyridin-4-yloxy)acetate, 20: Compound 19 (2.38 mmol) is dissolved in a dry dichloroethane (300 mL). To the mixture Rh$_2$(OCOCF$_3$)$_4$ (71 mg, 0.103 mmol) is added. The reaction mixture is heated to reflux and then to the reaction mixture a solution of ethyl diazoacetate (2.37 mmol) in dry dichloroethane (30 mL) is added dropwise over 6 h under refluxing. After addition the reaction mixture is stirred for 1.5 h under refluxing. Then the reaction mixture is cooled to room temperature. The mixture is concentrated and the residue is purified by silica gel chromatography to afford 20.

ethyl 2-(3-(2-amino-2-oxoacetyl)-1-(biphenyl-2-ylmethyl)-2-ethyl-1H-pyrrolo[3,2-c]pyridin-4-yloxy)acetate, 21: Compound 20 (1.15 mmol) is dissolved in a dry chloroform (37 mL). To the mixture the solution of oxalyl chloride (0.30 mL, 3.45 mmol) in chloroform (10 mL) is added dropwise at room temperature. Then pyridine (0.140 mL) is added slowly to the mixture at room temperature. After addition the mixture is stirred at room temperature for 18 h. The mixture is concentrated and the residue is purified by silica gel chromatography to afford 21.

2-(3-(2-amino-2-oxoacetyl)-1-(biphenyl-2-ylmethyl)-2-ethyl-1H-pyrrolo[3,2-c]pyridin-4-yloxy)acetic acid, Ily-II-10: Compound 21 (0.227 mmol) is dissolved in methanol (20 mL). To the mixture the solution of KOH (1M, 0.25 mL) is added at room temperature. After addition the mixture was stirred at room temperature for 18 h. Then solution of lithium hydroxide monohydrate (90 mg) in H$_2$O (5 mL) is added. After another hour stirring the mixture was concentrated and the residue is redissolved in methanol (10 mL) and ethanol (10 mL). The mixture is filtered and the filtrate was acidified by hydrogen chloride in ether (1.0 M) to pH=3-4. Solvent is evaporated and the residue is washed with a mixture of dichloromethane: ether (1:1), then water (5 mL) and ether to afford 2-(3-(2-amino-2-oxoacetyl)-1-benzyl-2-ethyl-1H-pyrrolo[3,2-c]pyridin-4-yloxy)acetic acid, Ily-II-10.

Example 12.9a

Compound (2-12)

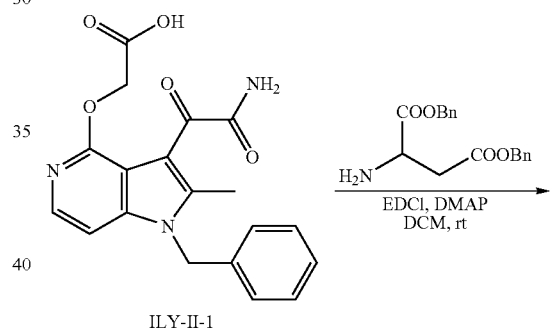

ILY-II-1

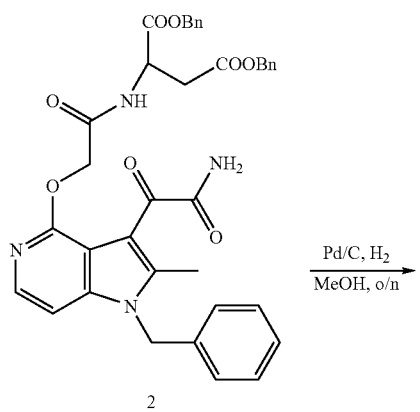

2

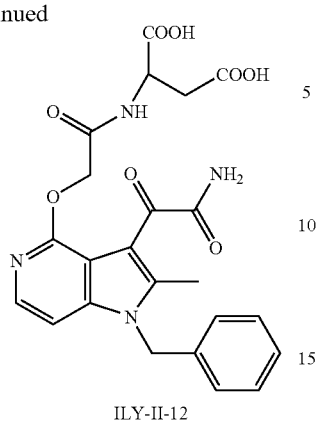

ILY-II-12

2-(2-(3-(2-amino-2-oxoacetyl)-1-benzyl-2-methyl-1H-pyrrolo[3,2-c]pyridin-4-yloxy)acetamido)succinic acid (ILY-II-12)

To a solution of 2-(3-(2-amino-2-oxoacetyl)-1-benzyl-2-methyl-1H-pyrrolo[3,2-c]pyridin-4-yloxy)acetic acid ILY-II-1 (1.5 mmol) in dichloromethane/dimethylformamide (5:1) is added aspartic acid dibenzyl ester (313 mg 1.5 mmol), 4-dimethylaminopyridine (18 mg 0.15 mmol), 1-hydroxybenzotriazole (202 mg, 1.5 mmol) and 1-(3-dimethylaminopropyl)-3-ethylcarbodiimide hydrochloride (286 mg, 1.5 mmol), respectively and reaction mixture allows to stir at room temperature. After 6 hrs the reaction is diluted with dichloromethane and washed twice with 1N HCl and brine. The organic layer is dried with Na$_2$SO$_4$ and evaporated in vacuum. The residue is chromatographed on silica gel to give the titled compound 2.

A solution of 2 (0.25 mmol) in ethanol 10 mL is stirred in hydrogen atmosphere using a balloon in the presence of Pd/C 50 mg. After stirring for 18 h the catalyst was filtered through celite and solvent is evaporated to give the target compound (2-(2-(3-(2-amino-2-oxoacetyl)-1-benzyl-2-methyl-1H-pyrrolo[3,2-c]pyridin-4-yloxy)acetamido)succinic acid) ILY-II-12.

Example 12.9b

Compound (2-12)

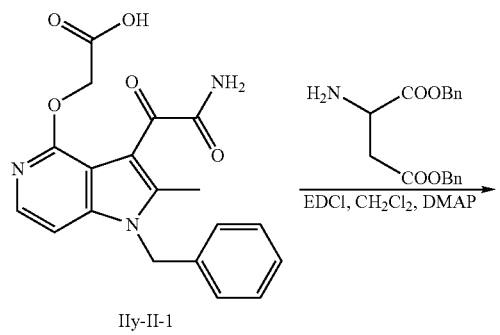

Ily-II-1

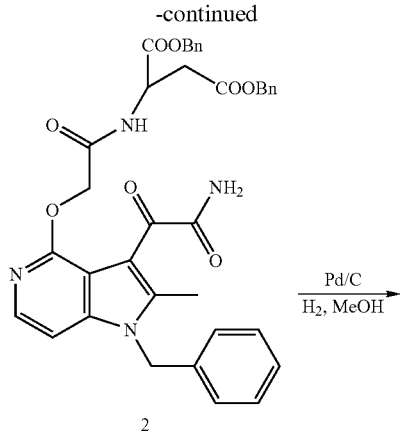

2

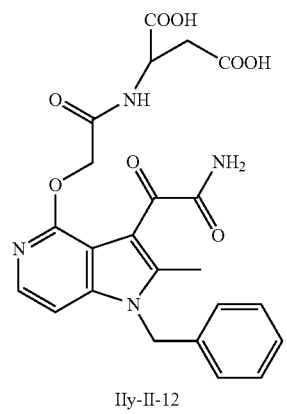

Ily-II-12

3-[2-(7-Aminooxalyl-5-benzyl-6-methyl-5H-[2]pyrindin-1-yloxy)-acetylamino]-pentanedioic acid dibenzyl ester (2)

To a mixture of Ily-II-1 (0.052 g, 0.177 mmole) in dichloromethane (10 mL) DMAP (0.045 g, 0.354 mmole), L-aspartic acid dibenzyl ester p-toluenesulfonate (0.173 g, 0.354 mmole), EDCI (0.068 g, 0.354 mmole) and HBTU (0.048 g, 0.354 mmole) were added. The mixture was stirred at room temperature for 18 h. The reaction mixture was diluted with dichloromethane (50 mL). The organic layer was washed with 1M HCl (50 mL), then water (50 mL). The organic layer was separated, dried over magnesium sulphate and concentrated. The residue was purified by column chromatography (4:1 EtOAc:Hexane) to afford intermediate (2) as a yellow solid. Yield: 0.03 g, 26%.

2-[2-(3-Aminooxalyl-1-benzyl-2-methyl-1H-pyrrolo[3,2-c]pyridin-4-yloxy)-acetylamino]-malonic acid (Ily-II-12): To a solution of intermediate (2) (0.040 g, 0.0604 mmole) in methanol (10 mL) Pd/C (10%, 0.015 g) was added. Hydrogen was passed through the mixture at 1 atm and room temperature for 1.5 h. The reaction mixture was filtered through Celite. The filtrate was concentrated to afford a white solid which was dissolved in methanol (10 mL) and passed through a PTFE filter. The filtrate was concentrated to afford Ily-II-12 as a yellow solid. Yield: 0.020 g, 68%. $^1$H NMR: 05-043-146-2 (DMSO-d$_6$, 400 MHz) δ, ppm: 8.15-8.05 (m, 2H), 7.22 (d, 1H), 7.35-7.22 (m, 4H), 7.07 (d, 2H), 5.58 (s, 2H), 5.20 (d, 1H), 4.80 (d, 1H), 4.30 (br, 1H), 2.55 (s, 3H). ES-MS: m/z=482.94 (M+1). Compound (2-12)

Example 12.10

Compound (2-13)

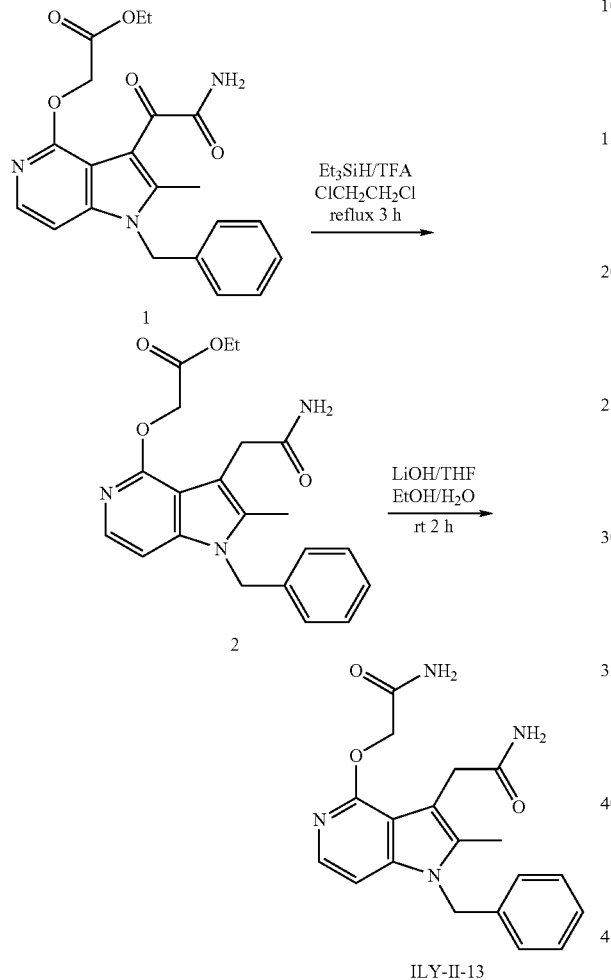

2-(4-(2-amino-2-oxoethoxy)-1-benzyl-2-m ethyl-1H-pyrrolo[3,2-c]pyridin-3-yl)acetamide (ILY-II-13)

To a stirred solution of ILY-II-1 ethyl ester 1 (0.22 mmol) in dichloroethane (7 mL), Et₃SiH (0.5 mL) and CF₃CO₂H (0.5 mL) are added. The mixture is heated to 85° C. and stirring is continued for 3 h. The reaction mixture is cooled to room temperature and evaporated. The obtained residue is diluted with EtOAc (50 mL), washed with cold saturated NaHCO₃ (20 mL), brine (20 mL), dried over Na₂SO₄ and evaporated to give crude product 2, which is used without further purification for the next step.

To a stirred solution of 1 (0.22 mmol) in THF/EtOH/H₂O (3 mL/3 mL/3 mL), LiOH (53 mg, 2.2 mmol) is added. The reaction mixture is stirred at room temperature for 2 h, evaporated and then acidified (pH=4) with 1 N HCl to form a precipitate, which is filtered off, washed with water and dried in vacuum to afford product Ily-II-13.

Example 12.11a

Compound (2-14)

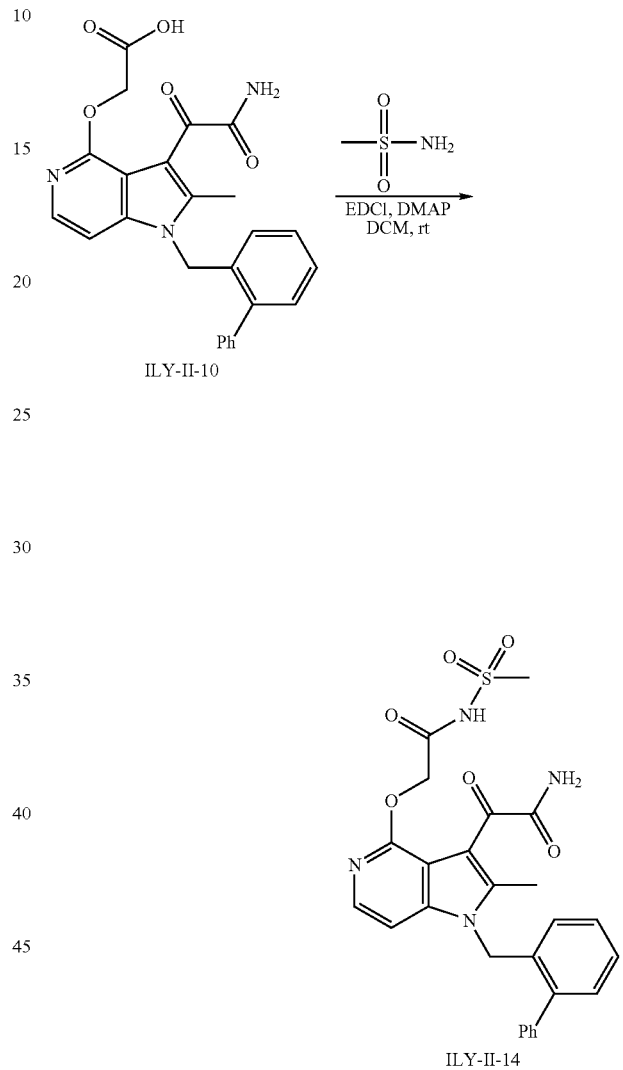

2-(3-(2-amino-2-oxoacetyl)-1-(biphenyl-2-ylmethyl)-2-methyl-1H-pyrrolo[3,2-c]pyridin-4-yloxy)-N-(methylsulfonyl)acetamide (ILY-II-14) To a solution of 2-(3-(2-amino-2-oxoacetyl)-1-(biphenyl-2-ylmethyl)-2-ethyl-1H-pyrrolo[3,2-c]pyridin-4-yloxy)acetic acid, Ily-II-10 (2.3 mmol) in dichloromethane/dimethylformamide mixture (4:1, 10 mL) is added 4-dimethylaminopyridine (3.4 mmol), methanesulfonamide (431 mg, 4.5 mmol) and 1-(3-dimethylaminopropyl)-3-ethylcarbodiimide hydrochloride (433 mg, 2.3 mmol) and the reaction mixture is stirred at room temperature. After 24 h the reaction mixture is diluted with dichloromethane and washed twice with 1N HCl and brine. The organic layer is dried with Na₂SO₄ and evaporated in vacuum. The residue is chromatographed on silica gel (CHCl₃ to 4% MeOH in CHCl₃) to give 2-(3-(2-amino-2-oxoacetyl)-1-(biphenyl-2-ylmethyl)-2-methyl-1H-pyrrolo[3,2-c]pyridin-4-yloxy)-N-(methylsulfonyl)acetamide (ILY-II-14).
Example 12.11b
Compound (2-14)
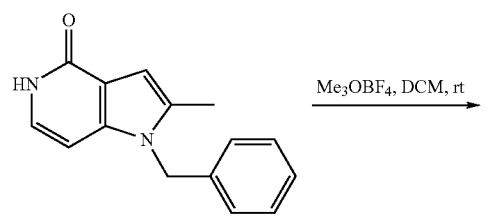
1
Me₃OBF₄, DCM, rt →
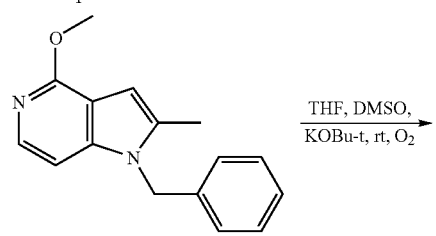
2
THF, DMSO,
KOBu-t, rt, O₂ →
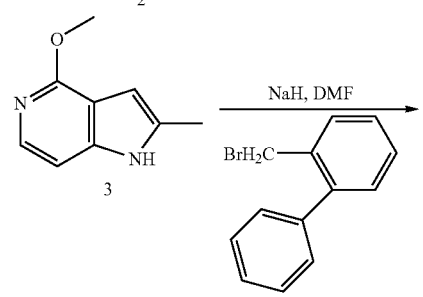
3
NaH, DMF
BrH₂C—(2-phenylphenyl) →
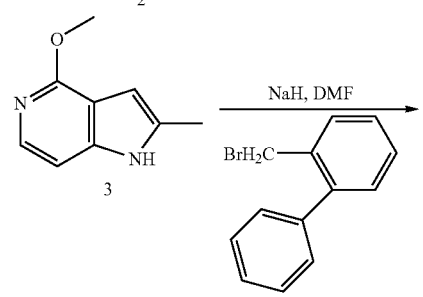
4
HOAc, HBr →
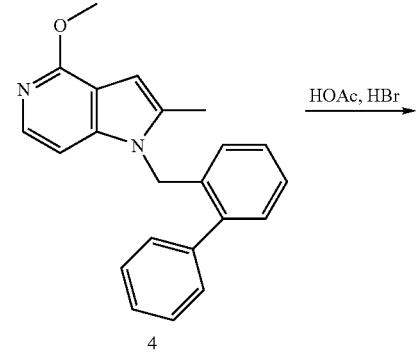
5
N₂CH₂COOEt
[Rh(OCOCF₃)₂]₂ →
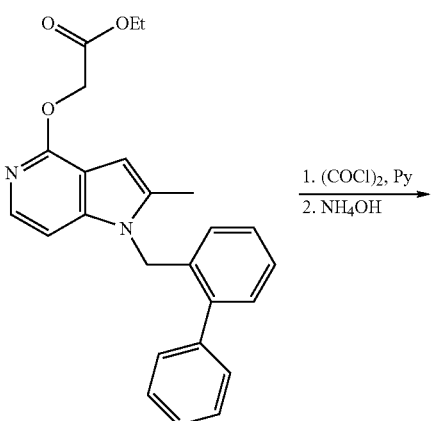
6
1. (COCl)₂, Py
2. NH₄OH →
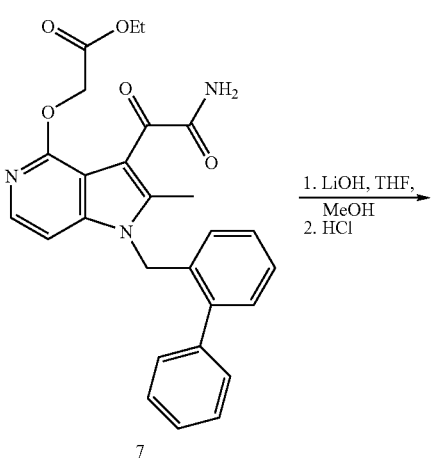
7
1. LiOH, THF,
MeOH
2. HCl →
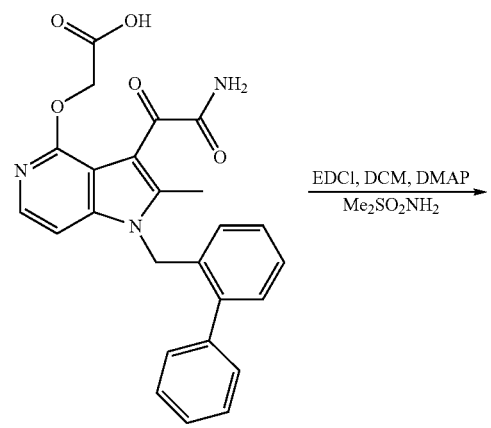
8
EDCl, DCM, DMAP
Me₂SO₂NH₂ →
-continued

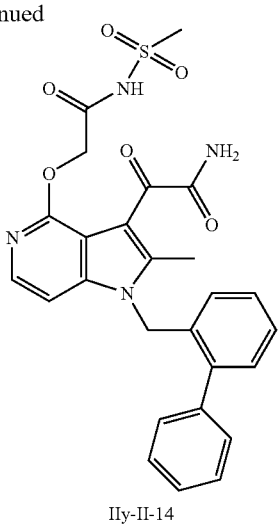

IIy-II-14

1-Benzyl-4-methoxy-2-methyl-1H-pyrrolo[3,2-c]pyridine (2): To a mixture of 1-benzyl-2-methyl-1,5-dihydropyrrolo[3,2-c]pyridin-4-one (1) (3.48 g, 16.62 mmole) in dichloromethane (160 mL) trimethyloxonium tetrafluoroborate (4.52 g, 29.24 mmole) was added. The mixture was stirred at room temperature for 18 h. Additional trimethyloxonium tetrafluoroborate (2.25 g, 14.55 mmole) was added and stirred for 18 h. The mixture was filtered and the filtrate was concentrated. The residue was purified by column chromatography (20:1 $CH_2Cl_2$:MeOH) to afford intermediate (2) Yield: 1.31 g, 35%.

4-Methoxy-2-methyl-1H-pyrrolo[3,2-c]pyridine (3): To a solution of 1-benzyl-4-methoxy-2-methyl-1H-pyrrolo[3,2-c]pyridine (2) (0.887 g, 3.51 mmole) in anhydrous THF (10 mL) dimethyl sulfoxide (25 mL) was added slowly (via a syringe) and the mixture was cooled to 0° C. Potassium tert-butoxide (1M in THF, 25 mL, 25 mmole) was added slowly. Oxygen was bubbled through the mixture for 45 minutes. The reaction was quenched with saturated ammonium chloride solution, the mixture was extracted with ethyl acetate (3×50 mL). The organic layer was separated, dried over magnesium sulphate and concentrated. The residue was purified by column chromatography (3:1 Hex:EtOAc) to afford intermediate (3). Yield: 1.06 g >100%

1-Biphenyl-2-ylmethyl-4-methoxy-2-methyl-1H-pyrrolo[3,2-c]pyridine (4): To a solution of intermediate (3) (0.70 g, 4.69 mmole) in anhydrous DMF (40 mL) sodium hydride (60% in mineral oil, 0.28 g, 7.04 mmole) was added, the mixture was stirred for 1 h. To the mixture 2-phenylbenzyl bromide (0.95 mL, 5.16 mmole) was added dropwise. The mixture was stirred at room temperature for 18 h. The reaction was quenched with saturated ammonium chloride solution (200 mL), the mixture was extracted with ethyl acetate (3×200 mL). The organic layer was separated and washed with water, dried over magnesium sulphate and concentrated. The residue was purified by column chromatography (3:1 Hex:EtOAc) to afford intermediate (4) as a yellow solid. Yield: 1.1 g 71%.

1-Biphenyl-2-ylmethyl-2-methyl-1H-pyrrolo[3,2-c]pyridin-4-ol (5): To a solution of intermediate (4) in acetic acid (45 mL) hydrogen bromide (48% solution, 15 mL) was added. The mixture was heated at 105° C. for 18 h. The reaction mixture was concentrated, then dissolved in dichloromethane (100 mL) and washed with ammonium chloride solution (100 mL). The organic layer was separated, dried over magnesium sulphate and concentrated to afford intermediate (5) as a solid. Yield: 0.65 g, 62%.

(1-Biphenyl-2-ylmethyl-2-methyl-1H-pyrrolo[3,2-c]pyridin-4-yloxy)-acetic acid ethyl ester (6): To a solution of intermediate (5) (0.557 g, 1.77 mmole) in 1,2-dichloroethane (250 mL) rhodium(II) trifluoroacetate dimmer (0.058 g, 0.0885 mmole) was added, the reaction was heated to reflux. Then the solution of ethyl diazoacetate (90%, 0.2 mL, 1.77 mmole) in dichloroethane (35 mL) was added via a syringe pump to the mixture over 16 h. The reaction mixture was refluxed for an additional 2 h. The solvent was evaporated and the residue was purified by column chromatography (3:1 Hex:EtOAc) to afford intermediate (6) as a yellow solid. Yield: 0.272 g, 38%.

(3-Aminooxalyl-1-biphenyl-2-ylmethyl-2-methyl-1H-pyrrolo[3,2-c]pyridin-4-yloxy)-acetic acid ethyl ester (7): To a solution of intermediate (6) (0.255 g, 0.637 mmole) in chloroform (20 mL) oxalyl chloride (0.169 mL, 1.898 mmole) in chloroform (6 mL) was added dropwise, followed by the addition of pyridine (0.1 mL). The mixture was stirred at room temperature for 18 h. The reaction mixture was poured onto ice cold ammonium chloride solution (50 mL), dichloromethane (50 mL) was added and the mixture was stirred for 1 h. The organic layer was separated and the aqueous layer was further extracted with chloroform (3×50 mL). The organic fractions were combined, dried over magnesium sulphate and concentrated. The residue was purified by column chromatography (3:1 EtOAc:Hex) to afford intermediate (7) as a yellow solid. Yield: 0.18 g, 60%)

(3-Aminooxalyl-1-biphenyl-2-ylmethyl-2-methyl-1H-pyrrolo[3,2-c]pyridin-4-yloxy)-acetic acid (8): To a solution of intermediate (7) (0.18 g, 0.382 mmole) in THF/MeOH (10 mL/10 mL) lithium hydroxide monohydrate (0.035 g, 0.852 mmole) was added. The reaction mixture was stirred at room temperature for 1.5 h. The mixture was acidified to pH 1-2 with 2M HCl, then adjusted to pH=6.5 with 1 M KOH solution. The solvent was evaporated and the water was decanted off. The residue was washed with water (2×5 mL), followed by diethyl ether (2×5 mL). The solid was collected by filtration and dried under high vacuum to afford intermediate (8) as a yellow solid. Yield: 0.13 g, 72%.

2-[1-Biphenyl-2-ylmethyl-4-(2-methanesulfonylamino-2-oxo-ethoxy)-2-methyl-1H-pyrrolo[3,2-c]pyridin-3-yl]-2-oxo-acetamide (Ily-II-14): To a mixture of intermediate (8) (0.13 g, 0.295 mmole) in dichloromethane (10 mL) DMAP (0.065 g, 0.45 mmole), methanesulfonamide (0.056 g, 0.58 mmole) and 1-(3-dimethylaminopropyl)-3-ethylcarbodiimide hydrochloride (EDAC) (0.056 g, 0.293 mmole) were added. The mixture was stirred at room temperature for 18 h. The solvent was concentrated and the residue was purified by preparative TLC (10:1 $CH_2Cl_2$:MeOH) afford to Ily-II-14. Yield: 0.035 g, 23%. $^1$H NMR: 05-043-167-2a (DMSO-$d_6$, 400 MHz) δ, ppm: 7.96 (s, 1H), 7.75 (d, 1H), 7.60-7.22 (m, 10 H), 7.02 (d, 1H), 6.42 (d, 1H), 5.40 (s, 2H), 4.75 (s, 2H), 3.00 (s, 3H), 2.30 (s, 3H). ES-MS: m/z=520.95 (M+1).

Certain such azaindole and azaindole related compounds were evaluated for phospholipase activity using the protocol of Example 8. The results are shown in Table 10.

TABLE 10

Inhibition of pancreas secreted human, mouse and porcine PLA$_2$

| structure | Compound ID | MW | ILYPSA IC50 (µM) | | | ILYPSA % inhibition at 15 µM | | |
|---|---|---|---|---|---|---|---|---|
| | | | hps PLA$_2$ | pps PLA$_2$ | mps PLA$_2$ | hps PLA$_2$ | pps PLA$_2$ | mps PLA$_2$ |
| | ILY-II-1 (2-1) | 367.36 | 1.15 | 0.07 | 0.23 | | | |
| | ILY-VII-1 (7-1) | 367.36 | 13.65 | 0.06 | 2.14 | | | |
| | ILY-II-7 (2-7) | 444.46 | 2.07 | 0.04 | 1.05 | | | |
| | ILY-II-4 (2-4) | 443.45 | 0.08 | <0.02 | 0.07 | | | |

TABLE 10-continued

Inhibition of pancreas secreted human, mouse and porcine $PLA_2$

| structure | Compound ID | MW | ILYPSA IC50 (µM) | | | ILYPSA % inhibition at 15 µM | | |
|---|---|---|---|---|---|---|---|---|
| | | | hps $PLA_2$ | pps $PLA_2$ | mps $PLA_2$ | hps $PLA_2$ | pps $PLA_2$ | mps $PLA_2$ |
| (structure) | ILY-II-8 (2-8) | 389.45 | 0.27 | 0.08 | 0.12 | | | |
| (structure) | ILY-II-11 (2-11) | 395.41 | 0.48 | <0.02 | 0.03 | | | |
| (structure) | ILY-II-9 (2-9) | 381.38 | 1.46 | 0.03 | 0.35 | | | |
| (structure) | ILY-II-12 (2-12) | 482.44 | | 3.71 | | 16.63 | | 35.68 |

TABLE 10-continued

Inhibition of pancreas secreted human, mouse and porcine PLA$_2$

| structure | Compound ID | MW | ILYPSA IC50 (µM) | | | ILYPSA % inhibition at 15 µM | | |
|---|---|---|---|---|---|---|---|---|
| | | | hps PLA$_2$ | pps PLA$_2$ | mps PLA$_2$ | hps PLA$_2$ | pps PLA$_2$ | mps PLA$_2$ |
| [structure] | ILY-II-14 (2-14) | 520.57 | 0.69 | 0.04 | 0.59 | | | |

Example 13

Mouse Pharmacokinetic Study

The plasma exposure of male CD-1 mice to indole and indole-related test articles (TAs) following intravenous (IV, 3 mg/kg) and oral (PO, 30 mg/kg) routes of administration was measured. This model was used to investigate the bioavailability of indole and indole-related TAs in mouse. Mice were selected for the study since they are an accepted species frequently used in pre-clinical evaluation of drugs intended for human use.

Male CD-1 mice (7-8 weeks old) were obtained from Charles River Laboratories (Wilmington, Mass.). Two groups (N=18 and 27) of male CD-1 mice were used for the study. Upon arrival, the animals were placed on Rodent Diet 5001 (Purina Mills, Inc., St. Louis, Mo.).

On study day (−1), indole and indole-related TAs were formulated for oral or IV dosing by mixing the formulation components with test article in the proportions described in Table 11.1. The components were mixed by vortexing and sonicating in a warming bath for 60 minutes. Animals were fasted overnight prior to start of the study. On study day (1), formulations were sonicated for an hour to make sure that no visible particles were present prior to dosing, or if present were evenly distributed in suspension. Formulated test article were stirred continuously during dosing.

TABLE 11.1

Oral and IV Dose Formulations

| | PO | IV |
|---|---|---|
| H$_2$O | 85 ml | 60 ml |
| PEG400 | 9 ml | |
| PEG300 | | 30 ml |
| Tween-80 | 50 ul | |
| Ethanol | | 5 ml |
| DMSO | 5 ml | 5 ml |
| CMC | 900 mg | |
| Test Article | 300 mg | 60 mg |

All animals were weighed on study day (1) and the body weights were recorded and used for dose calculation. The animals were dosed by either PO or IV route as outlined in Table 11.2. Blood samples (0.5 mL) were collected at specified time intervals into labeled, yellow-capped Microtainer tubes. The tubes were centrifuged (8,000×g, 10 min). Serum was then pipetted off into labeled Eppendorf® tubes and frozen at −80° C. Clinical observations were recorded as needed.

TABLE 11.2

Oral and IV Dosing Schedule

| Compound | Group No. | Dose | Time Points | Mice Per Time Point |
|---|---|---|---|---|
| Test Article | 1 | PO (30 mg/kg) | 0.5 h, 1 h, 1.5 h, 2 h, 6 h, 24 h | 3 |
| Test Article | 2 | IV (3 mg/kg) | 5 m, 10 m, 20 m, 30 m, 45 m, 1 h, 2 h, 6 h, 24 h | 3 |

Analysis of serum samples was performed by LC/MS/MS (Waters Quattro Premier, Milford, Mass.). The Limit Of Quantitation (LOQ) for each compound is listed in Table 11.3. Areas under curves (AUC) were calculated using Graphpad Prism Version 4. Bioavailability was calculated using the following equation:

$$(\text{Bioavailability}) = (AUC_{0-t,\,oral}/AUC_{0-t,\,iv}) \times (\text{Dose}_{iv}/\text{Dose}_{oral}) \times 100$$

where $AUC_{0-t}$=total area under curve at the last measurable time point

Based on the serum levels analyzed by LC/MS/MS, the calculated bioavailability of indole and indole-related TAs in CD-1 mice is summarized in Table 11.3.

TABLE 11.3

Bioavialability of Compounds

| Compound | Bioavailability (%) | LOQ (ng/ml) |
|---|---|---|
| ILY-V-26 | 0.00 | 200 |
| ILY-V-30 | 0.00 | 120 |
| ILY-V-32 | 0.00 | 200 |
| ILY-IV-40 | 0.50 | 3 |
| ILY-V-37 | 0.15 | 45 |

TABLE 11.3-continued

Bioavialability of Compounds

| Compound | Bioavailability (%) | LOQ (ng/ml) |
|---|---|---|
| ILV-V-27 | 1.49 | 60 |
| ILY-V-41 | 1.62 | 45 |
| ILV-V-31 | 5.15 | 45 |
| ILY-V-33 | 8.75 | 120 |
| ILY-II-1 | 11.00 | 1 |
| ILY-II-14 | 14.74 | 16 |

Example 14

Mouse Diet-Induced Obesity

The high-fat diet-fed C57BL/6J mouse model of human diabetes, originally introduced by Surwit and colleagues (Surwit, R S, et al. (1988) "Diet-induced type II diabetes in C57BL/6J mice", Diabetes 37: 1163-1167) is a widely accepted, clinically relevant, polygenic model that induces obesity, dyslipidemia, glucose- and insulin-resistance as early as 3 weeks after commencing the high fat diet (Winzell, M S and Ahren, B (2004) "The high-fat diet-fed mouse: a model for studying mechanisms and treatment of impaired glucose tolerance and type 2 diabetes", Diabetes 53 Suppl 3: S215-219). This model was used to investigate the effects of indole and indole-related Test Articles. Avandia (rosiglitazone) was used as a control Test Article.

Female C57Black/6J mice (5-6 weeks old) were obtained from Jackson laboratories (Bar Harbor, Me.). Upon arrival, the animals were placed on Laboratory Rodent Diet 5001 (Purina Mills, Inc., St. Louis, Mo.). Diet and water was provided ad libitum throughout the course of the study. Animals were acclimated for at least seven days, and then randomized by weight into twelve groups of eight animals each. Each group of animals was placed on diets with and without Test Articles as described in Table 12. All diets other than Laboratory Rodent Diet 5001 were provided by Research Diets (New Brunswick, N.J.).

In these studies and the accompanying figures, Diet D12328 from Research Diets is referred to as the "Low Fat" or Control diet/chow, while Diet D12331 from Research Diets is referred to as the "High Fat" diet. Groups 1-6 were fed diet D12328 that contained either no drug (Group 1) or varying amounts of Test Articles (Groups 2-6). Groups 7-12 were fed diet D12331 that contained either no drug (Group 7) or varying amounts of Test Articles (Groups 8-12). The Test Article content was calculated such that ad libitum consumption by the animals would deliver doses (in mg of Test Article per kg animal weight per day) approximating those listed in Table 12.

In this and other examples, Test Article ILY4008 is compound ILY-V-26 (5-26), Test Article ILY4013 is compound ILY-V-32 (5-32), Test Article ILY4011 is compound ILY-V-30 (5-30), and Test Article ILY4016 is compound ILY-V-40 (4-40).

TABLE 12

Mouse Diet-Induced Obesity Assay Diets

| Group | Diet | Added Test Article |
|---|---|---|
| 1 | D12328 | No added Test Article |
| 2 | D12328 | 50 mg/kg/d Rosiglitazone |
| 3 | D12328 | 90 mg/kg/d ILY4008 or ILY4013 |
| 4 | D12328 | 25 mg/kg/d ILY4008 or ILY4013 |
| 5 | D12328 | 90 mg/kg/d ILY4011 or ILY4016 |
| 6 | D12328 | 25 mg/kg/d ILY4011 or ILY4016 |
| 7 | D12331 | No added Test Article |
| 8 | D12331 | 50 mg/kg/d Rosiglitazone |
| 9 | D12331 | 90 mg/kg/d ILY4008 or ILY4013 |
| 10 | D12331 | 25 mg/kg/d ILY4008 or ILY4013 |
| 11 | D12331 | 90 mg/kg/d ILY4011 or ILY4016 |
| 12 | D12331 | 25 mg/kg/d ILY4011 or ILY4016 |

Animals were maintained on the diets for up to eleven weeks. Body weights were recorded weekly. Blood was drawn within 1-2 hrs of lights-on. without fasting. The serum was analyzed for glucose, total cholesterol, triglycerides (TG) and lysophospholipid (LPC) content.

Statistical analyses were performed using GraphPad Prism 4.03. (GraphPad Software, Inc., San Diego, Calif.). Two sets of statistical analyses were performed. First, the Low Fat Chow, no treatment group was compared by student's two-tailed T-test against the High Fat, High Sucrose diet, no treatment group. In all figures an "a" above the low fat chow, no treatment column signifies that the values are significantly different ($p<0.05$) from the High Fat, High Sucrose diet, no treatment group. Second, all treatment groups on the High Fat, High Sucrose diet were compared to the no-treatment group on that diet by 1-way ANOVA, followed by a Dunnett's post-test. A "b" above a graph column signifies that the values are significantly different ($p<0.05$) versus the no-treatment group on that diet.

Figure 12A:
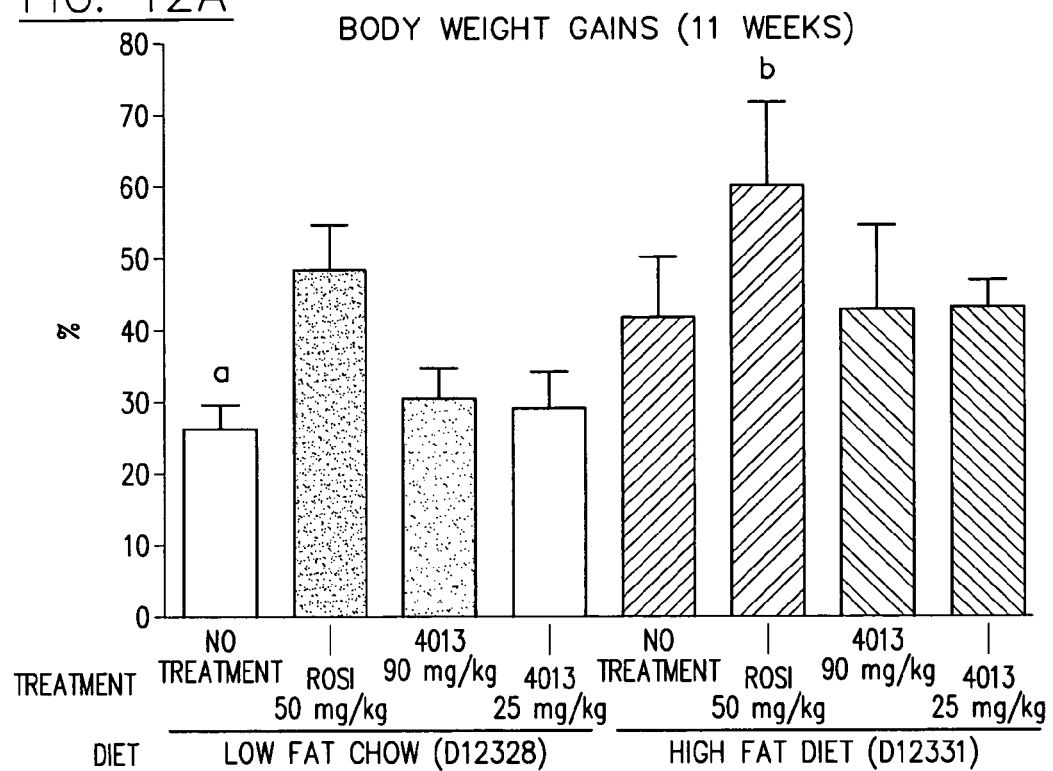
FIGS. 12A, 12B and 12C are graphs depicting results for Test Article ILY4013 (ILY-V-32) in a C57BL/6J mouse model of obesity.
Figure 12B:
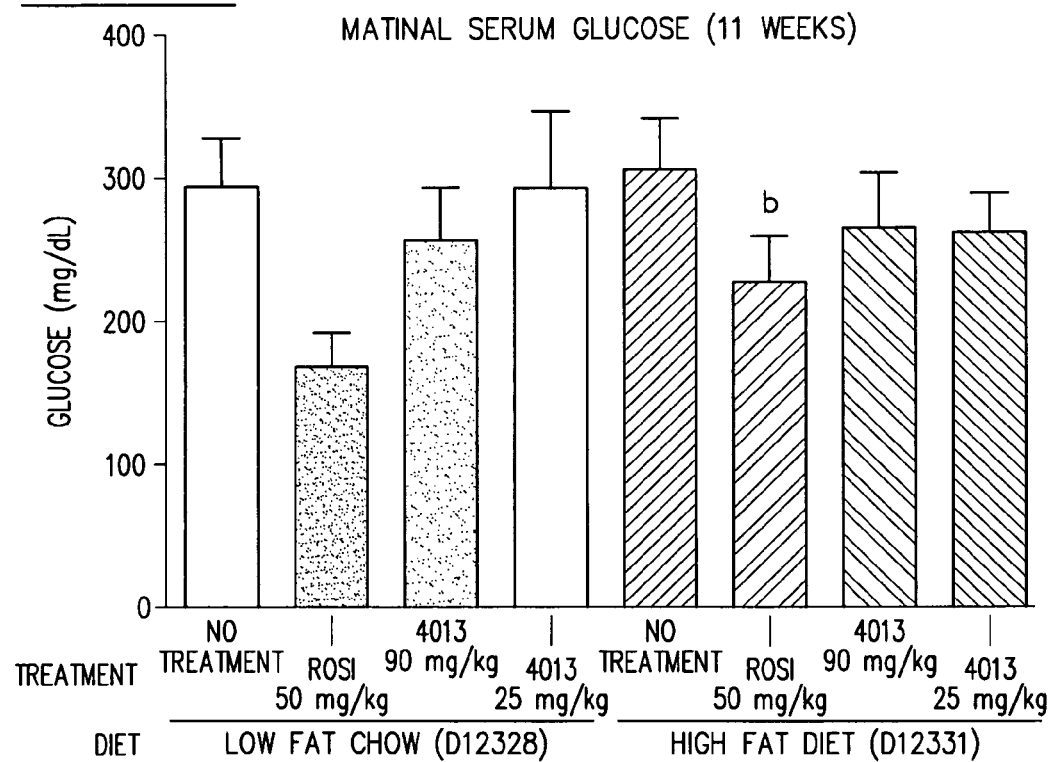
Figure 12C:
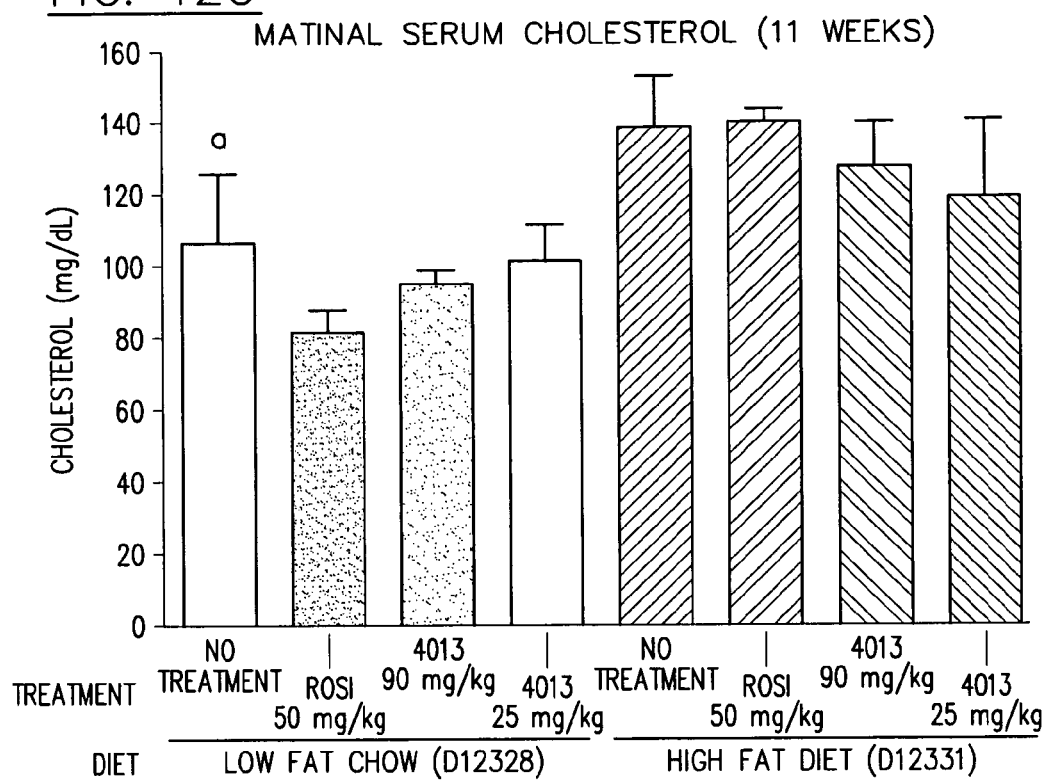
Figure 13A:
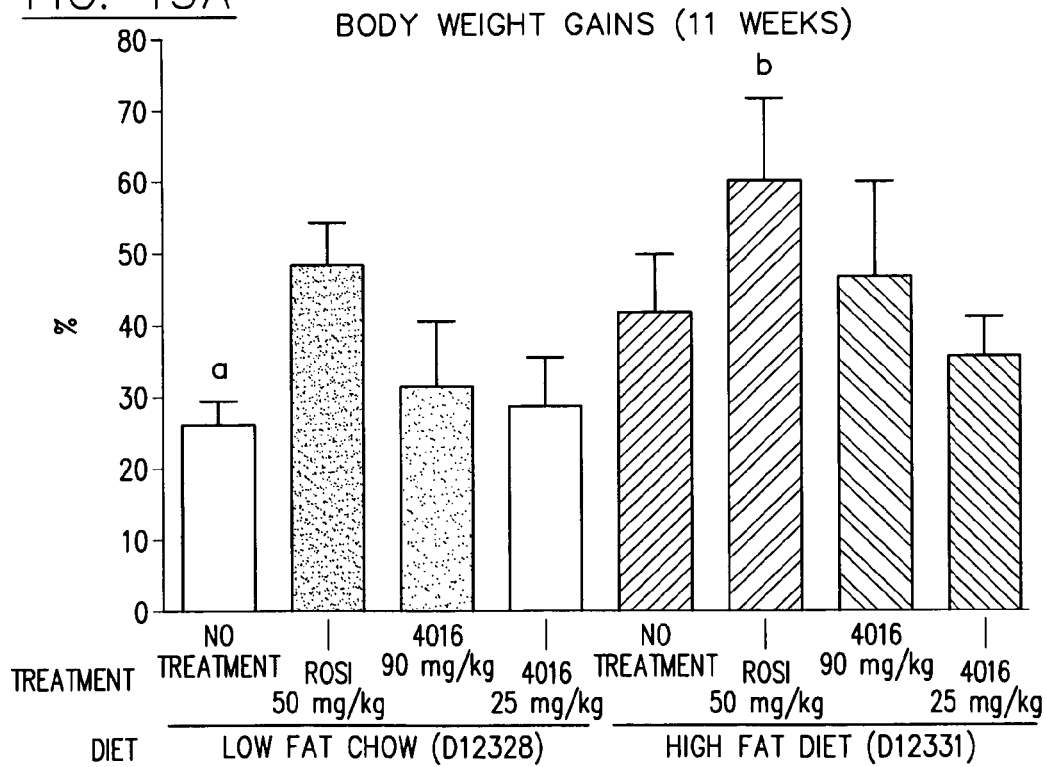
FIGS. 13A, 13B, and 13C are graphs depicting results for Test Article ILY4016 (ILY-IV-40) in a C57BL/6J mouse model of obesity.
Figure 13B:
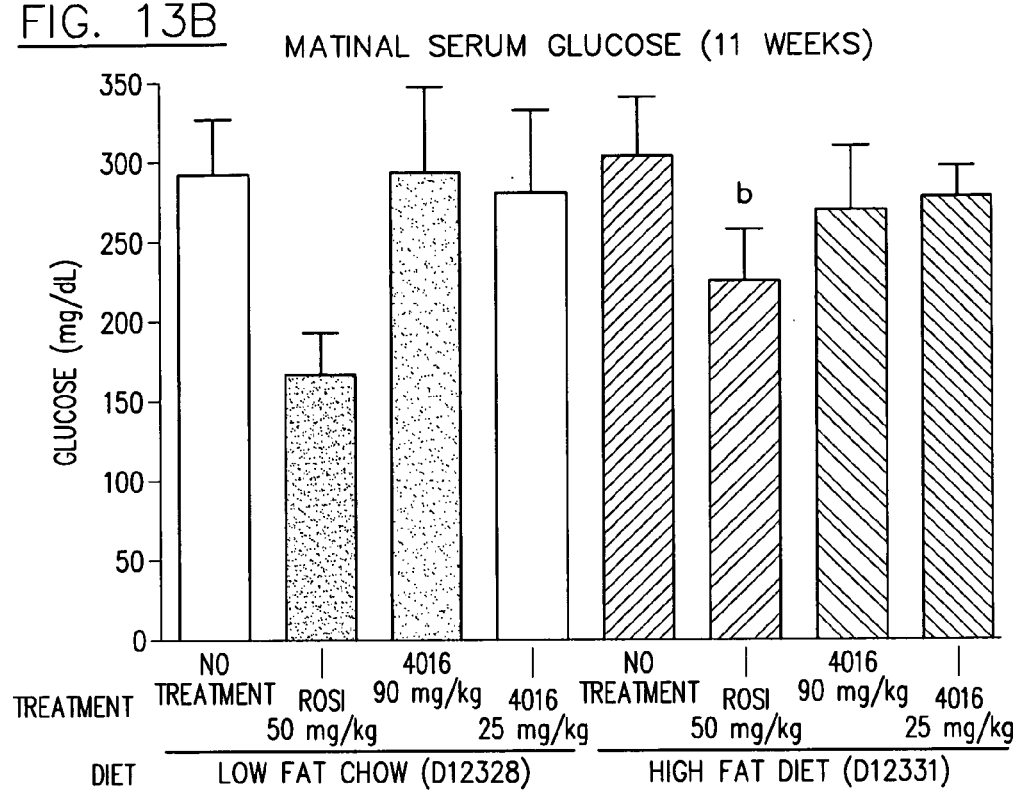
Figure 13C:
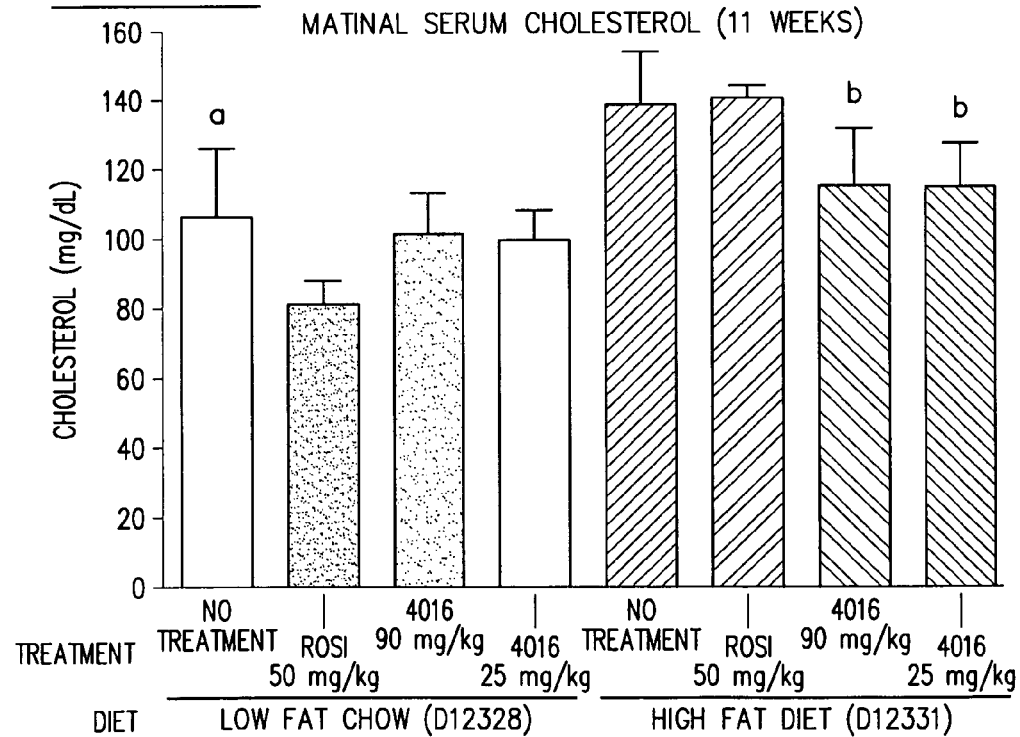
Figure 14A:
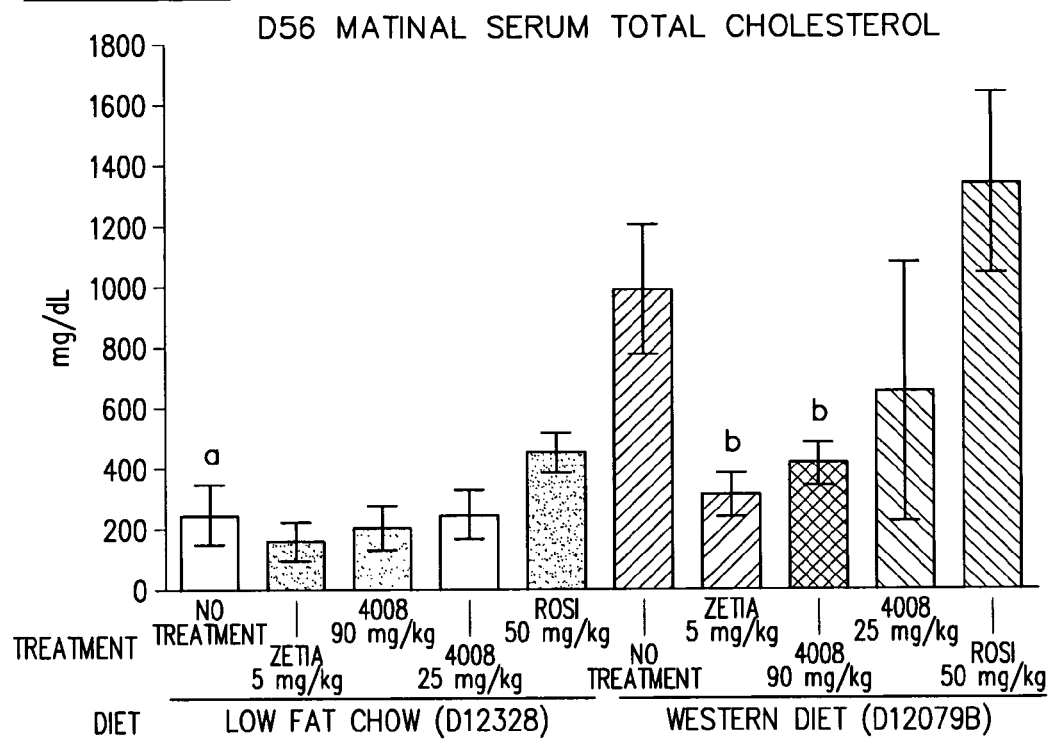
FIGS. 14A, 14B, 14C, 14D, 14E and 14F are graphs depicting results for Test Article ILY4008 (ILY-V-26) in a LDL receptor knockout mouse model.
Figure 14B:
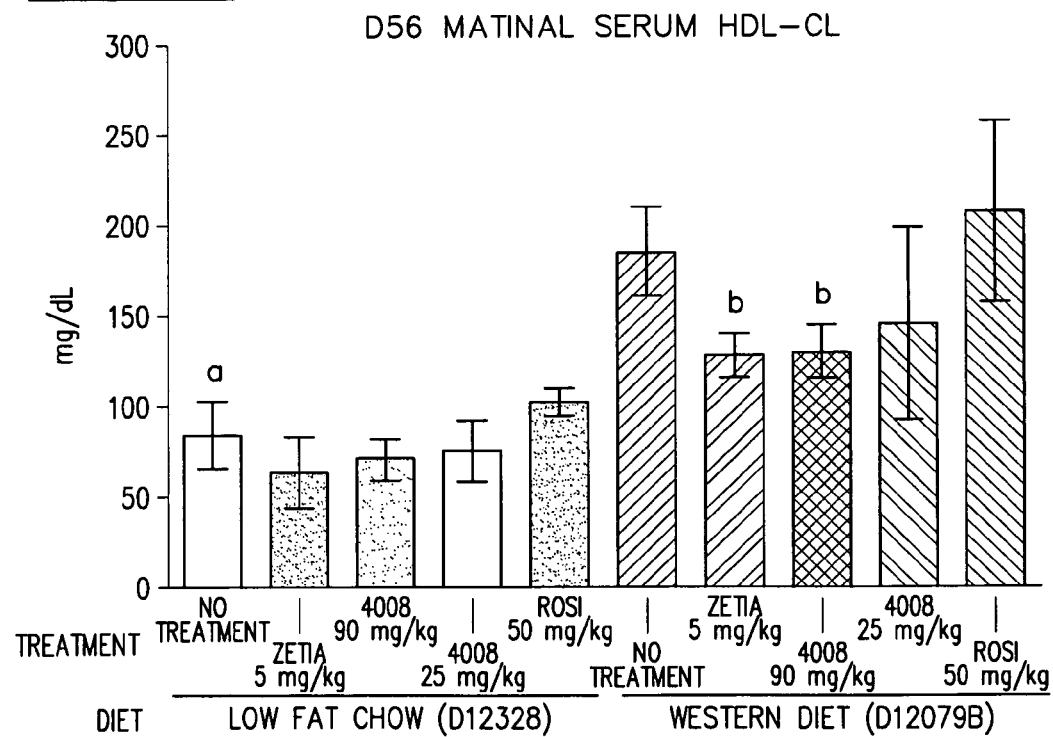
Figure 14C:
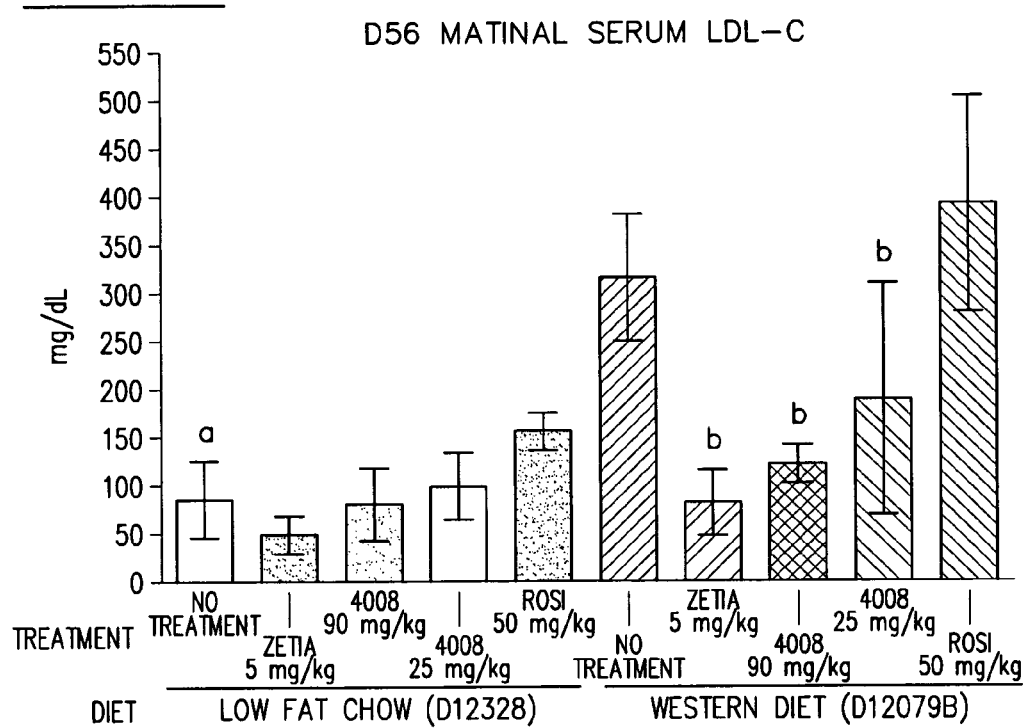
Figure 14D:
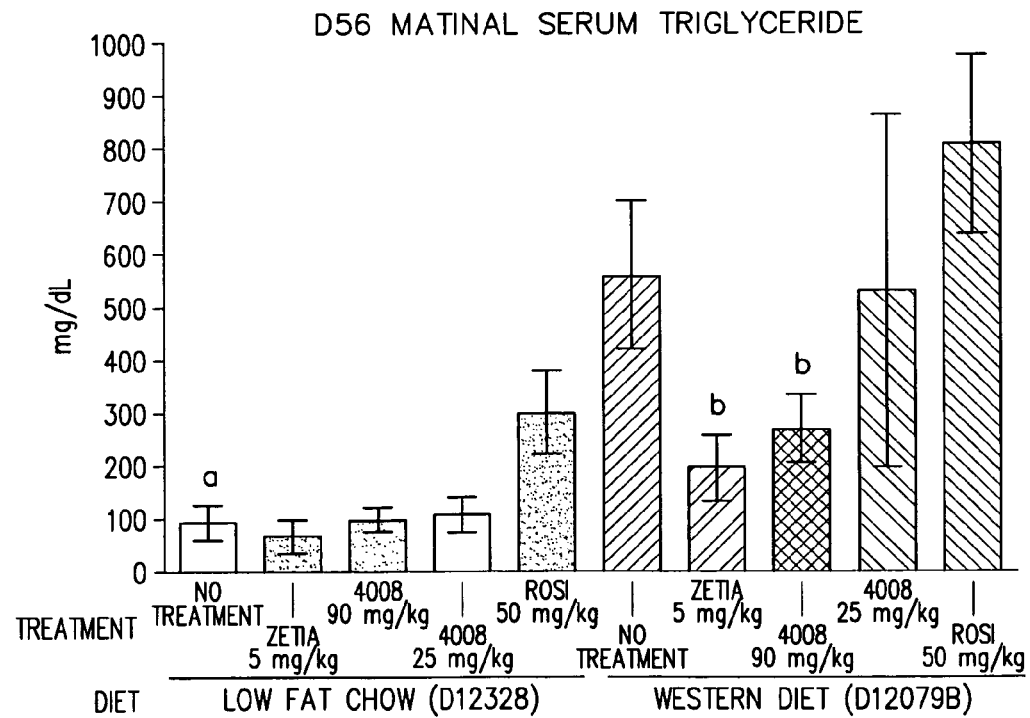
Figure 14E:
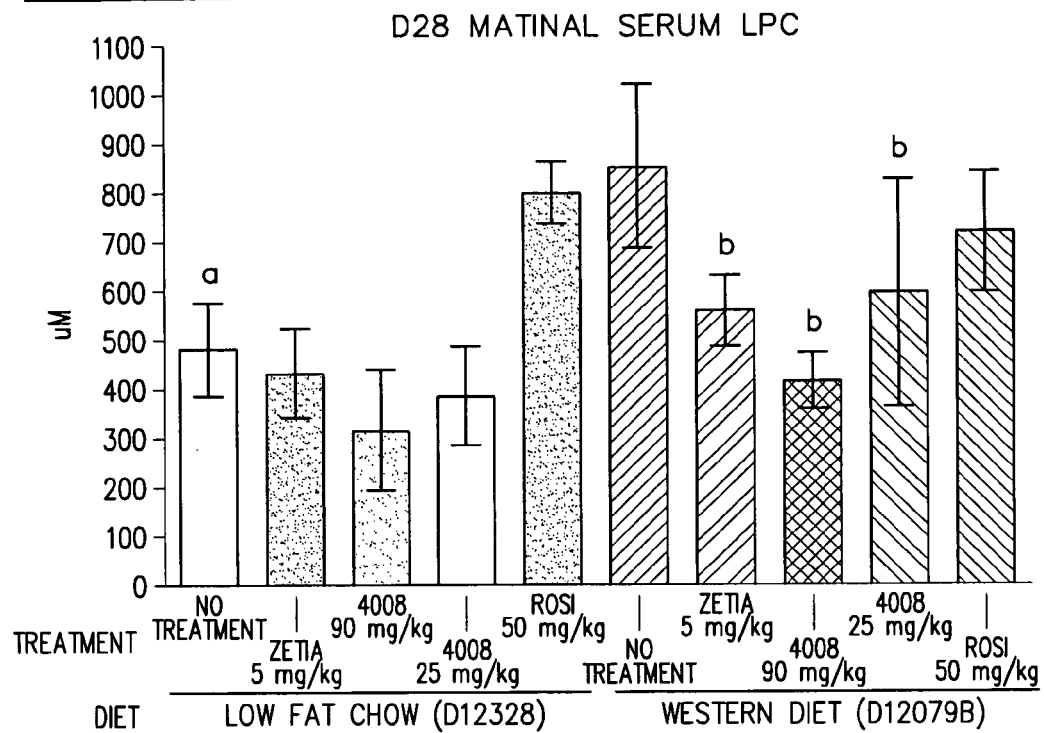
Figure 14F:
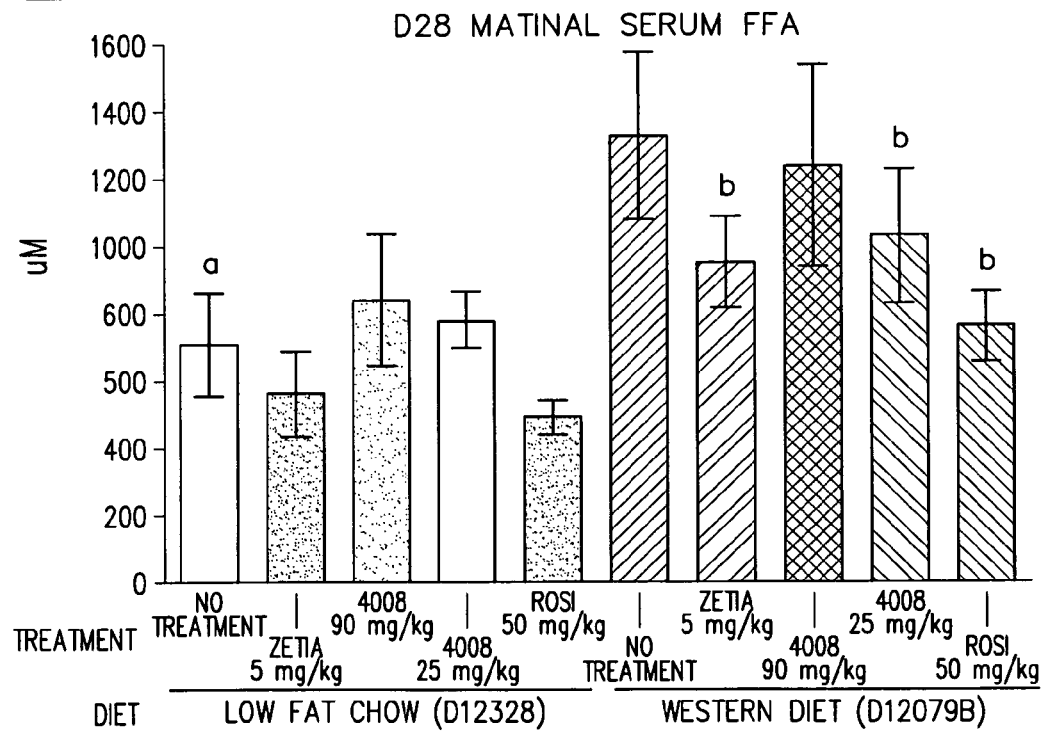
Figure 15A:
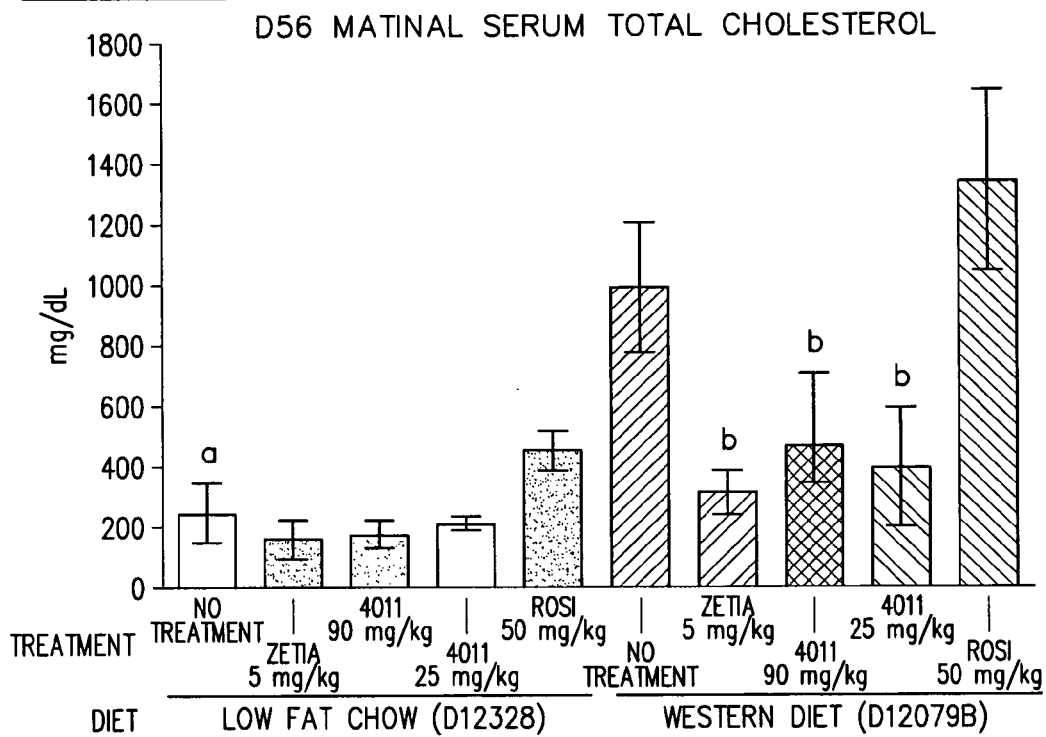
FIGS. 15A, 15B, 15C, 15D, 15E and 15F are graphs depicting results for Test Article ILY4011 (ILY-V-30) in a LDL receptor knockout mouse model.
Figure 15B:
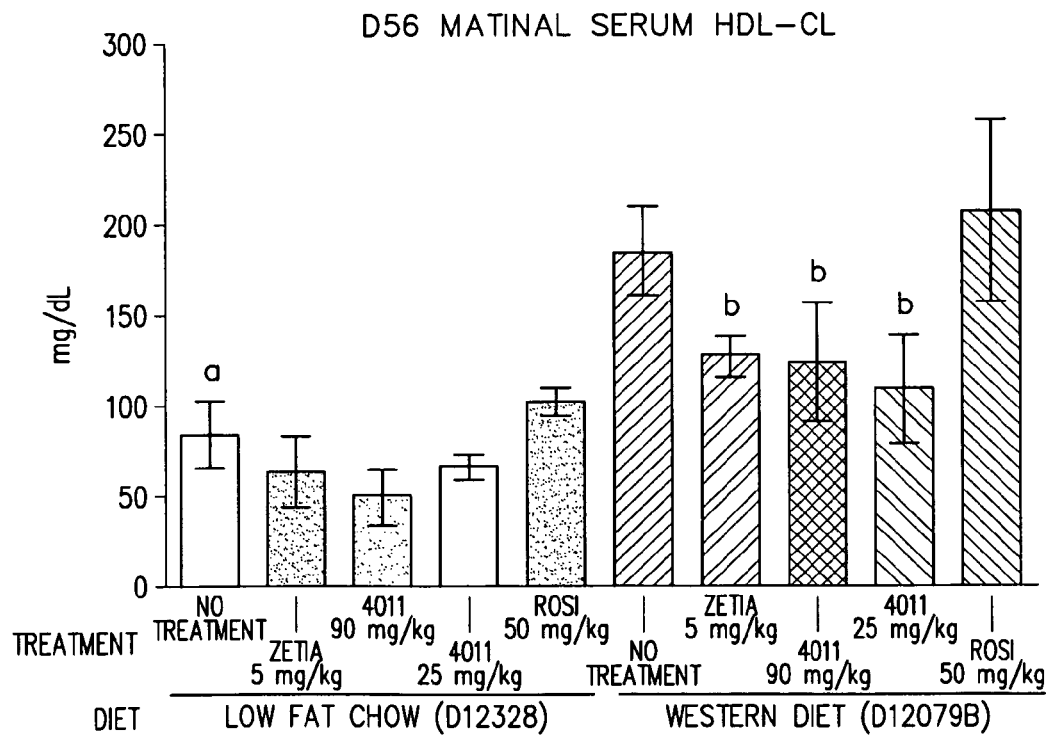
Figure 15C:
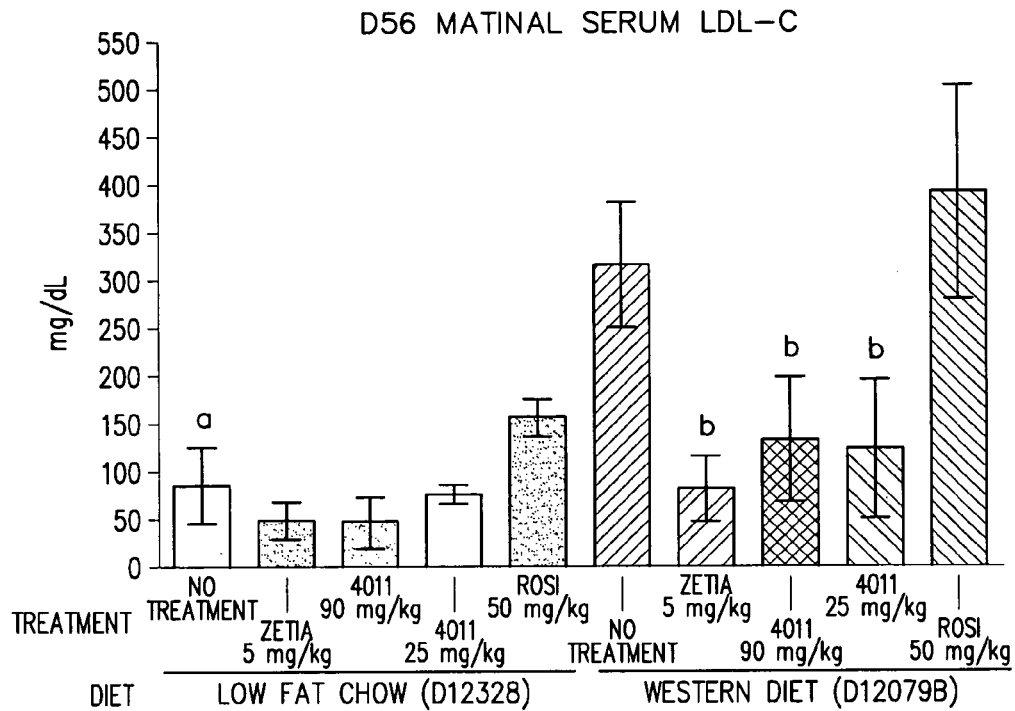
Figure 15D:
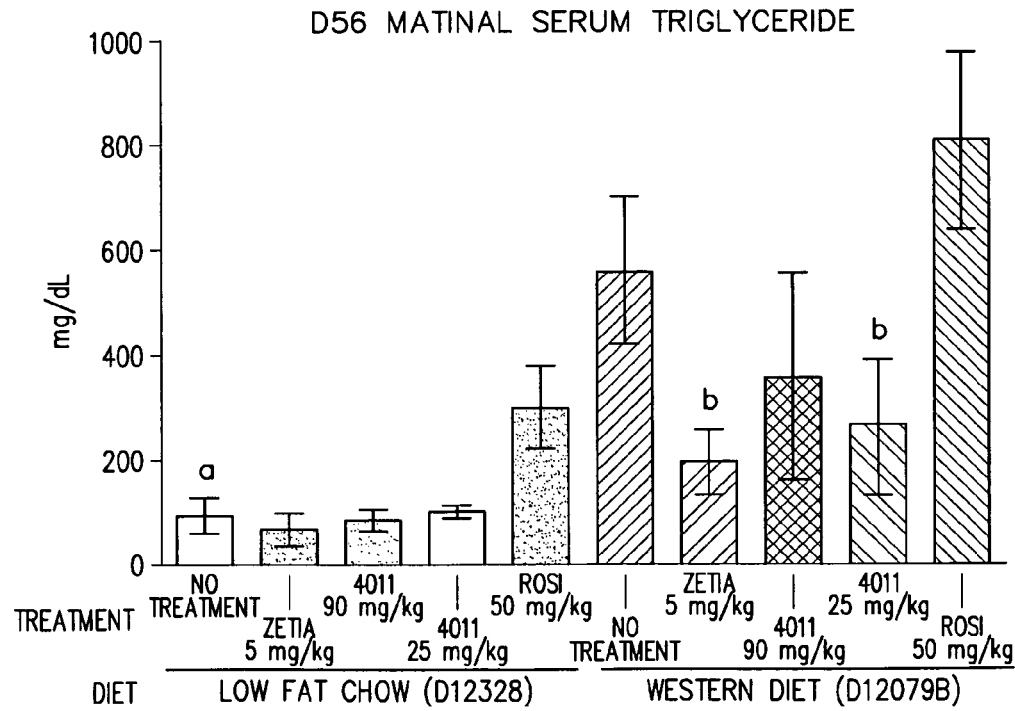
Figure 15E:
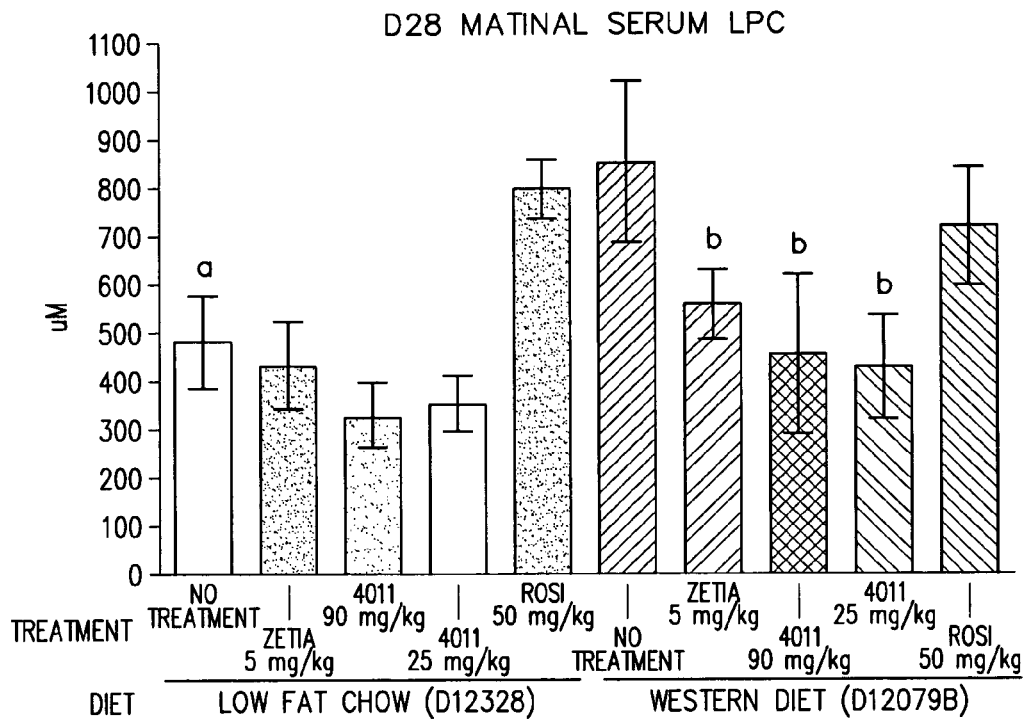
Figure 15F:
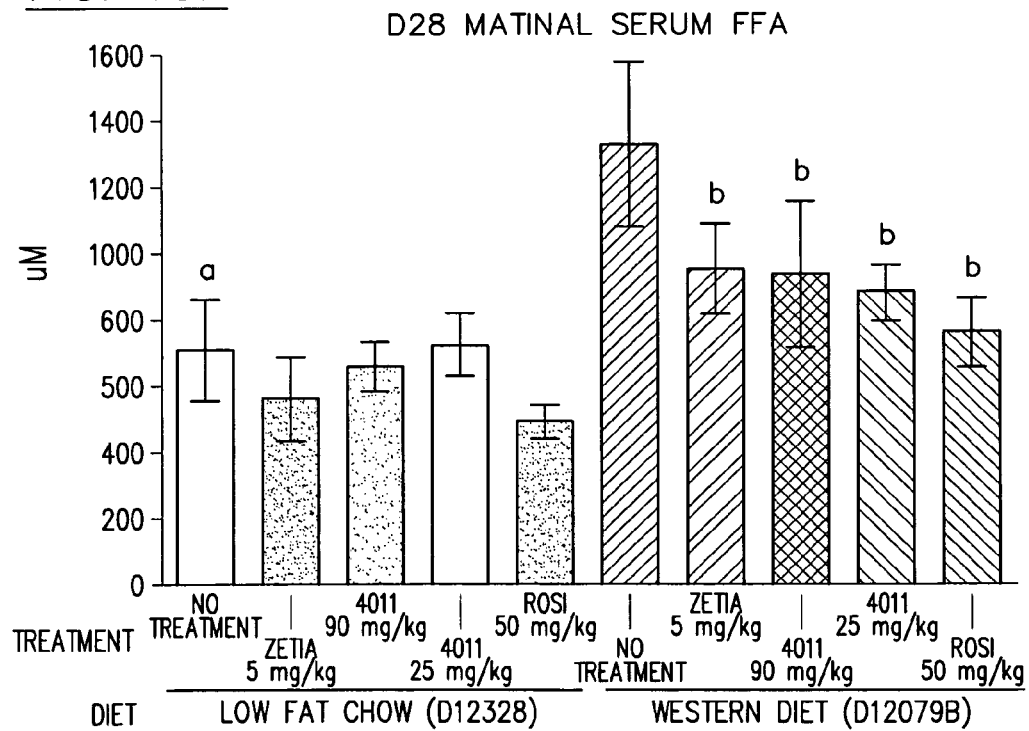
Figure 16A:
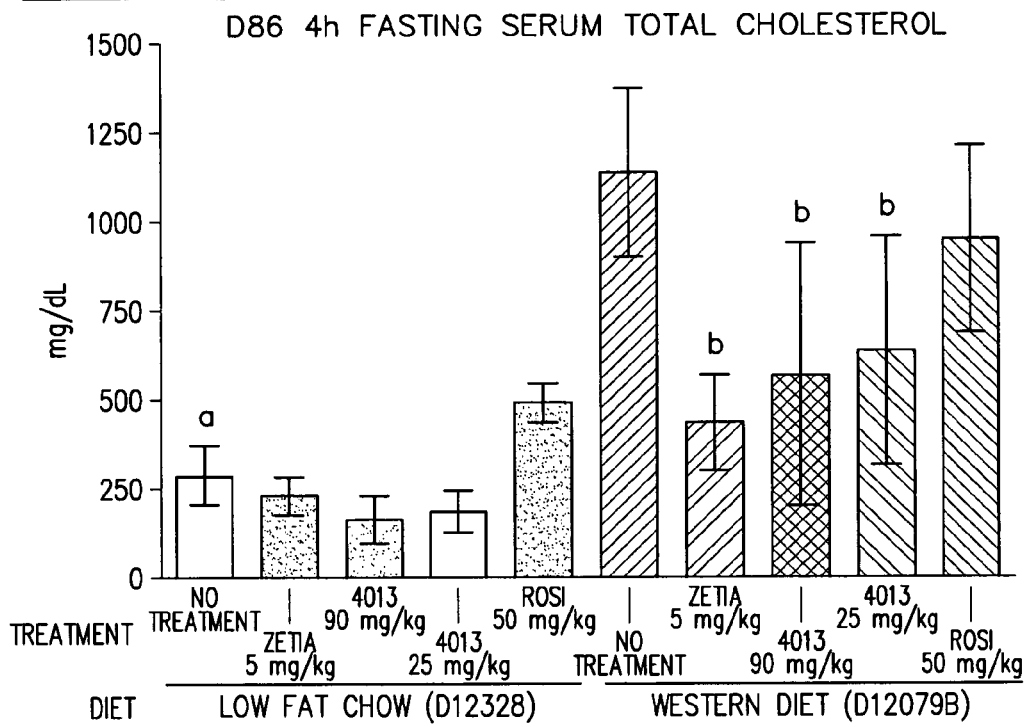
FIGS. 16A, 16B, 16C and 16D are graphs depicting results for Test Article ILY4013 (ILY-V-32) in a LDL receptor knockout mouse model.
Figure 16B:
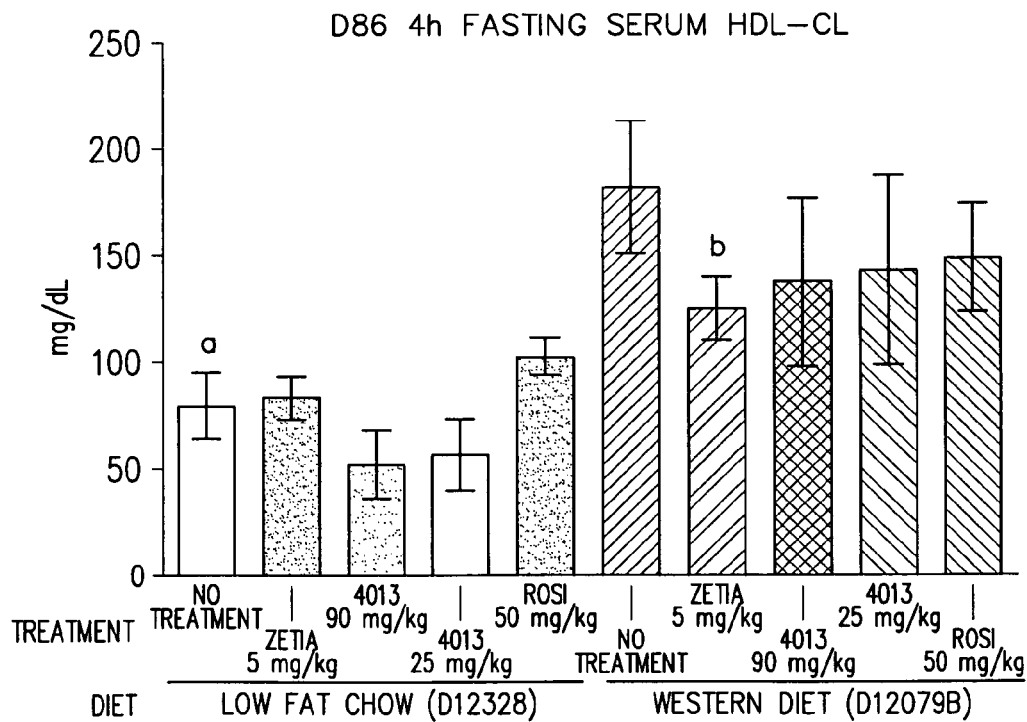
Figure 16C:
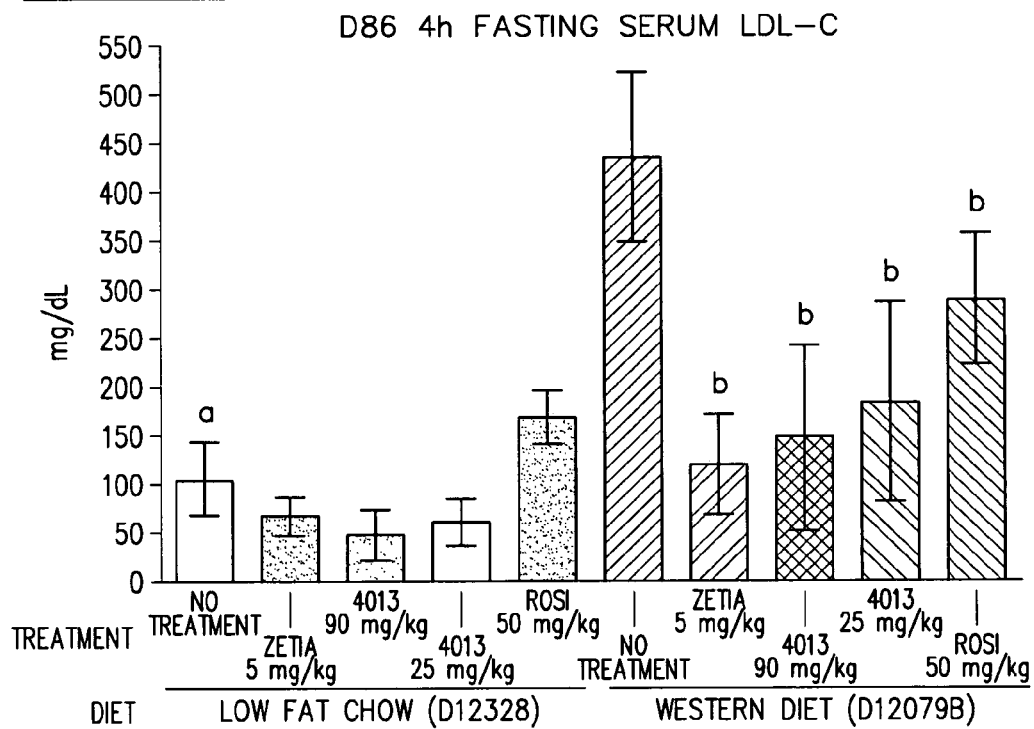
Figure 16D:
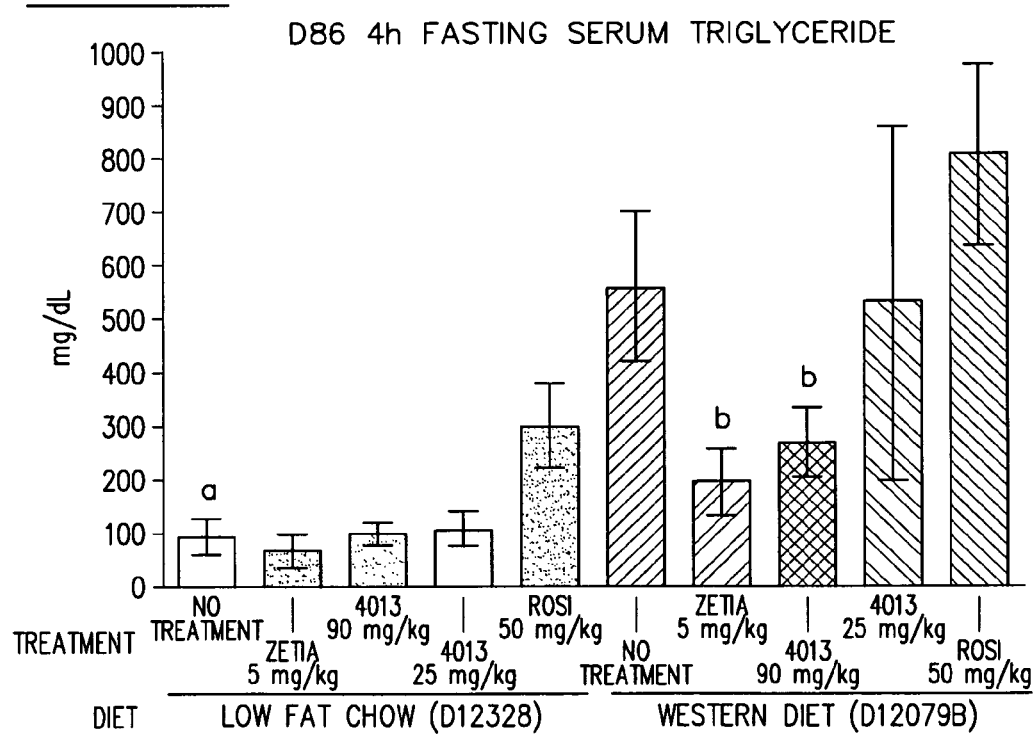
Figure 17A:
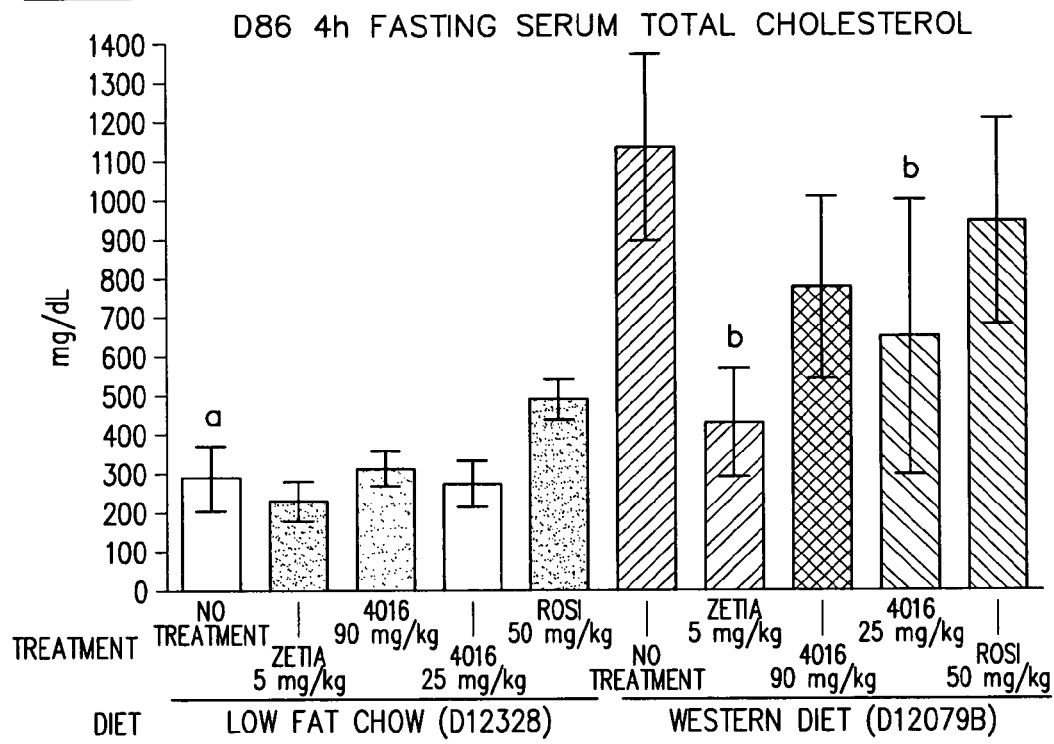
FIGS. 17A, 17B, 17C and 17D are graphs depicting results for Test Article ILY4016 (ILY-IV-40) in a LDL receptor knockout mouse model.
Figure 17B:
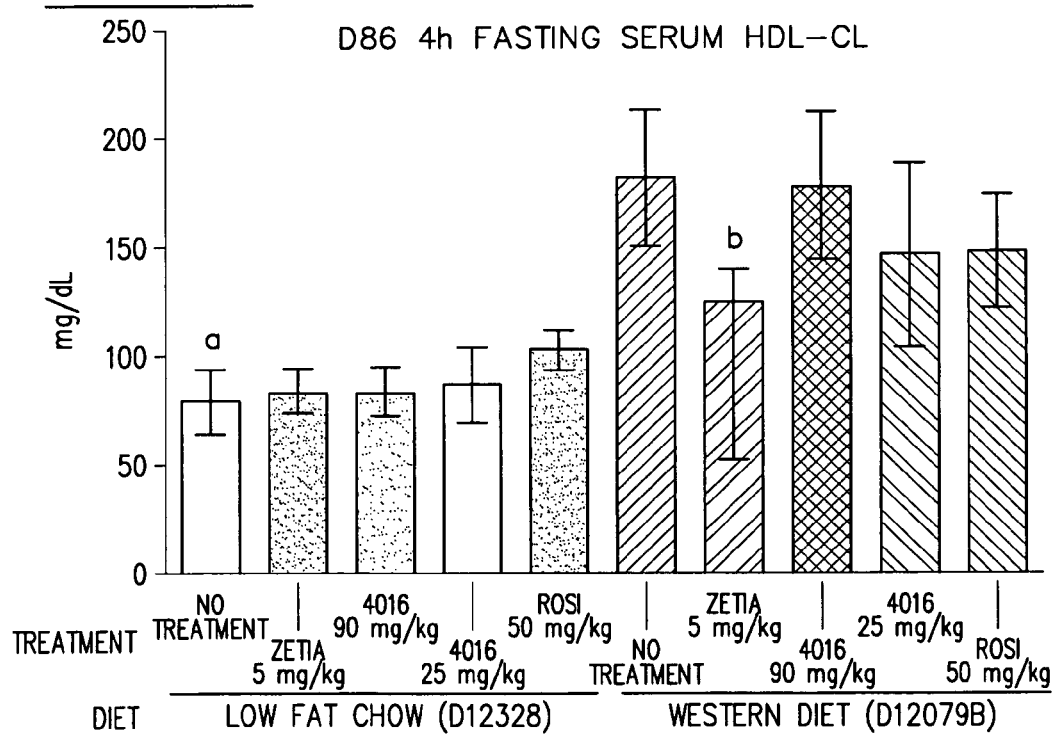
Figure 17C:
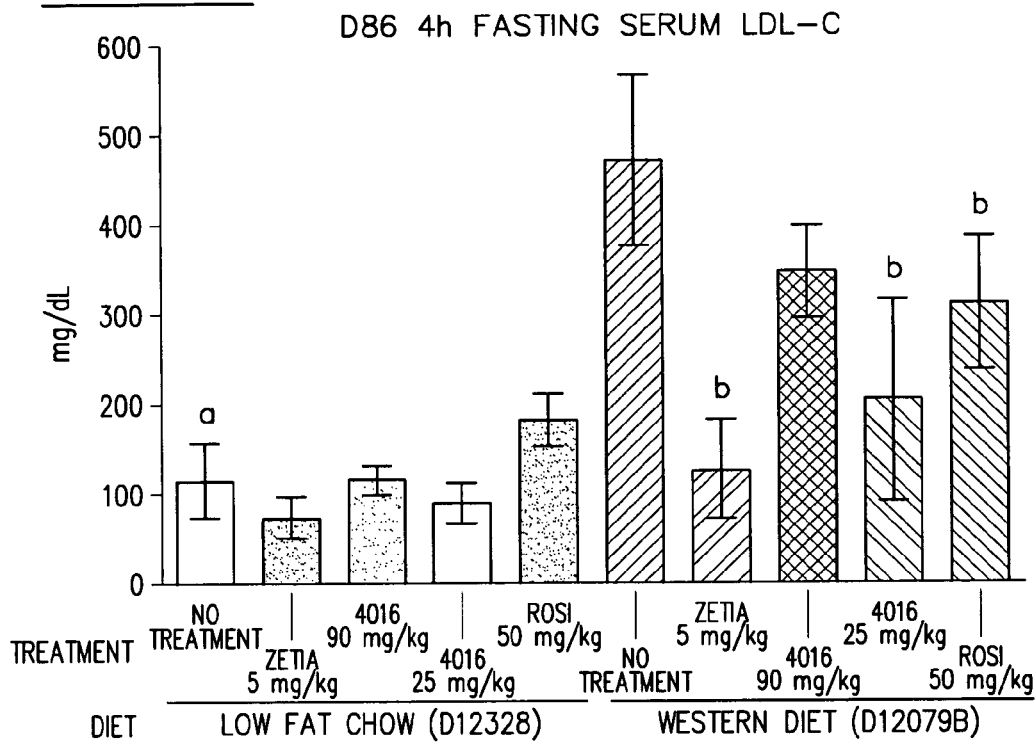
Figure 17D:
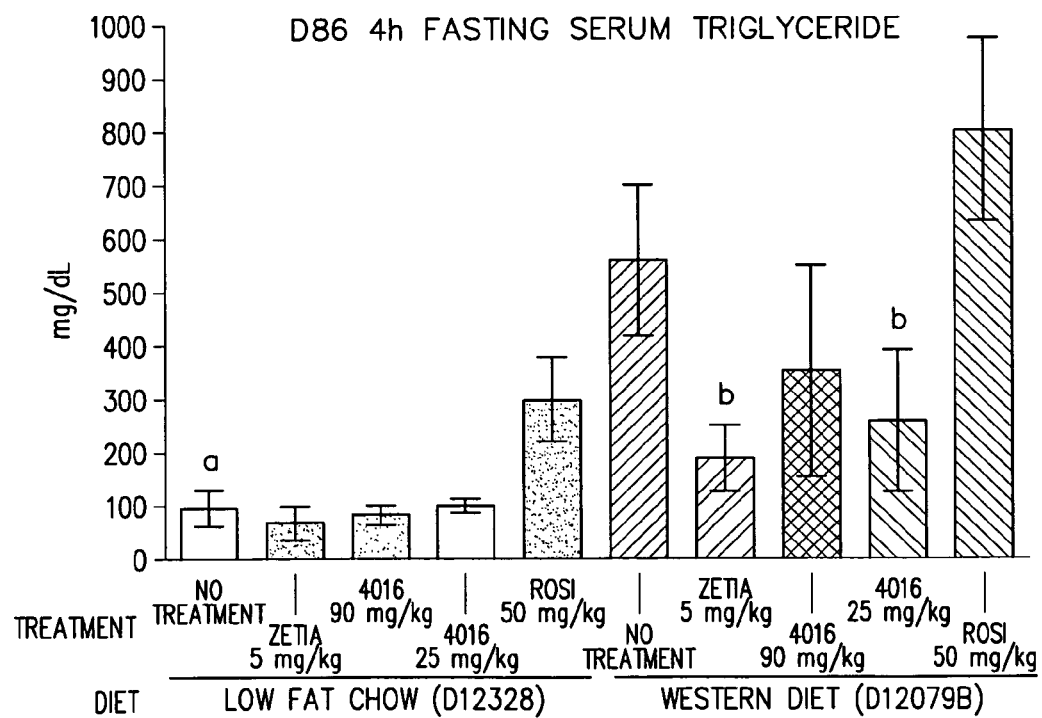
Figure 18A:
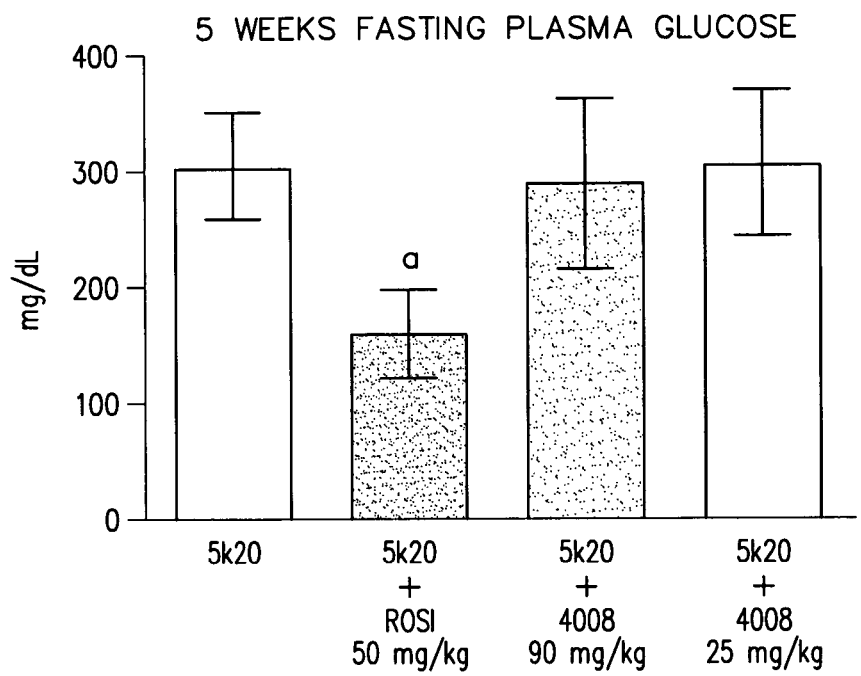
FIGS. 18A, 18B, 18C, 18D and 18E are graphs depicting results for Test Article ILY4008 (ILY-V-26) in a NONc-NZO10/LtJ mouse model of Type II diabetes.
Figure 18B:
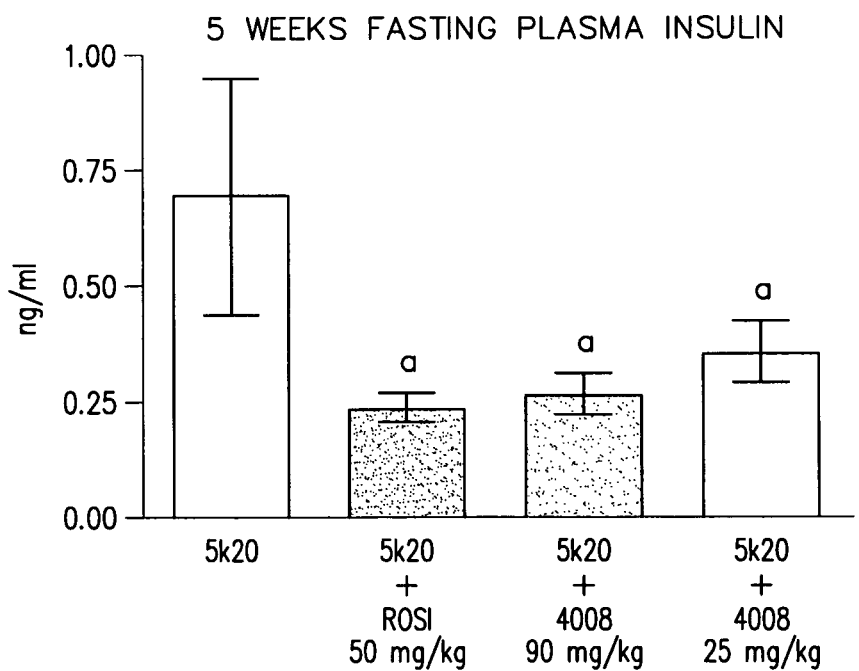
Figure 18C:
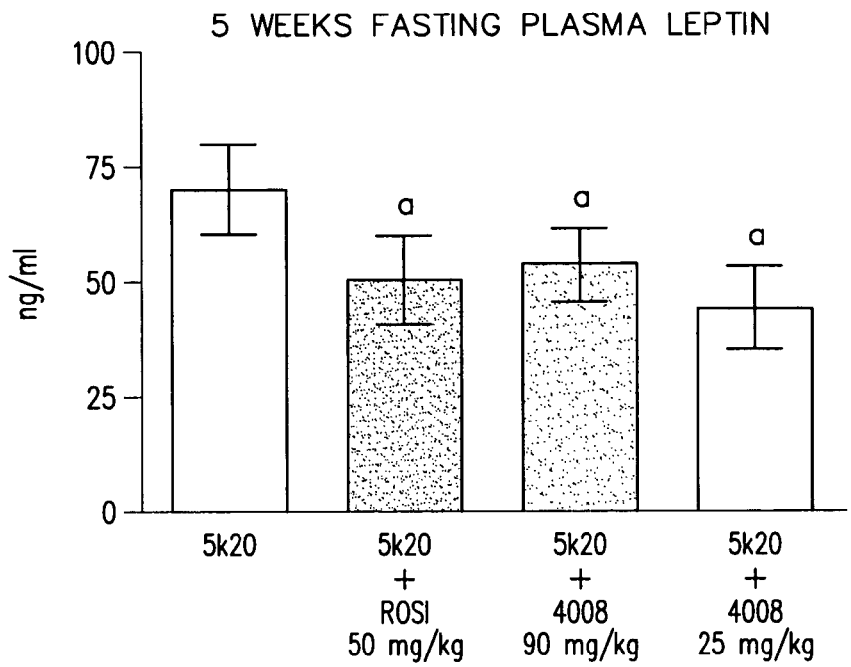
Figure 18D:
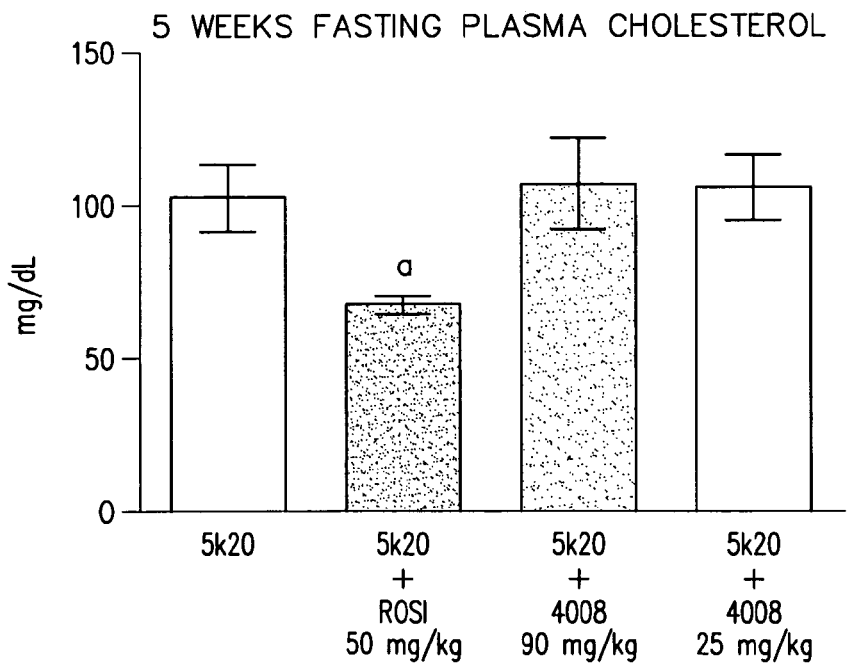
Figure 18E:
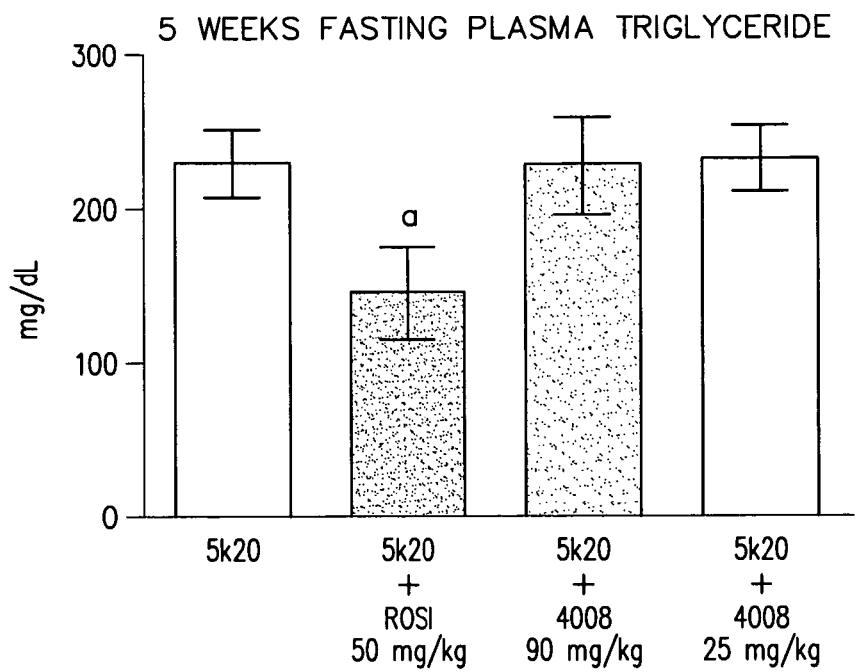
Figure 19A:
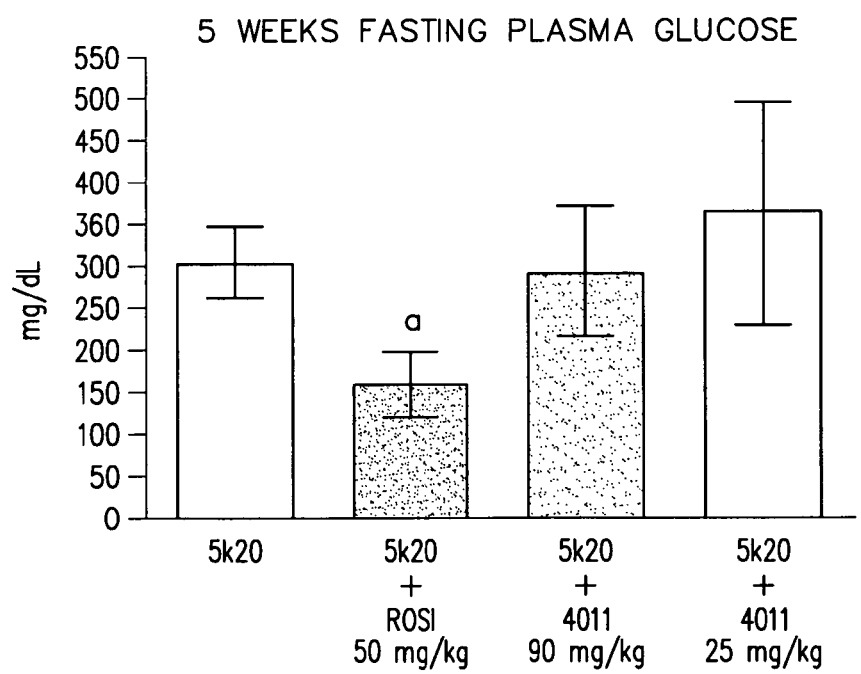
FIGS. 19A, 19B, 19C, 19D and 19E are graphs depicting results for Test Article ILY4011 (ILY-V-30) in a NONc-NZO10/LtJ mouse model of Type II diabetes.
Figure 19B:
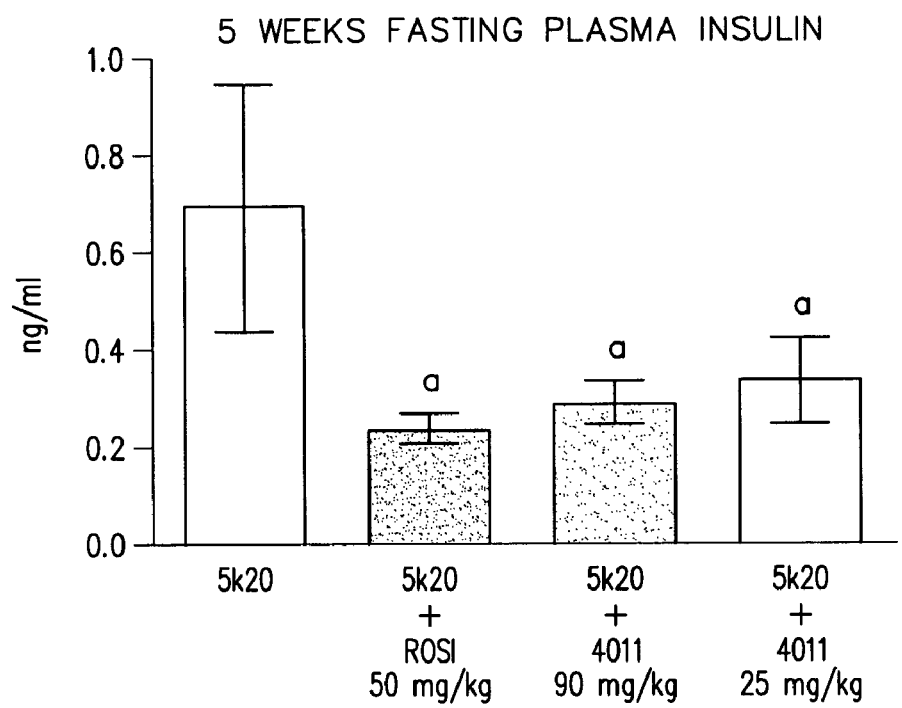
Figure 19C:
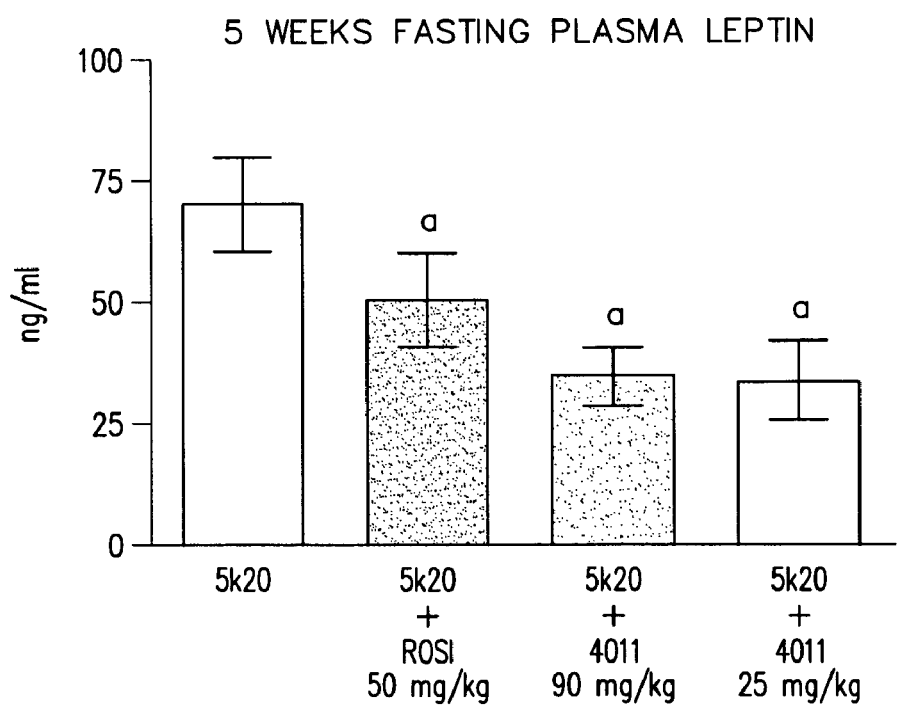
Figure 19D:
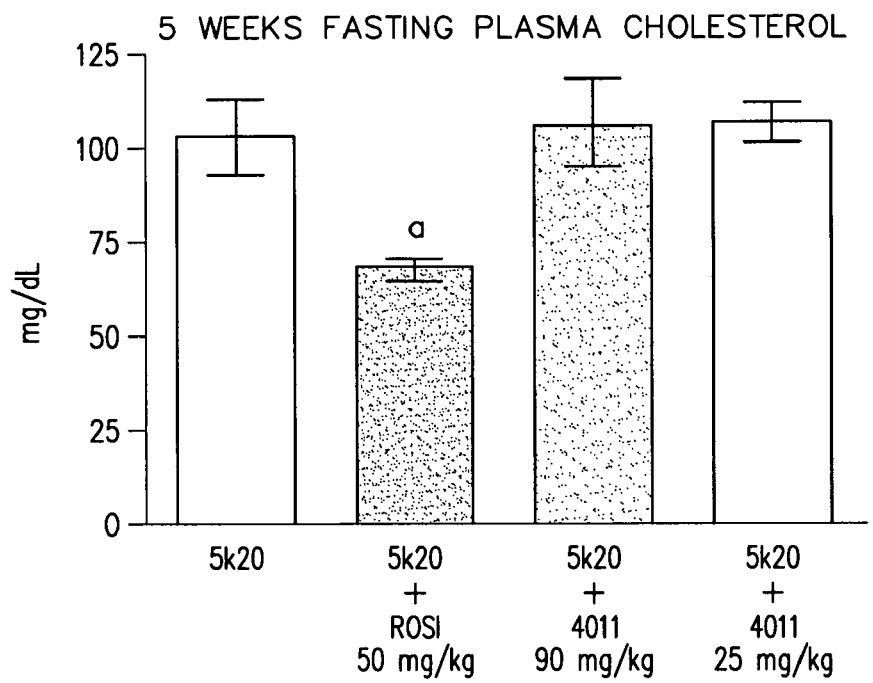
Figure 19E:
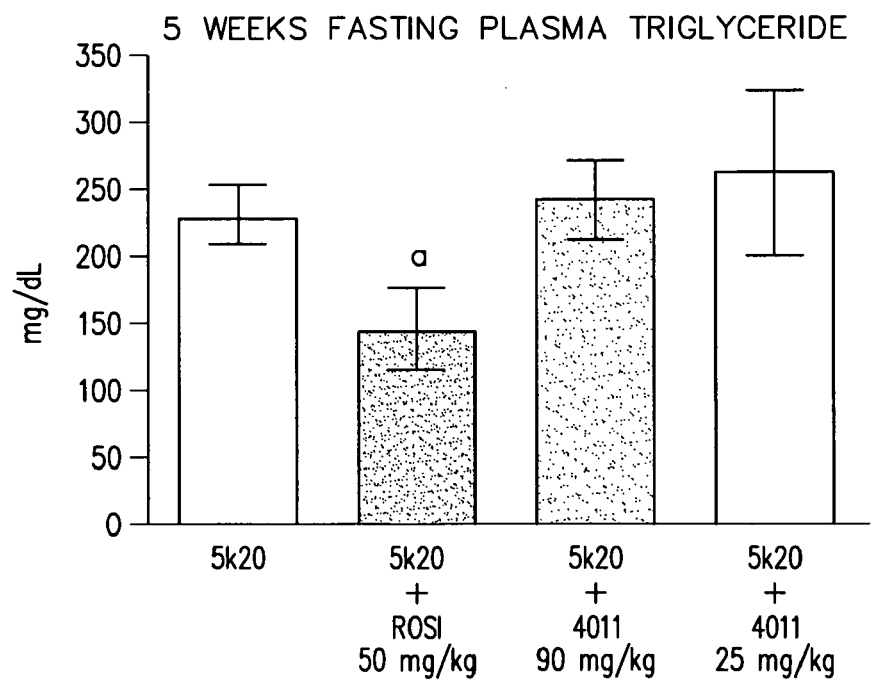
Figure 20A:
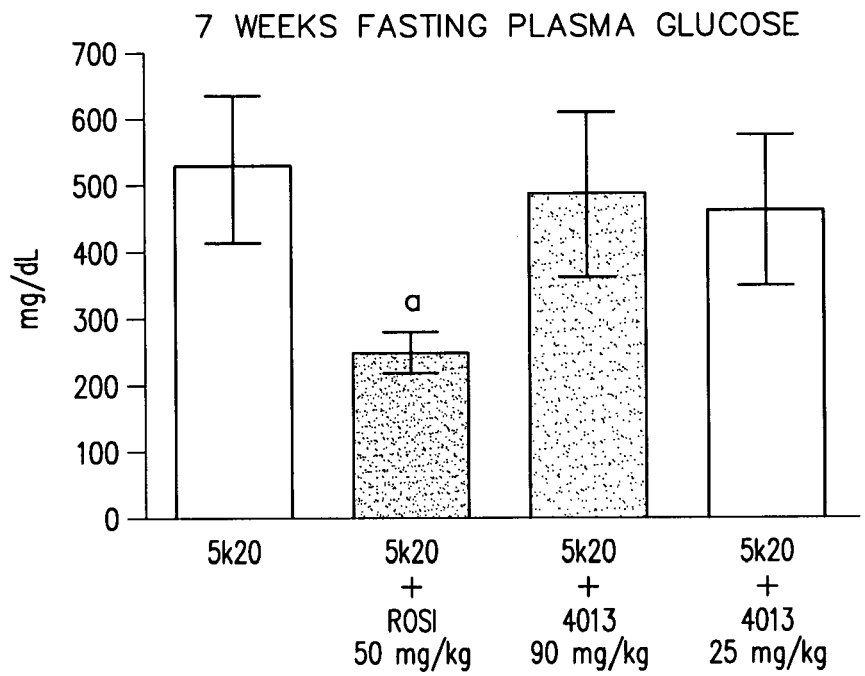
FIGS. 20A, 20B, 20C, 20D and 20E are graphs depicting results for Test Article ILY4013 (ILY-V-32) in a NONc-NZO10/LtJ mouse model of Type II diabetes.
Figure 20B:
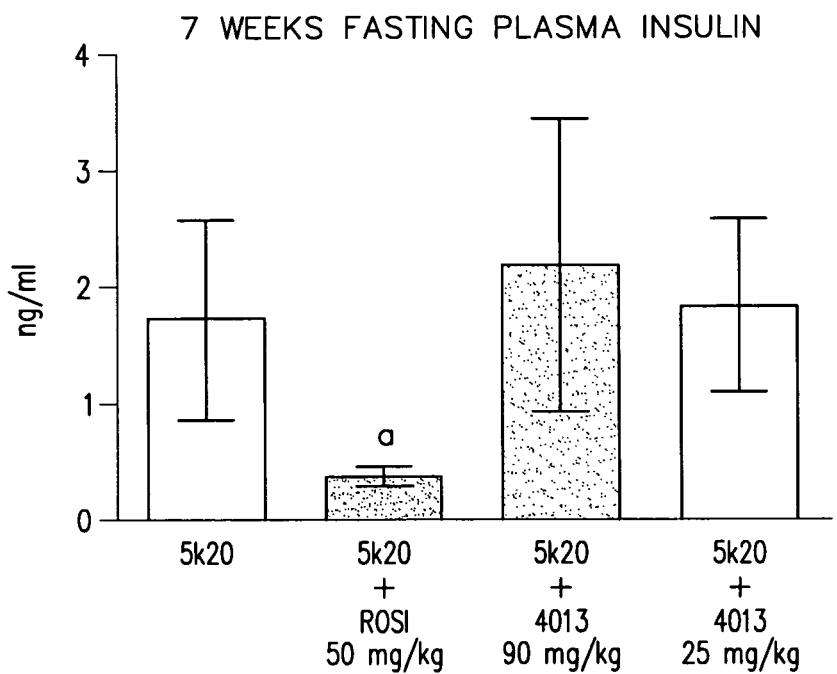
Figure 20C:
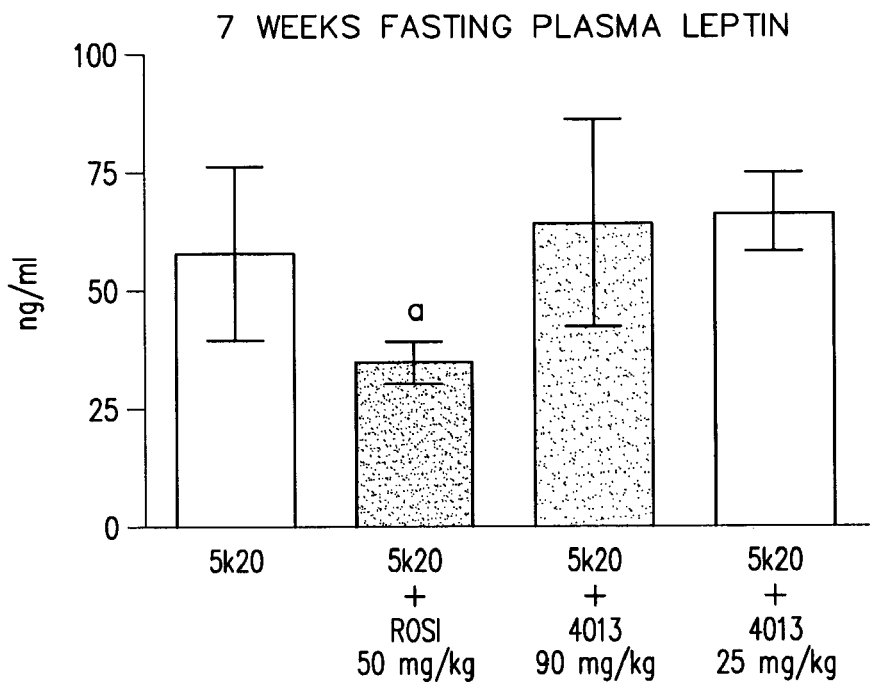
Figure 20D:
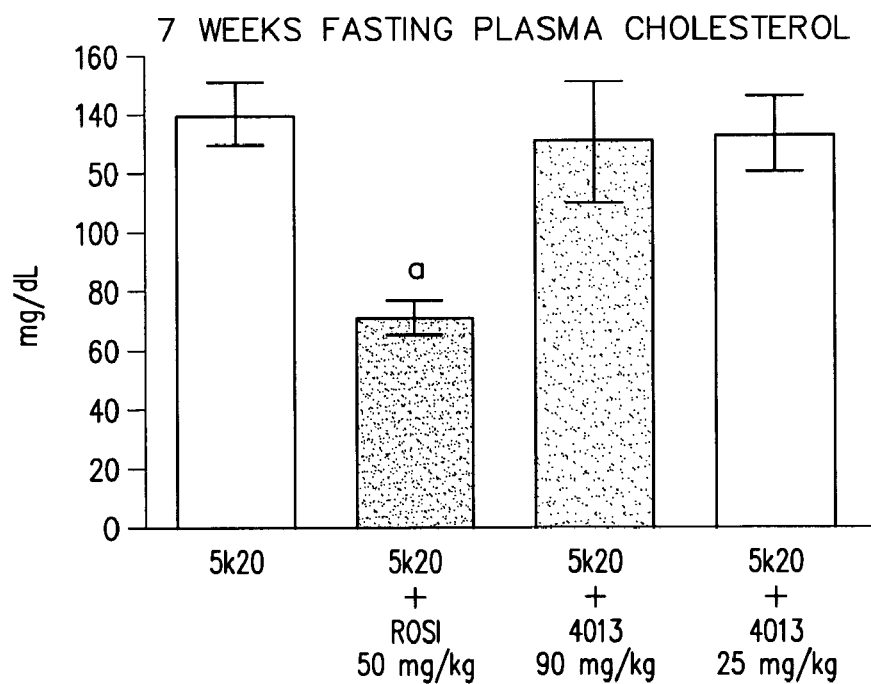
Figure 20E:
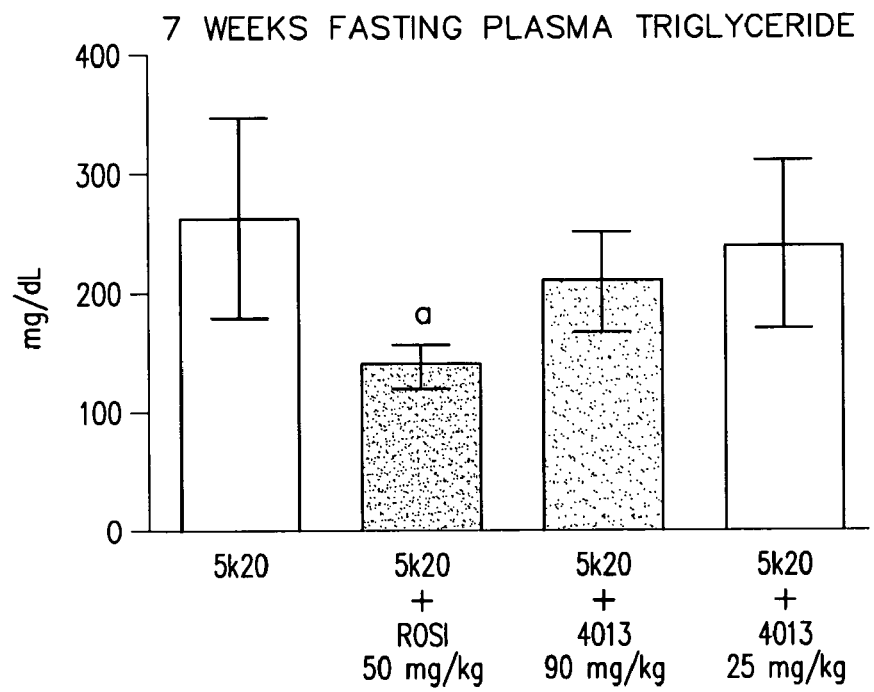
Figure 21A:
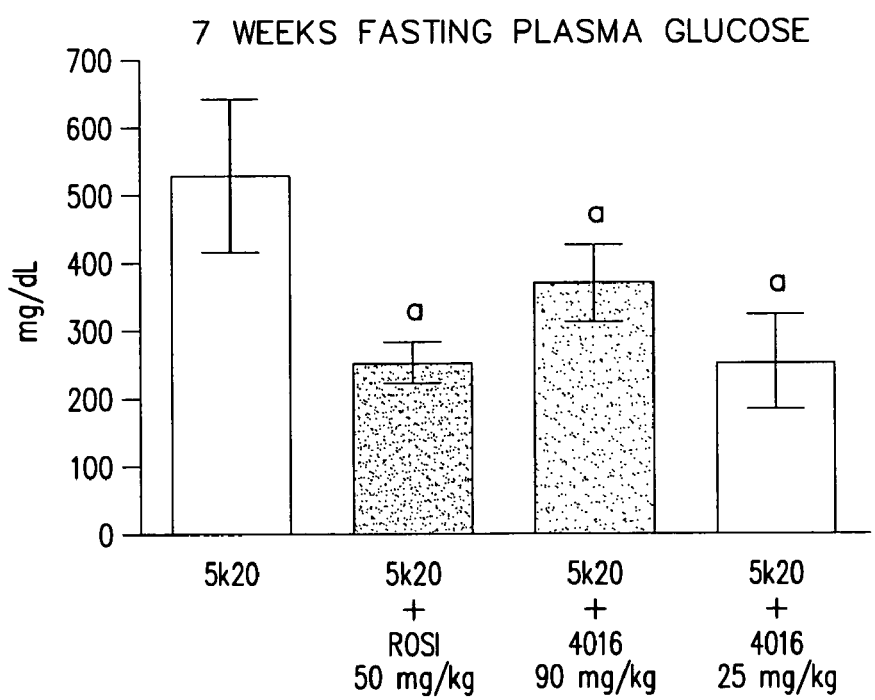
FIGS. 21A, 21B, 21C, 21D and 21E are graphs depicting results for Test Article ILY4016 (ILY-IV-40) in a NONc-NZO10/LtJ mouse model of Type II diabetes.
Figure 21B:
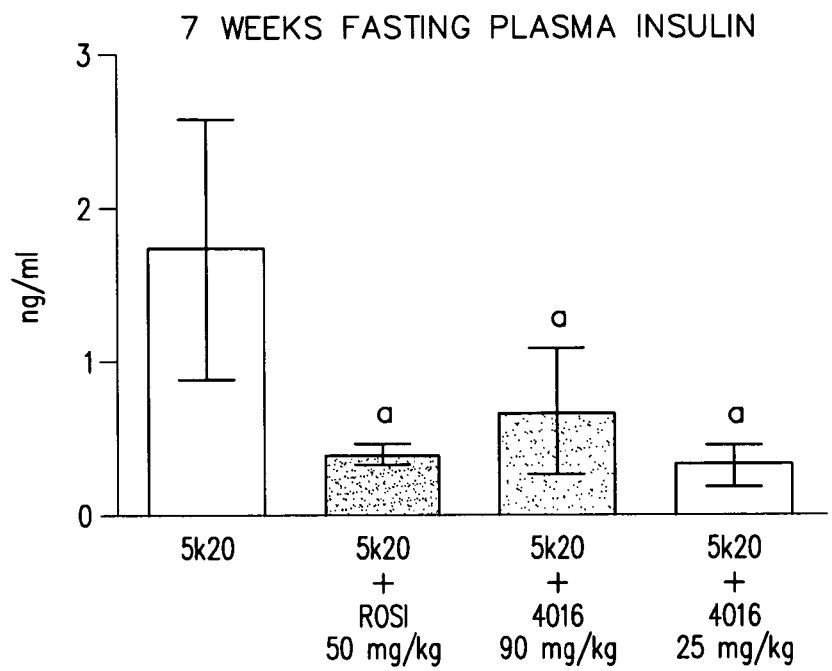
Figure 21C:
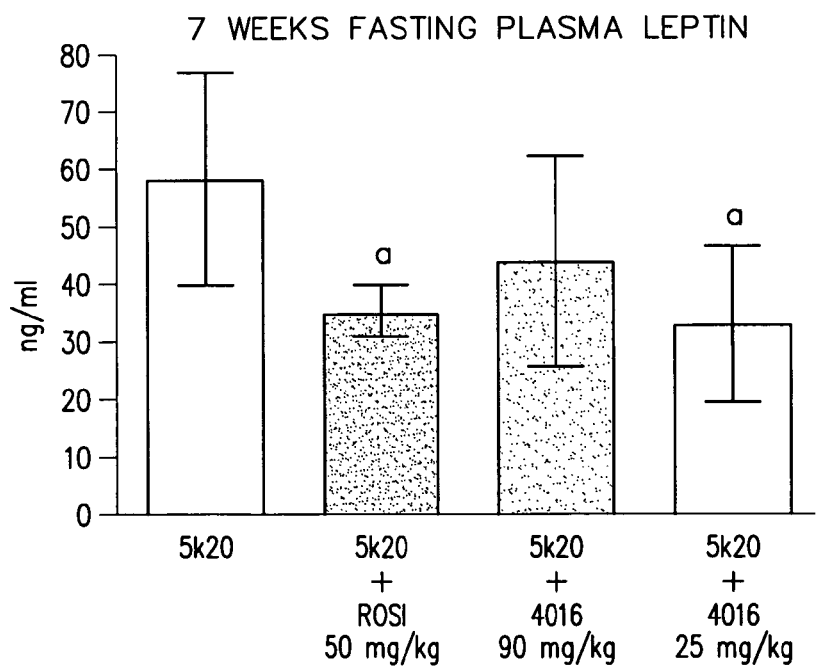
Figure 21D:
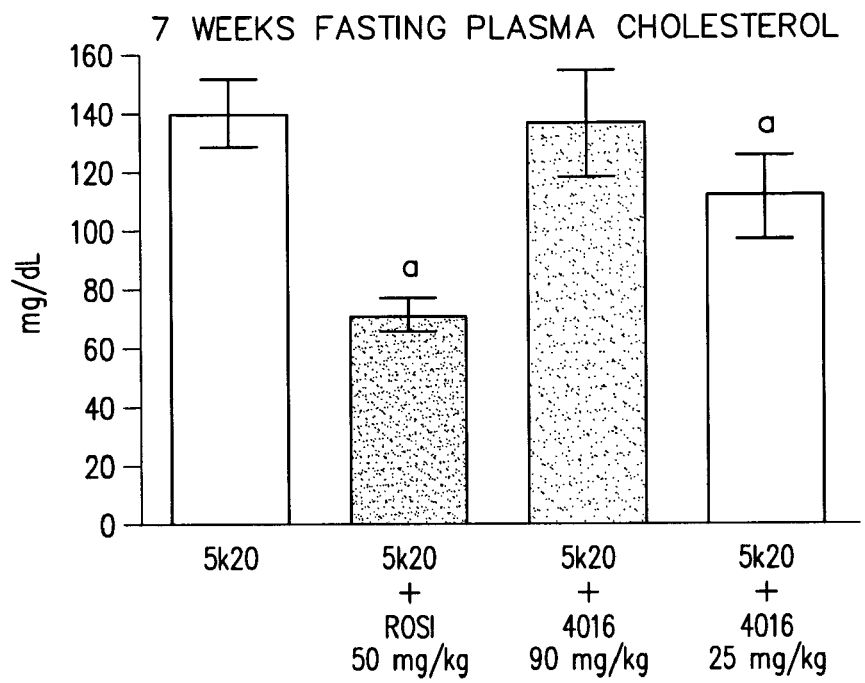
Figure 21E:
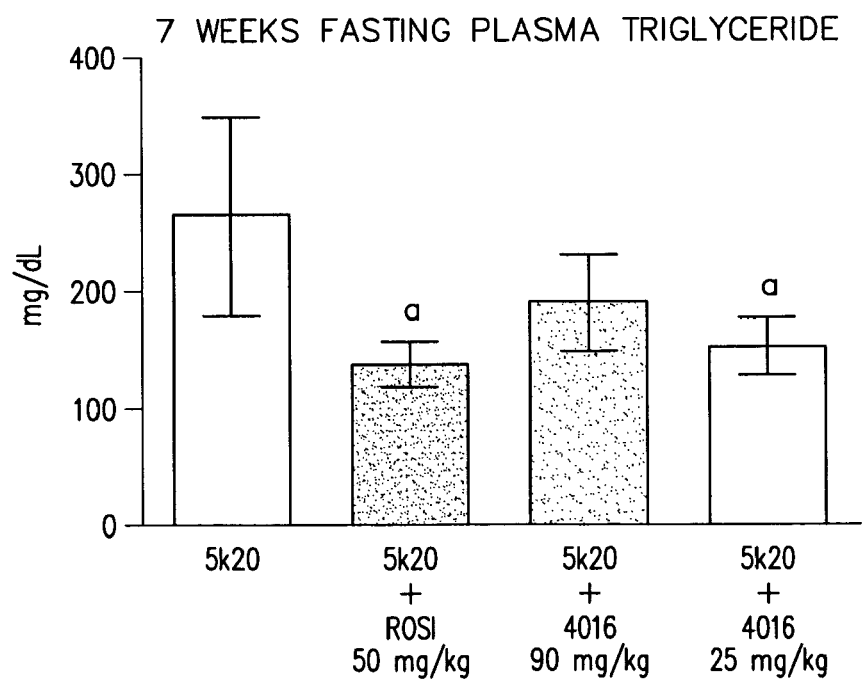

Results for Test Article ILY4008 (ILY-V-26) are shown in FIGS. 10A, 10B, 10C and 10D. Results for Test Article ILY4011 (ILY-V-30) are shown in FIGS. 11A, 11B, 11C and 11D. Results for Test Article ILY4013 (ILY-V-32) are shown in FIGS. 12A, 12B and 12C. Results for Test Article ILY4016 (ILY-IV40) are shown in FIGS. 13A, 13B, and 13C.

No or little effect was observed when animals fed a low fat control diet were compared to animals fed a low fat control diet containing ILY4008, ILY4011, ILY4013 or ILY4016. This observation suggests that some embodiments provide efficacy under high-risk diet conditions yet have no observable effect under lower risk diet conditions.

Example 15

LDL Receptor Knockout Mice

Mice lack an enzyme found in humans, cholesterol ester transfer protein (CETP), which is responsible for the transfer of cholesterol from high density lipoproteins (HDL) to the ApoB-containing lipoproteins such as very low density lipoproteins (VLDL) and low density lipoproteins (LDL). Consequently, LDL cholesterol levels in wild-type mice are very low compared to those seen in humans. The low density lipoprotein receptor (LDLR) is involved with clearing LDL and lipoprotein remnants containing apoE. If the LDLR is inactivated, LDL cholesterol levels rise to levels seen in humans. On a normal rodent diet, the LDL cholesterol levels in LDLR deficient mice are elevated compared to wild-type mice. If the LDLR deficient mice are fed a Western-type diet containing elevated levels of fats and cholesterol, then the total cholesterol and LDL cholesterol levels become highly elevated and can exceed 1000 mg/dL and 300 mg/dL, respectively. This model was used to investigate the effects of indole and indole-related Test Articles. Avandia (rosiglitazone) and Zetia (ezetimibe) were used as control test articles.

Male LDL receptor knockout mice (B6.129S7-Ldlrtm1Her) were obtained from Jackson Labs (Bar Harbor, Me.). Upon arrival, the animals were placed on Laboratory Rodent Diet 5001 (Purina Mills, Inc., St. Louis, Mo.). Diet and water was provided ad libitum throughout the course of the study. Animals were acclimated for at least seven days, and then randomized by body weight into fourteen groups of seven animals each. Each group of animals was placed on diets with and without Test Articles as described in Table 13. All diets other than Laboratory Rodent Diet 5001 were provided by Research Diets (New Brunswick, N.J.).

In these studies and the accompanying figures, Diet D12328 from Research Diets is referred to as the "Low Fat" or Control diet, while Diet D12079B from Research Diets is referred to as the "Western" diet. Groups 1-7 were fed diet D12328 that contained either no drug (Group 1) or varying amounts of Test Articles (Groups 2-7). Groups 8-14 were fed diet D12079 that contained either no drug (Group 8) or varying amounts of Test Articles (Groups 9-14). The Test Article content was calculated such that ad libitum consumption by the animals would deliver doses (in mg of Test Article per Kg animal weight per day) approximating those listed in Table 13.

TABLE 13

LDL Receptor Knockout Mice Assay Diets

| Group | Diet | Added Test Article |
|---|---|---|
| 1 | D12328 | No added Test Article |
| 2 | D12328 | 5 mg/kg/day ezetimibe |
| 3 | D12328 | 90 mg/kg/d ILY4008 or ILY4013 |
| 4 | D12328 | 25 mg/kg/d ILY4008 or ILY4013 |
| 5 | D12328 | 90 mg/kg/d ILY4011 or ILY4016 |
| 6 | D12328 | 25 mg/kg/d ILY4011 or ILY4016 |
| 7 | D12328 | 50 mg/kg/d Rosiglitazone |
| 8 | D12079B | No added Test Article |
| 9 | D12079B | 5 mg/kg/day ezetimibe |
| 10 | D12079B | 90 mg/kg/d ILY4008 or ILY4013 |
| 11 | D12079B | 25 mg/kg/d ILY4008 or ILY4013 |
| 12 | D12079B | 90 mg/kg/d ILY4011 or ILY4016 |
| 13 | D12079B | 25 mg/kg/d ILY4011 or ILY4016 |
| 14 | D12079B | 50 mg/kg/d Rosiglitazone |

Animals were maintained on the diets for eight weeks. Body weights were recorded weekly. Blood was drawn within 1-2 hrs of lights-on, without fasting. The serum was analyzed for total cholesterol, LDL cholesterol, HDL cholesterol, triglycerides (TG), free fatty acid (FFA) and lysophospholipid (LPC) content.

Statistical analyses were performed using GraphPad Prism 4.03. (GraphPad Software, Inc., San Diego, Calif.). Two sets of statistical analyses were performed. First, the Low Fat Chow, no treatment group was compared by student's two-tailed T-test against the Western Diet, no treatment group. In all figures an "a" above the low fat chow, no treatment column signifies that the values are significantly different ($p<0.05$) from the Western diet, no treatment group. Second, all treatment groups on the Western diet were compared to the no-treatment group on that diet by 1-way ANOVA, followed by a Dunnett's post-test.

A "b" above a graph column signifies that the values are significantly different ($p<0.05$) versus the no-treatment group on that diet.

Results for Test Article ILY4008 (ILY-V-26) are shown in FIGS. 14A, 14B, 14C, 14D, 14E and 14F. Results for Test Article ILY4011 (ILY-V-30) are shown in FIGS. 15A, 15B, 15C, 15D, 15E and 15F. Results for Test Article ILY4013 (ILY-V-32) are shown in FIGS. 16A, 16B, 16C and 16D. Results for Test Article ILY4016 (ILY-IV-40) are shown in FIGS. 17A, 17B, 17C and 17D.

No or little effect was observed when animals fed a low fat control diet were compared to animals fed a low fat control diet containing ILY4008, ILY4011, ILY4013 or ILY4016. This observation suggests that some embodiments provide efficacy under high-risk diet conditions yet have no observable effect under lower risk diet conditions.

Example 16

NONcNZO10/LtJ Mouse Model of Type II Diabetes

The NONcNZO10/LtJ mouse strain (Jackson Labs, Bar Harbor Me.) is a recombinant congenic strain developed specifically to model human Type 2 diabetes. Although other mouse strains with specific defects in the leptin signaling pathway (for example BKS.Cg-m+/+Leprdb/J, B6.V-Lepob/J and KK.Cg-Ay/J are excellent models of monogenic obesity and useful for researching type 2 diabetes, they do not reflect the more common human obesity-induced diabetes (diabesity) syndromes. Common human diabesity syndromes are polygenic, not monogenic, and the clinical phenotypes of the monogenic models are extreme: massive obesity and hyperphagia, either extremely high or no leptin in circulation, and extreme hyperinsulinism. In contrast, NONcNZO10/LtJ has moderate behavioral and endocrine phenotypes, and males exhibit a maturity-onset transition from impaired glucose tolerance to a stable non-fasting hyperglycemia without hyperphagia or reproductive failure, and only moderately elevated insulin and leptin concentrations in plasma (Leiter, E H, et al. (2005) "Differential Endocrine Responses to Rosiglitazone Therapy in New Mouse Models of Type 2 Diabetes", Endocrinology, Leiter, EH and Reifsnyder, PC (2004) "Differential levels of diabetogenic stress in two new mouse models of obesity and type 2 diabetes", Diabetes 53 Suppl 1: S4-11). Also in contrast to the diet-induced obesity (DIO) model used in other studies, NONcNZO10/LtJ male mice show robust hyperglycemia and elevated insulin when fed diets that have only moderately increased amount of fat compared to standard laboratory rodent chow. This model was used to investigate the effects of indole and indole-related Test Articles. Avandia (rosiglitazone) was used as a control test article.

Male NONcNZO10/LtJ mice, five weeks of age, were obtained from Jackson Labs (Bar Harbor, Me.). Upon arrival, the animals were placed on Laboratory Rodent Diet 5K20 (Purina Mills, Inc., St. Louis, Mo.). Diet and water was provided ad libitum throughout the course of the study. Animals were acclimated for at least four weeks, and then weighed on study day (1). Animals with outlying weights were removed from the study. The remaining animals were randomized by weight into six groups of seven animals each. Each group of animals was placed on diets with and without test articles as described in Table 14. All diets were provided by Research Diets (New Brunswick, N.J.). Maltodextrin (5% by weight) was added at Research Diets to each diet to aid reformulation into pellets after the addition of test articles into the 5K20 diet.

The test article content was calculated such that ad libitum consumption by the animals would deliver doses (in mgs Test Article per Kg animal weight per day) approximating those listed in Table 14.

Animals were maintained on the diets for up to two months. Body weights were recorded weekly. Blood was drawn by retroorbital bleeding. For these blood draws, the animals were fasted overnight. The serum was analyzed for glucose, insulin, leptin, total cholesterol and triglyceride (TG) content.

TABLE 14

NONcNZO10/LtJ Mouse Model of Type II Diabetes Assay Diets

| Group | Diet | Added Test Article |
|---|---|---|
| 1 | 5K20 | No added Test Article |
| 2 | 5K20 | 50 mg/kg/d Rosiglitazone |
| 3 | 5K20 | 90 mg/kg/d ILY4008 or ILY4013 |
| 4 | 5K20 | 25 mg/kg/d ILY4008 or ILY4013 |
| 5 | 5K20 | 90 mg/kg/d ILY4011 or ILY4016 |
| 6 | 5K20 | 25 mg/kg/d ILY4011 or ILY4016 |

Statistical analyses were performed using GraphPad Prism 4.03. (GraghPad Software, Inc., San Diego, Calif.). In all figures an "a" above a graph column signifies that the values are significantly different (p<0.05) by 1-way ANOVA, followed by a Dunnett's post-test versus the group fed 5K20 with no test article added.

Results for Test Article ILY4008 (ILY-V-26) are shown in FIGS. 18A, 18B, 18C, 18D and 18E. Results for Test Article ILY4011 (ILY-V-30) are shown in FIGS. 19A, 19B, 19C, 19D and 19E. Results for Test Article ILY4013 (ILY-IV-32) are shown in FIGS. 20A, 20B, 20C, 20D and 20E. Results for Test Article ILY4016 (ILY-IV-40) are shown in FIGS. 21A, 21B, 20C, 20D and 20E.

Example 17

Hamster Diet-Induced Dyslipidemia

Golden Syrian hamsters become hypercholesterolemic within one week of being fed a standard rodent diet that has been supplemented with 0.5% cholesterol (van Heek, M, et al. (2001) "Ezetimibe selectively inhibits intestinal cholesterol absorption in rodents in the presence and absence of exocrine panceatic function", Br J Pharmacol 134: 409-417). In contrast to wild-type mice, hamsters express cholesterol ester transfer protein (CETP) and have a lipid metabolic profile similar to that of humans. Consequently, hamsters are considered to be an excellent non-primate model of human lipid and cholesterol metabolism (Spady, D K and Dietschy, J M (1988) "Interaction of dietary cholesterol and triglycerides in the regulation of hepatic low density lipoprotein transport in the hamster", J Clin Invest 81: 300-309, Spady, D K and Dietschy, J M (1989) "Interaction of aging and dietary fat in the regulation of low density lipoprotein transport in the hamster", J Lipid Res 30: 559-569). This model was used to investigate the effects of indole and indole-related Test Articles. Zetia (ezetimibe) was used as a control test article. The Test Article content was calculated such that ad libitum consumption by the animals would deliver doses (in mg of Test Article per kg animal weight per day) approximating those listed in Table 15.

Golden Syrian hamsters were placed on Laboratory Rodent Diet 5001 (Purina Mills, Inc., St. Louis, Mo.) for a ten-day acclimation period. Diet and water was provided ad libitum throughout the course of the study. After acclimation, blood was drawn and serum cholesterol levels were measured. Animals with outlying cholesterol levels were removed from the study and the remaining animals were randomized by matinal serum cholesterol into eight groups of six animals each. Each group of animals was placed on diets with and without test articles as described in Table 15. All diets were provided by Research Diets (New Brunswick, N.J.). Blood draws via retro-orbital bleeding on lightly sedated hamsters were performed within two hours of lights on at baseline (pre-diet dosing, for randomization), and on study days 7, 14, and 21. The final blood draw, on day 28, was performed through terminal cardiocentesis after 24 hr food fasting. Results from the day 28 blood draw were thus not included in the 2-way ANOVA analysis. The serum was analyzed for total cholesterol, LDL-cholesterol, HDL-cholesterol and triglyceride (TG) content.

TABLE 15

Hamster Diet-Induced Dyslipidemia Assay Diets

| Group | Test Article | Base Diet | Dose (mg/kg) | Dose (mg/kg of diet) |
|---|---|---|---|---|
| 1 | none | Purina 5001 | ad lib. | N/A |
| 2 | none | Purina 5001 + 0.5% Cholesterol | ad lib | N/A |
| 3 | ezetimibe | Purina 5001 + 0.5% Cholesterol | ad lib (estimated 1 mg ezetimibe/kg/d). | 10 |
| 4 | ILY4008 | Purina 5001 + 0.5% Cholesterol | ad lib (estimated 90 mg ezetimibe/kg/d). | 900 |
| 5 | ILY4011 | Purina 5001 + 0.5% Cholesterol | ad lib (estimated 90 mg ezetimibe/kg/d). | 900 |
| 6 | ILY4013 | Purina 5001 + 0.5% Cholesterol | ad lib (estimated 90 mg ezetimibe/kg/d). | 900 |
| 7 | ILY4016 | Purina 5001 + 0.5% Cholesterol | ad lib (estimated 90 mg ezetimibe/kg/d). | 900 |
| 8 | ILY4017 | Purina 5001 + 0.5% Cholesterol | ad lib (estimated 90 mg ezetimibe/kg/d). | 900 |

Statistical analyses were performed using GraphPad Prism 4.03. (GraphPad Software, Inc., San Diego, Calif.). In all figures "*" above a graph column signifies that the values are significantly different (p<0.05) versus group 2 (Purina 5001 supplemented with 0.5% cholesterol and no test article added) by 2-way ANOVA, followed by a Bonferroni's post-test. Day 28 (fasting) values were not included in the 2-way ANOVA analysis.

The results for Test Articles ILY4016 (ILY-IV40), Test Article ILY4008 (ILY-V-26), Test Article ILY4013 (ILY-V-32), Test Article ILY4011 (ILY-V-30), and Test Article ILY4017 (ILY-V-37) are shown in FIGS. 22A and 22B.

Example 14

Toxicology

The purpose of this study was to evaluate the toxicity of indole and indole-related Test Articles when administered daily via oral gavage to mice for 5 consecutive days.

Assessment of toxicity was based on mortality; clinical signs, body weight, food consumption, clinical pathology, and macroscopic pathology data.

All animals survived to scheduled sacrifice. There were no treatment-related clinical observations. There were no remarkable changes in the body weight or food consumption data.

The clinical pathology data were generally unremarkable and similar among the groups. There were no differences between the vehicle control group and the treated groups that could be attributed to the administration of any of the test articles (ILY4008, ILY4011, ILY4013, ILY4016, and ILY4017).

There were no macroscopic findings at necropsy. There was no evidence of toxicity associated with any of the test articles at the dose levels use in this study.

The observation of no toxicity is consistent with embodiments having a characteristic property of low absorption or non-absorption.

All publications, patents, and patent applications mentioned in this specification are herein incorporated by reference to the same extent as if each individual publication, patent, or patent application was specifically and individually indicated to be incorporated by reference.

It can be appreciated to one of ordinary skill in the art that many changes and modifications can be made thereto without departing from the spirit or scope of the appended claims, and such changes and modifications are contemplated within the scope of the instant invention.

We claim:

1. A composition of matter comprising a substituted organic compound, or a salt thereof, wherein the substituted organic compound has two or more independently selected multi-ring structures, Z, linked by independently selected linking moieties, L, to a multifunctional bridge moiety, as represented by formula (D-I)

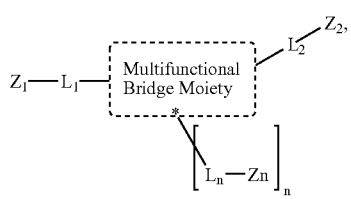

(D-I)

with n being an integer ranging from 0 to 2, the two or more multi-ring structures, Z, being covalently bonded to the multifunctional bridge moiety through corresponding linking moieties, L, each of the two or more multi-ring structures is a fused five-membered ring and six-membered ring represented by formulas (I) or (II)

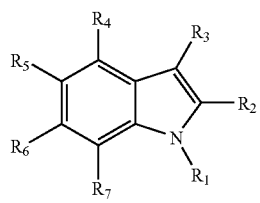

(I)

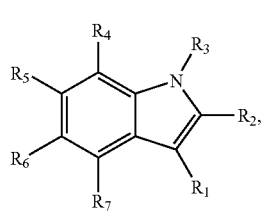

(II)

$R_1$ through $R_7$ each being independently selected from the group consisting of hydrogen, halide, oxygen, sulfur, phosphorus, hydroxyl, amine, thiol, alkyl, substituted alkyl, alkenyl, substituted alkenyl, alkynyl, substituted alkynyl, ether, carbonyl, acidic, carboxyl, ester, amide, carbocyclic, acylamino, oximyl, hydrazyl and combinations thereof, provided that $R_1$ is $C_4$-$C_{36}$ alkyl or substituted $C_4$-$C_{36}$ alkyl; wherein $R_1$ is linked to a linking moiety L; $R_2$ is alkyl or substituted alkyl;

L is selected from O and S; and the multifunctional bridge moiety having at least (n+2) reactive sites to which the corresponding linking groups of the two or more multi-ring structures are bonded, the multifunctional bridge moiety being selected from the group consisting of alkyl, phenyl, and combinations thereof.

2. The composition of claim 1 wherein $R_3$ is a moiety represented by formula (C3-I or C3-II)

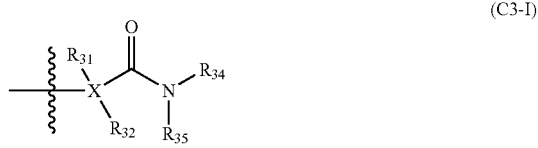

(C3-I)

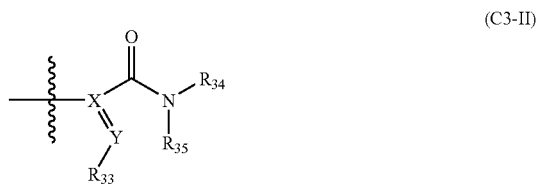

(C3-II)

with

X being selected from the group consisting of O, C and N, $R_{31}$ being optional, and if present being selected from the group consisting of hydrogen, halide, hydroxyl and cyano, $R_{32}$ being optional, and if present being selected from the group consisting of hydrogen, halide, hydroxyl, and cyano, Y being selected from the group consisting of O, S, and N, $R_{33}$ being optional, and if present being selected from the group consisting of hydrogen, hydroxyl, $C_1$-$C_6$ alkyl, substituted $C_1$-$C_6$ alkyl, $C_1$-$C_6$ alkoxyl, and substituted $C_1$-$C_6$ alkoxyl, and $R_{34}$ and $R_{35}$ each being independently selected from the group consisting of hydrogen, hydroxyl, alkoxyl, alkyl, substituted alkyl, amine, and alkylsulfonyl.

3. The composition of claim 1 wherein $R_3$ is a moiety represented by formula (C3-I-A or C3-II-A)

(C3-I-A)

-continued

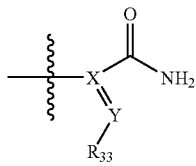
(C3-II-A)

with
- X being selected from the group consisting of O, C and N,
- $R_{31}$ being optional, and if present being selected from the group consisting of hydrogen, halide, hydroxyl and cyano,
- $R_{32}$ being optional, and if present being selected from the group consisting of hydrogen, halide, hydroxyl, and cyano,
- Y being selected from the group consisting of O, S, and N,
- $R_{33}$ being optional, and if present being selected from the group consisting of hydrogen, hydroxyl, $C_1$-$C_6$ alkyl, substituted $C_1$-$C_6$ alkyl, $C_1$-$C_6$ alkoxyl and substituted $C_1$-$C_6$ alkoxy.

4. The composition of claim 1 wherein $R_3$ is a moiety represented by a formula selected from the group consisting of

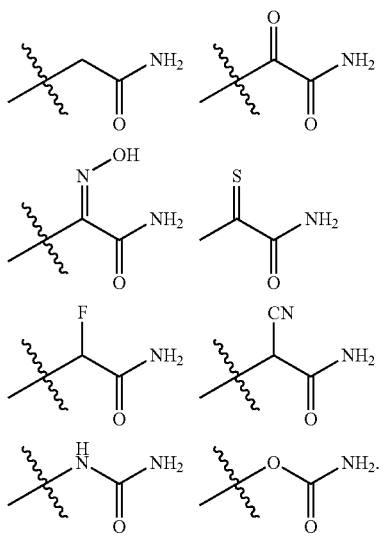

5. The composition of claim 4 wherein $R_4$ is a moiety represented by the formula

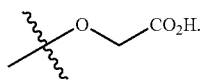

6. The composition of claim 1 wherein $R_4$ is a moiety represented by formula selected from (C4-Acidic) or (C-4 Amide)

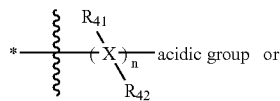
(C4-Acidic)

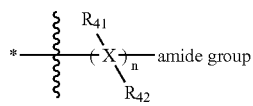
(C-4 Amide)

with
- n being an integer ranging from 1 to 5, and
- for each n,
  - X being independently selected from the group consisting of C, O, S, and N, and
  - $R_{41}$ and $R_{42}$ each being optional, but if present being independently selected from the group consisting of hydrogen, halide, alkyl, substituted alkyl, phenyl, aryl, amine, alkoxyl, alkylsulfonyl, alkylphosphonyl, alkylcarbonyl, carboxyl, phosphonic, sulfonic, carboxamide, and cyano.

7. The composition of claim 1 wherein $R_4$ is a moiety represented by formula (C4-Acidic)

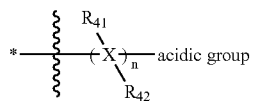
(C4-Acidic)

with
- n being an integer ranging from 1 to 5, and
- for each n,
  - X being independently selected from the group consisting of C, O, S, and N, and
  - $R_{41}$ and $R_{42}$ each being optional, but if present being independently selected from the group consisting of hydrogen, halide, alkyl, substituted alkyl, phenyl, aryl, amine, alkoxyl, alkylsulfonyl, alkylphosphonyl, alkylcarbonyl, carboxyl, phosphonic, sulfonic, carboxamide, and cyano.

8. The composition of claim 1 wherein $R_4$ is a moiety represented by formula (C4-I-A)

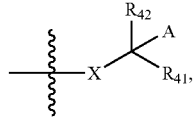
(C4-I-A)

with
- X being selected from the group consisting of O, C, S and N,
- A being an acidic group,
- $R_{41}$ being selected from the group consisting of hydrogen, halide, hydroxyl and cyano, and
- $R_{42}$ being selected from the group consisting of (i) $C_1$-$C_8$ alkyl, (ii) $C_1$-$C_8$ alkyl substituted with one or more substituents selected from halide, hydroxyl and amine, (iii) hydrogen, (iv) halide, and (v) carboxyl; preferably $R_{42}$ being selected from the group consisting of (i) $C_2$-$C_6$ alkyl, (ii) $C_2$-$C_6$ alkyl substituted with one or more substituents selected from halide, hydroxyl and amine, (iii) halide, and (iv) carboxyl.

9. The composition of claim 8 wherein $R_3$ is a moiety represented by the formula

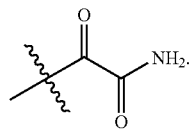

10. The composition of claim 1 wherein the linking moieties and the multifunctional bridge moiety are represented by formulas selected from the group consisting of

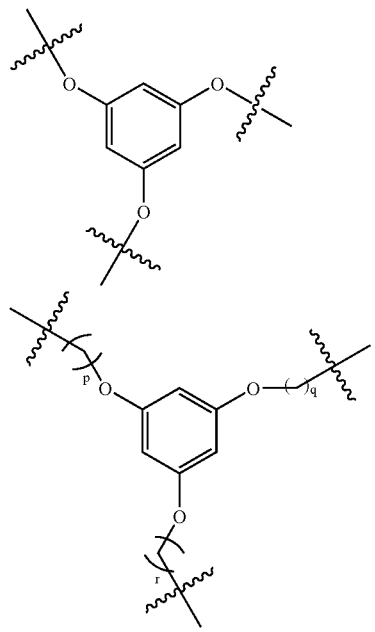

with in each case independently, and as applicable, p, q and r each being an independently selected integer ranging from 0 to about 16.

11. The composition of claim 10 wherein the composition is

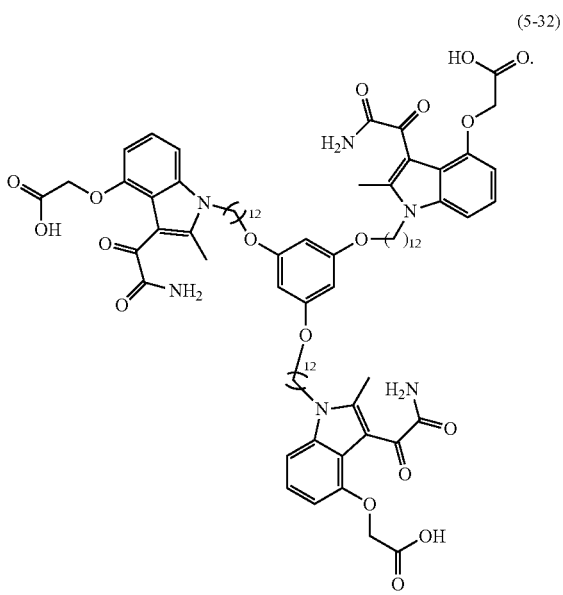

(5-32)

12. The composition of claim 1 represented by a formula selected from the group consisting of

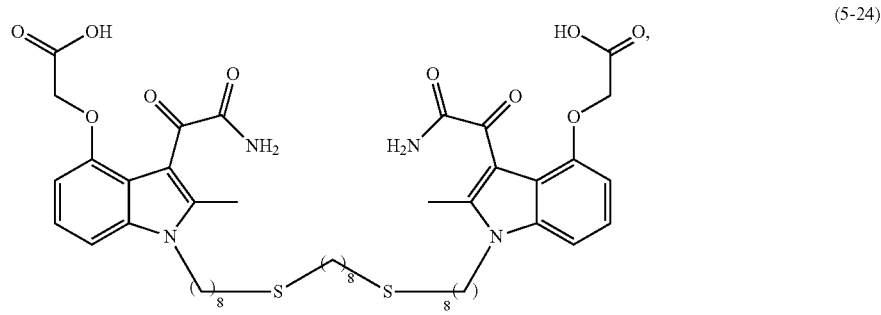

(5-24)

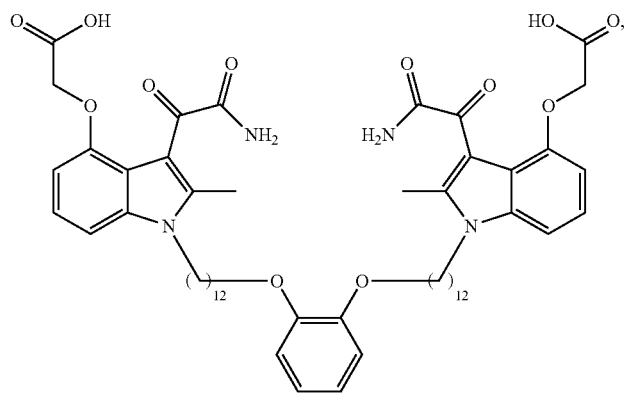
(5-27)
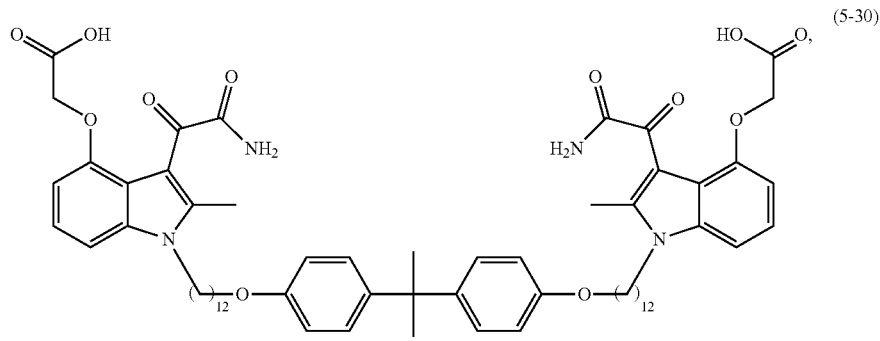
(5-30)
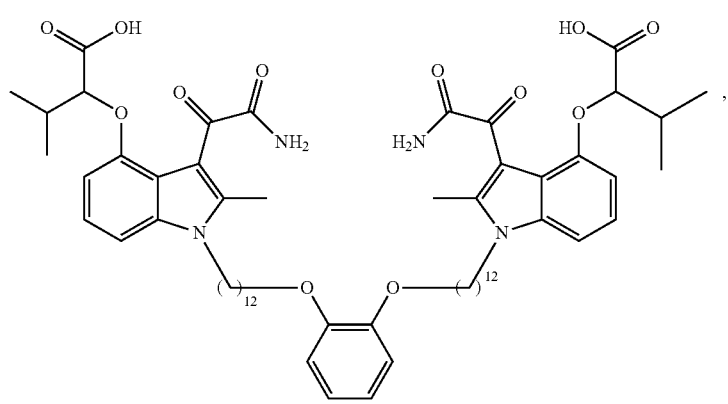
(5-33)
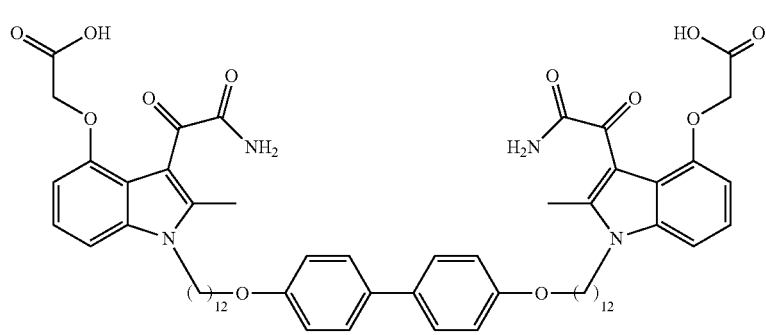
(5-36)

-continued

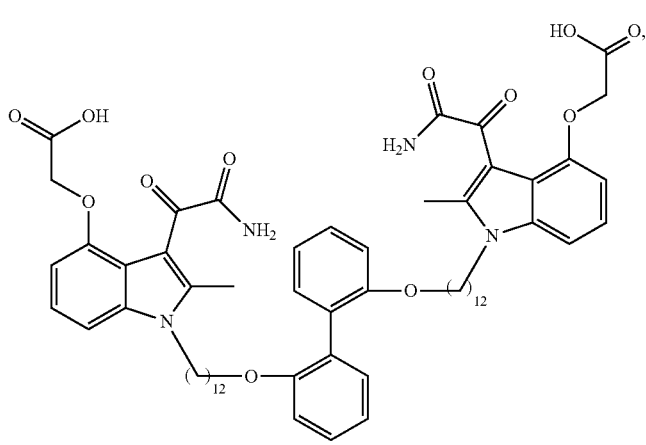

(5-37)

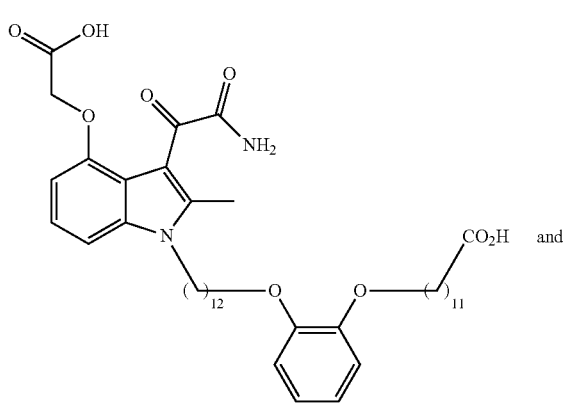

(5-41)

and

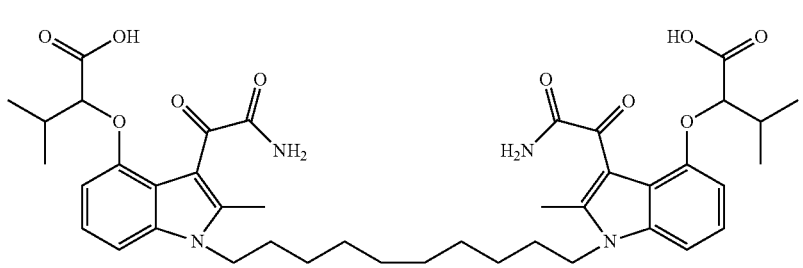

(5-44)

13. A method comprising of treating obesity, type 2 diabetes, insulin resistance, glucose intolerance, hypercholesterolemia and hypertriglyceridemia or any combinations thereof, to achieve a therapeutic benefit comprising administering an effective amount of a pharmaceutical composition to a subject, the pharmaceutical composition being a phospholipase-$A_2$ inhibitor comprising the composition of claim 1.

14. A method comprising of treating obesity, type 2 diabetes, insulin resistance, glucose intolerance, hypercholesterolemia and hypertriglyceridemia or any combinations thereof, to achieve a therapeutic benefit comprising administering an effective amount of a pharmaceutical composition to a subject, the pharmaceutical composition being a phospholipase-$A_2$ inhibitor comprising the composition of claim 12.

15. The composition of claim 1 wherein the linking moieties and the multifunctional bridge moiety are represented by formulas selected from the group consisting of
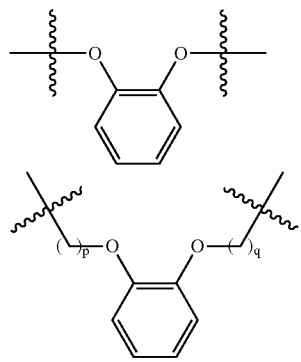
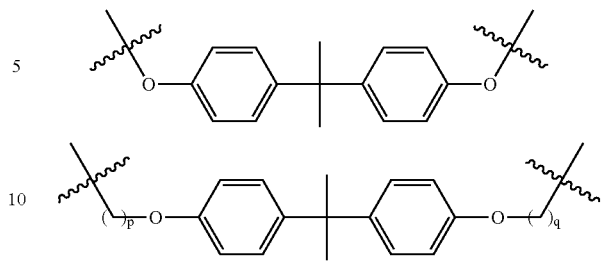
with in each case independently, and as applicable, p, q and r each being an independently selected integer ranging from 0 to about 16.
* * * * *